United States Patent
Amann et al.

(10) Patent No.: US 12,227,594 B2
(45) Date of Patent: Feb. 18, 2025

(54) BISPECIFIC 2+1 CONTORSBODIES

(71) Applicant: Hoffmann-La Roche Inc., Little Falls, NJ (US)

(72) Inventors: Maria Amann, Schlieren (CH); Claudia Ferrara Koller, Schlieren (CH); Reto Flury, Schlieren (CH); Guy Georges, Penzberg (DE); Sandra Grau-Richards, Schlieren (CH); Alexander Haas, Penzberg (DE); Friederike Hesse, Penzberg (DE); Sabine Imhof-Jung, Penzberg (DE); Christian Klein, Schlieren (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/760,820

(22) PCT Filed: Oct. 31, 2018

(86) PCT No.: PCT/EP2018/079785
§ 371 (c)(1),
(2) Date: Apr. 30, 2020

(87) PCT Pub. No.: WO2019/086500
PCT Pub. Date: May 9, 2019

(65) Prior Publication Data
US 2021/0324108 A1    Oct. 21, 2021

(30) Foreign Application Priority Data
Nov. 1, 2017  (EP) ..................... 17199537

(51) Int. Cl.
*C07K 16/40* (2006.01)
*A61K 45/06* (2006.01)
*C07K 16/28* (2006.01)
*C07K 16/30* (2006.01)

(52) U.S. Cl.
CPC .............. *C07K 16/40* (2013.01); *A61K 45/06* (2013.01); *C07K 16/2878* (2013.01); *C07K 16/30* (2013.01); *C07K 2317/31* (2013.01); *C07K 2317/524* (2013.01); *C07K 2317/526* (2013.01); *C07K 2317/53* (2013.01); *C07K 2317/55* (2013.01); *C07K 2317/565* (2013.01); *C07K 2319/30* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 5,500,362 A | 3/1996 | Robinson et al. |
| 5,571,894 A | 11/1996 | Wels et al. |
| 5,587,458 A | 12/1996 | King et al. |
| 5,731,168 A | 3/1998 | Carter et al. |
| 5,821,337 A | 10/1998 | Carter et al. |
| 5,869,046 A | 2/1999 | Presta et al. |
| 5,959,177 A | 9/1999 | Hein et al. |
| 5,969,108 A | 10/1999 | McCafferty et al. |
| 6,040,498 A | 3/2000 | Stomp et al. |
| 6,171,586 B1 | 1/2001 | Lam et al. |
| 6,248,516 B1 | 6/2001 | Winter et al. |
| 6,267,958 B1 | 7/2001 | Andya et al. |
| 6,417,429 B1 | 7/2002 | Hein et al. |
| 6,420,548 B1 | 7/2002 | Vezina et al. |
| 6,602,684 B1 | 8/2003 | Umana et al. |
| 6,737,056 B1 | 5/2004 | Presta |
| 6,818,418 B1 | 11/2004 | Lipovsek et al. |
| 7,125,978 B1 | 10/2006 | Vezina et al. |
| 7,166,697 B1 | 1/2007 | Galanis et al. |
| 7,250,297 B1 | 7/2007 | Beste et al. |
| 7,288,638 B2 | 10/2007 | Jure-Kunkel et al. |
| 7,332,581 B2 | 2/2008 | Presta |
| 7,521,541 B2 | 4/2009 | Eigenbrot et al. |
| 7,659,384 B2 | 2/2010 | Jure-Kunkel et al. |
| 7,695,936 B2 | 4/2010 | Carter et al. |
| 2003/0157108 A1 | 8/2003 | Presta |
| 2004/0093621 A1 | 5/2004 | Shitara et al. |
| 2004/0132028 A1 | 7/2004 | Stumpp et al. |
| 2004/0132066 A1 | 7/2004 | Balint et al. |
| 2005/0123546 A1 | 6/2005 | Umana et al. |
| 2007/0224633 A1 | 9/2007 | Skerra et al. |
| 2007/0258984 A1 | 11/2007 | Fyfe et al. |

(Continued)

FOREIGN PATENT DOCUMENTS

| | | |
|---|---|---|
| CN | 1603345 A | 4/2005 |
| CN | 102369214 | 3/2012 |

(Continued)

OTHER PUBLICATIONS

Lloyd et al., Protein Engineering, Design & Selection 22:159-168 (Year: 2009).*
Edwards et al., J Mol Biol. 334(1): 103-118 (Year: 2003).*
Piche-Nicholas et al., MABS 10(1): 81-94 (Year: 2018).*
Barrios et al., J Molecular Recognition 17: 332-338 (Year: 2004).*
MacCallum et al., Mol. Biol 262: 732-745 (Year: 1996).*
Wu et al., J. Mol. Biol. 294: 151-162 (Year: 1999).*
Hust et al., "Single Chain Fab (scFab) Fragment" BMC Biotechnology, Biomed Central Ltd. London, GB. (XP21023594), 7(1):14 (Mar. 8, 2007).
Song, L., et al. "A new model of trispecific antibody with cytotoxicity against tumor cells" Acta Biochimica et Biophysica Sinica 35(6):503-510 (Jun. 1, 2003).
Trabi, M., et al., "Circular proteins—no ends in sight" Trends Biochem Sci 27(3):132-138 (Mar. 1, 2002).

(Continued)

*Primary Examiner* — Phuong Huynh
(74) *Attorney, Agent, or Firm* — GENENTECH, INC.; Lawrence S. Graham

(57) ABSTRACT

The invention relates to novel bispecific antibodies consisting of two fusion polypeptides comprising two antigen binding domains capable of specific binding to a first target and one antigen binding domain capable of specific binding to a second target, and to methods of producing these molecules and to methods of using the same.

14 Claims, 53 Drawing Sheets

Specification includes a Sequence Listing.

(56) References Cited

U.S. PATENT DOCUMENTS

| | | | |
|---|---|---|---|
| 2008/0139791 A1 | 6/2008 | Lipovsek et al. | |
| 2014/0112927 A1* | 4/2014 | Chen ..................... | C07K 16/10 530/387.3 |
| 2014/0155581 A1 | 6/2014 | Gao et al. | |
| 2019/0389971 A1* | 12/2019 | Dengl .................... | C07K 16/00 |
| 2021/0122832 A1 | 4/2021 | Brinkmann et al. | |
| 2021/0347916 A1* | 11/2021 | Dengl .................... | C07K 16/46 |
| 2024/0166771 A1* | 5/2024 | Dengl .................... | C07K 16/46 |

FOREIGN PATENT DOCUMENTS

| | | |
|---|---|---|
| EP | 0404097 B1 | 12/1990 |
| EP | 1378520 A1 | 1/2004 |
| EP | 1870459 A1 | 12/2007 |
| EP | 1641818 B1 | 12/2008 |
| WO | 93/01161 A1 | 1/1993 |
| WO | 93/16185 A2 | 8/1993 |
| WO | 96/027011 A1 | 9/1996 |
| WO | 97/30087 A1 | 8/1997 |
| WO | 98/050431 A2 | 11/1998 |
| WO | 98/050431 A3 | 11/1998 |
| WO | 98/58964 A1 | 12/1998 |
| WO | 99/22764 A1 | 5/1999 |
| WO | 02/020565 A2 | 3/2002 |
| WO | 03/011878 A2 | 2/2003 |
| WO | 03/011878 A3 | 2/2003 |
| WO | 2005/056764 A2 | 6/2005 |
| WO | 2005/100402 A1 | 10/2005 |
| WO | 2006/029879 A2 | 3/2006 |
| WO | 2006/044908 A2 | 4/2006 |
| WO | 2006/044908 A3 | 4/2006 |
| WO | 2006/128103 A2 | 11/2006 |
| WO | 2007/110205 A2 | 10/2007 |
| WO | 2007/147901 A1 | 12/2007 |
| WO | 2008/098796 A1 | 8/2008 |
| WO | 2009/080252 A1 | 7/2009 |
| WO | 2009/089004 A1 | 7/2009 |
| WO | 2009/091912 A | 7/2009 |
| WO | 2010/129304 A2 | 2/2011 |
| WO | 2010/129304 A3 | 2/2011 |
| WO | 2011/090754 A1 | 7/2011 |
| WO | 2011/117330 A1 | 9/2011 |
| WO | 2011/143545 A1 | 11/2011 |
| WO | 2012/020006 A2 | 2/2012 |
| WO | 2012/058768 A1 | 6/2012 |
| WO | 2012/058768 A8 | 6/2012 |
| WO | 2012/130831 A1 | 10/2012 |
| WO | 2013/028231 A1 | 2/2013 |
| WO | 2013/096291 A2 | 6/2013 |
| WO | 2013/157954 A1 | 10/2013 |
| WO | 2014/116846 A2 | 7/2014 |
| WO | 2017/055398 A2 | 4/2017 |
| WO | 2017/060144 A1 | 4/2017 |
| WO | 2017/180913 A2 | 10/2017 |
| WO | 2017/180913 A3 | 10/2017 |
| WO | 2017/191101 A1 | 11/2017 |
| WO | 2018/127473 A1 | 7/2018 |
| WO | 2018/185045 A1 | 10/2018 |

OTHER PUBLICATIONS

Ali, Stuart A., et al., "Transferrin Trojan Horses as a Rational Approach for the Biological Delivery of Therapeutic Peptide Domains" J Biol Chem 274(34):24066-24073 (Aug. 20, 1999).
Armour, K., et al., "Recombinant Human IgG Molecules Lacking Fcγ Receptor I Binding and Monocyte Triggering Activities" Eur J Immunol 29(8):2613-2624 (May 10, 1999).
Atwell, S., et al., "Stable heterodimers from remodeling the domain interface of a homodimer using a phage display library" J Mol Biol 270(1):26-35 (Jul. 4, 1997).
Baumann, R., et al., "Functional expression of CD134 by neutrophils" Eur J Immunol 34(8):2268-2275 (Aug. 1, 2004).
Binz, H. Kaspar, et al., "Designing Repeat Proteins: Well-expressed, Soluble and Stable Proteins from Combinatorial Libraries of Consensus Ankyrin Repeat Proteins" J Mol Biol 332:489-503 (Jul. 10, 2003).
Borghouts, Corina, et al., "Peptide aptamers: recent developments for cancer therapy" Expert Opin Biol Th 5(6):783-797 (Nov. 24, 2005).
Bowie, J. et al., "Deciphering the message in protein sequences: tolerance to amino acid substitutions" Science 247(4948):1306-1310 (Mar. 16, 1990).
Braddock, Martin, "11th Annual Inflammatory and Immune Diseases Drug Discovery and Development Summit" Expert Opin Inv Drug 16(6):909-917 (Jun. 1, 2007).
Brinkmann, U., et al., "The making of bispecific antibodies" MABS 9(2):182-212 (Jan. 10, 2017).
Bruggemann, M., et al., "Comparison of the Effector Functions of Human Immunogobulins Using a Matched set of Chimeric Antibodies" J Exp Med 166(5):1351-1361 (Oct. 1, 1987).
Capel, P., et al., "Heterogeneity of human IgG Fc receptors" Immunothods 4(1):25-34 (Feb. 1, 1994).
Carter, Paul, "Bispecific human IgG by design" J Immunol Methods 248(1-2):7-15 (Feb. 1, 2001).
Clynes, R., et al., "Fc receptors are required in passive and active immunity to melanoma" PNAS USA 95(2):652-656 (Jan. 1, 1998).
Cragg, M., et al., "Antibody Specificity Controls in Vivo Effector Mechanisms of Anti-CD20 Regents" Blood 103(7):2738-2743 (Apr. 1, 2004).
Cragg, M., et al., "Complement-mediated lysis by anti-CD20 mAb correlates with segregation into lipid rafts" Blood 101(3):1045-1052 (Feb. 1, 2003).
Croft, M. et al., "The significance of OX40 and OX40L to T-cell biology and immune disease" Immunol Rev 229(1):173-191 (May 1, 2009).
De Haas, M., et al., "Fcγ receptors of phagocytes" J Lab Clin Med 126(4):330-341 (Oct. 1, 1995).
Gazzano-Santoro, H., et al., "A non-radioactive complement-dependent cytotoxicity assay for anti-CD20 monoclonal antibody" J Immunol Methods 202(2):163-171 (Mar. 28, 1997).
Gebauer, M., et al., "Engineered protein scaffolds as next-generation antibody therapeutics" Curr Opin Chem Biol 13(3):245-255 (Jun. 1, 2009).
Gerngross, T., "Advances in the Production of Human Therapeutic Proteins in Yeasts and Filamentous Fungi" 22:1409-1414 (Nov. 22, 2004).
Gessner, J., et al., "The IgG Fc Receptor Family" Ann Hematol 76(6):231-248 (Jun. 1, 1998).
Graham, F., et al., "Characteristics of a Human Cell Line Transformed by DNA form Human Adenovirus Type 5" J Gen Virol 36(1):59 (Jul. 1, 1977).
Harlow, E., et al. Antibodies: A Laboratory Manual Cold Spring Harbor, New York:Cold Spring Harbor Laboratory,:1-28 ( 1988).
Heeley, R. et al., "Mutations Flanking the Polyglutamine Repeat in the Modulatory Domain of Rat Glucocorticoid Receptor Lead to an Increase in Affinity for Hormone" Endocr Res 28(3):217-229 (Aug. 1, 2002).
Hellstrom, I et al., "Strong antitumor activities of IgG3 antibodies to a human melanoma-associated ganglioside" PNAS USA 82(5):1499-1502 (Mar. 1, 1985).
Hellstrom, I., et al., "Antitumor effects of L6, an IgG2a antibody that reacts with most human carcinomas" PNAS US 83(18):7059-7063 (Sep. 1, 1986).
Holliger, P., et al., "Diabodies: Small Bivalent and Bispecific Antibody Fragments" PNAS 90(14):6444-6448 (Jul. 15, 1993).
Hudson, P., et al., "Engineered antibodies" Nat Med 9(1):129-134 (Jan. 1, 2003).
"International Search Report—PCT/EP/2019/079785":pp. 1-7 (Jul. 29, 2019).
Irving, Robert A., et al., "Ribosome display and affinity maturation : from antibodies to single V-domains and a step towards cancer therapeutics" J Immunol Methods 248:31-45 (Jan. 1, 2001).
Kam, N., et al., "Carbon nanotubes as multifunctional biological transporters and near-infrared agents for selective cancer cell destruction" PNAS 102(33):11600-11605 (Aug. 16, 2005).

(56) References Cited

OTHER PUBLICATIONS

Kohl, A., et al., "Designed to be stable: Crystal structure of a consensus ankyrin repeat protein" PNAS 100(4):1700-1705 (Feb. 18, 2003).
Li, H., et al., "Optimization of humanized IgGs in glycoengineered Pichia pastoris" Nat Biotechnol 24(2):210-215 (Feb. 1, 2006).
Liljeblad, M., et al., "Analysis of agalacto-IgG in rheumatoid arthritis using surface plasmon resonance" Glycoconjugate J 17:323-329 (Jul. 14, 2000).
Mather, J., et al., "Culture of Testicular Cells in Hormone-Supplemented Serum-Free Medium" Ann NY Acad Sci 383:44-68 (Jan. 1, 1982).
Mather, Jennie, "Establishment and characterization of two distinct mouse testicular epithelial cell lines" Biol Reprod 23(1):243-252 (Aug. 1, 1980).
Merchant, A., et al., "An efficient route to human bispecific IgG" Nat Biotechnol 16(7):677-681 (Jul. 1, 1998).
Parker, M.H., et al., "Antibody mimics based on human fibronectin type three domain engineered for thermostability and high-affinity binding to vascular endothelial growth factor receptor two" Protein Eng Des Sel 18(9):435-444 (Aug. 8, 2005).
Pluckthun et al. The Pharmacology of Monoclonal Antibodies Rosenburg and Moore (eds.), New York:Springer-Verlag, vol. 113:269-315 ( 1994).
Ravetch, J. et al., "Fc receptors" Annu Rev Immunol 9:457-492 ( 1991).
Ridgway et al., "'Knobs-into-holes' Engineering of Antibody CH3 Domains for Heavy Chain Heterodimerization" Protein Eng 9(7):617-621 ( 1996).
Schaefer, W., et al., "Immunoglobulin domain crossover as a generic approach for the production of bispecific IgG antibodies" PNAS USA 108(27):11187-11192 (Jul. 5, 2011).
Shields, R., et al., "High resolution mapping of the binding site on human IgG1 for Fc gamma RI, Fc gamma RII, Fc gamma RIII, and FcRn and design of IgG1 variants with improved binding to the Fc gamma R" J Biol Chem 276(9):6591-6604 (Mar. 2, 2001).
Silverman, Joshua, et al., "Multivalent avimer proteins evolved by exon shuffling of a family of human receptor domains" Nat Biotechnol 23(12):1556-1561 (Dec. 1, 2005).
Song, J. et al., "Activation of Nf-kB1 by OX40 Contributes to Antigen-Driven T Cell Expansion and Survival" J Immunol 180(11):7240-7248 (Jun. 1, 2008).
Stamenkovic, I., et al., "A B-Lymphocyte Activation Molecule Related to the Nerve Growth Factor Receptor and Induced by Cytokines in Carcinomas." EMBO J 8(5):1403-1410 (May 1, 1989).
Stumpp, M., et al., "DARPins: a new generation of protein therapeutics" Drug Discov Today 13(15-16):695-701 (Aug. 1, 2008).
Underwood et al. et al., "Ovarian tumor cells express a novel multi-domain cell surface serine protease" Biochem Biophys Acta 1502(3):337-350 (Nov. 15, 2000).
Urlaub, G., et al., "Isolation of chinese hamster cell mutants deficient in dihydrofolate reductase activity" PNAS US 77(7):4216-4220 (Jul. 1, 1980).
Weinberg, A., et al., "Engagement of the OX-40 Receptor In Vivo Enhances Antitumor Immunity" J Immunol 164(4):2160-2169 (Feb. 15, 2000).
Weinberg, A., et al., "The generation of T cell memory: a review describing the molecular and cellular events following OX40 (CD134) engagement" J Leukocyte Biol 75(6):962-972 (Jun. 1, 2004).
Wikman, M., et al., "Selection and characterization of HER2/neu-binding affibody ligands" Protein Eng Des Sel 17(5):455-462 (Jun. 18, 2004).
Wright et al., "Effect of glycosylation on antibody function: implications for genetic engineering" Trends Biotechnol. 15(1):26-32 (Jan. 1, 1997).
Yazaki et al. Methods in Molecular Biology "Expression of recombinant antibodies in mammalian cell lines" Lo, B.K.C. (ed.), Totowa, NJ:Humana Press, vol. 248:255-268 ( 2004).
Zahnd, C. et al., "A designed ankyrin repeat protein evolved to picomolar affinity to Her2" J Mol Biol 369(4):1015-1028 (Mar. 13, 2007).
Hornig et al., "Evaluating combinations of costimulatory antibody—ligand fusion proteins for targeted cancer immunotherapy" Cancer Immunol Immunother 62:13691380 ( 2013).
Li et al., "Structure design of bispecific antibodies and progress in the assembly process" Chinese Journal of New Drugs 23(20):2430-2436 ( 2014).
Xie et al., "Construction formats of engineered bispecific antibodies" Bull Acad Mil Med Sci 28(4):375 ( 2004).
Mayer et al., "TriFabs-Trivalent IgG-Shaped Bispecific Antibody Derivatives: Design, Generation, Characterization and Application for Targeted Payload Delivery" International Journal of Molecular Sciences 16:27497-27507 ( 2015).
Vidarsson, G., et al., "IgG Subclasses and Allotypes: From Structure to Effector Functions"Front Immunol 5(520):1-17 (Oct. 20, 2014).

* cited by examiner

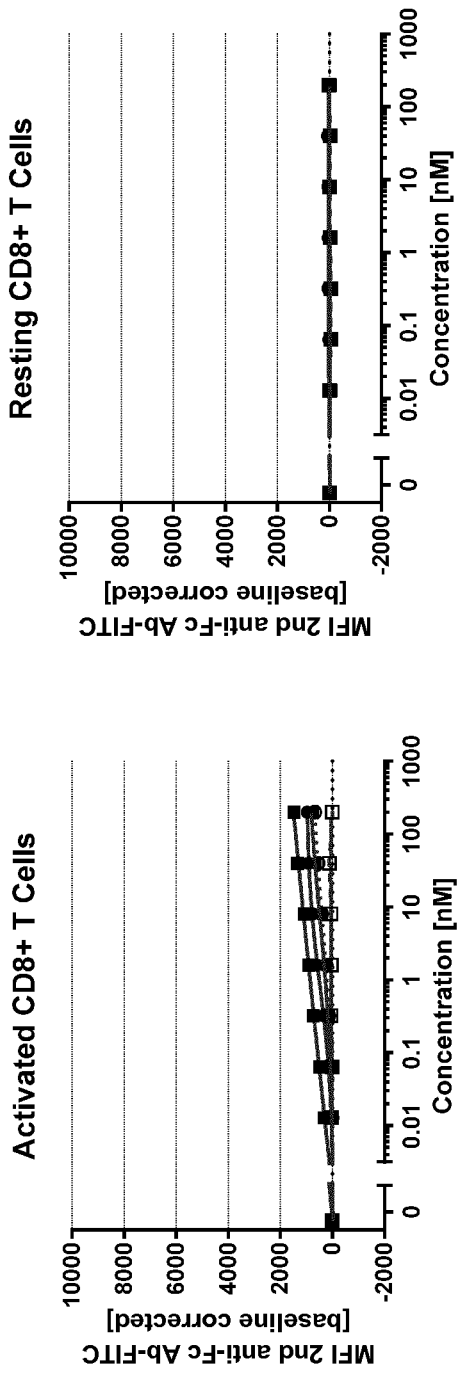

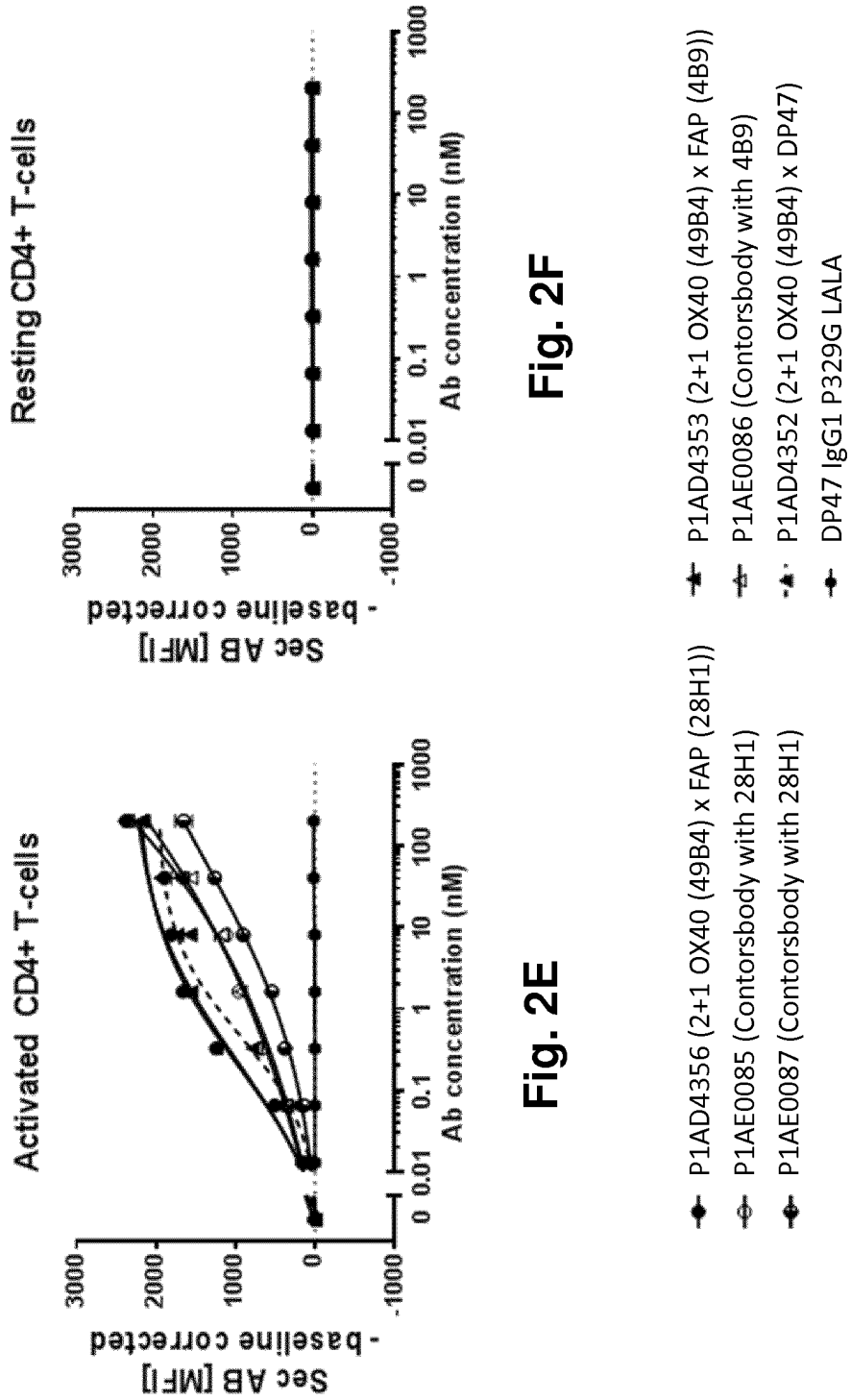

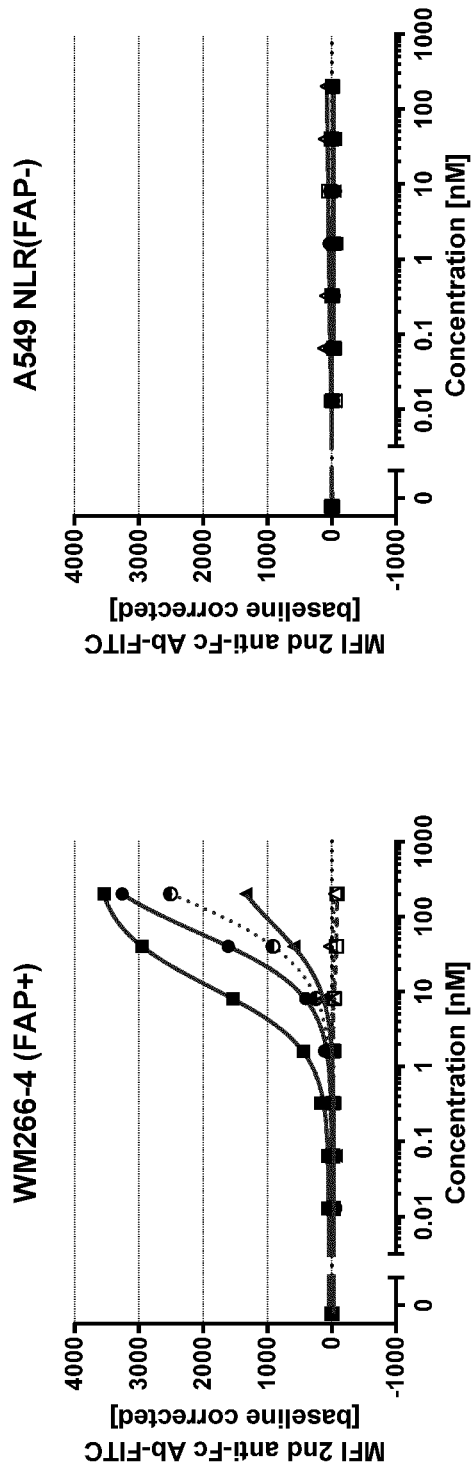

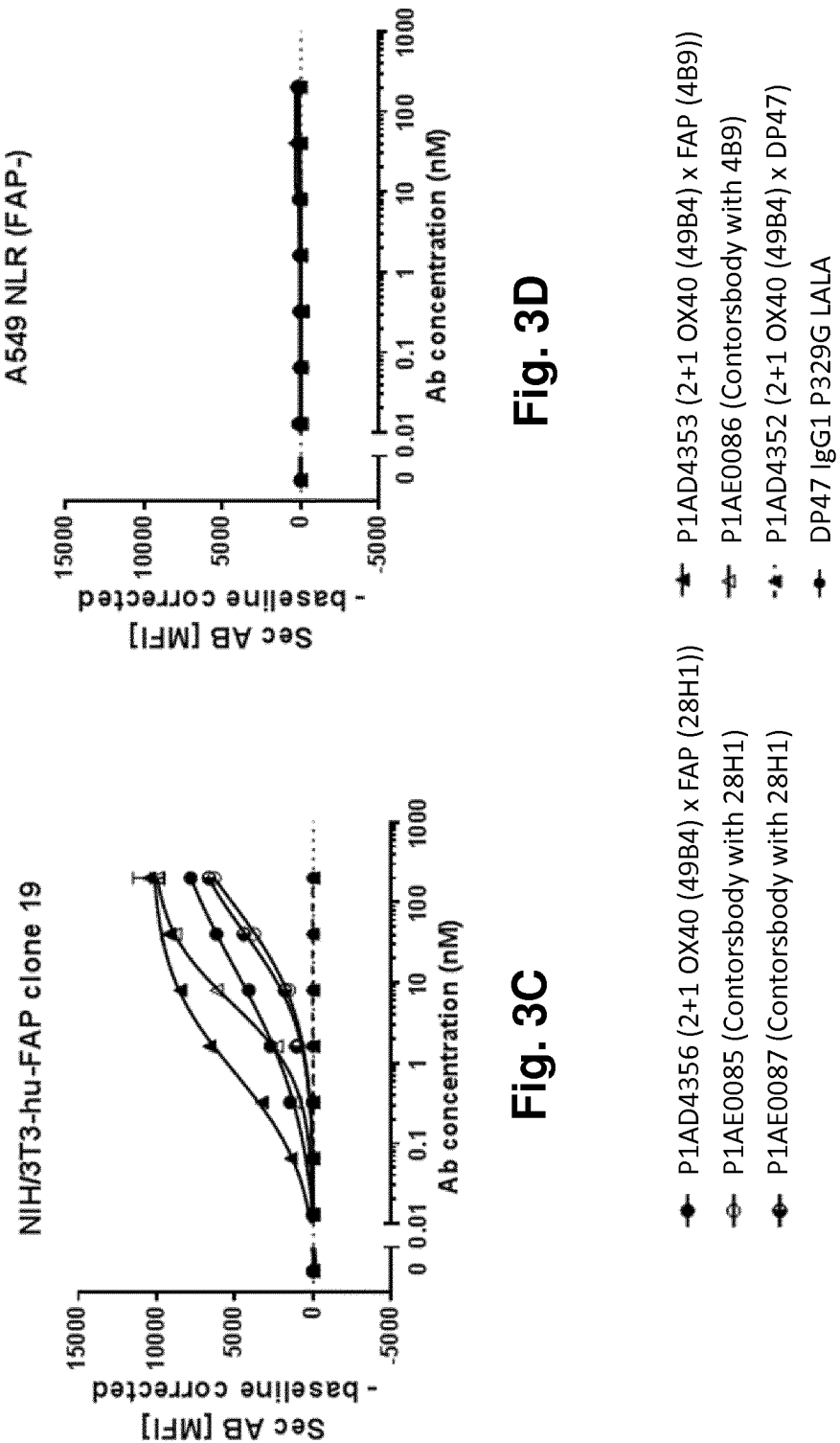

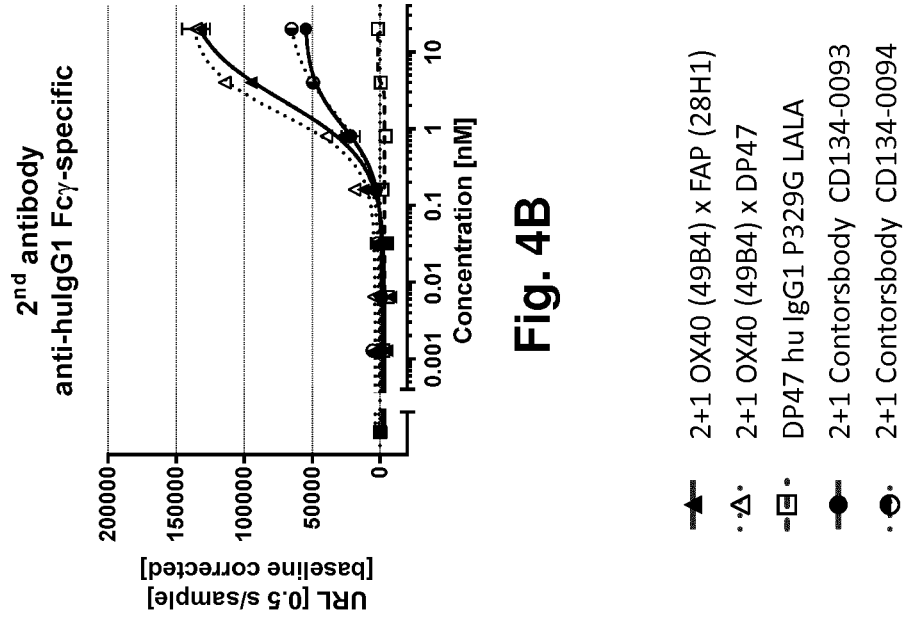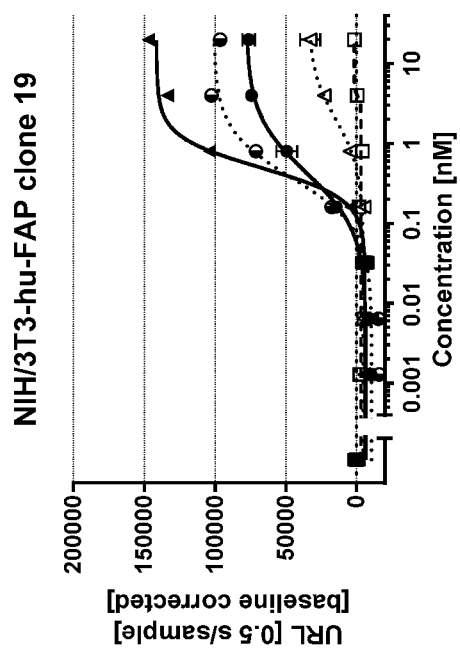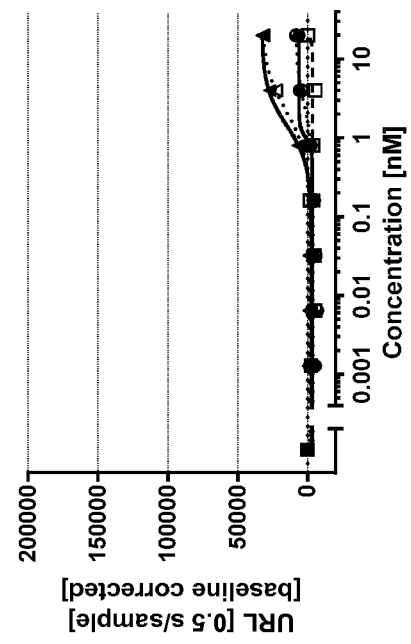

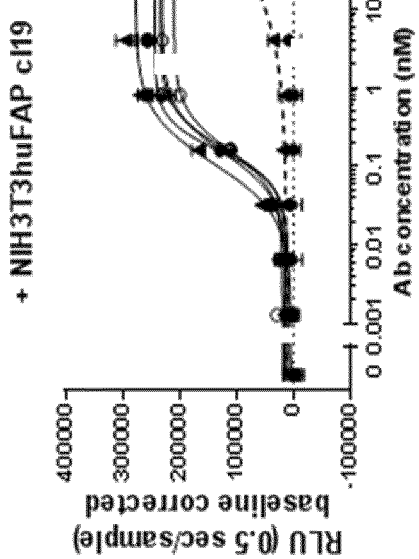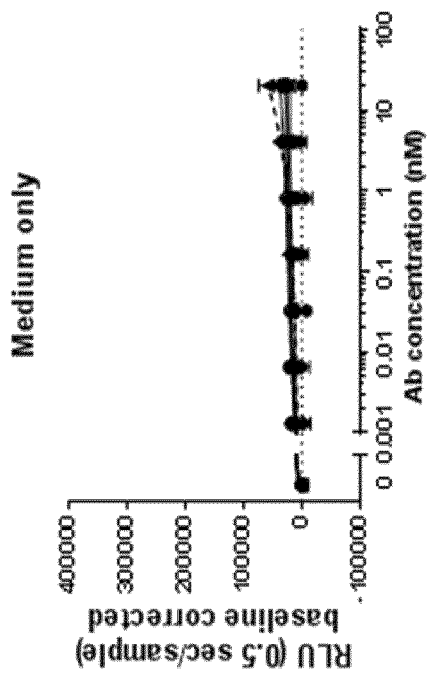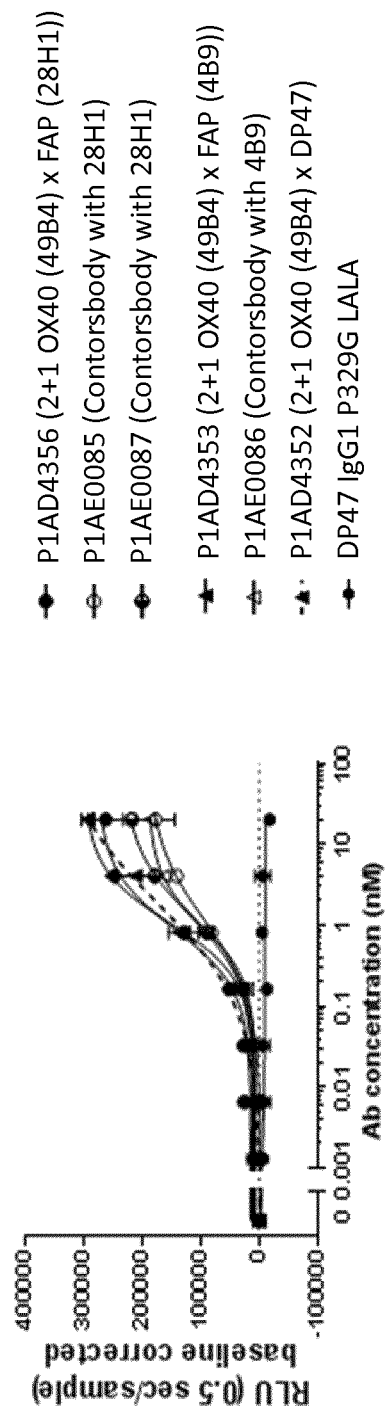
Fig. 4D
Fig. 4E
Fig. 4F

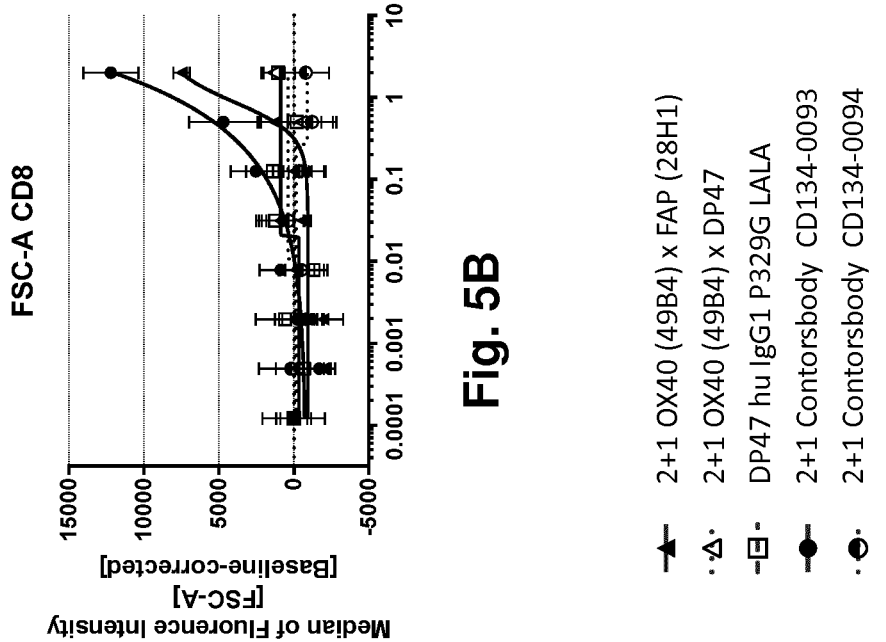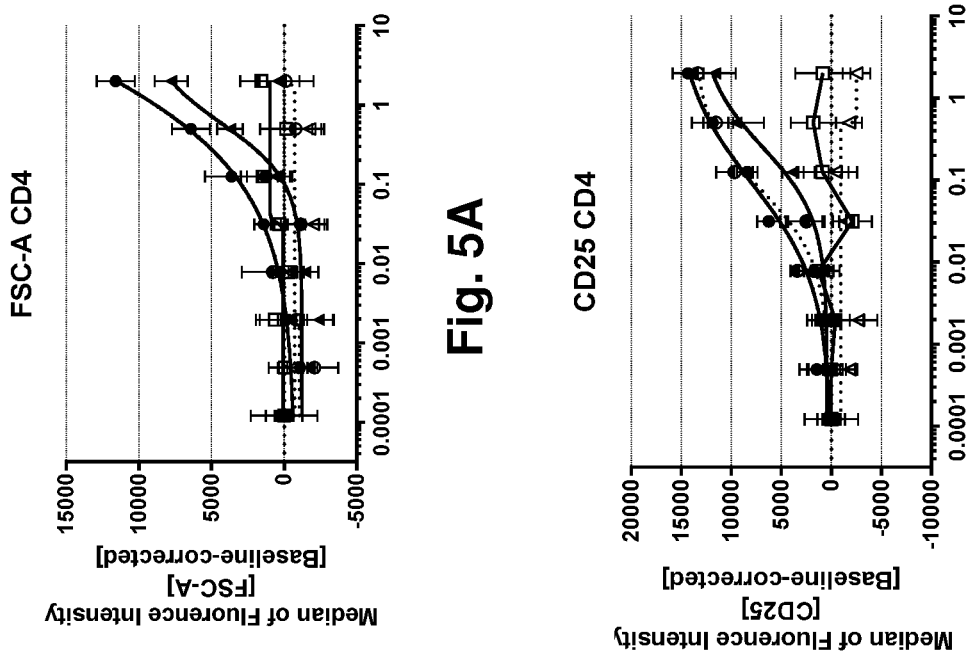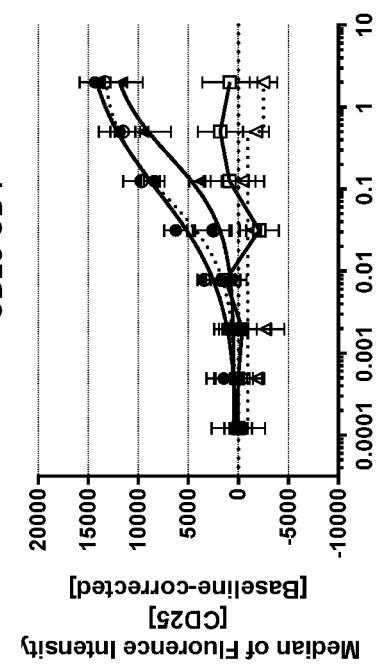

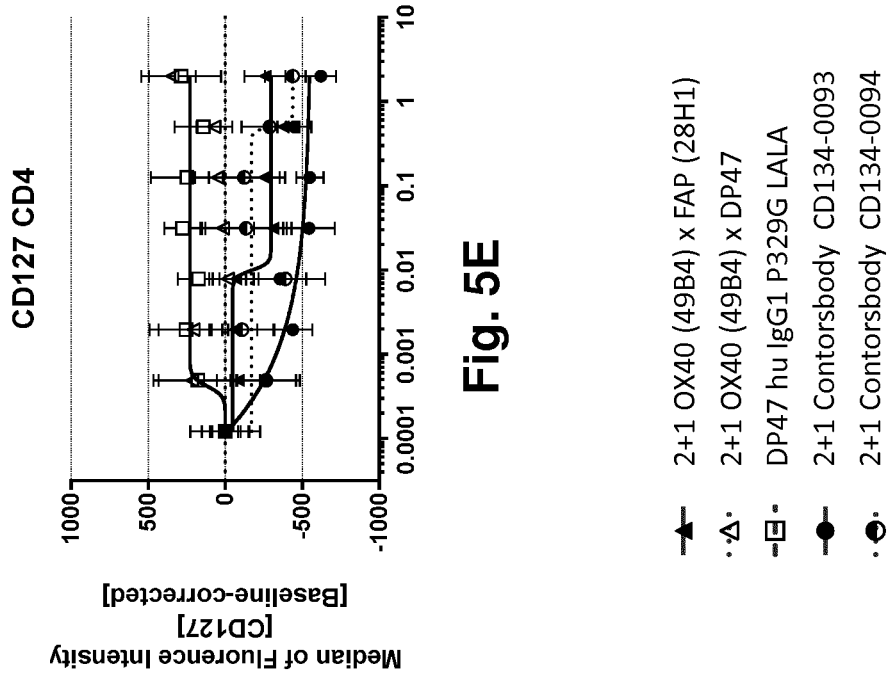
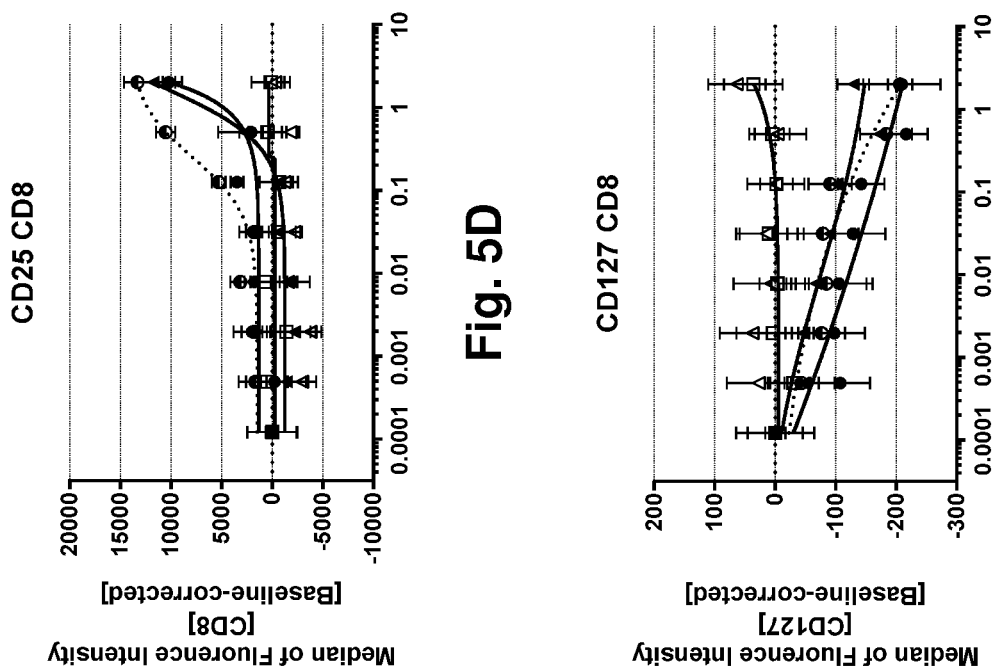
Fig. 5D, Fig. 5E, Fig. 5F

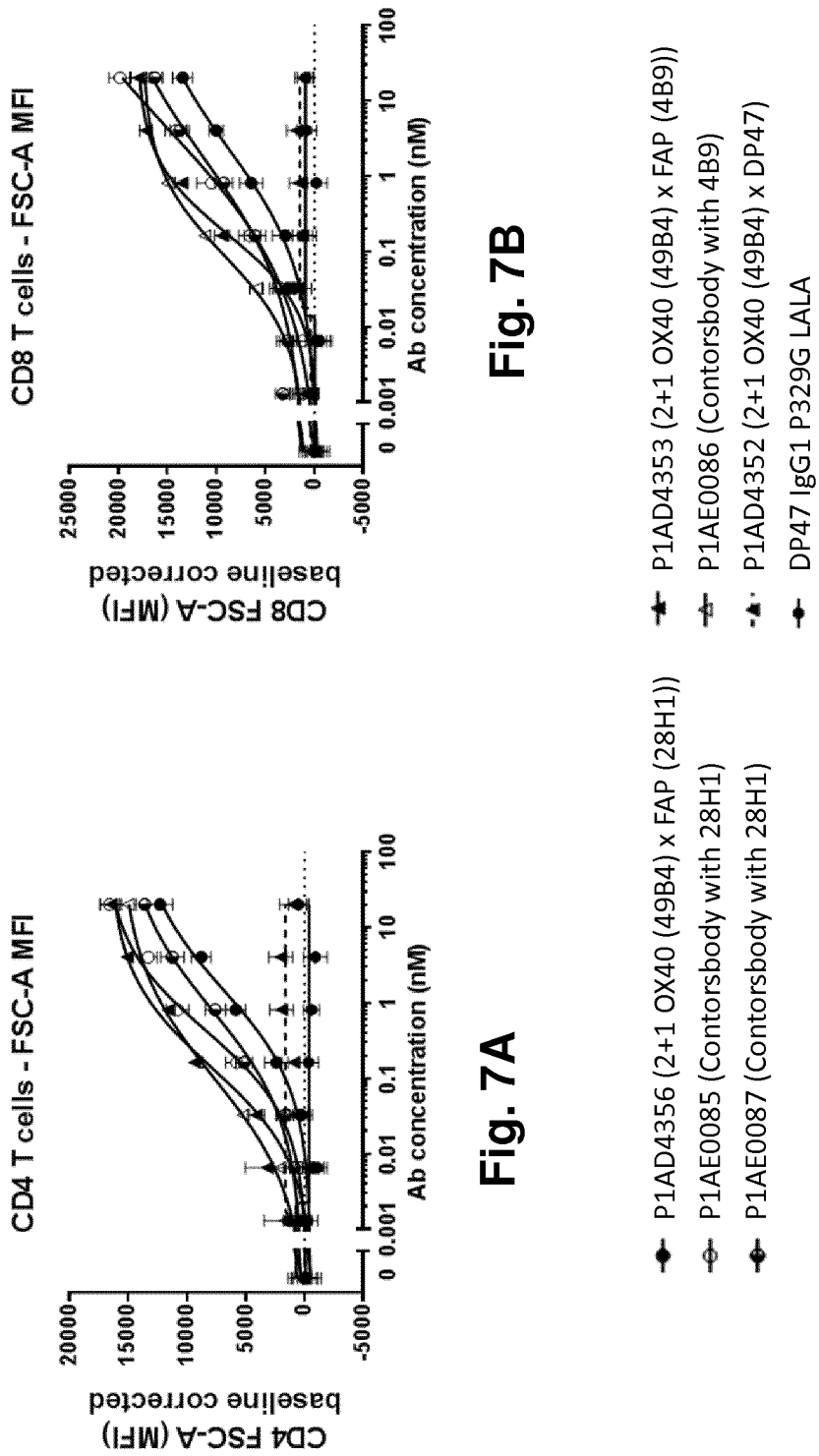

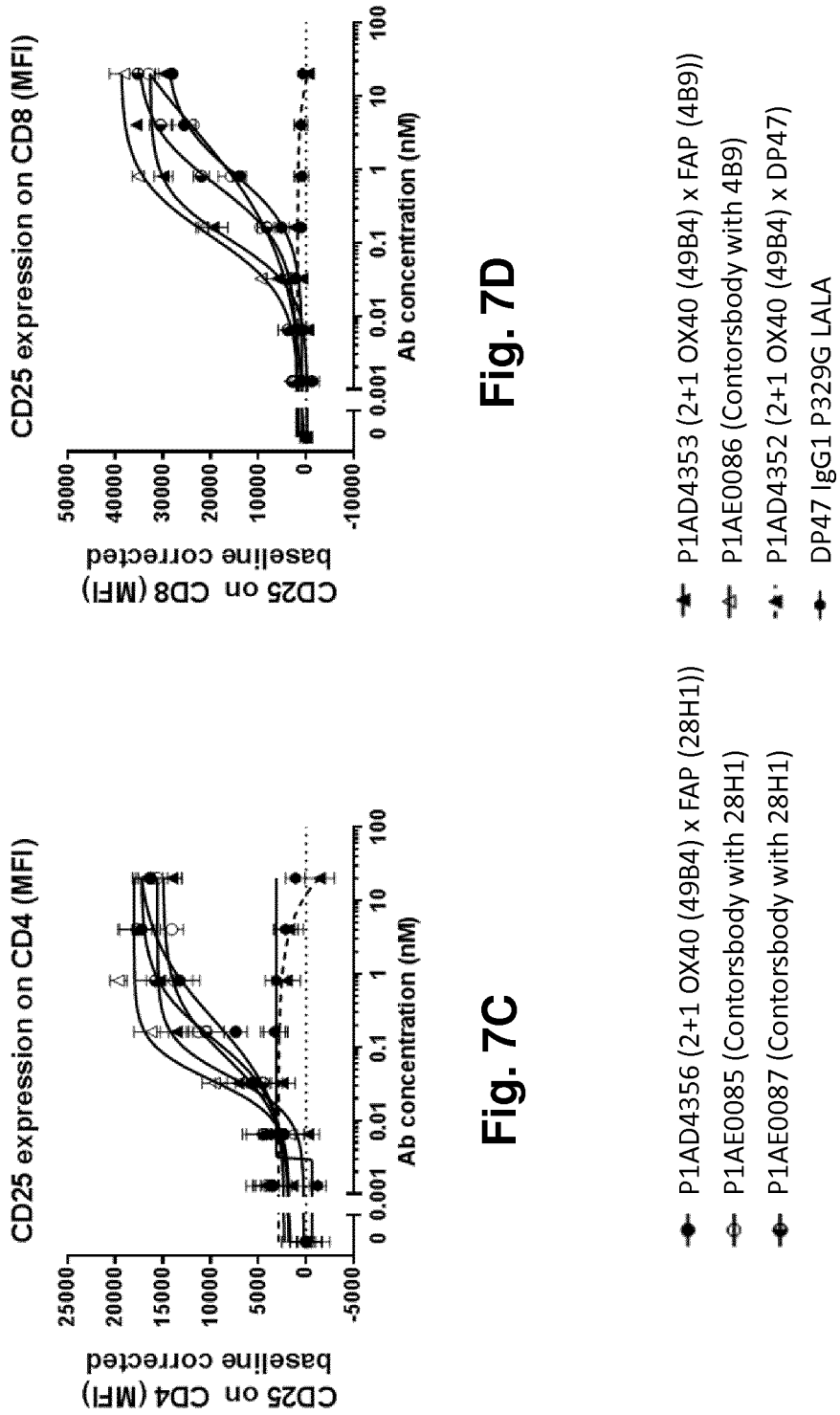

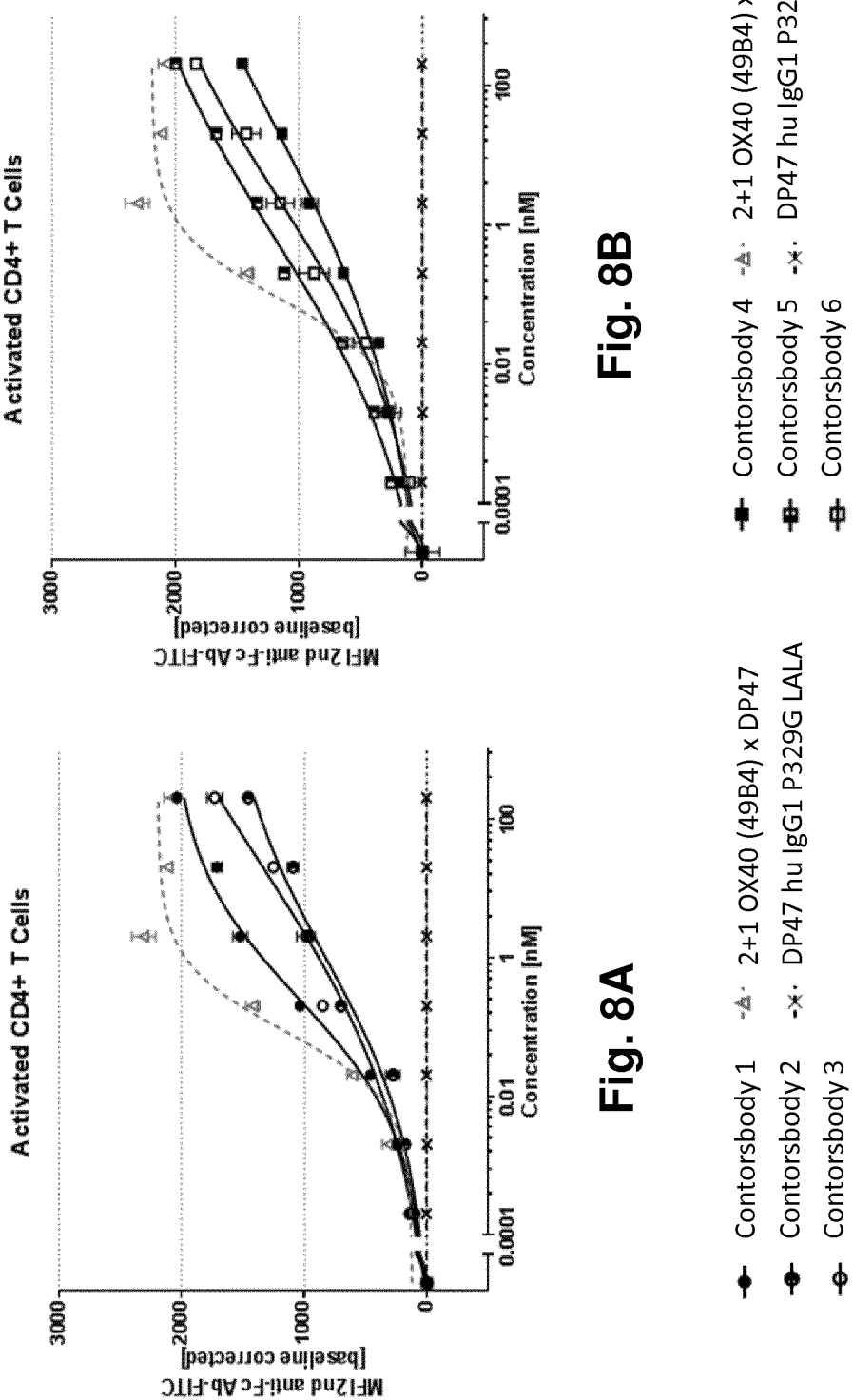

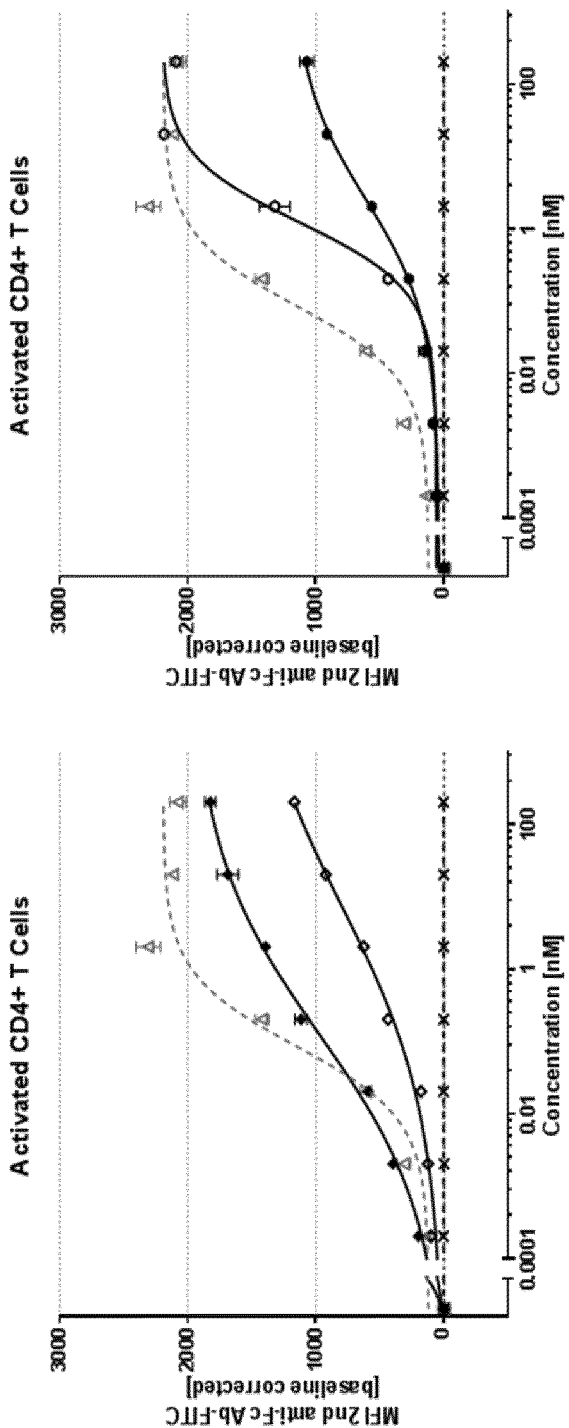

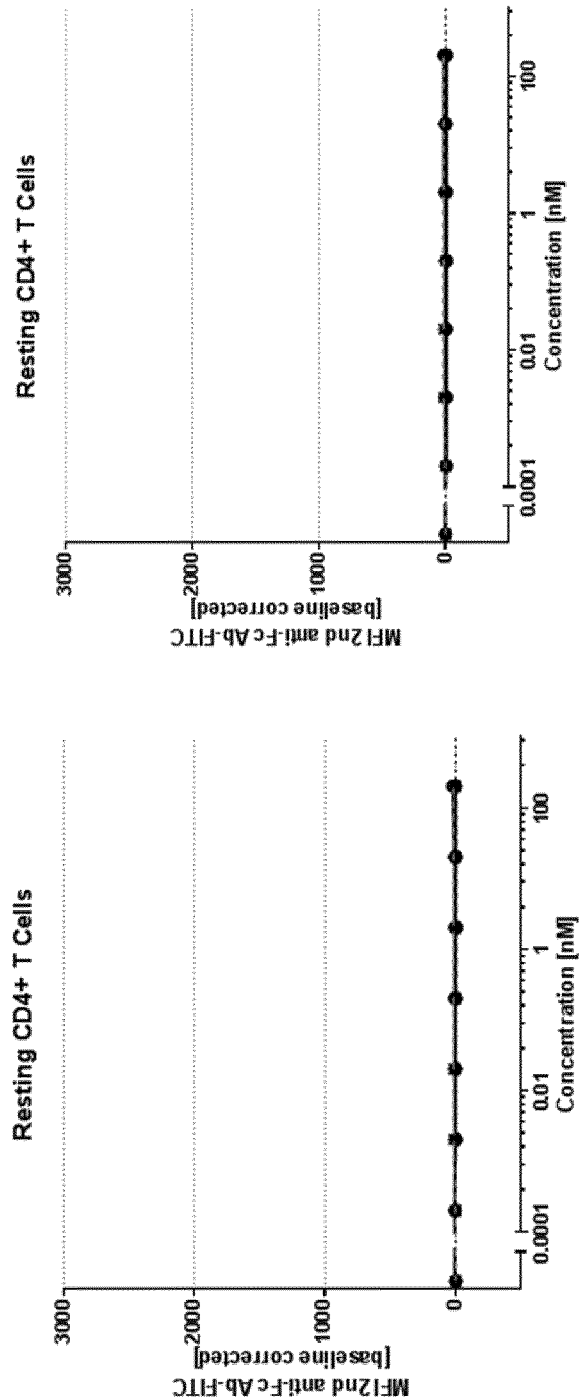
Fig. 9A / Fig. 9B

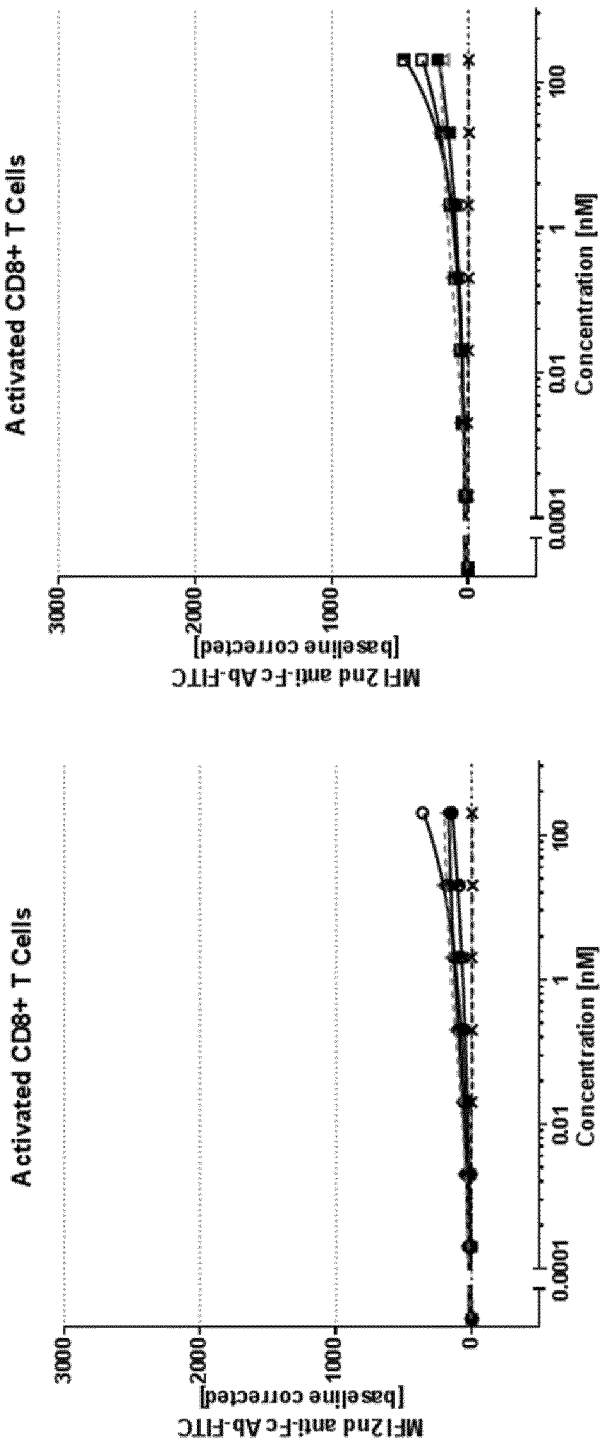

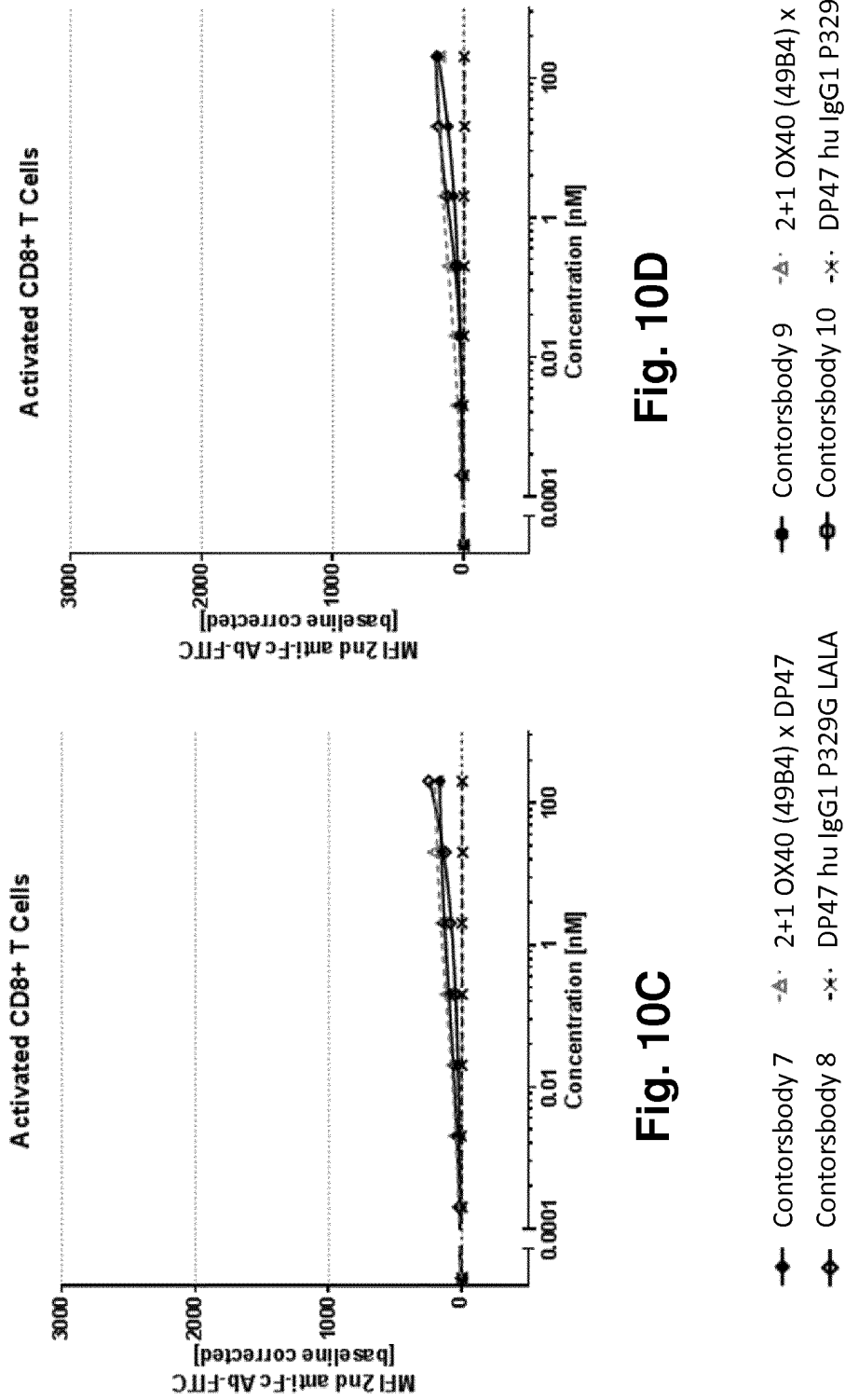

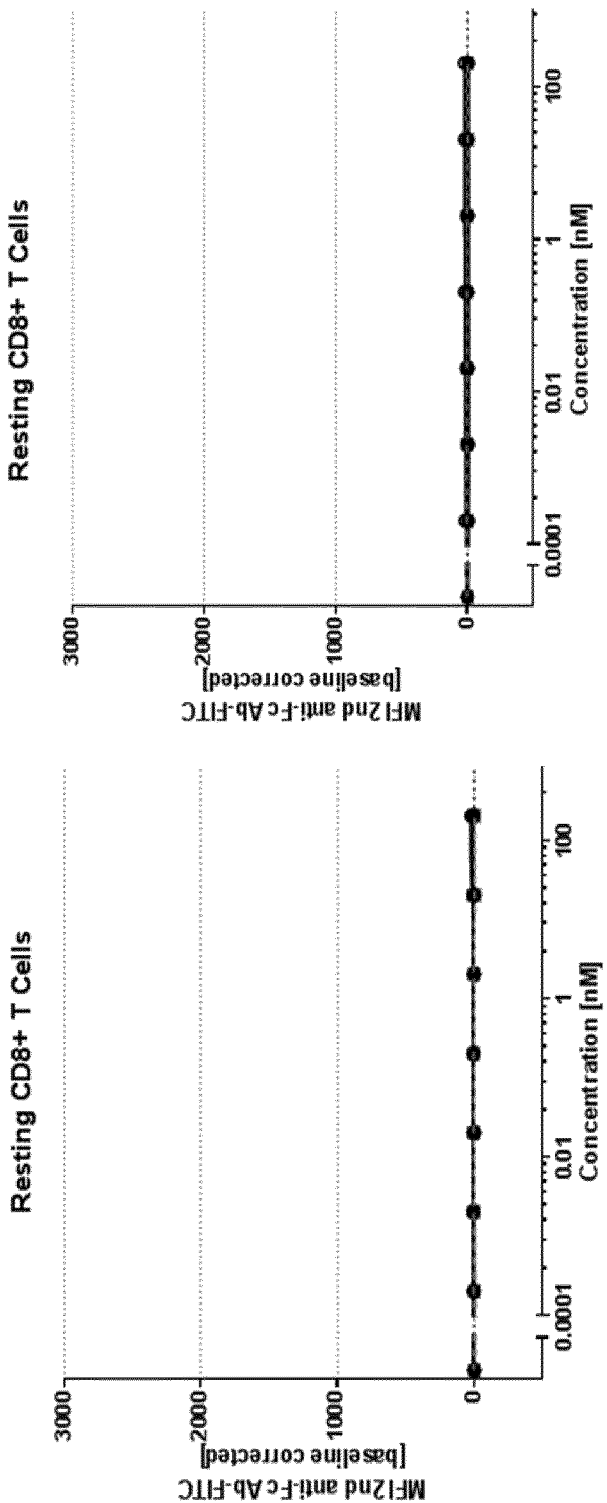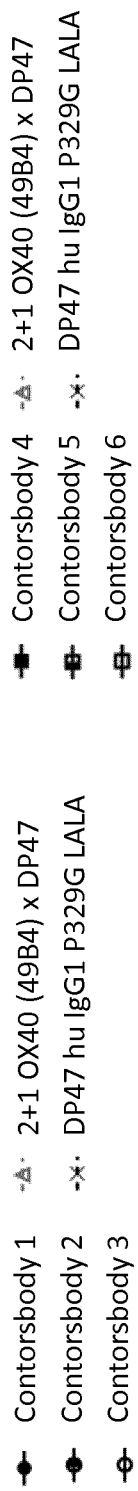

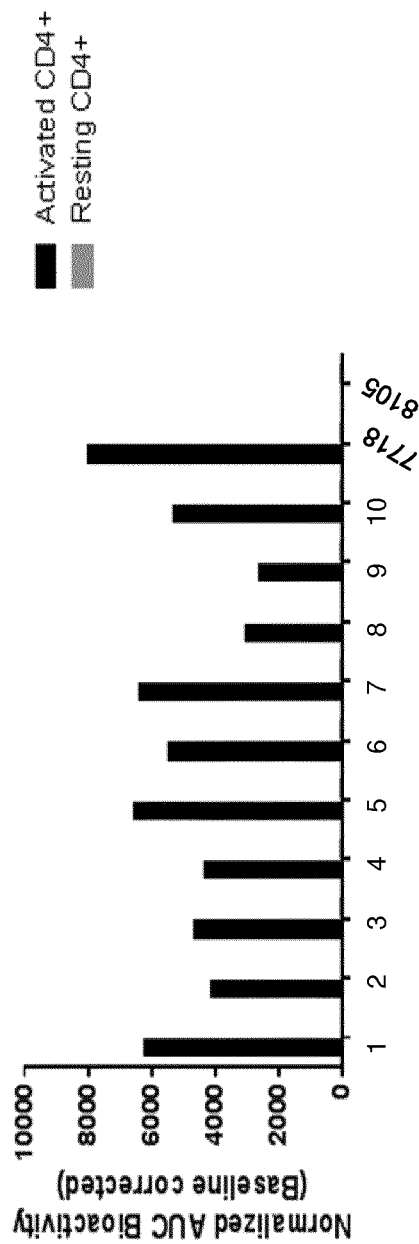
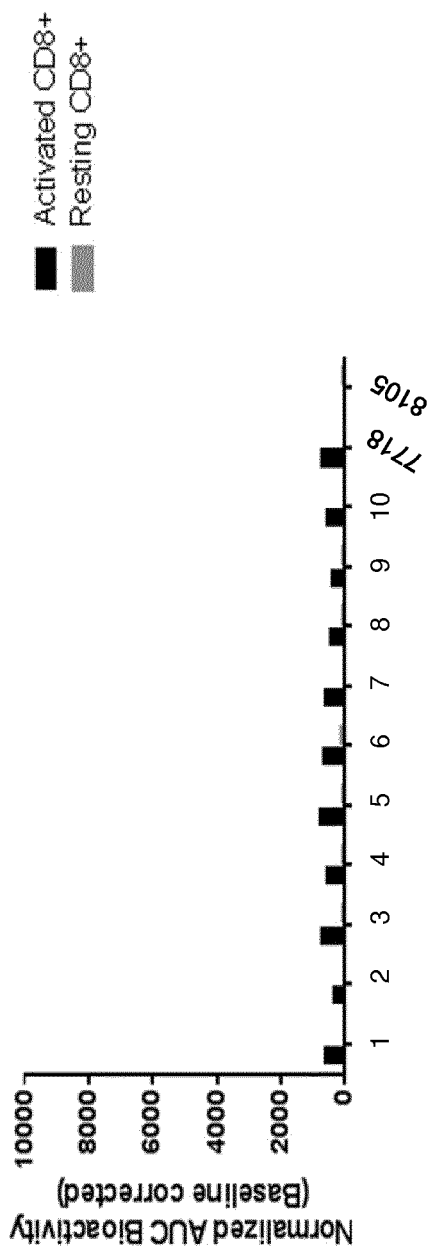

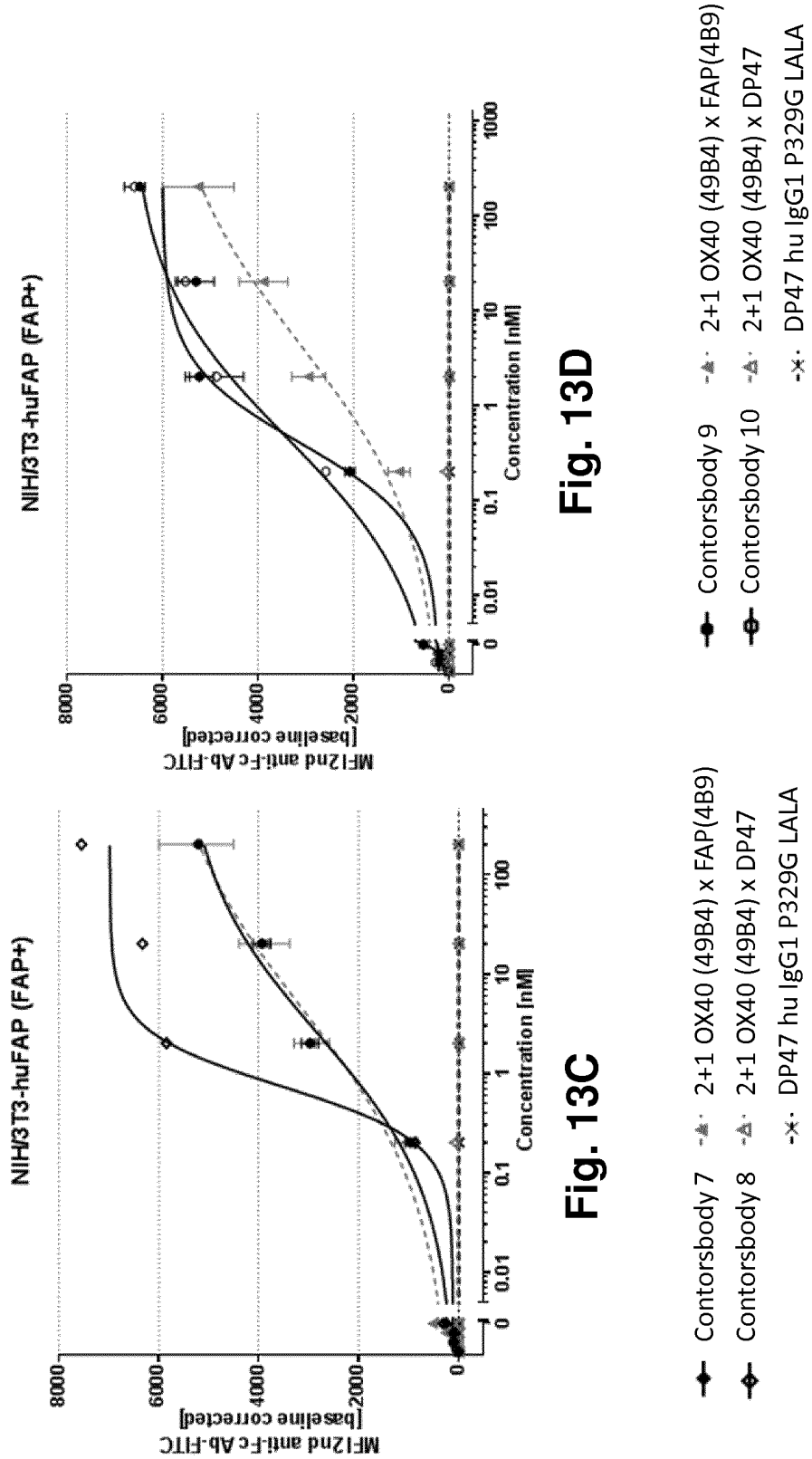

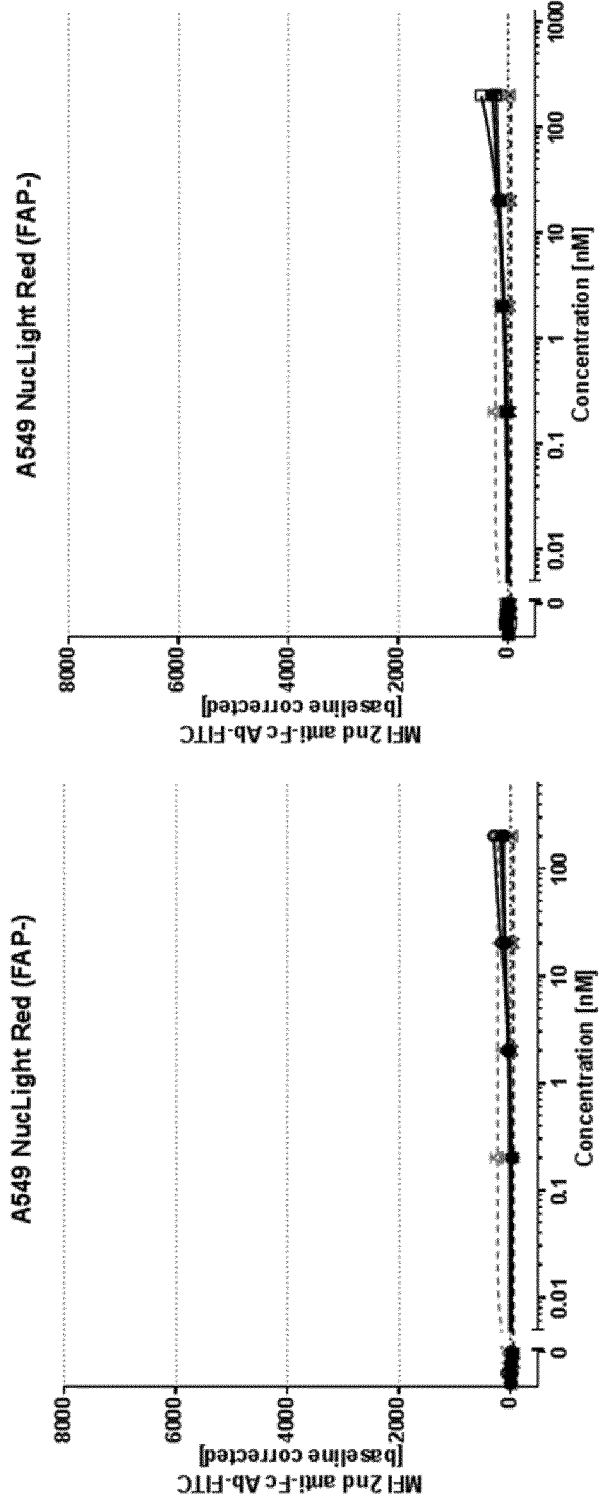
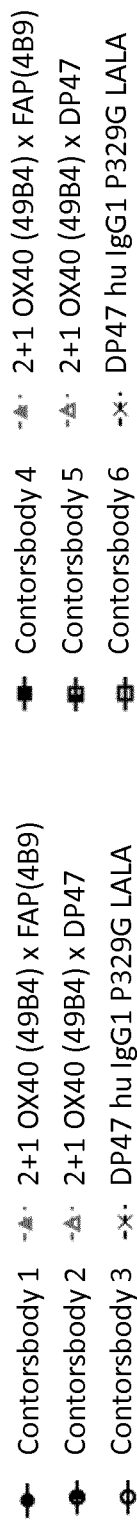
Fig. 14A
Fig. 14B

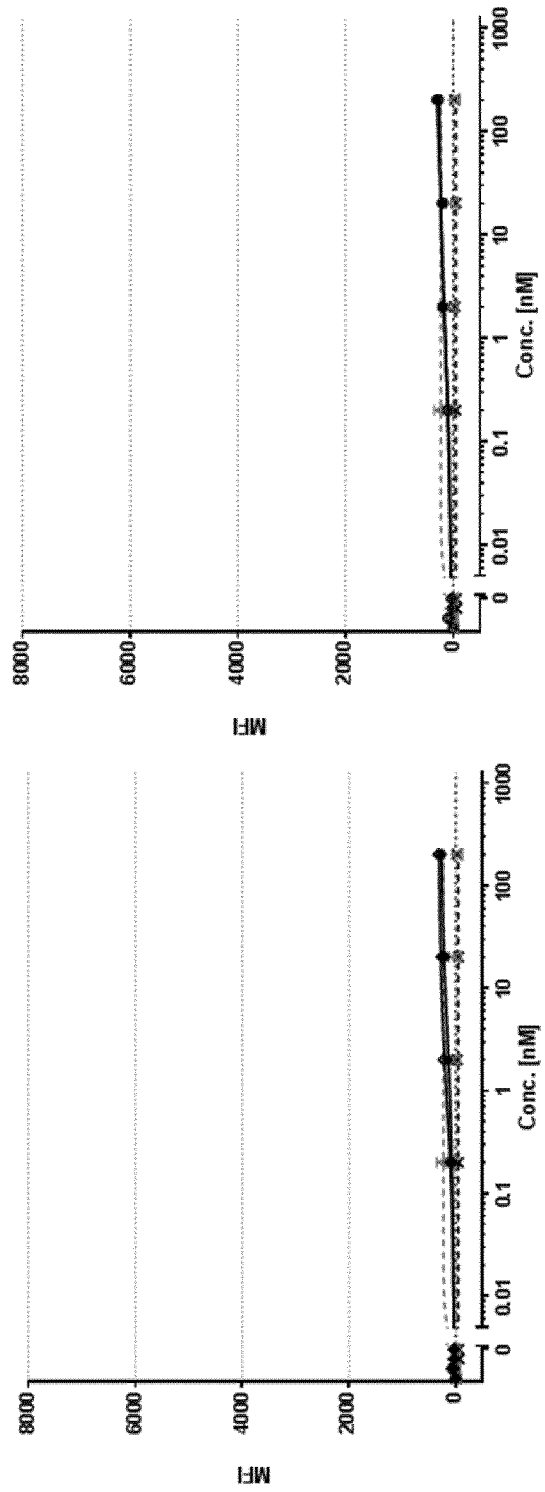

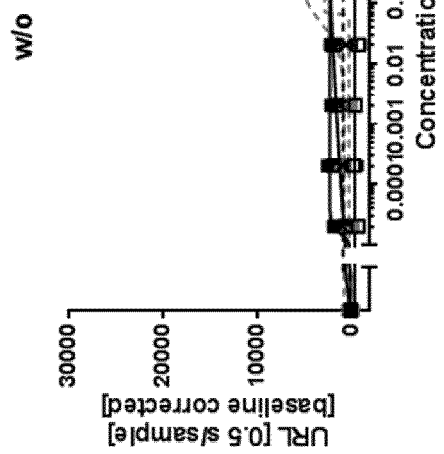
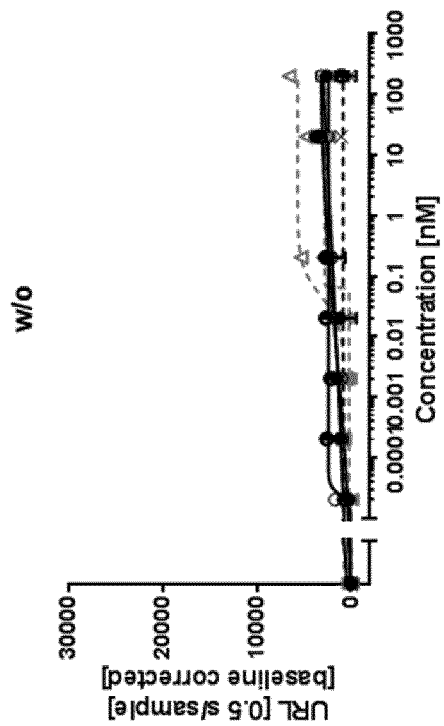
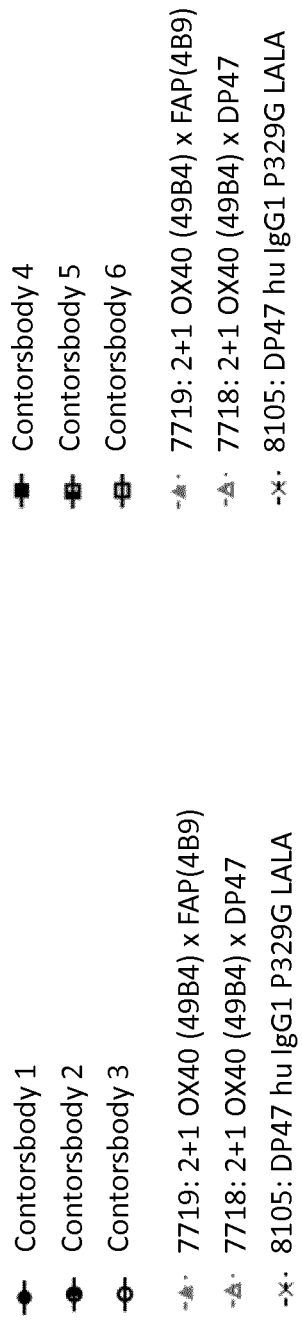

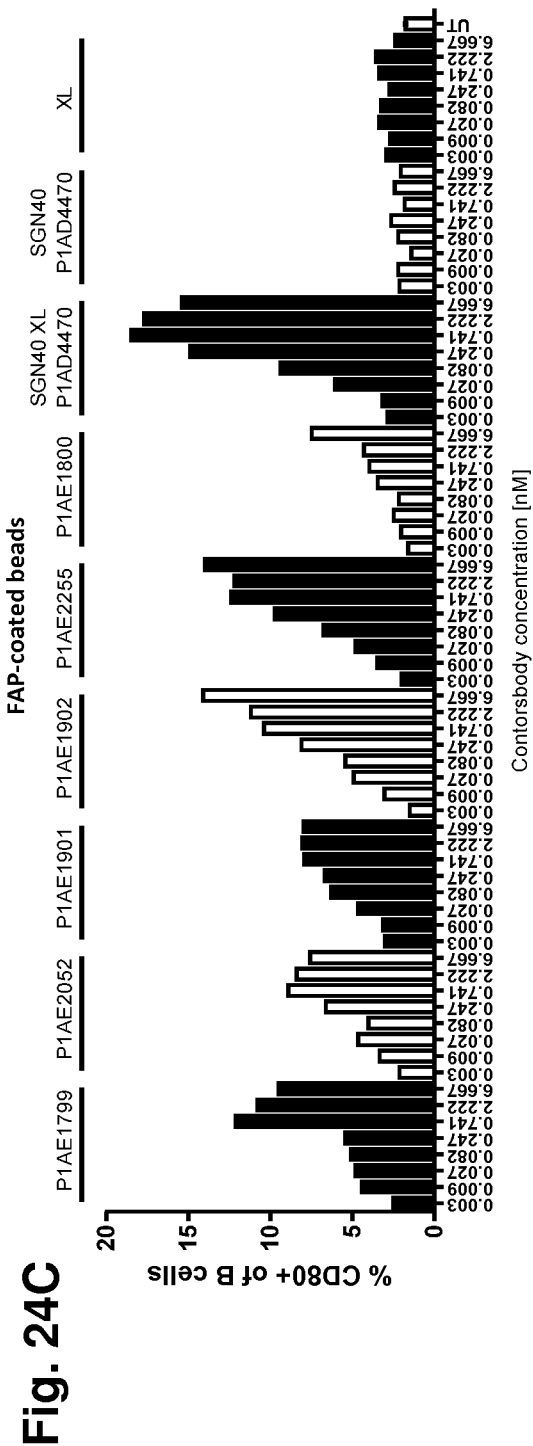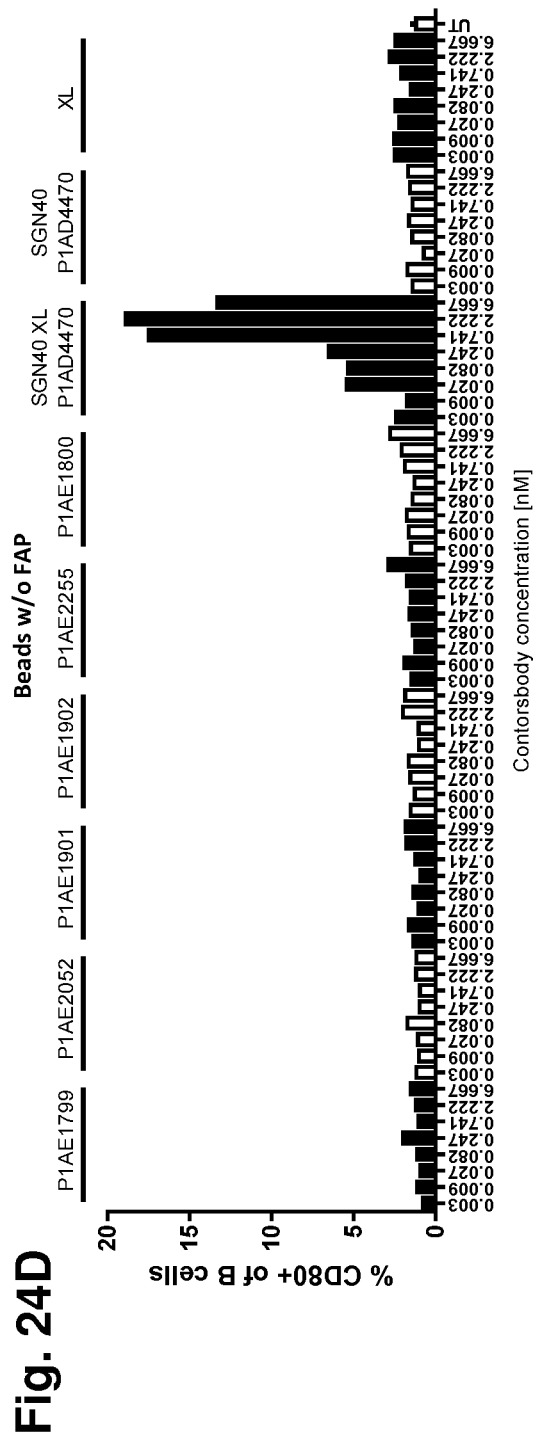

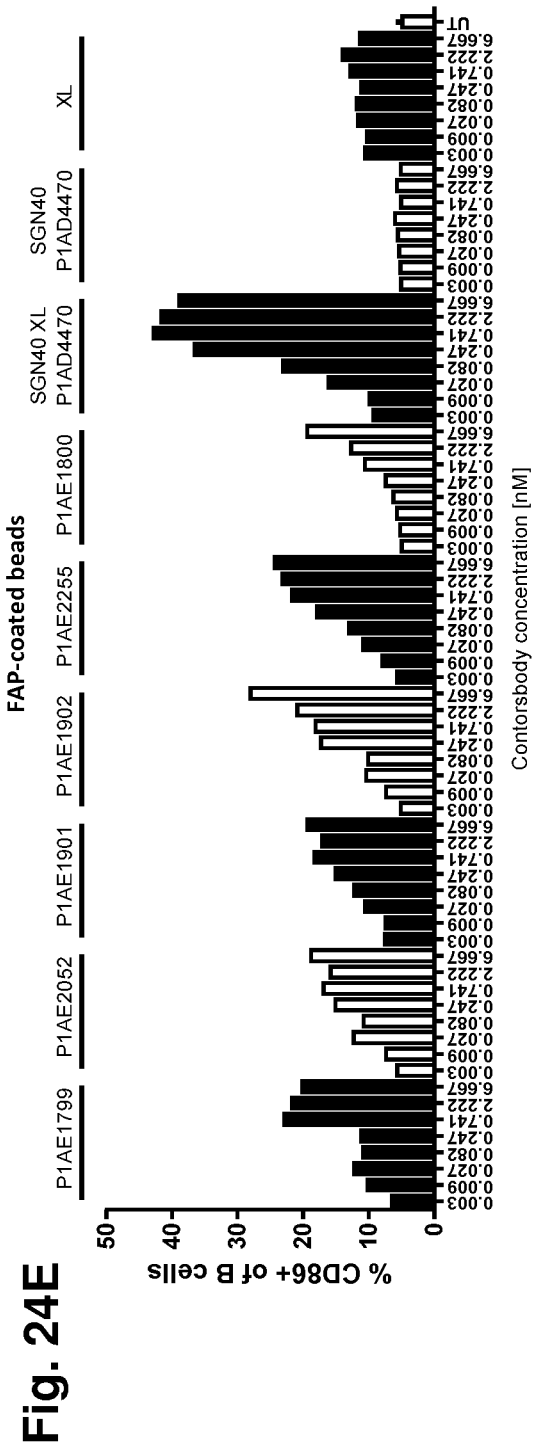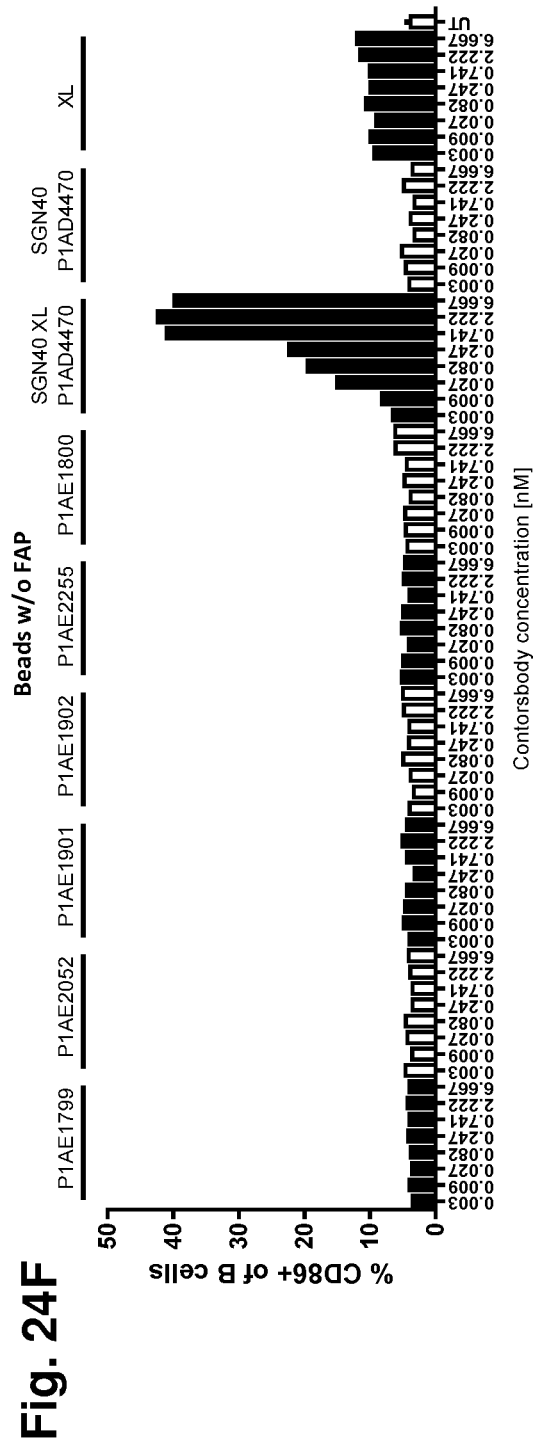

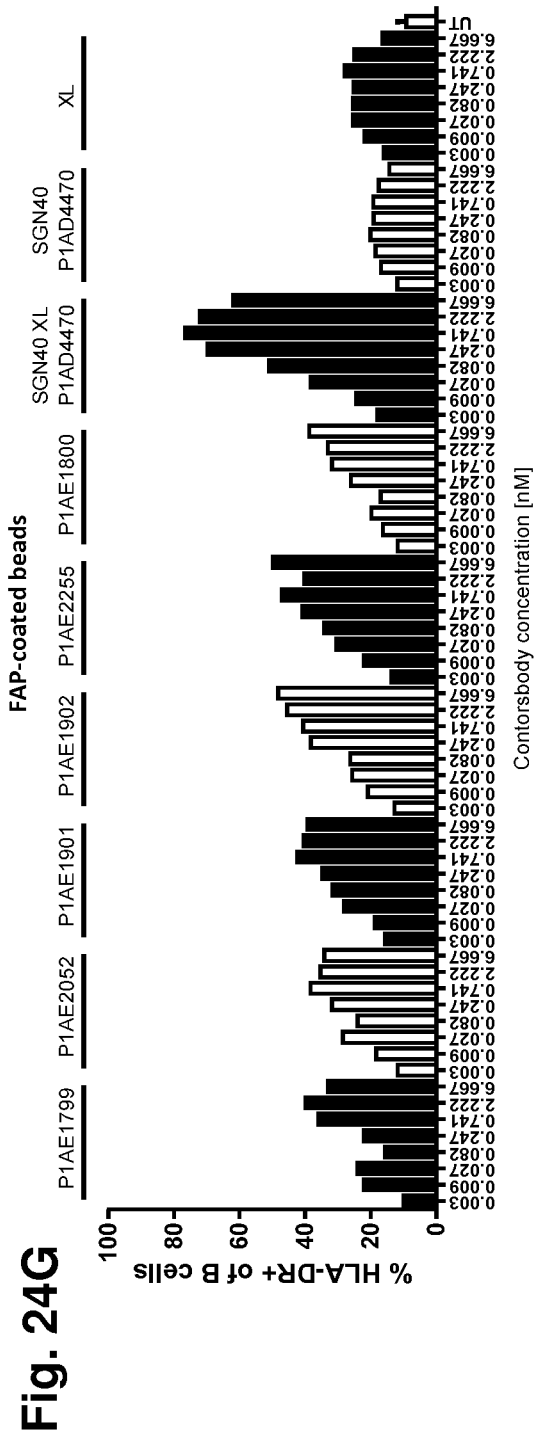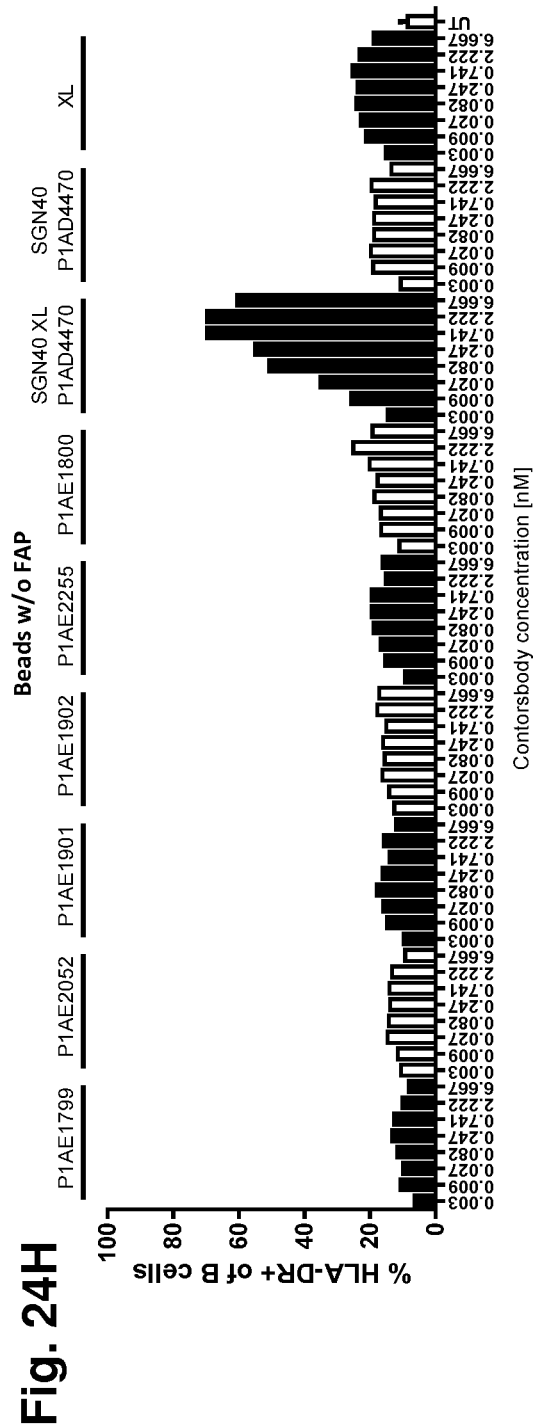

BISPECIFIC 2+1 CONTORSBODIES

CROSS REFERENCE TO RELATED APPLICATIONS

This application is a national phase application under 35 USC 371 of Patent Cooperation Treaty (PCT) Application No. PCT/EP2018/079785 filed Oct. 31, 2018, which claims priority to European Application No. 17199537.6 filed Nov. 1, 2017, which is incorporated herein by reference in its entirety.

SEQUENCE LISTING

This application contains a Sequence Listing which has been submitted electronically in ASCII format and is hereby incorporated by reference in its entirety. Said ASCII copy, created on Apr. 30, 2020 is named P34510-US_ST25.txt and is 525 KB in size.

FIELD OF THE INVENTION

The invention relates to novel bispecific antibodies (contorsbodies) consisting of two fusion polypeptides comprising two antigen binding domains capable of specific binding to a first target and one antigen binding domain capable of specific binding to a second target, and to methods of producing these molecules and to methods of using the same.

BACKGROUND

Since the development of the first monoclonal antibodies by Koehler and Milstein in 1974 a lot of efforts have been dedicated to the development of antibodies which are appropriate for therapy in humans. The first monoclonal antibodies which became available had been developed in mice and rats. These antibodies when used for therapy of a human being caused unwanted side effects due to anti-rodent antibodies. A lot of efforts have been dedicated to the reduction or even elimination of such unwanted side effects. In the past years an ever growing number of human monoclonal antibodies or humanized monoclonal antibodies have reached the market.

Bispecific antibodies have become of increasing interest for diagnostic and therapeutic applications. While natural antibodies are monospecific, bispecific antibodies recognize two different epitopes either on the same or on different antigens. Over the past years, a plethora of new antibody formats have been developed. The application of sophisticated molecular design and genetic engineering has solved many of the technical problems associated with the formation of bispecific antibodies such as stability, solubility and other parameters that confer drug properties and that are summarized under the term "developability". In addition, different desired features of the bispecific antibody to be generated (i.e. target product profiles) make it necessary to have access to a diverse panel of antibody formats. These formats may vary in size, geometry of their binding modules, valencies, flexibility as well as in their pharmacokinetic properties (Brinkmann U. and Kontermann R. E., MABS 2017, 9(2), 182-212).

However, it seems that there is not one best format for all needs and that there is still potential to optimize antibody formats derived from the wild-type four chain Y-shaped antibody format. For the use as pharmaceutical product, bispecific antibodies need to be produced in large amounts in a reproducible manner, preferably at high yields. The more complex composition (e.g. 3-4 chains in contrast to 2-chain IgGs) does often require more extensive optimization of expression systems. Furthermore, the presence or absence of undesired side products can be of high importance.

SUMMARY OF THE INVENTION

The present invention refers to bispecific antibodies that particularly consist of two chains although they comprise three antigen binding domains. The antibodies of the present invention differ in the spatial orientation of the antigen binding domain from classical antibodies in the IgG format.

The present invention provides a bispecific antibody consisting of two fusion polypeptides and comprising two antigen binding domains capable of specific binding to a first target and one antigen binding domain capable of specific binding to a second target, wherein (a) the first fusion polypeptide comprises a first part of a first antigen binding domain capable of specific binding to the first target, a spacer domain, a second part of a first antigen binding domain capable of specific binding to the first target and a first part of an antigen binding domain capable of specific binding to the second target, wherein the spacer domain is a polypeptide and comprises at least 25 amino acid residues, the first part of the first antigen binding domain capable of specific binding to the first target is fused either directly or via a first peptide linker to the N-terminus of the spacer domain, the second part of the first antigen binding domain capable of specific binding to the first target is fused either directly or via a second peptide linker to the C-terminus of the spacer domain, and the first part of an antigen binding domain capable of specific binding to a second target is fused either directly or via a third peptide linker to the C-terminus of the second part of the first antigen binding domain capable of specific binding to the first target or is fused either directly or via a third peptide linker to the N-terminus of the first part of the first antigen binding domain capable of specific binding to the first target, and (b) the second fusion polypeptide comprising a first part of a second antigen binding domain capable of specific binding to a first target, a spacer domain, a second part of the second antigen binding domain capable of specific binding to a first target and the second part of an antigen binding domain capable of specific binding to a second target, wherein the spacer domain is a polypeptide and comprises at least 25 amino acid residues, the first part of the second antigen binding domain capable of specific binding to a first target is fused either directly or via a first peptide linker to the N-terminus of the spacer domain, the second part of the second antigen binding domain capable of specific binding to a first target is fused either directly or via a second peptide linker to the C-terminus of the spacer domain, and the second part of an antigen binding domain capable of specific binding to a second target is fused either directly or via a third peptide linker to the C-terminus of the second part of the second antigen binding domain capable of specific binding to a first target or is fused either directly or via a third peptide linker to the N-terminus of the first part of the second antigen binding domain capable of specific binding to a first target, wherein the first part and the second part of the antigen binding domain capable of specific binding to the second target are associated with each other to form the antigen binding domain capable of specific binding to the second target and wherein the first part and the second part of the first and second antigen binding domain capable of specific binding to the first target are associated with each other to form a circular fusion polypeptide, and wherein the spacer domain of the first fusion polypeptide and the spacer domain of the second fusion polypeptide are associated covalently to each other by a disulfide bond and comprise modifications promoting the association of the first and second fusion polypeptide.

In one aspect, provided is a bispecific antibody as defined herein before, wherein in the first fusion polypeptide the first part of an antigen binding domain capable of specific binding to a second target is fused either directly or via a third peptide linker to the C-terminus of the second part of the first antigen binding domain capable of specific binding to the first target and wherein in the second fusion polypeptide the second part of an antigen binding domain capable of specific binding to a second target is fused either directly or via a third peptide linker to the C-terminus of the second part of the first antigen binding domain capable of specific binding to the first target.

In another aspect, provided is a bispecific antibody as defined herein before, wherein in the first fusion polypeptide the first part of an antigen binding domain capable of specific binding to a second target is fused either directly or via a third peptide linker to the N-terminus of the first part of the first antigen binding domain capable of specific binding to the first target and wherein in the second fusion polypeptide the second part of an antigen binding domain capable of specific binding to a second target is fused either directly or via a third peptide linker to the N-terminus of the first part of the first antigen binding domain capable of specific binding to the first target.

In one aspect, provided is a bispecific antibody as defined herein before, wherein the third peptide linker connecting the first part or the second part of an antigen binding domain capable of specific binding to a second target comprises at least 15 amino acids. In one aspect, the third peptide linker connecting the first part of an antigen binding domain capable of specific binding to a second target and the third peptide linker connecting the second part of an antigen binding domain capable of specific binding to a second target are identical. In one aspect, the third peptide linker comprises 15 to 25 amino acids. In one particular aspect, the third peptide linker comprises the amino acid sequence of SEQ ID NO:84.

In one aspect, the invention provides a bispecific antibody as defined herein before, wherein the first fusion polypeptide comprises the heavy chain variable domain of the antigen binding domain capable of specific binding to a second target and the second fusion polypeptide comprises the antibody light chain variable domain of the antigen binding domain capable of specific binding to a second target or vice versa. In one particular aspect, the first part of the antigen binding domain is an antibody heavy chain Fab fragment and the second part of the antigen binding domain is an antibody light chain Fab fragment or vice versa. In one aspect, the first part of the antigen binding domain and the second part of the antigen binding domain are associated covalently to each other by a disulfide bond.

Thus, in one aspect, the first part of the antigen binding domain is an antibody heavy chain Fab fragment (VH-CH1) and the second part of the antigen binding domain is an antibody light chain Fab fragment (VL-Ckappa). In another aspect, the first part of the antigen binding domain is an antibody light chain Fab fragment and the second part of the antigen binding domain is an antibody heavy chain Fab fragment. In another aspect, the first part of the antigen binding domain is an antibody cross Fab fragment comprising VH-Ckappa and the second part of the antigen binding domain is an antibody cross Fab fragment comprising VL-CH1. In a further aspect, the first part of the antigen binding domain is an antibody cross Fab fragment comprising VL-CH1 and the second part of the antigen binding domain is an antibody cross Fab fragment comprising VH-Ckappa.

As described above, the bispecific antibody consists of a first and a second fusion polypeptide, both comprising a spacer domain, the spacer domain of the first fusion polypeptide and the spacer domain of the second fusion polypeptide are associated covalently to each other by a disulfide bond and comprise modifications promoting the association of the first and second fusion polypeptide. The spacer domain comprises at least 25 amino acids.

In one aspect of the invention, the spacer domain comprises an antibody hinge region or a (C-terminal) fragment thereof and an antibody CH2 domain or a (N-terminal) fragment thereof. In another aspect, the spacer domain comprises an antibody hinge region or a fragment thereof, an antibody CH2 domain, and an antibody CH3 domain or a fragment thereof. Furthermore, the spacer domain of the first fusion polypeptide and the spacer domain of the second fusion polypeptide comprise modifications promoting the association of the first and second fusion polypeptide. In a particular aspect, the spacer domain of the first fusion polypeptide comprises holes and the spacer domain of the second fusion polypeptide comprises knobs according to the knobs into hole method. In a further aspect, the invention comprises a bispecific antibody, wherein the spacer domain comprises an antibody hinge region or a fragment thereof and an IgG1 Fc domain. Particularly, the IgG1 Fc domain comprises one or more amino acid substitution that reduces binding to an Fc receptor, in particular towards Fcγ receptor. More particularly, the IgG1 Fc domain comprises the amino acid substitutions L234A, L235A and P329G (numbering according to Kabat EU index).

In some aspects, provided is a bispecific antibody wherein the one antigen binding domain capable of specific binding to a second target is an antigen binding domain capable of specific binding to a tumor associated antigen (TAA). In particular, the tumor associated antigen is Fibroblast Activation Protein (FAP). In one aspect, provided is a bispecific antibody, wherein the antigen binding domain capable of specific binding to a second target is an antigen binding domain capable of specific binding to Fibroblast Activation Protein (FAP).

In some aspects, the antigen binding domain capable of specific binding to FAP comprises
(a) a heavy chain variable region (VHFAP) comprising (i) CDR-H1 comprising the amino acid sequence of SEQ ID NO:1, (ii) CDR-H2 comprising the amino acid sequence of SEQ ID NO:2, and (iii) CDR-H3 comprising the amino acid sequence of SEQ ID NO:3, and a light chain variable region (VLFAP) comprising (iv) CDR-L1 comprising the amino acid sequence of SEQ ID NO:4, (v) CDR-L2 comprising the amino acid sequence of SEQ ID NO:5, and (vi) CDR-L3 comprising the amino acid sequence of SEQ ID NO:6, or (b) a heavy chain variable region (VHFAP) comprising (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO:11, and a a light chain variable region (VLFAP) comprising (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14.

More particularly, the antigen binding domain capable of specific binding to FAP comprises (a) a heavy chain variable region (VHFAP) comprising an amino acid sequence that is at least about 95%, 96%, 97%, 98%, 99% or 100% identical to the amino acid sequence of SEQ ID NO:7, and a light chain variable region (VLFAP) comprising an amino acid sequence that is at least about 95%, 96%, 97%, 98%, 99% or 100% identical to the amino acid sequence of SEQ ID NO:8, or (b) a heavy chain variable region (VHFAP) comprising an amino acid sequence that is at least about 95%, 96%, 97%, 98%, 99% or 100% identical to the amino acid sequence of SEQ ID NO:15, and a light chain variable region (VLFAP) comprising an amino acid sequence that is at least about 95%, 96%, 97%, 98%, 99% or 100% identical to the amino acid sequence of SEQ ID NO:16.

In some aspects, provided is a bispecific antibody wherein the antigen binding domain capable of specific binding to a first target is an antigen binding domain capable of specific binding to a TNF receptor, in particular a costimulatory TNF receptor. Particularly, the costimulatory TNF receptor is OX40. In one aspect, provided is a bispecific antibody, wherein the antigen binding domain capable of specific binding to a first target is an antigen binding domain capable of specific binding to OX40. Particularly, the bispecific antibody of the invention comprises two antigen binding domains capable of specific binding to OX40.

In some aspects, the antigen binding domain capable of specific binding to OX40 comprises (a) a heavy chain variable region (VHOX40) comprising (i) CDR-H1 comprising the amino acid sequence of SEQ ID NO:17, (ii) CDR-H2 comprising the amino acid sequence of SEQ ID NO:19, and (iii) CDR-H3 comprising the amino acid sequence of SEQ ID NO:22, and a light chain variable region (VLOX40) comprising (iv) CDR-L1 comprising the amino acid sequence of SEQ ID NO:28, (v) CDR-L2 comprising the amino acid sequence of SEQ ID NO:31, and (vi) CDR-L3 comprising the amino acid sequence of SEQ ID NO:35, or (b) a heavy chain variable region (VHOX40) comprising (i) CDR-H1 comprising the amino acid sequence of SEQ ID NO:17, (ii) CDR-H2 comprising the amino acid sequence of SEQ ID NO:19, and (iii) CDR-H3 comprising the amino acid sequence of SEQ ID NO:21, and a light chain variable region (VLOX40) comprising (iv) CDR-L1 comprising the amino acid sequence of SEQ ID NO:28, (v) CDR-L2 comprising the amino acid sequence of SEQ ID NO:31, and (vi) CDR-L3 comprising the amino acid sequence of SEQ ID NO:34, or (c) a heavy chain variable region (VHOX40) comprising (i) CDR-H1 comprising the amino acid sequence of SEQ ID NO:17, (ii) CDR-H2 comprising the amino acid sequence of SEQ ID NO:19, and (iii) CDR-H3 comprising the amino acid sequence of SEQ ID NO:23, and a light chain variable region (VLOX40) comprising (iv) CDR-L1 comprising the amino acid sequence of SEQ ID NO:28, (v) CDR-L2 comprising the amino acid sequence of SEQ ID NO:31, and (vi) CDR-L3 comprising the amino acid sequence of SEQ ID NO:36, or (d) a heavy chain variable region (VHOX40) comprising (i) CDR-H1 comprising the amino acid sequence of SEQ ID NO:17, (ii) CDR-H2 comprising the amino acid sequence of SEQ ID NO:19, and (iii) CDR-H3 comprising the amino acid sequence of SEQ ID NO:24, and a light chain variable region (VLOX40) comprising (iv) CDR-L1 comprising the amino acid sequence of SEQ ID NO:28, (v) CDR-L2 comprising the amino acid sequence of SEQ ID NO:31, and (vi) CDR-L3 comprising the amino acid sequence of SEQ ID NO:37, or (e) a heavy chain variable region (VHOX40) comprising (i) CDR-H1 comprising the amino acid sequence of SEQ ID NO:18, (ii) CDR-H2 comprising the amino acid sequence of SEQ ID NO:20, and (iii) CDR-H3 comprising the amino acid sequence of SEQ ID NO:25, and a light chain variable region (VLOX40) comprising (iv) CDR-L1 comprising the amino acid sequence of SEQ ID NO:29, (v) CDR-L2 comprising the amino acid sequence of SEQ ID NO:32, and (vi) CDR-L3 comprising the amino acid sequence of SEQ ID NO:38, or (f) a heavy chain variable region (VHOX40) comprising (i) CDR-H1 comprising the amino acid sequence of SEQ ID NO:18, (ii) CDR-H2 comprising the amino acid sequence of SEQ ID NO:20, and (iii) CDR-H3 comprising the amino acid sequence of SEQ ID NO:26, and a light chain variable region (VLOX40) comprising (iv) CDR-L1 comprising the amino acid sequence of SEQ ID NO:29, (v) CDR-L2 comprising the amino acid sequence of SEQ ID NO:32, and (vi) CDR-L3 comprising the amino acid sequence of SEQ ID NO:38, or (g) a heavy chain variable region (VHOX40) comprising (i) CDR-H1 comprising the amino acid sequence of SEQ ID NO:18, (ii) CDR-H2 comprising the amino acid sequence of SEQ ID NO:20, and (iii) CDR-H3 comprising the amino acid sequence of SEQ ID NO:27, and a light chain variable region (VLOX40) comprising (iv) CDR-L1 comprising the amino acid sequence of SEQ ID NO:30, (v) CDR-L2 comprising the amino acid sequence of SEQ ID NO:33, and (vi) CDR-L3 comprising the amino acid sequence of SEQ ID NO:39.

In particular, the antigen binding domain capable of specific binding to OX40 comprises a heavy chain variable region (VHOX40) comprising (i) CDR-H1 comprising the amino acid sequence of SEQ ID NO:17, (ii) CDR-H2 comprising the amino acid sequence of SEQ ID NO:19, and (iii) CDR-H3 comprising the amino acid sequence of SEQ ID NO:22, and a light chain variable region (VLOX40) comprising (iv) CDR-L1 comprising the amino acid sequence of SEQ ID NO:28, (v) CDR-L2 comprising the amino acid sequence of SEQ ID NO:31, and (vi) CDR-L3 comprising the amino acid sequence of SEQ ID NO:35.

In some aspects, the antigen binding domain capable of specific binding to OX40 comprises (a) a heavy chain variable region (VHOX40) comprising an amino acid sequence of SEQ ID NO:40 and a light chain variable region (VLOX40) comprising an amino acid sequence of SEQ ID NO:41, or (b) a heavy chain variable region (VHOX40) comprising an amino acid sequence of SEQ ID NO:42 and a light chain variable region (VLOX40) comprising an amino acid sequence of SEQ ID NO:43, or (c) a heavy chain variable region (VHOX40) comprising an amino acid sequence of SEQ ID NO:44 and a light chain variable region (VLOX40) comprising an amino acid sequence of SEQ ID NO:45, or (d) a heavy chain variable region (VHOX40) comprising an amino acid sequence of SEQ ID NO:46 and a light chain variable region (VLOX40) comprising an amino acid sequence of SEQ ID NO:47, or (a) a heavy chain variable region (VHOX40) comprising an amino acid sequence of SEQ ID NO:48 and a light chain variable region (VLOX40) comprising an amino acid sequence of SEQ ID NO:49, or (a) a heavy chain variable region (VHOX40) comprising an amino acid sequence of SEQ ID NO:50 and a light chain variable region (VLOX40) comprising an amino acid sequence of SEQ ID NO:51, or (a) a heavy chain variable region (VHOX40) comprising an amino acid sequence of SEQ ID NO:52 and a light chain variable region (VLOX40) comprising an amino acid sequence of SEQ ID NO:53.

In one particular aspect, the antigen binding domain capable of specific binding to OX40 comprises (a) a heavy chain variable region (VHOX40) comprising an amino acid sequence that is at least about 95%, 96%, 97%, 98%, 99% or 100% identical to the amino acid sequence of SEQ ID NO:40, and a light chain variable region (VLOX40) comprising an amino acid sequence that is at least about 95%, 96%, 97%, 98%, 99% or 100% identical to the amino acid sequence of SEQ ID NO:41.

Particularly, the present invention provides a bispecific antibody, wherein the bispecific antibody comprises (a) a fusion polypeptide comprising an amino acid sequence that is at least about 95%, 96%, 97%, 98%, 99% or 100% identical to the amino acid sequence of SEQ ID NO:54, and a fusion polypeptide comprising an amino acid sequence that is at least about 95%, 96%, 97%, 98%, 99% or 100% identical to the amino acid sequence of SEQ ID NO:55, (b) a fusion polypeptide comprising an amino acid sequence that is at least about 95%, 96%, 97%, 98%, 99% or 100% identical to the amino acid sequence of SEQ ID NO:56, and a fusion polypeptide comprising an amino acid sequence that is at least about 95%, 96%, 97%, 98%, 99% or 100% identical to the amino acid sequence of SEQ ID NO:57, (c) a fusion polypeptide comprising an amino acid sequence that is at least about 95%, 96%, 97%, 98%, 99% or 100% identical to the amino acid sequence of SEQ ID NO:58, and a fusion polypeptide comprising an amino acid sequence that is at least about 95%, 96%, 97%, 98%, 99% or 100% identical to the amino acid sequence of SEQ ID NO:59, (d) a fusion polypeptide comprising an amino acid sequence that is at least about 95%, 96%, 97%, 98%, 99% or 100% identical to the amino acid sequence of SEQ ID NO:60, and a fusion polypeptide comprising an amino acid sequence that is at least about 95%, 96%, 97%, 98%, 99% or 100% identical to the amino acid sequence of SEQ ID NO:61, (e) a fusion polypeptide comprising an amino acid sequence that is at least about 95%, 96%, 97%, 98%, 99% or 100% identical to the amino acid sequence of SEQ ID NO:62, and a fusion polypeptide comprising an amino acid sequence that is at least about 95%, 96%, 97%, 98%, 99% or 100% identical to the amino acid sequence of SEQ ID NO:63, (f) a fusion polypeptide comprising an amino acid sequence that is at least about 95%, 96%, 97%, 98%, 99% or 100% identical to the amino acid sequence of SEQ ID NO:64, and a fusion polypeptide comprising an amino acid sequence that is at least about 95%, 96%, 97%, 98%, 99% or 100% identical to the amino acid sequence of SEQ ID NO:65, or (g) a fusion polypeptide comprising an amino acid sequence that is at least about 95%, 96%, 97%, 98%, 99% or 100% identical to the amino acid sequence of SEQ ID NO:66, and a fusion polypeptide comprising an amino acid sequence that is at least about 95%, 96%, 97%, 98%, 99% or 100% identical to the amino acid sequence of SEQ ID NO:67.

Furthermore, the present invention provides a bispecific antibody, wherein the bispecific antibody comprises (a) a fusion polypeptide comprising an amino acid sequence that is at least about 95%, 96%, 97%, 98%, 99% or 100% identical to the amino acid sequence of SEQ ID NO:116, and a fusion polypeptide comprising an amino acid sequence that is at least about 95%, 96%, 97%, 98%, 99% or 100% identical to the amino acid sequence of SEQ ID NO:117, (b) a fusion polypeptide comprising an amino acid sequence that is at least about 95%, 96%, 97%, 98%, 99% or 100% identical to the amino acid sequence of SEQ ID NO:118, and a fusion polypeptide comprising an amino acid sequence that is at least about 95%, 96%, 97%, 98%, 99% or 100% identical to the amino acid sequence of SEQ ID NO:119, (c) a fusion polypeptide comprising an amino acid sequence that is at least about 95%, 96%, 97%, 98%, 99% or 100% identical to the amino acid sequence of SEQ ID NO:120, and a fusion polypeptide comprising an amino acid sequence that is at least about 95%, 96%, 97%, 98%, 99% or 100% identical to the amino acid sequence of SEQ ID NO:121, (d) a fusion polypeptide comprising an amino acid sequence that is at least about 95%, 96%, 97%, 98%, 99% or 100% identical to the amino acid sequence of SEQ ID NO:122, and a fusion polypeptide comprising an amino acid sequence that is at least about 95%, 96%, 97%, 98%, 99% or 100% identical to the amino acid sequence of SEQ ID NO:123, (e) a fusion polypeptide comprising an amino acid sequence that is at least about 95%, 96%, 97%, 98%, 99% or 100% identical to the amino acid sequence of SEQ ID NO:124, and a fusion polypeptide comprising an amino acid sequence that is at least about 95%, 96%, 97%, 98%, 99% or 100% identical to the amino acid sequence of SEQ ID NO:125, (f) a fusion polypeptide comprising an amino acid sequence that is at least about 95%, 96%, 97%, 98%, 99% or 100% identical to the amino acid sequence of SEQ ID NO:126, a fusion polypeptide comprising an amino acid sequence that is at least about 95%, 96%, 97%, 98%, 99% or 100% identical to the amino acid sequence of SEQ ID NO:127, and a light chain that is at least about 95%, 96%, 97%, 98%, 99% or 100% identical to the amino acid sequence of SEQ ID NO:128, (g) a fusion polypeptide comprising an amino acid sequence that is at least about 95%, 96%, 97%, 98%, 99% or 100% identical to the amino acid sequence of SEQ ID NO:129, and a fusion polypeptide comprising an amino acid sequence that is at least about 95%, 96%, 97%, 98%, 99% or 100% identical to the amino acid sequence of SEQ ID NO:130, (h) a fusion polypeptide comprising an amino acid sequence that is at least about 95%, 96%, 97%, 98%, 99% or 100% identical to the amino acid sequence of SEQ ID NO:131, and a fusion polypeptide comprising an amino acid sequence that is at least about 95%, 96%, 97%, 98%, 99% or 100% identical to the amino acid sequence of SEQ ID NO:132, or (i) a fusion polypeptide comprising an amino acid sequence that is at least about 95%, 96%, 97%, 98%, 99% or 100% identical to the amino acid sequence of SEQ ID NO:133, and a fusion polypeptide comprising an amino acid sequence that is at least about 95%, 96%, 97%, 98%, 99% or 100% identical to the amino acid sequence of SEQ ID NO:134.

In some aspects, provided is a bispecific antibody wherein the costimulatory TNF receptor is 4-1BB. In one aspect, provided is a bispecific antibody, wherein the antigen binding domain capable of specific binding to a first target is an antigen binding domain capable of specific binding to 4-1BB. Particularly, the bispecific antibody of the invention comprises two antigen binding domains capable of specific binding to 4-1BB.

In some aspects, the antigen binding domain capable of specific binding to 4-1BB a heavy chain variable region (VH4-1BB) comprising (i) CDR-H1 comprising the amino acid sequence of SEQ ID NO:135, (ii) CDR-H2 comprising the amino acid sequence of SEQ ID NO:136, and (iii) CDR-H3 comprising the amino acid sequence of SEQ ID NO:137, and a light chain variable region (VL4-1BB) comprising (iv) CDR-L1 comprising the amino acid sequence of SEQ ID NO:138, (v) CDR-L2 comprising the amino acid sequence of SEQ ID NO:139, and (vi) CDR-L3 comprising the amino acid sequence of SEQ ID NO:140. In one aspect, the antigen binding domain capable of specific binding to 4-1BB comprises a heavy chain variable region (VH4-1BB) comprising an amino acid sequence that is at least about 95%, 96%, 97%, 98%, 99% or 100% identical to the amino acid sequence of SEQ ID NO:141, and a light chain variable region (VL4-1BB) comprising an amino acid sequence that is at least about 95%, 96%, 97%, 98%, 99% or 100% identical to the amino acid sequence of SEQ ID NO:142.

Particularly, the present invention provides a bispecific antibody, wherein the bispecific antibody comprises (a) a fusion polypeptide comprising an amino acid sequence that is at least about 95%, 96%, 97%, 98%, 99% or 100% identical to the amino acid sequence of SEQ ID NO:143, and a fusion polypeptide comprising an amino acid sequence that is at least about 95%, 96%, 97%, 98%, 99% or 100% identical to the amino acid sequence of SEQ ID NO:144, or (b) a fusion polypeptide comprising an amino acid sequence that is at least about 95%, 96%, 97%, 98%, 99% or 100% identical to the amino acid sequence of SEQ ID NO:145, and a fusion polypeptide comprising an amino acid sequence that is at least about 95%, 96%, 97%, 98%, 99% or 100% identical to the amino acid sequence of SEQ ID NO:146.

In some aspects, provided is a bispecific antibody wherein the costimulatory TNF receptor is CD40. In one aspect, provided is a bispecific antibody, wherein the antigen binding domain capable of specific binding to a first target is an antigen binding domain capable of specific binding to CD40. Particularly, the bispecific antibody of the invention comprises two antigen binding domains capable of specific binding to CD40.

In some aspects, the antigen binding domain capable of specific binding to CD40 comprises a heavy chain variable region (VHCD40) comprising (i) CDR-H1 comprising the amino acid sequence of SEQ ID NO:147, (ii) CDR-H2 comprising the amino acid sequence of SEQ ID NO:148, and (iii) CDR-H3 comprising the amino acid sequence of SEQ ID NO:149, and a light chain variable region (VLCD40) comprising (iv) CDR-L1 comprising the amino acid sequence of SEQ ID NO:150, (v) CDR-L2 comprising the amino acid sequence of SEQ ID NO:151, and (vi) CDR-L3 comprising the amino acid sequence of SEQ ID NO:152. In one aspect, the antigen binding domain capable of specific binding to CD40 comprises a heavy chain variable region (VHCD40) comprising an amino acid sequence that is at least about 95%, 96%, 97%, 98%, 99% or 100% identical to the amino acid sequence of SEQ ID NO:153, and a light chain variable region (VLCD40) comprising an amino acid sequence that is at least about 95%, 96%, 97%, 98%, 99% or 100% identical to the amino acid sequence of SEQ ID NO:154.

In another aspect, the antigen binding domain capable of specific binding to a first target is an antigen binding domain capable of specific binding to CD40 comprises (i) a heavy chain variable region (VHCD40) comprising an amino acid sequence selected from the group consisting of SEQ ID NO:167, SEQ ID NO:168, SEQ ID NO:169 and SEQ ID NO:170, and a light chain variable region (VLCD40) comprising the amino acid sequence selected from the group consisting of SEQ ID NO:171, SEQ ID NO:172, SEQ ID NO:173, and SEQ ID NO:174, or (ii) a heavy chain variable region (VHCD40) comprising an amino acid sequence selected from the group consisting of SEQ ID NO:175, SEQ ID NO:176, SEQ ID NO:177, SEQ ID NO:178, SEQ ID NO:179 and SEQ ID NO:180, and a light chain variable region (VLCD40) comprising the amino acid sequence selected from the group consisting of SEQ ID NO:181, SEQ ID NO:182, SEQ ID NO:183, and SEQ ID NO:184.

Particularly, the present invention provides a bispecific antibody, wherein the bispecific antibody comprises (a) a fusion polypeptide comprising an amino acid sequence that is at least about 95%, 96%, 97%, 98%, 99% or 100% identical to the amino acid sequence of SEQ ID NO:155, and a fusion polypeptide comprising an amino acid sequence that is at least about 95%, 96%, 97%, 98%, 99% or 100% identical to the amino acid sequence of SEQ ID NO:156, (b) a fusion polypeptide comprising an amino acid sequence that is at least about 95%, 96%, 97%, 98%, 99% or 100% identical to the amino acid sequence of SEQ ID NO:157, and a fusion polypeptide comprising an amino acid sequence that is at least about 95%, 96%, 97%, 98%, 99% or 100% identical to the amino acid sequence of SEQ ID NO:158, (c) a fusion polypeptide comprising an amino acid sequence that is at least about 95%, 96%, 97%, 98%, 99% or 100% identical to the amino acid sequence of SEQ ID NO:159, and a fusion polypeptide comprising an amino acid sequence that is at least about 95%, 96%, 97%, 98%, 99% or 100% identical to the amino acid sequence of SEQ ID NO:160, (d) a fusion polypeptide comprising an amino acid sequence that is at least about 95%, 96%, 97%, 98%, 99% or 100% identical to the amino acid sequence of SEQ ID NO:161, and a fusion polypeptide comprising an amino acid sequence that is at least about 95%, 96%, 97%, 98%, 99% or 100% identical to the amino acid sequence of SEQ ID NO:162, (e) a fusion polypeptide comprising an amino acid sequence that is at least about 95%, 96%, 97%, 98%, 99% or 100% identical to the amino acid sequence of SEQ ID NO:163, and a fusion polypeptide comprising an amino acid sequence that is at least about 95%, 96%, 97%, 98%, 99% or 100% identical to the amino acid sequence of SEQ ID NO:164, or (f) a fusion polypeptide comprising an amino acid sequence that is at least about 95%, 96%, 97%, 98%, 99% or 100% identical to the amino acid sequence of SEQ ID NO:165, and a fusion polypeptide comprising an amino acid sequence that is at least about 95%, 96%, 97%, 98%, 99% or 100% identical to the amino acid sequence of SEQ ID NO:166.

The present invention also provides isolated nucleic acid encoding the bispecific antibody of the present invention. Provided is also an expression vector comprising the nucleic acid of the present invention and and furthermore a host cell comprising the isolated nucleic acid or the expression vector of the present invention is provided. Also included is a method of producing a bispecific antibody, comprising culturing the host cell of the present invention under conditions suitable for the expression of the bispecific antibody. The method may also include the step of isolating the bispecific antibody.

The present invention also provides a pharmaceutical composition comprising the bispecific antibody of the present invention and at least one pharmaceutically acceptable excipient.

The present invention also provides the bispecific antibody of the present invention, or the pharmaceutical composition of the present invention, for use as a medicament. More particularly, provided is also the bispecific antibody of the invention for use in treating cancer or infectious diseases. In particular, the bispecific antibody of the invention for use in treating cancer is provided.

In a further aspect, provided is the use of bispecific antibody of the present invention, or the pharmaceutical composition of the present invention, in the manufacture of a medicament for use
(i) in stimulating T cell response,
(ii) in supporting survival of activated T cells,
(iii) in the treatment of infections,
(iv) in the treatment of cancer,
(v) in delaying progression of cancer, or
(vi) in prolonging the survival of a patient suffering from cancer.

The present invention also provides a method of treating an individual having cancer or infectious diseases comprising administering to the individual an effective amount of the bispecific antibody of the present invention, or the pharmaceutical composition of the present invention.

The present invention also provides the use of the bispecific antibody of the present invention, or the pharmaceutical composition of the present invention, in the manufacture of a medicament for up-regulating or prolonging cytotoxic T cell activity. Also provided is a method of up-regulating or prolonging cytotoxic T cell activity in an individual having cancer, comprising administering to the individual an effective amount of the bispecific antibody of the present invention, or the pharmaceutical composition of the present invention. In some embodiments in accordance with various aspects of the present invention the individual is a mammal, particularly a human.

BRIEF DESCRIPTION OF THE DRAWINGS

In FIG. 1A, the contorsbody consists of a first fusion polypeptide comprising the first half of a fab capable of specific binding to the first target (heavy chain fab) linked via a peptide linker (black line) to a spacer domain linked via peptide linker (black line) to the second half of the fab capable of specific binding to the first target (light chain fab) which is further linked to a first half of a cross fab capable of specific binding to the second target (VH-Ckappa) (from N to C) and of a second fusion polypeptide comprising the first half of a fab capable of specific binding to the first target (heavy chain fab) linked via a peptide linker (black line) to a spacer domain linked via peptide linker (black line) to the second half of the fab capable of specific binding to the first target (light chain fab) which is further linked to second half of a cross fab capable of specific binding to the second target (VL-CH1) (from N to C). The two spacer domains are different from each other and comprise modifications promoting the association of the first and second fusion polypeptide. An example for this type of contorsbody is CD134-0093 (see Example 2.1). In FIG. 1B, the contorsbody consists of a first fusion polypeptide comprising the first half of a cross fab capable of specific binding to the first target (VH-Ckappa) linked via a peptide linker (black line) to a spacer domain linked via peptide linker (black line) to the second half of the cross fab capable of specific binding to the first target (VL-CH1) which is further linked to a first half of a fab capable of specific binding to the second target (light chain fab) (from N to C) and of a second fusion polypeptide comprising the first half of a cross fab capable of specific binding to the first target (VH-Ckappa) linked via a peptide linker (black line) to a spacer domain linked via peptide linker (black line) to the second half of the cross fab capable of specific binding to the first target (VL-CH1) which is further linked to second half of the fab capable of specific binding to the second target (heavy chain fab) (from N to C). The two spacer domains are different from each other and comprise modifications promoting the association of the first and second fusion polypeptide. An example for this type of contorsbody is CD134-0094 (see Example 2.2). In FIG. 1C, the contorsbody consists of a first fusion polypeptide comprising the first half of a fab capable of specific binding to the first target (VL-Ckappa) linked via a peptide linker (black line) to a spacer domain linked via peptide linker (black line) to the second half of the fab capable of specific binding to the first target (VH-CH1) which is further linked to a first half of a cross fab capable of specific binding to the second target (VH-Ckappa) (from N to C) and of a second fusion polypeptide comprising the first half of a fab capable of specific binding to the first target (VL-Ckappa) linked via a peptide linker (black line) to a spacer domain linked via peptide linker (black line) to the second half of the fab capable of specific binding to the first target (VH-CH1) which is further linked to second half of the cross fab capable of specific binding to the second target (VL-CH1) (from N to C). The two spacer domains are different from each other and comprise modifications promoting the association of the first and second fusion polypeptide. An example for this type of contorsbody is P1AE0821 (see Example 2.7). In FIG. 1D, the contorsbody consists of a first fusion polypeptide comprising the first half of a cross fab capable of specific binding to the second target (VH-Ckappa) linked via a peptide linker (black line) to a first half of a cross fab capable of specific binding to the first target (VH-Ckappa) which is further linked via a peptide linker (black line) to a spacer domain linked via peptide linker (black line) to the second half of the cross fab capable of specific binding to the first target (VL-CH1) (from N to C) and of a second fusion polypeptide comprising the first half of a cross fab capable of specific binding to the second target (VL-CH1) linked via a peptide linker (black line) to a first half of a cross fab capable of specific binding to the first target (VH-Ckappa) which is further linked via a peptide linker (black line) to a spacer domain linked via peptide linker (black line) to the second half of the cross fab capable of specific binding to the first target (VH-CH1) (from N to C). The two spacer domains are different from each other and comprise modifications promoting the association of the first and second fusion polypeptide. An example for this type of contorsbody is P1AE2735 (see Example 2.14).

In FIGS. 2A, 2B, 2C and 2D is shown the binding of OX40×FAP bispecific antibodies to activated CD4+ and CD8+ T-cells (FIGS. 2A and 2C, respectively) and resting CD4+ and CD8+ T-cells (FIGS. 2B and 2D, respectively). The tetravalent 4+1 OX40×FAP (4B9) bispecific antibody showed the strongest binding to $CD4^+$ and $CD8^+$ T-cells. The 2+1 formats 2+1 OX40 (49B4)×FAP (28H1) and 2+1 OX40 (49B4)×DP47 showed intermediate binding. The Contorsbody CD134-0093 indicated stronger binding than the 2+1 formats, whereas the Contorsbody CD134-0094 bound less strong. Binding to $CD4^+$ T-cells was much stronger than that to $CD8^+$ T cells. The negative control DP47 hu IgG1 P329G LALA did not bind to $CD4^+$ or $CD8^+$ T-cells. None of the molecules bound to resting $CD4^+$ or $CD8^+$ T-cells (FIGS. 2B and 2D).

FIGS. 2E, 2F, 2G and 2H show the results as obtained with Contorsbodies P1AE0085, P1AE0086 and P1AE0087. All 2+1 formats OX40 (49B4)×FAP (28H1), OX40 (49B4)× FAP (4B9) and OX40 (49B4)×DP47 showed a similarly good binding to activated $CD4^+$ and $CD8^+$ T-cells (FIGS. 2E and 2G, respectively) whereas the binding to OX40 was partially impaired for the Contorsbody molecules, especially for the Contorsbody P1AE0087. DP47 hu IgG1 P329G LALA did not bind to $CD4^+$ or $CD8^+$ T-cells as expected. No binding was observed to resting $CD4^+$ or $CD8^+$ T-cells (FIGS. 2F and 2H, respectively) for any of the tested molecules.

The binding to human FAP-expressing tumor cells is shown in FIGS. 3A, 3B, 3C and 3D. In a first experiment, Contorsbodies CD134-0093 and CD134-0094 were compared with the control molecules. Binding to WM266-4 ($FAP^+$ positive) and A549NLR (FAP negative) tumor cells is shown in FIGS. 3A and 3B, respectively. All OX40×FAP bispecific antibodies bound efficiently to human FAP expressing target cells. The tetravalent 4+1 OX40×FAP (4B9, high affinity to FAP) bispecific antibody bound strongest to $FAP^+$ cells, followed by the Contorsbody CD134-0093, Contorsbody CD1334-0094 and the 2+1 OX40 (49B4)×FAP (28H1) bispecific antibody. The non-targeted 2+1 OX40 (49B4)×DP47 and the negative control (DP47 hu IgG1 P329G LALA) did not bind to any $FAP^+$ cells. FIGS. 3C and 3D show the binding of Contorsbodies P1AE0085, P1AE0086 and P1AE0087 to NIH/3T3huFAP clone 19 ($FAP^+$) (FIG. 3C) and A549NLR ($FAP^-$) tumor cells (FIG. 3D). All FAP-targeted anti OX40 antibodies bound efficiently to human FAP expressing target cells. The binding of the Contorsbody molecules was slightly impaired as compared to their respective controls. Again, the non-targeted 2+1 OX40 (49B4)×DP47 and the negative control (DP47 hu IgG1 P329G LALA) showed no binding to $FAP^+$ cells.

In FIGS. 4A, 4B, 4C, 4D, 4E and 4F the NFκB activation with different types of cross-linking is shown. Using FAP expressing cells (NIH/3T3 huFAP clone 19) as crosslinkers, the FAP targeted 2+1 OX40 (49B4)×FAP (28H1) construct induced the strongest NFκB activation, followed by Contorsbodies CD134-0093 and CD134-0094, whereas CD134-0094 showed a slightly stronger activation than CD134-0093. The non-targeted and therefore not crosslinked 2 non-targeted 2+1 OX40 (49B4)×DP47 induced weak NFκB activation (FIG. 4A). When using a secondary, anti hu IgG1 Fcγ-specific antibody as crosslinker, the two 2+1 constructs OX40 (49B4)×FAP (28H1) and OX40 (49B4)×DP47 behaved similar. The Contorsbodies CD134-0093 and CD134-0094 ran similar as well, but lower than the 2+1 constructs (FIG. 4B). The least NFκB activation was obtained by not using crosslinkers. The 2+1 constructs OX40 (49B4)×FAP (28H1) and OX40 (49B4)×DP47 showed a moderate NFκB activation, followed by the even less potent Contorsbodies CD134-0093 and CD134-0094. DP47 hu IgG1 P329G LALA did not induce any NFκB activation (FIG. 4C). The ability of Contorsbodies P1AE0085, P1AE0086 and P1AE0087 to induce NFκB activation with different types of cross-linking is shown in FIGS. 4D to 4F. In the absence of cross-linking, only a weak signal could be detected at the highest antibody concentration (FIG. 4D). The three Contorsbody molecules induced a very similar NFκB activation to that of FAP-targeted 2+1 formats OX40 (49B4)×FAP (28H1) and OX40 (49B4)×FAP (4B9) when cross-linked by human FAP-expressing cells (FIG. 4E). In the presence of secondary antibody cross-linking, all three Contorsbody molecules displayed slightly lower NFκB activation than the 2+1 control molecules (FIG. 4F). DP47 hu IgG1 P329G LALA did not induce any NFκB activation.

Ox40 mediated co-stimulation of sub-optimally TCR triggered resting human PBMCs and hyper-crosslinking by cell surface FAP is shown in FIGS. 5A, 5B, 5C, 5D, 5E and 5F. FIGS. 5A and 5B show the FSC-A ("area" of a Forward Side Scatter (FSC) pulse), respectively the size of CD4 and CD8 T-cells, respectively, after suboptimal CD3 stimulation as measured as intensity of light scattered at small angles by FACS analysis. The FAP targeted 2+1 construct OX40 (49B4)×FAP (28H1) showed an intermediate increase in size, whereas the Contorsbody CD134-0093 indicated a stronger increase. The untargeted 2+1 OX40 (49B4)×DP47, the Contorsbody CD134-0094 and the negative control (DP47 hu IgG1 P329G LALA) did not change the size of neither CD4 nor CD8 T-cells. FIGS. 5C and 5D show the activation of CD4 and CD8 T-cells using the surface marker CD25. For the CD4 T-cells (FIG. 5C) contorsbodies CD134-0093 and CD134-0094 demonstrated the highest activation, followed by the somehow less potent targeted 2+1 OX40 (49B4)×FAP (28H1). The untargeted OX40 (49B4)×DP47 and the negative control did not show any activation after baseline-correction. For the CD8 T-cells (FIG. 5D), the Contorsbody CD134-0094 demonstrated a stronger activation compared to the 2+1 OX40 (49B4)×FAP (28H1) and CD134-0093. FIGS. 5E and 5F show the upon activation downregulated IL-7Rα (CD127). The Contorsbody CD134-0093 showed the strongest CD127 downregulation for CD4 and CD8 T-cells, followed by the targeted 2+1 OX40 (49B4)×FAP (28H1) and the Contorsbody CD134-0094.

Figure 6:
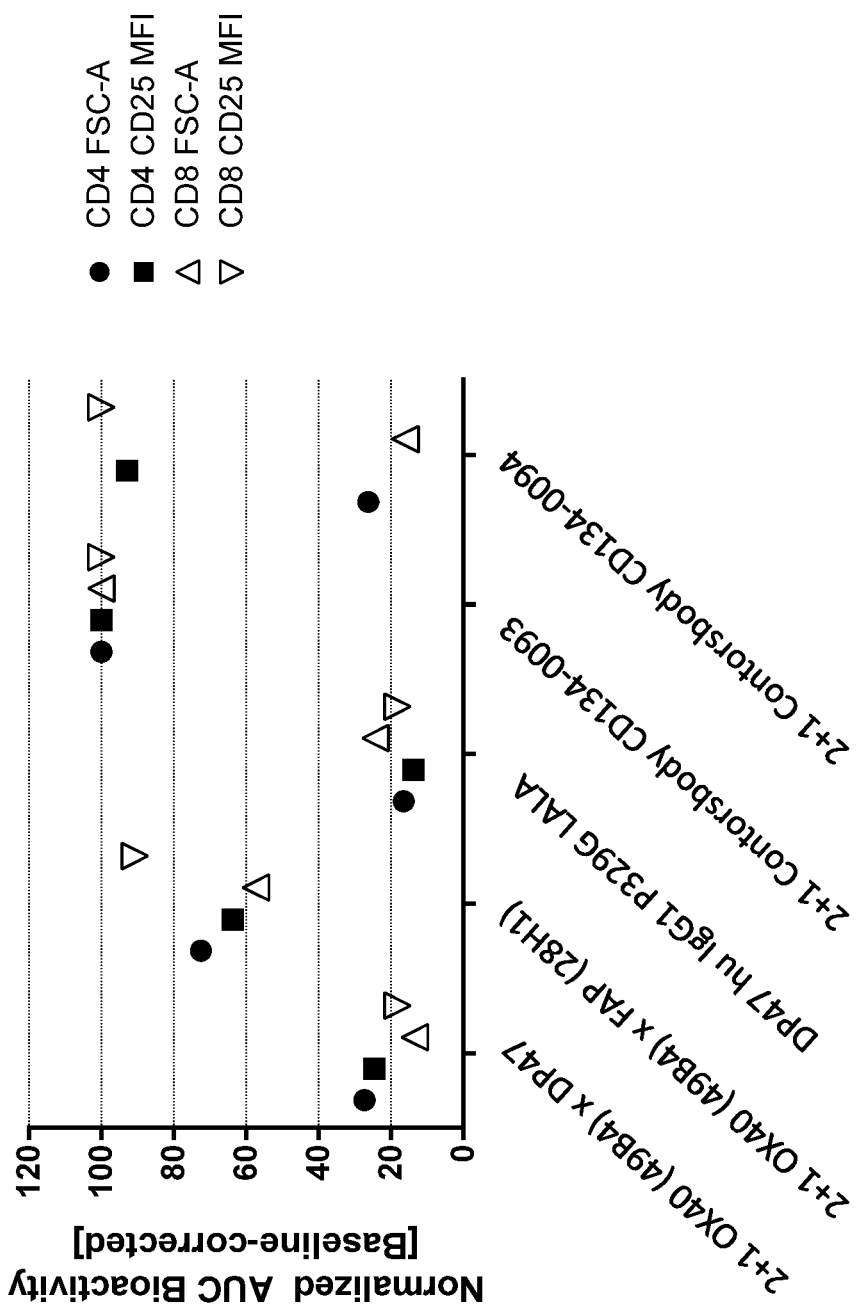
Figures 9C, 9D:
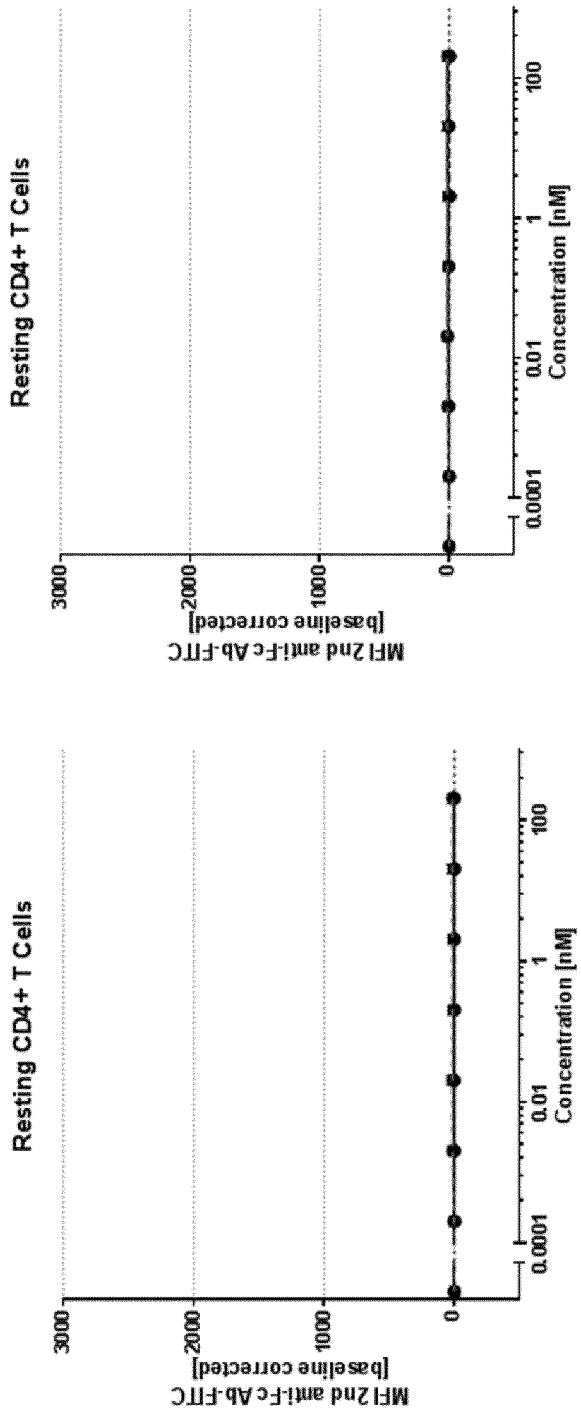
Figures 11C, 11D:
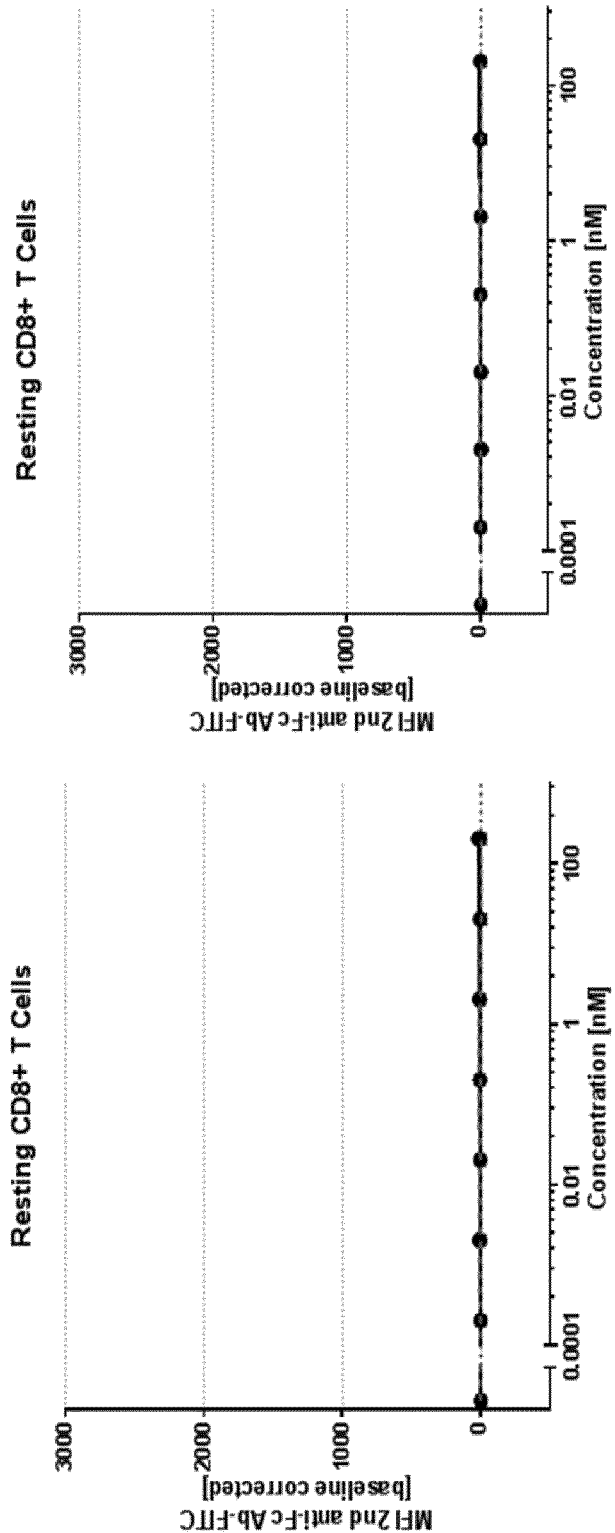

FIG. 6 illustrates the normalized area under the curve (AUC) values for FSC-A and CD25 on CD4 and CD8 T-cells. The filled symbols represent CD4 T-cells, the empty one CD8 T cells. All values were normalized to the top AUC values of the Contorsbody CD134-0093 (=100%). The untargeted 2+1 construct OX40 (49B4)×DP47 showed only minimal activation on CD4 and CD8 T cells, whereas the FAP targeted 2+1 construct OX40 (49B4)×FAP (28H1) demonstrated a higher potency (normalized values between 60 and 100) regarding FSC-A and CD25 on CD4 and CD8 T cells, but less potency compared to CD134-0093. For the Contorsbody CD134-0094, only the CD25 MFI AUC values of CD4 and CD8 T-cells showed similar activation compared to CD134-0093.

The effects of Contorsbodies P1AE0085, P1AE0086 and P1AE0087 on OX40 mediated co-stimulation of sub-optimally TCR triggered PBMCs and hyper-crosslinking by cell surface FAP are shown in FIGS. 7A, 7B, 7C and 7D. FIGS. 7A and 7B show the FSC-A, respectively the size of CD4 and CD8 T cells, respectively, after suboptimal CD3 stimulation. FIGS. 7C and 7D show the activation of CD4 and CD8 T-cells, respectively, using the expression of the surface marker CD25. All FAP-targeted molecules (controls and all three contorsbody molecules) induced a dose-dependent increase in the Forward Side Scatter Area and CD25 expression on both CD4 and CD8 T cells. The untargeted 2+1 construct OX40 (49B4)×DP47 and the negative control (DP47 hu IgG1 P329G LALA) did not show any activation after baseline-correction.

In FIGS. 8A, 8B, 8C and 8D is shown the binding of different OX40×FAP contorsbodies to activated CD4+ T-cells. The untargeted 2+1 construct OX40 (49B4)×DP47 was used as positive control and DP47 hu IgG1 P329G LALA as negative control. FIG. 8A shows the binding of Contorsbody 1 (P1AE1122), Contorsbody 2 (P1AE1942) and Contorsbody 3 (P1AE1887) and FIG. 8B shows the binding of Contorsbody 4 (P1AE1888), Contorsbody 5 (P1AE2254) and Contorsbody 6 (P1AE2340). The binding of Contorsbody 7 (P1AE0086) and Contorsbody 8 (P1AE2735) is shown in FIG. 8C and the binding of Contorsbody 9 (P1AE2743) and Contorsbody 10 (P1AE2762) is shown in FIG. 8D. In FIGS. 9A, 9B, 9C and 9D, respectively, it is shown that none of the tested Contorsbodies bound to resting CD4 T cells. In FIGS. 10A, 10B, 10C and 10D is shown the binding of the same OX40×FAP contorsbodies to activated CD8+ T-cells. The untargeted 2+1 construct OX40 (49B4)×DP47 was used as positive control and DP47 hu IgG1 P329G LALA as negative control. In FIGS. 11A, 11B, 11C and 11D, respectively, it is shown that none of the tested Contorsbodies bound to resting CD8 T cells. A summary of the area under the curve values for the binding to activated or resting CD4+ T-cells is shown in FIG. 12A and for the binding to activated or resting CD8+ T cell in FIG. 12B.

Figures 13A, 13B:
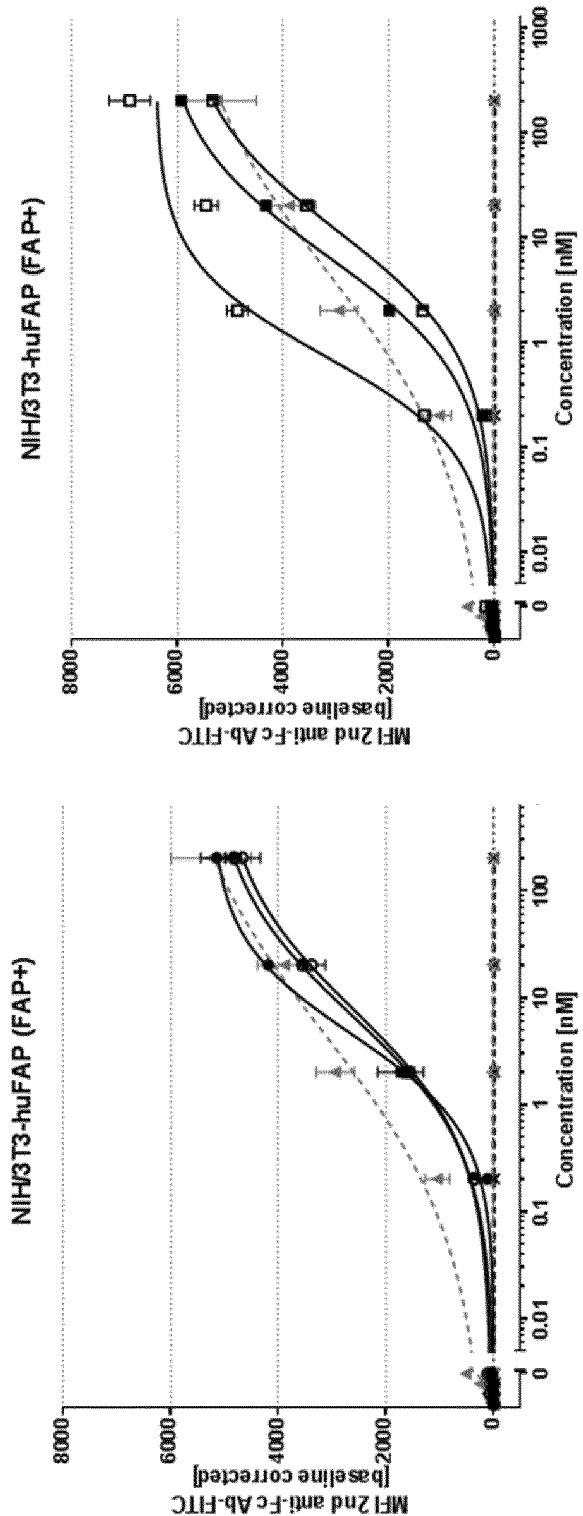
Figure 15A:
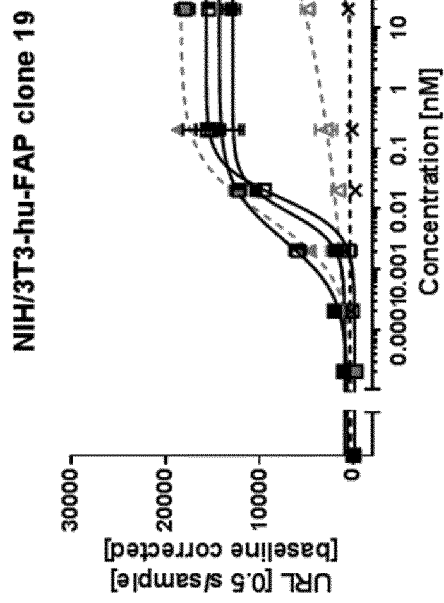
Figure 15B:
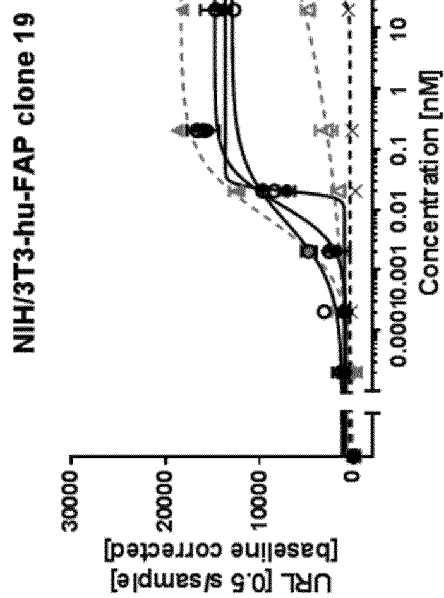
Figure 15C:
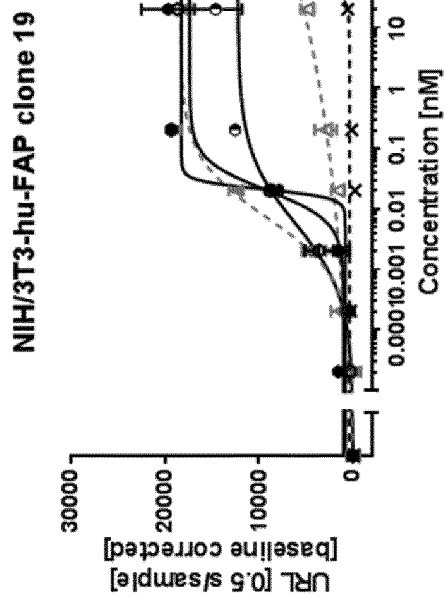
Figure 15D:
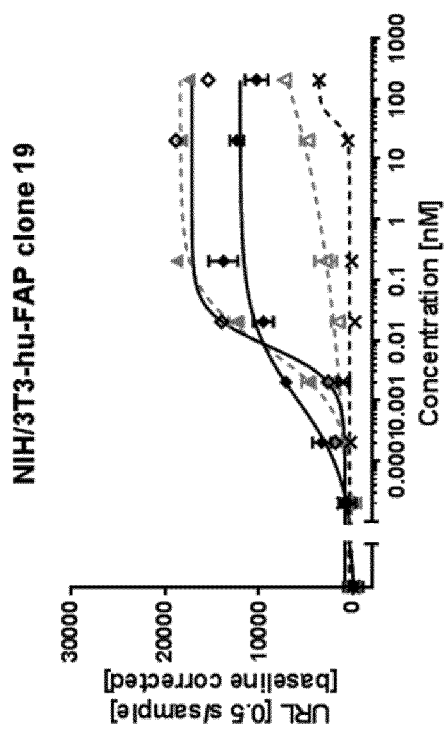

The binding to human FAP-expressing tumor cells of Contorsbodies 1 to 10 is shown in FIGS. 13A, 13B, 13C and 13D and FIGS. 14A, 14B, 14C and 14D, respectively. Binding to NIH/3T3-huFAP clone 19 (FAP+) tumor cells (FAP+ positive) is shown in FIGS. 12A to 12D, respectively. FIG. 13A shows the binding of Contorsbody 1 (P1AE1122), Contorsbody 2 (P1AE1942) and Contorsbody 3 (P1AE1887) and FIG. 13B shows the binding of Contorsbody 4 (P1AE1888), Contorsbody 5 (P1AE2254) and Contorsbody 6 (P1AE2340). The binding of Contorsbody 7 (P1AE0086) and Contorsbody 8 (P1AE2735) is shown in FIG. 13C and the binding of Contorsbody 9 (P1AE2743) and Contorsbody 10 (P1AE2762) is shown in FIG. 13D. All OX40×FAP bispecific contorsbodies bound efficiently to human FAP expressing target cells. Contorbody 8 (FIG. 12C) bound strongest to FAP+ cells, followed by Contorbody 10 (FIG. 12D) and Contorbody 6 (FIG. 12B), much stronger than the 2+1 bispecific antibody OX40 (49B4)× FAP (4B9). The untargeted 2+1 construct OX40 (49B4)× DP47 and the negative control (DP47 hu IgG1 P329G LALA) did not bind to any FAP+ cells. The corresponding binding of Contorsbodies 1 to 10 to A549NLR (FAP− negative) tumor cells is shown in FIGS. 14A to 14D. None of the FAP-targeted molecules (Contorsbodies 1 to 10 or 2+1 bispecific antibody OX40 (49B4)×FAP (4B9)) were able to bind to FAP− target cells.

Figure 16C:
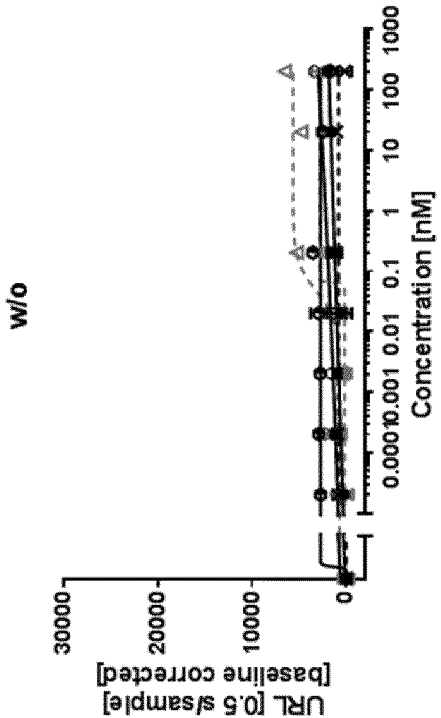
Figure 16D:
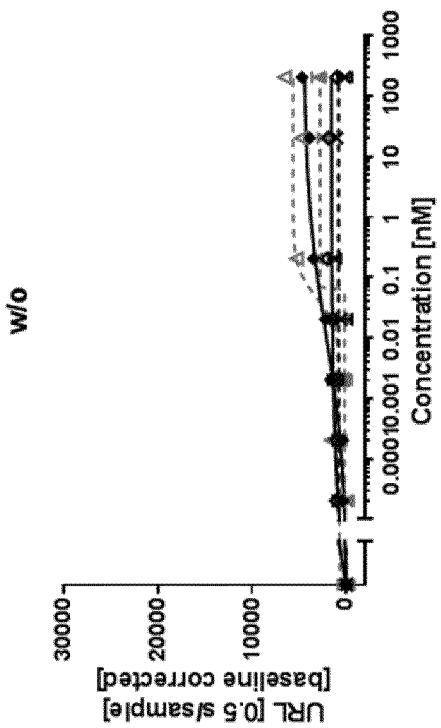

In FIGS. 15A, 15B, 15C and 15D the NFκB activation of Contorsbodies 1 to 11 with cross-linking is shown. Using FAP expressing cells (NIH/3T3 huFAP clone 19) as cross-linkers, the NFκB activation was comparable for all of the contorbodies, with Contorbody 11 (P1AE0821) being the least potent. The non-targeted and therefore not crosslinked 2 non-targeted 2+1 OX40 (49B4)×DP47 antibody (7718) induced weak NFκB activation, whereas bispecific OX40 (49B4)×FAP (4B9) antibody (7719) caused the highest NFκB activation. DP47 hu IgG1 P329G LALA (8105) did not induce any NFκB activation. NFκB activation without cross-linking by FAP is shown in FIGS. 16A, 16B, 16C and 16D. In the absence of cross-linking, only a weak signal could be detected at the higher antibody concentrations. The non-targeted 2+1 OX40 (49B4)×DP47 antibody (7718) showed a moderate NFκB activation, followed by the Contorbody 7 (FIG. 16C). The other contorbodies induced minor or zero levels. The negative control (8105) did not induce any NFκB activation. Normalized Area under the curve values for NFκB activation in HeLa cells with and without crosslinking with FAP+ cells are summarized in FIG. 17. The negative control (8105) did not induce any NFκB activation in both cases, while non-targeted 2+1 OX40 (49B4)×DP47 antibody (7718) showed only minimal activation in both cases. Bispecific OX40 (49B4)×FAP (4B9) antibody (7719) demonstrated the higher levels of activation, followed by Contorbodies 8, 9 and 10. Lower levels were observed for Contorbody 11 (P1AE0821).

Figure 18A:
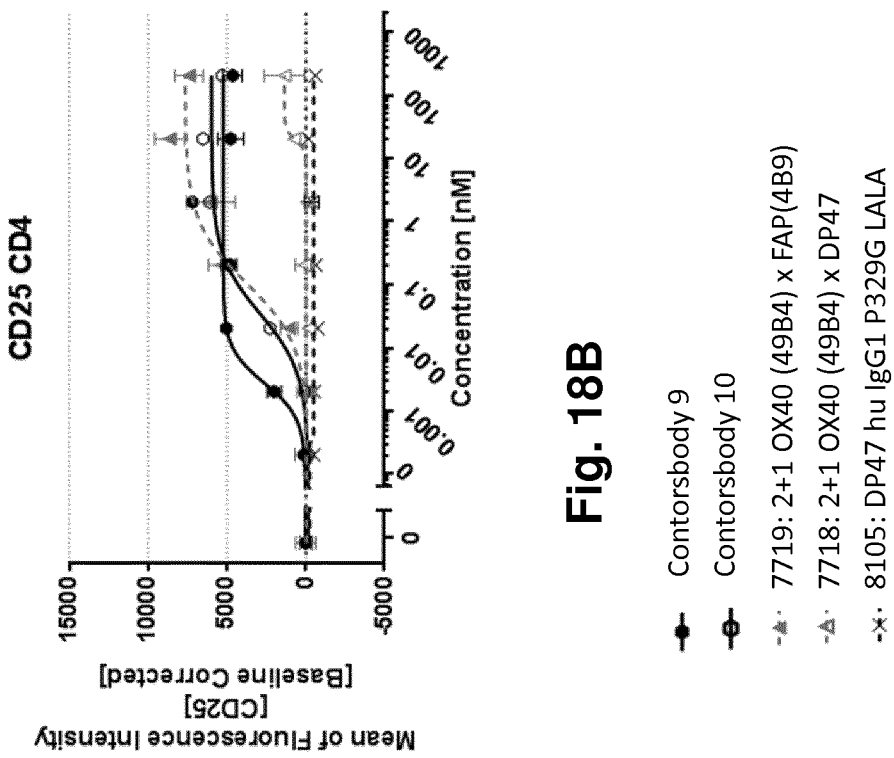
Figure 18B:
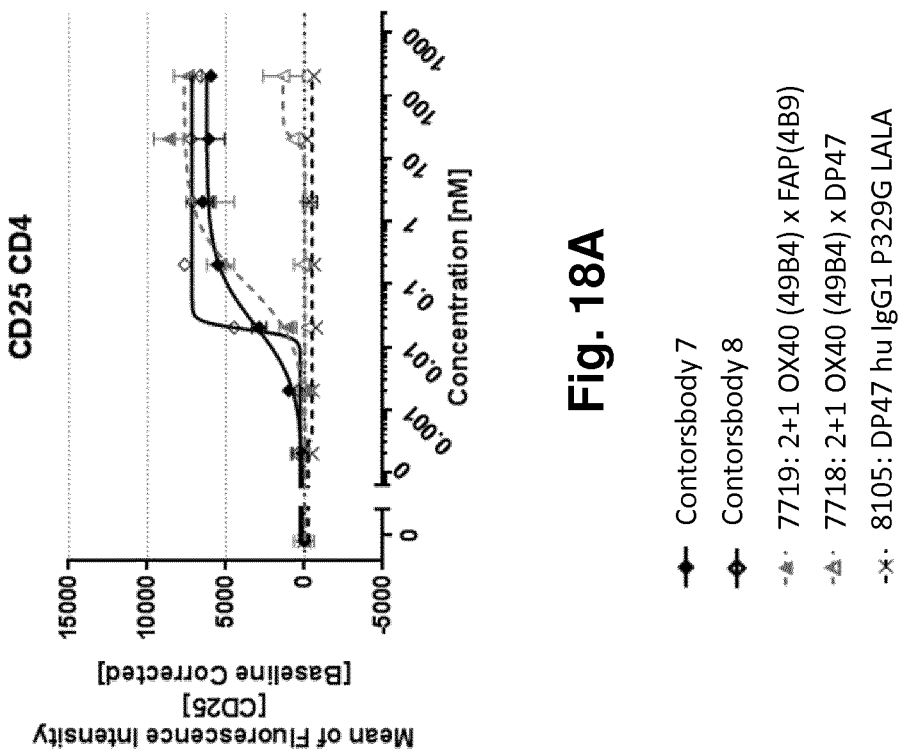
Figure 18C:
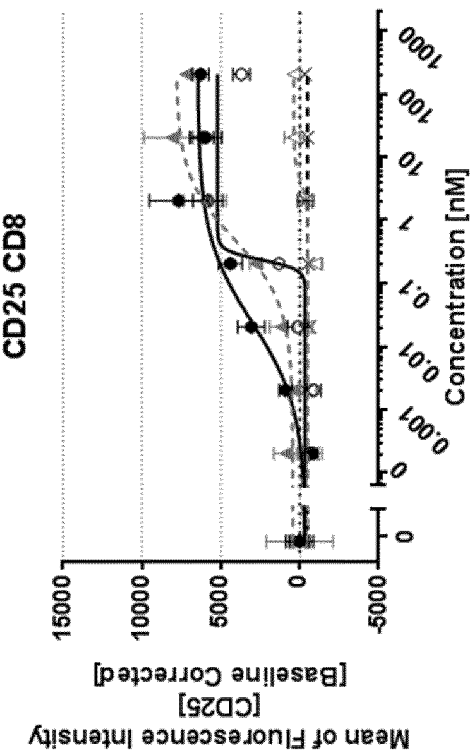
Figure 18D:
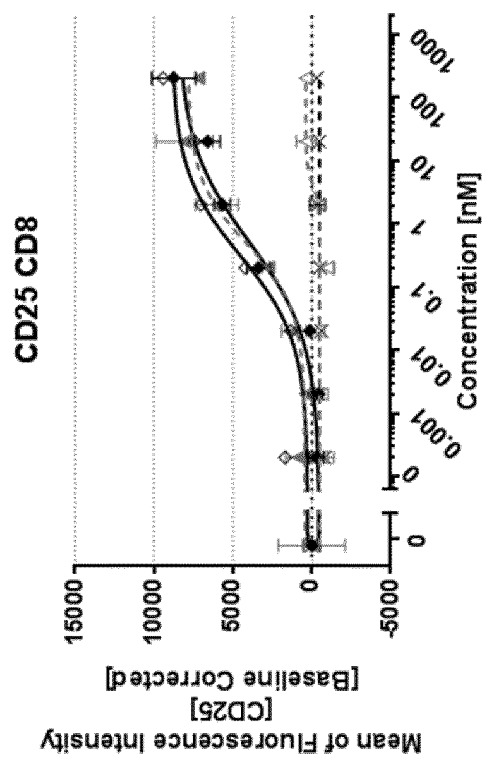
Figure 22A:
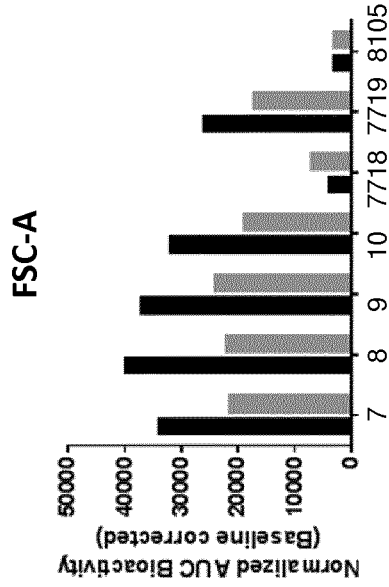
Figure 22B:
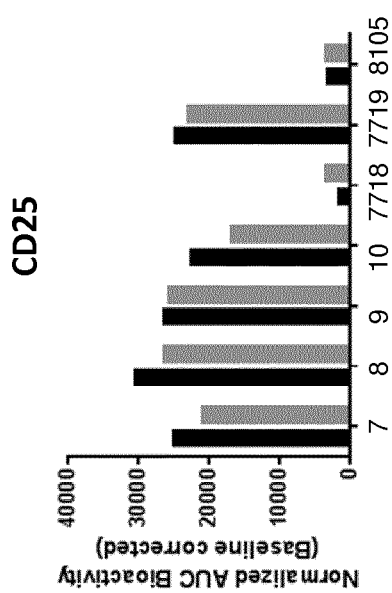
Figure 22C:
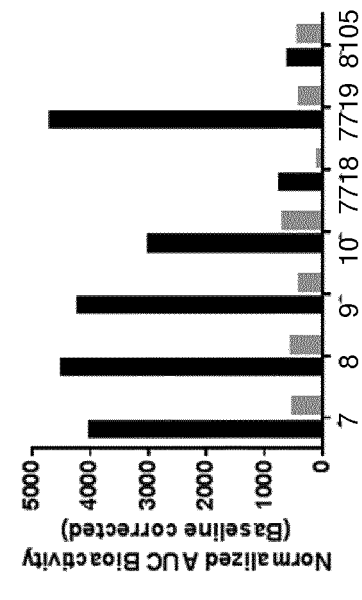
Figure 22D:
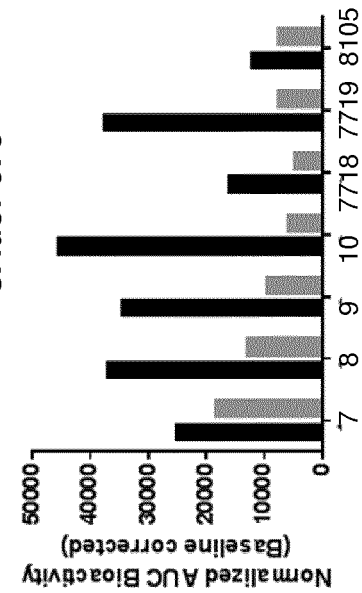

OX40 mediated co-stimulation of sub-optimally TCR triggered resting human PBMCs and hyper-crosslinking by cell surface FAP of Contorsbodies 7, 8, 9 and 10 is shown in FIGS. 18A, 18B, 18C and 18D. FIGS. 18A and 18B show the activation of CD4 T cells and FIGS. 18C and 18D show the activation of CD8 T cells using the surface marker CD25 after suboptimal CD3 stimulation. For the CD4 T-cells (FIGS. 18A and 18B), the bispecific OX40 (49B4)×FAP (4B9) antibody (7719) demonstrated the highest activation, followed by the minimally less potent Contorbody 8. The non-targeted 2+1 OX40 (49B4)×DP47 antibody (7718) and the negative control (8105) did not show any activation after baseline-correction. For the CD8 T-cells (FIGS. 18C and 18D), the Contorbodies 7, 8 and 9 as well as the bispecific OX40 (49B4)×FAP (4B9) antibody (7719) demonstrated a stronger activation compared to Contorbody 10. FIGS. 19A, 19B, 19C and 19D show the FSC-A, respectively the size of CD4 (FIGS. 19A and 19B) and CD8 T-cells (FIGS. 19C and 19D) after suboptimal CD3 stimulation. All contorbodies indicated a comparable intermediate increase. Addition of the untargeted 2+1 anti OX40 molecule (7718) and the negative control (8105) did not change the size of neither CD4 nor CD8 T-cells. FIGS. 20A, 20B, 20C and 20D show the eFluor 670 levels, respectively the proliferation of CD4 (FIGS. 20A and 20B) and CD8 T-cells (FIGS. 20C and 20D) after suboptimal CD3 stimulation. In CD4 subpopulations, Contorbodies 8 and 10 showed a considerable decrease in eFluor 670 levels, indicating stronger proliferation. In CD8 subpopulations Contorbodies 7 and 9 showed bigger decrease in eFluor 670 levels. The untargeted 2+1 anti OX40 molecule (7718) and the negative control (8105) showed only a minor decrease in all subpopulations. FIGS. 21A, 21B, 21C and 21D show the upon activation downregulated IL-7Rα (CD127). The the bispecific OX40 (49B4)×FAP (4B9) antibody (7719) showed the strongest downregulation for CD4 and CD8 T-cells, followed by Contorbody 10. Greater downregulation of CD127 was observed in CD4 cells than CD8 subpopulations. Normalized Area under the curve values for CD25 (FIG. 22A), FSC-A (FIG. 22B), eFluor 670 (FIG. 22C) and CD127 (FIG. 22D) on CD4 and CD8 T-cells are summarized in FIGS. 22A, 22B, 22C and 22D. The untargeted 2+1 anti OX40 molecule (7718) showed only minimal activation on CD4 and CD8 T cells, whereas the bispecific OX40 (49B4)×FAP (4B9) antibody (7719) demonstrated a higher potency regarding eFluor 679 and CD127 on CD4 and CD8 T-cells compared to the contorbodies. CD25 and FSC-A indicated similar activation levels in both the 7719 molecule and contorbodies in both CD4 and CD8 subpopulations.

Figures 23A, 23B:
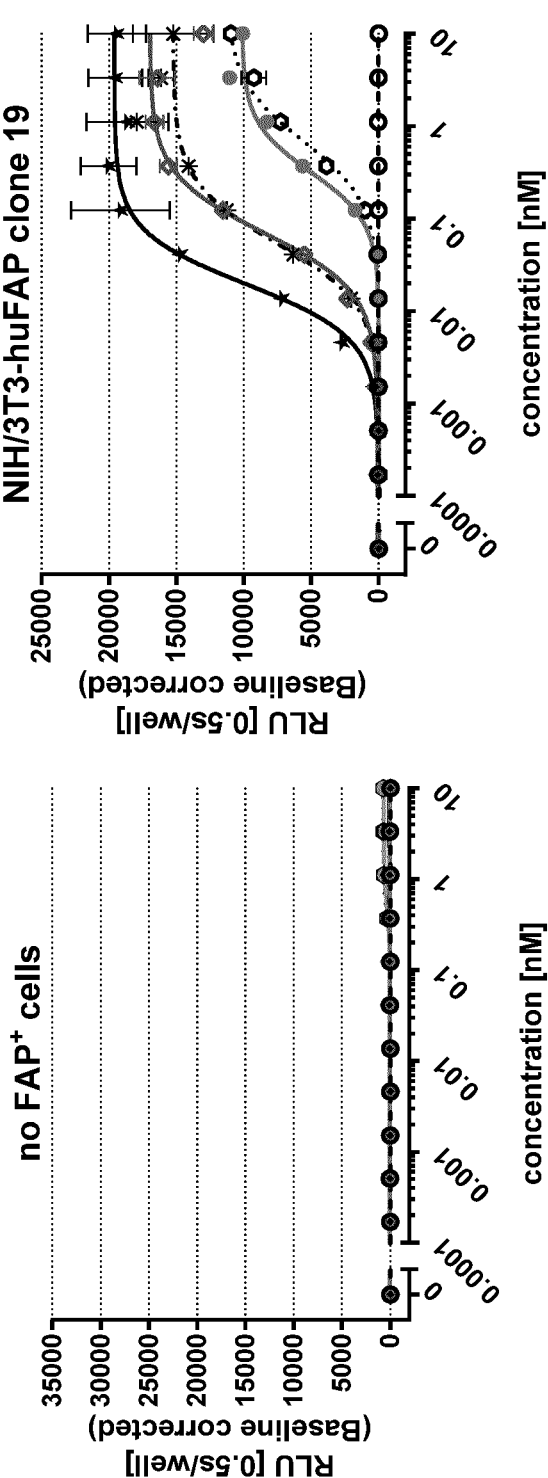
Figure 24A:
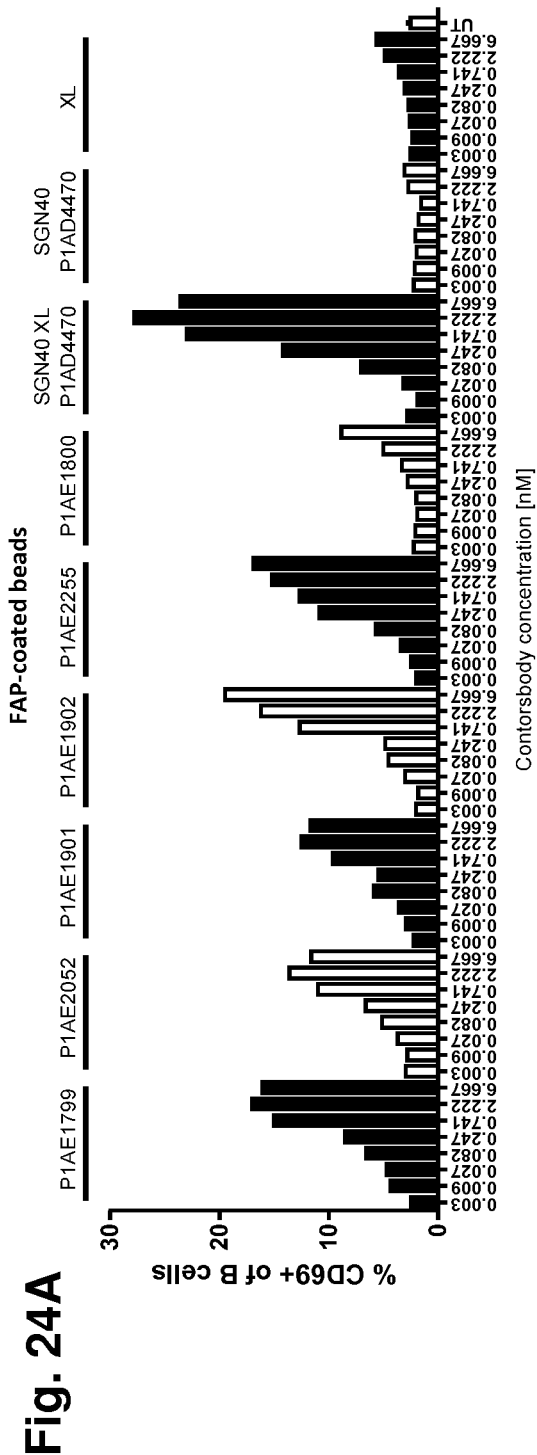
Figure 24B:
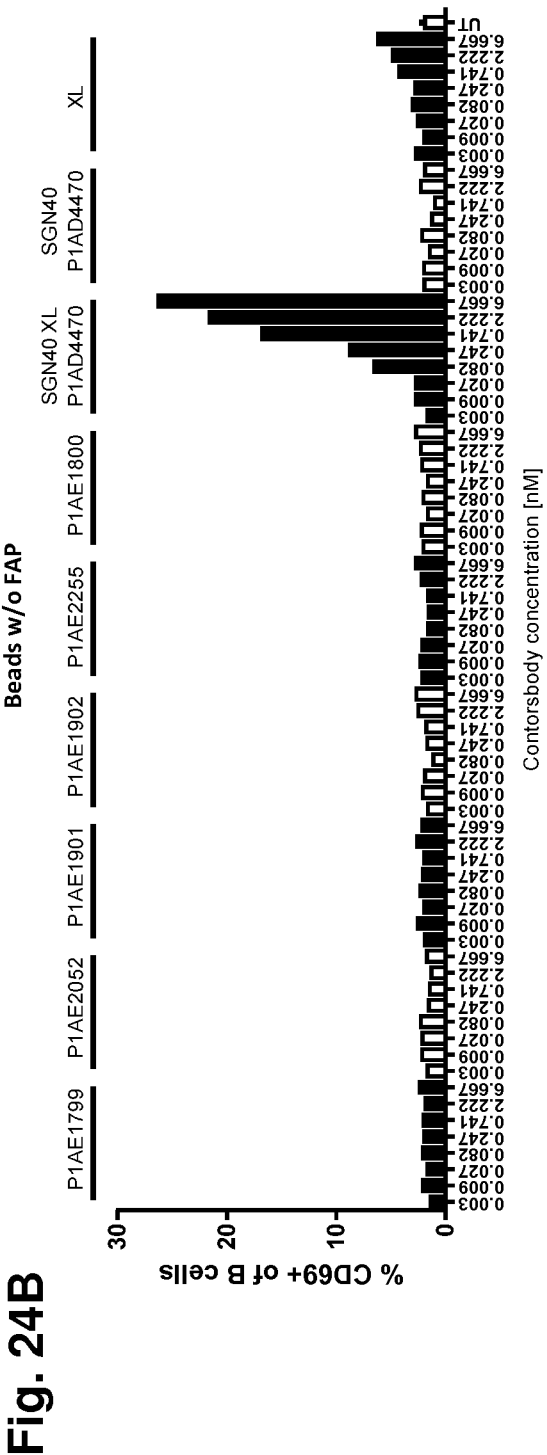

FIGS. 23A and 23B show the NFκB-mediated luciferase expression activity in 4-1BB expressing reporter cell line Jurkat-hu4-1BB-NFκB-luc2. To test the functionality of 2+1 anti-4-1BB (20H4.9)×anti-FAP(4B9) contorsbodies versus 2+1 anti-4-1BB (20H4.9)×anti-FAP (4B9) antigen binding molecules versus controls, molecules were incubated. The concentration of antigen binding molecules or its controls are blotted against the units of released light (RLU) measured after 6 h of incubation. All values are baseline corrected by subtracting the baseline values of the blank control (e.g. no antibodies added). In FIG. 23A FAP-target-independent 4-1BB activation is shown, whereby 4-1BB-binding induces NFκB-controlled luciferase expression in the reporter cell line without any FAP-mediated crosslinking. In FIG. 23B high FAP-expressing cell line NIH/3T3-huFAP clone 19 (human-FAP-transgenic mouse fibroblast cell line) was added. The FAP-expressing tumor cells lead to crosslinking of the bispecific 4-1BB (20H4.9)×FAP (4B9) antigen binding molecules and and a strong increase of its potential to induce NFκB-induced/luciferase activation in the 4-1BB-expressing reporter cell line. The bispecific 2+1 anti-4-1BB (20H4.9)×anti-FAP(4B9) antigen binding molecules (black filled star and line) showed a slightly better activation (lower EC50 values) than the contorsbodies. However, the activation caused by the contorsbodies was much higher the activation shown by the untargeted 4-1BB antibodies.

FIGS. 24A, 24B, 24C, 24D, 24E, 24F, 24G and 24H show the in vitro activation of human B cells by bivalent human anti-CD40×FAP contorsbodies in the presence of FAP-coated (FIGS. 24A, 24C, 24E and 24G) or uncoated Dynabeads® (FIGS. 24B, 24D, 24F and 24H) after 2 days incubation. Compared to the FAP-independent upregulation of CD69, CD80, CD86 and HLA-DR induced by cross-linked SGN40, upregulation of these activation markers induced by FAP-dependent bispecific antigen binding molecules in the presence of FAP-coated beads was slightly lower. In the absence of FAP (uncoated beads) no increase of CD69, CD80, CD86 or HLA-DR expression could be observed with the FAP-targeted anti-CD40 contorsbodies, while the cross-linked positive control antibody SGN40 induced an upregulation of these activation markers. Shown is the percentage of CD69, CD80, CD86 or HLA-DR positive vital B cells after 2 days of incubation with the indicated titrated contorsbodies or control antibody. XL stands for cross-linking with F(ab')$_2$ Fragment Goat anti-human IgG Fcγ fragment specific. The x-axis shows the concentration of contorsbody constructs or the control antibody.

DETAILED DESCRIPTION OF THE INVENTION

Definitions

Unless defined otherwise, technical and scientific terms used herein have the same meaning as generally used in the art to which this invention belongs. For purposes of interpreting this specification, the following definitions will apply and whenever appropriate, terms used in the singular will also include the plural and vice versa.

As used herein, the term "antigen binding molecule" refers in its broadest sense to a molecule that specifically binds an antigenic determinant. Examples of antigen binding molecules are antibodies, antibody fragments and scaffold antigen binding proteins.

The term "antigen binding domain" refers to the part of an antigen binding molecule that specifically binds to an antigenic determinant. In one aspect, the antigen binding domain is able to activate signaling through its target cell antigen. Antigen binding domains include the area or fragment of an antibody which specifically binds to and is complementary to part or all of an antigen. In addition, antigen binding domains include scaffold antigen binding proteins as further defined herein, e.g. binding domains which are based on designed repeat proteins or designed repeat domains (see e.g. WO 2002/020565). In particular, an antigen binding domain is comprised of a first part and a second part, wherein the first part comprises an antibody light chain variable region (VL) and the second part comprises an antibody heavy chain variable region (VH) or vice versa.

The term "antibody" herein is used in the broadest sense and encompasses various antibody structures, including but not limited to monoclonal antibodies, polyclonal antibodies, monospecific and multispecific antibodies (e.g., bispecific antibodies), and antibody fragments so long as they exhibit the desired antigen-binding activity.

The term "monoclonal antibody" as used herein refers to an antibody obtained from a population of substantially homogeneous antibodies, i.e., the individual antibodies comprising the population are identical and/or bind the same epitope, except for possible variant antibodies, e.g. containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen.

The term "monospecific" antibody as used herein denotes an antibody that has one or more binding sites each of which bind to the same epitope of the same antigen. The term "bispecific" means that the antigen binding molecule is able to specifically bind to at least two distinct antigenic determinants. A bispecific antigen binding molecule comprises at least two antigen binding sites, each of which is specific for a different antigenic determinant. In certain embodiments the bispecific antigen binding molecule is capable of simultaneously binding two antigenic determinants, particularly two antigenic determinants expressed on two distinct cells. For example, the antigen binding molecules of the present invention are bispecific, comprising an antigen binding domain capable of specific binding to a first target, and an antigen binding domain capable of specific binding to a second target. In one particular aspect, the antibody of the present invention comprises an antigen binding domain capable of specific binding to OX40 and an antigen binding domain capable of specific binding to FAP. In another particular aspect, the antibody of the present invention comprises an antigen binding domain capable of specific binding to 4-1BB and an antigen binding domain capable of specific binding to FAP. In one further aspect, the antibody of the present invention comprises an antigen binding domain capable of specific binding to CD40 and an antigen binding domain capable of specific binding to FAP.

The term "valent" as used within the current application denotes the presence of a specified number of binding sites in an antigen binding molecule. As such, the terms "bivalent", "tetravalent", and "hexavalent" denote the presence of two binding sites, four binding sites, and six binding sites, respectively, in an antigen binding molecule. Valency of an antigen binding molecule may also be expressed in relation to the number of binding sites for a given antigenic determinant. For example, the bispecific antibodies of the present invention are bivalent with respect to a first target, and monovalent with respect to a second target.

The terms "full length antibody", "intact antibody", and "whole antibody" are used herein interchangeably to refer to an antibody having a structure substantially similar to a native antibody structure. "Native antibodies" refer to naturally occurring immunoglobulin molecules with varying structures. For example, native IgG-class antibodies are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a light chain constant domain (CL), also called a light chain constant region. The heavy chain of an antibody may be assigned to one of five types, called α (IgA), δ (IgD), ε (IgE), γ (IgG), or μ (IgM), some of which may be further divided into subtypes, e.g. γ1 (IgG1), γ2 (IgG2), γ3 (IgG3), γ4 (IgG4), α1 (IgA1) and α2 (IgA2). The light chain of an antibody may be assigned to one of two types, called kappa (κ) and lambda (λ), based on the amino acid sequence of its constant domain.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies, triabodies, tetrabodies, cross-Fab fragments; linear antibodies; single-chain antibody molecules (e.g. scFv); and single domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. Diabodies are antibody fragments with two antigen-binding sites that may be bivalent or bispecific, see, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g. U.S. Pat. No. 6,248,516 B1). Antibody fragments can be made by various techniques, including but not limited to proteolytic digestion of an intact antibody as well as production by recombinant host cells (e.g. E. coli or phage), as described herein.

Papain digestion of intact antibodies produces two identical antigen-binding fragments, called "Fab" fragments containing each the heavy- and light-chain variable domains and also the constant domain of the light chain and the first constant domain (CH1) of the heavy chain. As used herein, Thus, the term "Fab fragment" refers to an antibody fragment comprising a light chain fragment comprising a VL and a constant domain of a light chain (CL), and a VH and a first constant domain (CH1) of a heavy chain. Fab' fragments differ from Fab fragments by the addition of a few residues at the carboxy terminus of the heavy chain CH1 domain including one or more cysteins from the antibody hinge region. Fab'-SH are Fab' fragments wherein the cysteine residue(s) of the constant domains bear a free thiol group. Pepsin treatment yields an F(ab')$_2$ fragment that has two antigen-combining sites (two Fab fragments) and a part of the Fc region. According to the present invention, the term "Fab fragment" also includes "cross-Fab fragments" or "crossover Fab fragments" as defined below.

The term "cross-Fab fragment" or "xFab fragment" or "crossover Fab fragment" refers to a Fab fragment, wherein either the variable regions or the constant regions of the heavy and light chain are exchanged. Two different chain compositions of a cross-Fab molecule are possible and comprised in the bispecific antibodies of the invention: On the one hand, the variable regions of the Fab heavy and light chain are exchanged, i.e. the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as CrossFab$_{(VLVH)}$. On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as CrossFab$_{(CLCH1)}$.

A "single chain Fab fragment" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments are stabilized via the natural disulfide bond between the CL domain and the CH1 domain. In addition, these single chain Fab molecules might be further stabilized by generation of interchain disulfide bonds via insertion of cysteine residues (e.g. position 44 in the variable heavy chain and position 100 in the variable light chain according to Kabat numbering).

A "crossover single chain Fab fragment" or "x-scFab" is a is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CL-linker-VL-CH1 and b) VL-CH1-linker-VH-CL; wherein VH and VL form together an antigen-binding site which binds specifically to an antigen and wherein said linker is a polypeptide of at least 30 amino acids. In addition, these x-scFab molecules might be further stabilized by generation of interchain disulfide bonds via insertion of cysteine residues (e.g. position 44 in the variable heavy chain and position 100 in the variable light chain according to Kabat numbering).

A "single-chain variable fragment (scFv)" is a fusion protein of the variable regions of the heavy ($V_H$) and light chains ($V_L$) of an antibody, connected with a short linker peptide of ten to about 25 amino acids. The linker is usually rich in glycine for flexibility, as well as serine or threonine for solubility, and can either connect the N-terminus of the VH with the C-terminus of the $V_L$, or vice versa. This protein retains the specificity of the original antibody, despite removal of the constant regions and the introduction of the linker. scFv antibodies are, e.g. described in Houston, J. S., Methods in Enzymol. 203 (1991) 46-96). In addition, antibody fragments comprise single chain polypeptides having the characteristics of a VH, namely being able to assemble together with a VL, or of a VL, namely being able to assemble together with a VH to a functional antigen binding site and thereby providing the antigen binding property of full length antibodies.

"Scaffold antigen binding proteins" are known in the art, for example, fibronectin and designed ankyrin repeat proteins (DARPins) have been used as alternative scaffolds for antigen-binding domains, see, e.g., Gebauer and Skerra, Engineered protein scaffolds as next-generation antibody therapeutics. Curr Opin Chem Biol 13:245-255 (2009) and Stumpp et al., Darpins: A new generation of protein therapeutics. Drug Discovery Today 13: 695-701 (2008). In one aspect of the invention, a scaffold antigen binding protein is selected from the group consisting of CTLA-4 (Evibody), Lipocalins (Anticalin), a Protein A-derived molecule such as Z-domain of Protein A (Affibody), an A-domain (Avimer/Maxibody), a serum transferrin (trans-body); a designed ankyrin repeat protein (DARPin), a variable domain of antibody light chain or heavy chain (single-domain antibody, sdAb), a variable domain of antibody heavy chain (nanobody, aVH), $V_{NAR}$ fragments, a fibronectin (AdNectin), a C-type lectin domain (Tetranectin); a variable domain of a new antigen receptor beta-lactamase ($V_{NAR}$ fragments), a human gamma-crystallin or ubiquitin (Affilin molecules); a kunitz type domain of human protease inhibitors, microbodies such as the proteins from the knottin family, peptide aptamers and fibronectin (adnectin). CTLA-4 (Cytotoxic T Lymphocyte-associated Antigen 4) is a CD28-family receptor expressed on mainly CD4$^+$ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies (e.g. U.S. Pat. No. 7,166,697B1). Evibodies are around the same size as the isolated variable region of an antibody (e.g. a domain antibody). For further details see Journal of Immunological Methods 248 (1-2), 31-45 (2001). Lipocalins are a family of extracellular proteins which transport small hydrophobic molecules such as steroids, bilins, retinoids and lipids. They have a rigid beta-sheet secondary structure with a number of loops at the open end of the conical structure which can be engineered to bind to different target antigens. Anticalins are between 160-180 amino acids in size, and are derived from lipocalins. For further details see Biochim Biophys Acta 1482: 337-350 (2000), U.S. Pat. No. 7,250,297B1 and US20070224633. An affibody is a scaffold derived from Protein A of *Staphylococcus aureus* which can be engineered to bind to antigen. The domain consists of a three-helical bundle of approximately 58 amino acids. Libraries have been generated by randomization of surface residues. For further details see Protein Eng. Des. Sel. 2004, 17, 455-462 and EP 1641818A1. Avimers are multidomain proteins derived from the A-domain scaffold family. The native domains of approximately 35 amino acids adopt a defined disulfide bonded structure. Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007). A transferrin is a monomeric serum transport glycoprotein. Transferrins can be engineered to bind different target antigens by insertion of peptide sequences in a permissive surface loop. Examples of engineered transferrin scaffolds include the Trans-body. For further details see J. Biol. Chem 274, 24066-24073

(1999). Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two alpha-helices and a beta-turn. They can be engineered to bind different target antigens by randomizing residues in the first alpha-helix and a beta-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1. A single-domain antibody is an antibody fragment consisting of a single monomeric variable antibody domain. The first single domains were derived from the variable domain of the antibody heavy chain from camelids (nanobodies or $V_H H$ fragments). Furthermore, the term single-domain antibody includes an autonomous human heavy chain variable domain (aVH) or $V_{NAR}$ fragments derived from sharks. Fibronectin is a scaffold which can be engineered to bind to antigen. Adnectins consists of a backbone of the natural amino acid sequence of the 10th domain of the 15 repeating units of human fibronectin type III (FN3). Three loops at one end of the .beta.-sandwich can be engineered to enable an Adnectin to specifically recognize a therapeutic target of interest. For further details see Protein Eng. Des. Sel. 18, 435-444 (2005), US20080139791, WO2005056764 and U.S. Pat. No. 6,818,418B1. Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5, 783-797 (2005). Microbodies are derived from naturally occurring microproteins of 25-50 amino acids in length which contain 3-4 cysteine bridges—examples of microproteins include KalataBI and conotoxin and knottins. The microproteins have a loop which can beengineered to include upto 25 amino acids without affecting the overall fold of the microprotein. For further details of engineered knottin domains, see WO2008098796.

An "antigen binding molecule that binds to the same epitope" as a reference molecule refers to an antigen binding molecule that blocks binding of the reference molecule to its antigen in a competition assay by 50% or more, and conversely, the reference molecule blocks binding of the antigen binding molecule to its antigen in a competition assay by 50% or more.

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins useful as antigens herein can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants.

The term "paratope" refers to that part of a given antibody molecule that is required for specific binding between a target and a binding site. A paratope may be continuous, i.e. formed by adjacent amino acid residues present in the binding site, or discontinuous, i.e. formed by amino acid residues that are at different positions in the primary sequence of the amino acid residues, such as in the amino acid sequence of the CDRs of the amino acid residues, but in close proximity in the three-dimensional structure, which the binding site adopts.

By "specific binding" is meant that the binding is selective for the antigen and can be discriminated from unwanted or non-specific interactions. The ability of an antigen binding molecule to bind to a specific antigen can be measured either through an enzyme-linked immunosorbent assay (ELISA) or other techniques familiar to one of skill in the art, e.g. Surface Plasmon Resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding molecule to an unrelated protein is less than about 10% of the binding of the antigen binding molecule to the antigen as measured, e.g. by SPR. In certain embodiments, a molecule that binds to the antigen has a dissociation constant (Kd) of $\leq 1$ μM, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M, e.g. from $10^{-9}$ M to $10^{-13}$ M).

"Affinity" or "binding affinity" refers to the strength of the sum total of non-covalent interactions between a single binding site of a molecule (e.g. an antibody) and its binding partner (e.g. an antigen). Unless indicated otherwise, as used herein, "binding affinity" refers to intrinsic binding affinity which reflects a 1:1 interaction between members of a binding pair (e.g. antibody and antigen). The affinity of a molecule X for its partner Y can generally be represented by the dissociation constant (Kd), which is the ratio of dissociation and association rate constants (koff and kon, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

A "tumor associated antigen" as used herein refers to an antigenic determinant presented on the surface of a target cell, which is a cell in a tumor such as a cancer cell, a cell of the tumor stroma or a B cell. In certain aspects, the tumor associated antigen is Fibroblast Activation Protein (FAP).

The term "capable of specific binding to Fibroblast activation protein (FAP)" refers to an antigen binding molecule that is capable of binding FAP with sufficient affinity such that the antigen binding molecule is useful as a diagnostic and/or therapeutic agent in targeting FAP. The antigen binding molecule includes but is not limited to, antibodies, Fab molecules, crossover Fab molecules, single chain Fab molecules, Fv molecules, scFv molecules, single domain antibodies, and VH and scaffold antigen binding protein. In one aspect, the extent of binding of an anti-FAP antigen binding molecule to an unrelated, non-FAP protein is less than about 10% of the binding of the antigen binding molecule to FAP as measured, e.g., by Surface Plasmon Resonance (SPR). In particular, an antigen binding molecule that is capable of specific binding to FAP has a dissociation constant ($K_d$) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$M to $10^{-13}$M, e.g., from $10^{-9}$M to $10^{-13}$ M). In certain embodiments, an anti-FAP antigen binding molecule binds to FAP from different species. In particular, the anti-FAP antigen binding molecule binds to human, cynomolgus and mouse FAP.

The term "Fibroblast activation protein (FAP)", also known as Prolyl endopeptidase FAP or Seprase (EC 3.4.21), refers to any native FAP from any vertebrate source, including mammals such as primates (e.g. humans) non-human primates (e.g. cynomolgus monkeys) and rodents (e.g. mice and rats), unless otherwise indicated. The term encompasses "full-length," unprocessed FAP as well as any form of FAP which results from processing in the cell. The term also encompasses naturally occurring variants of FAP, e.g., splice variants or allelic variants. In one embodiment, the antigen binding molecule of the invention is capable of specific binding to human, mouse and/or cynomolgus FAP. The amino acid sequence of human FAP is shown in UniProt (www.uniprot.org) accession no. Q12884 (version 149, SEQ ID NO:97), or NCBI (www.ncbi.nlm.nih.gov/) RefSeq NP_004451.2. The extracellular domain (ECD) of human FAP extends from amino acid position 26 to 760. The amino acid sequence of mouse FAP is shown in UniProt accession no. P97321 (version 126, SEQ ID NO:98), or NCBI RefSeq NP_032012.1. The extracellular domain (ECD) of mouse FAP extends from amino acid position 26 to 761. Preferably, an anti-FAP binding molecule of the invention binds to the extracellular domain of FAP. Exemplary anti-FAP binding molecules are described in International Patent Application No. WO 2012/020006 A2.

The term "variable region" or "variable domain" refers to the domain of an antibody heavy or light chain that is involved in binding the antigen binding molecule to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single VH or VL may be sufficient to confer antigen-binding specificity.

The term "hypervariable region" or "HVR" as used herein refers to each of the regions of an antibody variable domain which are hypervariable in sequence ("complementarity determining regions" or "CDRs") and/or structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR (e.g. CDR) residues and other residues in the variable domain (e.g., FR residues) are numbered herein according to Kabat et al., supra.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

As used herein, the term "affinity matured" in the context of antigen binding molecules (e.g., antibodies) refers to an antigen binding molecule that is derived from a reference antigen binding molecule, e.g., by mutation, binds to the same antigen, preferably binds to the same epitope, as the reference antibody; and has a higher affinity for the antigen than that of the reference antigen binding molecule. Affinity maturation generally involves modification of one or more amino acid residues in one or more CDRs of the antigen binding molecule. Typically, the affinity matured antigen binding molecule binds to the same epitope as the initial reference antigen binding molecule.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g. $IgG_1$, $IgG_2$, $IgG_3$, $IgG_4$, $IgA_1$, and IgA$_2$. The heavy chain constant domains that correspond to the different classes of immunoglobulins are called α, δ, ε, γ, and μ respectively.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

A "human" antibody is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "CH1 domain" denotes the part of an antibody heavy chain polypeptide that extends approximately from EU position 118 to EU position 215 (EU numbering system according to Kabat). In one aspect, a CH1 domain has the amino acid sequence of

```
                                      (SEQ ID NO: 94)
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKKV.
```

Usually, a segment having the amino acid sequence of EPKSC (SEQ ID NO:99) is following to link the CH1 domain to the hinge region, The term "hinge region" denotes the part of an antibody heavy chain polypeptide that joins in a wild-type antibody heavy chain the CH1 domain and the CH2 domain, e.g. from about position 216 to about position 230 according to the EU number system of Kabat, or from about position 226 to about position 230 according to the EU number system of Kabat. The hinge regions of other IgG subclasses can be determined by aligning with the hinge-region cysteine residues of the IgG1 subclass sequence. The hinge region is normally a dimeric molecule consisting of two polypeptides with identical amino acid sequence. The hinge region generally comprises up to 25 amino acid residues and is flexible allowing the associated target binding sites to move independently. The hinge region can be subdivided into three domains: the upper, the middle, and the lower hinge domain (see e.g. Roux, et al., J. Immunol. 161 (1998) 4083).

In one aspect, the hinge region has the amino acid sequence DKTHTCPXCP (SEQ ID NO: 100), wherein X is either S or P. In one aspect, the hinge region has the amino acid sequence HTCPXCP (SEQ ID NO: 101), wherein X is either S or P. In one aspect, the hinge region has the amino acid sequence CPXCP (SEQ ID NO: 102), wherein X is either S or P.

The term "Fc domain" or "Fc region" herein is used to define a C-terminal region of an antibody heavy chain that contains at least a portion of the constant region. The term includes native sequence Fc regions and variant Fc regions. In one aspect, a human IgG heavy chain Fc-domain extends from Cys226, or from Pro230, or from Ala231 to the carboxyl-terminus of the heavy chain. However, the C-terminal lysine (Lys447) of the Fc-region may or may not be present. An IgG Fc region comprises an IgG CH2 and an IgG CH3 domain.

The "CH2 domain" of a human IgG Fc region usually extends from an amino acid residue at about EU position 231 to an amino acid residue at about EU position 340 (EU numbering system according to Kabat). In one aspect, a CH2 domain has the amino acid sequence of APELLGGPSV FLFPPKPKDT LMISRTPEVT CVWDVSHEDP EVKFNWYVDG VEVHNAKTKP REEQESTYRW SVLTVLHQDW LNGKEYKCKV SNKALPAPIE KTISKAK (SEQ ID NO: 95). The CH2 domain is unique in that it is not closely paired with another domain. Rather, two N-linked branched carbohydrate chains are interposed between the two CH2 domains of an intact native Fc-region. It has been speculated that the carbohydrate may provide a substitute for the domain-domain pairing and help stabilize the CH2 domain. Burton, Mol. Immunol. 22 (1985) 161-206. In one embodiment, a carbohydrate chain is attached to the CH2 domain. The CH2 domain herein may be a native sequence CH2 domain or variant CH2 domain.

The "CH3 domain" comprises the stretch of residues C-terminal to a CH2 domain in an Fc region denotes the part of an antibody heavy chain polypeptide that extends approximately from EU position 341 to EU position 446 (EU numbering system according to Kabat). In one aspect, the CH3 domain has the amino acid sequence of GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPG (SEQ ID NO: 96). The CH3 region herein may be a native sequence CH3 domain or a variant CH3 domain (e.g. a CH3 domain with an introduced "protuberance" ("knob") in one chain thereof and a corresponding introduced "cavity" ("hole") in the other chain thereof; see U.S. Pat. No. 5,821,333, expressly incorporated herein by reference). Such variant CH3 domains may be used to promote heterodimerization of two non-identical antibody heavy chains as herein described. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

The "knob-into-hole" technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). The protuberance and cavity can be made by altering the nucleic acid encoding the polypeptides, e.g. by site-specific mutagenesis, or by peptide synthesis. In a specific embodiment a knob modification comprises the amino acid substitution T366W in one of the two subunits of the Fc domain, and the hole modification comprises the amino acid substitutions T366S, L368A and Y407V in the other one of the two subunits of the Fc domain. In a further specific embodiment, the subunit of the Fc domain comprising the knob modification additionally comprises the amino acid substitution S354C, and the subunit of the Fc domain comprising the hole modification additionally comprises the amino acid substitution Y349C. Introduction of these two cysteine residues results in the formation of a disulfide bridge between the two subunits of the Fc region, thus further stabilizing the dimer (Carter, J Immunol Methods 248, 7-15 (2001)). The numbering is according to EU index of Kabat et al, Sequences of Proteins of Immunological Interest, 5th Ed. Public Health Service, National Institutes of Health, Bethesda, Md., 1991.

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U. et al., Science 247:1306-10 (1990)).

The term "wild-type Fc domain" denotes an amino acid sequence identical to the amino acid sequence of an Fc domain found in nature. Wild-type human Fc domains include a native human IgG1 Fc-region (non-A and A allotypes), native human IgG2 Fc-region, native human IgG3 Fc-region, and native human IgG4 Fc-region as well as naturally occurring variants thereof. Wild-type Fc-regions are denoted in SEQ ID NO: 102 (IgG1, caucasian allotype), SEQ ID NO: 103 (IgG1, afroamerican allotype), SEQ ID NO: 104 (IgG2), SEQ ID NO: 105 (IgG3) and SEQ ID NO: 106 (IgG4).

The term "variant (human) Fc domain" denotes an amino acid sequence which differs from that of a "wild-type" (human) Fc domain amino acid sequence by virtue of at least one "amino acid mutation". In one aspect, the variant Fc-region has at least one amino acid mutation compared to a native Fc-region, e.g. from about one to about ten amino acid mutations, and in one aspect from about one to about five amino acid mutations in a native Fc-region. In one aspect, the (variant) Fc-region has at least about 95% homology with a wild-type Fc-region.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

Fc receptor binding dependent effector functions can be mediated by the interaction of the Fc-region of an antibody with Fc receptors (FcRs), which are specialized cell surface receptors on hematopoietic cells. Fc receptors belong to the immunoglobulin superfamily, and have been shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC) (see e.g. Van de Winkel, J. G. anderson, C. L., J. Leukoc. Biol. 49 (1991) 511-524). FcRs are defined by their specificity for immunoglobulin isotypes: Fc receptors for IgG antibodies are referred to as FcγR. Fc receptor binding is described e.g. in Ravetch, J. V. and Kinet, J. P., Annu. Rev. Immunol. 9 (1991) 457-492; Capel, P. J., et al., Immunomethods 4 (1994) 25-34; de Haas, M., et al., J. Lab. Clin. Med. 126 (1995) 330-341; and Gessner, J. E., et al., Ann. Hematol. 76 (1998) 231-248.

Cross-linking of receptors for the Fc-region of IgG antibodies (FcγR) triggers a wide variety of effector functions including phagocytosis, antibody-dependent cellular cytotoxicity, and release of inflammatory mediators, as well as immune complex clearance and regulation of antibody production. In humans, three classes of FcγR have been characterized, which are:

FcγRI (CD64) binds monomeric IgG with high affinity and is expressed on macrophages, monocytes, neutrophils and eosinophils. Modification in the Fc-region IgG at least at one of the amino acid residues E233-G236, P238, D265, N297, A327 and P329 (numbering according to EU index of Kabat) reduce binding to FcγRI. IgG2 residues at positions 233-236, substituted into IgG1 and IgG4, reduced binding to FcγRI by $10^3$-fold and eliminated the human monocyte response to antibody-sensitized red blood cells (Armour, K. L., et al., Eur. J. Immunol. 29 (1999) 2613-2624).

FcγRII (CD32) binds complexed IgG with medium to low affinity and is widely expressed. This receptor can be divided into two sub-types, FcγRIIA and FcγRIIB. FcγRIIA is found on many cells involved in killing (e.g. macrophages, monocytes, neutrophils) and seems able to activate the killing process. FcγRIIB seems to play a role in inhibitory processes and is found on B cells, macrophages and on mast cells and eosinophils. On B-cells it seems to function to suppress further immunoglobulin production and isotype switching to, for example, the IgE class. On macrophages, FcγRIIB acts to inhibit phagocytosis as mediated through FcγRIIA. On eosinophils and mast cells the B-form may help to suppress activation of these cells through IgE binding to its separate receptor. Reduced binding for FcγRIIA is found e.g. for antibodies comprising an IgG Fc-region with mutations at least at one of the amino acid residues E233-G236, P238, D265, N297, A327, P329, D270, Q295, A327, R292, and K414 (numbering according to EU index of Kabat).

FcγRIII (CD16) binds IgG with medium to low affinity and exists as two types. FcγRIIIA is found on NK cells, macrophages, eosinophils and some monocytes and T cells and mediates ADCC. FcγRIIIB is highly expressed on neutrophils. Reduced binding to FcγRIIIA is found e.g. for antibodies comprising an IgG Fc-region with mutation at least at one of the amino acid residues E233-G236, P238, D265, N297, A327, P329, D270, Q295, A327, 5239, E269, E293, Y296, V303, A327, K338 and D376 (numbering according to EU index of Kabat).

Mapping of the binding sites on human IgG1 for Fc receptors, the above mentioned mutation sites and methods for measuring binding to FcγRI and FcγRIIA are described in Shields, R. L., et al. J. Biol. Chem. 276 (2001) 6591-6604.

The term "ADCC" or "antibody-dependent cellular cytotoxicity" is a function mediated by Fc receptor binding and refers to lysis of target cells by an antibody as reported herein in the presence of effector cells. The capacity of the antibody to induce the initial steps mediating ADCC is investigated by measuring their binding to Fcγ receptors expressing cells, such as cells, recombinantly expressing FcγRI and/or FcγRIIA or NK cells (expressing essentially FcγRIIIA). In particular, binding to FcγR on NK cells is measured.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89). A particular activating Fc receptor is human FcγRIIIa (see UniProt accession no. P08637, version 141).

The "Tumor Necrosis factor receptor superfamily" or "TNF receptor superfamily" currently consists of 27 receptors. It is a group of cytokine receptors characterized by the ability to bind tumor necrosis factors (TNFs) via an extracellular cysteine-rich domain (CRD). These pseudorepeats are defined by intrachain disulphides generated by highly conserved cysteine residues within the receptor chains. With the exception of nerve growth factor (NGF), all TNFs are homologous to the archetypal TNF-alpha. In their active form, the majority of TNF receptors form trimeric complexes in the plasma membrane. Accordingly, most TNF receptors contain transmembrane domains (TMDs). Several of these receptors also contain intracellular death domains (DDs) that recruit caspase-interacting proteins following ligand binding to initiate the extrinsic pathway of caspase activation. Other TNF superfamily receptors that lack death domains bind TNF receptor-associated factors and activate intracellular signaling pathways that can lead to proliferation or differentiation. These receptors can also initiate apoptosis, but they do so via indirect mechanisms. In addition to regulating apoptosis, several TNF superfamily receptors are involved in regulating immune cell functions such as B cell homeostasis and activation, natural killer cell activation, and T cell co-stimulation. Several others regulate cell type-specific responses such as hair follicle development and osteoclast development. Members of the TNF receptor superfamily include the following: Tumor necrosis factor receptor 1 (1A) (TNFRSF1A, CD120a), Tumor necrosis factor receptor 2 (1B) (TNFRSF1B, CD120b), Lymphotoxin beta receptor (LTBR, CD18), OX40 (TNFRSF4, CD134), CD40 (Bp50), Fas receptor (Apo-1, CD95, FAS), Decoy receptor 3 (TR6, M68, TNFRSF6B), CD27 (S152, Tp55), CD30 (Ki-1, TNFRSF8), 4-1BB (CD137, TNFRSF9), DR4 (TRAILR1, Apo-2, CD261, TNFRSF10A), DR5 (TRAILR2, CD262, TNFRSF10B), Decoy Receptor 1 (TRAILR3, CD263, TNFRSF10C), Decoy Receptor 2 (TRAILR4, CD264, TNFRSF10D), RANK (CD265, TNFRSF11A), Osteoprotegerin (OCIF, TR1, TNFRSF11B), TWEAK receptor (Fn14, CD266, TNFRSF12A), TACI (CD267, TNFRSF13B), BAFF receptor (CD268, TNFRSF13C), Herpesvirus entry mediator (HVEM, TR2, CD270, TNFRSF14), Nerve growth factor receptor (p75NTR, CD271, NGFR), B-cell maturation antigen (CD269, TNFRSF17), Glucocorticoid-induced TNFR-related (GITR, AITR, CD357, TNFRSF18), TROY (TNFRSF19), DR6 (CD358, TNFRSF21), DR3 (Apo-3, TRAMP, WS-1, TNFRSF25) and Ectodysplasin A2 receptor (XEDAR, EDA2R).

Several members of the tumor necrosis factor receptor (TNFR) family function after initial T cell activation to sustain T cell responses. The term "costimulatory TNF receptor family member" or "costimulatory TNF family receptor" refers to a subgroup of TNF receptor family members, which are able to costimulate proliferation and cytokine production of T-cells. The term refers to any native TNF family receptor from any vertebrate source, including mammals such as primates (e.g. humans), non-human primates (e.g. cynomolgus monkeys) and rodents (e.g. mice and rats), unless otherwise indicated. In specific embodiments of the invention, costimulatory TNF receptor family members are selected from the group consisting of OX40 (CD134), 4-1BB (CD137), CD40, CD27, HVEM (CD270), CD30, and GITR, all of which can have costimulatory effects on T cells. More particularly, the antigen binding molecule of the present invention comprises at least moiety capable of specific binding to the costimulatory TNF receptor family member OX40.

Further information, in particular sequences, of the TNF receptor family members may be obtained from publically accessible databases such as Uniprot (www.uniprot.org). For instance, the human costimulatory TNF receptors have the following amino acid sequences: human OX40 (UniProt accession no. P43489, SEQ ID NO:108), human 4-1BB (UniProt accession no. Q07011, SEQ ID NO:109), human CD27 (UniProt accession no. P26842, SEQ ID NO:110), human HVEM (UniProt accession no. Q92956, SEQ ID NO:111), human CD30 (UniProt accession no. P28908, SEQ ID NO:112), human GITR (UniProt accession no. Q9Y5U5, SEQ ID NO:113) and human CD40 (UniProt accession no. P25942, SEQ ID NO. 115).

The term "OX40", as used herein, refers to any native OX40 from any vertebrate source, including mammals such as primates (e.g. humans) and rodents (e.g., mice and rats), unless otherwise indicated. The term encompasses "full-length," unprocessed OX40 as well as any form of OX40 that results from processing in the cell. The term also encompasses naturally occurring variants of OX40, e.g., splice variants or allelic variants. The amino acid sequence of an exemplary human OX40 is shown in SEQ ID NO: 107 (Uniprot P43489, version 112) and the amino acid sequence of an exemplary murine OX40 is shown in SEQ ID NO: 113 (Uniprot P47741, version 101).

Among several costimulatory molecules, the tumor necrosis factor (TNF) receptor family member OX40 (CD134) plays a key role in the survival and homeostasis of effector and memory T cells (Croft M. et al. (2009), Immunological Reviews 229, 173-191). OX40 (CD134) is expressed in several types of cells and regulates immune responses against infections, tumors and self-antigens and its expression has been demonstrated on the surface of T-cells, NKT-cells and NK-cells as well as neutrophils (Baumann R. et al. (2004), Eur. J. Immunol. 34, 2268-2275) and shown to be strictly inducible or strongly upregulated in response to various stimulatory signals. Functional activity of the molecule has been demonstrated in every OX40-expressing cell type suggesting complex regulation of OX40-mediated activity in vivo. Combined with T-cell receptor triggering, OX40 engagement on T-cells by its natural ligand or agonistic antibodies leads to synergistic activation of the PI3K and NFκB signalling pathways (Song J. et al. (2008) J. Immunology 180(11), 7240-7248). In turn, this results in enhanced proliferation, increased cytokine receptor and cytokine production and better survival of activated T-cells. In addition to its co-stimulatory activity in effector CD4+ or CD8+ T-cells, OX40 triggering has been recently shown to inhibit the development and immunosuppressive function of T regulatory cells. This effect is likely to be responsible, at least in part, for the enhancing activity of OX40 on anti-tumor or anti-microbial immune responses. Given that OX40 engagement can expand T-cell populations, promote cytokine secretion, and support T-cell memory, agonists including antibodies and soluble forms of the ligand OX40L have been used successfully in a variety of preclinical tumor models (Weinberg et al. (2000), J. Immunol. 164, 2160-2169).

The terms "anti-OX40 antibody", "anti-OX40", "OX40 antibody and "an antibody that specifically binds to OX40" refer to an antibody that is capable of binding OX40 with sufficient affinity such that the antibody is useful as a diagnostic and/or therapeutic agent in targeting OX40. In one embodiment, the extent of binding of an anti-OX40 antibody to an unrelated, non-OX40 protein is less than about 10% of the binding of the antibody to OX40 as measured, e.g., by flow cytometry (FACS). In certain embodiments, an antibody that binds to OX40 has a dissociation constant ($K_D$) of ≤1 μM, ≤100 nM, ≤10 nM, ≤1 nM, ≤0.1 nM, ≤0.01 nM, or ≤0.001 nM (e.g. $10^{-6}$ M or less, e.g. from $10^{-6}8$M to $10^{-13}$M, e.g., from $10^{-8}$ M to $10^{-10}$ M).

The term "4-1BB" or "CD137", as used herein, refers to any native 4-1BB from any vertebrate source, including mammals such as primates (e.g. humans) and rodents (e.g., mice and rats), unless otherwise indicated. The term encompasses "full-length," unprocessed 4-1BB as well as any form of 4-1BB that results from processing in the cell. The term also encompasses naturally occurring variants of 4-1BB, e.g., splice variants or allelic variants. The amino acid sequence of an exemplary human 4-1BB is shown in SEQ ID NO:109 (Uniprot accession no. Q07011).

The terms "anti-4-1BB antibody", "anti-4-1BB", "4-1BB antibody and "an antibody that specifically binds to 4-1BB" refer to an antibody that is capable of binding 4-1BB with sufficient affinity such that the antibody is useful as a diagnostic and/or therapeutic agent in targeting 4-1BB. In one embodiment, the extent of binding of an anti-4-1BB antibody to an unrelated, non-4-1BB protein is less than about 10% of the binding of the antibody to 4-1BB as measured, e.g., by a radioimmunoassay (RIA) or flow cytometry (FACS). In certain embodiments, an antibody that binds to 4-1BB has a dissociation constant ($K_D$) of ≤1 μM, ≤100 nM, ≤10 nM, ≤1 nM, ≤0.1 nM, ≤0.01 nM, or ≤0.001 nM (e.g. $10^{-6}$ M or less, e.g. from $10^{-6}8$M to $10^{-13}$M, e.g., from $10^{-8}$ M to $10^{-11}$ M). In particular, the anti-4-1BB antibody is clone 20H4.9 as disclosed in U.S. Pat. No. 7,288,638.

The term "CD40", as used herein, refers to any native CD40 from any vertebrate source, including mammals such as primates (e.g. humans) and rodents (e.g., mice and rats), unless otherwise indicated. The term encompasses "full-length," unprocessed CD40 as well as any form of CD40 that results from processing in the cell. The term also encompasses naturally occurring variants of CD40, e.g., splice variants or allelic variants. The amino acid sequence of an exemplary human CD40 is shown in SEQ ID NO:115 (UniProt no. P25942, version 200). The CD40 antigen is a 50 kDa cell surface glycoprotein which belongs to the Tumor Necrosis Factor Receptor (TNF-R) family. (Stamenkovic et al. (1989), EMBO J. 8: 1403-10). CD40 is expressed in many normal and tumor cell types, including B lymphocytes, dendritic cells, monocytes, macrophages, thymus epithelium, endothelial cells, fibroblasts, and smooth muscle cells. CD40 is expressed in all B-lymphomas and in 70% of all solid tumors and is up-regulated in antigen presenting cells (APCs) by maturation signals, such as IFN-gamma and GM-CSF. CD40 activation also induces differentiation of monocytes into functional dendritic cells (DCs) and enhances cytolytic activity of NK cells through APC-CD40 induced cytokines. Thus CD40 plays an essential role in the initiation and enhancement of immune responses by inducing maturation of APCs, secretion of helper cytokines, upregulation of costimulatory molecules, and enhancement of effector functions.

The term "CD40 agonist" as used herein includes any moiety that agonizes the CD40/CD40L interaction. CD40 as used in this context refers preferably to human CD40, thus the CD40 agonist is preferably an agonist of human CD40. Typically, the moiety will be an agonistic CD40 antibody or antibody fragment.

The terms "anti-CD40 antibody", "anti-CD40", "CD40 antibody" and "an antibody that specifically binds to CD40" refer to an antibody that is capable of binding CD40 with sufficient affinity such that the antibody is useful as a diagnostic and/or therapeutic agent in targeting CD40. In one aspect, the extent of binding of an anti-CD40 antibody to an unrelated, non-CD40 protein is less than about 10% of the binding of the antibody to CD40 as measured, e.g., by a radioimmunoassay (RIA) or flow cytometry (FACS). In certain embodiments, an antibody that binds to CD40 has a dissociation constant ($K_D$) of ≤1 μM, ≤100 nM, ≤10 nM, ≤1 nM, ≤0.1 nM, ≤0.01 nM, or ≤0.001 nM (e.g. $10^{-6}$ M or less, e.g. from $10^{-6}8$M to $10^{-13}$M, e.g., from $10^{-8}$ M to $10^{-10}$ M).

The term "peptide linker" refers to a peptide comprising one or more amino acids, typically about 2 to 20 amino acids. Peptide linkers are known in the art or are described herein. Suitable, non-immunogenic linker peptides are, for example, $(G_4S)_n$ (SEQ ID NO: 185), $(SG_4)_n$ (SEQ ID NO: 186) or $G_4(SG_4)_n$ (SEQ ID NO: 187) peptide linkers, wherein "n" is generally a number between 1 and 10, typically between 1 and 4, in particular 2, i.e. the peptides selected from the group consisting of GGGGS (SEQ ID NO:77), GGGGSGGGGS (SEQ ID NO:78), SGGGGSGGGG (SEQ ID NO:79), GGGGSGGGGSSGGGGS (SEQ ID NO:80), $(G_40.5)_3$ (SEQ ID NO: 81) or GGGGSGGGGSGGGGS (SEQ ID NO:81), GGGGSGGGGSGGGG (SEQ ID NO: 82) or G4(SG4)$_2$ (SEQ ID NO:82), $(G_4S)_4$ (SEQ ID NO: 83) or GGGGSGGGGSGGGGSGGGGS (SEQ ID NO:83), and GGGGSGGGGSGGGSGGGGS (SEQ ID NO:84), but also include the sequences GSPGSSSSGS (SEQ ID NO:85), GSGSGSGS (SEQ ID NO:86), GSGSGNGS (SEQ ID NO:87), GGSGSGSG (SEQ ID NO:88), GGSGSG (SEQ ID NO:89), GGSG (SEQ ID NO:90), GGSGNGSG (SEQ ID NO:91), GGNGSGSG (SEQ ID NO:92) and GGNGSG (SEQ ID NO:93). Peptide linkers of particular interest are $((G_4S)_2$ (SEQ ID NO: 78) or GGGGSGGGGS (SEQ ID NO:78) and GGGGSGGGGSGGGGSGGGGS (SEQ ID NO:84).

A "spacer domain" according to the present invention is a polypeptide forming a structural domain after folding. Thus, the spacer domain can be smaller than 100 amino acid residues, but needs to be structurally confined to fix the binding motifs. Exemplary spacer domains are pentameric coil-coils, antibody hinge regions or antibody Fc regions or fragments thereof. The spacer domain is a dimerization domain, i.e. the the spacer domain comprises amino acids that are able to provide the dimerization functionality.

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

By "fused" or "connected" is meant that the components (e.g. a heavy chain of an antibody and a Fab fragment) are linked by peptide bonds, either directly or via one or more peptide linkers.

A "fusion polypeptide" or "single fusion polypeptide" as used herein refers to a single chain polypeptide composed of different components such as the ectodomain of a TNF ligand family member that are fused to each either directly or via a peptide linker. By "fused" or "connected" is meant that the components (e.g. a polypeptide and an ectodomain of said TNF ligand family member) are linked by peptide bonds, either directly or via one or more peptide linkers.

"Percent (%) amino acid sequence identity" with respect to a reference polypeptide (protein) sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN. SAWI or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In certain embodiments, amino acid sequence variants of the antigen binding molecules provided herein are contemplated. For example, it may be desirable to improve the binding affinity and/or other biological properties of the antigen binding molecules. Amino acid sequence variants of the antigen binding molecules may be prepared by introducing appropriate modifications into the nucleotide sequence encoding the molecules, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding. Sites of interest for substitutional mutagenesis include the HVRs and Framework (FRs). Conservative substitutions are provided in Table B under the heading "Preferred Substitutions" and further described below in reference to amino acid side chain classes (1) to (6). Amino acid substitutions may be introduced into the molecule of interest and the products screened for a desired activity, e.g., retained/improved antigen binding, decreased immunogenicity, or improved ADCC or CDC.

TABLE A

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
  (1) hydrophobic: Norleucine, Met, Ala, Val, Leu, Ile;
  (2) neutral hydrophilic: Cys, Ser, Thr, Asn, Gln;
  (3) acidic: Asp, Glu;
  (4) basic: His, Lys, Arg;
  (5) residues that influence chain orientation: Gly, Pro;
  (6) aromatic: Trp, Tyr, Phe.

Non-conservative substitutions will entail exchanging a member of one of these classes for another class.

The term "amino acid sequence variants" includes substantial variants wherein there are amino acid substitutions in one or more hypervariable region residues of a parent antigen binding molecule (e.g. a humanized or human antibody). Generally, the resulting variant(s) selected for further study will have modifications (e.g., improvements) in certain biological properties (e.g., increased affinity, reduced immunogenicity) relative to the parent antigen binding molecule and/or will have substantially retained certain biological properties of the parent antigen binding molecule. An exemplary substitutional variant is an affinity matured antibody, which may be conveniently generated, e.g., using phage display-based affinity maturation techniques such as those described herein. Briefly, one or more HVR residues are mutated and the variant antigen binding molecules displayed on phage and screened for a particular biological activity (e.g. binding affinity). In certain embodiments, substitutions, insertions, or deletions may occur within one or more HVRs so long as such alterations do not substantially reduce the ability of the antigen binding molecule to bind antigen. For example, conservative alterations (e.g., conservative substitutions as provided herein) that do not substantially reduce binding affinity may be made in HVRs. A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antigen binding molecule complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include bispecific antigen binding molecules of the invention with an N-terminal methionyl residue. Other insertional variants of the molecule include the fusion to the N- or C-terminus to a polypeptide which increases the serum half-life of the bispecific antigen binding molecules.

In certain embodiments, the bispecific antigen binding molecules provided herein are altered to increase or decrease the extent to which the antibody is glycosylated. Glycosylation variants of the molecules may be conveniently obtained by altering the amino acid sequence such that one or more glycosylation sites is created or removed. Where the bispecific antigen binding molecule comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in the antigen binding molecule may be made in order to create variants with certain improved properties. In one aspect, variants of bispecific antigen binding molecules or antibodies of the invention are provided having a carbohydrate structure that lacks fucose attached (directly or indirectly) to an Fc region. Such fucosylation variants may have improved ADCC function, see e.g. US Patent Publication Nos. US 2003/0157108 (Presta, L.) or US 2004/0093621 (Kyowa Hakko Kogyo Co., Ltd). In another aspect, variants of the bispecific antigen binding molecules or antibodies of the invention are provided with bisected oligosaccharides, e.g., in which a biantennary oligosaccharide attached to the Fc region is bisected by GlcNAc. Such variants may have reduced fucosylation and/or improved ADCC function., see for example WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such antibody variants may have improved CDC function and are described, e.g., in WO 1997/30087 (Patel et al.); WO 1998/58964 (Raju, S.); and WO 1999/22764 (Raju, S.).

In certain aspects, it may be desirable to create cysteine engineered variants of the bispecific antigen binding molecules of the invention, e.g., "thioMAbs," in which one or more residues of the molecule are substituted with cysteine residues. In particular aspects, the substituted residues occur at accessible sites of the molecule. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain aspects, any one or more of the following residues may be substituted with cysteine: V205 (Kabat numbering) of the light chain; A118 (EU numbering) of the heavy chain; and S400 (EU numbering) of the heavy chain Fc region. Cysteine engineered antigen binding molecules may be generated as described, e.g., in U.S. Pat. No. 7,521,541.

In certain aspects, the bispecific antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the bispecific antibody derivative will be used in a therapy under defined conditions, etc. In another aspect, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

In another aspect, immunoconjugates of the bispecific antibodies provided herein maybe obtained. An "immunoconjugate" is an antibody conjugated to one or more heterologous molecule(s), including but not limited to a cytotoxic agent.

The term "nucleic acid" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the bispecific antigen binding molecules of the present invention. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable excipient" refers to an ingredient in a pharmaceutical composition, other than an active ingredient, which is nontoxic to a subject. A pharmaceutically acceptable excipient includes, but is not limited to, a buffer, a stabilizer, or a preservative.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the molecules of the invention are used to delay development of a disease or to slow the progression of a disease.

The term "cancer" as used herein refers to proliferative diseases, such as lymphomas, carcinoma, lymphoma, blastoma, sarcoma, leukemia, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colorectal cancer (CRC), pancreatic cancer, breast cancer, triple-negative breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, melanoma, multiple myeloma, B-cell cancer (lymphoma), chronic lymphocytic leukemia (CLL), acute lymphoblastic leukemia (ALL), hairy cell leukemia, chronic myeloblastic leukemia, including refractory versions of any of the above cancers, or a combination of one or more of the above cancers.

Bispecific Antigen Binding Molecules of the Invention

The invention provides novel bispecific antibodies with particularly advantageous properties such as producibility, stability, binding affinity, biological activity, targeting efficiency and reduced toxicity. The novel bispecific antibodies consist of two fusion polypeptides comprising two antigen binding domains capable of specific binding to a first target and one antigen binding domain capable of specific binding to a second target. Surprisingly, these two fusion polypeptides are engineered in a way that the three antigen binding domains can assemble correctly and that the bispecific binding is fully functional.

For a molecule intended to be developed towards clinical application, aggregates of functionally active molecules have to be avoided, meaning the purity and stability of the assembly of the different fusion polypeptides forming the antigen binding molecule is very critical. Importantly, in the bispecific antibodies of the invention, all three antigen binding domains are fused in a way that enables the correct assembly of the three antigen binding domains. And all three antigen binding domains are positioned in a way that every antigen binding domain can bind to their respective targets. The new bispecific antigen binding molecules of the invention are furthermore comprised only of two fusion polypeptides and do not comprise any light chains. Thus, the problem of correct pairing between heavy and light chains can be avoided. Important is also that the constructs are expressable with reasonably good titers and produce a good ratio of the wished product. The antibody-like architecture comprising a spacer domain for dimerization is stabile compared to other proteins; their expression is also very robust using different cell lines.

The novel bispecific antigen binding molecules of the invention are called 2+1 Contorsbodies.

Thus, a 2+1 Contorsbody is a bispecific antibody consisting of two fusion polypeptides and comprising two antigen binding domains capable of specific binding to a first target and one antigen binding domain capable of specific binding to a second target, wherein (a) the first fusion polypeptide comprises a first part of a first antigen binding domain capable of specific binding to the first target, a spacer domain, a second part of a first antigen binding domain capable of specific binding to the first target and a first part of an antigen binding domain capable of specific binding to the second target, wherein the spacer domain is a polypeptide and comprises at least 25 amino acid residues, the first part of the first antigen binding domain capable of specific binding to the first target is fused either directly or via a first peptide linker to the N-terminus of the spacer domain, the second part of the first antigen binding domain capable of specific binding to the first target is fused either directly or via a second peptide linker to the C-terminus of the spacer domain, and the first part of an antigen binding domain capable of specific binding to a second target is fused either directly or via a third peptide linker to the C-terminus of the second part of the first antigen binding domain capable of specific binding to the first target or is fused either directly or via a third peptide linker to the N-terminus of the first part of the first antigen binding domain capable of specific binding to the first target, and (b) the second fusion polypeptide comprising a first part of a second antigen binding domain capable of specific binding to a first target, a spacer domain, a second part of the second antigen binding domain capable of specific binding to a first target and the second part of an antigen binding domain capable of specific binding to a second target, wherein the spacer domain is a polypeptide and comprises at least 25 amino acid residues, the first part of the second antigen binding domain capable of specific binding to a first target is fused either directly or via a first peptide linker to the N-terminus of the spacer domain, the second part of the second antigen binding domain capable of specific binding to a first target is fused either directly or via a second peptide linker to the C-terminus of the spacer domain, and the second part of an antigen binding domain capable of specific binding to a second target is fused either directly or via a third peptide linker to the C-terminus of the second part of the second antigen binding domain capable of specific binding to a first target or is fused either directly or via a third peptide linker to the N-terminus of the first part of the second antigen binding domain capable of specific binding to a first target, wherein the first part and the second part of the antigen binding domain capable of specific binding to the second target are associated with each other to form the antigen binding domain capable of specific binding to the second target and wherein the first part and the second part of the first and second antigen binding domain capable of specific binding to the first target are associated with each other to form a circular fusion polypeptide, and wherein the spacer domain of the first fusion polypeptide and the spacer domain of the second fusion polypeptide are associated covalently to each other by a disulfide bond and comprise modifications promoting the association of the first and second fusion polypeptide.

In one aspect, provided is a bispecific antibody as defined herein before, wherein in the first fusion polypeptide the first part of an antigen binding domain capable of specific binding to a second target is fused either directly or via a third peptide linker to the C-terminus of the second part of the first antigen binding domain capable of specific binding to the first target and wherein in the second fusion polypeptide the second part of an antigen binding domain capable of specific binding to a second target is fused either directly or via a third peptide linker to the C-terminus of the second part of the first antigen binding domain capable of specific binding to the first target.

In another aspect, provided is a bispecific antibody as defined herein before, wherein in the first fusion polypeptide the first part of an antigen binding domain capable of specific binding to a second target is fused either directly or via a third peptide linker to the N-terminus of the first part of the first antigen binding domain capable of specific binding to the first target and wherein in the second fusion polypeptide the second part of an antigen binding domain capable of specific binding to a second target is fused either directly or via a third peptide linker to the N-terminus of the first part of the first antigen binding domain capable of specific binding to the first target.

Thus, in the bispecific antibody as defined herein before, the original antibody domains are fused by flexible peptide linkers. These linkers enable the correct domain association within the Contorsbody molecule, as well as proper folding of the antibody. This new chain topology results in a spatial orientation of Fab arms and Fc part that differs from the classical IgG1 format. Due to the parallel orientation of its antigen binding sites, the Contorsbody is a very suitable antibody format for agonistic mechanisms.

In one aspect, provided is a bispecific antibody as defined herein before, wherein the third peptide linker connecting the first part or the second part of an antigen binding domain capable of specific binding to a second target comprises at least 15 amino acids. In one aspect, the third peptide linker connecting the first part of an antigen binding domain capable of specific binding to a second target and the third peptide linker connecting the second part of an antigen binding domain capable of specific binding to a second target are identical. In one aspect, the third peptide linker comprises 15 to 25 amino acids. In one particular aspect, the third peptide linker comprises the amino acid sequence of SEQ ID NO:83 or SEQ ID NO:84. More particularly, the the third peptide linker comprises the amino acid sequence of SEQ ID NO:84. In a further aspect, the third peptide linker (in both fusion polypeptides) comprises the amino acid sequence of SEQ ID NO:83 or SEQ ID NO:84 and the first and second peptide linker comprises the amino acid sequence of SEQ ID NO:78.

In one aspect, the invention provides a bispecific antibody as defined herein before, wherein the first fusion polypeptide comprises the heavy chain variable domain of the antigen binding domain capable of specific binding to a second target and the second fusion polypeptide comprises the antibody light chain variable domain of the antigen binding domain capable of specific binding to a second target or vice versa.

In one aspect, the invention provides a bispecific antibody as defined herein before, wherein the first fusion polypeptide comprises the heavy chain variable domain of the antigen binding domain capable of specific binding to a second target and the second fusion polypeptide comprises the antibody light chain variable domain of the antigen binding domain capable of specific binding to a second target or vice versa. In one particular aspect, the first part of the antigen binding domain is an antibody heavy chain Fab fragment and the second part of the antigen binding domain is an antibody light chain Fab fragment or vice versa. In one aspect, the first part of the antigen binding domain and the second part of the antigen binding domain are associated covalently to each other by a disulfide bond.

In an alternative aspect, a bispecific antibody consisting of two fusion polypeptides and comprising two antigen binding domains capable of specific binding to a first target and one antigen binding domain capable of specific binding to a second target, wherein (a) the first fusion polypeptide comprises a first part of a first antigen binding domain capable of specific binding to the first target, a spacer domain, a second part of a first antigen binding domain capable of specific binding to the first target and a first part of an antigen binding domain capable of specific binding to the second target, wherein the spacer domain is a polypeptide and comprises at least 25 amino acid residues, the first part of the first antigen binding domain capable of specific binding to the first target is fused either directly or via a first peptide linker to the N-terminus of the spacer domain, the second part of the first antigen binding domain capable of specific binding to the first target is fused either directly or via a second peptide linker to the C-terminus of the spacer domain, and the first part of an antigen binding domain capable of specific binding to a second target is fused either directly or via a third peptide linker to the C-terminus of the second part of the first antigen binding domain capable of specific binding to the first target or is fused either directly or via a third peptide linker to the N-terminus of the first part of the first antigen binding domain capable of specific binding to the first target, and
(b) the second fusion polypeptide comprising a first part of a second antigen binding domain capable of specific binding to a first target, a spacer domain, a second part of the second antigen binding domain capable of specific binding to a first target and the second part of an antigen binding domain capable of specific binding to a second target, wherein
the spacer domain is a polypeptide and comprises at least 25 amino acid residues,
the first part of the second antigen binding domain capable of specific binding to a first target is fused either directly or via a first peptide linker to the N-terminus of the spacer domain,
the second part of the second antigen binding domain capable of specific binding to a first target is fused either directly or via a second peptide linker to the C-terminus of the spacer domain, and
(c) a light chain comprising the the second part of an antigen binding domain capable of specific binding to a second target,
wherein the first part and the second part of the antigen binding domain capable of specific binding to the second target are associated with each other to form the antigen binding domain capable of specific binding to the second target and wherein the first part and the second part of the first and second antigen binding domain capable of specific binding to the first target are associated with each other to form a circular fusion polypeptide, and
wherein the spacer domain of the first fusion polypeptide and the spacer domain of the second fusion polypeptide are associated covalently to each other by a disulfide bond and comprise modifications promoting the association of the first and second fusion polypeptide.

In some aspects, the first part of the antigen binding domain is an antibody heavy chain Fab fragment and the second part of the antigen binding domain is an antibody light chain Fab fragment or vice versa. In one aspect, the first part of the antigen binding domain and the second part of the antigen binding domain are associated covalently to each other by a disulfide bond.

In one aspect, provided is a bispecific antibody as defined herein before, wherein in both the first fusion polypeptide and the second fusion polypeptide the first part of the antigen binding domain capable of specific binding to the first target is an antibody heavy chain Fab fragment and the second part of the antigen binding domain capable of specific binding to the first target is an antibody light chain Fab fragment.

If the antigen binding domain is a Fab fragment, then the Fab can be a conventional Fab, a cross-Fab or a DutaFab.

In case of a conventional Fab, a first part of the antigen binding domain comprises an antibody heavy chain variable domain (VH) and at least an N-terminal fragment of a (or a complete) first antibody heavy chain constant domain (CH1) and the respective second part of the antigen binding domain comprises an antibody light chain variable domain (VL) and at least an N-terminal fragment of a (or a complete) antibody light chain constant domain (CL or Ckappa). The order of these domains may be any as long as association thereof and forming of a (functional) antigen binding domain is possible (i.e. not prevented). In one aspect, one part of the antigen binding domain comprises in N- to C-terminal direction VH-CH1 and the other part of the antigen binding domain comprises in N- to C-terminal direction VL-CL (Ckappa).

In case of a cross-Fab both parts of the antigen binding domain comprise each an antibody variable domain and at least an N-terminal fragment of a (or a complete) antibody constant domain whereby the pairs of variable domain and constant domain are not naturally associated with each other and are obtained by a domain cross-over/exchange of a heavy chain domain and a light chain domain. This can be the exchange of VH with VL or CH1 with CL. The order of these domains may be any as long as association thereof and forming of a (functional) binding site is possible (i.e. not prevented). In one aspect, the first part of the antigen binding domain comprises in N- to C-terminal direction VL-CH1 and the second part of the binding domain comprises in N- to C-terminal direction VH-CL (Ckappa). In another aspect, the first part of the antigen binding domain comprises in N- to C-terminal direction VH-CL and the second part of the binding domain comprises in N- to C-terminal direction VL-CH1.

In case of a DutaFab, a first part of the antigen binding domain comprises an antibody heavy chain variable domain (VH) and at least an N-terminal fragment of a (or a complete) first antibody heavy chain constant domain (CH1) and the respective second antigen binding domain comprises an antibody light chain variable domain (VL) and at least an N-terminal fragment of a (or a complete) antibody light chain constant domain (CL), wherein said antigen binding domain comprises two non-overlapping paratopes in the complementary pair of a heavy chain variable domain (VH) and a light chain variable domain (VL), wherein the first paratope comprises residues from CDR1 and CDR3 of the VL domain and CDR2 of the VH domain, and the second paratope comprises residues from CDR1 and CDR3 of the VH domain and CDR2 of the VL domain.

Thus, in one aspect, the first part of the antigen binding domain is an antibody heavy chain Fab fragment (VH-CH1) and the second part of the antigen binding domain is an antibody light chain Fab fragment (VL-Ckappa). In another aspect, the first part of the antigen binding domain is an antibody light chain Fab fragment and the second part of the antigen binding domain is an antibody heavy chain Fab fragment. In another aspect, the first part of the antigen binding domain is an antibody cross Fab fragment comprising VH-Ckappa and the second part of the antigen binding domain is an antibody cross Fab fragment comprising VL-CH1. In a further aspect, the first part of the antigen binding domain is an antibody cross Fab fragment comprising VL-CH1 and the second part of the antigen binding domain is an antibody cross Fab fragment comprising VH-Ckappa.

In a particular aspect, the invention provides a bispecific antibody, wherein the antigen binding domain capable of specific binding to a second target is a cross-Fab and wherein both antigen binding domains capable of specific binding to the first target are conventional Fabs.

In another aspect, the invention provides a bispecific antibody, wherein the antigen binding domain capable of specific binding to a second target is a conventional Fab and wherein both antigen binding domains capable of specific binding to the first target are cross-Fabs.

As described above, the bispecific antibody consists of a first and a second fusion polypeptide, both comprising a spacer domain, the spacer domain of the first fusion polypeptide and the spacer domain of the second fusion polypeptide are associated covalently to each other by a disulfide bond and comprise modifications promoting the association of the first and second fusion polypeptide. The spacer domain comprises at least 25 amino acids.

In one aspect of the invention, the spacer domain comprises an antibody hinge region or a (C-terminal) fragment thereof and an antibody CH2 domain or a (N-terminal) fragment thereof. In another aspect, the spacer domain comprises an antibody hinge region or a fragment thereof, an antibody CH2 domain, and an antibody CH3 domain or a fragment thereof. In one aspect, the spacer domain of the fusion polypeptide as described herein is an antibody Fc domain, in particular of IgG1, IgG2 or IgG4 subclass, more particularly of IgG1 subclass.

In one aspect, the spacer domain comprises a Fc domain with an amino acid sequence selected from the group consisting of SEQ ID NO:103, Seq ID NO:104, SEQ ID NO:105, SEQ ID NO:106 and SEQ ID NO:107, or a variant of 95% homology thereof.

Furthermore, the spacer domain of the first fusion polypeptide and the spacer domain of the second fusion polypeptide comprise modifications promoting the association of the first and second fusion polypeptide. In a particular aspect, the spacer domain of the first fusion polypeptide comprises holes and the spacer domain of the second fusion polypeptide comprises knobs according to the knobs into hole method. In a further aspect, the invention comprises a bispecific antibody, wherein the spacer domain comprises an antibody hinge region or a fragment thereof and an IgG1 Fc domain. Particularly, the IgG1 Fc domain comprises one or more amino acid substitution that reduces binding to an Fc receptor, in particular towards Fcγ receptor. In a particular aspect, the IgG1 Fc domain comprises the amino acid substitutions L234A and L235A. In another aspect, the IgG1 Fc domain comprises the mutation P329G. More particularly, the IgG1 Fc domain comprises the amino acid substitutions L234A, L235A and P329G (numbering according to Kabat EU index).

In another aspect, the Fc domain as reported herein is of IgG1 or IgG2 subclass and comprises the mutations PVA236, GLPSS331, and/or L234A/L235A/P329G (numbering according to Kabat EU index). In a further aspect, the Fc domain reported herein is of IgG4 subclass and comprises the mutation L235E. In one aspect, the Fc domain further comprises the mutation S228P. In one aspect, the Fc domain of IgG4 subclass comprises the mutation P329G. In one aspect, the Fc domain as reported herein is of IgG4 subclass and comprises the mutations S228P/L235E/P329G (all numbering according to EU index of Kabat).

In some aspects, provided is a bispecific antibody wherein the one antigen binding domain capable of specific binding to a second target is an antigen binding domain capable of specific binding to a tumor associated antigen (TAA). In particular, the tumor associated antigen is Fibroblast Activation Protein (FAP). In one aspect, provided is a bispecific antibody, wherein the antigen binding domain capable of specific binding to a second target is an antigen binding domain capable of specific binding to Fibroblast Activation Protein (FAP).

Fc Domain Modifications Promoting Heterodimerization

In one aspect, the bispecific antibodies of the invention may comprise (a) a first fusion polypeptide as defined herein before and a second fusion polypeptide as defined herein before, wherein the first and second fusion polypeptide comprise modifications promoting the association of the first and second fusion polypeptide. Typically, these modifications are introduced in the Fc domains. Recombinant co-expression of the two structurally different fusion polypeptides and subsequent dimerization would lead to several possible combinations of the two polypeptides. In order to improve the yield and purity of the bispecific antibodies in recombinant production, it will thus be advantageous to introduce in the Fc domain of the bispecific antigen binding molecule s of the invention modifications promoting the association of the desired polypeptides.

The site of most extensive protein-protein interaction between the two subunits of a human IgG Fc domain is in the CH3 domain of the Fc domain. Thus, said modification is particularly in the CH3 domain of the Fc domain.

In a specific aspect, said modification is a so-called "knob-into-hole" modification, comprising a "knob" modification in one of the two subunits of the Fc domain and a "hole" modification in the other one of the two subunits of the Fc domain. Thus, in a particular aspect, the invention relates to a bispecific antigen binding molecule as described herein before which comprises an IgG molecule, wherein the Fc part of the first heavy chain comprises a first dimerization module and the Fc part of the second heavy chain comprises a second dimerization module allowing a heterodimerization of the two heavy chains of the IgG molecule and the first dimerization module comprises knobs and the second dimerization module comprises holes according to the knob into hole technology.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

The CH3 domains in the first and second fusion polypeptide as reported herein can be altered by the "knob-into-holes" technology which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681. In this method the interaction surfaces of the two CH3 domains are altered to increase the heterodimerization of both heavy chains containing these two CH3 domains. Each of the two CH3 domains (of the two heavy chains) can be the "knob", while the other is the "hole". The introduction of a disulfide bridge further stabilizes the heterodimers (Merchant, A. M., et al., Nature Biotech. 16 (1998) 677-681; Atwell, S., et al., J. Mol. Biol. 270 (1997) 26-35) and increases the yield.

Accordingly, in a particular aspect, in the CH3 domain of the first subunit of the Fc domain of the bispecificantigen binding molecules of the invention an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

In a specific aspect, in the CH3 domain of the first subunit of the Fc domain ("knobs chain") the threonine residue at position 366 is replaced with a tryptophan residue (T366W), and in the CH3 domain of the second subunit of the Fc domain the tyrosine residue at position 407 is replaced with a valine residue (Y407V). More particularly, in the second subunit of the Fc domain ("hole chain") additionally the threonine residue at position 366 is replaced with a serine residue (T366S) and the leucine residue at position 368 is replaced with an alanine residue (L368A). More particularly, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). The introduction of these two cysteine residues results in the formation of a disulfide bridge between the two subunits of the Fc domain. The disulfide bridge further stabilizes the dimer (Carter, J Immunol Methods 248, 7-15 (2001)).

But also other knobs-in-holes technologies as described by EP 1870459 A1, can be used alternatively or additionally. In one embodiment the multicircular fusion polypeptide as reported herein comprises the R409D and K370E mutations in the CH3 domain of the "knobs chain" and the D399K and E357K mutations in the CH3 domain of the "hole-chain" (numbering according to Kabat EU index).

In a further aspect, the bispecificantigen binding molecule may comprises the Y349C and T366W mutations in one of the two CH3 domains and the S354C, T366S, L368A and Y407V mutations in the other of the two CH3 domains, or the bispecificantigen binding molecule as reported herein comprises the Y349C and T366W mutations in one of the two CH3 domains and the S354C, T366S, L368A and Y407V mutations in the other of the two CH3 domains and additionally the R409D and K370E mutations in the CH3 domain of the "knobs chain" and the D399K and E357K mutations in the CH3 domain of the "hole chain" (numbering according to the Kabat EU index).

In an alternative aspect, a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

Apart from the "knob-into-hole technology" other techniques for modifying the CH3 domains of the heavy chains to enforce heterodimerization are known in the art. These technologies, especially the ones described in WO 96/27011, WO 98/050431, EP 1870459, WO 2007/110205, WO 2007/147901, WO 2010/129304, WO 2011/90754, WO 2011/143545, WO 2012/058768, WO 2013/157954 and WO 2013/096291 are contemplated herein as alternatives to the "knob-into-hole technology" in combination with a bispecific antigen binding molecule as described herein.

In one aspect, charged amino acids with opposite charges at specific amino acid positions in the CH3/CH3-domain-interface between both, the first and the second heavy chain are introduced to further promote the association of the desired polypeptides. Accordingly, this aspect relates to bispecific antigen binding molecules as disclosed herein, wherein in the tertiary structure of the antibody the CH3 domain of the first heavy chain and the CH3 domain of the second heavy chain an interface is formed that is located between the respective antibody CH3 domains, wherein the respective amino acid sequences of the CH3 domain of the first heavy chain and the CH3 domain of the second heavy chain each comprise a set of amino acids that is located within said interface in the tertiary structure of the circular fusion polypeptide, and wherein from the set of amino acids that is located in the interface in the CH3 domain of one heavy chain a first amino acid is substituted by a positively charged amino acid and from the set of amino acids that is located in the interface in the CH3 domain of the other heavy chain a second amino acid is substituted by a negatively charged amino acid. The bispecific antigen binding molecule according to this aspect is herein also referred to as "CH3 (+/−)-engineered TNF family ligand trimer-containing antigen binding molecule" (wherein the abbreviation "+/−" stands for the oppositely charged amino acids that were introduced in the respective CH3 domains). In one aspect of said CH3(+/−)-engineered bispecific antigen binding molecule as reported herein the positively charged amino acid is selected from K, R and H, and the negatively charged amino acid is selected from E or D. In another aspect, in said CH3(+/−)-engineered bispecific antigen binding molecule as reported herein the positively charged amino acid is selected from K and R, and the negatively charged amino acid is selected from E or D. In a further aspect, in said CH3(+/−)-engineered bispecific antigen binding molecule as reported herein the positively charged amino acid is K, and the negatively charged amino acid is E. In one aspect, in said CH3(+/−)-engineered bispecific antigen binding molecule as reported herein in the CH3 domain of one heavy chain the amino acid R at position 409 is substituted by D and the amino acid K at position is substituted by E, and in the CH3 domain of the other heavy chain the amino acid D at position 399 is substituted by K and the amino acid E at position 357 is substituted by K (numbering according to Kabat EU index).

In a further aspect of the invention, the IgG1 Fc domain comprises one or more amino acid substitution that reduces binding to an Fc receptor, in particular towards Fcγ receptor.

Fc Domain Modifications Reducing Fc Receptor Binding and/or Effector Function

The bispecific antibodies of the invention may comprise as a spacer domain the heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. The Fc region confers favorable pharmacokinetic properties to the bispecific antibodies of the invention, including a long serum half-life which contributes to good accumulation in the target tissue and a favorable tissue-blood distribution ratio. At the same time it may, however, lead to undesirable targeting of the bispecific antibodies of the invention to cells expressing Fc receptors rather than to the preferred antigen-bearing cells. Accordingly, in particular embodiments the Fc region of the bispecific antibodies of the invention exhibits reduced binding affinity to an Fc receptor and/or reduced effector function, as compared to a native IgG Fc region, in particular an IgG1 Fc region or an IgG4 Fc region. More particularly, the Fc region is an IgG1 Fc region.

In one such aspect the Fc region (or the bispecific antigen binding molecule of the invention comprising said Fc region) exhibits less than 50%, preferably less than 20%, more preferably less than 10% and most preferably less than 5% of the binding affinity to an Fc receptor, as compared to a native IgG1 Fc region (or the bispecific antigen binding molecule of the invention comprising a native IgG1 Fc region), and/or less than 50%, preferably less than 20%, more preferably less than 10% and most preferably less than 5% of the effector function, as compared to a native IgG1 Fc region (or the bispecific antigen binding molecule of the invention comprising a native IgG1 Fc region). In one aspect, the Fc region (or the bispecific antigen binding molecule of the invention comprising said Fc region) does not substantially bind to an Fc receptor and/or induce effector function. In a particular aspect the Fc receptor is an Fcγ receptor. In one aspect, the Fc receptor is a human Fc receptor. In one aspect, the Fc receptor is an activating Fc receptor. In a specific aspect, the Fc receptor is an activating human Fcγ receptor, more specifically human FcγRIIIa, FcγRI or FcγRIIa, most specifically human FcγRIIIa. In one aspect, the Fc receptor is an inhibitory Fc receptor. In a specific aspect, the Fc receptor is an inhibitory human Fcγ receptor, more specifically human FcγRIIB. In one aspect the effector function is one or more of CDC, ADCC, ADCP, and cytokine secretion. In a particular aspect, the effector function is ADCC. In one aspect, the Fc region domain exhibits substantially similar binding affinity to neonatal Fc receptor (FcRn), as compared to a native IgG1 Fc region. Substantially similar binding to FcRn is achieved when the Fc region (or the bispecific antigen binding molecule of the invention comprising said Fc region) exhibits greater than about 70%, particularly greater than about 80%, more particularly greater than about 90% of the binding affinity of a native IgG1 Fc region (or the bispecific antigen binding molecule of the invention comprising a native IgG1 Fc region) to FcRn.

In a particular aspect, the Fc region is engineered to have reduced binding affinity to an Fc receptor and/or reduced effector function, as compared to a non-engineered Fc region. In a particular aspect, the Fc region of the bispecific antigen binding molecule of the invention comprises one or more amino acid mutation that reduces the binding affinity of the Fc region to an Fc receptor and/or effector function. Typically, the same one or more amino acid mutation is present in each of the two subunits of the Fc region. In one aspect, the amino acid mutation reduces the binding affinity of the Fc region to an Fc receptor. In another aspect, the amino acid mutation reduces the binding affinity of the Fc region to an Fc receptor by at least 2-fold, at least 5-fold, or at least 10-fold. In one aspect, the bispecific antigen binding molecule of the invention comprising an engineered Fc region exhibits less than 20%, particularly less than 10%, more particularly less than 5% of the binding affinity to an Fc receptor as compared to bispecific antibodies of the invention comprising a non-engineered Fc region. In a particular aspect, the Fc receptor is an Fcγ receptor. In other aspects, the Fc receptor is a human Fc receptor. In one aspect, the Fc receptor is an inhibitory Fc receptor. In a specific aspect, the Fc receptor is an inhibitory human Fcγ receptor, more specifically human FcγRIIB. In some aspects the Fc receptor is an activating Fc receptor. In a specific aspect, the Fc receptor is an activating human Fcγ receptor, more specifically human FcγRIIIa, FcγRI or FcγRIIa, most specifically human FcγRIIIa. Preferably, binding to each of these receptors is reduced. In some aspects, binding affinity to a complement component, specifically binding affinity to C1q, is also reduced. In one aspect, binding affinity to neonatal Fc receptor (FcRn) is not reduced. Substantially similar binding to FcRn, i.e. preservation of the binding affinity of the Fc region to said receptor, is achieved when the Fc region (or the bispecific antigen binding molecule of the invention comprising said Fc region) exhibits greater than about 70% of the binding affinity of a non-engineered form of the Fc region (or the bispecific antigen binding molecule of the invention comprising said non-engineered form of the Fc region) to FcRn. The Fc region, or the bispecific antigen binding molecule of the invention comprising said Fc region, may exhibit greater than about 80% and even greater than about 90% of such affinity. In certain embodiments the Fc region of the bispecific antigen binding molecule of the invention is engineered to have reduced effector function, as compared to a non-engineered Fc region. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced dendritic cell maturation, or reduced T cell priming.

In certain aspects, provided is a bispecific antibody that possesses some but not all effector functions, which make it a desirable candidate for applications in which the half-life in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the circular fusion polypeptide lacks FcγR binding (hence likely lacking ADCC activity), but retains FcRn binding ability.

Accordingly, in particular aspects, the Fc domain of the bispecific antibody of the invention exhibits reduced binding affinity to an Fc receptor and/or reduced effector function, as compared to a native IgG1 Fc domain. In one aspect, the Fc does not substantially bind to an Fc receptor and/or does not induce effector function. In a particular aspect the Fc receptor is an Fcγ receptor. In one aspect, the Fc receptor is a human Fc receptor. In a specific aspect, the Fc receptor is an activating human Fcγ receptor, more specifically human FcγRIIIa, FcγRI or FcγRIIa, most specifically human FcγRIIIa. In one aspect, the Fc domain does not induce effector function. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced dendritic cell maturation, or reduced T cell priming.

In certain aspects, one or more amino acid modifications may be introduced into the Fc region of the bispecific antigen binding molecule provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In a particular aspect, the invention provides a bispecificantigen binding molecule, wherein the spacer domain comprises Fc domain that comprises one or more amino acid substitution that reduces binding to an Fc receptor, in particular towards Fcγ receptor.

In one aspect, the Fc domain of the bispecificantigen binding molecule of the invention comprises one or more amino acid mutation that reduces the binding affinity of the Fc domain to an Fc receptor and/or effector function. Typically, the same one or more amino acid mutation is present in each of the two subunits of the Fc domain. In particular, the Fc domain comprises an amino acid substitution at a position of E233, L234, L235, N297, P331 and P329 (EU numbering). In particular, the Fc domain comprises amino acid substitutions at positions 234 and 235 (EU numbering) and/or 329 (EU numbering) of the IgG heavy chains. More particularly, provided is a bispecificantigen binding molecule according to the invention which comprises an Fc domain with the amino acid substitutions L234A, L235A and P329G ("P329G LALA", EU numbering according to Kabat) in the IgG heavy chains. The amino acid substitutions L234A and L235A refer to the so-called LALA mutation. The "P329G LALA" combination of amino acid substitutions almost completely abolishes Fcγ receptor binding of a human IgG1 Fc domain and is described in International Patent Appl. Publ. No. WO 2012/130831 A1 which also describes methods of preparing such mutant Fc domains and methods for determining its properties such as Fc receptor binding or effector functions. "EU numbering" refers to the numbering according to EU index of Kabat et al., Sequences of Proteins of Immunological Interest, 5th Ed. Public Health Service, National Institutes of Health, Bethesda, Md., 1991.

Fc domains with reduced Fc receptor binding and/or effector function also include those with substitution of one or more of Fc domain residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In another aspect, the Fc domain is an IgG4 Fc domain. IgG4 antibodies exhibit reduced binding affinity to Fc receptors and reduced effector functions as compared to IgG1 antibodies. In a more specific aspect, the Fc domain is an IgG4 Fc domain comprising an amino acid substitution at position S228 (Kabat numbering), particularly the amino acid substitution S228P. In a more specific aspect, the Fc domain is an IgG4 Fc domain comprising amino acid substitutions L235E and S228P and P329G (EU numbering). Such IgG4 Fc domain mutants and their Fcγ receptor binding properties are also described in WO 2012/130831.

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. A suitable such binding assay is described herein. Alternatively, binding affinity of Fc domains or cell activating bispecific antigen binding molecules comprising an Fc domain for Fc receptors may be evaluated using cell lines known to express particular Fc receptors, such as human NK cells expressing FcγIIIa receptor.

Effector function of an Fc domain, or bispecific antibodies of the invention comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the bispecific antibodies of the invention is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

In particular aspects, the bispecificantigen binding molecule comprises all positions according to EU index of Kabat)

i) a homodimeric Fc-region of the human IgG1 subclass optionally with the mutations P329G, L234A and L235A, or ii) a homodimeric Fc-region of the human IgG4 subclass optionally with the mutations P329G, S228P and L235E, or iii) a homodimeric Fc-region of the human IgG1 subclass optionally with the mutations P329G, L234A, L235A, I253A, H310A, and H435A, or optionally with the mutations P329G, L234A, L235A, H310A, H433A, and Y436A, or iv) a heterodimeric Fc-region whereof
a) one Fc-region polypeptide comprises the mutation T366W, and the other Fc-region polypeptide comprises the mutations T366S, L368A and Y407V, or
b) one Fc-region polypeptide comprises the mutations T366W and Y349C, and the other Fc-region polypeptide comprises the mutations T366S, L368A, Y407V, and S354C, or
c) one Fc-region polypeptide comprises the mutations T366W and S354C, and the other Fc-region polypeptide comprises the mutations T366S, L368A, Y407V and Y349C,
or v) a heterodimeric Fc-region of the human IgG1 subclass whereof both Fc-region polypeptides comprise the mutations P329G, L234A and L235A and
a) one Fc-region polypeptide comprises the mutation T366W, and the other Fc-region polypeptide comprises the mutations T366S, L368A and Y407V, or
b) one Fc-region polypeptide comprises the mutations T366W and Y349C, and the other Fc-region polypeptide comprises the mutations T366S, L368A, Y407V, and S354C, or c) one Fc-region polypeptide comprises the mutations T366W and S354C, and the other Fc-region polypeptide comprises the mutations T366S, L368A, Y407V and Y349C, or vi) a heterodimeric Fc-region of the human IgG4 subclass whereof both Fc-region polypeptides comprise the mutations P329G, S228P and L235E and a) one Fc-region polypeptide comprises the mutation T366W, and the other Fc-region polypeptide comprises the mutations T366S, L368A and Y407V, or b) one Fc-region polypeptide comprises the mutations T366W and Y349C, and the other Fc-region polypeptide comprises the mutations T366S, L368A, Y407V, and S354C, or c) one Fc-region polypeptide comprises the mutations T366W and S354C, and the other Fc-region polypeptide comprises the mutations T366S, L368A, Y407V and Y349C, or vii) a combination of one of i), ii), and iii) with one of vi), v) and vi).

The C-terminus of the fusion polypeptides comprised in the bispecific antibodies as reported herein can be a complete C-terminus ending with the amino acid residues PGK. The C-terminus can be a shortened C-terminus in which one or two of the C-terminal amino acid residues have been removed. In one preferred embodiment the C-terminus is a shortened C-terminus ending with the amino acid residues PG.

In some aspects, provided is a bispecific antibody wherein the one antigen binding domain capable of specific binding to a second target is an antigen binding domain capable of specific binding to a tumor associated antigen (TAA). In particular, the tumor associated antigen is Fibroblast Activation Protein (FAP). In one aspect, provided is a bispecific antibody, wherein the antigen binding domain capable of specific binding to a second target is an antigen binding domain capable of specific binding to Fibroblast Activation Protein (FAP).

Bispecific Antibodies Binding to a TNF Receptor and FAP

In some aspects, the antigen binding domain capable of specific binding to FAP comprises (a) a heavy chain variable region ($V_H$FAP) comprising (i) CDR-H1 comprising the amino acid sequence of SEQ ID NO:1, (ii) CDR-H2 comprising the amino acid sequence of SEQ ID NO:2, and (iii) CDR-H3 comprising the amino acid sequence of SEQ ID NO:3, and a light chain variable region ($V_L$FAP) comprising (iv) CDR-L1 comprising the amino acid sequence of SEQ ID NO:4, (v) CDR-L2 comprising the amino acid sequence of SEQ ID NO:5, and (vi) CDR-L3 comprising the amino acid sequence of SEQ ID NO:6, or (b) a heavy chain variable region ($V_H$FAP) comprising (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO:11, and a a light chain variable region ($V_L$FAP) comprising (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14.

More particularly, the antigen binding domain capable of specific binding to FAP comprises (a) a heavy chain variable region ($V_H$FAP) comprising an amino acid sequence that is at least about 95%, 96%, 97%, 98%, 99% or 100% identical to the amino acid sequence of SEQ ID NO:7, and a light chain variable region ($V_L$FAP) comprising an amino acid sequence that is at least about 95%, 96%, 97%, 98%, 99% or 100% identical to the amino acid sequence of SEQ ID NO:8, or (b) a heavy chain variable region ($V_H$FAP) comprising an amino acid sequence that is at least about 95%, 96%, 97%, 98%, 99% or 100% identical to the amino acid sequence of SEQ ID NO:15, and a light chain variable region ($V_L$FAP) comprising an amino acid sequence that is at least about 95%, 96%, 97%, 98%, 99% or 100% identical to the amino acid sequence of SEQ ID NO:16.

In one particular aspect, the antigen binding domain capable of specific binding to FAP comprises a heavy chain variable region ($V_H$FAP) comprising an amino acid sequence of SEQ ID NO:7 and a light chain variable region ($V_L$FAP) comprising an amino acid sequence of SEQ ID NO:8. In one aspect, the antigen binding domain capable of specific binding to FAP consists of a heavy chain variable region ($V_H$FAP) comprising an amino acid sequence of SEQ ID NO:7 and a light chain variable region ($V_L$FAP) comprising an amino acid sequence of SEQ ID NO:8.

In another aspect, the antigen binding domain capable of specific binding to FAP comprises a heavy chain variable region ($V_H$FAP) comprising an amino acid sequence of SEQ ID NO:15 and a light chain variable region ($V_L$FAP) comprising an amino acid sequence of SEQ ID NO:16. In one aspect, the antigen binding domain capable of specific binding to FAP consists of a heavy chain variable region ($V_H$FAP) comprising an amino acid sequence of SEQ ID NO:15 and a light chain variable region ($V_L$FAP) comprising an amino acid sequence of SEQ ID NO:16.

In one aspect, the bispecific antibodies provided herein bind monovalent to FAP.

Bispecific Antibodies Binding to OX40 and FAP

In some aspects, provided is a bispecific antibody wherein the antigen binding domain capable of specific binding to a first target is an antigen binding domain capable of specific binding to a TNF receptor, in particular a costimulatory TNF receptor. Particularly, the costimulatory TNF receptor is OX40. In one aspect, provided is a bispecific antibody, wherein the antigen binding domain capable of specific binding to a first target is an antigen binding domain capable of specific binding to OX40. Particularly, the bispecific antibody of the invention comprises two antigen binding domains capable of specific binding to OX40.

In some aspects, the antigen binding domain capable of specific binding to OX40 comprises (a) a heavy chain variable region (VHOX40) comprising (i) CDR-H1 comprising the amino acid sequence of SEQ ID NO:17, (ii) CDR-H2 comprising the amino acid sequence of SEQ ID NO:19, and (iii) CDR-H3 comprising the amino acid sequence of SEQ ID NO:22, and a light chain variable region (VLOX40) comprising (iv) CDR-L1 comprising the amino acid sequence of SEQ ID NO:28, (v) CDR-L2 comprising the amino acid sequence of SEQ ID NO:31, and (vi) CDR-L3 comprising the amino acid sequence of SEQ ID NO:35, or (b) a heavy chain variable region (VHOX40) comprising (i) CDR-H1 comprising the amino acid sequence of SEQ ID NO:17, (ii) CDR-H2 comprising the amino acid sequence of SEQ ID NO:19, and (iii) CDR-H3 comprising the amino acid sequence of SEQ ID NO:21, and a light chain variable region (VLOX40) comprising (iv) CDR-L1 comprising the amino acid sequence of SEQ ID NO:28, (v) CDR-L2 comprising the amino acid sequence of SEQ ID NO:31, and (vi) CDR-L3 comprising the amino acid sequence of SEQ ID NO:34, or (c) a heavy chain variable region (VHOX40) comprising (i) CDR-H1 comprising the amino acid sequence of SEQ ID NO:17, (ii) CDR-H2 comprising the amino acid sequence of SEQ ID NO:19, and (iii) CDR-H3 comprising the amino acid sequence of SEQ ID NO:23, and a light chain variable region (VLOX40) comprising (iv) CDR-L1 comprising the amino acid sequence of SEQ ID NO:28, (v) CDR-L2 comprising the amino acid sequence of SEQ ID NO:31, and (vi) CDR-L3 comprising the amino acid sequence of SEQ ID NO:36, or (d) a heavy chain variable region (VHOX40) comprising (i) CDR-H1 comprising the amino acid sequence of SEQ ID NO:17, (ii) CDR-H2 comprising the amino acid sequence of SEQ ID NO:19, and (iii) CDR-H3 comprising the amino acid sequence of SEQ ID NO:24, and a light chain variable region (VLOX40) comprising (iv) CDR-L1 comprising the amino acid sequence of SEQ ID NO:28, (v) CDR-L2 comprising the amino acid sequence of SEQ ID NO:31, and (vi) CDR-L3 comprising the amino acid sequence of SEQ ID NO:37, or (e) a heavy chain variable region (VHOX40) comprising (i) CDR-H1 comprising the amino acid sequence of SEQ ID NO:18, (ii) CDR-H2 comprising the amino acid sequence of SEQ ID NO:20, and (iii) CDR-H3 comprising the amino acid sequence of SEQ ID NO:25, and a light chain variable region (VLOX40) comprising (iv) CDR-L1 comprising the amino acid sequence of SEQ ID NO:29, (v) CDR-L2 comprising the amino acid sequence of SEQ ID NO:32, and (vi) CDR-L3 comprising the amino acid sequence of SEQ ID NO:38, or (f) a heavy chain variable region (VHOX40) comprising (i) CDR-H1 comprising the amino acid sequence of SEQ ID NO:18, (ii) CDR-H2 comprising the amino acid sequence of SEQ ID NO:20, and (iii) CDR-H3 comprising the amino acid sequence of SEQ ID NO:26, and a light chain variable region (VLOX40) comprising (iv) CDR-L1 comprising the amino acid sequence of SEQ ID NO:29, (v) CDR-L2 comprising the amino acid sequence of SEQ ID NO:32, and (vi) CDR-L3 comprising the amino acid sequence of SEQ ID NO:38, or (g) a heavy chain variable region (VHOX40) comprising (i) CDR-H1 comprising the amino acid sequence of SEQ ID NO:18, (ii) CDR-H2 comprising the amino acid sequence of SEQ ID NO:20, and (iii) CDR-H3 comprising the amino acid sequence of SEQ ID NO:27, and a light chain variable region (VLOX40) comprising (iv) CDR-L1 comprising the amino acid sequence of SEQ ID NO:30, (v) CDR-L2 comprising the amino acid sequence of SEQ ID NO:33, and (vi) CDR-L3 comprising the amino acid sequence of SEQ ID NO:39.

In particular, the antigen binding domain capable of specific binding to OX40 comprises a heavy chain variable region (VHOX40) comprising (i) CDR-H1 comprising the amino acid sequence of SEQ ID NO:17, (ii) CDR-H2 comprising the amino acid sequence of SEQ ID NO:19, and (iii) CDR-H3 comprising the amino acid sequence of SEQ ID NO:22, and a light chain variable region ($V_L$OX40) comprising (iv) CDR-L1 comprising the amino acid sequence of SEQ ID NO:28, (v) CDR-L2 comprising the amino acid sequence of SEQ ID NO:31, and (vi) CDR-L3 comprising the amino acid sequence of SEQ ID NO:35.

In some aspects, the antigen binding domain capable of specific binding to OX40 comprises (a) a heavy chain variable region (VHOX40) comprising an amino acid sequence of SEQ ID NO:40 and a light chain variable region (VLOX40) comprising an amino acid sequence of SEQ ID NO:41, or (b) a heavy chain variable region (VHOX40) comprising an amino acid sequence of SEQ ID NO:42 and a light chain variable region (VLOX40) comprising an amino acid sequence of SEQ ID NO:43, or (c) a heavy chain variable region (VHOX40) comprising an amino acid sequence of SEQ ID NO:44 and a light chain variable region (VLOX40) comprising an amino acid sequence of SEQ ID NO:45, or (d) a heavy chain variable region (VHOX40) comprising an amino acid sequence of SEQ ID NO:46 and a light chain variable region (VLOX40) comprising an amino acid sequence of SEQ ID NO:47, or (a) a heavy chain variable region (VHOX40) comprising an amino acid sequence of SEQ ID NO:48 and a light chain variable region (VLOX40) comprising an amino acid sequence of SEQ ID NO:49, or (a) a heavy chain variable region (VHOX40) comprising an amino acid sequence of SEQ ID NO:50 and a light chain variable region (VLOX40) comprising an amino acid sequence of SEQ ID NO:51, or (a) a heavy chain variable region (VHOX40) comprising an amino acid sequence of SEQ ID NO:52 and a light chain variable region (VLOX40) comprising an amino acid sequence of SEQ ID NO:53.

In a particular aspect, the the antigen binding domain capable of specific binding to OX40 comprises (a) a heavy chain variable region (VHOX40) comprising an amino acid sequence that is at least about 95%, 96%, 97%, 98%, 99% or 100% identical to the amino acid sequence of SEQ ID NO:40, and a light chain variable region (VLOX40) comprising an amino acid sequence that is at least about 95%, 96%, 97%, 98%, 99% or 100% identical to the amino acid sequence of SEQ ID NO:41.

In one particular aspect, the antigen binding domain capable of specific binding to OX40 comprises a heavy chain variable region (VHOX40) comprising an amino acid sequence of SEQ ID NO:40 and a light chain variable region (VLOX40) comprising an amino acid sequence of SEQ ID NO:41. In one aspect, the antigen binding domain capable of specific binding to OX40 consists of a heavy chain variable region (VHOX40) comprising an amino acid sequence of SEQ ID NO:40 and a light chain variable region (VLOX40) comprising an amino acid sequence of SEQ ID NO:41.

In one aspect, bispecific antibodies are provided that comprise two antigen binding domains capable of specific binding to OX40 comprises a heavy chain variable region (VHOX40) comprising an amino acid sequence of SEQ ID NO:40 and a light chain variable region (VLOX40) comprising an amino acid sequence of SEQ ID NO:41.

More particularly, the present invention provides a bispecific antibody, wherein the bispecific antibody comprises (a) a first fusion polypeptide comprising an amino acid sequence that is at least about 95%, 96%, 97%, 98%, 99% or 100% identical to the amino acid sequence of SEQ ID NO:54, and a second fusion polypeptide comprising an amino acid sequence that is at least about 95%, 96%, 97%, 98%, 99% or 100% identical to the amino acid sequence of SEQ ID NO:55, (b) a first fusion polypeptide comprising an amino acid sequence that is at least about 95%, 96%, 97%, 98%, 99% or 100% identical to the amino acid sequence of SEQ ID NO:56, and a second fusion polypeptide comprising an amino acid sequence that is at least about 95%, 96%, 97%, 98%, 99% or 100% identical to the amino acid sequence of SEQ ID NO:57, (c) a first fusion polypeptide comprising an amino acid sequence that is at least about 95%, 96%, 97%, 98%, 99% or 100% identical to the amino acid sequence of SEQ ID NO:58, and a second fusion polypeptide comprising an amino acid sequence that is at least about 95%, 96%, 97%, 98%, 99% or 100% identical to the amino acid sequence of SEQ ID NO:59, (d) a first fusion polypeptide comprising an amino acid sequence that is at least about 95%, 96%, 97%, 98%, 99% or 100% identical to the amino acid sequence of SEQ ID NO:60, and a second fusion polypeptide comprising an amino acid sequence that is at least about 95%, 96%, 97%, 98%, 99% or 100% identical to the amino acid sequence of SEQ ID NO:61, (e) a first fusion polypeptide comprising an amino acid sequence that is at least about 95%, 96%, 97%, 98%, 99% or 100% identical to the amino acid sequence of SEQ ID NO:62, and a second fusion polypeptide comprising an amino acid sequence that is at least about 95%, 96%, 97%, 98%, 99% or 100% identical to the amino acid sequence of SEQ ID NO:63, (f) a first fusion polypeptide comprising an amino acid sequence that is at least about 95%, 96%, 97%, 98%, 99% or 100% identical to the amino acid sequence of SEQ ID NO:64, and a second fusion polypeptide comprising an amino acid sequence that is at least about 95%, 96%, 97%, 98%, 99% or 100% identical to the amino acid sequence of SEQ ID NO:65, or (g) a first fusion polypeptide comprising an amino acid sequence that is at least about 95%, 96%, 97%, 98%, 99% or 100% identical to the amino acid sequence of SEQ ID NO:66, and a second fusion polypeptide comprising an amino acid sequence that is at least about 95%, 96%, 97%, 98%, 99% or 100% identical to the amino acid sequence of SEQ ID NO:67.

In one aspect, the bispecific antibody comprises (a) a first fusion polypeptide comprising an amino acid sequence of SEQ ID NO:54, and a second fusion polypeptide comprising an amino acid sequence of SEQ ID NO:55, (b) a first fusion polypeptide comprising an amino acid sequence of SEQ ID NO:56, and a second fusion polypeptide comprising an amino acid sequence of SEQ ID NO:57, (c) a first fusion polypeptide comprising an amino acid sequence of SEQ ID NO:58, and a second fusion polypeptide comprising an amino acid sequence of SEQ ID NO:59, (d) a first fusion polypeptide comprising an amino acid sequence of SEQ ID NO:60, and a second fusion polypeptide comprising an amino acid sequence of SEQ ID NO:61, (e) a first fusion polypeptide comprising an amino acid sequence of SEQ ID NO:62, and a second fusion polypeptide comprising an amino acid sequence of SEQ ID NO:63, (f) a first fusion polypeptide comprising an amino acid sequence of SEQ ID NO:64, and a second fusion polypeptide comprising an amino acid sequence of SEQ ID NO:65, or (g) a first fusion polypeptide comprising an amino acid sequence of SEQ ID NO:66, and a second fusion polypeptide comprising an amino acid sequence of SEQ ID NO:67.

Furthermore, the present invention provides a bispecific antibody, wherein the bispecific antibody comprises (a) a first fusion polypeptide comprising an amino acid sequence that is at least about 95%, 96%, 97%, 98%, 99% or 100% identical to the amino acid sequence of SEQ ID NO:116, and a second fusion polypeptide comprising an amino acid sequence that is at least about 95%, 96%, 97%, 98%, 99% or 100% identical to the amino acid sequence of SEQ ID NO:117, (b) a first fusion polypeptide comprising an amino acid sequence that is at least about 95%, 96%, 97%, 98%, 99% or 100% identical to the amino acid sequence of SEQ ID NO:118, and a second fusion polypeptide comprising an amino acid sequence that is at least about 95%, 96%, 97%, 98%, 99% or 100% identical to the amino acid sequence of SEQ ID NO:119, (c) a first fusion polypeptide comprising an amino acid sequence that is at least about 95%, 96%, 97%, 98%, 99% or 100% identical to the amino acid sequence of SEQ ID NO:120, and a second fusion polypeptide comprising an amino acid sequence that is at least about 95%, 96%, 97%, 98%, 99% or 100% identical to the amino acid sequence of SEQ ID NO:121, (d) a first fusion polypeptide comprising an amino acid sequence that is at least about 95%, 96%, 97%, 98%, 99% or 100% identical to the amino acid sequence of SEQ ID NO:122, and a second fusion polypeptide comprising an amino acid sequence that is at least about 95%, 96%, 97%, 98%, 99% or 100% identical to the amino acid sequence of SEQ ID NO:123, (e) a first fusion polypeptide comprising an amino acid sequence that is at least about 95%, 96%, 97%, 98%, 99% or 100% identical to the amino acid sequence of SEQ ID NO:124, and a second fusion polypeptide comprising an amino acid sequence that is at least about 95%, 96%, 97%, 98%, 99% or 100% identical to the amino acid sequence of SEQ ID NO:125, (f) a first fusion polypeptide comprising an amino acid sequence that is at least about 95%, 96%, 97%, 98%, 99% or 100% identical to the amino acid sequence of SEQ ID NO:126, a second fusion polypeptide comprising an amino acid sequence that is at least about 95%, 96%, 97%, 98%, 99% or 100% identical to the amino acid sequence of SEQ ID NO:127, and a light chain that is at least about 95%, 96%, 97%, 98%, 99% or 100% identical to the amino acid sequence of SEQ ID NO:128, (g) a first fusion polypeptide comprising an amino acid sequence that is at least about 95%, 96%, 97%, 98%, 99% or 100% identical to the amino acid sequence of SEQ ID NO:129, and a second fusion polypeptide comprising an amino acid sequence that is at least about 95%, 96%, 97%, 98%, 99% or 100% identical to the amino acid sequence of SEQ ID NO:130, (h) a first fusion polypeptide comprising an amino acid sequence that is at least about 95%, 96%, 97%, 98%, 99% or 100% identical to the amino acid sequence of SEQ ID NO:131, and a second fusion polypeptide comprising an amino acid sequence that is at least about 95%, 96%, 97%, 98%, 99% or 100% identical to the amino acid sequence of SEQ ID NO:132, or (i) a first fusion polypeptide comprising an amino acid sequence that is at least about 95%, 96%, 97%, 98%, 99% or 100% identical to the amino acid sequence of SEQ ID NO:133, and a second fusion polypeptide comprising an amino acid sequence that is at least about 95%, 96%, 97%, 98%, 99% or 100% identical to the amino acid sequence of SEQ ID NO:134.

In one aspect, the bispecific antibody comprises (a) a first fusion polypeptide comprising an amino acid sequence of SEQ ID NO:116, and a second fusion polypeptide comprising an amino acid sequence of SEQ ID NO:117, (b) a first fusion polypeptide comprising an amino acid sequence of SEQ ID NO:118, and a second fusion polypeptide comprising an amino acid sequence of SEQ ID NO:119, (c) a first fusion polypeptide comprising an amino acid sequence of SEQ ID NO:120, and a second fusion polypeptide comprising an amino acid sequence of SEQ ID NO:121, (d) a first fusion polypeptide comprising an amino acid sequence of SEQ ID NO:122, and a second fusion polypeptide comprising an amino acid sequence of SEQ ID NO:123, (e) a first fusion polypeptide comprising an amino acid sequence of SEQ ID NO:124, and a second fusion polypeptide comprising an amino acid sequence of SEQ ID NO:125, (f) a first fusion polypeptide comprising an amino acid sequence of SEQ ID NO:126, a second fusion polypeptide comprising an amino acid sequence of SEQ ID NO:127, and a light chain comprising the amino acid sequence of SEQ ID NO:128, (g) a first fusion polypeptide comprising an amino acid sequence of SEQ ID NO:129, and a second fusion polypeptide comprising an amino acid sequence of SEQ ID NO:130, (h) a first fusion polypeptide comprising an amino acid sequence of SEQ ID NO:131, and a second fusion polypeptide comprising an amino acid sequence of SEQ ID NO:132, or (i) a first fusion polypeptide comprising an amino acid sequence of SEQ ID NO:133, and a second fusion polypeptide comprising an amino acid sequence of SEQ ID NO:134.

Bispecific Antibodies Binding to 4-1BB and FAP

In some aspects, provided is a bispecific antibody wherein the antigen binding domain capable of specific binding to a first target is an antigen binding domain capable of specific binding to a TNF receptor, wherein the costimulatory TNF receptor is 4-1BB. In one aspect, provided is a bispecific antibody, wherein the antigen binding domain capable of specific binding to a first target is an antigen binding domain capable of specific binding to 4-1BB. Particularly, the bispecific antibody of the invention comprises two antigen binding domains capable of specific binding to 4-1BB.

In some aspects, the antigen binding domain capable of specific binding to 4-1BB a heavy chain variable region ($V_H$4-1BB) comprising (i) CDR-H1 comprising the amino acid sequence of SEQ ID NO:135, (ii) CDR-H2 comprising the amino acid sequence of SEQ ID NO:136, and (iii) CDR-H3 comprising the amino acid sequence of SEQ ID NO:137, and a light chain variable region ($V_L$4-1BB) comprising (iv) CDR-L1 comprising the amino acid sequence of SEQ ID NO:138, (v) CDR-L2 comprising the amino acid sequence of SEQ ID NO:139, and (vi) CDR-L3 comprising the amino acid sequence of SEQ ID NO:140. In one aspect, the antigen binding domain capable of specific binding to 4-1BB comprises a heavy chain variable region ($V_H$4-1BB) comprising an amino acid sequence that is at least about 95%, 96%, 97%, 98%, 99% or 100% identical to the amino acid sequence of SEQ ID NO:141, and a light chain variable region (VL4-1BB) comprising an amino acid sequence that is at least about 95%, 96%, 97%, 98%, 99% or 100% identical to the amino acid sequence of SEQ ID NO:142.

In one particular aspect, the antigen binding domain capable of specific binding to 4-1BB comprises a heavy chain variable region ($V_H$4-1BB) comprising an amino acid sequence of SEQ ID NO:141 and a light chain variable region ($V_L$4-1BB) comprising an amino acid sequence of SEQ ID NO:142. In one aspect, the antigen binding domain capable of specific binding to 4-1BB consists of a heavy chain variable region ($V_H$4-1BB) comprising an amino acid sequence of SEQ ID NO:141 and a light chain variable region ($V_L$4-1BB) comprising an amino acid sequence of SEQ ID NO:142.

Particularly, the present invention provides a bispecific antibody, wherein the bispecific antibody comprises (a) a first fusion polypeptide comprising an amino acid sequence that is at least about 95%, 96%, 97%, 98%, 99% or 100% identical to the amino acid sequence of SEQ ID NO:143, and a second fusion polypeptide comprising an amino acid sequence that is at least about 95%, 96%, 97%, 98%, 99% or 100% identical to the amino acid sequence of SEQ ID NO:144, or (b) a first fusion polypeptide comprising an amino acid sequence that is at least about 95%, 96%, 97%, 98%, 99% or 100% identical to the amino acid sequence of SEQ ID NO:145, and a second fusion polypeptide comprising an amino acid sequence that is at least about 95%, 96%, 97%, 98%, 99% or 100% identical to the amino acid sequence of SEQ ID NO:146.

In one aspect, the bispecific antibody comprises (a) a first fusion polypeptide comprising an amino acid sequence of SEQ ID NO:143, and a second fusion polypeptide comprising an amino acid sequence of SEQ ID NO:144, or (b) a first fusion polypeptide comprising an amino acid sequence of SEQ ID NO:145, and a second fusion polypeptide comprising an amino acid sequence of SEQ ID NO:146.

Bispecific Antibodies Binding to CD40 and FAP

In some aspects, provided is a bispecific antibody wherein the antigen binding domain capable of specific binding to a first target is an antigen binding domain capable of specific binding to a TNF receptor, wherein the costimulatory TNF receptor is CD40. In one aspect, provided is a bispecific antibody, wherein the antigen binding domain capable of specific binding to a first target is an antigen binding domain capable of specific binding to CD40. Particularly, the bispecific antibody of the invention comprises two antigen binding domains capable of specific binding to CD40.

In some aspects, the antigen binding domain capable of specific binding to CD40 comprises a heavy chain variable region (VHCD40) comprising (i) CDR-H1 comprising the amino acid sequence of SEQ ID NO:147, (ii) CDR-H2 comprising the amino acid sequence of SEQ ID NO:148, and (iii) CDR-H3 comprising the amino acid sequence of SEQ ID NO:149, and a light chain variable region (VLCD40) comprising (iv) CDR-L1 comprising the amino acid sequence of SEQ ID NO:150, (v) CDR-L2 comprising the amino acid sequence of SEQ ID NO:151, and (vi) CDR-L3 comprising the amino acid sequence of SEQ ID NO:152. In one aspect, the antigen binding domain capable of specific binding to CD40 comprises a heavy chain variable region (VHCD40) comprising an amino acid sequence that is at least about 95%, 96%, 97%, 98%, 99% or 100% identical to the amino acid sequence of SEQ ID NO:153, and a light chain variable region (VLCD40) comprising an amino acid sequence that is at least about 95%, 96%, 97%, 98%, 99% or 100% identical to the amino acid sequence of SEQ ID NO:154.

In another aspect, the antigen binding domain capable of specific binding to a first target is an antigen binding domain capable of specific binding to CD40 comprises
(i) a heavy chain variable region (VHCD40) comprising an amino acid sequence selected from the group consisting of SEQ ID NO:167, SEQ ID NO:168, SEQ ID NO:169 and SEQ ID NO:170, and a light chain variable region (VLCD40) comprising the amino acid sequence selected from the group consisting of SEQ ID NO:171, SEQ ID NO:172, SEQ ID NO:173, and SEQ ID NO:174, or (ii) a heavy chain variable region (VHCD40) comprising an amino acid sequence selected from the group consisting of SEQ ID NO:175, SEQ ID NO:176, SEQ ID NO:177, SEQ ID NO:178, SEQ ID NO:179 and SEQ ID NO:180, and a light chain variable region (VLCD40) comprising the amino acid sequence selected from the group consisting of SEQ ID NO:181, SEQ ID NO:182, SEQ ID NO:183, and SEQ ID NO:184.

In one aspect, the antigen binding domain capable of specific binding to a first target is an antigen binding domain capable of specific binding to CD40 comprises (a) a heavy chain variable region (VHCD40) comprising an amino acid sequence of SEQ ID NO:153, and a light chain variable region (VLCD40) comprising an amino acid sequence of SEQ ID NO:154, or (b) a heavy chain variable region (VHCD40) comprising an amino acid sequence of SEQ ID NO:167, and a light chain variable region (VLCD40) comprising an amino acid sequence of SEQ ID NO:171.

Particularly, the present invention provides a bispecific antibody, wherein the bispecific antibody comprises (a) a first fusion polypeptide comprising an amino acid sequence that is at least about 95%, 96%, 97%, 98%, 99% or 100% identical to the amino acid sequence of SEQ ID NO:155, and a second fusion polypeptide comprising an amino acid sequence that is at least about 95%, 96%, 97%, 98%, 99% or 100% identical to the amino acid sequence of SEQ ID NO:156, (b) a first fusion polypeptide comprising an amino acid sequence that is at least about 95%, 96%, 97%, 98%, 99% or 100% identical to the amino acid sequence of SEQ ID NO:157, and a second fusion polypeptide comprising an amino acid sequence that is at least about 95%, 96%, 97%, 98%, 99% or 100% identical to the amino acid sequence of SEQ ID NO:158, (c) a first fusion polypeptide comprising an amino acid sequence that is at least about 95%, 96%, 97%, 98%, 99% or 100% identical to the amino acid sequence of SEQ ID NO:159, and a second fusion polypeptide comprising an amino acid sequence that is at least about 95%, 96%, 97%, 98%, 99% or 100% identical to the amino acid sequence of SEQ ID NO:160, (d) a first fusion polypeptide comprising an amino acid sequence that is at least about 95%, 96%, 97%, 98%, 99% or 100% identical to the amino acid sequence of SEQ ID NO:161, and a second fusion polypeptide comprising an amino acid sequence that is at least about 95%, 96%, 97%, 98%, 99% or 100% identical to the amino acid sequence of SEQ ID NO:162, (e) a first fusion polypeptide comprising an amino acid sequence that is at least about 95%, 96%, 97%, 98%, 99% or 100% identical to the amino acid sequence of SEQ ID NO:163, and a second fusion polypeptide comprising an amino acid sequence that is at least about 95%, 96%, 97%, 98%, 99% or 100% identical to the amino acid sequence of SEQ ID NO:164, or (f) a first fusion polypeptide comprising an amino acid sequence that is at least about 95%, 96%, 97%, 98%, 99% or 100% identical to the amino acid sequence of SEQ ID NO:165, and a second fusion polypeptide comprising an amino acid sequence that is at least about 95%, 96%, 97%, 98%, 99% or 100% identical to the amino acid sequence of SEQ ID NO:166.

In one aspect, the the bispecific antibody comprises (a) a first fusion polypeptide comprising an amino acid sequence of SEQ ID NO:155, and a second fusion polypeptide comprising an amino acid sequence of SEQ ID NO:156, (b) a first fusion polypeptide comprising an amino acid sequence of SEQ ID NO:157, and a second fusion polypeptide comprising an amino acid sequence of SEQ ID NO:158, (c) a first fusion polypeptide comprising an amino acid sequence of SEQ ID NO:159, and a second fusion polypeptide comprising an amino acid sequence of SEQ ID NO:160, (d) a first fusion polypeptide comprising an amino acid sequence of SEQ ID NO:161, and a second fusion polypeptide comprising an amino acid sequence of SEQ ID NO:162, (e) a first fusion polypeptide comprising an amino acid sequence of SEQ ID NO:163, and a second fusion polypeptide comprising an amino acid sequence of SEQ ID NO:164, or (f) a first fusion polypeptide comprising an amino acid sequence of SEQ ID NO:165, and a second fusion polypeptide comprising an amino acid sequence of SEQ ID NO:166.

Modifications in the Fab Domains

In one aspect, the invention relates to a bispecific antibody comprising (a) two Fab fragments capable of specific binding to OX40 and (b) one Fab fragment capable of specific binding to FAP, wherein in one of (a) and (b) in the Fab fragments either the variable domains VH and VL or the constant domains CH1 and CL are exchanged. The bispecific antibodies are prepared according to the Crossmab technology.

Multispecific antibodies with a domain replacement/exchange in one binding arm (CrossMabVH-VL or CrossMabCH-CL) are described in detail in WO2009/080252 and Schaefer, W. et al, PNAS, 108 (2011) 11187-11192. They clearly reduce the byproducts caused by the mismatch of a light chain against a first antigen with the wrong heavy chain against the second antigen (compared to approaches without such domain exchange).

In one aspect, the invention relates to a bispecific antibody comprising (a) two Fab fragments capable of specific binding to OX40 and (b) a cross-Fab fragment capable of specific binding to FAP, wherein the constant domains CL (Ckappa) and CH1 are replaced by each other so that the CH1 domain is fused to the VL domain and the CL domain is fused to the VH domain.

In another aspect, the invention relates to a bispecific antibody, comprising (a) two cross-Fab fragments capable of specific binding to OX40, wherein the VH domain is fused to the CL (Ckappa) domain and the VL domain is fused to the CH1 domain and (b) a Fab fragment capable of specific binding to FAP.

In another aspect, and to further improve correct pairing, the bispecific antibody can contain different charged amino acid substitutions (so-called "charged residues"). These modifications are introduced in the crossed or non-crossed CH1 and CL domains. In a particular aspect, the invention relates to a bispecific antibody, wherein in one of CL domains the amino acid at position 123 (EU numbering) has been replaced by arginine (R) and the amino acid at position 124 (EU numbering) has been substituted by lysine (K) (positive charges) and wherein in one of the CH1 domains the amino acids at position 147 (EU numbering) and at position 213 (EU numbering) have been substituted by glutamic acid (E) (negative charges).

More particularly, the invention relates to a bispecific antigen binding molecule comprising a Fab, wherein in the CL domain the amino acid at position 123 (EU numbering) has been replaced by arginine (R) and the amino acid at position 124 (EU numbering) has been substituted by lysine (K), and wherein in the CH1 domain the amino acids at position 147 (EU numbering) and at position 213 (EU numbering) have been substituted by glutamic acid (E).

Accordingly, in some embodiments one or more of the Fab fragments (e.g. Fab fragments capable of specific binding to OX40) of the bispecific antigen binding molecule of the present invention comprise a CL domain comprising an arginine (R) at amino acid at position 123 (EU numbering) and a lysine (K) at amino acid at position 124 (EU numbering), and a CH1 domain comprising a glutamic acid (E) at amino acid at position 147 (EU numbering) and a glutamic acid (E) at amino acid at position 213 (EU numbering).

Polynucleotides

The invention further provides isolated nucleic acid encoding a bispecific antibody of the invention as described herein, or a fragment thereof.

The isolated nucleic acid encoding a bispecific antibody of the invention may be expressed as a single polynucleotide that encodes the entire antigen binding molecule or as multiple (e.g., two or more) polynucleotides that are co-expressed. Polypeptides encoded by polynucleotides that are co-expressed may associate through, e.g., disulfide bonds or other means to form a functional antigen binding molecule. When co-expressed, the fusion polypeptides will associate to form the antigen binding domain capable of specific binding to the second target (e.g. FAP). The antigen binding domains capable of specific binding to the first target (e.g. OX40) may be encoded by one polynucleotide. When co-expressed, the fusion polypeptides will associate to form the bispecific antibody.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

According to another aspect of the invention, there is provided an isolated polynucleotide encoding a fusion polypeptide as described herein before. The invention further provides a vector, particularly an expression vector, comprising the isolated polynucleotide of the invention and a host cell comprising the isolated polynucleotide or the vector of the invention. In some embodiments the host cell is a eukaryotic cell, particularly a mammalian cell.

In another aspect, provided is a method for producing the bispecific antibody of the invention, comprising the steps of (i) culturing the host cell of the invention under conditions suitable for expression of said antibody, and (ii) isolating said bispecific antibody. The invention also encompasses a bispecific antibody produced by the method of the invention.

Recombinant Methods

Bispecific antigen binding molecules of the invention may be obtained, for example, by solid-state peptide synthesis (e.g. Merrifield solid phase synthesis) or recombinant production. For recombinant production one or more polynucleotide encoding the antigen binding molecule or polypeptide fragments thereof, e.g., as described above, is isolated and inserted into one or more vectors for further cloning and/or expression in a host cell. Such polynucleotide may be readily isolated and sequenced using conventional procedures. In one aspect of the invention, a vector, preferably an expression vector, comprising one or more of the polynucleotides of the invention is provided. Methods which are well known to those skilled in the art can be used to construct expression vectors containing the coding sequence of the bispecific antigen binding molecule (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y. (1989). The expression vector can be part of a plasmid, virus, or may be a nucleic acid fragment. The expression vector includes an expression cassette into which the polynucleotide encoding the bispecific antigen binding molecule or polypeptide fragments thereof (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the bispecific antigen binding molecule of the invention or polypeptide fragments thereof, or variants or derivatives thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription.

Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit α-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the bispecific antigen binding molecule or polypeptide fragments thereof is desired, DNA encoding a signal sequence may be placed upstream of the nucleic acid encoding a bispecific antigen binding molecule of the invention or polypeptide fragments thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the fusion protein may be included within or at the ends of the polynucleotide encoding a bispecific antigen binding molecule of the invention or polypeptide fragments thereof.

In a further aspect of the invention, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one aspect, a host cell comprises (e.g. has been transformed or transfected with) a vector comprising a polynucleotide that encodes (part of) a bispecific antigen binding molecule of the invention. As used herein, the term "host cell" refers to any kind of cellular system which can be engineered to generate the fusion proteins of the invention or fragments thereof. Host cells suitable for replicating and for supporting expression of antigen binding molecules are well known in the art. Such cells may be transfected or transduced as appropriate with the particular expression vector and large quantities of vector containing cells can be grown for seeding large scale fermenters to obtain sufficient quantities of the antigen binding molecule for clinical applications. Suitable host cells include prokaryotic microorganisms, such as E. coli, or various eukaryotic cells, such as Chinese hamster ovary cells (CHO), human embryonic kidney (HEK) cells, insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gemgross, Nat Biotech 22, 1409-1414 (2004), and Li et al., Nat Biotech 24, 210-215 (2006).

Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts. See e.g. U.S. Pat. Nos. 5,959,177, 6,040, 498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr- CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., YO, NS0, Sp20 cell). Standard technologies are known in the art to express foreign genes in these systems. Cells expressing a polypeptide comprising either the heavy or the light chain of an antigen binding domain, may be engineered so as to also express the other of the immunoglobulin chains such that the expressed product is an antigen binding domain that has both a heavy and a light chain.

In another aspect, provided is a method for producing the bispecific antibody of the invention, comprising the steps of (i) culturing the host cell of the invention under conditions suitable for expression of said bispecific antibody, and (ii) isolating said bispecific antibody form the host cell or host cell culture medium.

The components of the bispecific antibody are genetically fused to each other. Bispecific antigen binding molecules can be designed such that its components are fused directly to each other or indirectly through a linker sequence. The composition and length of the linker may be determined in accordance with methods well known in the art and may be tested for efficacy. Examples of linker sequences between different components of bispecific antigen binding molecules are found in the sequences provided herein. Additional sequences may also be included to incorporate a cleavage site to separate the individual components of the fusion if desired, for example an endopeptidase recognition sequence.

In certain aspects, the antigen binding domain capable of specific binding to FAP (e.g. Fab fragments or scFv) forming part of the antibody comprises at least an immunoglobulin variable region capable of binding to FAP. Similarly, in certain aspects, the moieties capable of specific binding to OX40 (e.g. Fab fragments or scFv) forming part of the bispecific antibody comprise at least an immunoglobulin variable region capable of binding to OX40. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,816,567) or can be obtained, for example, by screening combinatorial libraries comprising variable heavy chains and variable light chains (see e.g. U.S. Pat. No. 5,969,108 to McCafferty).

In certain aspects, the antigen binding domains capable of specific binding to the relevant target (e.g. Fab fragments or scFv) comprised in the antigen binding molecules of the present invention are engineered to have enhanced binding affinity according to, for example, the methods disclosed in PCT publication WO 2012/020006 (see Examples relating to affinity maturation) or U.S. Pat. Appl. Publ. No. 2004/0132066. The ability of the antigen binding molecules of the invention to bind to a specific antigenic determinant can be measured either through an enzyme-linked immunosorbent assay (ELISA) or other techniques familiar to one of skill in the art, e.g. surface plasmon resonance technique (Liljeblad, et al., Glyco J 17, 323-329 (2000)), and traditional binding assays (Heeley, Endocr Res 28, 217-229 (2002)). Competition assays may be used to identify an antigen binding molecule that competes with a reference antibody for binding to a particular antigen. In certain embodiments, such a competing antigen binding molecule binds to the same epitope (e.g. a linear or a conformational epitope) that is bound by the reference antigen binding molecule. Detailed exemplary methods for mapping an epitope to which an antigen binding molecule binds are provided in Morris (1996) "Epitope Mapping Protocols", in Methods in Molecular Biology vol. 66 (Humana Press, Totowa, N.J.). In an exemplary competition assay, immobilized antigen is incubated in a solution comprising a first labeled antigen binding molecule that binds to the antigen and a second unlabeled antigen binding molecule that is being tested for its ability to compete with the first antigen binding molecule for binding to the antigen. The second antigen binding molecule may be present in a hybridoma supernatant. As a control, immobilized antigen is incubated in a solution comprising the first labeled antigen binding molecule but not the second unlabeled antigen binding molecule. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antigen binding molecule is competing with the first antigen binding molecule for binding to the antigen. See Harlow and Lane (1988) Antibodies: A Laboratory Manual ch. 14 (Cold Spring Harbor Laboratory, Cold Spring Harbor, N.Y.).

Bispecific antibodies of the invention prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the bispecific antigen binding molecule binds. For example, for affinity chromatography purification of fusion proteins of the invention, a matrix with protein A or protein G may be used. Sequential Protein A or G affinity chromatography and size exclusion chromatography can be used to isolate an antigen binding molecule essentially as described in the Examples. The purity of the bispecific antigen binding molecule or fragments thereof can be determined by any of a variety of well-known analytical methods including gel electrophoresis, high pressure liquid chromatography, and the like. For example, the bispecific antigen binding molecules expressed as described in the Examples were shown to be intact and properly assembled as demonstrated by reducing and non-reducing SDS-PAGE.

The invention also encompasses a bispecific antibodies produced by the methods of the invention.

Assays

The bispecific antigen binding molecules provided herein may be identified, screened for, or characterized for their physical/chemical properties and/or biological activities by various assays known in the art.

1. Affinity Assays

The affinity of the bispecific antigen binding molecule provided herein for OX40 or FAP can be determined in accordance with the methods set forth in the Examples by surface plasmon resonance (SPR), using standard instrumentation such as a BIAcore instrument (GE Healthcare), and receptors or target proteins such as may be obtained by recombinant expression. A specific illustrative and exemplary embodiment for measuring binding affinity is described in Example 3. According to one aspect, $K_D$ is measured by surface plasmon resonance using a BIACORE® T200 machine (GE Healthcare) at 25° C.

2. Binding Assays and Other Assays

Binding of the bispecific antigen binding molecule provided herein to the corresponding OX40 and/or FAP expressing cells may be evaluated using cell lines expressing the particular receptor or target antigen, for example by flow cytometry (FACS). In one aspect, fresh peripheral blood mononuclear cells (PBMCs) expressing OX40 are used in the binding assay. These cells are used directly after isolation (naïve PMBCs) or after stimulation (activated PMBCs). A specific illustrative and exemplary embodiment for measuring binding to OX40 is described in Example 4.1.

In a further aspect, cancer cell lines expressing FAP were used to demonstrate the binding of the bispecific antibodies to FAP (see Example 4.2).

In another aspect, competition assays may be used to identify an antigen binding molecule that competes with a specific antibody or antigen binding molecule for binding to FAP or OX40, respectively. In certain embodiments, such a competing antibody binds to the same epitope (e.g., a linear or a conformational epitope) that is bound by a specific anti-FAP antibody or a specific anti-OX40 antibody. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

3. Activity Assays

In one aspect, assays are provided for identifying bispecific antigen binding molecules that bind to FAP and to OX40 having biological activity. Biological activity may include, e.g., agonistic signalling through OX40 on cells expressing OX40. Bispecific antigen binding molecules identified by the assays as having such biological activity in vitro are also provided. In particular, a reporter cell assay detecting NFκB activation in Hela cells expressing human OX40 and co-cultured with FAP-expressing tumor cells is provided (see e.g. Example 5.1).

In another aspect, assays are provided for identifying bispecific antigen binding molecules that bind to FAP and to 4-1BB having biological activity. In particular, a reporter cell assay detecting NF-κB activation in human 4-1BB and NFκB-luciferase reporter gene expressing reporter cell line Jurkat-hu4-1BB-NFκB-luc2 is provided (see e.g. Example 7.2).

In another aspect, assays are provided for identifying bispecific antigen binding molecules that bind to FAP and to CD40 having biological activity. In particular, a method of measuring the activation of human B cells by FAP-targeted anti-human CD40 binding molecules using FAP-coated Dynabeads® as source of antigen is provided (see e.g. Example 10.1).

In certain aspects, bispecific antigen binding molecules of the invention are tested for such biological activity. Assays for detecting the biological activity of the molecules of the invention are those described in Example 5. Furthermore, assays for detecting cell lysis (e.g. by measurement of LDH release), induced apoptosis kinetics (e.g. by measurement of Caspase 3/7 activity) or apoptosis (e.g. using the TUNEL assay) are well known in the art. In addition, the biological activity of such complexes can be assessed by evaluating their effects on survival, proliferation and lymphokine secretion of various lymphocyte subsets such as NK cells, NKT-cells or γδ T-cells or assessing their capacity to modulate phenotype and function of antigen presenting cells such as dendritic cells, monocytes/macrophages or B-cells.

Pharmaceutical Compositions, Formulations and Routes of Administation

In a further aspect, the invention provides pharmaceutical compositions comprising any of the bispecific antibodies provided herein, e.g., for use in any of the below therapeutic methods. In one embodiment, a pharmaceutical composition comprises any of the bispecific antibodies provided herein and at least one pharmaceutically acceptable excipient. In another embodiment, a pharmaceutical composition comprises any of the bispecific antibodies provided herein and at least one additional therapeutic agent, e.g., as described below.

Pharmaceutical compositions of the present invention comprise a therapeutically effective amount of one or more bispecific antibodies dissolved or dispersed in a pharmaceutically acceptable excipient. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one bispecific antibody and optionally an additional active ingredient will be known to those of skill in the art in light of the present disclosure, as exemplified by Remington's Pharmaceutical Sciences, 18th Ed. Mack Printing Company, 1990, incorporated herein by reference. In particular, the compositions are lyophilized formulations or aqueous solutions. As used herein, "pharmaceutically acceptable excipient" includes any and all solvents, buffers, dispersion media, coatings, surfactants, antioxidants, preservatives (e.g. antibacterial agents, antifungal agents), isotonic agents, salts, stabilizers and combinations thereof, as would be known to one of ordinary skill in the art.

Parenteral compositions include those designed for administration by injection, e.g. subcutaneous, intradermal, intralesional, intravenous, intraarterial intramuscular, intrathecal or intraperitoneal injection. For injection, the bispecific antibodies of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the fusion proteins may be in powder form for constitution with a suitable vehicle, e.g., sterile pyrogen-free water, before use. Sterile injectable solutions are prepared by incorporating the fusion proteins of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable excipients include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

Exemplary pharmaceutically acceptable excipients herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171, 586 and WO2006/044908, the latter formulations including a histidine-acetate buffer.

In addition to the compositions described previously, the fusion proteins may also be formulated as a depot preparation. Such long acting formulations may be administered by implantation (for example subcutaneously or intramuscularly) or by intramuscular injection. Thus, for example, the fusion proteins may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the fusion proteins of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The bispecific antibodies may be formulated into a composition in a free acid or base, neutral or salt form. Pharmaceutically acceptable salts are salts that substantially retain the biological activity of the free acid or base. These include the acid addition salts, e.g. those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

The composition herein may also contain more than one active ingredients as necessary for the particular indication being treated, preferably those with complementary activities that do not adversely affect each other. Such active ingredients are suitably present in combination in amounts that are effective for the purpose intended.

The formulations to be used for in vivo administration are generally sterile. Sterility may be readily accomplished, e.g., by filtration through sterile filtration membranes.

Therapeutic Methods and Compositions

Any of the bispecific antibodies provided herein may be used in therapeutic methods. For use in therapeutic methods, the antigen binding molecules of the invention can be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, the bispecific antibodies of the invention are provided for use as a medicament. In further aspects, the bispecific antigen binding molecules of the invention are provided for use in treating a disease, in particular for use in the treatment of cancer. In certain embodiments, the bispecific antibodies of the invention are provided for use in a method of treatment. In one embodiment, the invention provides a bispecific antibody as described herein for use in the treatment of a disease in an individual in need thereof. In certain embodiments, the invention provides a bispecific antibody for use in a method of treating an individual having a disease comprising administering to the individual a therapeutically effective amount of the bispecific antigen binding molecule. In certain embodiments the disease to be treated is cancer. In certain embodiments the disease to be treated is a proliferative disorder, particularly cancer. Examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that can be treated using a bispecific antigen binding molecule of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer. The subject, patient, or "individual" in need of treatment is typically a mammal, more specifically a human.

Also encompassed by the invention is the bispecific antibody of the invention, or the pharmaceutical composition of the invention, for use in up-regulating or prolonging cytotoxic T cell activity.

In a further aspect, the invention provides for the use of a bispecific antibody of the invention in the manufacture or preparation of a medicament for the treatment of a disease in an individual in need thereof. In one aspect, the medicament is for use in a method of treating a disease comprising administering to an individual having the disease a therapeutically effective amount of the medicament. In certain embodiments the disease to be treated is a proliferative disorder, particularly cancer. Examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that can be treated using a bispecific antigen binding molecule of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer. A skilled artisan readily recognizes that in many cases the bispecific antigen binding molecule may not provide a cure but may only provide partial benefit. In some embodiments, a physiological change having some benefit is also considered therapeutically beneficial. Thus, in some embodiments, an amount of bispecific antibody that provides a physiological change is considered an "effective amount" or a "therapeutically effective amount". In any of the above embodiments the individual is preferably a mammal, particularly a human.

In a further aspect, the invention relates to the use of a bispecific antibody as described herein in the manufacture or preparation of a medicament for the treatment of infectious diseases, in particular for the treatment of viral infections or for the treatment of autoimmune diseases, for example Lupus disease.

In a further aspect, the invention provides a method for treating a disease in an individual, comprising administering to said individual a therapeutically effective amount of a bispecific antigen binding molecule of the invention. In one embodiment a composition is administered to said individual, comprising a fusion protein of the invention in a pharmaceutically acceptable form. In certain embodiments the disease to be treated is a proliferative disorder. In a particular embodiment the disease is cancer. In certain embodiments the method further comprises administering to the individual a therapeutically effective amount of at least one additional therapeutic agent, e.g. an anti-cancer agent if the disease to be treated is cancer. An "individual" according to any of the above embodiments may be a mammal, preferably a human.

For the prevention or treatment of disease, the appropriate dosage of a bispecific antibody of the invention (when used alone or in combination with one or more other additional therapeutic agents) will depend on the type of disease to be treated, the route of administration, the body weight of the patient, the type of fusion protein, the severity and course of the disease, whether the fusion protein is administered for preventive or therapeutic purposes, previous or concurrent therapeutic interventions, the patient's clinical history and response to the fusion protein, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The bispecific antibody is suitably administered to the patient at one time or over a series of treatments. Depending on the type and severity of the disease, about 1 μg/kg to 15 mg/kg (e.g. 0.1 mg/kg-10 mg/kg) of the antigen binding molecule can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the fusion protein would be in the range from about 0.005 mg/kg to about 10 mg/kg. In other examples, a dose may also comprise from about 1 μg/kg body weight, about 5 μg/kg body weight, about 10 μg/kg body weight, about 50 μg/kg body weight, about 100 μg/kg body weight, about 200 μg/kg body weight, about 350 μg/kg body weight, about 500 μg/kg body weight, about 1 mg/kg body weight, about 5 mg/kg body weight, about 10 mg/kg body weight, about 50 mg/kg body weight, about 100 mg/kg body weight, about 200 mg/kg body weight, about 350 mg/kg body weight, about 500 mg/kg body weight, to about 1000 mg/kg body weight or more per administration, and any range derivable therein. In examples of a derivable range from the numbers listed herein, a range of about 5 mg/kg body weight to about 100 mg/kg body weight, about 5 μg/kg body weight to about 500 mg/kg body weight etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the bispecific antigen binding molecule). An initial higher loading dose, followed by one or more lower doses may be administered. However, other dosage regimens may be useful. The progress of this therapy is easily monitored by conventional techniques and assays.

The bispecific antibody of the invention will generally be used in an amount effective to achieve the intended purpose. For use to treat or prevent a disease condition, the bispecific antigen binding molecules of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data. Dosage amount and interval may be adjusted individually to provide plasma levels of the bispecific antigen binding molecules which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

In cases of local administration or selective uptake, the effective local concentration of the bispecific antigen binding molecules may not be related to plasma concentration. One skilled in the art will be able to optimize therapeutically effective local dosages without undue experimentation.

A therapeutically effective dose of the bispecific antibody described herein will generally provide therapeutic benefit without causing substantial toxicity. Toxicity and therapeutic efficacy of a fusion protein can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Bispecific antigen binding molecules that exhibit large therapeutic indices are preferred. In one embodiment, the bispecific antigen binding molecule according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with the bispecific antigen binding molecules of the invention will know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The bispecific antibodies of the invention may be administered in combination with one or more other agents in therapy. For instance, a bispecific antibody of the invention may be co-administered with at least one additional therapeutic agent. The term "therapeutic agent" encompasses any agent that can be administered for treating a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is another anti-cancer agent.

Such other agents are suitably present in combination in amounts that are effective for the purpose intended. The effective amount of such other agents depends on the amount of fusion protein used, the type of disorder or treatment, and other factors discussed above. The bispecific antigen binding molecules are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the bispecific antigen binding molecule of the invention can occur prior to, simultaneously, and/or following, administration of the additional therapeutic agent and/or adjuvant.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper that is pierceable by a hypodermic injection needle). At least one active agent in the composition is a bispecific antibody as described herein.

The label or package insert indicates that the composition is used for treating the condition of choice. Moreover, the article of manufacture may comprise (a) a first container with a composition contained therein, wherein the composition comprises a bispecific antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition.

Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

TABLE B

Sequences

| SEQ ID NO: | Name | Sequence |
|---|---|---|
| 1 | FAP(4B9) CDR-H1 | SYAMS |
| 2 | FAP(4B9) CDR-H2 | AIIGSGASTYYADSVKG |
| 3 | FAP(4B9) CDR-H3 | GWFGGFNY |
| 4 | FAP(4B9) CDR-L1 | RASQSVTSSYLA |
| 5 | FAP(4B9) CDR-L2 | VGSRRAT |
| 6 | FAP(4B9) CDR-L3 | QQGIMLPPT |
| 7 | FAP(4B9) VH | EVQLLESGGGLVQPGGSLRLSCAASGFTFSSYAMSWVRQ APGKGLEWVSAIIGSGASTYYADSVKGRFTISRDNSKNT LYLQMNSLRAEDTAVYYCAKGWFGGFNYWGQGTLVTVSS |
| 8 | FAP(4B9) VL | EIVLTQSPGTLSLSPGERATLSCRASQSVTSSYLAWYQQ KPGQAPRLLINVGSRRATGIPDRFSGSGSGTDFTLTISR LEPEDFAVYYCQQGIMLPPTFGQGTKVEIK |
| 9 | FAP (28H1) CDR-H1 | SHAMS |
| 10 | FAP (28H1) CDR-H2 | AIWASGEQYYADSVKG |
| 11 | FAP (28H1) CDR-H3 | GWLGNFDY |
| 12 | FAP (28H1) CDR-L1 | RASQSVSRSYLA |
| 13 | FAP (28H1) CDR-L2 | GASTRAT |
| 14 | FAP (28H1) CDR-L3 | QQGQVIPPT |
| 15 | FAP(28H1) VH | EVQLLESGGGLVQPGGSLRLSCAASGFTFSSHAMSWVRQ APGKGLEWVSAIWASGEQYYADSVKGRFTISRDNSKNTL YLQMNSLRAEDTAVYYCAKGWLGNFDYWGQGTLVTVSS |
| 16 | FAP(28H1) VL | EIVLTQSPGTLSLSPGERATLSCRASQSVSRSYLAWYQQ KPGQAPRLLIIGASTRATGIPDRFSGSGSGTDFTLTISR LEPEDFAVYYCQQGQVIPPTFGQGTKVEIK |
| 17 | OX40(8H9, 49B4, 1G4, 20B7) CDR-H1 | SYAIS |
| 18 | OX40(CLC-563, CLC-564, 17A9) CDR-H1 | SYAMS |
| 19 | OX40(8H9, 49B4, 1G4, 20B7) CDR-H2 | GIIPIFGTANYAQKFQG |
| 20 | OX40(CLC-563, CLC-564, 17A9) CDR-H2 | AISGSGGSTYYADSVKG |
| 21 | OX40(8H9) CDR-H3 | EYGWMDY |
| 22 | OX40(49B4) CDR-H3 | EYYRGPYDY |
| 23 | OX40(1G4) CDR-H3 | EYGSMDY |
| 24 | OX40(20B7) CDR-H3 | VNYPYSYWGDFDY |
| 25 | OX40(CLC-563) CDR-H3 | DVGAFDY |
| 26 | OX40(CLC-564) CDR-H3 | DVGPFDY |
| 27 | OX40(17A9)-CDR-H3 | VFYRGGVSMDY |
| 28 | OX40(8H9, 49B4, 1G4, 20B7) CDR-L1 | RASQSISSWLA |

TABLE B-continued

Sequences

| SEQ ID NO: | Name | Sequence |
|---|---|---|
| 29 | OX40(CLC-563, CLC564) CDR-L1 | RASQSVSSSYLA |
| 30 | OX40(17A9) CDR-L1 | QGDSLRSYYAS |
| 31 | OX40(8H9, 49B4, 1G4, 20B7) CDR-L2 | DASSLES |
| 32 | OX40(CLC-563, CLC564) CDR-L2 | GASSRAT |
| 33 | OX40(17A9) CDR-L2 | GKNNRPS |
| 34 | OX40(8H9) CDR-L3 | QQYLTYSRFT |
| 35 | OX40(49B4) CDR-L3 | QQYSSQPYT |
| 36 | OX40(1G4) CDR-L3 | QQYISYSMLT |
| 37 | OX40(20B7) CDR-L3 | QQYQAFSLT |
| 38 | OX40(CLC-563, CLC-564) CDR-L3 | QQYGSSPLT |
| 39 | OX40(17A9) CDR-L3 | NSRVMPHNRV |
| 40 | OX40(49B4) VH | QVQLVQSGAEVKKPGSSVKVSCKASGGTFSSYAISWVRQ APGQGLEWMGGIIPIFGTANYAQKFQGRVTITADKSTST AYMELSSLRSEDTAVYYCAREYYRGPYDYWGQGTTVTVSS |
| 41 | OX40(49B4) VL | DIQMTQSPSTLSASVGDRVTITCRASQSISSWLAWYQQK PGKAPKLLIYDASSLESGVPSRFSGSGSGTEFTLTISSL QPDDFATYYCQQYSSQPYTFGQGTKVEIK |
| 42 | OX40(8H9) VH | QVQLVQSGAEVKKPGSSVKVSCKASGGTFSSYAISWVRQ APGQGLEWMGGIIPIFGTANYAQKFQGRVTITADKSTST AYMELSSLRSEDTAVYYCAREYGWMDYWGQGTTVTVSS |
| 43 | OX40(8H9) VL | DIQMTQSPSTLSASVGDRVTITCRASQSISSWLAWYQQK PGKAPKLLIYDASSLESGVPSRFSGSGSGTEFTLTISSL QPDDFATYYCQQYLTYSRFTFGQGTKVEIK |
| 44 | OX40(1G4) VH | QVQLVQSGAEVKKPGSSVKVSCKASGGTFSSYAISWVRQ APGQGLEWMGGIIPIFGTANYAQKFQGRVTITADKSTST AYMELSSLRSEDTAVYYCAREYGSMDYWGQGTTVTVSS |
| 45 | OX40(1G4) VL | DIQMTQSPSTLSASVGDRVTITCRASQSISSWLAWYQQK PGKAPKLLIYDASSLESGVPSRFSGSGSGTEFTLTISSL QPDDFATYYCQQYISYSMLTFGQGTKVEIK |
| 46 | OX40(20B7) VH | QVQLVQSGAEVKKPGSSVKVSCKASGGTFSSYAISWVRQ APGQGLEWMGGIIPIFGTANYAQKFQGRVTITADKSTST AYMELSSLRSEDTAVYYCARVNYPYSYWGDFDYWGQGTT VTVSS |
| 47 | OX40(20B7) VL | DIQMTQSPSTLSASVGDRVTITCRASQSISSWLAWYQQK PGKAPKLLIYDASSLESGVPSRFSGSGSGTEFTLTISSL QPDDFATYYCQQYQAFSLTFGQGTKVEIK |
| 48 | OX40(CLC-563) VH | EVQLLESGGGLVQPGGSLRLSCAASGFTFSSYAMSWVRQ APGKGLEWVSAISGSGGSTYYADSVKGRFTISRDNSKNT LYLQMNSLRAEDTAVYYCALDVGAFDYWGQGALVTVSS |
| 49 | OX40(CLC-563) VL | EIVLTQSPGTLSLSPGERATLSCRASQSVSSSYLAWYQQ KPGQAPRLLIYGASSRATGIPDRFSGSGSGTDFTLTISR LEPEDFAVYYCQQYGSSPLTFGQGTKVEIK |
| 50 | OX40(CLC-564) VH | EVQLLESGGGLVQPGGSLRLSCAASGFTFSSYAMSWVRQ APGKGLEWVSAISGSGGSTYYADSVKGRFTISRDNSKNT LYLQMNSLRAEDTAVYYCAFDVGPFDYWGQGTLVTVSS |
| 51 | OX40(CLC-564) VL | EIVLTQSPGTLSLSPGERATLSCRASQSVSSSYLAWYQQ KPGQAPRLLIYGASSRATGIPDRFSGSGSGTDFTLTISR LEPEDFAVYYCQQYGSSPLTFGQGTKVEIK |

TABLE B-continued

Sequences

| SEQ ID NO: | Name | Sequence |
|---|---|---|
| 52 | OX40(17A9) VH | EVQLLESGGGLVQPGGSLRLSCAASGFTFSSYAMSWVRQ APGKGLEWVSAISGSGGSTYYADSVKGRFTISRDNSKNT LYLQMNSLRAEDTAVYYCARVFYRGGVSMDYWGQGTLVT VSS |
| 53 | OX40(17A9) VL | SSELTQDPAVSVALGQTVRITCQGDSLRSYYASWYQQKP GQAPVLVIYGKNNRPSGIPDRFSGSSSGNTASLTITGAQ AEDEADYYCNSRVMPHNRVFGGGTKLTV |
| 54 | Fc knob chain of CD134-0093 | Table 1 |
| 55 | Fc hole chain of CD134-0093 | Table 1 |
| 56 | Fc knob chain of CD134-0094 | Table 2 |
| 57 | Fc hole chain of CD134-0094 | Table 2 |
| 58 | Fc knob chain of P1AE0085 | Table 3 |
| 59 | Fc hole chain of P1AE0085 | Table 3 |
| 60 | Fc knob chain of P1AE0086 | Table 4 |
| 61 | Fc hole chain of P1AE0086 | Table 4 |
| 62 | Fc knob chain of P1AE0087 | Table 5 |
| 63 | Fc hole chain of P1AE0087 | Table 5 |
| 64 | Fc knob chain of P1AE0839 | Table 6 |
| 65 | Fc hole chain of P1AE0839 | Table 6 |
| 66 | Fc knob chain of P1AE0821 | Table 7 |
| 67 | Fc hole chain of P1AE0821 | Table 7 |
| 68 | (49B4) VHCH1 Fc knob VH (28H1) (heavy chain 1) | QVQLVQSGAEVKKPGSSVKVSCKASGGTFSSYAISWVRQ APGQGLEWMGGIIPIFGTANYAQKFQGRVTITADKSTST AYMELSSLRSEDTAVYYCAREYYRGPYDYWGQGTTVTVS SASTKGPSVFPLAPSSKSTSGGTAALGCLVKDYFPEPVT VSWNSGALTSGVHTFPAVLQSSGLYSLSSVVTVPSSSLG TQTYICNVNHKPSNTKVDKKVEPKSCDKTHTCPPCPAPE AAGGPSVFLFPPKPKDTLMISRTPEVTCVVVDVSHEDPE VKFNWYVDGVEVHNAKTKPREEQYNSTYRVVSVLTVLHQ DWLNGKEYKCKVSNKALGAPIEKTISKAKGQPREPQVYT LPPCRDELTKNQVSLWCLVKGFYPSDIAVEWESNGQPEN NYKTTPPVLDSDGSFFLYSKLTVDKSRWQQGNVFSCSVM HEALHNHYTQKSLSLSPGGGGSGGGGSGGGGSGGGGSE VQLLESGGGLVQPGGSLRLSCAASGFTFSSHAMSWVRQA PGKGLEWVSAIWASGEQYYADSVKGRFTISRDNSKNTLY LQMNSLRAEDTAVYYCAKGWLGNFDYWGQGTLVTVSS |
| 69 | (49B4) VHCH1 Fc hole VL (28H1) (heavy chain 2) | QVQLVQSGAEVKKPGSSVKVSCKASGGTFSSYAISWVRQ APGQGLEWMGGIIPIFGTANYAQKFQGRVTITADKSTST AYMELSSLRSEDTAVYYCAREYYRGPYDYWGQGTTVTVS SASTKGPSVFPLAPSSKSTSGGTAALGCLVKDYFPEPVT VSWNSGALTSGVHTFPAVLQSSGLYSLSSVVTVPSSSLG TQTYICNVNHKPSNTKVDKKVEPKSCDKTHTCPPCPAPE AAGGPSVFLFPPKPKDTLMISRTPEVTCVVVDVSHEDPE VKFNWYVDGVEVHNAKTKPREEQYNSTYRVVSVLTVLHQ DWLNGKEYKCKVSNKALGAPIEKTISKAKGQPREPQVCT LPPSRDELTKNQVSLSCAVKGFYPSDIAVEWESNGQPEN NYKTTPPVLDSDGSFFLVSKLTVDKSRWQQGNVFSCSVM HEALHNHYTQKSLSLSPGGGGSGGGGSGGGGSGGGGSE IVLTQSPGTLSLSPGERATLSCRASQSVSRSYLAWYQQK PGQAPRLLIIGASTRATGIPDRFSGSGSGTDFTLTISRL EPEDFAVYYCQQGQVIPPTFGQGTKVEIK |
| 70 | (49B4) VLCL-light chain | DIQMTQSPSTLSASVGDRVTITCRASQSISSWLAWYQQK PGKAPKLLIYDASSLESGVPSRFSGSGSGTEFTLTISSL QPDDFATYYCQQYSSQPYTFGQGTKVEIKRTVAAPSVFI FPPSDEQLKSGTASVVCLLNNFYPREAKVQWKVDNALQS GNSQESVTEQDSKDSTYSLSSTLTLSKADYEKHKVYACE V |

TABLE B-continued

Sequences

| SEQ ID NO: | Name | Sequence |
|---|---|---|
| 71 | (49B4) VHCH1 Fc knob VH (4B9) (heavy chain 1) | QVQLVQSGAEVKKPGSSVKVSCKASGGTFSSYAISWVRQ APGQGLEWMGGIIPIFGTANYAQKFQGRVTITADKSTST AYMELSSLRSEDTAVYYCAREYYRGPYDYWGQGTTVTVS SASTKGPSVFPLAPSSKSTSGGTAALGCLVKDYFPEPVT VSWNSGALTSGVHTFPAVLQSSGLYSLSSVVTVPSSSLG TQTYICNVNHKPSNTKVDKKVEPKSCDKTHTCPPCPAPE AAGGPSVFLFPPKPKDTLMISRTPEVTCVVVDVSHEDPE VKFNWYVDGVEVHNAKTKPREEQYNSTYRVVSVLTVLHQ DWLNGKEYKCKVSNKALGAPIEKTISKAKGQPREPQVYT LPPCRDELTKNQVSLWCLVKGFYPSDIAVEWESNGQPEN NYKTTPPVLDSDGSFFLYSKLTVDKSRWQQGNVFSCSVM HEALHNHYTQKSLSLSPGGGGSGGGGSGGGGSGGGGSE VQLLESGGGLVQPGGSLRLSCAASGFTFSSYAMSWVRQA PGKGLEWVSAIIGSGASTYYADSVKGRFTISRDNSKNTL YLQMNSLRAEDTAVYYCAKGWFGGFNYWGQGTLVTVSS |
| 72 | (49B4) VHCH1 Fc hole VL (4B9) (heavy chain 2) | QVQLVQSGAEVKKPGSSVKVSCKASGGTFSSYAISWVRQ APGQGLEWMGGIIPIFGTANYAQKFQGRVTITADKSTST AYMELSSLRSEDTAVYYCAREYYRGPYDYWGQGTTVTVS SASTKGPSVFPLAPSSKSTSGGTAALGCLVKDYFPEPVT VSWNSGALTSGVHTFPAVLQSSGLYSLSSVVTVPSSSLG TQTYICNVNHKPSNTKVDKKVEPKSCDKTHTCPPCPAPE AAGGPSVFLFPPKPKDTLMISRTPEVTCVVVDVSHEDPE VKFNWYVDGVEVHNAKTKPREEQYNSTYRVVSVLTVLHQ DWLNGKEYKCKVSNKALGAPIEKTISKAKGQPREPQVCT LPPSRDELTKNQVSLSCAVKGFYPSDIAVEWESNGQPEN NYKTTPPVLDSDGSFFLVSKLTVDKSRWQQGNVFSCSVM HEALHNHYTQKSLSLSPGGGGSGGGGSGGGGSGGGGSE IVLTQSPGTLSLSPGERATLSCRASQSVTSSYLAWYQQK PGQAPRLLINVGSRRATGIPDRFSGSGSGTDFTLTISRL EPEDFAVYYCQQGIMLPPTFGQGTKVEIK |
| 73 | (49B4) VHCH1 Fc knob VH (DP47) (heavy chain 1) | QVQLVQSGAEVKKPGSSVKVSCKASGGTFSSYAISWVRQ APGQGLEWMGGIIPIFGTANYAQKFQGRVTITADKSTST AYMELSSLRSEDTAVYYCAREYYRGPYDYWGQGTTVTVS SASTKGPSVFPLAPSSKSTSGGTAALGCLVKDYFPEPVT VSWNSGALTSGVHTFPAVLQSSGLYSLSSVVTVPSSSLG TQTYICNVNHKPSNTKVDKKVEPKSCDKTHTCPPCPAPE AAGGPSVFLFPPKPKDTLMISRTPEVTCVVVDVSHEDPE VKFNWYVDGVEVHNAKTKPREEQYNSTYRVVSVLTVLHQ DWLNGKEYKCKVSNKALGAPIEKTISKAKGQPREPQVYT LPPCRDELTKNQVSLWCLVKGFYPSDIAVEWESNGQPEN NYKTTPPVLDSDGSFFLYSKLTVDKSRWQQGNVFSCSVM HEALHNHYTQKSLSLSPGGGGSGGGGSGGGGSGGGGSE VQLLESGGGLVQPGGSLRLSCAASGFTFSSYAMSWVRQA PGKGLEWVSAISGSGGSTYYADSVKGRFTISRDNSKNTL YLQMNSLRAEDTAVYYCAKGSGFDYWGQGTLVTVSS |
| 74 | (49B4) VHCH1 Fc hole VL (DP47) (heavy chain 2) | QVQLVQSGAEVKKPGSSVKVSCKASGGTFSSYAISWVRQ APGQGLEWMGGIIPIFGTANYAQKFQGRVTITADKSTST AYMELSSLRSEDTAVYYCAREYYRGPYDYWGQGTTVTVS SASTKGPSVFPLAPSSKSTSGGTAALGCLVKDYFPEPVT VSWNSGALTSGVHTFPAVLQSSGLYSLSSVVTVPSSSLG TQTYICNVNHKPSNTKVDKKVEPKSCDKTHTCPPCPAPE AAGGPSVFLFPPKPKDTLMISRTPEVTCVVVDVSHEDPE VKFNWYVDGVEVHNAKTKPREEQYNSTYRVVSVLTVLHQ DWLNGKEYKCKVSNKALGAPIEKTISKAKGQPREPQVCT LPPSRDELTKNQVSLSCAVKGFYPSDIAVEWESNGQPEN NYKTTPPVLDSDGSFFLVSKLTVDKSRWQQGNVFSCSVM HEALHNHYTQKSLSLSPGGGGSGGGGSGGGGSGGGGSE IVLTQSPGTLSLSPGERATLSCRASQSVSSSYLAWYQQK PGQAPRLLIYGASSRATGIPDRFSGSGSGTDFTLTISRL EPEDFAVYYCQQYGSSPLTFGQGTKVEIK |
| 75 | HC1 (49B4) VHCH1_VHCH1 Fc knob VH (4B9) | QVQLVQSGAEVKKPGSSVKVSCKASGGTFSSYAISWVRQ APGQGLEWMGGIIPIFGTANYAQKFQGRVTITADKSTST AYMELSSLRSEDTAVYYCAREYYRGPYDYWGQGTTVTVS SASTKGPSVFPLAPSSKSTSGGTAALGCLVKDYFPEPVT VSWNSGALTSGVHTFPAVLQSSGLYSLSSVVTVPSSSLG TQTYICNVNHKPSNTKVDKKVEPKSCDGGGSGGGGSQV QLVQSGAEVKKPGSSVKVSCKASGGTFSSYAISWVRQAP GQGLEWMGGIIPIFGTANYAQKFQGRVTITADKSTSTAY MELSSLRSEDTAVYYCAREYYRGPYDYWGQGTTVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKKVEPKSCDKTHTCPPCPAPEAA |

TABLE B-continued

Sequences

| SEQ ID NO: | Name | Sequence |
|---|---|---|
|  |  | GGPSVFLFPPKPKDTLMISRTPEVTCVVVDVSHEDPEVK FNWYVDGVEVHNAKTKPREEQYNSTYRVVSVLTVLHQDW LNGKEYKCKVSNKALGAPIEKTISKAKGQPREPQVYTLP PCRDELTKNQVSLWCLVKGFYPSDIAVEWESNGQPENNY KTTPPVLDSDGSFFLYSKLTVDKSRWQQGNVFSCSVMHE ALHNHYTQKSLSLSPGGGGSGGGGSGGGGSGGGGSEVQ LLESGGGLVQPGGSLRLSCAASGFTFSSYAMSWVRQAPG KGLEWVSAIIGSGASTYYADSVKGRFTISRDNSKNTLYL QMNSLRAEDTAVYYCAKGWFGGFNYWGQGTLVTVSS |
| 76 | HC2 (49B4) VHCH1_VHCH1 Fc hole VL (4B9) | QVQLVQSGAEVKKPGSSVKVSCKASGGTFSSYAISWVRQ APGQGLEWMGGIIPIFGTANYAQKFQGRVTITADKSTST AYMELSSLRSEDTAVYYCAREYYRGPYDYWGQGTTVTVS SASTKGPSVFPLAPSSKSTSGGTAALGCLVKDYFPEPVT VSWNSGALTSGVHTFPAVLQSSGLYSLSSVVTVPSSSLG TQTYICNVNHKPSNTKVDKKVEPKSCDGGGGSGGGGSQV QLVQSGAEVKKPGSSVKVSCKASGGTFSSYAISWVRQAP GQGLEWMGGIIPIFGTANYAQKFQGRVTITADKSTSTAY MELSSLRSEDTAVYYCAREYYRGPYDYWGQGTTVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKKVEPKSCDKTHTCPPCPAPEAA GGPSVFLFPPKPKDTLMISRTPEVTCVVVDVSHEDPEVK FNWYVDGVEVHNAKTKPREEQYNSTYRVVSVLTVLHQDW LNGKEYKCKVSNKALGAPIEKTISKAKGQPREPQVCTLP PSRDELTKNQVSLSCAVKGFYPSDIAVEWESNGQPENNY KTTPPVLDSDGSFFLVSKLTVDKSRWQQGNVFSCSVMHE ALHNHYTQKSLSLSPGGGGSGGGGSGGGGSGGGGSEIV LTQSPGTLSLSPGERATLSCRASQSVTSSYLAWYQQKPG QAPRLLINVGSRRATGIPDRFSGSGSGTDFTLTISRLEP EDFAVYYCQQGIMLPPTFGQGTKVEIK |
| 77 | Peptide linker G4S | GGGGS |
| 78 | Peptide linker (G4S)2 | GGGGSGGGGS |
| 79 | Peptide linker (SG4)2 | SGGGGSGGGG |
| 80 | Peptide linker | GGGGSGGGGSSGGGGS |
| 81 | Peptide linker (G4S)3 | GGGGSGGGGSGGGGS |
| 82 | Peptide linker G4(SG4)2 | GGGGSGGGGSGGGG |
| 83 | Peptide linker (G4S)4 | GGGGSGGGGSGGGGSGGGGS |
| 84 | Peptide linker | GGGGSGGGGSGGGSGGGGS |
| 85 | Peptide linker | GSPGSSSSGS |
| 86 | Peptide linker | GSGSGSGS |
| 87 | Peptide linker | GSGSGNGS |
| 88 | Peptide linker | GGSGSGSG |
| 89 | Peptide linker | GGSGSG |
| 90 | Peptide linker | GGSG |
| 91 | Peptide linker | GGSGNGSG |
| 92 | Peptide linker | GGNGSGSG |
| 93 | Peptide linker | GGNGSG |
| 94 | IgG CH1 domain | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKV |
| 95 | IgG CH2 domain | APELLGGPSVFLFPPKPKDTLMISRTPEVTCVWDVSHED PEVKFNWYVDGVEVHNAKTKPREEQESTYRWSVLTVLHQ DWLNGKEYKCKVSNKALPAPIEKTISKAK |

TABLE B-continued

Sequences

| SEQ ID NO: | Name | Sequence |
|---|---|---|
| 96 | IgG CH3 domain | GQPREPQVYTLPPSRDELTKNQVSLTCLVKGFYPSDIAV EWESNGQPENNYKTTPPVLDSDGSFFLYSKLTVDKSRWQ QGNVFSCSVMHEALHNHYTQKSLSLSPG |
| 97 | human FAP | Uniprot accession no. Q12884 |
| 98 | mouse FAP | UniProt accession no. P97321 |
| 99 | CH1 connector | EPKSC |
| 100 | hinge | DKTHTCPXCP with X being S or P |
| 101 | hinge | HTCPXCP with X being S or P |
| 102 | hinge | CPXCP with X being S or P |
| 103 | IgG1, caucasian allotype | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSCDKTHTCPPCPAPEL LGGPSVFLFPPKPKDTLMISRTPEVTCVVVDVSHEDPEV KFNWYVDGVEVHNAKTKPREEQYNSTYRVVSVLTVLHQD WLNGKEYKCKVSNKALPAPIEKTISKAKGQPREPQVYTL PPSRDELTKNQVSLTCLVKGFYPSDIAVEWESNGQPENN YKTTPPVLDSDGSFFLYSKLTVDKSRWQQGNVFSCSVMH EALHNHYTQKSLSLSPGK |
| 104 | IgG1, afroamerican allotype | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSCDKTHTCPPCPAPEL LGGPSVFLFPPKPKDTLMISRTPEVTCVVVDVSHEDPEV KFNWYVDGVEVHNAKTKPREEQYNSTYRVVSVLTVLHQD WLNGKEYKCKVSNKALPAPIEKTISKAKGQPREPQVYTL PPSREEMTKNQVSLTCLVKGFYPSDIAVEWESNGQPENN YKTTPPVLDSDGSFFLYSKLTVDKSRWQQGNVFSCSVMH EALHNHYTQKSLSLSPGK |
| 105 | IgG2 | ASTKGPSVFPLAPCSRSTSESTAALGCLVKDYFPEPVTV SWNSGALTSGVHTFPAVLQSSGLYSLSSVVTVPSSNFGT QTYTCNVDHKPSNTKVDKTVERKCCVECPPCPAPPVAGP SVFLFPPKPKDTLMISRTPEVTCVVVDVSHEDPEVQFNW YVDGVEVHNAKTKPREEQFNSTFRVVSVLTVVHQDWLNG KEYKCKVSNKGLPAPIEKTISKTKGQPREPQVYTLPPSR EEMTKNQVSLTCLVKGFYPSDISVEWESNGQPENNYKTT PPMLDSDGSFFLYSKLTVDKSRWQQGNVFSCSVMHEALH NHYTQKSLSLSPGK |
| 106 | IgG3 | ASTKGPSVFPLAPCSRSTSGGTAALGCLVKDYFPEPVTV SWNSGALTSGVHTFPAVLQSSGLYSLSSVVTVPSSSLGT QTYTCNVNHKPSNTKVDKRVELKTPLGDTTHTCPRCPEP KSCDTPPPCPRCPEPKSCDTPPPCPRCPEPKSCDTPPPC PRCPAPELLGGPSVFLFPPKPKDTLMISRTPEVTCVVVD VSHEDPEVQFKWYVDGVEVHNAKTKPREEQYNSTFRVVS VLTVLHQDWLNGKEYKCKVSNKALPAPIEKTISKTKGQP REPQVYTLPPSREEMTKNQVSLTCLVKGFYPSDIAVEWE SSGQPENNYNTTPPMLDSDGSFFLYSKLTVDKSRWQQGN IFSCSVMHEALHNRFTQKSLSLSPGK |
| 107 | IgG4 | ASTKGPSVFPLAPCSRSTSESTAALGCLVKDYFPEPVTV SWNSGALTSGVHTFPAVLQSSGLYSLSSVVTVPSSSLGT KTYTCNVDHKPSNTKVDKRVESKYGPPCPSCPAPEFLGG PSVFLFPPKPKDTLMISRTPEVTCVVVDVSQEDPEVQFN WYVDGVEVHNAKTKPREEQFNSTYRVVSVLTVLHQDWLN GKEYKCKVSNKGLPSSIEKTISKAKGQPREPQVYTLPPS QEEMTKNQVSLTCLVKGFYPSDIAVEWESNGQPENNYKT TPPVLDSDGSFFLYSRLTVDKSRWQEGNVFSCSVMHEAL HNHYTQKSLSLSLGK |
| 108 | human OX40 | UniProt no. P43489 |
| 109 | human 4-1BB | UniProt no. Q07011 |
| 110 | human CD27 | UniProt no. P26842 |
| 111 | human HVEM | UniProt no. Q92956 |

TABLE B-continued

| SEQ ID NO: | Name | Sequence |
|---|---|---|
| 112 | human CD30 | UniProt no. P28908 |
| 113 | human GITR | UniProt no. Q9Y5U5 |
| 114 | murine OX40 | UniProt no. P47741 |
| 115 | human CD40 | UniProt no. P25942 |
| 116 | Fc knob chain of P1AE1122 | See Table 8 |
| 117 | Fc hole chain of P1AE1122 | See Table 8 |
| 118 | Fc knob chain of P1AE1942 | See Table 9 |
| 119 | Fc hole chain of P1AE1942 | See Table 9 |
| 120 | Fc knob chain of P1AE1887 | See Table 10 |
| 121 | Fc hole chain of P1AE1887 | See Table 10 |
| 122 | Fc knob chain of P1AE1888 | See Table 11 |
| 123 | Fc hole chain of P1AE1888 | See Table 11 |
| 124 | Fc knob chain of P1AE2254 | See Table 12 |
| 125 | Fc hole chain of P1AE2254 | See Table 12 |
| 126 | Fc knob chain of P1AE2340 | See Table 13 |
| 127 | Fc hole chain of P1AE2340 | See Table 13 |
| 128 | Light chain of P1AE2340 | See Table 13 |
| 129 | Fc knob chain of P1AE2735 | See Table 14 |
| 130 | Fc hole chain of P1AE2735 | See Table 14 |
| 131 | Fc knob chain of P1AE2743 | See Table 15 |
| 132 | Fc hole chain of P1AE2743 | See Table 15 |
| 133 | Fc knob chain of P1AE2762 | See Table 16 |
| 134 | Fc hole chain of P1AE2762 | See Table 16 |
| 135 | 4-1BB (20H4.9) CDR-H1 | GYYWS |
| 136 | 4-1BB (20H4.9) CDR-H2 | EINFIGGYVTYNPSLES |
| 137 | 4-1BB (20H4.9) CDR-H3 | DYGPGNYDWYFDL |
| 138 | 4-1BB (20H4.9) CDR-L1 | RASQSVSSYLA |
| 139 | 4-1BB (20H4.9) CDR-L2 | DASNRAT |
| 140 | 4-1BB (20H4.9) CDR-L3 | QQRSNWPPALT |
| 141 | 4-1BB (20H4.9) VH | QVQLQQWGAGLLKPSETLSLTCAVYGGSFSGYYWSWIRQSPEKGLEWIGEINFIGGYVTYNPSLESRVTISVDTSKNQFSLKLSSVTAADTAVYYCARDYGPGNYDWYFDLWGRGTLVTVSS |
| 142 | 4-1BB (20H4.9) VL | EIVLTQSPATLSLSPGERATLSCRASQSVSSYLAWYQQKPGQAPRLLIYDASNRATGIPARFSGSGSGTDFTLTISSLEPEDFAVYYCQQRSNWPPALTFGGGTKVEIK |
| 143 | Fc knob chain of P1AE1899 | See Table 26 |
| 144 | Fc hole chain of P1AE1899 | See Table 26 |
| 145 | Fc knob chain of P1AE2051 | See Table 27 |
| 146 | Fc hole chain of P1AE2051 | See Table 27 |
| 147 | hu CD40 CDR-H1 | GYYIH |

TABLE B-continued

| SEQ ID NO: | Name | Sequence |
|---|---|---|
| 148 | hu CD40 CDR-H2 | RVIPNAGGTSYNQKFKG |
| 149 | hu CD40 CDR-H3 | EGIYW |
| 150 | hu CD40 CDR-L1 | RSSQSLVHSNGNTFLH |
| 151 | hu CD40 CDR-L2 | TVSNRFS |
| 152 | hu CD40 CDR-L3 | SQTTHVPWT |
| 153 | hu CD40 VH | EVQLVESGGGLVQPGGSLRLSCAASGYSFTGYYIHWVRQAPGKGLEWVARVIPNAGGTSYNQKFKGRFTLSVDNSKNTAYLQMNSLRAEDTAVYYCAREGIYWWGQGTLVTVSS |
| 154 | hu CD40 VL | DIQMTQSPSSLSASVGDRVTITCRSSQSLVHSNGNTFLHWYQQKPGKAPKLLIYTVSNRFSGVPSRFSGSGSGTDFTLTISSLQPEDFATYFCSQTTHVPWTFGQGTKVEIK |
| 155 | Fc knob chain of P1AE1799 | See Table 32 |
| 156 | Fc hole chain of P1AE1799 | See Table 32 |
| 157 | Fc knob chain of P1AE1902 | See Table 33 |
| 158 | Fc hole chain of P1AE1902 | See Table 33 |
| 159 | Fc knob chain of P1AE1800 | See Table 34 |
| 160 | Fc hole chain of P1AE1800 | See Table 34 |
| 161 | Fc knob chain of P1AE2052 | See Table 35 |
| 162 | Fc hole chain of P1AE2052 | See Table 35 |
| 163 | Fc knob chain of P1AE1901 | See Table 36 |
| 164 | Fc hole chain of P1AE1901 | See Table 36 |
| 165 | Fc knob chain of P1AE2255 | See Table 37 |
| 166 | Fc hole chain of P1AE2255 | See Table 37 |
| 167 | VH1a (CD40) | QVQLVQSGAEVKKPGASVKVSCKASGYSFTGYYIHWVRQAPGQSLEWMGRVIPNAGGTSYNQKFKGRVTLTVDKSISTAYMELSRLRSDDTAVYYCAREGIYWWGQGTTVTVSS |
| 168 | VH1b (CD40) | QVQLVQSGAEVKKPGASVKVSCKASGYSFTGYYIHWVRQAPGKSLEWMGRVIPNAGGTSYNQKFKGRVTLTVDKSISTAYMELSRLRSDDTAVYYCAREGIYWWGQGTTVTVSS |
| 169 | VH1c (CD40) | QVQLVQSGAEVKKPGASVKVSCKASGYSFTGYYIHWVRQAPGQSLEWMGRVIPNAGGTSYNQKFKGRVTLTVDKSISTAYMELSRLRSDDTAVYYCAREGIYWWGHGTTVTVSS |
| 170 | VH1d (CD40) | QVQLVQSGAEVKKPGASVKVSCKASGYSFTGYYIHWVRQAPGQSLEWMGRVIPNAGGTSYNQKFKGRVTLSVDKSISTAYMELSRLRSDDTAVYYCAREGIYWWGQGTTVTVSS |
| 171 | VL1a (CD40) | DIVMTQTPLSLSVTPGQPASISCRSSQSLVHSNGNTFLHWYLQKPGQSPQLLIYTVSNRFSGVPDRFSGSGSGTDFTLKISRVEAEDVGVYFCSQTTHVPWTFGGGTKVEIK |
| 172 | VL1b (CD40) | DIVVTQTPLSLSVTPGQPASISCRSSQSLVHSNGNTFLHWYLQKPGQSPQLLIYTVSNRFSGVPDRFSGSGSGTDFTLKISRVEAEDVGVYFCSQTTHVPWTFGGGTKVEIK |
| 173 | VL1c (CD40) | DVVVTQTPLSLSVTPGQPASISCRSSQSLVHSNGNTFLHWYLQKPGQSPQLLIYTVSNRFSGVPDRFSGSGSGTDFTLKISRVEAEDVGVYFCSQTTHVPWTFGGGTKVEIK |

TABLE B-continued

Sequences

| SEQ ID NO: | Name | Sequence |
|---|---|---|
| 174 | VL1d (CD40) | DVVVTQTPLSLSVTPGQPASISCRSSQSLVHSNGNTFLH<br>WYLQKPGQSPQLLIYTVSNRFSGVPDRFSGSGSGTDFTL<br>KISRVEAEDVGVYFCSQTTHVPWTFGGGTKLEIK |
| 175 | VH2a (CD40) | EVQLLESGGGLVQPGGSLRLSCAASGYSFTGYYIHWVRQ<br>APGKGLEWVGRVIPNAGGTSYNQKFKGRFTISVDNSKNT<br>AYLQMNSLRAEDTAVYYCAREGIYWWGQGTTVTVSS |
| 176 | VH2b (CD40) | EVQLLESGGGLVQPGGSLRLSCAASGYSFTGYYIHWVRQ<br>APGKSLEWVGRVIPNAGGTSYNQKFKGRFTISVDNSKNT<br>AYLQMNSLRAEDTAVYYCAREGIYWWGQGTTVTVSS |
| 177 | VH2c (CD40) | EVQLLESGGGLVQPGGSLRLSCAASGYSFTGYYIHWVRQ<br>APGKGLEWVGRVIPNAGGTSYNQKFKGRFTISVDNSKNT<br>AYLQMNSLRAEDTAVYYCAREGIYWWGHGTTVTVSS |
| 178 | VH2d (CD40) | EVQLLESGGGLVQPGGSLRLSCAASGYSFTGYYIHWVRQ<br>APGKGLEWVGRVIPNAGGTSYGDSVKGRFTISVDNSKNT<br>AYLQMNSLRAEDTAVYYCAREGIYWWGQGTTVTVSS |
| 179 | VH2ab (CD40) | EVQLLESGGGLVQPGGSLRLSCAASGYSFTGYYMHVRQW<br>VRQAPGKGLEWVGRVIPNAGGTSYNQKFKGRFTISVDNS<br>KNTAYLQMNSLRAEDTAVYYCAREGIYWWGQGTTVTVSS |
| 180 | VH2ac (CD40) | EVQLLESGGGLVQPGGSLRLSCAASGYSFTGYYIHWVRQ<br>APGKGLEWVGRVIPNAGGTSYNQKVKGRFTISVDNSKNT<br>AYLQMNSLRAEDTAVYYCAREGIYWWGQGTTVTVSS |
| 181 | VL2a (CD40) | DIQMTQSPSSLSASVGDRVTITCRSSQSLVHSNGNTFLH<br>WYQQKPGKAPKLLIYTVSNRFSGVPSRFSGSGSGTDFTL<br>TISSLQPEDFATYFCSQTTHVPWTFGGGTKVEIK |
| 182 | VL2b (CD40) | DIQMTQSPSSLSASVGDRVTITCRSSQSLVHSNGNTFLH<br>WYQQKPGQSPKLLIYTVSNRFSGVPSRFSGSGSGTDFTL<br>TISSLQPEDFATYFCSQTTHVPWTFGGGTKVEIK |
| 183 | VL2ab (CD40) | DIQMTQSPSSLSASVGDRVTITCRASQSLVHSNGNTFLH<br>WYQQKPGKAPKLLIYTVSNRFSGVPSRFSGSGSGTDFTL<br>TISSLQPEDFATYFCSQTTHVPWTFGGGTKVEIK |
| 184 | VL2ac (CD40) | DIQMTQSPSSLSASVGDRVTITCRSSQSIVHSNGNTFLH<br>WYQQKPGKAPKLLIYTVSNRFSGVPSRFSGSGSGTDFTL<br>TISSLQPEDFATYFCSQTTHVPWTFGGGTKVEIK |

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991). Amino acids of antibody chains are numbered and referred to according to the EU numbering systems according to Kabat (Kabat, E. A., et al., Sequences of Proteins of Immunological Interest, 5th ed., Public Health Service, National Institutes of Health, Bethesda, Md. (1991)) as defined above.

EXAMPLES

The following are examples of methods and compositions of the invention. It is understood that various other embodiments may be practiced, given the general description provided above.

Recombinant DNA Techniques

Standard methods were used to manipulate DNA as described in Sambrook et al., Molecular cloning: A laboratory manual; Cold Spring Harbor Laboratory Press, Cold Spring Harbor, N.Y., 1989. The molecular biological reagents were used according to the manufacturer's instructions. General information regarding the nucleotide sequences of human immunoglobulin light and heavy chains is given in: Kabat, E. A. et al., (1991) Sequences of Proteins of Immunological Interest, Fifth Ed., NIH Publication No 91-3242.

DNA Sequencing

DNA sequences were determined by double strand sequencing.

Gene Synthesis

Desired gene segments were prepared by chemical synthesis at Geneart AG (Regensburg, Germany) from synthetic oligonucleotides by automated gene synthesis. The synthesized gene fragments were cloned into an *E. coli* plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany).

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Reagents

All commercial chemicals, antibodies and kits were used as provided according to the manufacturer's protocol if not stated otherwise.

Example 1

Generation of Bispecific Contorsbodies 1.1 Construction of the Expression Plasmids for the Bispecific Contorsbodies For the expression of bispecific contorsbodies as reported herein a transcription unit comprising the following functional elements was used:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a nucleic acid encoding the respective circular fusion polypeptide, and
- the bovine growth hormone polyadenylation sequence (BGH pA).

Beside the expression unit/cassette including the desired gene to be expressed the basic/standard mammalian expression plasmid contains
- an origin of replication from the vector pUC18 which allows replication of this plasmid in *E. coli*, and
- a beta-lactamase gene which confers ampicillin resistance in *E. coli*.

1.2 Expression of the Bispecific Contorsbodies

Transient expression of the bispecificantigen binding molecules was performed in suspension-adapted HEK293F (FreeStyle 293-F cells; Invitrogen) cells with Transfection Reagent 293-free (Novagen).

Cells were passaged, by dilution, at least four times (volume 30 ml) after thawing in a 125 ml shake flask (Incubate/Shake at 37° C., 7% $CO_2$, 85% humidity, 135 rpm). The cells were expanded to $3\times10^5$ cells/ml in 250 ml volume. Three days later, cells were split and new seeded with a density of $7*10^5$ cells/ml in a 250 ml volume in a 1 liter shake flask. Transfection will be 24 hours later at a cell density around $1.4-2.0\times10^6$ cells/ml.

Before transfection 250 µg plasmid-DNA were diluted in a final volume of 10 ml with pre-heated (water bath; 37° C.) Opti-MEM (Gibco). The solution was gently mixed and incubated at room temperature for not longer than 5 min. Then 333.3 µl of the 293-free transfection reagent were added to the DNA-OptiMEM-solution. Thereafter the solution was gently mixed and incubated at room temperature for 15-20 minutes. The whole volume of mixture was added to 1 L shake flask with 250 ml HEK-cell-culture-volume.

Incubate/Shake at 37° C., 7% $CO_2$, 85% humidity, 135 rpm for 6 or 7 days.

The supernatant was harvested by a first centrifugation-step at 2,000 rpm, 4° C., for 10 minutes. Then the supernatant was transferred into a new centrifugation-flask for a second centrifuge at 4,000 rpm, 4° C., for 20 minutes. Thereafter the cell-free-supernatant was filtered through a 0.22 µm bottle-top-filter and stored in a freezer (−20° C.).

1.3 Purification of the Bispecific Contorsbodies

The antigen binding molecule-containing culture supernatants were filtered and purified by two chromatographic steps. The antibodies were captured by affinity chromatography using HiTrap MabSelectSuRe (GE Healthcare) equilibrated with PBS (1 mM $KH_2PO_4$, 10 mM $Na_2HPO_4$, 137 mM NaCl, 2.7 mM KCl), pH 7.4. Unbound proteins were removed by washing with equilibration buffer, and the antigen binding molecule was recovered with 50 mM citrate buffer, pH 2.8, and immediately after elution neutralized to pH 6.0 with 1 M Tris-base, pH 9.0. Size exclusion chromatography on Superdex 200™ (GE Healthcare) was used as second purification step. The size exclusion chromatography was performed in 20 mM histidine buffer, 0.14 M NaCl, pH 6.0. The bispecificantigen binding molecules containing solutions were concentrated with an Ultrafree-CL centrifugal filter unit equipped with a Biomax-SK membrane (Millipore, Billerica, Mass.) and stored at −80° C.

1.4 Mass Spectrometric Analysis of the Bispecific Contorsbodies

PNGase F was obtained from Roche Diagnostics GmbH (14.3 U/µl; solution in sodium phosphate, EDTA and glycerol). A protease specifically cleaving in the hinge region of an IgG antibody was freshly reconstituted from a lyophilisate prior to digestion.

Enzymatic Deglycosylation of with PNGase F

50 µg of antigen binding molecule was diluted to a final concentration of 0.6 mg/ml with 10 mM sodium phosphate buffer, pH 7.1, and deglycosylated with 1 µl PNGase F at 37° C. for 16 hours.

Enzymatic Cleavage

The deglycosylated sample was diluted to a final concentration of 0.5 mg/ml with 200 mM Tris buffer, pH 8.0, and subsequently digested with the IgG specific protease at 37° C. for 1 hour.

ESI-QTOF Mass Spectrometry

The sample was desalted by HPLC on a Sephadex G25 column (Kronlab, 5×250 mm, TAC05/250G0-SR) using 40% acetonitrile with 2% formic acid (v/v). The total mass was determined via ESI-QTOF MS on the maXis 4G UHR-QTOF MS system (Bruker Daltonik) equipped with a TriVersa NanoMate source (Advion). Calibration was performed with sodium iodide (Waters ToF G2-Sample Kit 2 Part: 700008892-1). For the digested antigen binding molecule, data acquisition was done at 1000-4000 m/z (ISCID: 30 eV). The raw mass spectra were evaluated and transformed into individual relative molar masses. For visualization of the results proprietary software was used to generate deconvoluted mass spectra.

Example 2

Preparation of Bispecific Antibodies with Two Antigen Binding Domains Binding to OX40 and One Antigen Binding Domain Binding to FAP (FAP-OX40 Contorsbodies)

The generation and preparation of the FAP binders is described in WO 2012/020006 A2, which is incorporated herein by reference. The OX40 binder is described in WO 2017/055398 A2.

2.1 Preparation of FAP (4B9)-OX40 (49B4) Contorsbody CD134-0093

Figure 1A:
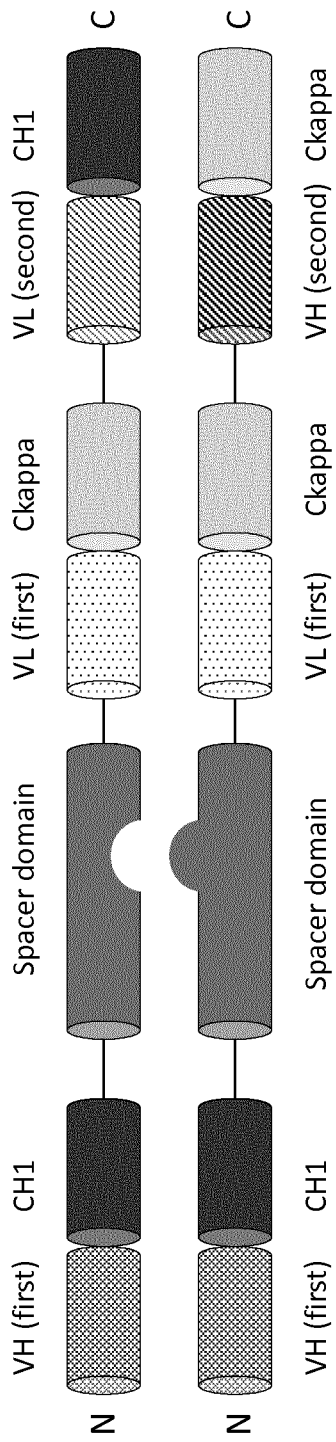
FIGS. 1A, 1B, 1C and 1D show examples, how the contorsbodies of the invention can be assembled.

A bispecific antibody comprising two fusion polypeptides was cloned as depicted in FIG. 1A:
- first fusion polypeptide (from N- to C-terminus): VH (OX40)-CH1, (G4S)2 connector (SEQ ID NO: 78), IgG1 hinge, Fc knob, (G4S)2 connector (SEQ ID NO: 78), VL(OX40)-Ckappa, (G4S)2 connector (SEQ ID NO: 78), VH(FAP)-Ckappa
- second fusion polypeptide (from N- to C-terminus): VH (OX40)-CH1, (G4S)2 connector (SEQ ID NO: 78), IgG1 hinge, Fc hole, (G4S)2 connector (SEQ ID NO: 78), VL(OX40)-Ckappa, (G4S)2 connector (SEQ ID NO: 78), VL(FAP)-CH1.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)).

Table 1 shows the amino acid sequences of the bispecific antibody CD134-0093.

TABLE 1

| | | Sequences of CD134-0093 |
|---|---|---|
| SEQ ID NO: | Description | Sequence |
| 54 | first fusion polypeptide (Fc knob) | QVQLVQSGAEVKKPGSSVKVSCKASGGTFSSYAISWVRQA PGQGLEWMGGIIPIFGTANYAQKFQGRVTITADKSTSTAY MELSSLRSEDTAVYYCAREYYRGPYDYWGQGTTVTVSSAS TKGPSVFPLAPSSKSTSGGTAALGCLVKDYFPEPVTVSWN SGALTSGVHTFPAVLQSSGLYSLSSVVTVPSSSLGTQTYI CNVNHKPSNTKVDKKVEPKSCGGGGSGGGGSDKTHTCPPC PAPEAAGGPSVFLFPPKPKDTLMISRTPEVTCVVVDVSHE DPEVKFNWYVDGVEVHNAKTKPREEQYNSTYRVVSVLTVL HQDWLNGKEYKCKVSNKALGAPIEKTISKAKGQPREPQVY TLPPCRDELTKNQVSLWCLVKGFYPSDIAVEWESNGQPEN NYKTTPPVLDSDGSFFLYSKLTVDKSRWQQGNVFSCSVMH EALHNHYTQKSLSLSPGKGGGGSGGGGSDIQMTQSPSTLS ASVGDRVTITCRASQSISSWLAWYQQKPGKAPKLLIYDAS SLESGVPSRFSGSGSGTEFTLTISSLQPDDFATYYCQQYS SQPYTFGQGTKVEIKRTVAAPSVFIFPPSDEQLKSGTASV VCLLNNFYPREAKVQWKVDNALQSGNSQESVTEQDSKDST YSLSSTLTLSKADYEKHKVYACEVTHQGLSSPVTKSFNRG ECGGGGSGGGGSEVQLLESGGGLVQPGGSLRLSCAASGFT FSSYAMSWVRQAPGKGLEWVSAIIGSGASTYYADSVKGRF TISRDNSKNTLYLQMNSLRAEDTAVYYCAKGWFGGFNYWG QGTLVTVSSASVAAPSVFIFPPSDEQLKSGTASVVCLLNN FYPREAKVQWKVDNALQSGNSQESVTEQDSKDSTYSLSST LTLSKADYEKHKVYACEVTHQGLSSPVTKSFNRGEC |
| 55 | second fusion polypeptide (Fc hole) | QVQLVQSGAEVKKPGSSVKVSCKASGGTFSSYAISWVRQA PGQGLEWMGGIIPIFGTANYAQKFQGRVTITADKSTSTAY MELSSLRSEDTAVYYCAREYYRGPYDYWGQGTTVTVSSAS TKGPSVFPLAPSSKSTSGGTAALGCLVKDYFPEPVTVSWN SGALTSGVHTFPAVLQSSGLYSLSSVVTVPSSSLGTQTYI CNVNHKPSNTKVDKKVEPKSCGGGGSGGGGSDKTHTCPPC PAPEAAGGPSVFLFPPKPKDTLMISRTPEVTCVVVDVSHE DPEVKFNWYVDGVEVHNAKTKPREEQYNSTYRVVSVLTVL HQDWLNGKEYKCKVSNKALGAPIEKTISKAKGQPREPQVC TLPPSRDELTKNQVSLSCAVKGFYPSDIAVEWESNGQPEN NYKTTPPVLDSDGSFFLVSKLTVDKSRWQQGNVFSCSVMH EALHNHYTQKSLSLSPGKGGGGSGGGGSDIQMTQSPSTLS ASVGDRVTITCRASQSISSWLAWYQQKPGKAPKLLIYDAS SLESGVPSRFSGSGSGTEFTLTISSLQPDDFATYYCQQYS SQPYTFGQGTKVEIKRTVAAPSVFIFPPSDEQLKSGTASV VCLLNNFYPREAKVQWKVDNALQSGNSQESVTEQDSKDST YSLSSTLTLSKADYEKHKVYACEVTHQGLSSPVTKSFNRG ECGGGGSGGGGSEIVLTQSPGTLSLSPGERATLSCRASQS VTSSYLAWYQQKPGQAPRLLINVGSRRATGIPDRFSGSGS GTDFTLTISRLEPEDFAVYYCQQGIMLPPTFGQGTKVEIK SSASTKGPSVFPLAPSSKSTSGGTAALGCLVKDYFPEPVT VSWNSGALTSGVHTFPAVLQSSGLYSLSSVVTVPSSSLGT QTYICNVNHKPSNTKVDKKVEPKSC |

Figure 1B:
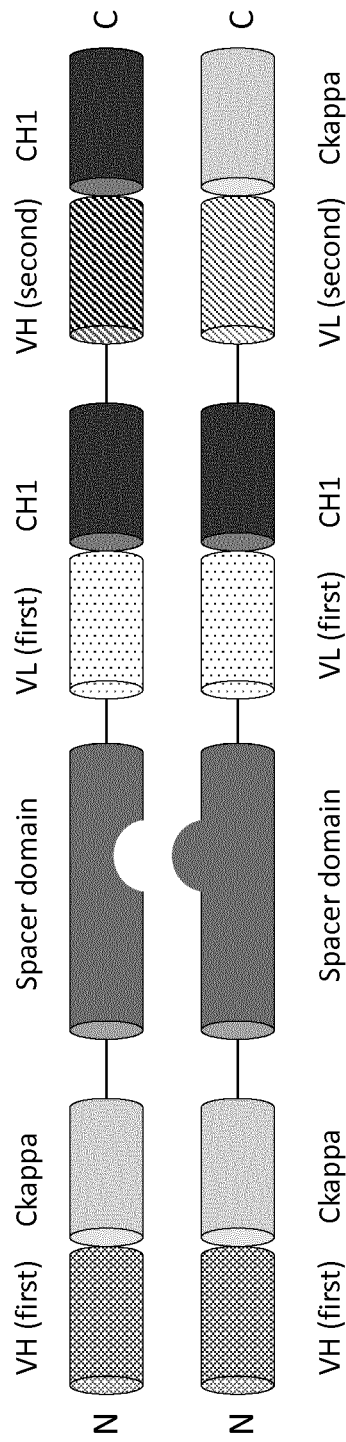
Figure 1C:
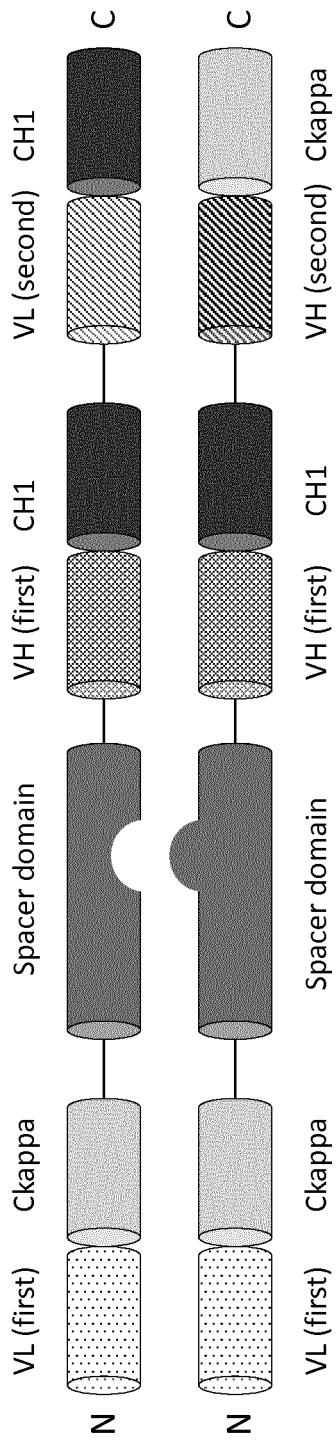
Figure 1D:
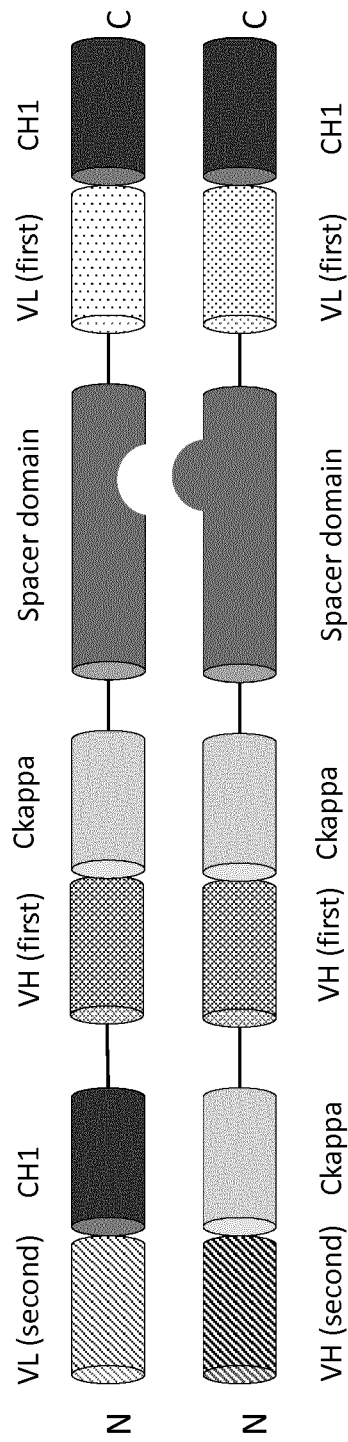
Figure 1F:
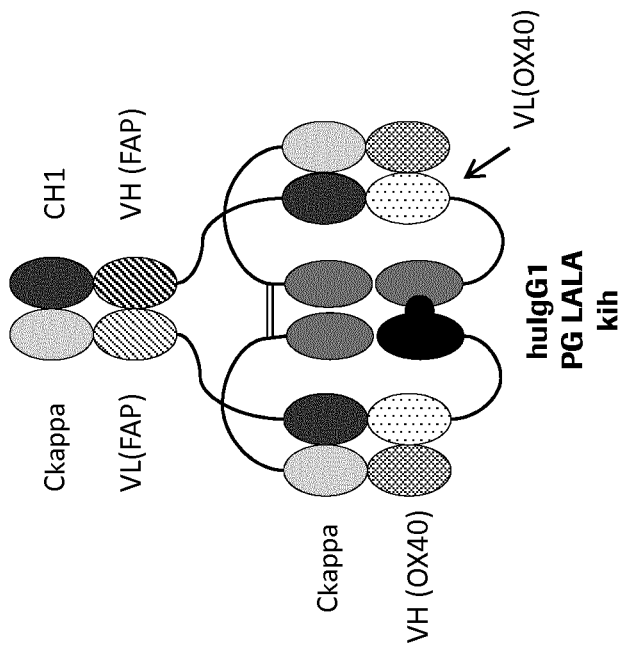
In FIG. 1F a schematic drawing of the assembled structure of Contorsbody CD134-0094 (Example 2.2) is shown.
Figure 1E:
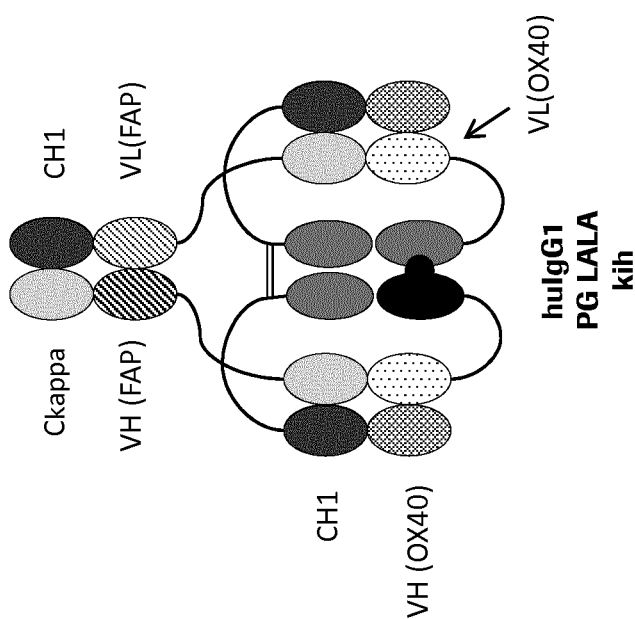
FIG. 1E is a schematic drawing of the assembled structure of Contorsbody CD134-0093 (Example 2.1).

A schematic scheme of the assembled structure is shown in FIG. 1E.

2.2 Preparation of FAP (4B9)-OX40 (49B4) Contorsbody CD134-0094

A bispecific antibody comprising two fusion polypeptides was cloned as depicted in FIG. 1B:

first fusion polypeptide (from N- to C-terminus): VH (OX40)-Ckappa, (G4S)2 connector (SEQ ID NO: 78), IgG1 hinge, Fc knob, (G4S)2 connector (SEQ ID NO: 78), VL(OX40)-CH1, (G4S)2 connector (SEQ ID NO: 78), VL(FAP)-Ckappa second fusion polypeptide (from N- to C-terminus): VH (OX40)-Ckappa, (G4S)2 connector (SEQ ID NO: 78), IgG1 hinge, Fc hole, (G4S)2 connector (SEQ ID NO: 78), VL(OX40)-CH1, (G4S)2 connector (SEQ ID NO: 78), VH(FAP)-CH1.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)).

Table 2 shows the amino acid sequences of the bispecific antibody CD134-0094.

TABLE 2

Sequences of CD134-0094

| SEQ ID NO: | Description | Sequence |
|---|---|---|
| 56 | first fusion polypeptide (Fc knob) | QVQLVQSGAEVKKPGSSVKVSCKASGGTFSSYAISWVRQAPGQGLEWMGGIIPIFGTANYAQKFQGRVTITADKSTSTAYMELSSLRSEDTAVYYCAREYYRGPYDYWGQGTTVTVSSASVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECDGGGGSGGGGSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGKGGGGSGGGGSDIQMTQSPSTLSASVGDRVTITCRASQSISSWLAWYQQKPGKAPKLLIYDASSLESGVPSRFSGSGSGTEFTLTISSLQPDDFATYYCQQYSSQPYTFGQGTKVEIKSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCGGGGSGGGGSEIVLTQSPGTLSLSPGERATLSCRASQSVTSSYLAWYQQKPGQAPRLLINVGSRRATGIPDRFSGSGSGTDFTLTISRLEPEDFAVYYCQQGIMLPPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 57 | second fusion polypeptide (Fc hole) | QVQLVQSGAEVKKPGSSVKVSCKASGGTFSSYAISWVRQAPGQGLEWMGGIIPIFGTANYAQKFQGRVTITADKSTSTAYMELSSLRSEDTAVYYCAREYYRGPYDYWGQGTTVTVSSASVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECDGGGGSGGGGSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGKGGGGSGGGGSDIQMTQSPSTLSASVGDRVTITCRASQSISSWLAWYQQKPGKAPKLLIYDASSLESGVPSRFSGSGSGTEFTLTISSLQPDDFATYYCQQYSSQPYTFGQGTKVEIKSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCGGGGSGGGGSEVQLLESGGGLVQPGGSLRLSCAASGFTFSSYAMSWVRQAPGKGLEWVSAIIGSGASTYYADSVKGRFTISRDNSKNTLYLQMNSLRAEDTAVYYCAKGWFGGFNYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |

A schematic scheme of the assembled structure is shown in FIG. 1F.

2.3 Preparation of FAP (28H1)-OX40 (49B4) Contorsbody P1AE0085

A bispecific antibody comprising two fusion polypeptides was cloned as depicted in FIG. 1A:

first fusion polypeptide (from N- to C-terminus): VH (OX40)-CH1, (G4S)2 connector (SEQ ID NO: 78), IgG1 hinge, Fc knob, (G4S)2 connector (SEQ ID NO: 78), VL(OX40)-Ckappa, GGGGSGGGGSGGGSGGGGS (SEQ ID NO:84) connector, VH(FAP)-Ckappa second fusion polypeptide (from N- to C-terminus): VH (OX40)-CH1, (G4S)2 connector (SEQ ID NO: 78), IgG1 hinge, Fc hole, (G4S)2 connector (SEQ ID NO: 78), VL(OX40)-Ckappa, GGGGSGGGGSGGGSGGGGS (SEQ ID NO:84) connector, VL(FAP)-CH1.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)).

Table 3 shows the amino acid sequences of the bispecific antibody P1AE0085.

TABLE 3

Sequences of P1AE0085

| SEQ ID NO: | Description | Sequence |
|---|---|---|
| 58 | first fusion polypeptide (Fc knob) | QVQLVQSGAEVKKPGSSVKVSCKASGGTFSSYAISWVRQAPGQGLEWM GGIIPIFGTANYAQKFQGRVTITADKSTSTAYMELSSLRSEDTAVYYC AREYYRGPYDYWGQGTTVTVSSASTKGPSVFPLAPSSKSTSGGTAALG CLVKDYFPEPVTVSWNSGALTSGVHTFPAVLQSSGLYSLSSVVTVPSS SLGTQTYICNVNHKPSNTKVDKKVEPKSCGGGGSGGGGSDKTHTCPPC PAPEAAGGPSVFLFPPKPKDTLMISRTPEVTCVVVDVSHEDPEVKFNW YVDGVEVHNAKTKPREEQYNSTYRVVSVLTVLHQDWLNGKEYKCKVSN KALGAPIEKTISKAKGQPREPQVYTLPPCRDELTKNQVSLWCLVKGFY PSDIAVEWESNGQPENNYKTTPPVLDSDGSFFLYSKLTVDKSRWQQGN VFSCSVMHEALHNHYTQKSLSLSPGKGGGGSGGGGSDIQMTQSPSTLS ASVGDRVTITCRASQSISSWLAWYQQKPGKAPKLLIYDASSLESGVPS RFSGSGSGTEFTLTISSLQPDDFATYYCQQYSSQPYTFGQGTKVEIKR TVAAPSVFIFPPSDEQLKSGTASVVCLLNNFYPREAKVQWKVDNALQS GNSQESVTEQDSKDSTYSLSSTLTLSKADYEKHKVYACEVTHQGLSSP VTKSFNRGECGGGGSGGGGSGGGSGGGGSEVQLLESGGGLVQPGGSLR LSCAASGFTFSSHAMSWVRQAPGKGLEWVSAIWASGEQYYADSVKGRF TISRDNSKNTLYLQMNSLRAEDTAVYYCAKGWLGNFDYWGQGTLVTVS SASVAAPSVFIFPPSDEQLKSGTASVVCLLNNFYPREAKVQWKVDNAL QSGNSQESVTEQDSKDSTYSLSSTLTLSKADYEKHKVYACEVTHQGLS SPVTKSFNRGEC |
| 59 | second fusion polypeptide (Fc hole) | QVQLVQSGAEVKKPGSSVKVSCKASGGTFSSYAISWVRQAPGQGLEWM GGIIPIFGTANYAQKFQGRVTITADKSTSTAYMELSSLRSEDTAVYYC AREYYRGPYDYWGQGTTVTVSSASTKGPSVFPLAPSSKSTSGGTAALG CLVKDYFPEPVTVSWNSGALTSGVHTFPAVLQSSGLYSLSSVVTVPSS SLGTQTYICNVNHKPSNTKVDKKVEPKSCGGGGSGGGGSDKTHTCPPC PAPEAAGGPSVFLFPPKPKDTLMISRTPEVTCVVVDVSHEDPEVKFNW YVDGVEVHNAKTKPREEQYNSTYRVVSVLTVLHQDWLNGKEYKCKVSN KALGAPIEKTISKAKGQPREPQVCTLPPSRDELTKNQVSLSCAVKGFY PSDIAVEWESNGQPENNYKTTPPVLDSDGSFFLVSKLTVDKSRWQQGN VFSCSVMHEALHNHYTQKSLSLSPGKGGGGSGGGGSDIQMTQSPSTLS ASVGDRVTITCRASQSISSWLAWYQQKPGKAPKLLIYDASSLESGVPS RFSGSGSGTEFTLTISSLQPDDFATYYCQQYSSQPYTFGQGTKVEIKR TVAAPSVFIFPPSDEQLKSGTASVVCLLNNFYPREAKVQWKVDNALQS GNSQESVTEQDSKDSTYSLSSTLTLSKADYEKHKVYACEVTHQGLSSP VTKSFNRGECGGGGSGGGGSGGGSGGGGSEIVLTQSPGTLSLSPGERA TLSCRASQSVSRSYLAWYQQKPGQAPRLLIIGASTRATGIPDRFSGSG SGTDFTLTISRLEPEDFAVYYCQQGQVIPPTFGQGTKVEIKSSASTKG PSVFPLAPSSKSTSGGTAALGCLVKDYFPEPVTVSWNSGALTSGVHTF PAVLQSSGLYSLSSVVTVPSSSLGTQTYICNVNHKPSNTKVDKKVEPK SC |

Figures 1G, 1H:
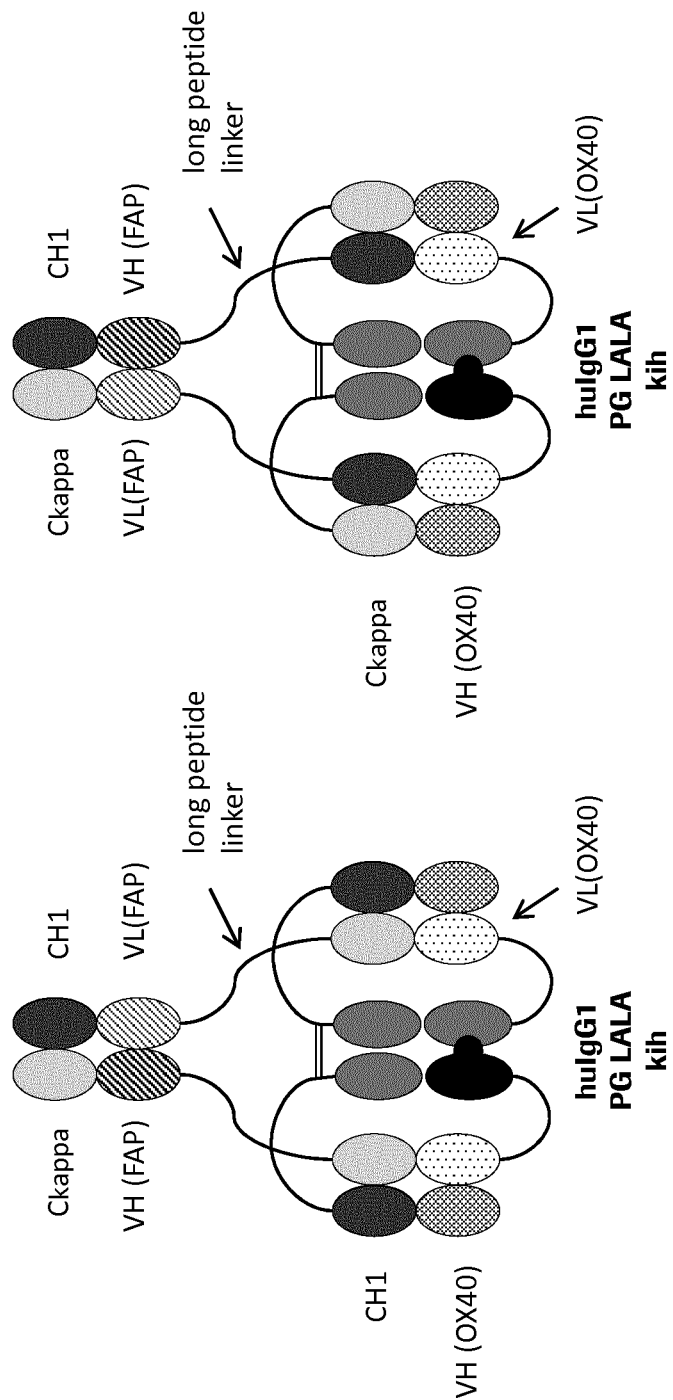
FIG. 1G is a schematic drawing of the assembled structure of Contorsbodies P1AE0085 and P1AE0086 (Examples 2.3 and 2.4). The antigen binding domain capable of specific binding to the second target (cross fab) is connected via a longer peptide linker that changes the geometry of the molecule.
FIG. 1H is a schematic drawing of the assembled structure of Contorsbody P1AE0087 (Example 2.5) and Contorsbody P1AE0839 (Example 2.6). In this case the antigen binding domain capable of specific binding to the second target is a fab and both antigen binding domains capable of specific binding to the first target are cross fabs.

A schematic scheme of the assembled structure is shown in FIG. 1G.

2.4 Preparation of FAP (4B9)-OX40 (49B4) Contorsbody P1AE0086

A bispecific antibody comprising two fusion polypeptides was cloned as depicted in FIG. 1A:
first fusion polypeptide (from N- to C-terminus): VH (OX40)-CH1, (G4S)2 connector (SEQ ID NO: 78), IgG1 hinge, Fc knob, (G4S)2 connector (SEQ ID NO: 78), VL(OX40)-Ckappa, GGGGSGGGGSGGGSGGGGS (SEQ ID NO:84) connector, VH(FAP)-Ckappa
second fusion polypeptide (from N- to C-terminus): VH (OX40)-CH1, (G4S)2 connector (SEQ ID NO: 78), IgG1 hinge, Fc hole, (G4S)2 connector (SEQ ID NO: 78), VL(OX40)-Ckappa, GGGGSGGGGSGGGSGGGGS (SEQ ID NO:84) connector, VL(FAP)-CH1.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)).

Table 4 shows the amino acid sequences of the bispecific antibody P1AE0086 (Contorsbody 7).

TABLE 4

Sequences of P1AE0086

| SEQ ID NO: | Description | Sequence |
|---|---|---|
| 60 | first fusion polypeptide (Fc knob) | QVQLVQSGAEVKKPGSSVKVSCKASGGTFSSYAISWVRQAPGQGLEWM GGIIPIFGTANYAQKFQGRVTITADKSTSTAYMELSSLRSEDTAVYYC AREYYRGPYDYWGQGTTVTVSSASTKGPSVFPLAPSSKSTSGGTAALG |

TABLE 4-continued

Sequences of P1AE0086

| SEQ ID NO: | Description | Sequence |
|---|---|---|
| | | CLVKDYFPEPVTVSWNSGALTSGVHTFPAVLQSSGLYSLSSVVTVPSS<br>SLGTQTYICNVNHKPSNTKVDKKVEPKSCGGGGSGGGGSDKTHTCPPC<br>PAPEAAGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSN<br>KALGAPIEKTISKAKGQPREPQVYTLPPCRDELTKNQVSLWCLVKGFY<br>PSDIAVEWESNGQPENNYKTTPPVLDSDGSFFLYSKLTVDKSRWQQGN<br>VFSCSVMHEALHNHYTQKSLSLSPGKGGGGSGGGGSDIQMTQSPSTLS<br>ASVGDRVTITCRASQSISSWLAWYQQKPGKAPKLLIYDASSLESGVPS<br>RFSGSGSGTEFTLTISSLQPDDFATYYCQQYSSQPYTFGQGTKVEIKR<br>TVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSP<br>VTKSFNRGECGGGGSGGGGSGGGSGGGGSEVQLLESGGGLVQPGGSLR<br>LSCAASGFTFSSYAMSWVRQAPGKGLEWVSAIIGSGASTYYADSVKGR<br>FTISRDNSKNTLYLQMNSLRAEDTAVYYCAKGWFGGFNYWGQGTLVTV<br>SSASVAAPSVFIFPPSDEQLKSGTASVVCLLNNFYPREAKVQWKVDNA<br>LQSGNSQESVTEQDSKDSTYSLSSTLTLSKADYEKHKVYACEVTHQGL<br>SSPVTKSFNRGEC |
| 61 | second fusion polypeptide (Fc hole) | QVQLVQSGAEVKKPGSSVKVSCKASGGTFSSYAISWVRQAPGQGLEWM<br>GGIIPIFGTANYAQKFQGRVTITADKSTSTAYMELSSLRSEDTAVYYC<br>AREYYRGPYDYWGQGTTVTVSSASTKGPSVFPLAPSSKSTSGGTAALG<br>CLVKDYFPEPVTVSWNSGALTSGVHTFPAVLQSSGLYSLSSVVTVPSS<br>SLGTQTYICNVNHKPSNTKVDKKVEPKSCGGGGSGGGGSDKTHTCPPC<br>PAPEAAGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSN<br>KALGAPIEKTISKAKGQPREPQVCTLPPSRDELTKNQVSLSCAVKGFY<br>PSDIAVEWESNGQPENNYKTTPPVLDSDGSFFLVSKLTVDKSRWQQGN<br>VFSCSVMHEALHNHYTQKSLSLSPGKGGGGSGGGGSDIQMTQSPSTLS<br>ASVGDRVTITCRASQSISSWLAWYQQKPGKAPKLLIYDASSLESGVPS<br>RFSGSGSGTEFTLTISSLQPDDFATYYCQQYSSQPYTFGQGTKVEIKR<br>TVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSP<br>VTKSFNRGECGGGGSGGGGSGGGSGGGGSEIVLTQSPGTLSLSPGERA<br>TLSCRASQSVTSSYLAWYQQKPGQAPRLLINVGSRRATGIPDRFSGSG<br>SGTDFTLTISRLEPEDFAVYYCQQGIMLPPTFGQGTKVEIKSSASTKG<br>PSVFPLAPSSKSTSGGTAALGCLVKDYFPEPVTVSWNSGALTSGVHTF<br>PAVLQSSGLYSLSSVVTVPSSSLGTQTYICNVNHKPSNTKVDKKVEPK<br>SC |

A schematic scheme of the assembled structure is shown in FIG. 1G.

2.5 Preparation of FAP (28H1)-OX40 (49B4) Contorsbody P1AE0087

A bispecific antibody comprising two fusion polypeptides was cloned as depicted in FIG. 1B:

first fusion polypeptide (from N- to C-terminus): VH (OX40)-Ckappa, (G4S)2 connector (SEQ ID NO: 78), IgG1 hinge, Fc knob, (G4S)2 connector (SEQ ID NO: 78), VL(OX40)-CH1, GGGGSGGGGSGGGSGGGGS (SEQ ID NO:84) connector, VL(FAP)-Ckappa.

second fusion polypeptide (from N- to C-terminus): VH (OX40)-Ckappa, (G4S)2 connector (SEQ ID NO: 78), IgG1 hinge, Fc hole, (G4S)2 connector (SEQ ID NO: 78), VL(OX40)-CH1, GGGGSGGGGSGGGSGGGGS (SEQ ID NO:84) connector, VH(FAP)-CH1.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)).

Table 5 shows the amino acid sequences of the bispecific antibody P1AE0087.

TABLE 5

Sequences of P1AE0087

| SEQ ID NO: | Description | Sequence |
|---|---|---|
| 62 | first fusion polypeptide (Fc knob) | QVQLVQSGAEVKKPGSSVKVSCKASGGTFSSYAISWVRQAPGQGLEWM<br>GGIIPIFGTANYAQKFQGRVTITADKSTSTAYMELSSLRSEDTAVYYC<br>AREYYRGPYDYWGQGTTVTVSSASVAAPSVFIFPPSDEQLKSGTASVV<br>CLLNNFYPREAKVQWKVDNALQSGNSQESVTEQDSKDSTYSLSSTLTL<br>SKADYEKHKVYACEVTHQGLSSPVTKSFNRGECGGGGSGGGGSDKTH<br>TCPPCPAPEAAGGPSVFLFPPKPKDTLMISRTPEVTCVVVDVSHEDPE<br>VKFNWYVDGVEVHNAKTKPREEQYNSTYRVVSVLTVLHQDWLNGKEYK<br>CKVSNKALGAPIEKTISKAKGQPREPQVYTLPPCRDELTKNQVSLWCL<br>VKGFYPSDIAVEWESNGQPENNYKTTPPVLDSDGSFFLYSKLTVDKSR<br>WQQGNVFSCSVMHEALHNHYTQKSLSLSPGKGGGGSGGGGSDIQMTQS |

TABLE 5-continued

Sequences of P1AE0087

| SEQ ID NO: | Description | Sequence |
|---|---|---|
| | | PSTLSASVGDRVTITCRASQSISSWLAWYQQKPGKAPKLLIYDASSLE SGVPSRFSGSGSGTEFTLTISSLQPDDFATYYCQQYSSQPYTFGQGTK VEIKSSASTKGPSVFPLAPSSKSTSGGTAALGCLVKDYFPEPVTVSWN SGALTSGVHTFPAVLQSSGLYSLSSVVTVPSSSLGTQTYICNVNHKPS NTKVDKKVEPKSCGGGGSGGGGSGGGSGGGGSEIVLTQSPGTLSLSPG ERATLSCRASQSVSRSYLAWYQQKPGQAPRLLIIGASTRATGIPDRFS GSGSGTDFTLTISRLEPEDFAVYYCQQGQVIPPTFGQGTKVEIKRTVA APSVFIFPPSDEQLKSGTASVVCLLNNFYPREAKVQWKVDNALQSGNS QESVTEQDSKDSTYSLSSTLTLSKADYEKHKVYACEVTHQGLSSPVTK SFNRGEC |
| 63 | second fusion polypeptide (Fc hole) | QVQLVQSGAEVKKPGSSVKVSCKASGGTFSSYAISWVRQAPGQGLEWM GGIIPIFGTANYAQKFQGRVTITADKSTSTAYMELSSLRSEDTAVYYC AREYYRGPYDYWGQGTTVTVSSASVAAPSVFIFPPSDEQLKSGTASVV CLLNNFYPREAKVQWKVDNALQSGNSQESVTEQDSKDSTYSLSSTLTL SKADYEKHKVYACEVTHQGLSSPVTKSFNRGECDGGGGSGGGGSDKTH TCPPCPAPEAAGGPSVFLFPPKPKDTLMISRTPEVTCVVVDVSHEDPE VKFNWYVDGVEVHNAKTKPREEQYNSTYRVVSVLTVLHQDWLNGKEYK CKVSNKALGAPIEKTISKAKGQPREPQVCTLPPSRDELTKNQVSLSCA VKGFYPSDIAVEWESNGQPENNYKTTPPVLDSDGSFFLVSKLTVDKSR WQQGNVFSCSVMHEALHNHYTQKSLSLSPGKGGGGSGGGGSDIQMTQS PSTLSASVGDRVTITCRASQSISSWLAWYQQKPGKAPKLLIYDASSLE SGVPSRFSGSGSGTEFTLTISSLQPDDFATYYCQQYSSQPYTFGQGTK VEIKSSASTKGPSVFPLAPSSKSTSGGTAALGCLVKDYFPEPVTVSWN SGALTSGVHTFPAVLQSSGLYSLSSVVTVPSSSLGTQTYICNVNHKPS NTKVDKKVEPKSCGGGGSGGGGSGGGSGGGGSEVQLLESGGGLVQPGG SLRLSCAASGFTFSSHAMSWVRQAPGKGLEWVSAIWASGEQYYADSVK GRFTISRDNSKNTLYLQMNSLRAEDTAVYYCAKGWLGNFDYWGQGTLV TVSSASTKGPSVFPLAPSSKSTSGGTAALGCLVKDYFPEPVTVSWNSG ALTSGVHTFPAVLQSSGLYSLSSVVTVPSSSLGTQTYICNVNHKPSNT KVDKKVEPKSC |

A schematic scheme of the assembled structure is shown in FIG. 1H.

2.6 Preparation of FAP (4B9)-OX40 (49B4) Contorsbody P1AE0839

A bispecific antibody comprising two fusion polypeptides was cloned as depicted in FIG. 1B:
first fusion polypeptide (from N- to C-terminus): VH (OX40)-Ckappa, (G4S)2 connector (SEQ ID NO: 78), IgG1 hinge, Fc knob, (G4S)2 connector (SEQ ID NO: 78), VL(OX40)-CH1, GGGGSGGGGSGGGSGGGGS (SEQ ID NO:84) connector, VL(FAP)-Ckappa.
second fusion polypeptide (from N- to C-terminus): VH (OX40)-Ckappa, (G4S)2 connector (SEQ ID NO: 78), IgG1 hinge, Fc hole, (G4S)2 connector (SEQ ID NO: 78), VL(OX40)-CH1, GGGGSGGGGSGGGSGGGGS (SEQ ID NO:84) connector, VH(FAP)-CH1.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)).

Table 6 shows the amino acid sequences of the bispecific antibody P1AE0839.

TABLE 6

Sequences of P1AE0839

| SEQ ID NO: | Description | Sequence |
|---|---|---|
| 64 | first fusion polypeptide (Fc knob) | QVQLVQSGAEVKKPGSSVKVSCKASGGTFSSYAISWVRQAPGQGLEWMG GIIPIFGTANYAQKFQGRVTITADKSTSTAYMELSSLRSEDTAVYYCAR EYYRGPYDYWGQGTTVTVSSASVAAPSVFIFPPSDEQLKSGTASVVCLL NNFYPREAKVQWKVDNALQSGNSQESVTEQDSKDSTYSLSSTLTLSKAD YEKHKVYACEVTHQGLSSPVTKSFNRGECDGGGGSGGGGSDKTHTCPPC PAPEAAGGPSVFLFPPKPKDTLMISRTPEVTCVVVDVSHEDPEVKFNWY VDGVEVHNAKTKPREEQYNSTYRVVSVLTVLHQDWLNGKEYKCKVSNKA LGAPIEKTISKAKGQPREPQVYTLPPCRDELTKNQVSLWCLVKGFYPSD IAVEWESNGQPENNYKTTPPVLDSDGSFFLYSKLTVDKSRWQQGNVFSC SVMHEALHNHYTQKSLSLSPGKGGGGSGGGGSDIQMTQSPSTLSASVGD RVTITCRASQSISSWLAWYQQKPGKAPKLLIYDASSLESGVPSRFSGSG SGTEFTLTISSLQPDDFATYYCQQYSSQPYTFGQGTKVEIKSSASTKGP SVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCG GGGSGGGGSGGGSGGGGSEIVLTQSPGTLSLSPGERATLSCRASQSVTS SYLAWYQQKPGQAPRLLINVGSRRATGIPDRFSGSGSGTDFTLTISRLE PEDFAVYYCQQGIMLPPTFGQGTKVEIKRTVAAPSVFIFPPSDEQLKSG |

TABLE 6-continued

Sequences of P1AE0839

| SEQ ID NO: | Description | Sequence |
|---|---|---|
|  |  | TASVVCLLNNFYPREAKVQWKVDNALQSGNSQESVTEQDSKDSTYSLSS<br>TLTLSKADYEKHKVYACEVTHQGLSSPVTKSFNRGEC |
| 65 | second fusion polypeptide (Fc hold) | QVQLVQSGAEVKKPGSSVKVSCKASGGTFSSYAISWVRQAPGQGLEWMG<br>GIIPIFGTANYAQKFQGRVTITADKSTSTAYMELSSLRSEDTAVYYCAR<br>EYYRGPYDYWGQGTTVTVSSASVAAPSVFIFPPSDEQLKSGTASVVCLL<br>NNFYPREAKVQWKVDNALQSGNSQESVTEQDSKDSTYSLSSTLTLSKAD<br>YEKHKVYACEVTHQGLSSPVTKSFNRGECDGGGGSGGGGSDKTHTCPPC<br>PAPEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVSNKA<br>LGAPIEKTISKAKGQPREPQVCTLPPSRDELTKNQVSLSCAVKGFYPSD<br>IAVEWESNGQPENNYKTTPPVLDSDGSFFLVSKLTVDKSRWQQGNVFSC<br>SVMHEALHNHYTQKSLSLSPGKGGGGSGGGGSDIQMTQSPSTLSASVGD<br>RVTITCRASQSISSWLAWYQQKPGKAPKLLIYDASSLESGVPSRFSGSG<br>SGTEFTLTISSLQPDDFATYYCQQYSSQPYTFGQGTKVEIKSSASTKGP<br>SVFPLAPSSKSTSGGTAALGCLVKDYFPEPVTVSWNSGALTSGVHTFPA<br>VLQSSGLYSLSSVVTVPSSSLGTQTYICNVNHKPSNTKVDKKVEPKSCG<br>GGGSGGGGSGGGSGGGGSEVQLLESGGGLVQPGGSLRLSCAASGFTFSS<br>YAMSWVRQAPGKGLEWVSAIIGSGASTYYADSVKGRFTISRDNSKNTLY<br>LQMNSLRAEDTAVYYCAKGWFGGFNYWGQGTLVTVSSASTKGPSVFPLA<br>PSSKSTSGGTAALGCLVKDYFPEPVTVSWNSGALTSGVHTFPAVLQSSG<br>LYSLSSVVTVPSSSLGTQTYICNVNHKPSNTKVDKKVEPKSC |

A schematic scheme of the assembled structure is shown in FIG. 1H.

2.7 Preparation of FAP (4B9)-OX40 (49B4) Contorsbody P1AE0821

A bispecific antibody comprising two fusion polypeptides was cloned as depicted in FIG. 1C:

first fusion polypeptide (from N- to C-terminus): VL (OX40)-Ckappa, (G4S)2 connector (SEQ ID NO: 78), IgG1 hinge, Fc knob, (G4S)2 connector (SEQ ID NO: 78), VH(OX40)-CH1, GGGGSGGGGSGGGSGGGGS (SEQ ID NO:84) connector, VH(FAP)-Ckappa.

second fusion polypeptide (from N- to C-terminus): VL (OX40)-Ckappa, (G4S)2 connector (SEQ ID NO: 78), IgG1 hinge, Fc hole, (G4S)2 connector (SEQ ID NO: 78), VH(OX40)-CH1, GGGGSGGGGSGGGSGGGGS (SEQ ID NO:84) connector, VL(FAP)-CH1.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)).

Table 7 shows the amino acid sequences of the bispecific antibody P1AE0821 (Contorsbody 11).

TABLE 7

Sequences of P1AE0821

| SEQ ID NO: | Description | Sequence |
|---|---|---|
| 66 | first fusion polypeptide (Fc knob) | DIQMTQSPSTLSASVGDRVTITCRASQSISSWLAWYQQKPGKAPKLLIYD<br>ASSLESGVPSRFSGSGSGTEFTLTISSLQPDDFATYYCQQYSSQPYTFGQ<br>GTKVEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>LSSPVTKSFNRGECGGGGSGGGGSDKTHTCPPCPAPEAAGGPSVFLFPPK<br>PKDTLMISRTPEVTCVVVDVSHEDPEVKFNWYVDGVEVHNAKTKPREEQY<br>NSTYRVVSVLTVLHQDWLNGKEYKCKVSNKALGAPIEKTISKAKGQPREP<br>QVYTLPPCRDELTKNQVSLWCLVKGFYPSDIAVEWESNGQPENNYKTTPP<br>VLDSDGSFFLYSKLTVDKSRWQQGNVFSCSVMHEALHNHYTQKSLSLSPG<br>KGGGGSGGGGSQVQLVQSGAEVKKPGSSVKVSCKASGGTFSSYAISWVRQ<br>APGQGLEWMGGIIPIFGTANYAQKFQGRVTITADKSTSTAYMELSSLRSE<br>DTAVYYCAREYYRGPYDYWGQGTTVTVSSASTKGPSVFPLAPSSKSTSGG<br>TAALGCLVKDYFPEPVTVSWNSGALTSGVHTFPAVLQSSGLYSLSSVVTV<br>PSSSLGTQTYICNVNHKPSNTKVDKKVEPKSCGGGGSGGGGSGGGSGGGG<br>SEVQLLESGGGLVQPGGSLRLSCAASGFTFSSYAMSWVRQAPGKGLEWVS<br>AIIGSGASTYYADSVKGRFTISRDNSKNTLYLQMNSLRAEDTAVYYCAKG<br>WFGGFNYWGQGTLVTVSSASVAAPSVFIFPPSDEQLKSGTASVVCLLNNF<br>YPREAKVQWKVDNALQSGNSQESVTEQDSKDSTYSLSSTLTLSKADYEKH<br>KVYACEVTHQGLSSPVTKSFNRGEC |
| 67 | second fusion polypeptide (Fc hole) | DIQMTQSPSTLSASVGDRVTITCRASQSISSWLAWYQQKPGKAPKLLIYD<br>ASSLESGVPSRFSGSGSGTEFTLTISSLQPDDFATYYCQQYSSQPYTFGQ<br>GTKVEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>LSSPVTKSFNRGECGGGGSGGGGSDKTHTCPPCPAPEAAGGPSVFLFPPK |

TABLE 7-continued

Sequences of P1AE0821

| SEQ ID NO: Description | Sequence |
|---|---|
| | PKDTLMISRTPEVTCVVVDVSHEDPEVKFNWYVDGVEVHNAKTKPREEQY<br>NSTYRVVSVLTVLHQDWLNGKEYKCKVSNKALGAPIEKTISKAKGQPREP<br>QVCTLPPSRDELTKNQVSLSCAVKGFYPSDIAVEWESNGQPENNYKTTPP<br>VLDSDGSFFLVSKLTVDKSRWQQGNVFSCSVMHEALHNHYTQKSLSLSPG<br>KGGGGSGGGGSQVQLVQSGAEVKKPGSSVKVSCKASGGTFSSYAISWVRQ<br>APGQGLEWMGGIIPIFGTANYAQKFQGRVTITADKSTSTAYMELSSLRSE<br>DTAVYYCAREYYRGPYDYWGQGTTVTVSSASTKGPSVFPLAPSSKSTSGG<br>TAALGCLVKDYFPEPVTVSWNSGALTSGVHTFPAVLQSSGLYSLSSVVTV<br>PSSSLGTQTYICNVNHKPSNTKVDKKVEPKSCGGGGSGGGGSGGGSGGGG<br>SEIVLTQSPGTLSLSPGERATLSCRASQSVTSSYLAWYQQKPGQAPRLLI<br>NVGSRRATGIPDRFSGSGSGTDFTLTISRLEPEDFAVYYCQQGIMLPPTF<br>GQGTKVEIKSSASTKGPSVFPLAPSSKSTSGGTAALGCLVKDYFPEPVTV<br>SWNSGALTSGVHTFPAVLQSSGLYSLSSVVTVPSSSLGTQTYICNVNHKP<br>SNTKVDKKVEPKSC |

A schematic scheme of the assembled structure is shown in Figure H.

2.8 Preparation of FAP (4B9)-OX40 (49B4) Contorsbody P1AE1122 (Contorsbody 1)

A bispecific antibody comprising two fusion polypeptides was cloned as depicted in FIG. 1D:

first fusion polypeptide (from N- to C-terminus): VH (OX40)-CH1, (G4S)2 connector (SEQ ID NO: 78), IgG1 hinge, Fc knob, (G4S)2 connector (SEQ ID NO: 78), VL(OX40)-Ckappa, GGGGSGGGGSGGGSGGGGS (SEQ ID NO:84) connector, VL(FAP)-CH1.

second fusion polypeptide (from N- to C-terminus): VH (OX40)-CH1, (G4S)2 connector (SEQ ID NO: 78), IgG1 hinge, Fc hole, (G4S)2 connector (SEQ ID NO: 78), VL(OX40)-Ckappa, GGGGSGGGGSGGGSGGGGS (SEQ ID NO:84) connector, VH(FAP)-Ckappa.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)).

Table 8 shows the amino acid sequences of the bispecific antibody P1AE1122.

TABLE 8

Sequences of P1AE1122:

| SEQ ID NO: | Description | Sequence |
|---|---|---|
| 116 | first fusion polypeptide (Fc knob) | QVQLVQSGAEVKKPGSSVKVSCKASGGTFSSYAISWVRQAPGQGLEWMG<br>GIIPIFGTANYAQKFQGRVTITADKSTSTAYMELSSLRSEDTAVYYCAR<br>EYYRGPYDYWGQGTTVTVSSASTKGPSVFPLAPSSKSTSGGTAALGCLV<br>KDYFPEPVTVSWNSGALTSGVHTFPAVLQSSGLYSLSSVVTVPSSSLGT<br>QTYICNVNHKPSNTKVDKKVEPKSCGGGGSGGGGSDKTHTCPPCPAPEA<br>AGGPSVFLFPPKPKDTLMISRTPEVTCVVVDVSHEDPEVKFNWYVDGVE<br>VHNAKTKPREEQYNSTYRVVSVLTVLHQDWLNGKEYKCKVSNKALGAPI<br>EKTISKAKGQPREPQVYTLPPCRDELTKNQVSLWCLVKGFYPSDIAVEW<br>ESNGQPENNYKTTPPVLDSDGSFFLYSKLTVDKSRWQQGNVFSCSVMHE<br>ALHNHYTQKSLSLSPGKGGGGSGGGGSDIQMTQSPSTLSASVGDRVTIT<br>CRASQSISSWLAWYQQKPGKAPKLLIYDASSLESGVPSRFSGSGSGTEF<br>TLTISSLQPDDFATYYCQQYSSQPYTFGQGTKVEIKRTVAAPSVFIFPP<br>SDEQLKSGTASVVCLLNNFYPREAKVQWKVDNALQSGNSQESVTEQDSK<br>DSTYSLSSTLTLSKADYEKHKVYACEVTHQGLSSPVTKSFNRGECGGGG<br>SGGGGSGGGSGGGGSEIVLTQSPGTLSLSPGERATLSCRASQSVTSSYL<br>AWYQQKPGQAPRLLINVGSRRATGIPDRFSGSGSGTDFTLTISRLEPED<br>FAVYYCQQGIMLPPTFGQGTKVEIKSSASTKGPSVFPLAPSSKSTSGGT<br>AALGCLVKDYFPEPVTVSWNSGALTSGVHTFPAVLQSSGLYSLSSVVTV<br>PSSSLGTQTYICNVNHKPSNTKVDKKVEPKSC |
| 117 | second fusion polypeptide (Fc hole) | QVQLVQSGAEVKKPGSSVKVSCKASGGTFSSYAISWVRQAPGQGLEWMG<br>GIIPIFGTANYAQKFQGRVTITADKSTSTAYMELSSLRSEDTAVYYCAR<br>EYYRGPYDYWGQGTTVTVSSASTKGPSVFPLAPSSKSTSGGTAALGCLV<br>KDYFPEPVTVSWNSGALTSGVHTFPAVLQSSGLYSLSSVVTVPSSSLGT<br>QTYICNVNHKPSNTKVDKKVEPKSCGGGGSGGGGSDKTHTCPPCPAPEA<br>AGGPSVFLFPPKPKDTLMISRTPEVTCVVVDVSHEDPEVKFNWYVDGVE<br>VHNAKTKPREEQYNSTYRVVSVLTVLHQDWLNGKEYKCKVSNKALGAPI<br>EKTISKAKGQPREPQVCTLPPSRDELTKNQVSLSCAVKGFYPSDIAVEW<br>ESNGQPENNYKTTPPVLDSDGSFFLVSKLTVDKSRWQQGNVFSCSVMHE<br>ALHNHYTQKSLSLSPGKGGGGSGGGGSDIQMTQSPSTLSASVGDRVTIT<br>CRASQSISSWLAWYQQKPGKAPKLLIYDASSLESGVPSRFSGSGSGTEF<br>TLTISSLQPDDFATYYCQQYSSQPYTFGQGTKVEIKRTVAAPSVFIFPP<br>SDEQLKSGTASVVCLLNNFYPREAKVQWKVDNALQSGNSQESVTEQDSK |

TABLE 8-continued

Sequences of P1AE1122:

| SEQ ID NO: Description | Sequence |
|---|---|
| | DSTYSLSSTLTLSKADYEKHKVYACEVTHQGLSSPVTKSFNRGECGGGG
SGGGGSGGGSGGGGSEVQLLESGGGLVQPGGSLRLSCAASGFTFSSYAM
SWVRQAPGKGLEWVSAIIGSGASTYYADSVKGRFTISRDNSKNTLYLQM
NSLRAEDTAVYYCAKGWFGGFNYWGQGTLVTVSSASVAAPSVFIFPPSD
EQLKSGTASVVCLLNNFYPREAKVQWKVDNALQSGNSQESVTEQDSKDS
TYSLSSTLTLSKADYEKHKVYACEVTHQGLSSPVTKSFNRGEC |

Figures 1I, 1J:
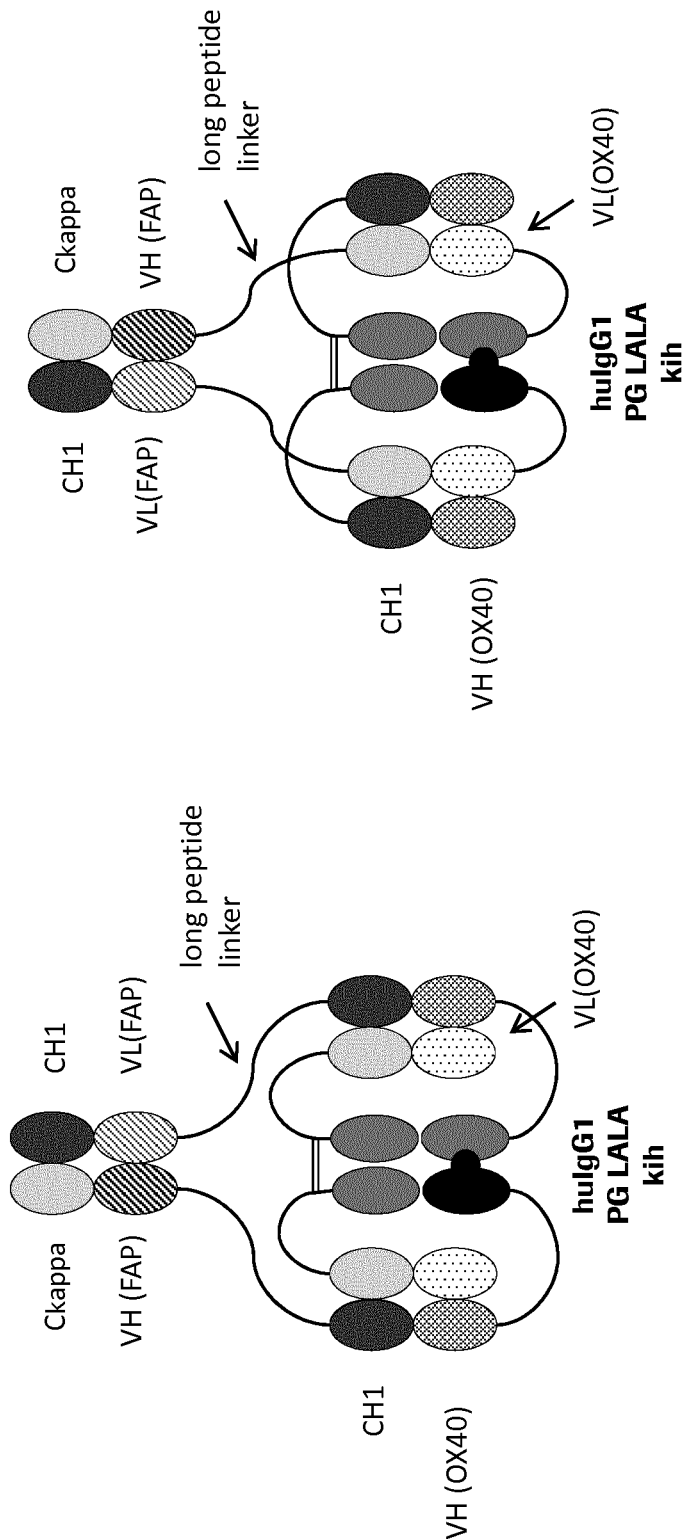
In FIG. 1I a schematic drawing of the assembled structure of Contorsbody P1AE0821 (Contorsbody 11, Example 2.7) is shown.
FIG. 1J is a schematic drawing of the assembled structure of Contorsbody P1AE1122 (Contorsbody 1, Example 2.8).

A schematic scheme of the assembled structure is shown in FIG. 1J.

2.9 Preparation of FAP (4B9)-OX40 (49B4) Contorsbody P1AE1942 (Contorsbody 2)

A bispecific antibody comprising two fusion polypeptides was cloned as follows:

first fusion polypeptide (from N- to C-terminus): VL (OX40)-Ckappa, (G4S)2 connector (SEQ ID NO: 78), IgG1 hinge, Fc knob, (G4S)2 connector (SEQ ID NO: 78), VH(OX40)-CH1, GGGGSGGGGSGGGSGGGGS (SEQ ID NO:84) connector, VL(FAP)-CH1.

second fusion polypeptide (from N- to C-terminus): VL (OX40)-Ckappa, (G4S)2 connector (SEQ ID NO: 78), IgG1 hinge, Fc hole, (G4S)2 connector (SEQ ID NO: 78), VH(OX40)-CH1, GGGGSGGGGSGGGSGGGGS (SEQ ID NO:84) connector, VH(FAP)-Ckappa.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)).

Table 9 shows the amino acid sequences of the bispecific antibody P1AE1942.

TABLE 9

Sequences of P1AE1942:

| SEQ ID NO: | Description | Sequence |
|---|---|---|
| 118 | first fusion polypeptide (Fc knob) | DIQMTQSPSTLSASVGDRVTITCRASQSISSWLAWYQQKPGKAPKLLIY
DASSLESGVPSRFSGSGSGTEFTLTISSLQPDDFATYYCQQYSSQPYTF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGECGGGGSGGGGSDKTHTCPPCPAPEAAGGPSVF
LFPPKPKDTLMISRTPEVTCVVVDVSHEDPEVKFNWYVDGVEVHNAKTK
PREEQYNSTYRVVSVLTVLHQDWLNGKEYKCKVSNKALGAPIEKTISKA
KGQPREPQVYTLPPCRDELTKNQVSLWCLVKGFYPSDIAVEWESNGQPE
NNYKTTPPVLDSDGSFFLYSKLTVDKSRWQQGNVFSCSVMHEALHNHYT
QKSLSLSPGKGGGGSGGGGSQVQLVQSGAEVKKPGSSVKVSCKASGGTF
SSYAISWVRQAPGQGLEWMGGIIPIFGTANYAQKFQGRVTITADKSTST
AYMELSSLRSEDTAVYYCAREYYRGPYDYWGQGTTVTVSSASTKGPSVF
PLAPSSKSTSGGTAALGCLVKDYFPEPVTVSWNSGALTSGVHTFPAVLQ
SSGLYSLSSVVTVPSSSLGTQTYICNVNHKPSNTKVDKKVEPKSCGGGG
SGGGGSGGGSGGGGSEIVLTQSPGTLSLSPGERATLSCRASQSVTSSYL
AWYQQKPGQAPRLLINVGSRRATGIPDRFSGSGSGTDFTLTISRLEPED
FAVYYCQQGIMLPPTFGQGTKVEIKSSASTKGPSVFPLAPSSKSTSGGT
AALGCLVKDYFPEPVTVSWNSGALTSGVHTFPAVLQSSGLYSLSSVVTV
PSSSLGTQTYICNVNHKPSNTKVDKKVEPKSC |
| 119 | second fusion polypeptide (Fc hole) | DIQMTQSPSTLSASVGDRVTITCRASQSISSWLAWYQQKPGKAPKLLIY
DASSLESGVPSRFSGSGSGTEFTLTISSLQPDDFATYYCQQYSSQPYTF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGECGGGGSGGGGSDKTHTCPPCPAPEAAGGPSVF
LFPPKPKDTLMISRTPEVTCVVVDVSHEDPEVKFNWYVDGVEVHNAKTK
PREEQYNSTYRVVSVLTVLHQDWLNGKEYKCKVSNKALGAPIEKTISKA
KGQPREPQVCTLPPSRDELTKNQVSLSCAVKGFYPSDIAVEWESNGQPE
NNYKTTPPVLDSDGSFFLVSKLTVDKSRWQQGNVFSCSVMHEALHNHYT
QKSLSLSPGKGGGGSGGGGSQVQLVQSGAEVKKPGSSVKVSCKASGGTF
SSYAISWVRQAPGQGLEWMGGIIPIFGTANYAQKFQGRVTITADKSTST
AYMELSSLRSEDTAVYYCAREYYRGPYDYWGQGTTVTVSSASTKGPSVF
PLAPSSKSTSGGTAALGCLVKDYFPEPVTVSWNSGALTSGVHTFPAVLQ
SSGLYSLSSVVTVPSSSLGTQTYICNVNHKPSNTKVDKKVEPKSCGGGG
SGGGGSGGGSGGGGSEVQLLESGGGLVQPGGSLRLSCAASGFTFSSYAM
SWVRQAPGKGLEWVSAIIGSGASTYYADSVKGRFTISRDNSKNTLYLQM
NSLRAEDTAVYYCAKGWFGGFNYWGQGTLVTVSSASVAAPSVFIFPPSD
EQLKSGTASVVCLLNNFYPREAKVQWKVDNALQSGNSQESVTEQDSKDS
TYSLSSTLTLSKADYEKHKVYACEVTHQGLSSPVTKSFNRGEC |

2.10 Preparation of FAP (4B9)-OX40 (49B4) Contorsbody P1AE1887 (Contorsbody 3)

A bispecific antibody comprising two fusion polypeptides was cloned as follows:

first fusion polypeptide (from N- to C-terminus): VL (OX40)-Ckappa, (G4S)2 connector (SEQ ID NO: 78), IgG1 hinge, Fc knob, (G4S)2 connector (SEQ ID NO: 78), VH(OX40)-CH1, GGGGSGGGGSGGGSGGGGS (SEQ ID NO:84) connector, VH(FAP)-Ckappa.

second fusion polypeptide (from N- to C-terminus): VH (OX40)-CH1, (G4S)2 connector (SEQ ID NO: 78), IgG1 hinge, Fc hole, (G4S)2 connector (SEQ ID NO: 78), VL(OX40)-Ckappa, GGGGSGGGGSGGGSGGGGS (SEQ ID NO:84) connector, VL(FAP)-CH1.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)).

Table 10 shows the amino acid sequences of the bispecific antibody P1AE1887.

Figures 1K, 1L:
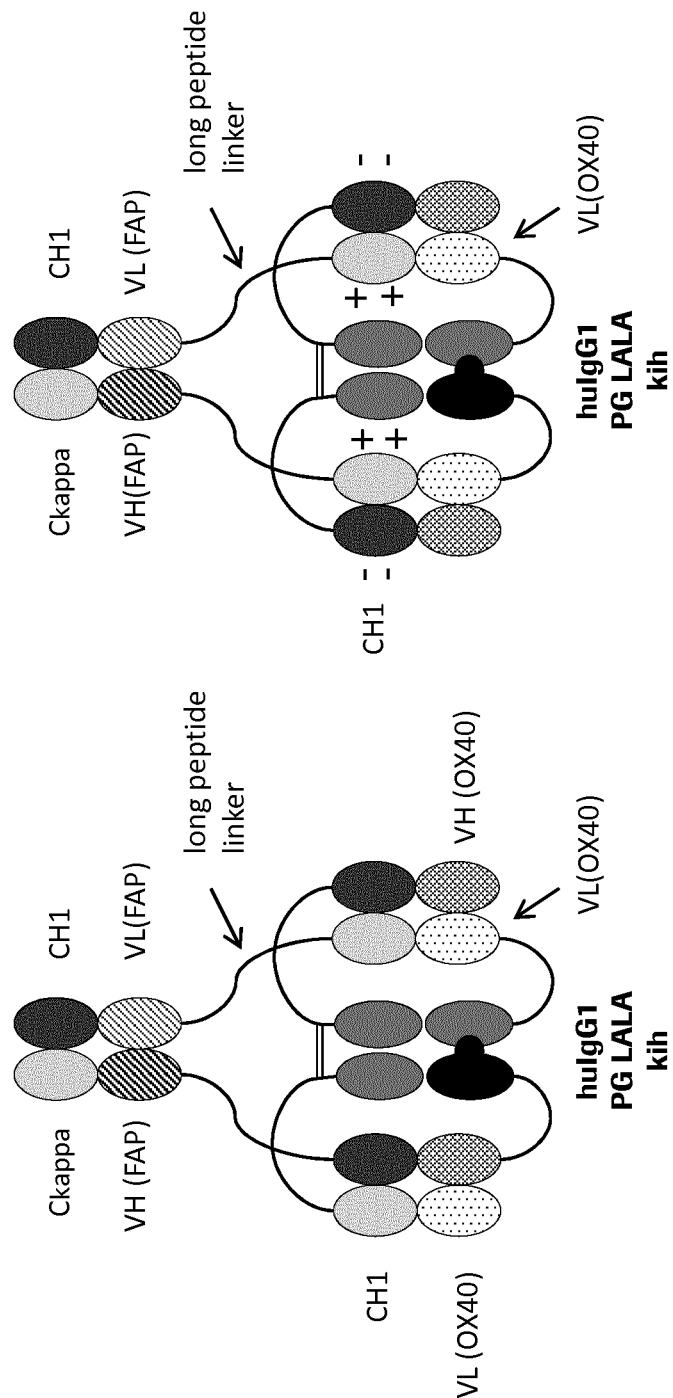
In FIG. 1K a schematic drawing of the assembled structure of Contorsbody P1AE1887 (Contorsbody 3, Example 2.10) is shown.
In FIG. 1L a schematic drawing of the assembled structure of Contorsbody P1AE2254 (Contorsbody 5, Example 2.12) is shown. In the CH and Ckappa fused to the VL and VH of OX40, respectively, amino acid mutations (so-called charged residues) were introduced to prevent the generation of Bence Jones proteins and to further facilitate the correct pairing.

A schematic scheme of the assembled structure is shown in FIG. 1K.

2.11 Preparation of FAP (4B9)-OX40 (49B4) Contorsbody P1AE1888 (Contorsbody 4)

A bispecific antibody comprising two fusion polypeptides was cloned as follows:

first fusion polypeptide (from N- to C-terminus): VH(OX40)-CH1, (G4S)2 connector (SEQ ID NO: 78), IgG1 hinge, Fc knob, (G4S)2 connector (SEQ ID NO: 78), VL(OX40)-Ckappa, GGGGSGGGGSGGGSGGGGS (SEQ ID NO:84) connector, VH(FAP)-Ckappa.

second fusion polypeptide (from N- to C-terminus): VL(OX40)-Ckappa, (G4S)2 connector (SEQ ID NO: 78), IgG1 hinge, Fc hole, (G4S)2 connector (SEQ ID NO: 78), VH(OX40)-CH1, GGGGSGGGGSGGGSGGGGS (SEQ ID NO:84) connector, VL(FAP)-CH1.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)).

TABLE 10

Sequences of P1AE1887:

| SEQ ID NO: | Description | Sequence |
|---|---|---|
| 120 | first fusion polypeptide (Fc knob) | DIQMTQSPSTLSASVGDRVTITCRASQSISSWLAWYQQKPGKAPKLLIYDA SSLESGVPSRFSGSGSGTEFTLTISSLQPDDFATYYCQQYSSQPYTFGQGT KVEIKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSP VTKSFNRGECGGGGSGGGGSDKTHTCPPCPAPEAAGGPSVFLFPPKPKDTL MISRTPEVTCVVVDVSHEDPEVKFNWYVDGVEVHNAKTKPREEQYNSTYRV VSVLTVLHQDWLNGKEYKCKVSNKALGAPIEKTISKAKGQPREPQVYTLPP CRDELTKNQVSLWCLVKGFYPSDIAVEWESNGQPENNYKTTPPVLDSDGSF FLYSKLTVDKSRWQQGNVFSCSVMHEALHNHYTQKSLSLSPGKGGGGSGGG GSQVQLVQSGAEVKKPGSSVKVSCKASGGTFSSYAISWVRQAPGQGLEWMG GIIPIFGTANYAQKFQGRVTITADKSTSTAYMELSSLRSEDTAVYYCAREY YRGPYDYWGQGTTVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCGGGGSGGGGSGGGSGGGGSEVQLLESGGGLVQ PGGSLRLSCAASGFTFSSYAMSWVRQAPGKGLEWVSAIIGSGASTYYADSV KGRFTISRDNSKNTLYLQMNSLRAEDTAVYYCAKGWFGGFNYWGQGTLVTV SSASVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTK SFNRGEC |
| 121 | second fusion polypeptide (Fc hole) | QVQLVQSGAEVKKPGSSVKVSCKASGGTFSSYAISWVRQAPGQGLEWMGGI IPIFGTANYAQKFQGRVTITADKSTSTAYMELSSLRSEDTAVYYCAREYYR GPYDYWGQGTTVTVSSASTKGPSVFPLAPSSKSTSGGTAALGCLVKDYFPE PVTVSWNSGALTSGVHTFPAVLQSSGLYSLSSVVTVPSSSLGTQTYICNVN HKPSNTKVDKKVEPKSCGGGGSGGGGSDKTHTCPPCPAPEAAGGPSVFLFP PKPKDTLMISRTPEVTCVVVDVSHEDPEVKFNWYVDGVEVHNAKTKPREEQ YNSTYRVVSVLTVLHQDWLNGKEYKCKVSNKALGAPIEKTISKAKGQPREP QVCTLPPSRDELTKNQVSLSCAVKGFYPSDIAVEWESNGQPENNYKTTPPV LDSDGSFFLVSKLTVDKSRWQQGNVFSCSVMHEALHNHYTQKSLSLSPGKG GGGSGGGGSDIQMTQSPSTLSASVGDRVTITCRASQSISSWLAWYQQKPGK APKLLIYDASSLESGVPSRFSGSGSGTEFTLTISSLQPDDFATYYCQQYSS QPYTFGQGTKVEIKRTVAAPSVFIFPPSDEQLKSGTASVVCLLNNFYPREA KVQWKVDNALQSGNSQESVTEQDSKDSTYSLSSTLTLSKADYEKHKVYACE VTHQGLSSPVTKSFNRGECGGGGSGGGGSGGGSGGGGSEIVLTQSPGTLSL SPGERATLSCRASQSVTSSYLAWYQQKPGQAPRLLINVGSRRATGIPDRFS GSGSGTDFTLTISRLEPEDFAVYYCQQGIMLPPTFGQGTKVEIKSSASTKG PSVFPLAPSSKSTSGGTAALGCLVKDYFPEPVTVSWNSGALTSGVHTFPAV LQSSGLYSLSSVVTVPSSSLGTQTYICNVNHKPSNTKVDKKVEPKSC |

Table 11 shows the amino acid sequences of the bispecific antibody P1AE1888.

TABLE 11

Sequences of P1AE1888:

| SEQ ID NO: | Description | Sequence |
|---|---|---|
| 122 | first fusion polypeptide (Fc knob) | QVQLVQSGAEVKKPGSSVKVSCKASGGTFSSYAISWVRQAPGQGLEWMGG<br>IIPIFGTANYAQKFQGRVTITADKSTSTAYMELSSLRSEDTAVYYCAREY<br>YRGPYDYWGQGTTVTVSSASTKGPSVFPLAPSSKSTSGGTAALGCLVKDY<br>FPEPVTVSWNSGALTSGVHTFPAVLQSSGLYSLSSVVTVPSSSLGTQTYI<br>CNVNHKPSNTKVDKKVEPKSCGGGGSGGGGSDKTHTCPPCPAPEAAGGPS<br>VFLFPPKPKDTLMISRTPEVTCVVVDVSHEDPEVKFNWYVDGVEVHNAKT<br>KPREEQYNSTYRVVSVLTVLHQDWLNGKEYKCKVSNKALGAPIEKTISKA<br>KGQPREPQVYTLPPCRDELTKNQVSLWCLVKGFYPSDIAVEWESNGQPEN<br>NYKTTPPVLDSDGSFFLYSKLTVDKSRWQQGNVFSCSVMHEALHNHYTQK<br>SLSLSPGKGGGGSGGGGSDIQMTQSPSTLSASVGDRVTITCRASQSISSW<br>LAWYQQKPGKAPKLLIYDASSLESGVPSRFSGSGSGTEFTLTISSLQPDD<br>FATYYCQQYSSQPYTFGQGTKVEIKRTVAAPSVFIFPPSDEQLKSGTASV<br>VCLLNNFYPREAKVQWKVDNALQSGNSQESVTEQDSKDSTYSLSSTLTLS<br>KADYEKHKVYACEVTHQGLSSPVTKSFNRGECGGGGSGGGGSGGGSGGGG<br>SEVQLLESGGGLVQPGGSLRLSCAASGFTFSSYAMSWVRQAPGKGLEWVS<br>AIIGSGASTYYADSVKGRFTISRDNSKNTLYLQMNSLRAEDTAVYYCAKG<br>WFGGFNYWGQGTLVTVSSASVAAPSVFIFPPSDEQLKSGTASVVCLLNNF<br>YPREAKVQWKVDNALQSGNSQESVTEQDSKDSTYSLSSTLTLSKADYEKH<br>KVYACEVTHQGLSSPVTKSFNRGEC |
| 123 | second fusion polypeptide (Fc hole) | DIQMTQSPSTLSASVGDRVTITCRASQSISSWLAWYQQKPGKAPKLLIYD<br>ASSLESGVPSRFSGSGSGTEFTLTISSLQPDDFATYYCQQYSSQPYTFGQ<br>GTKVEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>LSSPVTKSFNRGECGGGGSGGGGSDKTHTCPPCPAPEAAGGPSVFLFPPK<br>PKDTLMISRTPEVTCVVVDVSHEDPEVKFNWYVDGVEVHNAKTKPREEQY<br>NSTYRVVSVLTVLHQDWLNGKEYKCKVSNKALGAPIEKTISKAKGQPREP<br>QVCTLPPSRDELTKNQVSLSCAVKGFYPSDIAVEWESNGQPENNYKTTPP<br>VLDSDGSFFLVSKLTVDKSRWQQGNVFSCSVMHEALHNHYTQKSLSLSPG<br>KGGGGSGGGGSQVQLVQSGAEVKKPGSSVKVSCKASGGTFSSYAISWVRQ<br>APGQGLEWMGGIIPIFGTANYAQKFQGRVTITADKSTSTAYMELSSLRSE<br>DTAVYYCAREYRGPYDYWGQGTTVTVSSASTKGPSVFPLAPSSKSTSGG<br>TAALGCLVKDYFPEPVTVSWNSGALTSGVHTFPAVLQSSGLYSLSSVVTV<br>PSSSLGTQTYICNVNHKPSNTKVDKKVEPKSCGGGGSGGGGSGGGSGGGG<br>SEIVLTQSPGTLSLSPGERATLSCRASQSVTSSYLAWYQQKPGQAPRLLI<br>NVGSRRATGIPDRFSGSGSGTDFTLTISRLEPEDFAVYYCQQGIMLPPTF<br>GQGTKVEIKSSASTKGPSVFPLAPSSKSTSGGTAALGCLVKDYFPEPVTV<br>SWNSGALTSGVHTFPAVLQSSGLYSLSSVVTVPSSSLGTQTYICNVNHKP<br>SNTKVDKKVEPKSC |

2.12 Preparation of FAP (4B9)-OX40 (49B4) Contorsbody P1AE2254 (Contorsbody 5)

A bispecific antibody comprising two fusion polypeptides was cloned as follows:

first fusion polypeptide (from N- to C-terminus): VH(OX40)-CH1_EE (K147E, K213E), (G4S)2 connector (SEQ ID NO: 78), IgG1 hinge, Fc knob, (G4S)2 connector (SEQ ID NO: 78), VL(OX40)-Ckappa_RK (E123R, Q124K), GGGGSGGGGSGGGSGGGGS (SEQ ID NO:84) connector, VH(FAP)-Ckappa.

second fusion polypeptide (from N- to C-terminus): VH(OX40)-CH1_EE (K147E, K213E), (G4S)2 connector (SEQ ID NO: 78), IgG1 hinge, Fc hole, (G4S)2 connector (SEQ ID NO: 78), VL(OX40)-Ckappa_RK (E123R, Q124K), GGGGSGGGGSGGGSGGGGS (SEQ ID NO:84) connector, VL(FAP)-CH1.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)). Furthermore, in the CH and Ckappa fused to the VL and VH of OX40, respectively, amino acid mutations (so-called charged residues) were introduced to prevent the generation of Bence Jones proteins and to further facilitate the correct pairing, i.e negative charges in the CH1 domain (K147E, K213E, numbering according Kabat EU index) and positive charges in the CL domain of the anti-OX40 binder 49B4 (E123R and Q124K, numbering according to Kabat EU index).

Table 12 shows the amino acid sequences of the bispecific antibody P1AE2254.

TABLE 12

Sequences of P1AE2254:

| SEQ ID NO: | Description | Sequence |
|---|---|---|
| 124 | first fusion polypeptide (Fc knob) | QVQLVQSGAEVKKPGSSVKVSCKASGGTFSSYAISWVRQAPGQGLEWMGGII PIFGTANYAQKFQGRVTITADKSTSTAYMELSSLRSEDTAVYYCAREYYRGP YDYWGQGTTVTVSSASTKGPSVFPLAPSSKSTSGGTAALGCLVEDYFPEPVT VSWNSGALTSGVHTFPAVLQSSGLYSLSSVVTVPSSSLGTQTYICNVNHKPS NTKVDEKVEPKSCGGGGSGGGGSDKTHTCPPCPAPEAAGGPSVFLFPPKPKD TLMISRTPEVTCVVVDVSHEDPEVKFNWYVDGVEVHNAKTKPREEQYNSTYR VVSVLTVLHQDWLNGKEYKCKVSNKALGAPIEKTISKAKGQPREPQVYTLPP CRDELTKNQVSLWCLVKGFYPSDIAVEWESNGQPENNYKTTPPVLDSDGSFF LYSKLTVDKSRWQQGNVFSCSVMHEALHNHYTQKSLSLSPGKGGGGSGGGGS DIQMTQSPSTLSASVGDRVTITCRASQSISSWLAWYQQKPGKAPKLLIYDAS SLESGVPSRFSGSGSGTEFTLTISSLQPDDFATYYCQQYSSQPYTFGQGTKV EIKRTVAAPSVFIFPPSDRKLKSGTASVVCLLNNFYPREAKVQWKVDNALQS GNSQESVTEQDSKDSTYSLSSTLTLSKADYEKHKVYACEVTHQGLSSPVTKS FNRGECGGGGSGGGGSGGGSGGGGSEVQLLESGGGLVQPGGSLRLSCAASGF TFSSYAMSWVRQAPGKGLEWVSAIIGSGASTYYADSVKGRFTISRDNSKNTL YLQMNSLRAEDTAVYYCAKGWFGGFNYWGQGTLVTVSSASVAAPSVFIFPPS DEQLKSGTASVVCLLNNFYPREAKVQWKVDNALQSGNSQESVTEQDSKDSTY SLSSTLTLSKADYEKHKVYACEVTHQGLSSPVTKSFNRGEC |
| 125 | second fusion polypeptide (Fc hole) | QVQLVQSGAEVKKPGSSVKVSCKASGGTFSSYAISWVRQAPGQGLEWMGGII PIFGTANYAQKFQGRVTITADKSTSTAYMELSSLRSEDTAVYYCAREYYRGP YDYWGQGTTVTVSSASTKGPSVFPLAPSSKSTSGGTAALGCLVEDYFPEPVT VSWNSGALTSGVHTFPAVLQSSGLYSLSSVVTVPSSSLGTQTYICNVNHKPS NTKVDEKVEPKSCGGGGSGGGGSDKTHTCPPCPAPEAAGGPSVFLFPPKPKD TLMISRTPEVTCVVVDVSHEDPEVKFNWYVDGVEVHNAKTKPREEQYNSTYR VVSVLTVLHQDWLNGKEYKCKVSNKALGAPIEKTISKAKGQPREPQVCTLPP SRDELTKNQVSLSCAVKGFYPSDIAVEWESNGQPENNYKTTPPVLDSDGSFF LVSKLTVDKSRWQQGNVFSCSVMHEALHNHYTQKSLSLSPGKGGGGSGGGGS DIQMTQSPSTLSASVGDRVTITCRASQSISSWLAWYQQKPGKAPKLLIYDAS SLESGVPSRFSGSGSGTEFTLTISSLQPDDFATYYCQQYSSQPYTFGQGTKV EIKRTVAAPSVFIFPPSDRKLKSGTASVVCLLNNFYPREAKVQWKVDNALQS GNSQESVTEQDSKDSTYSLSSTLTLSKADYEKHKVYACEVTHQGLSSPVTKS FNRGECGGGGSGGGGSGGGSGGGGSEIVLTQSPGTLSLSPGERATLSCRASQ SVTSSYLAWYQQKPGQAPRLLINVGSRRATGIPDRFSGSGSGTDFTLTISRL EPEDFAVYYCQQGIMLPPTFGQGTKVEIKSSASTKGPSVFPLAPSSKSTSGG TAALGCLVKDYFPEPVTVSWNSGALTSGVHTFPAVLQSSGLYSLSSVVTVPS SSLGTQTYICNVNHKPSNTKVDKKVEPKSC |

A schematic scheme of the assembled structure is shown in FIG. 1L.

2.13 Preparation of FAP (4B9)-OX40 (49B4) Contorsbody P1AE2340 (Contorsbody 6)

A bispecific antibody comprising two fusion polypeptides and a light chain was cloned as follows:

first fusion polypeptide (from N- to C-terminus): VH(OX40)-CH1_EE (K147E, K213E), (G4S)2 connector (SEQ ID NO: 78), IgG1 hinge, Fc knob, (G4S)2 connector (SEQ ID NO: 78), VL(OX40)-Ckappa_RK (E123R, Q124K), GGGGSGGGGSGGGSGGGGS (SEQ ID NO:84) connector, VH(FAP)-Ckappa.

second fusion polypeptide (from N- to C-terminus): VH(OX40)-CH1_EE (K147E, K213E), (G4S)2 connector (SEQ ID NO: 78), IgG1 hinge, Fc hole, (G4S)2 connector (SEQ ID NO: 78), VL(OX40)-Ckappa_RK (E123R, Q124K).

light chain: VL(FAP)-CH1.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)). Furthermore, the CH and Ckappa fused to the VL and VH of OX40, respectively, amino acid mutations (so-called charged residues) were introduced to prevent the generation of Bence Jones proteins and to further facilitate the correct pairing, i.e negative charges in the CH1 domain (K147E, K213E, numbering according Kabat EU index) and positive charges in the CL domain of the anti-OX40 binder 49B4 (E123R and Q124K, numbering according to Kabat EU index).

Table 13 shows the amino acid sequences of the bispecific antibody P1AE2340.

TABLE 13

Sequences of P1AE2340:

| SEQ ID NO: | Description | Sequence |
|---|---|---|
| 126 | first fusion polypeptide | QVQLVQSGAEVKKPGSSVKVSCKASGGTFSSYAISWVRQAPGQGLEWMGGI IPIFGTANYAQKFQGRVTITADKSTSTAYMELSSLRSEDTAVYYCAREYYR |

TABLE 13-continued

Sequences of P1AE2340:

| SEQ ID NO: | Description | Sequence |
|---|---|---|
| | (Fc knob) | GPYDYWGQGTTVTVSSASTKGPSVFPLAPSSKSTSGGTAALGCLVEDYFPE PVTVSWNSGALTSGVHTFPAVLQSSGLYSLSSVVTVPSSSLGTQTYICNVN HKPSNTKVDEKVEPKSCGGGGSGGGGSDKTHTCPPCPAPEAAGGPSVFLFP PKPKDTLMISRTPEVTCVVVDVSHEDPEVKFNWYVDGVEVHNAKTKPREEQ YNSTYRVVSVLTVLHQDWLNGKEYKCKVSNKALGAPIEKTISKAKGQPREP QVYTLPPCRDELTKNQVSLWCLVKGFYPSDIAVEWESNGQPENNYKTTPPV LDSDGSFFLYSKLTVDKSRWQQGNVFSCSVMHEALHNHYTQKSLSLSPGKG GGGSGGGGSDIQMTQSPSTLSASVGDRVTITCRASQSISSWLAWYQQKPGK APKLLIYDASSLESGVPSRFSGSGSGTEFTLTISSLQPDDFATYYCQQYSS QPYTFGQGTKVEIKRTVAAPSVFIFPPSDRKLKSGTASVVCLLNNFYPREA KVQWKVDNALQSGNSQESVTEQDSKDSTYSLSSTLTLSKADYEKHKVYACE VTHQGLSSPVTKSFNRGECGGGGSGGGGSGGGSGGGGSEVQLLESGGGLVQ PGGSLRLSCAASGFTFSSYAMSWVRQAPGKGLEWVSAIIGSGASTYYADSV KGRFTISRDNSKNTLYLQMNSLRAEDTAVYYCAKGWFGGFNYWGQGTLVTV SSASVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTK SFNRGEC |
| 127 | second fusion polypeptide (Fc hole) | QVQLVQSGAEVKKPGSSVKVSCKASGGTFSSYAISWVRQAPGQGLEWMGGI IPIFGTANYAQKFQGRVTITADKSTSTAYMELSSLRSEDTAVYYCAREYYR GPYDYWGQGTTVTVSSASTKGPSVFPLAPSSKSTSGGTAALGCLVEDYFPE PVTVSWNSGALTSGVHTFPAVLQSSGLYSLSSVVTVPSSSLGTQTYICNVN HKPSNTKVDEKVEPKSCGGGGSGGGGSDKTHTCPPCPAPEAAGGPSVFLFP PKPKDTLMISRTPEVTCVVVDVSHEDPEVKFNWYVDGVEVHNAKTKPREEQ YNSTYRVVSVLTVLHQDWLNGKEYKCKVSNKALGAPIEKTISKAKGQPREP QVCTLPPSRDELTKNQVSLSCAVKGFYPSDIAVEWESNGQPENNYKTTPPV LDSDGSFFLVSKLTVDKSRWQQGNVFSCSVMHEALHNHYTQKSLSLSPGKG GGGSGGGGSDIQMTQSPSTLSASVGDRVTITCRASQSISSWLAWYQQKPGK APKLLIYDASSLESGVPSRFSGSGSGTEFTLTISSLQPDDFATYYCQQYSS QPYTFGQGTKVEIKRTVAAPSVFIFPPSDRKLKSGTASVVCLLNNFYPREA KVQWKVDNALQSGNSQESVTEQDSVTEQDSKDSTYSLSSTLTLSKADYEKH KVYACEVTHQGLSSPVTKSFNRGEC |
| 128 | Light Chain | EIVLTQSPGTLSLSPGERATLSCRASQSVTSSYLAWYQQKPGQAPRLLINV GSRRATGIPDRFSGSGSGTDFTLTISRLEPEDFAVYYCQQGIMLPPTFGQG TKVEIKSSASTKGPSVFPLAPSSKSTSGGTAALGCLVKDYFPEPVTVSWNS GALTSGVHTFPAVLQSSGLYSLSSVVTVPSSSLGTQTYICNVNHKPSNTKV DKKVEPKSC |

Figures 1M, 1N:
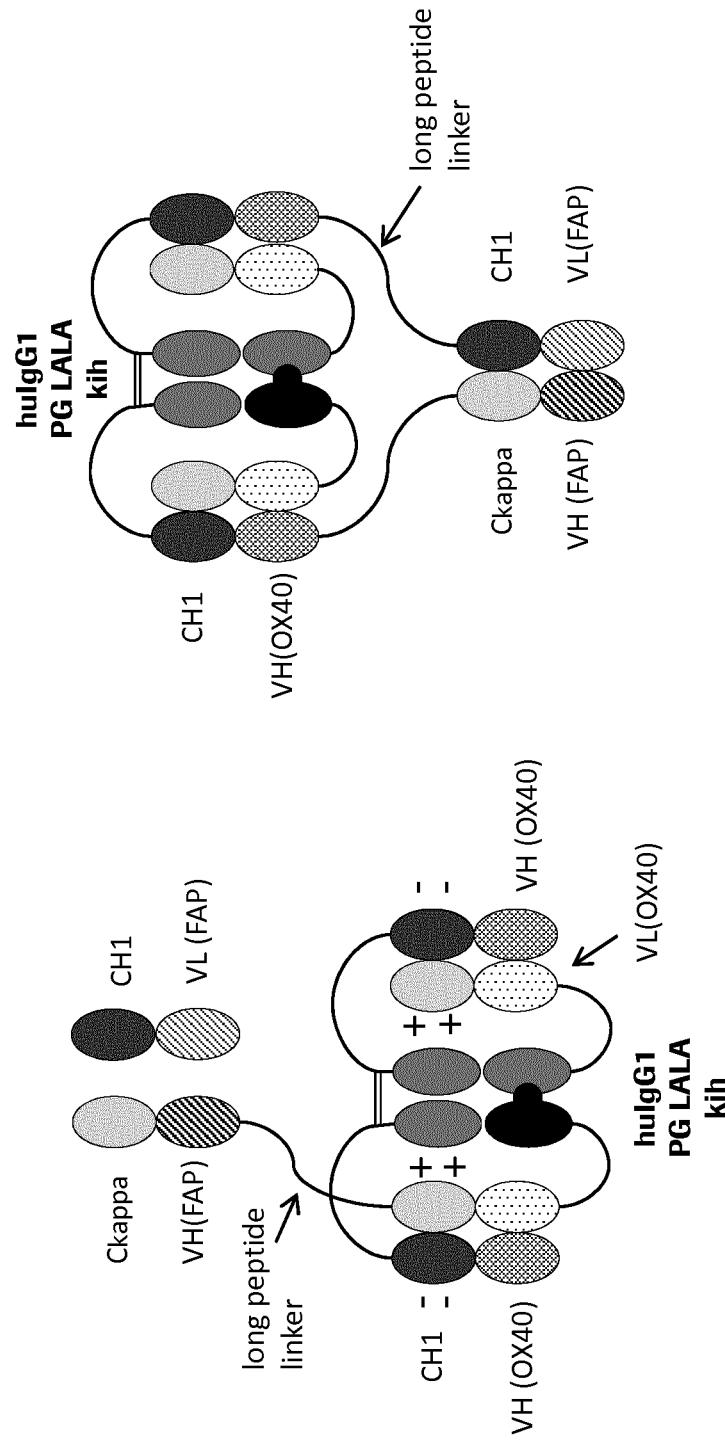
FIG. 1M is a schematic drawing of the assembled structure of Contorsbody P1AE2340 (Contorsbody 6, Example 2.13). In this case the molecule is composed of two fusion proteins and a light chain.
FIG. 1N is a schematic drawing of the assembled structure of Contorsbody P1AE2735 (Contorsbody 8, Example 2.14).

A schematic scheme of the assembled structure is shown in FIG. 1M.

2.14 Preparation of FAP (4B9)-OX40 (49B4) Contorsbody P1AE2735 (Contorsbody 8)

A bispecific antibody comprising two fusion polypeptides was cloned as follows:

first fusion polypeptide (from N- to C-terminus): VH(FAP)-Ckappa, GGGGSGGGGSGGGSGGGGS (SEQ ID NO:84) connector, VH(OX40)-CH1, (G4S)2 connector (SEQ ID NO: 78), IgG1 hinge, Fc knob, (G4S)2 connector (SEQ ID NO: 78), VL(OX40)-Ckappa.

second fusion polypeptide (from N- to C-terminus): VL(FAP)-CH1, GGGGSGGGGSGGGSGGGGS (SEQ ID NO:84) connector, VH(OX40)-CH1, (G4S)2 connector (SEQ ID NO: 78), IgG1 hinge, Fc hole, (G4S)2 connector (SEQ ID NO: 78), VL(OX40)-Ckappa.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)).

Table 14 shows the amino acid sequences of the bispecific antibody P1AE2735.

TABLE 14

Sequences of P1AE2735:

| SEQ ID NO: | Description | Sequence |
|---|---|---|
| 129 | first fusion polypeptide (Fc knob) | EVQLLESGGGLVQPGGSLRLSCAASGFTFSSYAMSWVRQAPGKGLEWVSAII GSGASTYYADSVKGRFTISRDNSKNTLYLQMNSLRAEDTAVYYCAKGWFGGF NYWGQGTLVTVSSASVAAPSVFIFPPSDEQLKSGTASVVCLLNNFYPREAKV QWKVDNALQSGNSQESVTEQDSKDSTYSLSSTLTLSKADYEKHKVYACEVTH QGLSSPVTKSFNRGECGGGGSGGGGSGGGSGGGGSQVQLVQSGAEVKKPGSS VKVSCKASGGTFSSYAISWVRQAPGQGLEWMGGIIPIFGTANYAQKFQGRVT ITADKSTSTAYMELSSLRSEDTAVYYCAREYYRGPYDYWGQGTTVTVSSAST KGPSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCGGGG |

TABLE 14-continued

Sequences of P1AE2735:

| SEQ ID NO: | Description | Sequence |
|---|---|---|
|  |  | SGGGGSDKTHTCPPCPAPEAAGGPSVFLFPPKPKDTLMISRTPEVTCVVVDV<br>SHEDPEVKFNWYVDGVEVHNAKTKPREEQYNSTYRVVSVLTVLHQDWLNGKE<br>YKCKVSNKALGAPIEKTISKAKGQPREPQVYTLPPCRDELTKNQVSLWCLVK<br>GFYPSDIAVEWESNGQPENNYKTTPPVLDSDGSFFLYSKLTVDKSRWQQGNV<br>FSCSVMHEALHNHYTQKSLSLSPGKGGGGSGGGGSDIQMTQSPSTLSASVGD<br>RVTITCRASQSISSWLAWYQQKPGKAPKLLIYDASSLESGVPSRFSGSGSGT<br>EFTLTISSLQPDDFATYYCQQYSSQPYTFGQGTKVEIKRTVAAPSVFIFPPS<br>DEQLKSGTASVVCLLNNFYPREAKVQWKVDNALQSGNSQESVTEQDSKDSTY<br>SLSSTLTLSKADYEKHKVYACEVTHQGLSSPVTKSFNRGEC |
| 130 | second fusion<br>polypeptide<br>(Fc hole) | EIVLTQSPGTLSLSPGERATLSCRASQSVTSSYLAWYQQKPGQAPRLLINVG<br>SRRATGIPDRFSGSGSGTDFTLTISRLEPEDFAVYYCQQGIMLPPTFGQGTK<br>VEIKSSASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNTKVDKKV<br>EPKSCGGGGSGGGGSGGGSGGGGSQVQLVQSGAEVKKPGSSVKVSCKASGGT<br>FSSYAISWVRQAPGQGLEWMGGIIPIFGTANYAQKFQGRVTITADKSTSTAY<br>MELSSLRSEDTAVYYCAREYYRGPYDYWGQGTTVTVSSASTKGPSVFPLAPS<br>SKSTSGGTAALGCLVKDYFPEPVTVSWNSGALTSGVHTFPAVLQSSGLYSLS<br>SVVTVPSSSLGTQTYICNVNHKPSNTKVDKKVEPKSCGGGGSGGGGSDKTHT<br>CPPCPAPEAAGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALG<br>APIEKTISKAKGQPREPQVCTLPPSRDELTKNQVSLSCAVKGFYPSDIAVEW<br>ESNGQPENNYKTTPPVLDSDGSFFLVSKLTVDKSRWQQGNVFSCSVMHEALH<br>NHYTQKSLSLSPGKGGGGSGGGGSDIQMTQSPSTLSASVGDRVTITCRASQS<br>ISSWLAWYQQKPGKAPKLLIYDASSLESGVPSRFSGSGSGTEFTLTISSLQP<br>DDFATYYCQQYSSQPYTFGQGTKVEIKRTVAAPSVFIFPPSDEQLKSGTASV<br>VCLLNNFYPREAKVQWKVDNALQSGNSQESVTEQDSKDSTYSLSSTLTLSKA<br>DYEKHKVYACEVTHQGLSSPVTKSFNRGEC |

A schematic scheme of the assembled structure is shown in FIG. 1N.

2.15 Preparation of FAP (4B9)-OX40 (49B4) Contorsbody P1AE2743 (Contorsbody 9)

A bispecific antibody comprising two fusion polypeptides was cloned as follows:

first fusion polypeptide (from N- to C-terminus): VH(FAP)-Ckappa, GGGGSGGGGSGGGSGGGGS (SEQ ID NO:84) connector, VL(OX40)-Ckappa, (G4S)2 connector (SEQ ID NO: 78), IgG1 hinge, Fc knob, (G4S)2 connector (SEQ ID NO: 78), VH(OX40)-CH1.

second fusion polypeptide (from N- to C-terminus): VL(FAP)-CH1, GGGGSGGGGSGGGSGGGGS (SEQ ID NO:84) connector, VL(OX40)-Ckappa, (G4S)2 connector (SEQ ID NO: 78), IgG1 hinge, Fc hole, (G4S)2 connector (SEQ ID NO: 78), VH(OX40)-CH1.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)).

Table 15 shows the amino acid sequences of the bispecific antibody P1AE2743.

TABLE 15

Sequences of P1AE2743:

| SEQ ID NO: | Description | Sequence |
|---|---|---|
| 131 | first fusion<br>polypeptide<br>(Fc knob) | EVQLLESGGGLVQPGGSLRLSCAASGFTFSSYAMSWVRQAPGKGLEWVSAII<br>GSGASTYYADSVKGRFTISRDNSKNTLYLQMNSLRAEDTAVYYCAKGWFGGF<br>NYWGQGTLVTVSSASVAAPSVFIFPPSDEQLKSGTASVVCLLNNFYPREAKV<br>QWKVDNALQSGNSQESVTEQDSKDSTYSLSSTLTLSKADYEKHKVYACEVTH<br>QGLSSPVTKSFNRGECGGGGSGGGGSGGGSGGGGSDIQMTQSPSTLSASVGD<br>RVTITCRASQSISSWLAWYQQKPGKAPKLLIYDASSLESGVPSRFSGSGSGT<br>EFTLTISSLQPDDFATYYCQQYSSQPYTFGQGTKVEIKRTVAAPSVFIFPPS<br>DEQLKSGTASVVCLLNNFYPREAKVQWKVDNALQSGNSQESVTEQDSKDSTY<br>SLSSTLTLSKADYEKHKVYACEVTHQGLSSPVTKSFNRGECGGGGSGGGGSD<br>KTHTCPPCPAPEAAGGPSVFLFPPKPKDTLMISRTPEVTCVVVDVSHEDPEV<br>KFNWYVDGVEVHNAKTKPREEQYNSTYRVVSVLTVLHQDWLNGKEYKCKVSN<br>KALGAPIEKTISKAKGQPREPQVYTLPPCRDELTKNQVSLWCLVKGFYPSDI<br>AVEWESNGQPENNYKTTPPVLDSDGSFFLYSKLTVDKSRWQQGNVFSCSVMH<br>EALHNHYTQKSLSLSPGKGGGGSGGGGSQVQLVQSGAEVKKPGSSVKVSCKA<br>SGGTFSSYAISWVRQAPGQGLEWMGGIIPIFGTANYAQKFQGRVTITADKST<br>STAYMELSSLRSEDTAVYYCAREYYRGPYDYWGQGTTVTVSSASTKGPSVFP<br>LAPSSKSTSGGTAALGCLVKDYFPEPVTVSWNSGALTSGVHTFPAVLQSSGL<br>YSLSSVVTVPSSSLGTQTYICNVNHKPSNTKVDKKVEPKSC |

TABLE 15-continued

Sequences of P1AE2743:

| SEQ ID NO: | Description | Sequence |
|---|---|---|
| 132 | second fusion polypeptide (Fc hole) | EIVLTQSPGTLSLSPGERATLSCRASQSVTSSYLAWYQQKPGQAPRLLINVG SRRATGIPDRFSGSGSGTDFTLTISRLEPEDFAVYYCQQGIMLPPTFGQGTK VEIKSSASTKGPSVFPLAPSSKSTSGGTAALGCLVKDYFPEPVTVSWNSGAL TSGVHTFPAVLQSSGLYSLSSVVTVPSSSLGTQTYICNVNHKPSNTKVDKKV EPKSCGGGGSGGGGSGGGSGGGGSDIQMTQSPSTLSASVGDRVTITCRASQS ISSWLAWYQQKPGKAPKLLIYDASSLESGVPSRFSGSGSGTEFTLTISSLQP DDFATYYCQQYSSQPYTFGQGTKVEIKRTVAAPSVFIFPPSDEQLKSGTASV VCLLNNFYPREAKVQWKVDNALQSGNSQESVTEQDSKDSTYSLSSTLTLSKA DYEKHKVYACEVTHQGLSSPVTKSFNRGECGGGGSGGGGSDKTHTCPPCPAP EAAGGPSVFLFPPKPKDTLMISRTPEVTCVVVDVSHEDPEVKFNWYVDGVEV HNAKTKPREEQYNSTYRVVSVLTVLHQDWLNGKEYKCKVSNKALGAPIEKTI SKAKGQPREPQVCTLPPSRDELTKNQVSLSCAVKGFYPSDIAVEWESNGQPE NNYKTTPPVLDSDGSFFLVSKLTVDKSRWQQGNVFSCSVMHEALHNHYTQKS LSLSPGKGGGGSGGGGSQVQLVQSGAEVKKPGSSVKVSCKASGGTFSSYAIS WVRQAPGQGLEWMGGIIPIFGTANYAQKFQGRVTITADKSTSTAYMELSSLR SEDTAVYYCAREYYRGPYDYWGQGTTVTVSSASTKGPSVFPLAPSSKSTSGG TAALGCLVKDYFPEPVTVSWNSGALTSGVHTFPAVLQSSGLYSLSSVVTVPS SSLGTQTYICNVNHKPSNTKVDKKVEPKSC |

2.16 Preparation of FAP (4B9)-OX40 (49B4) Contorsbody P1AE2762 (Contorsbody 10)

A bispecific antibody comprising two fusion polypeptides was cloned as follows:

first fusion polypeptide (from N- to C-terminus): VH(FAP)-Ckappa, GGGGSGGGGSGGGSGGGGS (SEQ ID NO:84) connector, VH(OX40)-Ckappa, (G4S)2 connector (SEQ ID NO: 78), IgG1 hinge, Fc knob, (G4S)2 connector (SEQ ID NO: 78), VL(OX40)-CH1.

second fusion polypeptide (from N- to C-terminus): VH(FAP)-Ckappa, GGGGSGGGGSGGGSGGGGS (SEQ ID NO:84) connector, VH(OX40)-Ckappa, (G4S)2 connector (SEQ ID NO: 78), IgG1 hinge, Fc hole, (G4S)2 connector (SEQ ID NO: 78), VL(OX40)-CH1.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)).

Table 16 shows the amino acid sequences of the bispecific antibody P1AE2762.

TABLE 16

Sequences of P1AE2762:

| SEQ ID NO: | Description | Sequence |
|---|---|---|
| 133 | first fusion polypeptide (Fc knob) | EIVLTQSPGTLSLSPGERATLSCRASQSVTSSYLAWYQQKPGQAPRLLINVGSRR ATGIPDRFSGSGSGTDFTLTISRLEPEDFAVYYCQQGIMLPPTFGQGTKVEIKRT VAAPSVFIFPPSDEQLKSGTASVVCLLNNFYPREAKVQWKVDNALQSGNSQESVT EQDSKDSTYSLSSTLTLSKADYEKHKVYACEVTHQGLSSPVTKSFNRGECGGGGS GGGGSGGGSGGGGSQVQLVQSGAEVKKPGSSVKVSCKASGGTFSSYAISWVRQAP GQGLEWMGGIIPIFGTANYAQKFQGRVTITADKSTSTAYMELSSLRSEDTAVYYC AREYYRGPYDYWGQGTTVTVSSASVAAPSVFIFPPSDEQLKSGTASVVCLLNNFY PREAKVQWKVDNALQSGNSQESVTEQDSKDSTYSLSSTLTLSKADYEKHKVYACE VTHQGLSSPVTKSFNRGECDGGGGSGGGGSDKTHTCPPCPAPEAAGGPSVFLFPP KPKDTLMISRTPEVTCVVVDVSHEDPEVKFNWYVDGVEVHNAKTKPREEQYNSTY RVVSVLTVLHQDWLNGKEYKCKVSNKALGAPIEKTISKAKGQPREPQVYTLPPCR DELTKNQVSLWCLVKGFYPSDIAVEWESNGQPENNYKTTPPVLDSDGSFFLYSKL TVDKSRWQQGNVFSCSVMHEALHNHYTQKSLSLSPGKGGGGSGGGGSDIQMTQSP STLSASVGDRVTITCRASQSISSWLAWYQQKPGKAPKLLIYDASSLESGVPSRFS GSGSGTEFTLTISSLQPDDFATYYCQQYSSQPYTFGQGTKVEIKSSASTKGPSVF PLAPSSKSTSGGTAALGCLVKDYFPEPVTVSWNSGALTSGVHTFPAVLQSSGLYS LSSVVTVPSSSLGTQTYICNVNHKPSNTKVDKKVEPKSC |
| 134 | second fusion polypeptide (Fc hole) | EVQLLESGGGLVQPGGSLRLSCAASGFTFSSYAMSWVRQAPGKGLEWVSAIIGSG ASTYYADSVKGRFTISRDNSKNTLYLQMNSLRAEDTAVYYCAKGWFGGFNYWGQG TLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSC GGGGSGGGGSGGGSGGGGSQVQLVQSGAEVKKPGSSVKVSCKASGGTFSSYAISW VRQAPGQGLEWMGGIIPIFGTANYAQKFQGRVTITADKSTSTAYMELSRSEDT AVYYCAREYYRGPYDYWGQGTTVTVSSASVAAPSVFIFPPSDEQLKSGTASVVCL LNNFYPREAKVQWKVDNALQSGNSQESVTEQDSKDSTYSLSSTLTLSKADYEKHK VYACEVTHQGLSSPVTKSFNRGECDGGGGSGGGGSDKTHTCPPCPAPEAAGGPSV FLFPPKPKDTLMISRTPEVTCVVVDVSHEDPEVKFNWYVDGVEVHNAKTKPREEQ YNSTYRVVSVLTVLHQDWLNGKEYKCKVSNKALGAPIEKTISKAKGQPREPQVCT LPPSRDELTKNQVSLSCAVKGFYPSDIAVEWESNGQPENNYKTTPPVLDSDGSFF |

TABLE 16-continued

Sequences of P1AE2762:

| SEQ ID NO: Description | Sequence |
|---|---|
| | LVSKLTVDKSRWQQGNVFSCSVMHEALHNHYTQKSLSLSPGKGGGGSGGGGSDIQ<br>MTQSPSTLSASVGDRVTITCRASQSISSWLAWYQQKPGKAPKLLIYDASSLESGV<br>PSRFSGSGSGTEFTLTISSLQPDDFATYYCQQYSSQPYTFGQGTKVEIKSSASTK<br>GPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSC |

2.17 Biochemical Analysis of the Molecules after Purification

Table 17 summarizes the yield and final monomer content of the FAP OX40 contorsbodies.

TABLE 17

Biochemical analysis of the FAP OX40 contorsbodies

| Construct | MW [kD] | Monomer [%] (SEC) | Yield [mg/l] |
|---|---|---|---|
| contorsbody CD134-0093 | 194.5 | 100 | 1.0 |
| contorsbody CD134-0094 | 194.8 | 100 | 0.5 |
| contorsbody P1AE0085 | 195.7 | 97.0 | 16.4 |
| contorsbody P1AE0086 | 195.6 | 96.4 | 11.2 |
| contorsbody P1AE0087 | 196.0 | 96.5 | 2.0 |
| contorsbody P1AE0839 | | 100 | 1.2 |
| contorsbody P1AE0821 | | 100 | 0.12 |
| contorsbody P1AE1122 | | 98.6 | 4.0 |
| contorsbody P1AE1942 | | 100 | 1.32 |
| contorsbody P1AE1887 | | 100 | 1.44 |
| contorsbody P1AE1888 | | 100 | 1.24 |
| contorsbody P1AE2254 | | 100 | 3.52 |
| contorsbody P1AE2340 | | 100 | 6.44 |
| contorsbody P1AE2735 | | 100 | 1.52 |
| contorsbody P1AE2743 | | 100 | 1.96 |
| contorsbody P1AE2762 | | 100 | 2.72 |

2.18 Preparation of Bispecific OX40 Antibodies as Control Molecules

As control the following bispecific anti-OX40 antibodies were prepared:

a) a bispecific antibody with bivalent binding for OX40 and monovalent binding for FAP was prepared in analogy with example 4.4 of WO 2017/055398 A2 (2+1 format). In this molecule, the first heavy chain (HC 1) was comprised of one Fab unit (VHCH1) of the anti-OX40 binder 49B4 followed by Fc knob chain fused by a (G$_4$S) linker (SEQ ID NO: 77) to a VH domain of the anti-FAP binder 28H1 or 4B9. The second heavy chain (HC 2) of the construct was comprised of one Fab units (VHCH1) of the anti-OX40 binder 49B4 followed Fc hole chain fused by a (G$_4$S) linker (SEQ ID NO: 77) to a VL domain of the anti-FAP binder 28H1 or 4B9.

Figure 1P:
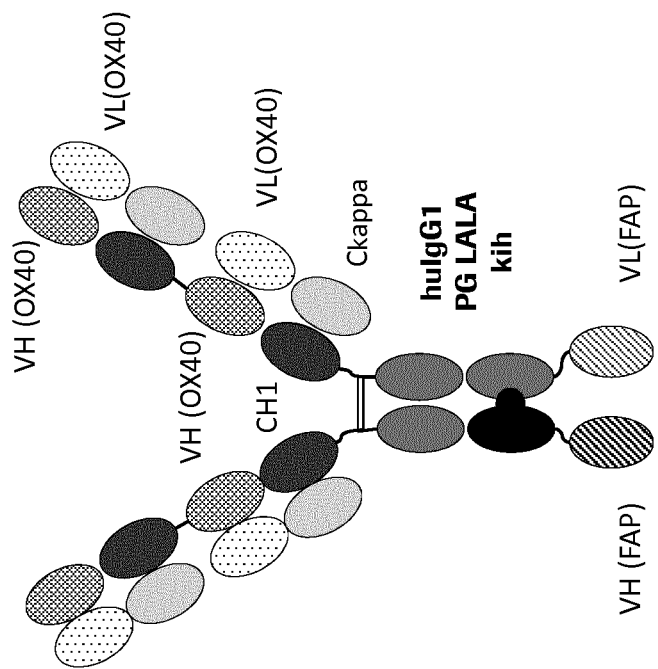
FIG. 1P is a schematic drawing of the 4+1 OX40×FAP bispecific antibody with tetravalent binding for OX40 and monovalent binding for FAP. These control molecules are described in more detail in Example 2.18.
Figure 1O:
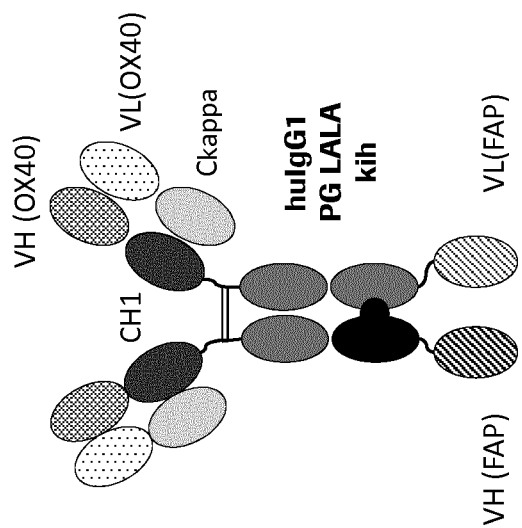
FIG. 1O is a schematic drawing of the 2+1 OX40×FAP bispecific antibody with bivalent binding for OX40 and monovalent binding for FAP (positive control molecule). A negative control molecule with the same structure was made wherein the FAP binding domain was replaced by DP47 germline (2+1 OX40×DP47 antibody).

A schematic scheme of the molecules is shown in FIG. 1O.

b) an antibody with bivalent binding for OX40 as above, wherein the the VH and VL domain of the anti-FAP binder were replaced by a germline control, termed DP47, not binding to the antigen. This molecule is used as negative, "untargeted" control.

c) a bispecific antibody with bivalent binding for OX40 and monovalent binding for FAP was prepared in analogy with example 4.4 of WO 2017/060144 A1 (4+1 format). In this molecule, the first heavy chain (HC 1) was comprised of two Fab units (VHCH1_VHCH1) of the anti-OX40 binder 49B4 followed by Fc knob chain fused by a (G4S) linker (SEQ ID NO: 77) to a VH domain of the anti-FAP binder 4B9. The second heavy chain (HC 2) of the construct was comprised of two Fab units (VHCH1_VHCH1) of the anti-OX40 binder 49B4 followed Fc hole chain fused by a (G4S) linker (SEQ ID NO: 77) to a VL domain of the anti-FAP binder 4B9. A schematic scheme of the molecule is shown in FIG. 1P.

Bispecific agonistic Ox40 antibodies with tetravalent binding for Ox40 and monovalent binding for FAP were prepared by applying the knob-into-hole technology to allow the assembling of two different heavy chains. The Pro329Gly, Leu234Ala and Leu235Ala mutations were introduced in the constant region of the heavy chains to abrogate binding to Fc gamma receptors according to the method described in International Patent Appl. Publ. No. WO 2012/130831 A1.

TABLE 18

Control molecules used in the experiments

| | disclosed in | composed of |
|---|---|---|
| OX40 (49B4) FAP (28H1)<br>2 + 1 construct<br>(P1AD4356) | Example 4.4 of<br>WO 2017/055398 | SEQ ID NO: 68,<br>SEQ ID NO: 69<br>2 x SEQ ID NO: 70 |
| OX40 (49B4) FAP (4B9)<br>2 + 1 construct<br>(P1AD4353, 7719) | Example 4.4 of<br>WO 2017/055398 | SEQ ID NO: 71,<br>SEQ ID NO: 72<br>2 x SEQ ID NO: 70 |
| OX40 (49B4) DP47<br>2 + 1 untargeted construct<br>(P1AD4352, 7718) | Example 4.4 of<br>WO 2017/055398 | SEQ ID NO: 73,<br>SEQ ID NO: 74<br>2 x SEQ ID NO: 70 |
| OX40 (49B4) FAP (4B9)<br>4 + 1 construct | Example 4.4 of<br>WO 2017/060144 A1 | SEQ ID NO: 75,<br>SEQ ID NO: 76<br>4 x SEQ ID NO: 70 |

Example 3

Characterization of FAP OX Antibodies 3.1 Binding on Human OX40 (Kinetic Affinity)

Binding of bispecific FAP-OX40 antibodies to human OX40 was investigated by surface plasmon resonance using a BIACORE T100 instrument (GE Healthcare). Around 8000 resonance units (RU) of the capturing system (20 µg/ml anti-human IgG (Fc); Order Code: BR100839; GE Healthcare Bio-Sciences AB, Sweden) were coupled on a CM5 chip (GE Healthcare BR-1005-30) at pH 5.0 by using an amine coupling kit supplied by the GE Healthcare. Running buffer was PBS-P pH 7.4 (20 mM phosphate buffer, 2.7 mM KCl, 137 mM NaCl, 0.05% Surfactant P20). The flow cell was set to 25° C.—and the sample block set to 12° C.—and primed with running buffer twice. The bispecific antibody was captured by injecting a 2 µg/ml solution for 60 s at a flow rate of 5 µl/min. Association was measured by injection of human OX40 for 120 s at a flow rate of 30 µl/min starting with 600 nM in 1:3 dilution. The dissociation phase was monitored for up to 720 s and triggered by switching from the sample solution to running buffer. The surface was regenerated by washing with 3 M MgCl$_2$ for 60 s at a flow rate of 10 μl/min. Bulk refractive index differences were corrected by subtracting the response obtained from an anti-human IgG (Fc) surface. Blank injections are also subtracted (=double referencing). For calculation of K$_D$ and kinetic parameters the Langmuir 1:1 model was used.

TABLE 19

Binding of anti-FAP/anti-OX40 antibodies to recombinant human OX40

| Molecule | ka (1/Ms) | kd (1/s) | KD (M) | Rmax (RU) | t ½ (min) |
|---|---|---|---|---|---|
| Contorsbody CD134-0093 | 6.82E+05 | 0.1853 | 2.72E−07 | 15.68 | 0.06 |
| Contorsbody CD134-0094 | 6.33E+05 | 0.2051 | 3.24E−07 | 15.09 | 0.06 |
| Control 4 + 1 | 5.29E+05 | 0.1856 | 3.51E−07 | 29.41 | 0.06 |

Both contorsbodies have similar K$_D$ values compared to a "4+1" IgG-like format for a tetravalent anti-OX40 antibody; affinity is comparable between the molecules and the Rmax is indicative of the valency of the various molecules tested.

Further FAP-OX40 contorsbodies were tested and showed K$_D$ values as listed in Table 20 below.

TABLE 20

Binding of anti-FAP/anti-OX40 antibodies to recombinant human OX40

| Molecule | ka (1/Ms) | kd (1/s) | KD (M) | Rmax (RU) | t ½ (ses) |
|---|---|---|---|---|---|
| Contorsbody 1 (P1AE1122) | 1.66E+06 | 2.12E−01 | 1.27E−07 | 11.7 | 3.3 |
| Contorsbody 2 (P1AE1942) | 8.74E+05 | 2.72E−01 | 3.11E−07 | 9.5 | 2.5 |
| Contorsbody 3 (P1AE1887) | 1.16E+06 | 3.12E−01 | 2.68E−07 | 18.9 | 2.2 |
| Contorsbody 6 (P1AE2340) | 1.66E+06 | 2.90E−01 | 1.75E−07 | 9.8 | 2.4 |
| Contorsbody P1AE0839 | 2.20E+06 | 3.62E−01 | 1.65E−07 | 6.5 | 1.9 |
| Contorsbody 4 (P1AE1888) | 1.03E+06 | 2.84E−01 | 2.76E−07 | 16.9 | 2.4 |
| Contorsbody 5 (P1AE2254) | 1.83E+06 | 2.39E−01 | 1.30E−07 | 8.7 | 2.9 |
| Contorsbody 11 (P1AE0821) | 8.94E+05 | 3.30E−01 | 3.69E−07 | 9.8 | 2.1 |
| Contorsbody 8 (P1AE2735) | 1.26E+06 | 2.27E−01 | 1.80E−07 | 8.2 | 3.1 |
| Contorsbody 9 (P1AE2743) | 7.30E+05 | 2.89E−01 | 3.95E−07 | 11.5 | 2.4 |
| Contorsbody 10 (P1AE2762) | 1.00E+06 | 3.30E−01 | 3.30E−07 | 9.3 | 2.1 |

3.2 Binding on Human FAP (Kinetic Affinity)

Binding of bispecific FAP-OX40 antibodies to human FAP was investigated by surface plasmon resonance using a BIACORE T100 instrument (GE Healthcare). Around 12000 resonance units (RU) of the capturing system (15 μg/ml anti-histidine antibody; Order Code: 28995056; GE Healthcare Bio-Sciences AB, Sweden) were coupled on a CM5 chip (GE Healthcare BR-1005-30) at pH 4.5 by using an amine coupling kit supplied by the GE Healthcare. Running buffer for Immobilization was HBS-N pH 7.4 (10 mM HEPES, 150 mM NaCl, pH 7.4, GE Healthcare). For the following kinetic characterization running buffer was PBS-P pH 7.4 (20 mM phosphate buffer, 2.7 mM KCl, 137 mM NaCl, 0.05% surfactant P20). The flow cell was set to 25° C.—and the sample block set to 12° C.—and primed with running buffer twice. The recombinant human FAP was captured by injecting a 25 μg/ml solution for 60 s at a flow rate of 5 μl/min. Association was measured by injection of the bispecific antibody for 120 s at a flow rate of 30 μl/min starting with 300 nM in 1:2 dilution. The dissociation phase was monitored for up to 720 s and triggered by switching from the sample solution to running buffer. The surface was regenerated by washing with 10 mM Glycine pH 1.5 for 60 s at a flow rate of 30 μl/min. Bulk refractive index differences were corrected by subtracting the response obtained from an anti-histidine surface. Blank injections are also subtracted (=double referencing). For calculation of K$_D$ and kinetic parameters the Langmuir 1:1 model was used.

TABLE 21

Binding of anti-FAP/anti-OX40 antibodies to recombinant human FAP

| Molecule | ka (1/Ms) | kd (1/s) | KD (M) | Rmax (RU) | t ½ (min) |
|---|---|---|---|---|---|
| Contorsbody CD134-0093 | 3.54E+04 | 7.08E−04 | 2.00E−08 | 21.01 | 16.32 |
| Contorsbody CD134-0094 | 1.23E+04 | 4.62E−04 | 3.75E−08 | 28.54 | 24.98 |
| Control 4 + 1 | 4.04E+05 | 5.84E−04 | 1.45E−09 | 28.62 | 19.80 |

Both molecules have similar KD values. The association to the FAP ECD was less optimal in the Contorsbody format compared to a standard control molecule. However, in the control molecule, two 4xG$_4$S peptide linker (SEQ ID NO: 83) were used to link the anti-FAP moiety C-terminally to the Fc part, whereas in the contorsbodies two 2xG4S peptide linker (SEQ ID NO: 78) were used to link the anti-FAP moiety to the contorsbody. Further FAP-OX40 contorsbodies were tested and showed K$_D$ values as listed in Table 22 below.

TABLE 22

Binding of anti-FAP/anti-OX40 antibodies to recombinant human FAP

| Molecule | ka (1/Ms) | kd (1/s) | KD (M) | Rmax (RU) | t ½ (sec) |
|---|---|---|---|---|---|
| Contorsbody 4 (P1AE1888) | 5.49E+04 | 1.95E−04 | 3.55E−09 | 29.9 | 3557.8 |
| Contorsbody P1AE0839 | 4.74E+04 | 1.83E−04 | 3.87E−09 | 17.2 | 3778.1 |
| Contorsbody 1 (P1AE1122) | 5.29E+04 | 2.02E−04 | 3.81E−09 | 26.1 | 3432.9 |
| Contorsbody 2 (P1AE1942) | 4.71E+04 | 2.54E−04 | 5.39E−09 | 18.5 | 2727.1 |
| Contorsbody 5 (P1AE2254) | 4.79E+04 | 2.66E−04 | 5.54E−09 | 20.6 | 2610.2 |
| Contorsbody 6 (P1AE2340) | 1.96E+05 | 2.18E−04 | 1.11E−09 | 28.1 | 3176 |
| Contorsbody 3 (P1AE1887) | 5.34E+04 | 2.06E−04 | 3.86E−09 | 35.4 | 3362.1 |
| Contorsbody 11 (P1AE0821) | 5.18E+04 | 3.03E−04 | 5.86E−09 | 16.9 | 2285 |
| Contorsbody 8 (P1AE2735) | 2.91E+05 | 5.13E−04 | 1.76E−09 | 33.4 | 1352.2 |
| Contorsbody 9 (P1AE2743) | 3.01E+05 | 4.86E−04 | 1.62E−09 | 36.9 | 1425.6 |
| Contorsbody 10 (P1AE2762) | 3.01E+05 | 3.59E−04 | 1.19E−09 | 40.9 | 1932.4 |

3.3 Simultaneous Binding on Human OX40 and Human FAP (Kinetic Affinity)

The capacity of binding simultaneously human OX40 and human FAP was also assessed by surface plasmon resonance (SPR) using a BIACORE T100 instrument (GE Healthcare). Around 8000 resonance units (RU) of the capturing system (20 µg/ml anti-human IgG (Fc); Order Code: BR100839; GE Healthcare Bio-Sciences AB, Sweden) were coupled on a CM5 chip (GE Healthcare BR-1005-30) at pH 5.0 by using an amine coupling kit supplied by the GE Healthcare. Running buffer was PBS-P pH 7.4 (20 mM phosphate buffer, 2.7 mM KCl, 137 mM NaCl, 0.05% Surfactant P20). The flow cell was set to 25° C.—and the sample block set to 12° C.—and primed with running buffer twice. The bispecific antibody was captured by injecting a 2 µg/ml solution for 60 seconds at a flow rate of 5 µl/min. Association was measured by injection of the first analyte (human OX40 or human FAP, respectively) for 120 seconds at a flow rate of 30 µl/min. Then the second analyte (human FAP or human OX40, respectively) was injected with a flow rate of 30 µl/min for 120 seconds. The dissociation phase was monitored for up to 720 seconds and triggered by switching from the sample solution to running buffer. The surface was regenerated by washing with 3 M $MgCl_2$ for 60 seconds at a flow rate of 10 µl/min. Bulk refractive index differences were corrected by subtracting the response obtained from an anti-human IgG (Fc) surface. Blank injections are also subtracted (=double referencing). For calculation of $K_D$ and kinetic parameters the Langmuir 1:1 model was used. All FAP-OX40 contorsbodies were able to bind simultaneously and independently to both antigens.

Example 4

Binding on Cells 4.1 Binding to Naïve Versus Activated Human PBMCs

Buffy coats were obtained from the Zurich blood donation center. Human PBMC were isolated by ficoll density gradient centrifugation. To isolate fresh peripheral blood mononuclear cells (PBMCs) the buffy coat was diluted with the same volume of DPBS (Gibco by Life Technologies, Cat. No. 14190 326). 50 mL polypropylene centrifuge tubes (TPP, Cat. No. 91050) were supplied with 15 mL Histopaque 1077 (SIGMA Life Science, Cat. No. 10771, polysucrose and sodium diatrizoate, adjusted to a density of 1.077 g/mL) and the buffy coat solution was layered above the Histopaque 1077. The tubes were centrifuged for 30 min at 400×g, room temperature and with low acceleration and no break. Afterwards the PBMCs were collected from the interface, washed three times with DPBS and resuspended in T cell medium consisting of RPMI 1640 medium (Gibco by Life Technology, Cat. No. 42401-042) supplied with 10% Fetal Bovine Serum (FBS, Gibco by Life Technology, Cat. No. 16000-044, Lot 941273, gamma-irradiated, mycoplasma-free and heat inactivated at 56° C. for 35 min), 1% (v/v) GlutaMAX I (GIBCO by Life Technologies, Cat. No. 35050 038), 1 mM Sodium Pyruvate (SIGMA, Cat. No. S8636), 1% (v/v) MEM non-essential amino acids (SIGMA, Cat.-No. M7145) and 50 µM β-Mercaptoethanol (SIGMA, M3148). PBMCs were frozen in FBS containing 10% (v/v) dimethyl sulfoxide.

Frozen PBMCs were thawed in T cell medium and PBMCs were used directly after isolation (binding on resting human PBMCs) or they were stimulated to receive a strong human OX40 expression on the cell surface of T cells (binding on activated human PBMCs). Therefore naïve PBMCs were cultured for two days in T cell medium supplied with 200 U/mL Proleukin and 2 µg/mL PHA-L in 6-well tissue culture plate and then 1 day on pre-coated 6-well tissue culture plates [4 µg/mL anti-human CD3 (clone OKT3) and 2 µg/mL anti-human CD28 (clone CD28.2)] in T cell medium.

For detection of OX40 naïve human PBMC and activated human PBMC were mixed. To enable distinction of naïve from activated human PBMC naïve cells were labeled prior to the binding assay using the eFluor670 cell proliferation dye (eBioscience, Cat.-No. 65-0840-85). A 1 to 1 mixture of $1×10^5$ naïve, eFluor670 labeled human PBMC and unlabeled activated human PBMC were then added to each well of a round-bottom suspension cell 96-well plates (greiner bio-one, cellstar, Cat. No. 650185) and the binding assay was performed.

Cells were stained for 120 minutes at 4° C. in the dark in 50 µL/well 4° C. cold FACS buffer containing titrated anti-Ox40 antibody constructs. After three times of washing with excess FACS buffer, cells were stained for 45 minutes at 4° C. in the dark in 25 µL/well 4° C. cold FACS buffer containing a mixture of fluorescently labeled anti-human CD4 (clone RPA-T4, mouse IgG1 k, BioLegend, Cat.-No. 300532), anti-human CD8 (clone RPA-T8, mouse IgG1k, BioLegend, Cat.-No. 3010441) and Fluorescein isothiocyanate (FITC)-conjugated AffiniPure anti-human IgG Fcγ-fragment-specific goat IgG F(ab')2 fragment (Jackson ImmunoResearch, Cat.-No. 109-096-098). Plates were finally resuspended in 85 µL/well FACS-buffer containing 0.2 µg/mL DAPI (Santa Cruz Biotec, Cat. No. Sc-3598) and acquired the same day using 5-laser LSR-Fortessa (BD Bioscience with DIVA software).

Figure 2A:
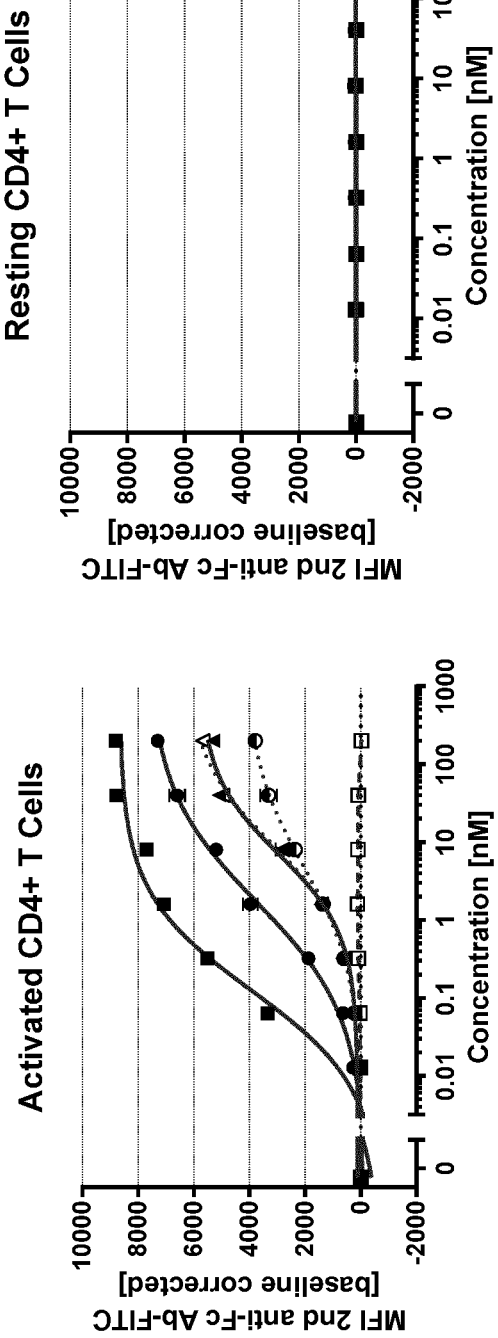
Figure 2B:
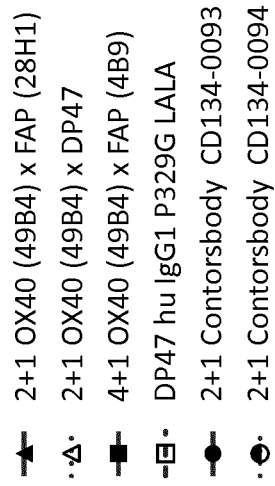

As shown in FIGS. 2B and 2D, no antigen binding molecule specific for OX40 bound to resting human CD4 T-cells or CD8 T-cells. In contrast, all antigen binding molecules (OX40 (49B4) FAP (28H1) 2+1 bispecific antibody, OX40 (49B4) DP47 2+1 bispecific antibody, OX40 (49B4) FAP (4B9) 4+1 bispecific antibody, Contorsbodies CD134-0093 and CD134-0094) bound to activated $CD8^+$ or $CD4^+$ T-cells (FIGS. 2A and 2C). Binding to $CD4^+$ T-cells was much stronger than that to $CD8^+$ T cells. All formats of a 2+1 design bound with similar strength to OX40 expressing (positive) cells, independently of the binding moiety of the second specificity. Additionally, the 4+1 construct showed the strongest binding. The Contorsbody CD134-0093 showed an intermediate binding between the 2+1 and 4+1 formats, the second Contorsbody CD134-0094 bound less strong to $CD4^+$ and $CD8^+$ T-cells than the 2+1 formats. The negative control DP47 hu IgG1 antibody (P329G LALA) did not bind to activated nor to resting T-cells. Since OX40 is not upregulated on resting CD4 or CD8 T-cells, none of the tested molecules bound to resting cells. Moreover, binding of all constructs (except the negative control) was stronger on CD4 T-cells, since OX40 expression is higher on these cells than on CD8 T-cells.

Figures 2G, 2H:
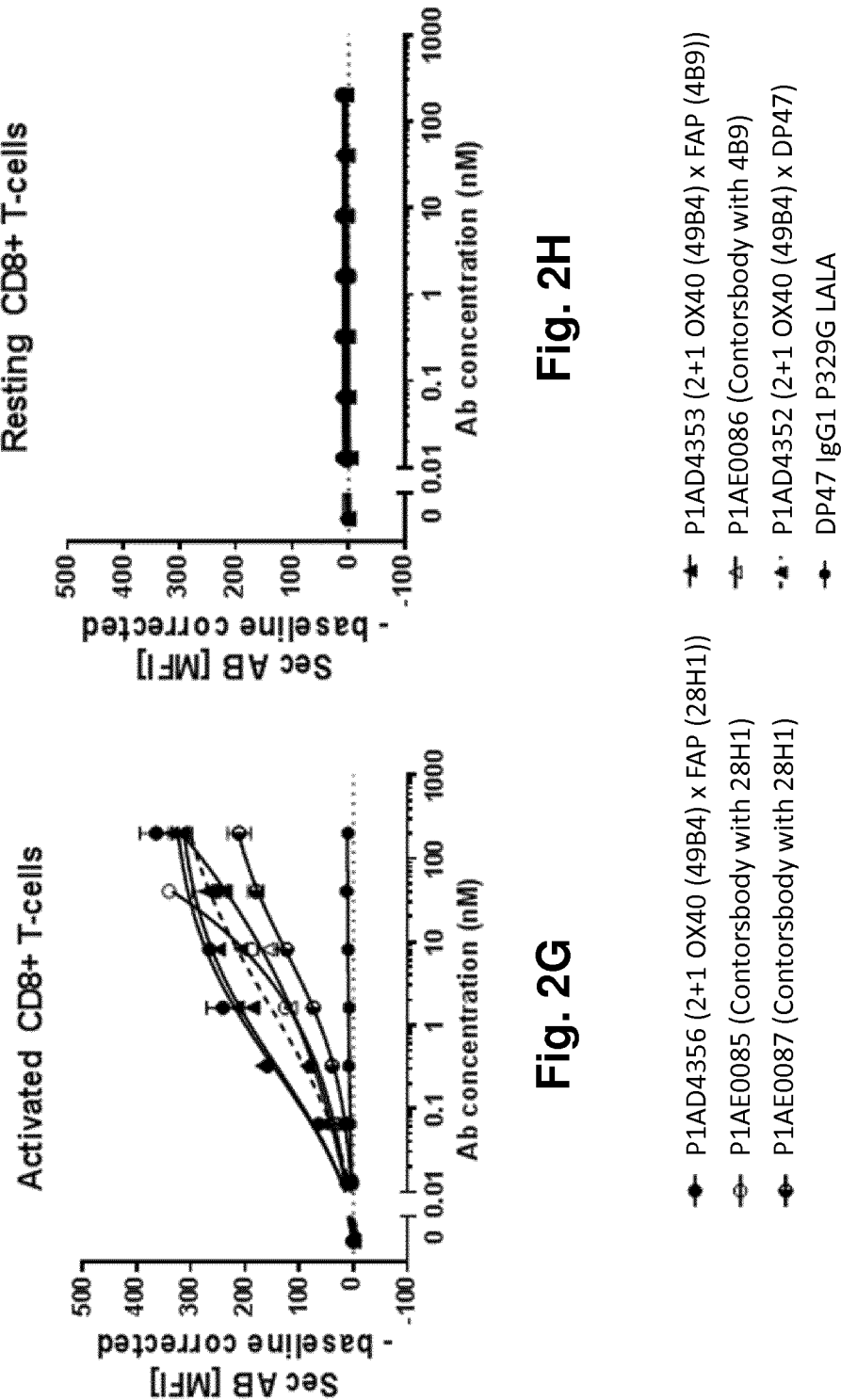

The results of a second experiment are shown in FIGS. 2E to 2H. As shown in these figures, none of the molecules tested (OX40 (49B4) FAP (28H1) 2+1 bispecific antibody, OX40 (49B4) FAP (4B9) 2+1 bispecific antibody, OX40 (49B4) DP47 2+1 bispecific antibody, Contorsbodies P1AE0085, P1AE0086 and P1AE0087) bound to resting human $CD4^+$ T-cells or $CD8^+$ T-cells as expected since OX40 is not expressed on resting cells (FIGS. 2F and 2H). In contrast, all antigen binding molecules displayed binding to activated $CD8^+$ and $CD4^+$ T-cells (FIGS. 2E and 2G). The signal amplitude was lower on $CD8^+$ T cells than on CD4 T cells which correlated with OX40 expression level (high on CD4+ T cells). However, binding pattern of each tested molecule was comparable between CD4+ and CD8+ T cells. All three contorsbody molecules did bind to OX40 expressing cells, however they showed reduced binding capacity to OX40 as compared to the 2+1 control molecules, irrespective of the FAP binding clone. In particular, the binding of contorsbody P1AE0087 was slightly more impaired than that of contorsbody P1AE0085.

The binding of further contorsbodies (Contorsbodies 1 to 11) to activated CD4+ T-cells is shown in FIGS. 8A to 8D and binding to activated CD8+ T-cells is shown in FIGS. 10A to 10D. In FIGS. 9A to 9D and FIGS. 11A to 11D, respectively, it is shown that none of Contorsbodies 1 to 11 bound to resting human CD4 T-cells or CD8 T-cells as expected. In contrast, all antigen binding molecules bound to activated CD8+ or CD4+ T-cells. Binding to CD4+ T-cells was much stronger than that to CD8+ T cells. All formats of a 2+1 design bound with similar strength to OX40 positive cells, independently of the binding moiety of the second specificity. The negative control (DP47 hu IgG1 P329G LALA) did not bind to activated nor resting T-cells. Since OX40 is not upregulated on resting CD4 or CD8 T-cells, none of the tested molecules bound to resting cells. Moreover, binding of all constructs (except the negative control) was stronger on CD4+ T-cells, since OX40 expression is higher on these cells than on CD8+ T-cells.

4.2 Binding to Human FAP-Expressing Tumor Cells

The binding to cell surface FAP was tested using human fibroblast activating protein (huFAP) expressing WM266-4 cells (ATCC CRL-1676). The lack of binding to OX40 negative FAP negative tumor cells was tested using A549 NucLight™ Red Cells (Essen Bioscience, Cat. No. 4491) expressing the NucLight Red fluorescent protein restricted to the nucleus to allow separation from unlabeled human FAP positive WM266-4 cells. Parental A549 (ATCC CCL-185) were transduced with the Essen CellPlayer NucLight Red Lentivirus (Essen Bioscience, Cat. No. 4476; EF1α, puromycin) at an MOI of 3 (TU/cell) in the presence of 8 μg/ml polybrene following the standard Essen protocol. This resulted in ≥70% transduction efficiency.

A mixture of $5 \times 10^4$ unlabeled WM266-4 cells and unlabeled A549 NucLight™ Red Cells in FACS buffer were added to each well of a round-bottom suspension cell 96-well plates (greiner bio-one, cellstar, Cat. No. 650185) and the binding assay was performed. Plates were centrifuged 4 minutes, 400×g at 4° C. and supernatants were flicked off. Cells were washed once with 200 μL DPBS and pellets were resuspended by a short and gentle vortex. All samples were resuspended in 50 μL/well of 4° C. cold FACS buffer containing the bispecific antigen binding molecules (primary antibody) at the indicated range of concentrations (titrated) and incubated for 120 minutes at 4° C. Afterwards the cells were washed four times with 200 μL 4° C. FACS buffer and resuspended by a short vortex. Cells were further stained with 25 μL/well of 4° C. cold secondary antibody solution containing Fluorescein isothiocyanate (FITC)-conjugated AffiniPure anti-human IgG Fcγ-fragment-specific goat IgG F(ab')2 fragment (Jackson ImmunoResearch, Cat. No. 109-096-098) and incubated for 60 minutes at 4° C. in the dark. Plates were finally resuspended in 90 μL/well FACS-buffer containing 0.2 μg/mL DAPI (Santa Cruz Biotec, Cat. No. Sc-3598) and acquired the same day using 5-laser LSR-Fortessa (BD Bioscience with DIVA software).

As shown in FIGS. 3A and 3B, the FAP-targeted anti-OX40 bispecific antibodies bound efficiently to human FAP-expressing target cells. Therefore, only FAP-targeted anti-OX40 antigen binding molecules show direct tumor-targeting properties. The FAP 4B9 has a high affinity to human FAP, whereas the 28H1 has a low affinity to human FAP. The FAP-targeted (OX40 (49B4) FAP (4B9) 4+1 bispecific antibody indicated the strongest binding to FAP+ cells, followed by the 2+1 Contorsbody CD134-0093, Contorsbody CD134-0094 and then the OX40 (49B4) FAP (28H1) 2+1 bispecific antibody. It has to be noted that FAP 4B9 has a higher affinity to human FAP compared to 28H1. The binding to FAP+ cells of both contorsbodies was slightly improved compared to a VHVL containing targeted 2+1 antibody construct. The non-targeted OX40 (49B4) DP47 2+1 bispecific antibody and the negative control (DP47 hu IgG1 antibody (P329G LALA)) did not bind to any FAP+ cells. $EC_{50}$ values of binding to activated human CD4 T cells and FAP positive tumor cells are summarized in Table 23.

TABLE 23

$EC_{50}$ values for binding of FAP targeted OX40 (49B4) bispecific antibodies in different formats to cell surface human FAP and human OX40 (on CD4+ T-cells)

| Format | FAP+ cell $EC_{50}$ [nM] | OX40+ cell $EC_{50}$ [nM] |
|---|---|---|
| OX40 (49B4) FAP (4B9) 4 + 1 construct | 11.342 | 0.127 |
| Contorsbody 1 (CD134-0093) | 61.231 | 1.693 |
| Contorsbody 2 (CD134-0094) | 227.281 | 4.988 |
| OX40 (49B4) FAP (28H1) 2 + 1 construct | 78.873 | 7.023 |
| OX40 (49B4) DP47 2 + 1 construct control | — | — |

In a further experiment, Contorsbodies P1AE0085, P1AE0086 and P1AE0087 were tested in comparison with OX40 (49B4) FAP (28H1) 2+1 bispecific antibody, OX40 (49B4) FAP (4B9) 2+1 bispecific antibody and OX40 (49B4) DP47 2+1 bispecific antibody (negative control). The results are shown in FIGS. 3C and 3D. All FAP-targeted anti-OX40 antigen binding molecules bound to human FAP-expressing cells. The FAP 4B9 clone has a higher affinity to human FAP as the 28H1. Consequently, the best binding properties were observed with OX40 (49B4) FAP (4B9) 2+1 bispecific antibody and OX40 (49B4) FAP (28H1) 2+1 bispecific antibody showed reduced binding as expected. All three contorsbodies showed binding to FAP, although the binding to FAP+ cells was slightly impaired compared to the OX40 (49B4) FAP 2+1 bispecific antibodies for both FAP clones (4B9 and 28H1). The linker length did not seem to affect the binding to huFAP since contorsbody P1AE0085 and P1AE0087 displayed very similar binding properties. The non-targeted 2 OX40 (49B4) DP47 2+1 bispecific antibody and the negative control (DP47 hu IgG1 antibody (P329G LALA)) did not bind to any FAP+ cells. In addition, none of the molecules showed binding to FAP-A549NLR cells, indicating that the binding was specific to human FAP. $EC_{50}$ values of binding to activated human CD4 and CD8 T cells and FAP positive cells are summarized in Table 24.

TABLE 24

EC$_{50}$ values for binding of FAP targeted OX40 (49B4)
bispecific antibodies in different formats to cell surface
human FAP and human Ox40 (on CD4$^+$ T-cells)

| Format | FAP$^+$ cell EC$_{50}$ [nM] | OX40$^+$ CD4$^+$ T cell EC$_{50}$ [nM] | OX40$^+$ CD8$^+$ T cell EC$_{50}$ [nM] |
|---|---|---|---|
| Contorsbody P1AE0085 (28H1) | 102.34 | n.c | n.c |
| Contorsbody P1AE0086 (4B9) | 5.48 | n.c | n.c |
| Contorsbody P1AE0087 (28H1) | 42.26 | 63.89 | 7.30 |
| OX40 (49B4) FAP (28H1) 2 + 1 bispecific antibody | 14.94 | 0.20 | 0.30 |
| OX40 (49B4) FAP (4B9) 2 + 1 bispecific antibody | 0.75 | 0.22 | 0.31 |
| OX40 (49B4) DP47 2 + 1 bispecific antibody | n.a | 0.47 | 1.79 | n.c. No curve fit. EC$_{50}$ calculation not possible
n.a. Not applicable

The binding results for Contorsbodies 1 to 10 to FAP$^+$ cells (NIH/3T3-huFAP tumor cells) are shown in FIGS. 13A to 13D. All FAP-targeted anti-OX40 antigen binding molecules bound to human FAP-expressing cells. As shown in FIGS. 14A to 14D, none of the FAP-targeted anti-OX40 antigen binding molecules were able to bind to A549NLR (FAP negative) tumor cells. Contorbody 8 bound strongest to FAP$^+$ cells, followed by Contorbody 10 and Contorbody 6. The binding to FAP$^+$ cells of both contorbodies was slightly improved compared to a VHVL containing targeted 2+1 antibody construct. The non-targeted 2+1 anti OX40 construct (7718) and the negative control (8105) did not bind to any FAP$^+$ cells. EC$_{50}$ values of binding to activated human CD4$^+$ T cells and FAP positive tumor cells are summarized in Table 25.

TABLE 25

EC$_{50}$ values for binding of FAP targeted OX40 (49B4)
bispecific antibodies in different formats to cell surface
human FAP and human Ox40 (on CD4$^+$ T-cells)

| Format | FAP$^+$ cell EC$_{50}$ [nM] | OX40$^+$ CD4$^+$ T cell EC$_{50}$ [nM] |
|---|---|---|
| Contorsbody 1 (P1AE1122) | 4.45 | 0.257 |
| Contorsbody 2 (P1AE1942) | 6.86 | 1.02 |
| Contorsbody 3 (P1AE1887) | 7.68 | 25.39 |
| Contorsbody 4 (P1AE1888) | 6.74 | 31.82 |
| Contorsbody 5 (P1AE2254) | 11.74 | 0.677 |
| Contorsbody 6 (P1AE2340) | 0.74 | n.c. |
| Contorsbody 7 (P1AE0086) | 2.47 | 0.126 |
| Contorsbody 8 (P1AE2735) | 0.736 | 7.02 |
| Contorsbody 9 (P1AE2743) | 0.398 | 2.56 |
| Contorsbody 10 (P1AE2762) | 0.464 | 1.22 |
| OX40 (49B4) DP47 2 + 1 bispecific antibody (P1AD4352) | n.d. | 0.086 |
| OX40 (49B4) FAP (4B9) 2 + 1 bispecific antibody (P1AD4353) | 4.46 | n.d. |
| OX40 (49B4) DP47 4+1 bispecific antibody (P1AD4524) | 3.98 | 0.0001 | n.c. No curve fit. EC$_{50}$ calculation not possible
n.a. Not applicable

Example 5

Functional Properties of Bispecific Anti-Human OX40 Binding Molecules 5.1 HeLa Cells Expressing Human OX40 and Reporter Gene NFκB-Luciferase Agonistic binding of OX40 to its ligand induces downstream signaling via activation of nuclear factor kappa B (NFkB) (A. D. Weinberg et al., J. Leukoc. Biol. 2004, 75(6), 962-972). The recombinant reporter cell line HeLa_hOx40_NFκB_Luc1 was generated to express human Ox40 on its surface. Additionally, it harbors a reporter plasmid containing the luciferase gene under the control of an NFκB-sensitive enhancer segment. Ox40 triggering induces dose-dependent activation of NFκB, which translocates in the nucleus, where it binds on the NFκB sensitive enhancer of the reporter plasmid to increase expression of the luciferase protein. Luciferase catalyzes luciferin-oxidation resulting in oxyluciferin which emits light. This can be quantified by a luminometer.

Thus, the capacity of the various anti-OX40 molecules to induce NFκB activation in HeLa_hOx40_NFκB_Luc1 reporter cells was analyzed as a measure for bioactivity.

The NFκB activating capacity of selected bispecific OX40(49B4) antibodies (in a bivalent FAP-targeted VHVL or Contorsbody format alone and with hyper-crosslinking of the constructs by either a secondary antibody or a FAP+ tumor cell line was tested. The crosslinking of FAP-binding antibodies by cell surface FAP was tested using human fibroblast activating protein (huFAP) expressing NIH/3T3-huFAP clone 19. This cell line was generated by the transfection of the mouse embryonic fibroblast NIH/3T3 cell line (ATCC CRL-1658) with the expression vector pETR4921 to express huFAP under 1.5 μg/mL Puromycin selection.

Adherent HeLa_hOX40_NFκB_Luc1 cells were cultured over night at a cell density of 0.2*10$^5$ cells per well and were stimulated for 5 hours with assay medium containing titrated bispecific anti-OX40 (49B4) antibodies (OX40 (49B4) FAP (28H1) 2+1 bispecific antibody, OX40 (49B4) DP47 2+1 bispecific antibody, Contorsbodies CD134-0093 and CD134-0094). For testing the effect of hyper-crosslinking by secondary antibodies, 25 μL/well of medium containing secondary antibody anti-human IgG Fcγ-fragment-specific goat IgG F(ab')2 fragment (Jackson ImmunoResearch, 109-006-098) was added in a 1:2 ratio (primary to secondary antibodies). To test the effect of hyper-crosslinking by cell surface FAP binding, 25 μL/well of medium containing FAP+ tumor cells (NIH/3T3-huFAP clone 19) were co-cultured in a 4 to 1 ratio (four time as much FAP+ tumor cells than reporter cells per well).

After incubation, assay supernatant was aspirated and plates washed two times with DPBS. Quantification of light emission was done using the luciferase 100 assay system and the reporter lysis buffer (both Promega, Cat.-No. E4550 and Cat-No: E3971) according to manufacturer instructions. Briefly, cells were lysed for 10 minutes at −20° C. by addition of 30 μL per well 1× lysis buffer. Cells were thawed for 20 minutes at 37° C. before 90 μL per well provided luciferase assay reagent was added. Light emission was quantified immediately with a SpectraMax M5/M5e microplate reader (Molecular Devices, USA) using 500 ms integration time, without any filter to collect all wavelengths. Emitted relative light units (URL) were corrected by basal luminescence of HeLa_hOx40_NFκB_Luc1 cells and were blotted against the logarithmic primary antibody concentration using Prism4 (GraphPad Software, USA). Curves were fitted using the inbuilt sigmoidal dose response.

As shown in FIGS. 4A to 4C, the presence of all anti-OX40 constructs induced NFκB activation. Hyper-crosslinking via secondary anti-huIgG Fcγ-specific antibody increased NFκB activation for all binders in a FAP independent manner. The two bispecific antibodies, 2+1 constructs OX40 (49B4) FAP (28H1) and OX40 (49B4) DP47, ran similar because the FAP targeting seemed not to impact the NFκB induction. The Contorsbodies CD134-0093 and CD134-0094 performed comparable, but showed a less strong NFκB activation under crosslinking (their effect seems to be intrinsic and not crosslinking dependant). FAP-expressing tumor cells strongly increased induction of NFκB-mediated luciferase-activation in a concentration-dependent manner when FAP targeted molecules (filled triangle, semi-filled circle, filled circle) were used. No such effect was seen with the OX40 (49B4) DP47 2+1 bispecific antibody (open circle) as the construct could not be further hyper-crosslinked by $FAP^+$ tumor cells. Additionally, the FAP targeted OX40 (49B4) FAP (28H1) 2+1 bispecific antibody induced a stronger NFκB activation than Contorsbody CD134-0093 and Contorsbody CD134-0094, whereas the CD134-0094 showed stronger activation than the CD134-0093 (FIG. 4A). Altogether, the contorsbody constructs were able to induce OX40 mediated NFκB activation however they were less active than FAP targeted OX40 (49B4) FAP (28H1) 2+1 bispecific antibody, either crosslinked by secondary antibody or cell surface expressed FAP. However, there was also less activity when added w/o secondary oligomerization.

The results of a second experiment are shown in FIGS. 4D to 4F. As shown in these figures, the presence of all anti-OX40 molecules tested (OX40 (49B4) FAP (28H1) 2+1 bispecific antibody, OX40 (49B4) FAP (4B9) 2+1 bispecific antibody, OX40 (49B4) DP47 2+1 bispecific antibody, Contorsbodies P1AE0085, P1AE0086 and P1AE0087) induced a very minimal NFκB activation in the absence of crosslinking (FIG. 4D). All three 2+1 control molecules (OX40 (49B4) FAP (28H1) 2+1 bispecific antibody, OX40 (49B4) FAP (4B9) 2+1 bispecific antibody and OX40 (49B4) DP47 2+1 bispecific antibody) showed very similar NFκB activation when hyper-crosslinking was provided by a secondary antibody (FIG. 4F). The three contorsbody molecules showed a slightly reduced activity as compared to the controls. This difference in NFκB activation between the tested contorsbody and control molecules was not observed in the presence of FAP-expressing cells. The curves corresponding to the contorsbody molecules and their respective FAP-targeted control molecules were analyzed with GraphPad Prism software as sharing one global curve fit, indicating that there was no significant difference in potency. Even though there is a different binding affinity for FAP between the two clones tested (4B9 and 28H1), it did not translate into a noticeable difference in potency in this assay. DP47-targeted 2+1 control molecule displayed only minimal activity since it does not have an FAP binding moiety. The negative control (DP47 hu IgG1 antibody (P329G LALA)) showed no activity, independent of cross-linking.

Figure 17:
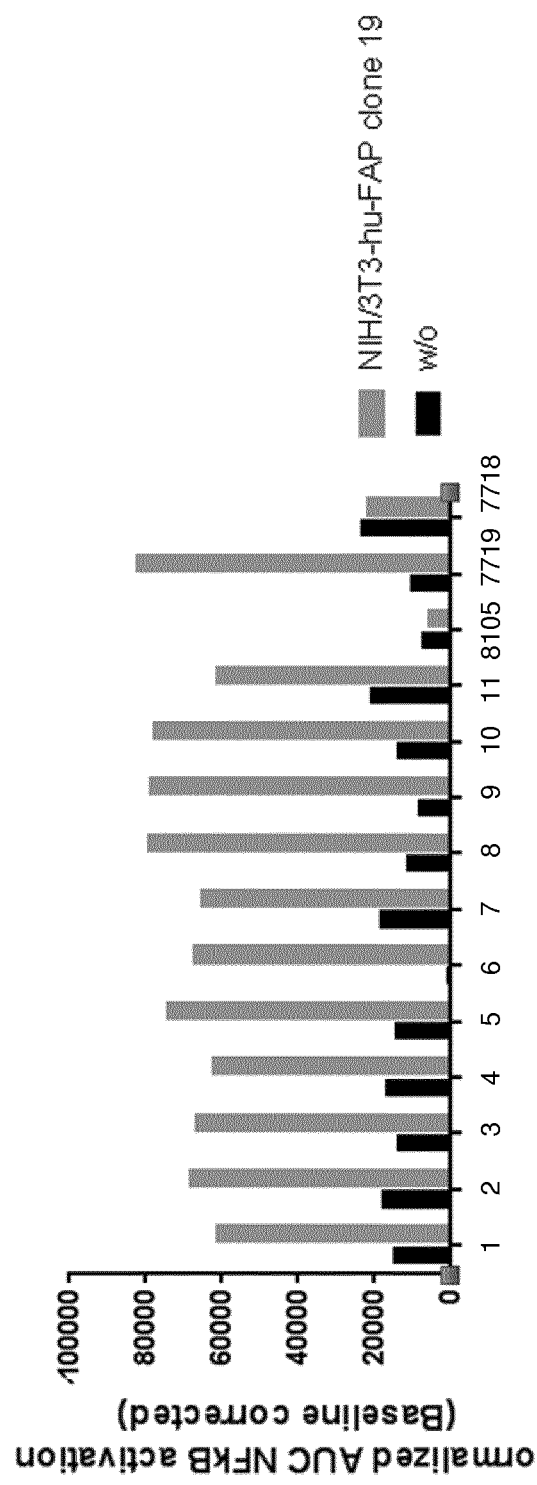

We further tested the NFκB activating capacity of Contorsbodies 1 to 11 alone and with hyper-crosslinking of the bispecific antibody constructs by the $FAP^+$ tumor cell line. In FIGS. 15A to 15D is shown the NFκB activation in the presence of FAP expressing tumor cells. The NFκB activation without crosslinking by FAP can be seen in FIGS. 16A to 16D. A summary of the area under the curve values for NFκB activation in HeLa cells with and without crosslinking with $FAP^+$ cells is shown in FIG. 17. The presence of all anti-OX40 constructs induced NFκB activation. Hyper-crosslinking via $FAP^+$ tumor cells increased NFκB activation for all tested bispecific antibodies. FAP-expressing tumor cell strongly increased induction of NFκB-mediated luciferase-activation in a concentration-dependent manner when FAP targeted molecules were used. No such effect was seen when in the 2+1 format the FAP binding moiety was replaced by a non-binding DP47 unit (open triangle) as the construct could not be further hyper-crosslinked by $FAP^+$ tumor cells. All of the contorsbodies performed comparably to the OX40 (49B4) FAP (4B9) 2+1 bispecific antibody.

5.2 Ox40 Mediated Co-Stimulation of Sub-Optimally TCR Triggered Resting Human PBMC and Hyper-Cross-linking by Cell Surface FAP It was shown in section 5.1 that addition of $FAP^+$ tumor cells can strongly increase the NFκB activity induced by FAP targeted bivalent anti-OX40 antibodies in human OX40 positive reporter cell lines by providing strong oligomerization of OX40 receptors. Likewise, we tested FAP-targeted bivalent anti-OX40 antibodies in the presence of NIH/3T3-huFAP clone 19 cells for their ability to rescue suboptimal TCR stimulation of resting human PBMC cells.

Human PBMC preparations contain (1) resting OX40 negative CD4+ and CD8+ T cells and (2) antigen presenting cells with various Fcγ receptor molecules on their cell surface e.g. B cells and monocytes. Anti-human CD3 antibody of human IgG1 isotype can bind with its Fc part to the present Fcγ receptor molecules and mediate a prolonged TCR activation on resting OX40 negative $CD4^+$ and $CD8^+$ T cells. These cells then start to express OX40 within several hours. Functional agonistic compounds against OX40 can signal via the OX40 receptor present on activated $CD8^+$ and $CD4^+$ T cells and support TCR-mediated stimulation.

Resting human PBMC were stimulated for five days with a suboptimal concentration of anti-CD3 antibody in the presence of irradiated $FAP^+$ NIH/3T3-huFAP clone 19 cells and titrated anti-OX40 constructs. Effects on T-cell survival and proliferation were analyzed through monitoring of total cell counts and co-staining with fluorescently-labeled antibodies against T-cell activation and maturation markers (CD25/CD127) by flow cytometry.

Mouse embryonic fibroblast NIH/3T3-huFAP clone 19 cells were harvested using cell dissociation buffer (Invitrogen, Cat.-No. 13151-014) for 10 minutes at 37° C. Cells were washed once with DPBS. NIH/3T3-huFAP clone 19 cells were cultured at a density of 0.2*105 cells per well in T cell media in a sterile 96-well round bottom adhesion tissue culture plate (TPP, Cat. No 92097) over night at 37° C. and 5% $CO_2$ in an incubator (Hera Cell 150). The next day they were irradiated in an xRay irradiator using a dose of 4500 RAD to prevent later overgrowth of human PBMC by the tumor cell line.

Human PBMCs were isolated by ficoll density centrifugation. Cells were added to each well at a density of 0.6*105 cells per well. Anti-human CD3 antibody (clone V9, human IgG1) at a final concentration of [10 nM] and FAP targeted bivalent anti-OX40 antigen binding molecules and Contorsbodies were added at the indicated concentrations. Cells were activated for four days at 37° C. and 5% $CO_2$ in an incubator (Hera Cell 150).

Then, cells were surface-stained with fluorescent dye-conjugated antibodies anti-human CD4 (clone RPA-T4, BioLegend, Cat.-No. 300532), CD8 (clone RPa-T8, BioLegend, Cat.-No. 3010441), CD25 (clone M-A251, BioLegend, Cat.-No. 356112) and CD127 (clone A019D5, BioLegend, Cat.-No. 351324) for 20 min at 4° C. Cell pellets were washed once with FACS buffer. Plates were finally resuspended in 85 µL/well FACS-buffer containing 0.2 µg/mL DAPI (Santa Cruz Biotec, Cat. No. Sc-3598) and acquired the same day using 5-laser LSR-Fortessa (BD Bioscience with DIVA software).

As shown in FIGS. 5A to 5F, co-stimulation with non-targeted OX40 (49B4) DP47 2+1 bispecific antibody (open triangle) did not rescue sub-optimally TCR stimulated CD4 and CD8 T cells. Hyper-crosslinking of the FAP targeted OX40 (49B4) FAP (28H1) 2+1 bispecific antibody (filled triangle) and the 2+1 Contorsbodies CD134-0093 and CD134-0094 by the presence of NIH/3T3-huFAP clone 19 cells strongly promoted survival and induced an enhanced activated phenotype in human CD4 and CD8 T cells. Furthermore, especially the Contorsbody CD134-0093 (filled circle) seems to show the most similar properties compared to the targeted OX40 (49B4) FAP (28H1) 2+1 bispecific antibody regarding activation. Moreover, the Contorsbody CD134-0094 (half filled circles) showed a stronger activation for CD8 T-cells than for CD4 T-cells (FIG. 5D), whereas it demonstrated comparable activation to the Contorsbody CD134-0093 and the FAP targeted OX40 (49B4) FAP (28H1) 2+1 bispecific antibody on CD4 T-cells. Altogether, results of the bioactivity and T-cell activation were normalized and summarized in FIG. 6, where the agonistic capacity of each construct was quantified for the analyzed markers as area under the curve and plotted against each other. As shown in FIG. 6, the Contorsbody CD134-0093 showed the strongest activation of both CD4 and CD8 T-cells regarding FSC-A and CD25. This molecule seems to be more potent than the FAP targeted OX40 (49B4) FAP (28H1) 2+1 bispecific antibody, which is roughly about 75% as strong as CD134-0093. The Contorsbody CD134-0094 seemed to be a bit less potent, since only CD25 got unregulated, but the size (FSC-A) of CD4 and CD8 T cells did not increase. Furthermore, the untargeted 2+1 molecule and the negative control did not show any activation (very low normalized AUC values).

In a further experiment, co-stimulation with non-targeted OX40 (49B4) DP47 2+1 bispecific antibody did not rescue sub-optimally TCR stimulated CD4$^+$ and CD8$^+$ T-cells. Hyper-crosslinking of the FAP targeted bivalent anti-OX40 antibodies OX40 (49B4) FAP (28H1) 2+1 bispecific antibody and OX40 (49B4) FAP (4B9) bispecific antibody, and the three contorsbody molecules (P1AE0085, P1AE0086 and P1AE 0087) by the presence of NIH/3T3-huFAP clone 19 cells strongly promoted an enhanced activation of primary human CD4 and CD8 T cells. P1AE0086 triggered a very similar activation of T cells than the corresponding 2+1 4B9 control antibody OX40 (49B4) FAP (4B9) bispecific antibody. They led to a more activated phenotype than the molecules with 28H1 FAP binder that is known to have a lower affinity for human FAP. Contorsbodies P1AE0085 and P1AE0087 showed a similar CD25 expression on CD4 and CD8 T-cells and a slightly higher FSC-A MFI as compared to 2+1 control molecule OX40 (49B4) FAP (28H1) 2+1 bispecific antibody. This assay with primary PBMCs showed that the potency of FAP-targeted molecules containing the high affinity binder (4B9) is higher than that of the molecules with low affinity FAP binder (28H1). The results of the bioactivity and T-cell activation are shown in FIGS. 7A to 7D.

Figure 19A:
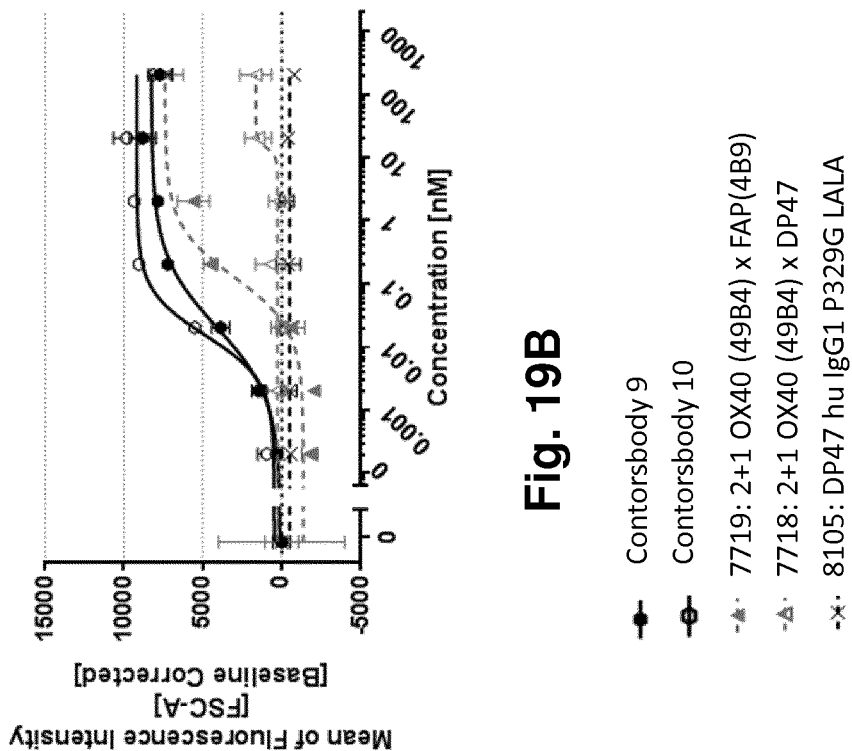
Figure 19B:
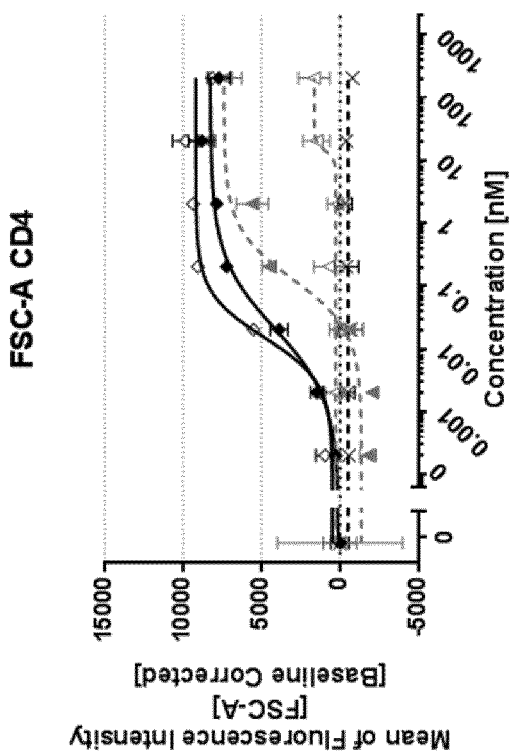
Figure 19C:
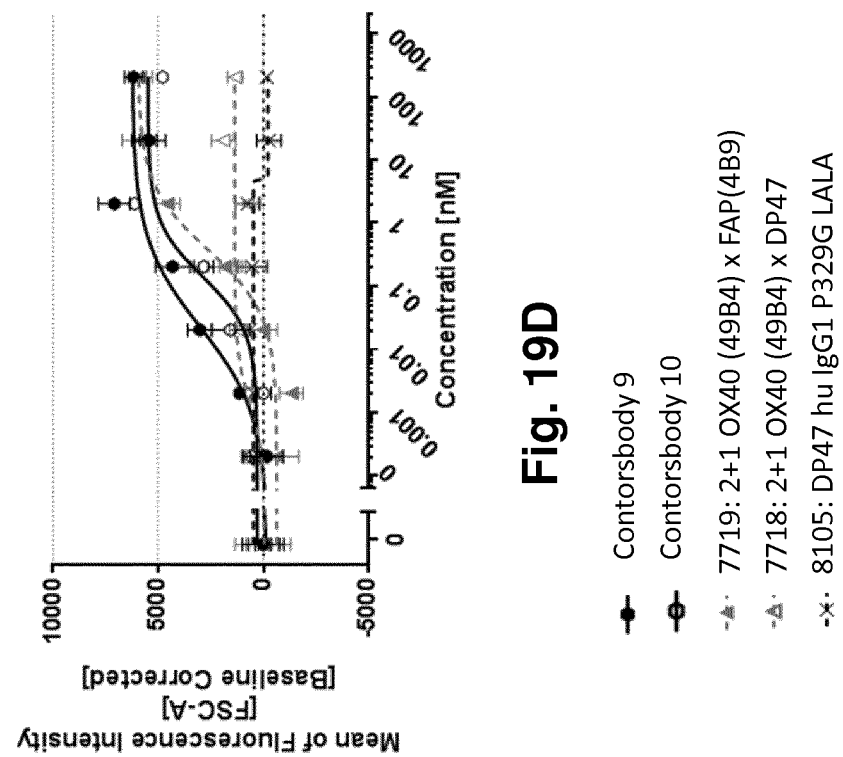
Figure 19D:
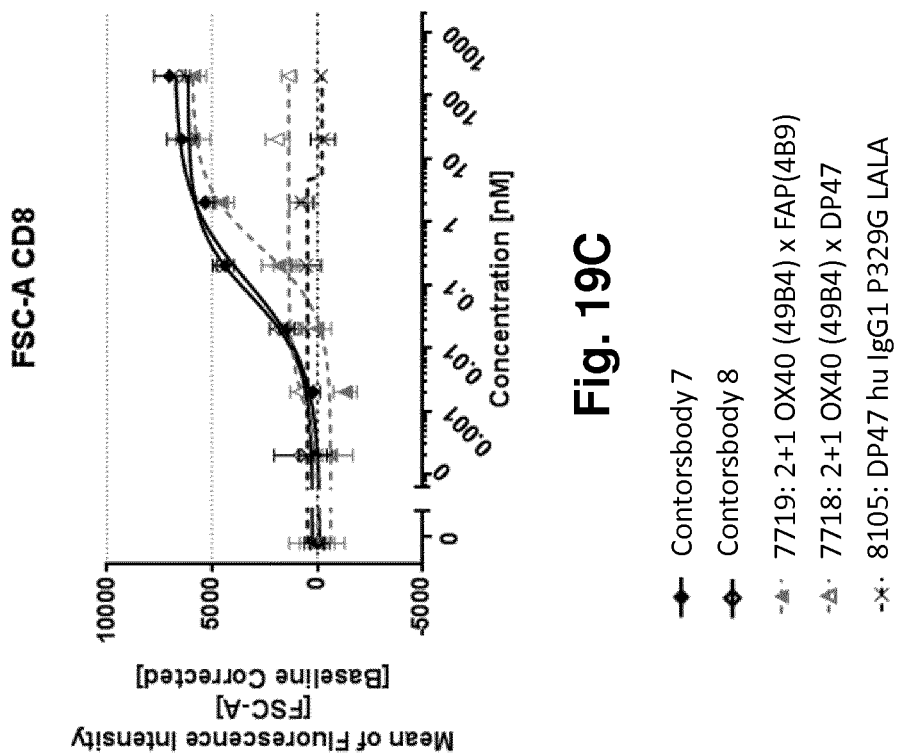
Figures 20A, 20B:
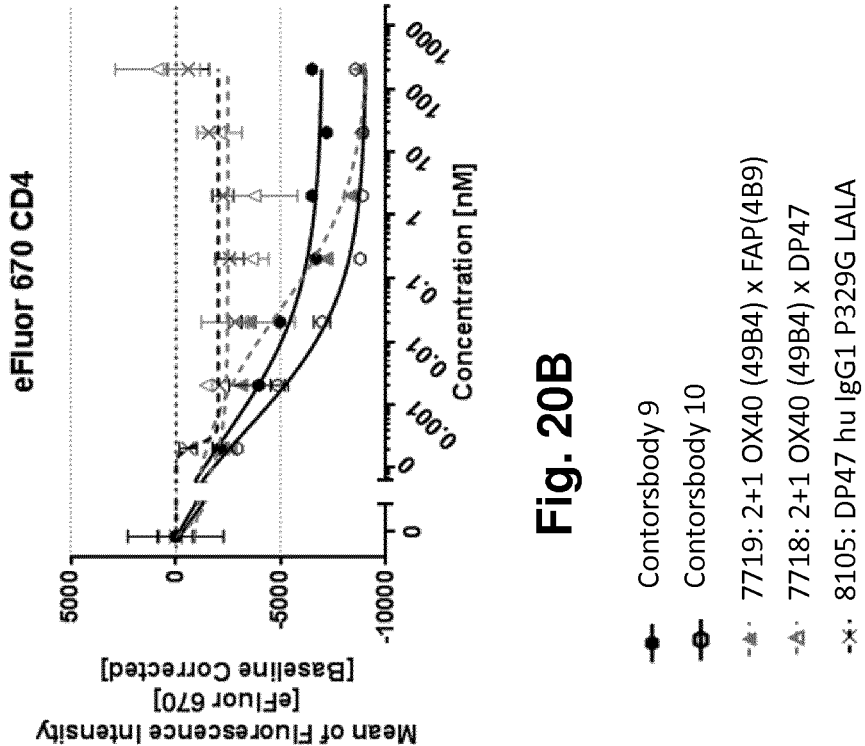
Figure 20D:
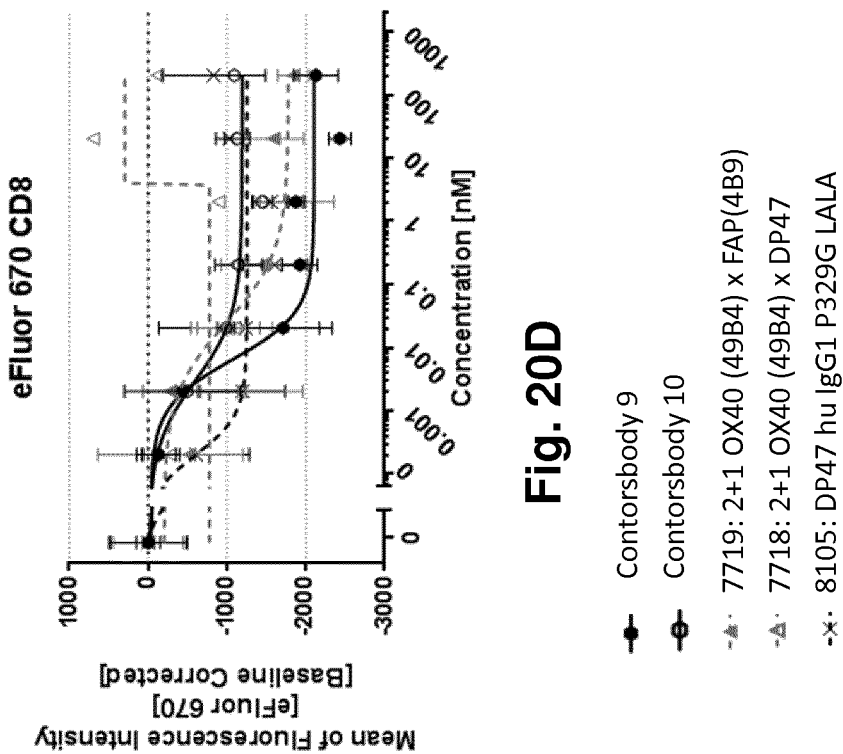
Figure 20C:
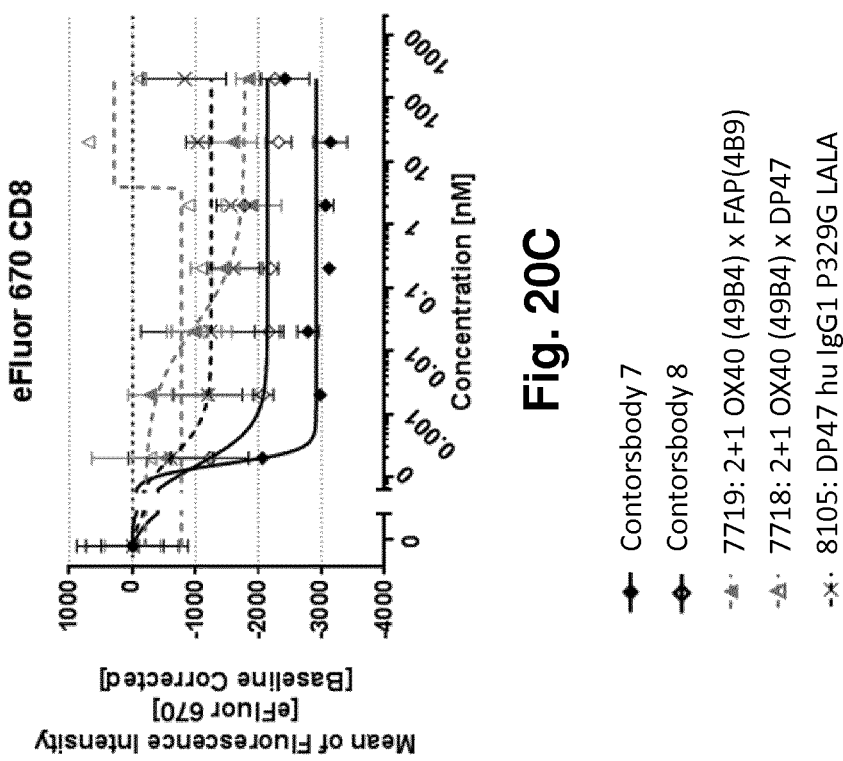
Figure 21A:
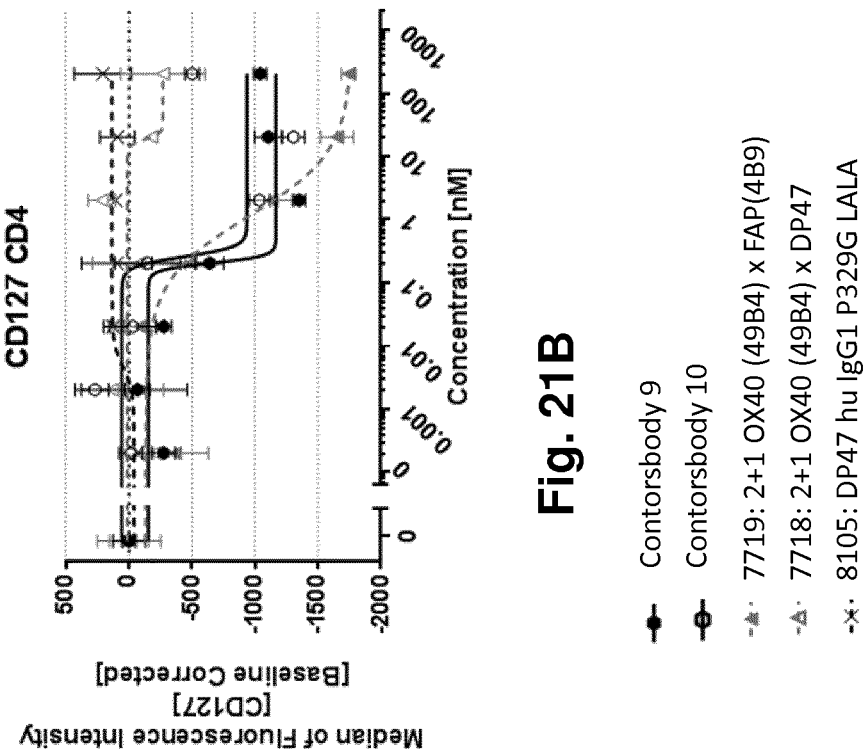
Figure 21B:
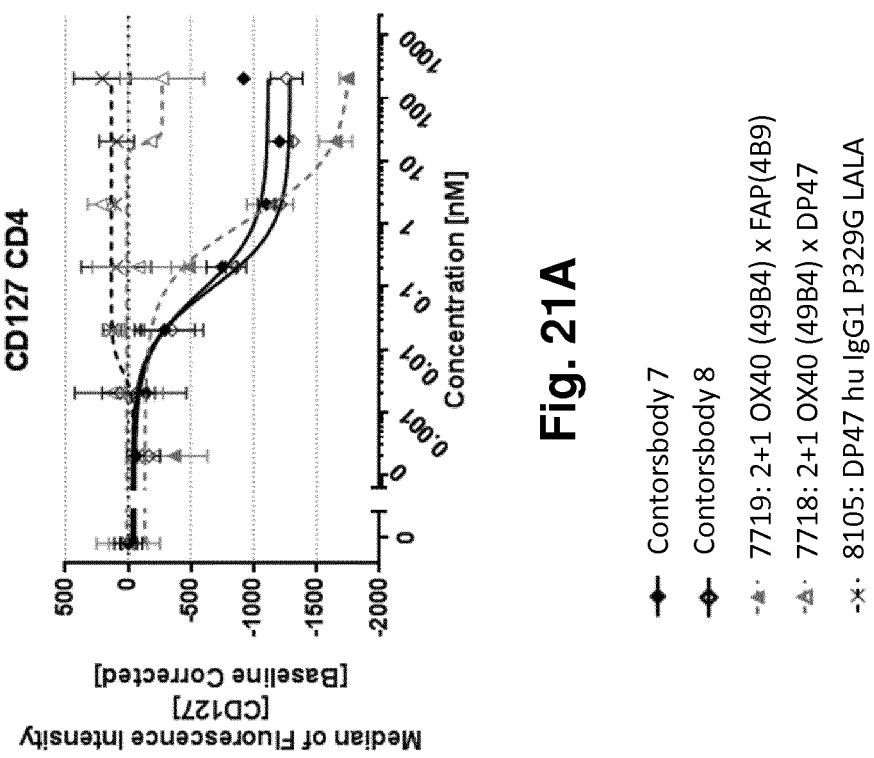
Figure 21C:
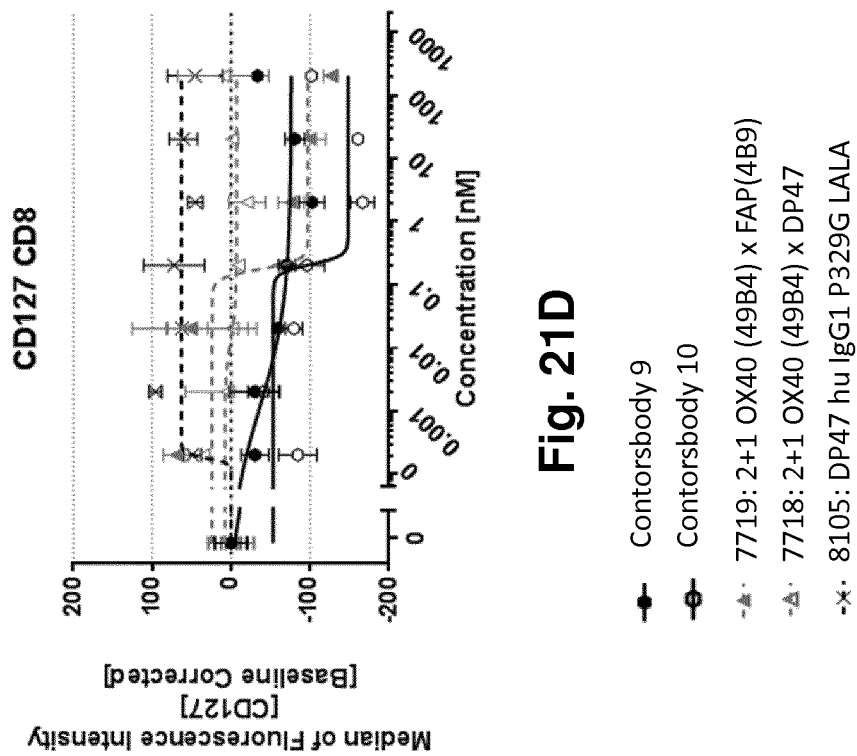
Figure 21D:
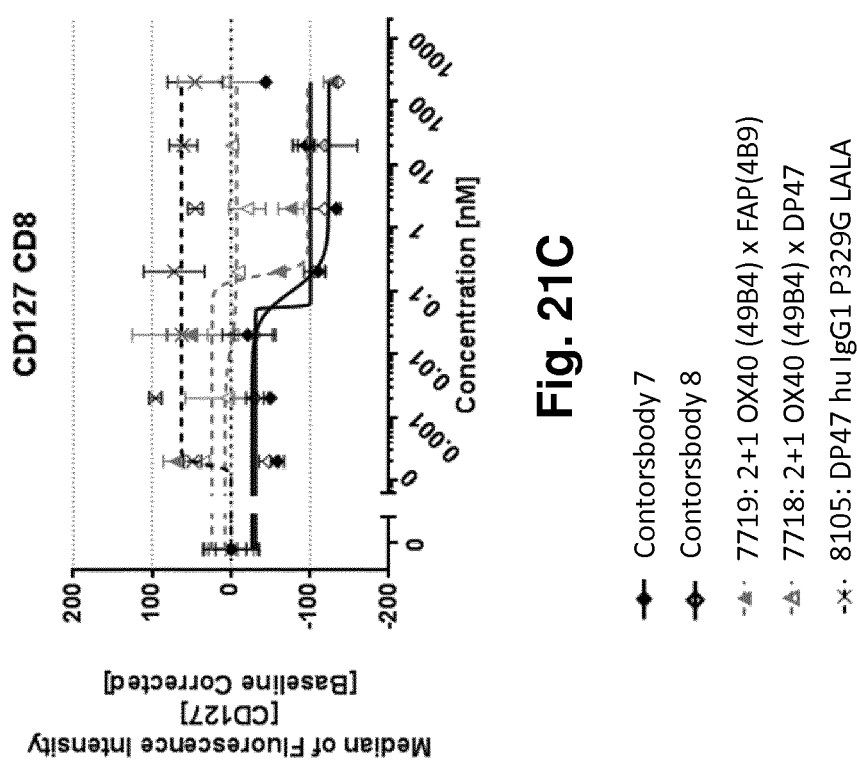

The ability of Contorsbodies 7, 8, 9 and 10 to rescue sub-optimally TCR stimulated CD4$^+$ and CD8$^+$ T-cells was also tested. FIGS. 18A and 18B show the activation of CD4 T cells indicated by the surface marker CD25 after suboptimal CD3 stimulation. In FIGS. 18C and 18D the activation of CD8 T cells indicated by the surface marker CD25 is shown. FIGS. 19A and 19B show the FSC-A MFI of CD4 T cells and FIGS. 19C and 19D the the FSC-A MFI of CD8 T cells. eFluor 670 is a proliferation dye for the measurement of cell divisions. The eFluor 670 levels, respectively the proliferation of CD4 T cells is shown in FIGS. 20A and 20B and the proliferation of CD8 T cells is shown in FIGS. 20C and 20D. The downregulation of IL-7Ra (CD127) is shown for CD4 T cells in FIGS. 21A and 21B and for CD8 T cells in FIGS. 21C and 21D. All results demonstrate that hyper-crosslinking of the contorsbodies and OX40 (49B4) FAP (4B9) bispecific antibody (filled triangle) in the presence of NIH/3T3-huFAP clone 19 cells strongly promoted survival and induced an enhanced activated phenotype in human CD4 and in a smaller degree in CD8 T cells. In FIGS. 22A to 22D the results of the various bioactivity assays are summarized as area under the curve.

5.3 Summary of Results

Altogether, the 2+1 Contorsbody CD134-0093 performed better than the 2+1 Contorsbody CD134-0094. The binding of CD134-0093 on activated CD4 T-cells was stronger than the one of the FAP targeted OX40 (49B4) FAP (28H1) 2+1 bispecific antibody and of CD134-0094, which both showed similar binding properties (FIG. 2A). Both Contorsbodies demonstrated good binding to human surface FAP on WM266-4 cells (FIG. 3A), the binding strength was between the ones from OX40 (49B4) FAP (4B9) 4+1 bispecific antibody (comprising the high affinity binder 4B9) and OX40 (49B4) FAP (28H1) 2+1 bispecific antibody (comprising the low affinity binder 28H1). Even if the format of the contorsbodies is different from the OX40 (49B4) FAP (28H1) 2+1 bispecific antibody as describe din Example 2.9, the binding properties seem to be as good or even better. Nevertheless, they do not reach the MFIs of the OX40 (49B4) FAP (4B9) 4+1 bispecific antibody (Example 2.9). Looking at NFκB activation with crosslinking NIH 3T3 huFAP cells, the Contorsbodies showed an intermediate activation of NFκB compared to the (49B4) FAP (28H1) 2+1 bispecific antibody, but still stronger than the untargeted OX40 (49B4) DP47 2+1 bispecific antibody (FIG. 4A). The FAP domain on both Contorsbodies seems to be able to act as crosslinkers and activate OX40 signaling. Using a secondary Fcγ specific antibody as crosslinker, both Contorsbodies demonstrated similar NFκB activation, but performed less good than the targeted control molecules (FIG. 4B). The bioactivity testing of the Contorsbodies revealed that CD134-0093 seemed to induce a more pronounced activated phenotype on CD4 and CD8 T-cells than CD134-0094 (FIG. 5A-D). The Contorsbody CD134-0093 even demonstrated a stronger activation of T-cells than the bivalent 2+1 format (FIG. 6).

Contorsbodies P1AE0085, P1AE0086 and P1AE 0087 showed a slightly reduced capacity to bind to OX40 expressed on the surface of activated CD4$^+$ and CD8$^+$ T-cells, as compared to bivalent anti OX40 control molecules (FIGS. 2E-2H). P1AE0085, P1AE0086 and P1AE0087 also displayed a partially impaired binding to human FAP expressed on the surface of NIH-3T3 huFAP clone 19 cells (FIGS. 3C and 3D) in comparison to their respective controls (2+1 4B9 and 28H1 FAP binders). The molecules containing the high affinity FAP binder 4B9 demonstrated a superior binding capacity to human FAP than that of the molecules with the lower affinity 28H1 binder. The NFκB activation assay revealed that the three contorsbody molecules P1AE0085, P1AE0086 and P1AE 0087 induced a similar activation of NFκB than the control FAP-targeted molecules when cross-linked via NIH-3T3 huFAP clone 19 cells (FIG. 4F). There was no discrimination in the potency of the low and high affinity FAP-targeted anti-OX40 molecules in the HeLa NFκB reporter assay. The bioactivity of the contorsbody molecules was also tested using primary human PBMCs and NIH-3T3 huFAP clone 19 cells as cross-linking cells in a five-day activation assay. Molecules with 4B9 FAP binder induced a more activated phenotype in CD4+ and CD8+ T-cells as compared to 28H1 binder. The contorsbody molecules performed as well as their respective control molecules. Taken together, these data indicated that the contorsbody molecules P1AE0085, P1AE0086 and P1AE0087 have a similar potency than that of the control molecules, despite a slightly reduced binding capacity to OX40 and huFAP.

All in all, despite the different format, Contorsbodies (and especially CD134-0093) seem to have comparable, if not better properties regarding binding and T-cell activation, than the FAP targeted 2+1 anti OX40 antibodies described in Example 2.18.

Example 6

Preparation of Bispecific Antibodies with Two Antigen Binding Domains Binding to 4-1BB and One Antigen Binding Domain Binding to FAP (FAP-4-1BB Contorsbodies)

The generation and preparation of the FAP binders is described in WO 2012/020006 A2, which is incorporated herein by reference. For the 4-1BB binder, the VH and VL sequences of clone 20H4.9 were obtained in accordance with U.S. Pat. No. 7,288,638 B2 or U.S. Pat. No. 7,659,384 B2.

6.1 Preparation of FAP (4B9)-4-1BB (20H4.9) Contorsbody P1AE1899

A bispecific antibody comprising two fusion polypeptides was cloned as depicted in FIG. 1A:

first fusion polypeptide (from N- to C-terminus): VH (4-1BB)-CH1, (G4S)2 connector (SEQ ID NO: 78), IgG1 hinge, Fc knob, (G4S)2 connector (SEQ ID NO: 78), VL(4-1BB)-Ckappa, (GGGGSGGGGSGGGGSGGGGS (SEQ ID NO:84) connector, VH(FAP)-Ckappa second fusion polypeptide (from N- to C-terminus): VH (4-1BB)-CH1, (G4S)2 connector (SEQ ID NO: 78), IgG1 hinge, Fc hole, (G4S)2 connector (SEQ ID NO: 78), VL(4-1BB)-Ckappa, GGGGSGGGGSGGGGSGGGGS (SEQ ID NO:84) connector, VL(FAP)-CH1.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)).

Table 26 shows the amino acid sequences of the bispecific antibody P1AE1899.

TABLE 26

Sequences of P1AE1899

| SEQ ID NO: | Description | Sequence |
|---|---|---|
| 143 | first fusion polypeptide (Fc knob) | QVQLQQWGAGLLKPSETLSLTCAVYGGSFSGYYWSWIRQSPEKGLEWIGEIN HGGYVTYNPSLESRVTISVDTSKNQFSLKLSSVTAADTAVYYCARDYGPGNY DWYFDLWGRGTLVTVSSASTKGPSVFPLAPSSKSTSGGTAALGCLVKDYFPE PVTVSWNSGALTSGVHTFPAVLQSSGLYSLSSVVTVPSSSLGTQTYICNVNH KPSNTKVDKKVEPKSCGGGGSGGGGSDKTHTCPPCPAPEAAGGPSVFLFPPK PKDTLMISRTPEVTCVVVDVSHEDPEVKFNWYVDGVEVHNAKTKPREEQYNS TYRVVSVLTVLHQDWLNGKEYKCKVSNKALGAPIEKTISKAKGQPREPQVYT LPPCRDELTKNQVSLWCLVKGFYPSDIAVEWESNGQPENNYKTTPPVLDSDG SFFLYSKLTVDKSRWQQGNVFSCSVMHEALHNHYTQKSLSLSPGKGGGGSGG GGSEIVLTQSPATLSLSPGERATLSCRASQSVSSYLAWYQQKPGQAPRLLIY DASNRATGIPARFSGSGSGTDFTLTISSLEPEDFAVYYCQQRSNWPPALTFG GGTKVEIKRTVAAPSVFIFPPSDEQLKSGTASVVCLLNNFYPREAKVQWKVD NALQSGNSQESVTEQDSKDSTYSLSSTLTLSKADYEKHKVYACEVTHQGLSS PVTKSFNRGECGGGGSGGGGSGGGSGGGGSEVQLLESGGGLVQPGGSLRLSC AASGFTFSSYAMSWVRQAPGKGLEWVSAIIGSGASTYYADSVKGRFTISRDN SKNTLYLQMNSLRAEDTAVYYCAKGWFGGFNYWGQGTLVTVSSASVAAPSVF IFPPSDEQLKSGTASVVCLLNNFYPREAKVQWKVDNALQSGNSQESVTEQDS KDSTYSLSSTLTLSKADYEKHKVYACEVTHQGLSSPVTKSFNRGEC |
| 144 | second fusion polypeptide (Fc hole) | QVQLQQWGAGLLKPSETLSLTCAVYGGSFSGYYWSWIRQSPEKGLEWIGEIN HGGYVTYNPSLESRVTISVDTSKNQFSLKLSSVTAADTAVYYCARDYGPGNY DWYFDLWGRGTLVTVSSASTKGPSVFPLAPSSKSTSGGTAALGCLVKDYFPE PVTVSWNSGALTSGVHTFPAVLQSSGLYSLSSVVTVPSSSLGTQTYICNVNH KPSNTKVDKKVEPKSCGGGGSGGGGSDKTHTCPPCPAPEAAGGPSVFLFPPK PKDTLMISRTPEVTCVVVDVSHEDPEVKFNWYVDGVEVHNAKTKPREEQYNS TYRVVSVLTVLHQDWLNGKEYKCKVSNKALGAPIEKTISKAKGQPREPQVCT LPPSRDELTKNQVSLSCAVKGFYPSDIAVEWESNGQPENNYKTTPPVLDSDG SFFLVSKLTVDKSRWQQGNVFSCSVMHEALHNHYTQKSLSLSPGKGGGGSGG GGSEIVLTQSPATLSLSPGERATLSCRASQSVSSYLAWYQQKPGQAPRLLIY DASNRATGIPARFSGSGSGTDFTLTISSLEPEDFAVYYCQQRSNWPPALTFG GGTKVEIKRTVAAPSVFIFPPSDEQLKSGTASVVCLLNNFYPREAKVQWKVD NALQSGNSQESVTEQDSKDSTYSLSSTLTLSKADYEKHKVYACEVTHQGLSS PVTKSFNRGECGGGGSGGGGSGGGSGGGGSEIVLTQSPGTLSLSPGERATLS CRASQSVTSSYLAWYQQKPGQAPRLLINVGSRRATGIPDRFSGSGSGTDFTL TISRLEPEDFAVYYCQQGIMLPPTFGQGTKVEIKSSASTKGPSVFPLAPSSK STSGGTAALGCLVKDYFPEPVTVSWNSGALTSGVHTFPAVLQSSGLYSLSSV VTVPSSSLGTQTYICNVNHKPSNTKVDKKVEPKSC |

A schematic scheme of the assembled structure is shown in FIG. 1E (OX40 to be replaced by 4-1BB).

6.2 Preparation of FAP (4B9)-4-1BB (20H4.9) Contorsbody P1AE2051

A bispecific antibody comprising two fusion polypeptides was cloned as follows:

first fusion polypeptide (from N- to C-terminus): VH(4-1BB)-CH1_EE (K147E, K213E), (G4S)2 connector (SEQ ID NO: 78), IgG1 hinge, Fc knob, (G4S)2 connector (SEQ ID NO: 78), VL(4-1BB)-Ckappa_RK (E123R, Q124K), GGGGSGGGGSGGGSGGGGS (SEQ ID NO:84) connector, VH(FAP)-Ckappa.

second fusion polypeptide (from N- to C-terminus): VH(4-1BB)-CH1_EE (K147E, K213E), (G4S)2 connector (SEQ ID NO: 78), IgG1 hinge, Fc hole, (G4S)2 connector (SEQ ID NO: 78), VL(4-1BB)-Ckappa_RK (E123R, Q124K), GGGGSGGGGSGGGSGGGGS (SEQ ID NO:84) connector, VL(FAP)-CH1.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)). Furthermore, in the CH and Ckappa fused to the VL and VH of OX40, respectively, amino acid mutations (so-called charged residues) were introduced to prevent the generation of Bence Jones proteins and to further facilitate the correct pairing, i.e negative charges in the CH1 domain (K147E, K213E, numbering according Kabat EU index) and positive charges in the CL domain of the anti-OX40 binder 49B4 (E123R and Q124K, numbering according to Kabat EU index).

Table 27 shows the amino acid sequences of the bispecific antibody P1AE2051.

TABLE 27

| Sequences of P1AE2051: | | |
|---|---|---|
| SEQ ID NO: | Description | Sequence |
| 145 | first fusion polypeptide (Fc knob) | QVQLQQWGAGLLKPSETLSLTCAVYGGSFSGYYWSWIRQSPEKGLEWIGE INHGGYVTYNPSLESRVTISVDTSKNQFSLKLSSVTAADTAVYYCARDYG PGNYDWYFDLWGRGTLVTVSSASTKGPSVFPLAPSSKSTSGGTAALGCLV EDYFPEPVTVSWNSGALTSGVHTFPAVLQSSGLYSLSSVVTVPSSSLGTQ TYICNVNHKPSNTKVDEKVEPKSCGGGGSGGGGSDKTHTCPPCPAPEAAG GPSVFLFPPKPKDTLMISRTPEVTCVVVDVSHEDPEVKFNWYVDGVEVHN AKTKPREEQYNSTYRVVSVLTVLHQDWLNGKEYKCKVSNKALGAPIEKTI SKAKGQPREPQVYTLPPCRDELTKNQVSLWCLVKGFYPSDIAVEWESNGQ PENNYKTTPPVLDSDGSFFLYSKLTVDKSRWQQGNVFSCSVMHEALHNHY TQKSLSLSPGKGGGGSGGGGSEIVLTQSPATLSLSPGERATLSCRASQSV SSYLAWYQQKPGQAPRLLIYDASNRATGIPARFSGSGSGTDFTLTISSLE PEDFAVYYCQQRSNWPPALTFGGGTKVEIKRTVAAPSVFIFPPSDRKLKS GTASVVCLLNNFYPREAKVQWKVDNALQSGNSQESVTEQDSKDSTYSLSS TLTLSKADYEKHKVYACEVTHQGLSSPVTKSFNRGECGGGGSGGGGSGGG SGGGGSEVQLLESGGGLVQPGGSLRLSCAASGFTFSSYAMSWVRQAPGKG LEWVSAIIGSGASTYYADSVKGRFTISRDNSKNTLYLQMNSLRAEDTAVY YCAKGWFGGFNYWGQGTLVTVSSASVAAPSVFIFPPSDEQLKSGTASVVC LLNNFYPREAKVQWKVDNALQSGNSQESVTEQDSKDSTYSLSSTLTLSKA DYEKHKVYACEVTHQGLSSPVTKSFNRGEC |
| 146 | second fusion polypeptide (Fc hole) | QVQLQQWGAGLLKPSETLSLTCAVYGGSFSGYYWSWIRQSPEKGLEWIGE INHGGYVTYNPSLESRVTISVDTSKNQFSLKLSSVTAADTAVYYCARDYG PGNYDWYFDLWGRGTLVTVSSASTKGPSVFPLAPSSKSTSGGTAALGCLV EDYFPEPVTVSWNSGALTSGVHTFPAVLQSSGLYSLSSVVTVPSSSLGTQ TYICNVNHKPSNTKVDEKVEPKSCGGGGSGGGGSDKTHTCPPCPAPEAAG GPSVFLFPPKPKDTLMISRTPEVTCVVVDVSHEDPEVKFNWYVDGVEVHN AKTKPREEQYNSTYRVVSVLTVLHQDWLNGKEYKCKVSNKALGAPIEKTI SKAKGQPREPQVCTLPPSRDELTKNQVSLSCAVKGFYPSDIAVEWESNGQ PENNYKTTPPVLDSDGSFFLVSKLTVDKSRWQQGNVFSCSVMHEALHNHY TQKSLSLSPGKGGGGSGGGGSEIVLTQSPATLSLSPGERATLSCRASQSV SSYLAWYQQKPGQAPRLLIYDASNRATGIPARFSGSGSGTDFTLTISSLE PEDFAVYYCQQRSNWPPALTFGGGTKVEIKRTVAAPSVFIFPPSDRKLKS GTASVVCLLNNFYPREAKVQWKVDNALQSGNSQESVTEQDSKDSTYSLSS TLTLSKADYEKHKVYACEVTHQGLSSPVTKSFNRGECGGGGSGGGGSGGG SGGGGSEIVLTQSPGTLSLSPGERATLSCRASQSVTSSYLAWYQQKPGQA PRLLINVGSRRATGIPDRFSGSGSGTDFTLTISRLEPEDFAVYYCQQGIM LPPPTFGQGTKVEIKSSASTKGPSVFPLAPSSKSTSGGTAALGCLVKDYFP EPVTVSWNSGALTSGVHTFPAVLQSSGLYSLSSVVTVPSSSLGTQTYICN VNHKPSNTKVDKKVEPKSC |

A schematic scheme of the assembled structure is shown in FIG. 1L (OX40 to be replaced by 4-1BB).

6.3 Biochemical Analysis of the Molecules after Purification

Table 28 summarizes the yield and final monomer content of the FAP-4-1BB contorsbodies.

TABLE 28

Biochemical analysis of the FAP 4-1BB contorsbodies

| Construct | Monomer [%] (SEC) | Yield after ProtA [mg/l] |
|---|---|---|
| contorsbody P1AE1899 | 100 | 0.72 |
| contorsbody P1AE2051 | 100 | 0.06 |

Example 7

Characterization of FAP-4-BB Contorsbodies 7.1 Binding on Human FAP (Kinetic Affinity)

Binding of bispecific FAP-4-1BB antibodies to human FAP was investigated by surface plasmon resonance using a BIACORE T100 instrument (GE Healthcare) as described in Example 3.2. For calculation of $K_D$ and kinetic parameters the Langmuir 1:1 model was used.

TABLE 29

Binding of anti-FAP/anti-4-1BB antibodies to recombinant human FAP

| Molecule | ka (1/Ms) | kd (1/s) | KD (M) | Rmax (RU) | t ½ (s) |
|---|---|---|---|---|---|
| Contorsbody P1AE1899 | 5.41E+04 | 2.80E−04 | 5.17E−09 | 18.8 | 2475.7 |
| Contorsbody P1AE2051 | 4.40E+04 | 3.67E−04 | 8.32E−09 | 6.7 | 1891.1 |

Both molecules have similar KD values.

7.2 NF-κB Activation in Human 4-1BB and NFκB-Luciferase Reporter Gene Expressing Reporter Cell Line Jurkat-Hu4-1BB-NFκB-Luc2

Agonistic binding of the 4-1BB (CD137) receptor to its ligand (4-1BBL) induces 4-1BB-downstream signaling via activation of nuclear factor kappa B (NFkB) and promotes survival and activity of CD8 T cells (Lee H W, Park S J, Choi B K, Kim H H, Nam K O, Kwon B S. 4-1BB promotes the survival of CD8 (+) T lymphocytes by increasing expression of Bcl-x(L) and Bfl-1. J Immunol 2002; 169:4882-4888). To monitor this NFκB-activation mediated by 2+1 H2H anti-4-1BB, anti-FAP huIgG1 PGLALA bispecific antibody, Jurkat-hu4-1BB-NFκB-luc2 reporter cell line was purchased from Promega (Germany). The cells were cultured as suspension cells in RPMI 1640 medium (GIBCO by Life Technologies, Cat No 42401-042) supplied with 10% (v/v) fetal bovine serum (FBS, GIBCO by Life Technologies, Cat.-No. 16000-044, Lot 941273, gamma irradiated mycoplasma free, heat inactivated), 2 mM L-alanyl-L-glutamine dipeptide (Glutqa-MAX-I, GIBCO by Life Technologies, Cat.-No. 35050-038), 1 mM Sodium Pyruvate (SIGMA-Aldrich Cat.-No. S8636), 1% (v/v) MEM-Non essential Aminoacid Solution 100× (SIGMA-Aldrich, Cat.-No. M7145), 600 µg/ml G-418 (Roche, Cat.-No. 04727894001), 400 µg/ml Hygromycin B (Roche, Cat.-No.: 10843555001) and 25 mM HEPES (Sigma Life Science, Cat.-No.: H0887-100 mL. For the assay, cells were harvested and resuspended in assay medium RPMI 1640 medium supplied with 10% (v/v) FBS and 1% (v/v) GlutaMAX-I. 10 µl containing $2 \times 10^3$ Jurkat-hu4-1BB-NFκB-luc2 reporter cells were transferred to each well of a sterile white 384-well flat bottom tissue culture plate with lid (Corning, Cat.-No.:3826). 10 µL of assay medium containing titrated concentrations of the contorsbodies, 2+1 bispecific agonistic anti-4-1BB (20H4.9)×anti-FAP (4B9) huIgG1 P329GLALA antibody, anti-4-1BB (20H4.9) huIgG1 P329GLALA antibody, anti-4-1BB (20H4.9) huIgG4 and isotype control (DP47 hu IgG1 P329GLALA antibody) were added. Finally, 10 µL of assay medium alone or containing $1 \times 10^4$ cells FAP-expressing cells, NIH/3T3-huFAP clone 19 (as described above) was supplied and plates were incubated for 6 hours at 37° C. and 5% $CO_2$ in a cell incubator. 6 µl freshly thawed One-Glo Luciferase assay detection solution (Promega, Cat.-No.: E6110) were added to each well and Luminescence light emission were measured immediately using Tecan microplate reader (500 ms integration time, no filter collecting all wavelength).

As shown in FIG. 23A, in the absence of FAP expressing cells none of the molecules was able to induce strong human 4-1BB receptor activation in the Jurkat-hu4-1BB-NFkB-luc2 reporter cell line, leading to NFkB-activation and therefore Luciferase expression. In the presence of FAP-expressing cells like NIH/3T3-huFAP clone 19 (human-FAP-transgenic mouse fibroblast cell line) (see FIG. 23B) crosslinking of bispecific 2+1 FAP 4-1BB contorsbodies as well as 2+1 bispecific agonistic anti-4-1BB (20H4.9)×anti-FAP (4B9) huIgG1 P329GLALA antibody (black filled star) led to a strong increase of NFkB-activated Luciferase activity in the Jurkat-hu4-1BB-NFkB-luc2 reporter cell line, which was above the activation mediated by the untargeted control 4-1BB antibodies. EC50 values and area under the curve (AUC) of activation curves are listed in Table 30 and Table 31.

TABLE 30

$EC_{50}$ values of activation curves shown in FIG. 23B

| $EC_{50}$ [nM] | NIH/3T3-huFAP clone 19 |
|---|---|
| Contorsbody P1AE1899 | 0.070 |
| Contorsbody P1AE2052 | 0.055 |
| 2 + 1 bispecific agonistic anti-4-1BB (20H4.9) x anti-FAP (4B9) huIgG1 P329GLALA antibody | 0.020 |
| 4-1BB (20H4.9) huIgG1 P329GLALA | 0.321 |
| 4-1BB (20H4.9) huIgG4 | 0.701 |
| Untargeted (DP47) huIgG1 P329G LALA | n.d. |

TABLE 31

Values of area under the curve (AUC) of activation curves shown in FIG. 23B

| AUC | NIH/3T3-huFAP clone 19 |
|---|---|
| Contorsbody P1AE1899 | 36079 |
| Contorsbody P1AE2052 | 36239 |
| 2 + 1 bispecific agonistic anti-4-1BB (20H4.9) x anti-FAP (4B9) huIgG1 P329GLALA antibody | 53529 |
| 4-1BB (20H4.9) huIgG1 P329GLALA | 15458 |
| 4-1BB (20H4.9) huIgG4 | 13032 |
| Untargeted (DP47) huIgG1 P329G LALA | n.d. |

Example 8

Preparation of Bispecific Antibodies with Two Antigen Binding Domains Binding to CD40 and One Antigen Binding Domain Binding to FAP (FAP-CD40 Contorsbodies)

The generation and preparation of the FAP binders is described in WO 2012/020006 A2, which is incorporated herein by reference. For the CD40 binder, the VH and VL sequences of clone 20H4.9 were obtained in accordance with SEQ ID NO:10 and SEQ ID NO:16 of WO 2006/128103.

8.1 Preparation of FAP (4B9)-CD40 Contorsbody P1AE1799

A bispecific antibody comprising two fusion polypeptides was cloned as depicted in FIG. 1A:
- first fusion polypeptide (from N- to C-terminus): VH (CD40)-CH1, (G4S)2 connector (SEQ ID NO: 78), IgG1 hinge, Fc knob, (G4S)2 connector (SEQ ID NO: 78), VL(CD40)-Ckappa, (GGGGSGGGGSGGGSGGGGS (SEQ ID NO:84) connector, VH(FAP)-Ckappa
- second fusion polypeptide (from N- to C-terminus): VH (CD40)-CH1, (G4S)2 connector (SEQ ID NO: 78), IgG1 hinge, Fc hole, (G4S)2 connector (SEQ ID NO: 78), VL(CD40)-Ckappa, GGGGSGGGGSGGGSGGGGS (SEQ ID NO:84) connector, VL(FAP)-CH1.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)).

Table 32 shows the amino acid sequences of the bispecific antibody P1AE1799.

TABLE 32

| | | Sequences of P1AE1799 |
|---|---|---|
| SEQ ID NO: | Description | Sequence |
| 155 | first fusion polypeptide (Fc knob) | EVQLLESGGGLVQPGGSLRLSCAASGYSFTGYYIHWVRQAPGKGLEWVGRVIPNAGGTSYNQKFKGRFTISVDNSKNTAYLQMNSLRAEDTAVYYCAREGIYWWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCGGGGSGGGGSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGKGGGGSGGGGSDIQMTQSPSSLSASVGDRVTITCRSSQSLVHSNGNTFLHWYQQKPGKAPKLLIYTVSNRFSGVPSRFSGSGSGTDFTLTISSLQPEDFATYFCSQTTHVPWTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGGGGSGGGGSGGGSGGGGSEVQLLESGGGLVQPGGSLRLSCAASGFTFSSYAMSWVRQAPGKGLEWVSAIIGSGASTYYADSVKGRFTISRDNSKNTLYLQMNSLRAEDTAVYYCAKGWFGGFNYWGQGTLVTVSSASVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 156 | second fusion polypeptide (Fc hole) | EVQLLESGGGLVQPGGSLRLSCAASGYSFTGYYIHWVRQAPGKGLEWVGRVIPNAGGTSYNQKFKGRFTISVDNSKNTAYLQMNSLRAEDTAVYYCAREGIYWWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCGGGGSGGGGSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGKGGGGSGGGGSDIQMTQSPSSLSASVGDRVTITCRSSQSLVHSNGNTFLHWYQQKPGKAPKLLIYTVSNRFSGVPSRFSGSGSGTDFTLTISSLQPEDFATYFCSQTTHVPWTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGGGGSGGGGSGGGSGGGGSEIVLTQSPGTLSLSPGERATLSCRASQSVTSSYLAWYQQKPGQAPRLLINVGSRRATGIPDRFSGSGSGTDFTLTISRLEPEDFAVYYCQQGIMLPPTFGQGTKVEIKSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKVEPKSC |

A schematic scheme of the assembled structure is shown in FIG. 1E (OX40 to be replaced by CD40).

8.2 Preparation of FAP (4B9)-CD40 Contorsbody P1AE1902

A bispecific antibody comprising two fusion polypeptides was cloned as follows:

first fusion polypeptide (from N- to C-terminus): VH (CD40)-CH1, (G4S)2 connector (SEQ ID NO: 78), IgG1 hinge, Fc knob, (G4S)2 connector (SEQ ID NO: 78), VL(CD40)-Ckappa, (GGGGSGGGGSGGGSGGGGS (SEQ ID NO:84) connector, VL(FAP)-CH1 second fusion polypeptide (from N- to C-terminus): VH (CD40)-CH1, (G4S)2 connector (SEQ ID NO: 78), IgG1 hinge, Fc hole, (G4S)2 connector (SEQ ID NO: 78), VL(CD40)-Ckappa, GGGGSGGGGSGGGSGGGGS (SEQ ID NO:84) connector, VH(FAP)-Ckappa.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)).

Table 33 shows the amino acid sequences of the bispecific antibody P1AE1902.

8.3 Preparation of FAP (4B9)-CD40 Contorsbody P1AE1800

A bispecific antibody comprising two fusion polypeptides was cloned as follows:

first fusion polypeptide (from N- to C-terminus): VH (CD40)-CH1, (G4S)2 connector (SEQ ID NO: 78), IgG1 hinge, Fc knob, (G4S)2 connector (SEQ ID NO: 78), VL(CD40)-Ckappa, GGGGSGGGGSGGGSGGGGS (SEQ ID NO:84) connector, VH(FAP)-Ckappa.

second fusion polypeptide (from N- to C-terminus): VL(CD40)-Ckappa, (G4S)2 connector (SEQ ID NO: 78), IgG1 hinge, Fc hole, (G4S)2 connector (SEQ ID NO: 78), VH(CD40)-CH1, GGGGSGGGGSGGGSGGGGS (SEQ ID NO:84) connector, VL(FAP)-CH1.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)).

TABLE 33

Sequences of P1AE1902:

| SEQ ID NO: | Description | Sequence |
|---|---|---|
| 157 | first fusion polypeptide (Fc knob) | EVQLLESGGGLVQPGGSLRLSCAASGYSFTGYYIHWVRQAPGKGLEWVGRVI PNAGGTSYNQKFKGRFTISVDNSKNTAYLQMNSLRAEDTAVYYCAREGIYWW GQGTTVTVSSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKV DKKVEPKSCGGGGSGGGGSDKTHTCPPCPAPEAAGGPSVFLFPPKPKDTLMI SRTPEVTCVVVDVSHEDPEVKFNWYVDGVEVHNAKTKPREEQYNSTYRVVSV LTVLHQDWLNGKEYKCKVSNKALGAPIEKTISKAKGQPREPQVYTLPPCRDE LTKNQVSLWCLVKGFYPSDIAVEWESNGQPENNYKTTPPVLDSDGSFFLYSK LTVDKSRWQQGNVFSCSVMHEALHNHYTQKSLSLSPGKGGGGSGGGGSDIQM TQSPSSLSASVGDRVTITCRSSQSLVHSNGNTFLHWYQQKPGKAPKLLIYTV SNRFSGVPSRFSGSGSGTDFTLTISSLQPEDFATYFCSQTTHVPWTFGGGTK VEIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTK SFNRGECGGGGSGGGGSGGGSGGGGSEIVLTQSPGTLSLSPGERATLSCRAS QSVTSSYLAWYQQKPGQAPRLLINVGSRRATGIPDRFSGSGSGTDFTLTISR LEPEDFAVYYCQQGIMLPPTFGQGTKVEIKSSASTKGPSVFPLAPSSKSTSG GTAALGCLVKDYFPEPVTVSWNSGALTSGVHTFPAVLQSSGLYSLSSVVTVP SSSLGTQTYICNVNHKPSNTKVDKKVEPKSC |
| 158 | second fusion polypeptide (Fc hole) | EVQLLESGGGLVQPGGSLRLSCAASGYSFTGYYIHWVRQAPGKGLEWVGRVI PNAGGTSYNQKFKGRFTISVDNSKNTAYLQMNSLRAEDTAVYYCAREGIYWW GQGTTVTVSSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKV DKKVEPKSCGGGGSGGGGSDKTHTCPPCPAPEAAGGPSVFLFPPKPKDTLMI SRTPEVTCVVVDVSHEDPEVKFNWYVDGVEVHNAKTKPREEQYNSTYRVVSV LTVLHQDWLNGKEYKCKVSNKALGAPIEKTISKAKGQPREPQVCTLPPSRDE LTKNQVSLSCAVKGFYPSDIAVEWESNGQPENNYKTTPPVLDSDGSFFLVSK LTVDKSRWQQGNVFSCSVMHEALHNHYTQKSLSLSPGKGGGGSGGGGSDIQM TQSPSSLSASVGDRVTITCRSSQSLVHSNGNTFLHWYQQKPGKAPKLLIYTV SNRFSGVPSRFSGSGSGTDFTLTISSLQPEDFATYFCSQTTHVPWTFGGGTK VEIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTK SFNRGECGGGGSGGGGSGGGSGGGGSEVQLLESGGGLVQPGGSLRLSCAASG FTFSSYAMSWVRQAPGKGLEWVSAIIGSGASTYYADSVKGRFTISRDNSKNT LYLQMNSLRAEDTAVYYCAKGWFGGFNYWGQGTLVTVSSASVAAPSVFIFPP SDEQLKSGTASVVCLLNNFYPREAKVQWKVDNALQSGNSQESVTEQDSKDST YSLSSTLTLSKADYEKHKVYACEVTHQGLSSPVTKSFNRGEC |

Table 34 shows the amino acid sequences of the bispecific antibody P1AE1800.

TABLE 34

Sequences of P1AE1800

| SEQ ID NO: | Description | Sequence |
|---|---|---|
| 159 | first fusion polypeptide (Fc knob) | EVQLLESGGGLVQPGGSLRLSCAASGYSFTGYYIHWVRQAPGKGLEWVGRVIP NAGGTSYNQKFKGRFTISVDNSKNTAYLQMNSLRAEDTAVYYCAREGIYWWGQ GTTVTVSSASTKGPSVFPLAPSSKSTSGGTAALGCLVKDYFPEPVTVSWNSGA LTSGVHTFPAVLQSSGLYSLSSVVTVPSSSLGTQTYICNVNHKPSNTKVDKKV EPKSCGGGGSGGGGSDKTHTCPPCPAPEAAGGPSVFLFPPKPKDTLMISRTPE VTCVVVDVSHEDPEVKFNWYVDGVEVHNAKTKPREEQYNSTYRVVSVLTVLHQ DWLNGKEYKCKVSNKALGAPIEKTISKAKGQPREPQVYTLPPCRDELTKNQVS LWCLVKGFYPSDIAVEWESNGQPENNYKTTPPVLDSDGSFFLYSKLTVDKSRW QQGNVFSCSVMHEALHNHYTQKSLSLSPGKGGGGSGGGGSDIQMTQSPSSLSA SVGDRVTITCRSSQSLVHSNGNTFLHWYQQKPGKAPKLLIYTVSNRFSGVPSR FSGSGSGTDFTLTISSLQPEDFATYFCSQTTHVPWTFGGGTKVEIKRTVAAPS VFIFPPSDEQLKSGTASVVCLLNNFYPREAKVQWKVDNALQSGNSQESVTEQD SKDSTYSLSSTLTLSKADYEKHKVYACEVTHQGLSSPVTKSFNRGECGGGGSG GGGSGGGGSGGGGSEVQLLESGGGLVQPGGSLRLSCAASGFTFSSYAMSWVRQA PGKGLEWVSAIIGSGASTYYADSVKGRFTISRDNSKNTLYLQMNSLRAEDTAV YYCAKGWFGGFNYWGQGTLVTVSSASVAAPSVFIFPPSDEQLKSGTASVVCLL NNFYPREAKVQWKVDNALQSGNSQESVTEQDSKDSTYSLSSTLTLSKADYEKH KVYACEVTHQGLSSPVTKSFNRGEC |
| 160 | second fusion polypeptide (Fc hole) | DIQMTQSPSSLSASVGDRVTITCRSSQSLVHSNGNTFLHWYQQKPGKAPKLLI YTVSNRFSGVPSRFSGSGSGTDFTLTISSLQPEDFATYFCSQTTHVPWTFGGG TKVEIKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPVTK SFNRGECGGGGSGGGGSDKTHTCPPCPAPEAAGGPSVFLFPPKPKDTLMISRT PEVTCVVVDVSHEDPEVKFNWYVDGVEVHNAKTKPREEQYNSTYRVVSVLTVL HQDWLNGKEYKCKVSNKALGAPIEKTISKAKGQPREPQVCTLPPSRDELTKNQ VSLSCAVKGFYPSDIAVEWESNGQPENNYKTTPPVLDSDGSFFLVSKLTVDKS RWQQGNVFSCSVMHEALHNHYTQKSLSLSPGKGGGGSGGGGSEVQLLESGGGL VQPGGSLRLSCAASGYSFTGYYIHWVRQAPGKGLEWVGRVIPNAGGTSYNQKF KGRFTISVDNSKNTAYLQMNSLRAEDTAVYYCAREGIYWWGQGTTVTVSSAST KGPSVFPLAPSSKSTSGGTAALGCLVKDYFPEPVTVSWNSGALTSGVHTFPAV LQSSGLYSLSSVVTVPSSSLGTQTYICNVNHKPSNTKVDKKVEPKSCGGGGSG GGGSGGGGSGGGGSEIVLTQSPGTLSLSPGERATLSCRASQSVTSSYLAWYQQK PGQAPRLLINVGSRRATGIPDRFSGSGSGTDFTLTISRLEPEDFAVYYCQQGI MLPPTFGQGTKVEIKSSASTKGPSVFPLAPSSKSTSGGTAALGCLVKDYFPEP VTVSWNSGALTSGVHTFPAVLQSSGLYSLSSVVTVPSSSLGTQTYICNVNHKP SNTKVDKKVEPKSC |

8.4 Preparation of FAP (4B9)-CD40 Contorsbody P1AE2052

A bispecific antibody comprising two fusion polypeptides was cloned as follows:

first fusion polypeptide (from N- to C-terminus): VL(CD40)-Ckappa, (G4S)2 connector (SEQ ID NO: 78), IgG1 hinge, Fc knob, (G4S)2 connector (SEQ ID NO: 78), VH(CD40)-CH1, GGGGSGGGGSGGGSGGGGS (SEQ ID NO:84) connector, VH(FAP)-Ckappa.

second fusion polypeptide (from N- to C-terminus): VL(CD40)-Ckappa, (G4S)2 connector (SEQ ID NO: 78), IgG1 hinge, Fc hole, (G4S)2 connector (SEQ ID NO: 78), VH(CD40)-CH1, GGGGSGGGGSGGGSGGGGS (SEQ ID NO:84) connector, VL(FAP)-CH1.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)).

Table 35 shows the amino acid sequences of the bispecific antibody P1AE2052.

TABLE 35

Sequences of P1AE2052

| SEQ ID NO: | Description | Sequence |
|---|---|---|
| 161 | first fusion polypeptide (Fc knob) | DIQMTQSPSSLSASVGDRVTITCRSSQSLVHSNGNTFLHWYQQKPGKAPKLLIYT VSNRFSGVPSRFSGSGSGTDFTLTISSLQPEDFATYFCSQTTHVPWTFGGGTKVE IKRTVAAPSVFIFPPSDEQLKSGTASVVCLLNNFYPREAKVQWKVDNALQSGNSQ ESVTEQDSKDSTYSLSSTLTLSKADYEKHKVYACEVTHQGLSSPVTKSFNRGECG GGGSGGGGSDKTHTCPPCPAPEAAGGPSVFLFPPKPKDTLMISRTPEVTCVVVDV SHEDPEVKFNWYVDGVEVHNAKTKPREEQYNSTYRVVSVLTVLHQDWLNGKEYKC KVSNKALGAPIEKTISKAKGQPREPQVYTLPPCRDELTKNQVSLWCLVKGFYPSD IAVEWESNGQPENNYKTTPPVLDSDGSFFLYSKLTVDKSRWQQGNVFSCSVMHEA |

TABLE 35-continued

Sequences of P1AE2052

| SEQ ID NO: | Description | Sequence |
|---|---|---|
| | | LHNHYTQKSLSLSPGKGGGGSGGGGSEVQLLESGGGLVQPGGSLRLSCAASGYSF<br>TGYYIHWVRQAPGKGLEWVGRVIPNAGGTSYNQKFKGRFTISVDNSKNTAYLQMN<br>SLRAEDTAVYYCAREGIYWWGQGTTVTVSSASTKGPSVFPLAPSSKSTSGGTAAL<br>GCLVKDYFPEPVTVSWNSGALTSGVHTFPAVLQSSGLYSLSSVVTVPSSSLGTQT<br>YICNVNHKPSNTKVDKKVEPKSCGGGGSGGGGSGGGSGGGGSEVQLLESGGGLVQ<br>PGGSLRLSCAASGFTFSSYAMSWVRQAPGKGLEWVSAIIGSGASTYYADSVKGRF<br>TISRDNSKNTLYLQMNSLRAEDTAVYYCAKGWFGGFNYWGQGTLVTVSSASVAAP<br>SVFIFPPSDEQLKSGTASVVCLLNNFYPREAKVQWKVDNALQSGNSQESVTEQDS<br>KDSTYSLSSTLTLSKADYEKHKVYACEVTHQGLSSPVTKSFNRGEC |
| 162 | second fusion polypeptide (Fc hole) | DIQMTQSPSSLSASVGDRVTITCRSSQSLVHSNGNTFLHWYQQKPGKAPKLLIYT<br>VSNRFSGVPSRFSGSGSGTDFTLTISSLQPEDFATYFCSQTTHVPWTFGGGTKVE<br>IKRTVAAPSVFIFPPSDEQLKSGTASVVCLLNNFYPREAKVQWKVDNALQSGNSQ<br>ESVTEQDSKDSTYSLSSTLTLSKADYEKHKVYACEVTHQGLSSPVTKSFNRGECG<br>GGGSGGGGSDKTHTCPPCPAPEAAGGPSVFLFPPKPKDTLMISRTPEVTCVVVDV<br>SHEDPEVKFNWYVDGVEVHNAKTKPREEQYNSTYRVVSVLTVLHQDWLNGKEYKC<br>KVSNKALGAPIEKTISKAKGQPREPQVCTLPPSRDELTKNQVSLSCAVKGFYPSD<br>IAVEWESNGQPENNYKTTPPVLDSDGSFFLVSKLTVDKSRWQQGNVFSCSVMHEA<br>LHNHYTQKSLSLSPGKGGGGSGGGGSEVQLLESGGGLVQPGGSLRLSCAASGYSF<br>TGYYIHWVRQAPGKGLEWVGRVIPNAGGTSYNQKFKGRFTISVDNSKNTAYLQMN<br>SLRAEDTAVYYCAREGIYWWGQGTTVTVSSASTKGPSVFPLAPSSKSTSGGTAAL<br>GCLVKDYFPEPVTVSWNSGALTSGVHTFPAVLQSSGLYSLSSVVTVPSSSLGTQT<br>YICNVNHKPSNTKVDKKVEPKSCGGGGSGGGGSGGGSGGGGSEIVLTQSPGTLSL<br>SPGERATLSCRASQSVTSSYLAWYQQKPGQAPRLLINVGSRRATGIPDRFSGSGS<br>GTDFTLTISRLEPEDFAVYYCQQGIMLPPTFGQGTKVEIKSSASTKGPSVFPLAP<br>SSKSTSGGTAALGCLVKDYFPEPVTVSWNSGALTSGVHTFPAVLQSSGLYSLSSV<br>VTVPSSSLGTQTYICNVNHKPSNTKVDKKVEPKSC |

8.5 Preparation of FAP (4B9)-CD40 Contorsbody P1AE1901

A bispecific antibody comprising two fusion polypeptides was cloned as follows:

first fusion polypeptide (from N- to C-terminus): VL(CD40)-Ckappa, (G4S)2 connector (SEQ ID NO: 78), IgG1 hinge, Fc knob, (G4S)2 connector (SEQ ID NO: 78), VH(CD40)-CH1, GGGGSGGGGSGGGSGGGGS (SEQ ID NO:84) connector, VL(FAP)-CH1.

second fusion polypeptide (from N- to C-terminus): VL(CD40)-Ckappa, (G4S)2 connector (SEQ ID NO: 78), IgG1 hinge, Fc hole, (G4S)2 connector (SEQ ID NO: 78), VH(CD40)-CH1, GGGGSGGGGSGGGSGGGGS (SEQ ID NO:84) connector, VH(FAP)-Ckappa.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)).

Table 36 shows the amino acid sequences of the bispecific antibody P1AE1901.

TABLE 36

Sequences of P1AE1901

| SEQ ID NO: | Description | Sequence |
|---|---|---|
| 163 | first fusion polypeptide (Fc knob) | DIQMTQSPSSLSASVGDRVTITCRSSQSLVHSNGNTFLHWYQQKPGKAPKLLIY<br>TVSNRFSGVPSRFSGSGSGTDFTLTISSLQPEDFATYFCSQTTHVPWTFGGGTK<br>VEIKRTVAAPSVFIFPPSDEQLKSGTASVVCLLNNFYPREAKVQWKVDNALQSG<br>NSQESVTEQDSKDSTYSLSSTLTLSKADYEKHKVYACEVTHQGLSSPVTKSFNR<br>GECGGGGSGGGGSDKTHTCPPCPAPEAAGGPSVFLFPPKPKDTLMISRTPEVTC<br>VVVDVSHEDPEVKFNWYVDGVEVHNAKTKPREEQYNSTYRVVSVLTVLHQDWLN<br>GKEYKCKVSNKALGAPIEKTISKAKGQPREPQVYTLPPCRDELTKNQVSLWCLV<br>KGFYPSDIAVEWESNGQPENNYKTTPPVLDSDGSFFLYSKLTVDKSRWQQGNVF<br>SCSVMHEALHNHYTQKSLSLSPGKGGGGSGGGGSEVQLLESGGGLVQPGGSLRL<br>SCAASGYSFTGYYIHWVRQAPGKGLEWVGRVIPNAGGTSYNQKFKGRFTISVDN<br>SKNTAYLQMNSLRAEDTAVYYCAREGIYWWGQGTTVTVSSASTKGPSVFPLAPS<br>SKSTSGGTAALGCLVKDYFPEPVTVSWNSGALTSGVHTFPAVLQSSGLYSLSSV<br>VTVPSSSLGTQTYICNVNHKPSNTKVDKKVEPKSCGGGGSGGGGSGGGSGGGGS<br>EIVLTQSPGTLSLSPGERATLSCRASQSVTSSYLAWYQQKPGQAPRLLINVGSR<br>RATGIPDRFSGSGSGTDFTLTISRLEPEDFAVYYCQQGIMLPPTFGQGTKVEIK<br>SSASTKGPSVFPLAPSSKSTSGGTAALGCLVKDYFPEPVTVSWNSGALTSGVHT<br>FPAVLQSSGLYSLSSVVTVPSSSLGTQTYICNVNHKPSNTKVDKKVEPKSC |
| 164 | second fusion polypeptide (Fc hole) | DIQMTQSPSSLSASVGDRVTITCRSSQSLVHSNGNTFLHWYQQKPGKAPKLLIY<br>TVSNRFSGVPSRFSGSGSGTDFTLTISSLQPEDFATYFCSQTTHVPWTFGGGTK<br>VEIKRTVAAPSVFIFPPSDEQLKSGTASVVCLLNNFYPREAKVQWKVDNALQSG |

TABLE 36-continued

Sequences of P1AE1901

| SEQ ID NO: Description | Sequence |
|---|---|
| | NSQESVTEQDSKDSTYSLSSTLTLSKADYEKHKVYACEVTHQGLSSPVTKSFNR<br>GECGGGGSGGGGSDKTHTCPPCPAPEAAGGPSVFLFPPKPKDTLMISRTPEVTC<br>VVVDVSHEDPEVKFNWYVDGVEVHNAKTKPREEQYNSTYRVVSVLTVLHQDWLN<br>GKEYKCKVSNKALGAPIEKTISKAKGQPREPQVCTLPPSRDELTKNQVSLSCAV<br>KGFYPSDIAVEWESNGQPENNYKTTPPVLDSDGSFFLVSKLTVDKSRWQQGNVF<br>SCSVMHEALHNHYTQKSLSLSPGKGGGGSGGGGSEVQLLESGGGLVQPGGSLRL<br>SCAASGYSFTGYYIHWVRQAPGKGLEWVGRVIPNAGGTSYNQKFKGRFTISVDN<br>SKNTAYLQMNSLRAEDTAVYYCAREGIYWWGQGTTVTVSSASTKGPSVFPLAPS<br>SKSTSGGTAALGCLVKDYFPEPVTVSWNSGALTSGVHTFPAVLQSSGLYSLSSV<br>VTVPSSSLGTQTYICNVNHKPSNTKVDKKVEPKSCGGGGSGGGGSGGGSGGGGS<br>EVQLLESGGGLVQPGGSLRLSCAASGFTFSSYAMSWVRQAPGKGLEWVSAIIGS<br>GASTYYADSVKGRFTISRDNSKNTLYLQMNSLRAEDTAVYYCAKGWFGGFNYWG<br>QGTLVTVSSASVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSPVT<br>KSFNRGEC |

8.6 Preparation of FAP (4B9)-CD40 Contorsbody P1AE2255

A bispecific antibody comprising two fusion polypeptides was cloned as follows:

first fusion polypeptide (from N- to C-terminus): VH(CD40)-CH1_EE (K147E, K213E), (G4S)2 connector (SEQ ID NO: 78), IgG1 hinge, Fc knob, (G4S)2 connector (SEQ ID NO: 78), VL(CD40)-Ckappa_RK (E123R, Q124K), GGGGSGGGGSGGGSGGGGS (SEQ ID NO:84) connector, VH(FAP)-Ckappa.

second fusion polypeptide (from N- to C-terminus): VH(CD40)-CH1_EE (K147E, K213E), (G4S)2 connector (SEQ ID NO: 78), IgG1 hinge, Fc hole, (G4S)2 connector (SEQ ID NO: 78), VL(CD40)-Ckappa_RK (E123R, Q124K), GGGGSGGGGSGGGSGGGGS (SEQ ID NO:84) connector, VL(FAP)-CH1.

The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831. The knobs into hole heterodimerization technology was used with the S354C/T366W mutations in the CH3 domain of the knob chain and the corresponding Y349C/T366S/L368A/Y407V mutations in the CH3 domain of the hole chain (Carter, J Immunol Methods 248, 7-15 (2001)). Furthermore, in the CH and Ckappa fused to the VL and VH of OX40, respectively, amino acid mutations (so-called charged residues) were introduced to prevent the generation of Bence Jones proteins and to further facilitate the correct pairing, i.e negative charges in the CH1 domain (K147E, K213E, numbering according Kabat EU index) and positive charges in the CL domain of the anti-OX40 binder 49B4 (E123R and Q124K, numbering according to Kabat EU index).

Table 37 shows the amino acid sequences of the bispecific antibody P1AE2255.

TABLE 37

Sequences of P1AE2255:

| SEQ ID NO: | Description | Sequence |
|---|---|---|
| 165 | first fusion polypeptide (Fc knob) | EVQLLESGGGLVQPGGSLRLSCAASGYSFTGYYIHWVRQAPGKGLEWVGRVIP<br>NAGGTSYNQKFKGRFTISVDNSKNTAYLQMNSLRAEDTAVYYCAREGIYWWGQ<br>GTTVTVSSASTKGPSVFPLAPSSKSTSGGTAALGCLVEDYFPEPVTVSWNSGA<br>LTSGVHTFPAVLQSSGLYSLSSVVTVPSSSLGTQTYICNVNHKPSNTKVDEKV<br>EPKSCGGGGSGGGGSDKTHTCPPCPAPEAAGGPSVFLFPPKPKDTLMISRTPE<br>VTCVVVDVSHEDPEVKFNWYVDGVEVHNAKTKPREEQYNSTYRVVSVLTVLHQ<br>DWLNGKEYKCKVSNKALGAPIEKTISKAKGQPREPQVYTLPPCRDELTKNQVS<br>LWCLVKGFYPSDIAVEWESNGQPENNYKTTPPVLDSDGSFFLYSKLTVDKSRW<br>QQGNVFSCSVMHEALHNHYTQKSLSLSPGKGGGGSGGGGSDIQMTQSPSSLSA<br>SVGDRVTITCRSSQSLVHSNGNTFLHWYQQKPGKAPKLLIYTVSNRFSGVPSR<br>FSGSGSGTDFTLTISSLQPEDFATYFCSQTTHVPWTFGGGTKVEIKRTVAAPS<br>VFIFPPSDRKLKSGTASVVCLLNNFYPREAKVQWKVDNALQSGNSQESVTEQD<br>SKDSTYSLSSTLTLSKADYEKHKVYACEVTHQGLSSPVTKSFNRGECGGGGSG<br>GGGSGGGSGGGGSEVQLLESGGGLVQPGGSLRLSCAASGFTFSSYAMSWVRQA<br>PGKGLEWVSAIIGSGASTYYADSVKGRFTISRDNSKNTLYLQMNSLRAEDTAV<br>YYCAKGWFGGFNYWGQGTLVTVSSASVAAPSVFIFPPSDEQLKSGTASVVCLL<br>NNFYPREAKVQWKVDNALQSGNSQESVTEQDSKDSTYSLSSTLTLSKADYEKH<br>KVYACEVTHQGLSSPVTKSFNRGEC |
| 166 | second fusion polypeptide (Fc hole) | EVQLLESGGGLVQPGGSLRLSCAASGYSFTGYYIHWVRQAPGKGLEWVGRVIP<br>NAGGTSYNQKFKGRFTISVDNSKNTAYLQMNSLRAEDTAVYYCAREGIYWWGQ<br>GTTVTVSSASTKGPSVFPLAPSSKSTSGGTAALGCLVEDYFPEPVTVSWNSGA<br>LTSGVHTFPAVLQSSGLYSLSSVVTVPSSSLGTQTYICNVNHKPSNTKVDEKV<br>EPKSCGGGGSGGGGSDKTHTCPPCPAPEAAGGPSVFLFPPKPKDTLMISRTPE<br>VTCVVVDVSHEDPEVKFNWYVDGVEVHNAKTKPREEQYNSTYRVVSVLTVLHQ<br>DWLNGKEYKCKVSNKALGAPIEKTISKAKGQPREPQVCTLPPSRDELTKNQVS<br>LSCAVKGFYPSDIAVEWESNGQPENNYKTTPPVLDSDGSFFLVSKLTVDKSRW<br>QQGNVFSCSVMHEALHNHYTQKSLSLSPGKGGGGSGGGGSDIQMTQSPSSLSA |

TABLE 37-continued

Sequences of P1AE2255:

| SEQ ID NO: Description | Sequence |
|---|---|
| | SVGDRVTITCRSSQSLVHSNGNTFLHWYQQKPGKAPKLLIYTVSNRFSGVPSR
FSGSGSGTDFTLTISSLQPEDFATYFCSQTTHVPWTFGGGTKVEIKRTVAAPS
VFIFPPSDRKLKSGTASVVCLLNNFYPREAKVQWKVDNALQSGNSQESVTEQD
SKDSTYSLSSTLTLSKADYEKHKVYACEVTHQGLSSPVTKSFNRGECGGGSG
GGGSGGGSGGGGSEIVLTQSPGTLSLSPGERATLSCRASQSVTSSYLAWYQQK
PGQAPRLLINVGSRRATGIPDRFSGSGSGTDFTLTISRLEPEDFAVYYCQQGI
MLPPTFGQGTKVEIKSSASTKGPSVFPLAPSSKSTSGGTAALGCLVKDYFPEP
VTVSWNSGALTSGVHTFPAVLQSSGLYSLSSVVTVPSSSLGTQTYICNVNHKP
SNTKVDKKVEPKSC |

A schematic scheme of the assembled structure is shown in FIG. 1L (OX40 to be replaced by CD40).

8.7 Biochemical Analysis of the Molecules after Purification

Table 38 summarizes the yield and final monomer content of the FAP-4-1BB contorsbodies.

TABLE 38

Biochemical analysis of the FAP 4-1BB contorsbodies

| Construct | Monomer [%] (SEC) | Titer [mg/l] |
|---|---|---|
| contorsbody P1AE1799 | 100 | 3.40 |
| contorsbody P1AE1902 | 100 | 4.42 |
| contorsbody P1AE1800 | 98.8 | 2.44 |
| contorsbody P1AE2052 | 100 | 4.06 |
| contorsbody P1AE1901 | 100 | 3.60 |
| contorsbody P1AE2255 | 100 | 1.82 |

Example 9

Characterization of FAP CD40 Antibodies 9.1 Binding to Human CD40

The capacity of the bispecific constructs to bind human CD40 was assessed by surface plasmon resonance (SPR). All SPR experiments were performed on a Biacore T200 (Biacore) at 25° C. with HBS-EP as running buffer (0.01 M HEPES pH 7.4, 0.15 M NaCl, 3 mM EDTA, 0.005% Surfactant P20, (Biacore). Association was measured by injection of human CD40 extra cellular domain in various concentrations in solution for 300 sec at a flow of 30 µl/min starting with 300 nM in 1:3 dilutions. The dissociation phase was monitored for up to 1200 sec and triggered by switching from the sample solution to running buffer. The surface was regenerated by 60 sec washing with a Glycine pH 2.1 solution at a flow rate of 30 µl/min. Bulk refractive index differences were corrected by subtracting the response obtained from a goat anti human F(ab')2 surface. Blank injections are also subtracted (=double referencing). For calculation of apparent $K_D$ and other kinetic parameters the Langmuir 1:1 model was used. The apparent Kd was calculated using the Biacore™ B4000 evaluation software (version 1.1).

TABLE 39

Binding of bispecific CD40 x FAP Contorsbodies to recombinant human CD40_ECD (Biacore)

| Molecule | ka (1/Ms) | kd (1/s) | KD (M) | Rmax (RU) | t ½ (s) |
|---|---|---|---|---|---|
| contorsbody P1AE1800 | 1.35E+06 | 1.27E−02 | 9.43E−09 | 5.2 | 55 |
| contorsbody P1AE1799 | 9.57E+05 | 1.51E−02 | 1.57E−08 | 10.7 | 46 |
| contorsbody P1AE1901 | 9.91E+05 | 6.92E−03 | 6.98E−09 | 12.3 | 100 |
| contorsbody P1AE1902 | 7.76E+05 | 1.45E−02 | 1.87E−08 | 9.9 | 48 |
| contorsbody P1AE2052 | 9.45E+05 | 6.81E−03 | 7.20E−09 | 10.9 | 102 |
| contorsbody P1AE2255 | 9.18E+05 | 1.59E−02 | 1.73E−08 | 14.2 | 44 |

9.2 Binding on Human FAP (Kinetic Affinity)

Binding of bispecific FAP-OX40 antibodies to human FAP was investigated by surface plasmon resonance using a BIACORE T100 instrument (GE Healthcare). Around 12000 resonance units (RU) of the capturing system (15 µg/ml anti-histidine antibody; Order Code: 28995056; GE Healthcare Bio-Sciences AB, Sweden) were coupled on a CM5 chip (GE Healthcare BR-1005-30) at pH 4.5 by using an amine coupling kit supplied by the GE Healthcare. Running buffer for Immobilization was HBS-N pH 7.4 (10 mM HEPES, 150 mM NaCl, pH 7.4, GE Healthcare). For the following kinetic characterization running buffer was PBS-P pH 7.4 (20 mM phosphate buffer, 2.7 mM KCl, 137 mM NaCl, 0.05% surfactant P20). The flow cell was set to 25° C.—and the sample block set to 12° C.—and primed with running buffer twice. The recombinant human FAP was captured by injecting a 25 µg/ml solution for 60 s at a flow rate of 5 µl/min. Association was measured by injection of the bispecific antibody for 120 s at a flow rate of 30 µl/min starting with 300 nM in 1:2 dilution. The dissociation phase was monitored for up to 720 s and triggered by switching from the sample solution to running buffer. The surface was regenerated by washing with 10 mM Glycine pH 1.5 for 60 s at a flow rate of 30 µl/min. Bulk refractive index differences were corrected by subtracting the response obtained from an anti-histidine surface. Blank injections are also subtracted (=double referencing). For calculation of $K_D$ and kinetic parameters the Langmuir 1:1 model was used.

TABLE 40

Binding of anti-FAP/anti-CD40 antibodies to recombinant human FAP

| Molecule | ka (1/Ms) | kd (1/s) | KD (M) | Rmax (RU) | t ½ (sec) |
|---|---|---|---|---|---|
| contorsbody P1AE1800 | 8.57E+04 | 7.78E−04 | 9.07E−09 | 18.4 | 891 |
| contorsbody P1AE1799 | 5.53E+04 | 2.53E−04 | 4.58E−09 | 28.9 | 2741 |
| contorsbody P1AE1901 | 3.82E+04 | 2.69E−04 | 7.05E−09 | 32.0 | 2578 |
| contorsbody P1AE1902 | 5.41E+04 | 2.88E−04 | 5.33E−09 | 26.0 | 2405 |
| contorsbody P1AE2052 | 3.56E+04 | 2.96E−04 | 8.31E−09 | 28.2 | 2345 |
| contorsbody P1AE2255 | 5.28E+04 | 2.35E−04 | 4.44E−09 | 36.7 | 2955 |

9.3 Simultaneous Binding on Human CD40 and Human FAP (Kinetic Affinity)

The capacity of binding simultaneously human CD40 and human FAP was also assessed by surface plasmon resonance (SPR) using a BIACORE T100 instrument (GE Healthcare). Around 8000 resonance units (RU) of the capturing system (20 µg/ml anti-human IgG (Fc); Order Code: BR100839; GE Healthcare Bio-Sciences AB, Sweden) were coupled on a CMS chip (GE Healthcare BR-1005-30) at pH 5.0 by using an amine coupling kit supplied by the GE Healthcare. Running buffer was PBS-P pH 7.4 (20 mM phosphate buffer, 2.7 mM KCl, 137 mM NaCl, 0.05% Surfactant P20). The flow cell was set to 25° C.—and the sample block set to 12° C.—and primed with running buffer twice. The bispecific antibody was captured by injecting a 2 µg/ml solution for 60 seconds at a flow rate of 5 µl/min. Association was measured by injection of the first analyte (human CD40 or human FAP, respectively) for 120 seconds at a flow rate of 30 µl/min. Then the second analyte (human FAP or human CD40, respectively) was injected with a flow rate of 30 µl/min for 120 seconds. The dissociation phase was monitored for up to 720 seconds and triggered by switching from the sample solution to running buffer. The surface was regenerated by washing with 3 M $MgCl_2$ for 60 seconds at a flow rate of 10 µl/min. Bulk refractive index differences were corrected by subtracting the response obtained from an anti-human IgG (Fc) surface. Blank injections are also subtracted (=double referencing). For calculation of $K_D$ and kinetic parameters the Langmuir 1:1 model was used. All FAP-CD40 contorsbodies were able to bind simultaneously and independently to both antigens.

Example 10

Functional Properties of FAP-Targeted Anti-Human CD40 Binding Molecules 10.1 Activation of Human B Cells by FAP-Targeted Anti-Human CD40 Binding Molecules Using FAP-Coated Dynabeads as Source of Antigen B cells were isolated from buffy coats obtained from the Stiftung Zürcher Blutspendedienst SRK. In order to isolate peripheral blood mononuclear cells (PBMCs), a buffy coat of 50 mL was diluted in the same volume of PBS (gibco, Cat. No. 10010023). 50 mL polypropylene centrifuge tubes (TPP, Cat. No. 91050) were supplied with 15 mL of Lymphoprep™ (STEMCELL Technologies, Cat. No. 07851) and 25 mL of the buffy coat solution per tube were carefully layered above the Lymphorep™. The tubes were centrifuged at 2000 rpm for 24 minutes at room temperature with low acceleration and without break. Afterwards, the PBMCs were collected from the interface, washed three times with PBS, resuspended in 10 mL of PBS and cells were analyzed for cell type and number with a Beckman Coulter cell counter Ac•T™ 5diff OV (Beckman Coulter, Cat. No. 6605580). Prior to the B cell isolation from the PBMCs, the CD14 positive fraction was removed by magnetic labeling of the CD14 positive cells with CD14 microbeads (Miltenyi, Cat. No. 130-050-201) and subsequent isolation with the autoMACS® Pro Separator (Miltenyi, Cat. No. 130-092-545). The CD14 negative fraction was used for subsequent B cell isolation with the Miltenyi B cell isolation kit II (Cat. No. 130-091-151) and autoMACS® separation. $1\times10^5$ B cells in 100 µl of R10 medium consisting of Roswell Park Memorial Institute (RPMI) medium 1640 (gibco, Cat. No. 31870-025) supplied with 10% (v/v) Fetal Bovine Serum (FBS) (life technologies, Cat. No. 16140, Lot No. 1797306A), 1% (v/v) Penicillin/Streptomycin (gibco, Cat. No. 15070-063), 1% (v/v) L-Glutamine (gibco, Cat. No. 25030-024), 1% (v/v) Sodium-Pyruvate (gibco, Cat. No. 11360-039), 1% (v/v) MEM non-essential amino acids (gibco, Cat. No. 11140-035) and 50 µM β-Mercaptoethanol (gibco, Cat. No. 31350-010) were added per well of a 96-well flat-bottom plate. Streptavidin Dynabeads® (ThermoFisher Scientific, Cat. No.: 11205D) were coated with biotinylated human FAP (produced in-house, binding capacity of $6.5\times10^4$ beads: 0.01 µg of protein) according to the manufacturer's protocol and added to the B cells in a bead to cell ratio of 2:1 in 50 µl of R10 medium. As control non-coated beads were added to the B cells.

FAP-targeted anti-human CD40 contorsbodies were added in 50 µl of R10 medium to the B cells at concentrations ranging from 6.7 to 0.003 nM (3× dilution series). As a positive FAP-independent control the agonistic anti-human CD40 antibody SGN40 (IgG1, INN: Dacetuzumab) was used. Since it is described in the literature that the SGN40 antibody requires Fc receptor cross-linking for biological activity (C. Law et al., Cancer Res 2005, 65, 8331-8338), the antibody was incubated with a cross-linking goat anti-human IgG Fcγ fragment specific F(ab')2 fragment (Jackson ImmunoResearch, Cat. No. 109-006-008) for 30 minutes before addition to the B cells. After 48 hours, cells were transferred into a 96-well round-bottom plate, washed once with PBS and incubated with 50 µl of 3 µg/mL of Fc receptor blocking Mouse IgG Isotype Control (ThermoFisher Scientific, Cat. No. 10400C) in PBS. After 15 minutes of incubation at 4° C., cells were washed with PBS and 50 µl of a mixture of fluorescently labelled antibodies in PBS was added to the cells. The following fluorescently labelled antibodies were used: anti-human CD80 BV605 (BD Biosciences, clone L307.4, Cat. No. 563315), anti-human CD69 Alexa Fluor® 488 (Biolegend, clone FN50, Cat. No. 310916), anti-human CD14 PerCP-Cy5.5 (Biolegend, clone HCD14, Cat. No. 325622), anti-human CD3 PerCP-Cy5.5 (Biolegend, clone UCHT1, Cat. No. 300430), anti-human CD86 PE-CF594 (BD Biosciences, clone FUN-1, Cat. No. 562390), anti-HLA-DR BUV395 (BD Biosciences, clone G46-6, Cat. No. 564040) and anti-human CD19 APC-H7 (BD Biosciences, clone SJ25C1, Cat. No. 560177). In order to distinguish between live and dead cells, the viability dye Zombie Aqua (Biolegend, Cat. No. 423102) was added to the antibody mixture. After 30 minutes of incubation at 4° C., cells were washed twice with PBS and resuspended in 200 µl of PBS. Cells were analyzed the same day using a 5-laser LSR-Fortessa (BD Bioscience with DIVA software). Data analysis was performed using the FlowJo version 10 software (FlowJo LLC). Live (aqua negative) cells, negative for CD14 and CD3 and positive for CD19 were analyzed for CD69, CD80, CD86 and HLA-DR expression.

B cells analyzed after 2 days of incubation with agonistic anti-CD40 contorsbodies or cross-linked SGN40 antibody showed an increase in CD69, CD80, CD86 and HLA-DR expression for all tested constructs (see FIGS. 24A to 24H). Upregulation of these expression markers was dependent on FAP in case of the different FAP-targeted contorsbodies and increase of expression induced by these FAP-dependent antibodies was comparable or slightly lower to the increase induced by the cross-linked SGN40 antibody.

The invention claimed is:

1. A bispecific antibody comprising two fusion polypeptides and comprising 2+1 binding domains binding domain capable of specific binding to a tumor-specific antigen comprising:

(a)
- (1) a first fusion polypeptide from N-terminus to C-terminus comprising a first heavy chain variable domain (first VH), a CH1 domain, a first peptide linker, a spacer domain, a second peptide linker, a first light chain variable domain (first VL), a CL domain (Ckappa), a third peptide linker, a second light chain variable domain (second VL), and a CH1 domain, wherein the first VH and the first VL forms a first binding domain, and
- (2) a second fusion polypeptide from N terminus to C-terminus comprising a first heavy chain variable domain (first VH), a CH1 domain, a first peptide linker, a spacer domain, a second peptide linker, a first light chain variable domain (first VL), a CL domain (Ckappa), a third peptide linker, a second heavy chain variable domain (second VH), and a CL domain (Ckappa),
wherein the first VH and the first VL forms a first binding domain, and wherein the second VH and the second VL domain forms a second antigen binding domain, wherein the spacer domain comprises a hinge, a CH2 domain and a CH3 domain or a fragment thereof;

or (b)
- (1) a first fusion polypeptide from N-terminus to C-terminus comprising a first heavy chain variable domain (first VH), a CL domain (Ckappa), a first peptide linker, a spacer domain, a second peptide linker, a first light chain variable domain (first VL), a CH1 domain, a third peptide linker, a second heavy chain variable domain (second VH), and a CH1 domain, wherein the first VH and the first VL forms a first binding domain, and
- (2) a second fusion polypeptide from N-terminus to C-terminus comprising a first heavy chain variable domain (first VH), a CL domain (Ckappa), a first peptide linker, a spacer domain, a second peptide linker, a first light chain variable domain (first VL), a CH1 domain, a third peptide linker, a second light chain variable domain (second VL), and a CL domain (Ckappa),
wherein the first VH and the first VL forms a first binding domain, and wherein the second VH and the second VL domain forms a second antigen binding domain, wherein the spacer domain comprises a hinge, a CH2 domain and a CH3 domain or a fragment thereof, or (c)
  (1) a first fusion polypeptide from N-terminus to C-terminus comprising a first light chain variable domain (first VL), a CL domain (Ckappa), a first peptide linker, a spacer domain, a second peptide linker, a first heavy chain variable domain (first VH), a CH1 domain, a third peptide linker, a second light chain variable domain (second VL), and a CH1 domain, wherein the first VH and the first VL forms a first binding domain, and
  (2) a second fusion polypeptide from N-terminus to C-terminus comprising a first light chain variable domain (first VL), a CL domain (Ckappa), a first peptide linker, a spacer domain, a second peptide linker, a first heavy chain variable domain (first VH), a CH1 domain, a third peptide linker, a second heavy chain variable domain (second VH), and a CL domain (Ckappa),
  wherein the first VH and the first VL forms a first binding domain, and wherein the second VH and the second VL domain forms a second antigen binding domain, wherein the spacer domain comprises a hinge, a CH2 domain and a CH3 domain or a fragment thereof, or (d)
  (1) a first fusion polypeptide from N-terminus to C-terminus comprising a second light chain variable domain (second VL), a CH1 domain, a first peptide linker, a first heavy chain variable domain (first VH), a CL domain (Ckappa) a second peptide linker, a spacer domain, a third peptide linker, a first light chain variable domain (first VL) and a CH1 domain, wherein the first VH and the first VL forms a first binding domain, and
  (2) a second fusion polypeptide from N-terminus to C-terminus comprising a second heavy chain variable domain (second VH), a CL domain (Ckappa), a first peptide linker, a first heavy chain variable domain (first VH), a CL domain (Ckappa), a second peptide linker, a spacer domain, a third peptide linker, a first light chain variable domain (first VL) and a CH1 domain,
  wherein the first VH and the first VL forms a first binding domain, and wherein the second VH and the second VL domain forms a second antigen binding domain, wherein the spacer domain comprises a hinge, a CH2 domain and a CH3 domain or a fragment thereof;

wherein for each of (a)-(d) above, the first and second antigen binding domain are associated with each other to form a circular fusion polypeptide, and wherein the spacer domain of the first fusion polypeptide and the spacer domain of the second fusion polypeptide are associated covalently to each other by a disulfide bond and comprise at least one modification promoting the association of the first fusion polypeptide and second fusion polypeptide.

2. The bispecific antibody of claim 1, wherein:
(a) each of said first VH comprises (i) CDR-H1 comprising the amino acid sequence of SEQ ID NO:17, (ii) CDR-H2 comprising the amino acid sequence of SEQ ID NO: 19, and (iii) CDR-H3 comprising the amino acid sequence of SEQ ID NO:22, and each of said first VL comprises (iv) CDR-L1 comprising the amino acid sequence of SEQ ID NO:28, (v) CDR-L2 comprising the amino acid sequence of SEQ ID NO:31, and (vi) CDR-L3 comprising the amino acid sequence of SEQ ID NO:35, or
(b) each of said first VH comprises (1) CDR-H1 comprising the amino acid sequence of SEQ ID NO:17, (ii) CDR-H2 comprising the amino acid sequence of SEQ ID NO:19, and (iii) CDR-H3 comprising the amino acid sequence of SEQ ID NO:21, and each of said first VL comprises (iv) CDR-L1 comprising the amino acid sequence of SEQ ID NO:28, (v) CDR-L2 comprising the amino acid sequence of SEQ ID NO:31, and (vi) CDR-L3 comprising the amino acid sequence of SEQ ID NO:34, or
(c) each of said first VH comprises (i) CDR-H1 comprising the amino acid sequence of SEQ ID NO:17, (ii) CDR-H2 comprising the amino acid sequence of SEQ ID NO:19, and (iii) CDR-H3 comprising the amino acid sequence of SEQ ID NO:23, and each of said first VL comprises (iv) CDR-L1 comprising the amino acid sequence of SEQ ID NO:28, (v) CDR-L2 comprising the amino acid sequence of SEQ ID NO:31, and (vi) CDR-L3 comprising the amino acid sequence of SEQ ID NO:36, or
(d) each of said first VH comprises (i) CDR-H1 comprising the amino acid sequence of SEQ ID NO:17, (ii) CDR-H2 comprising the amino acid sequence of SEQ ID NO:19, and (iii) CDR-H3 comprising the amino acid sequence of SEQ ID NO:24, and each of said first VL comprises (iv) CDR-L1 comprising the amino acid sequence of SEQ ID NO:28, (v) CDR-L2 comprising the amino acid sequence of SEQ ID NO:31, and (vi) CDR-L3 comprising the amino acid sequence of SEQ ID NO:37, or
(e) each of said first VH comprises (i) CDR-H1 comprising the amino acid sequence of SEQ ID NO:18, (ii) CDR-H2 comprising the amino acid sequence of SEQ ID NO:20, and (iii) CDR-H3 comprising the amino acid sequence of SEQ ID NO:25, and each of said first VL comprises (iv) CDR-L1 comprising the amino acid sequence of SEQ ID NO:29, (v) CDR-L2 comprising the amino acid sequence of SEQ ID NO:32, and (vi) CDR-L3 comprising the amino acid sequence of SEQ ID NO:38, or
(f) each of said first VH comprises (i) CDR-H1 comprising the amino acid sequence of SEQ ID NO:18, (ii) CDR-H2 comprising the amino acid sequence of SEQ ID NO:20, and (iii) CDR-H3 comprising the amino acid sequence of SEQ ID NO:26, and each of said first VL comprises (iv) CDR-L1 comprising the amino acid sequence of SEQ ID NO:29, (v) CDR-L2 comprising the amino acid sequence of SEQ ID NO:32, and (vi) CDR-L3 comprising the amino acid sequence of SEQ ID NO:38, or
(g) each of said first VH comprises (i) CDR-H1 comprising the amino acid sequence of SEQ ID NO:18, (ii) CDR-H2 comprising the amino acid sequence of SEQ ID NO:20, and (iii) CDR-H3 comprising the amino acid sequence of SEQ ID NO:27, and each of said first VL comprises (iv) CDR-L1 comprising the amino acid sequence of SEQ ID NO:30, (v) CDR-L2 comprising the amino acid sequence of SEQ ID NO:33, and (vi) CDR-L3 comprising the amino acid sequence of SEQ ID NO:39.

3. The bispecific antibody of claim 1, wherein:
(a) said second VH comprises (i) CDR-H1 comprising the amino acid sequence of SEQ ID NO:1, (ii) CDR-H2 comprising the amino acid sequence of SEQ ID NO:2, and (iii) CDR-H3 comprising the amino acid sequence of SEQ ID NO:3, and said second VL comprises (iv) CDR-L1 comprising the amino acid sequence of SEQ ID NO:4, (v) CDR-L2 comprising the amino acid sequence of SEQ ID NO:5, and (vi) CDR-L3 comprising the amino acid sequence of SEQ ID NO:6, or
(b) said second VH comprises (i) CDR-H1 comprising the amino acid sequence of SEQ ID NO:9, (ii) CDR-H2 comprising the amino acid sequence of SEQ ID NO:10, and (iii) CDR-H3 comprising the amino acid sequence of SEQ ID NO:11, and said second VL comprises (iv) CDR-L1 comprising the amino acid sequence of SEQ ID NO:12, (v) CDR-L2 comprising the amino acid sequence of SEQ ID NO:13, and (vi) CDR-L3 comprising the amino acid sequence of SEQ ID NO:14.

4. The bispecific antibody of claim 1, wherein:
(a)
  (i) each of said first VH comprises (1) CDR-H1 comprising the amino acid sequence of SEQ ID NO:17, (2) CDR-H2 comprising the amino acid sequence of SEQ ID NO:19, and (3) CDR-H3 comprising the amino acid sequence of SEQ ID NO:22, and a light chain variable region comprising (4) CDR-L1 comprising the amino acid sequence of SEQ ID NO:28, (5) CDR-L2 comprising the amino acid sequence of SEQ ID NO:31, and (6) CDR-L3 comprising the amino acid sequence of SEQ ID NO:35, or
  (ii) each of said first VH comprises (1) CDR-H1 comprising the amino acid sequence of SEQ ID NO:17, (2) CDR-H2 comprising the amino acid sequence of SEQ ID NO:19, and (3) CDR-H3 comprising the amino acid sequence of SEQ ID NO:21, and a light chain variable region comprising (4) CDR-L1 comprising the amino acid sequence of SEQ ID NO:28, (5) CDR-L2 comprising the amino acid sequence of SEQ ID NO:31, and (6) CDR-L3 comprising the amino acid sequence of SEQ ID NO:34, or
  (iii) each of said first VH comprises (1) CDR-H1 comprising the amino acid sequence of SEQ ID NO:17, (2) CDR-H2 comprising the amino acid sequence of SEQ ID NO:19, and (3) CDR-H3 comprising the amino acid sequence of SEQ ID NO:23, and a light chain variable region comprising (4) CDR-L1 comprising the amino acid sequence of SEQ ID NO:28, (5) CDR-L2 comprising the amino acid sequence of SEQ ID NO:31, and (6) CDR-L3 comprising the amino acid sequence of SEQ ID NO:36, or
  (iv) each of said first VH comprises (1) CDR-H1 comprising the amino acid sequence of SEQ ID NO:17, (2) CDR-H2 comprising the amino acid sequence of SEQ ID NO:19, and (3) CDR-H3 comprising the amino acid sequence of SEQ ID NO:24, and a light chain variable region comprising (4) CDR-L1 comprising the amino acid sequence of SEQ ID NO:28, (5) CDR-L2 comprising the amino acid sequence of SEQ ID NO:31, and (6) CDR-L3 comprising the amino acid sequence of SEQ ID NO:37, or
  (v) each of said first VH comprises (1) CDR-H1 comprising the amino acid sequence of SEQ ID NO:18, (2) CDR-H2 comprising the amino acid sequence of SEQ ID NO:20, and (3) CDR-H3 comprising the amino acid sequence of SEQ ID NO:25, and a light chain variable region comprising (4) CDR-L1 comprising the amino acid sequence of SEQ ID NO:29, (5) CDR-L2 comprising the amino acid sequence of SEQ ID NO:32, and (6) CDR-L3 comprising the amino acid sequence of SEQ ID NO:38, or
  (vi) each of said first VH comprises (1) CDR-H1 comprising the amino acid sequence of SEQ ID NO:18, (2) CDR-H2 comprising the amino acid sequence of SEQ ID NO:20, and (3) CDR-H3 comprising the amino acid sequence of SEQ ID NO:26, and a light chain variable region comprising (4) CDR-L1 comprising the amino acid sequence of SEQ ID NO:29, (5) CDR-L2 comprising the amino acid sequence of SEQ ID NO:32, and (6) CDR-L3 comprising the amino acid sequence of SEQ ID NO:38, or
  (vii) each of said first VH comprises (1) CDR-H1 comprising the amino acid sequence of SEQ ID NO:18, (2) CDR-H2 comprising the amino acid sequence of SEQ ID NO:20, and (3) CDR-H3 comprising the amino acid sequence of SEQ ID NO:27, and a light chain variable region comprising (4) CDR-L1 comprising the amino acid sequence of SEQ ID NO:30, (5) CDR-L2 comprising the amino acid sequence of SEQ ID NO:33, and (6) CDR-L3 comprising the amino acid sequence of SEQ ID NO:39;
and
(b) wherein
  (i) said second VH comprises (1) CDR-H1 comprising the amino acid sequence of SEQ ID NO:1, (2) CDR-H2 comprising the amino acid sequence of SEQ ID NO:2, and (3) CDR-H3 comprising the amino acid sequence of SEQ ID NO:3, and said second VL comprises (4) CDR-L1 comprising the amino acid sequence of SEQ ID NO:4, 5) CDR-L2 comprising the amino acid sequence of SEQ ID NO:5, and (6) CDR-L3 comprising the amino acid sequence of SEQ ID NO:6, or
  (ii) said second VH comprises (1) CDR-H1 comprising the amino acid sequence of SEQ ID NO:9, (2) CDR-H2 comprising the amino acid sequence of SEQ ID NO:10, and (3) CDR-H3 comprising the amino acid sequence of SEQ ID NO:11, and said second VL comprises (4) CDR-L1 comprising the amino acid sequence of SEQ ID NO:12, (5) CDR-L2 comprising the amino acid sequence of SEQ ID NO:13, and (6) CDR-L3 comprising the amino acid sequence of SEQ ID NO:14.

5. The bispecific antibody of claim 1 wherein
(a) said first VH comprises the amino acid sequence of SEQ ID NO: 40 and the first VL comprises the amino acid sequence of SEQ ID NO: 41, or
(b) said first VH comprises the amino acid sequence of SEQ ID NO: 42 and the first VL comprises the amino acid sequence of SEQ ID NO: 43, or
(c) said first VH comprises the amino acid sequence of SEQ ID NO: 44 and the first VL comprises the amino acid sequence of SEQ ID NO: 45, or
(d) said first VH comprises the amino acid sequence of SEQ ID NO: 46 and the first VL comprises the amino acid sequence of SEQ ID NO: 47, or (e) said first VH comprises the amino acid sequence of SEQ ID NO: 48 and the first VL comprises the amino acid sequence of SEQ ID NO:49, or
(f) said first VH comprises the amino acid sequence of SEQ ID NO: 50 and the first VL comprises the amino acid sequence of SEQ ID NO:51, or
(g) said first VH comprises the amino acid sequence of SEQ ID NO: 52 and first VL comprises the amino acid sequence of SEQ ID NO: 53.

6. The bispecific antibody of claim 1, wherein
(a) said second VH comprises the amino acid sequence of SEQ ID NO:7 and the second VL comprises the amino add sequence of SEQ ID NO:8; or
(b) said second VH comprises the amino acid sequence of SEQ ID NO: 15 and the second VL comprises the amino acid sequence of SEQ ID NO: 16.

7. The bispecific antibody of claim 1 wherein
(a)
(i) said first VH comprises the amino acid sequence of SEQ ID NO: 40 and the first VL comprises the amino acid sequence of SEQ ID NO: 41, or
(ii) said first VH comprises the amino acid sequence of SEQ ID NO: 42 and the first VL comprises the amino acid sequence of SEQ ID NO: 43, or
(iii) said first VH comprises the amino acid sequence of SEQ ID NO: 44 and the first VL comprises the amino acid sequence of SEQ ID NO: 45, or
(iv) said first VH comprises the amino acid sequence of SEQ ID NO: 46 and the first VL comprises the amino acid sequence of SEQ ID NO: 47, or
(v) said first VH comprises the amino acid sequence of SEQ ID NO: 48 and the first VL comprises the amino acid sequence of SEQ ID NO:49, or
(vi) said first VH comprises the amino acid sequence of SEQ ID NO: 50 and the first VL comprises the amino acid sequence of SEQ ID NO:51, or
(vii) said first VH comprises the amino acid sequence of SEQ ID NO: 52 and first VL comprises the amino acid sequence of SEQ ID NO: 53;
and
(b)
(i) said second VH comprises the amino acid sequence of SEQ ID NO:7 and the second VL comprises the amino add sequence of SEQ ID NO:8; or
(ii) said second VH comprises the amino acid sequence of SEQ ID NO: 15 and the second VL comprises the amino acid sequence of SEQ ID NO: 16.

8. The bispecific antibody of claim 1, wherein the spacer domain of the first fusion polypeptide comprises an antibody hinge region or a fragment thereof and an IgG1 Fc domain comprising an Fc knob, and wherein the Fc knob comprises S354C and T366W substitutions; and wherein the spacer domain of the second fusion polypeptide comprises an antibody hinge region or a fragment thereof and an IgG1 Fc domain comprising an Fc hole, and wherein the Fc hole comprises Y349C, T366S, L368A and Y407V substitutions; wherein for each of said substitutions, numbering is according to EU numbering.

9. The bispecific antibody of claim 1, wherein the spacer domain of the first fusion polypeptide comprises an antibody hinge region or a fragment thereof and an IgG1 Fc domain comprising an Fc hole, and wherein the Fc hole comprises Y349C, T366S, L368A and Y407V substitutions; and wherein the spacer domain of the second fusion polypeptide comprises an antibody hinge region or a fragment thereof and an IgG1 Fc domain comprising an Fc knob, and wherein the Fc knob comprises S354C and T366W substitutions; wherein for each of said substitutions, numbering is according to EU numbering.

10. The bispecific antibody of claim 4, wherein the spacer domain of the first fusion polypeptide comprises an antibody hinge region or a fragment thereof and an IgG1 Fc domain comprising an Fc knob, and wherein the Fc knob comprises S354C and T366W substitutions; and wherein the spacer domain of the second fusion polypeptide comprises an antibody hinge region or a fragment thereof and an IgG1 Fc domain comprising an Fc hole, and wherein the Fc hole comprises Y349C, T366S, L368A and Y407V substitutions; wherein for each of said substitutions, numbering is according to EU numbering.

11. The bispecific antibody of claim 4, wherein the spacer domain of the first fusion polypeptide comprises an antibody hinge region or a fragment thereof and an IgG1 Fc domain comprising an Fc hole, and wherein the Fc hole comprises Y349C, T366S, L368A and Y407V substitutions; and wherein the spacer domain of the second fusion polypeptide comprises an antibody hinge region or a fragment thereof and an IgG1 Fc domain comprising an Fc knob, and wherein the Fc knob comprises S354C and T366W substitutions; wherein for each of said substitutions, numbering is according to EU numbering.

12. The bispecific antibody of claim 1, wherein
(a) the first fusion polypeptide comprises the amino acid sequence of SEQ ID NO: 54 and the second fusion polypeptide comprises the amino acid sequence of SEQ ID NO: 55; or
(b) the first fusion polypeptide comprises the amino acid sequence of SEQ ID NO: 56 and the second fusion polypeptide comprises the amino acid sequence of SEQ ID NO: 57; or
(c) the first fusion polypeptide comprises the amino acid sequence of SEQ ID NO: 58 and the second fusion polypeptide comprises the amino acid sequence of SEQ ID NO: 59; or
(d) the first fusion polypeptide comprises the amino acid sequence of SEQ ID NO: 60 and the second fusion polypeptide comprises the amino acid sequence of SEQ ID NO: 61; or
(e) the first fusion polypeptide comprises the amino acid sequence of SEQ ID NO: 62 and the second fusion polypeptide comprises the amino acid sequence of SEQ ID NO: 63; or
(f) the first fusion polypeptide comprises the amino acid sequence of SEQ ID NO: 64 and the second fusion polypeptide comprises the amino acid sequence of SEQ ID NO: 65; or
(g) the first fusion polypeptide comprises the amino acid sequence of SEQ ID NO: 66 and the second fusion polypeptide comprises the amino acid sequence of SEQ ID NO: 67; or
(h) the first fusion polypeptide comprises the amino acid sequence of SEQ ID NO: 116 and the second fusion polypeptide comprises the amino acid sequence of SEQ ID NO: 117.

13. A pharmaceutical composition comprising the bispecific antibody of any of claims 2-12, and a pharmaceutically acceptable carrier.

14. A method of treating a FAP-expressing cancer in a human subject in need thereof, comprising administering a therapeutically effective amount of the bispecific antibody of any of claims 2-12 to said subject.

* * * * *

SEQUENCE LISTING

```
<160> NUMBER OF SEQ ID NOS: 184

<210> SEQ ID NO 1
<211> LENGTH: 5
<212> TYPE: PRT
<213> ORGANISM: Artificial Sequence
<220> FEATURE:
<223> OTHER INFORMATION: FAP(4B9)  CDR-H1

<400> SEQUENCE: 1

Ser Tyr Ala Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: FAP(4B9)  CDR-H2

<400> SEQUENCE: 2

Ala Ile Ile Gly Ser Gly Ala Ser Thr Tyr Tyr Ala Asp Ser Val Lys
1               5                   10                  15

Gly

<210> SEQ ID NO 3
<211> LENGTH: 8
<212> TYPE: PRT
<213> ORGANISM: Artificial Sequence
<220> FEATURE:
<223> OTHER INFORMATION: FAP(4B9)  CDR-H3

<400> SEQUENCE: 3

Gly Trp Phe Gly Gly Phe Asn Tyr
1               5

<210> SEQ ID NO 4
<211> LENGTH: 12
<212> TYPE: PRT
<213> ORGANISM: Artificial Sequence
<220> FEATURE:
<223> OTHER INFORMATION: FAP(4B9)  CDR-L1

<400> SEQUENCE: 4

Arg Ala Ser Gln Ser Val Ser Arg Ser Tyr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: FAP(4B9)  CDR-L2

<400> SEQUENCE: 5

Val Gly Ser Arg Arg Ala Thr
1               5
```

```
<210> SEQ ID NO 6
<211> LENGTH: 9
<212> TYPE: PRT
<213> ORGANISM: Artificial Sequence
<220> FEATURE:
<223> OTHER INFORMATION: FAP(4B9) CDR-L3

<400> SEQUENCE: 6

Gln Gln Gly Ile Met Leu Pro Pro Thr
1               5

<210> SEQ ID NO 7
<211> LENGTH: 117
<212> TYPE: PRT
<213> ORGANISM: Artificial Sequence
<220> FEATURE:
<223> OTHER INFORMATION: FAP(4B9) VH

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115

<210> SEQ ID NO 8
<211> LENGTH: 108
<212> TYPE: PRT
<213> ORGANISM: Artificial Sequence
<220> FEATURE:
<223> OTHER INFORMATION: FAP(4B9) VL

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

<210> SEQ ID NO 9
```

```
<211> LENGTH: 5
<212> TYPE: PRT
<213> ORGANISM: Artificial Sequence
<220> FEATURE:
<223> OTHER INFORMATION: FAP(28H1) CDR-H1

<400> SEQUENCE: 9

Ser His Ala Met Ser
1               5

<210> SEQ ID NO 10
<211> LENGTH: 16
<212> TYPE: PRT
<213> ORGANISM: Artificial Sequence
<220> FEATURE:
<223> OTHER INFORMATION: FAP(28H1) CDR-H2

<400> SEQUENCE: 10

Ala Ile Trp Ala Ser Gly Glu Gln Tyr Tyr Ala Asp Ser Val Lys Gly
1               5                   10                  15

<210> SEQ ID NO 11
<211> LENGTH: 8
<212> TYPE: PRT
<213> ORGANISM: Artificial Sequence
<220> FEATURE:
<223> OTHER INFORMATION: FAP(28H1) CDR-H3

<400> SEQUENCE: 11

Gly Trp Leu Gly Asn Phe Asp Tyr
1               5

<210> SEQ ID NO 12
<211> LENGTH: 12
<212> TYPE: PRT
<213> ORGANISM: Artificial Sequence
<220> FEATURE:
<223> OTHER INFORMATION: FAP(28H1) CDR-L1

<400> SEQUENCE: 12

Arg Ala Ser Gln Ser Val Ser Arg Ser Tyr Leu Ala
1               5                   10

<210> SEQ ID NO 13
<211> LENGTH: 7
<212> TYPE: PRT
<213> ORGANISM: Artificial Sequence
<220> FEATURE:
<223> OTHER INFORMATION: FAP(28H1) CDR-L2

<400> SEQUENCE: 13

Gly Ala Ser Thr Arg Ala Thr
1               5

<210> SEQ ID NO 14
<211> LENGTH: 9
<212> TYPE: PRT
<213> ORGANISM: Artificial Sequence
<220> FEATURE:
<223> OTHER INFORMATION: FAP(28H1) CDR-L3

<400> SEQUENCE: 14

Gln Gln Gly Gln Val Ile Pro Pro Thr
1               5

<210> SEQ ID NO 15
<211> LENGTH: 116
```

```
<212> TYPE: PRT
<213> ORGANISM: Artificial Sequence
<220> FEATURE:
<223> OTHER INFORMATION: FAP(28H1) VH

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser
            115

<210> SEQ ID NO 16
<211> LENGTH: 108
<212> TYPE: PRT
<213> ORGANISM: Artificial Sequence
<220> FEATURE:
<223> OTHER INFORMATION: FAP(28H1) VL

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105

<210> SEQ ID NO 17
<211> LENGTH: 5
<212> TYPE: PRT
<213> ORGANISM: Artificial sequence
<220> FEATURE:
<223> OTHER INFORMATION: OX40(8H9,49B4,1G4, 20B7)  CDR-H1

<400> SEQUENCE: 17

Ser Tyr Ala Ile Ser
1               5

<210> SEQ ID NO 18
<211> LENGTH: 5
<212> TYPE: PRT
```

```
<213> ORGANISM: Artificial sequence
<220> FEATURE:
<223> OTHER INFORMATION: OX40(CLC-563, CLC-564, 17A9) CDR-H1

<400> SEQUENCE: 18

Ser Tyr Ala Met Ser
1               5

<210> SEQ ID NO 19
<211> LENGTH: 17
<212> TYPE: PRT
<213> ORGANISM: Artificial sequence
<220> FEATURE:
<223> OTHER INFORMATION: OX40(8H9,49B4,1G4, 20B7) CDR-H2

<400> SEQUENCE: 19

Gly Ile Ile Pro Ile Phe Gly Thr Ala Asn Tyr Ala Gln Lys Phe Gln
1               5                   10                  15

Gly

<210> SEQ ID NO 20
<211> LENGTH: 17
<212> TYPE: PRT
<213> ORGANISM: Artificial sequence
<220> FEATURE:
<223> OTHER INFORMATION: OX40(CLC-563, CLC-564, 17A9) CDR-H2

<400> SEQUENCE: 20

Ala Ile Ser Gly Ser Gly Gly Ser Thr Tyr Tyr Ala Asp Ser Val Lys
1               5                   10                  15

Gly

<210> SEQ ID NO 21
<211> LENGTH: 7
<212> TYPE: PRT
<213> ORGANISM: Artificial sequence
<220> FEATURE:
<223> OTHER INFORMATION: OX40(8H9) CDR-H3

<400> SEQUENCE: 21

Glu Tyr Gly Trp Met Asp Tyr
1               5

<210> SEQ ID NO 22
<211> LENGTH: 9
<212> TYPE: PRT
<213> ORGANISM: Artificial sequence
<220> FEATURE:
<223> OTHER INFORMATION: OX40(49B4) CDR-H3

<400> SEQUENCE: 22

Glu Tyr Tyr Arg Gly Pro Tyr Asp Tyr
1               5

<210> SEQ ID NO 23
<211> LENGTH: 7
<212> TYPE: PRT
<213> ORGANISM: Artificial sequence
<220> FEATURE:
<223> OTHER INFORMATION: OX40(1G4) CDR-H3

<400> SEQUENCE: 23

Glu Tyr Gly Ser Met Asp Tyr
1               5
```

```
<210> SEQ ID NO 24
<211> LENGTH: 13
<212> TYPE: PRT
<213> ORGANISM: Artificial sequence
<220> FEATURE:
<223> OTHER INFORMATION: OX40(20B7)  CDR-H3

<400> SEQUENCE: 24

Val Asn Tyr Pro Tyr Ser Tyr Trp Gly Asp Phe Asp Tyr
1               5                   10

<210> SEQ ID NO 25
<211> LENGTH: 7
<212> TYPE: PRT
<213> ORGANISM: Artificial sequence
<220> FEATURE:
<223> OTHER INFORMATION: OX40(CLC-563)  CDR-H3

<400> SEQUENCE: 25

Asp Val Gly Ala Phe Asp Tyr
1               5

<210> SEQ ID NO 26
<211> LENGTH: 7
<212> TYPE: PRT
<213> ORGANISM: Artificial sequence
<220> FEATURE:
<223> OTHER INFORMATION: OX40(CLC-564)  CDR-H3

<400> SEQUENCE: 26

Asp Val Gly Pro Phe Asp Tyr
1               5

<210> SEQ ID NO 27
<211> LENGTH: 11
<212> TYPE: PRT
<213> ORGANISM: Artificial sequence
<220> FEATURE:
<223> OTHER INFORMATION: OX40(17A9)-CDR-H3

<400> SEQUENCE: 27

Val Phe Tyr Arg Gly Gly Val Ser Met Asp Tyr
1               5                   10

<210> SEQ ID NO 28
<211> LENGTH: 11
<212> TYPE: PRT
<213> ORGANISM: Artificial sequence
<220> FEATURE:
<223> OTHER INFORMATION: OX40(8H9,49B4,1G4, 20B7)  CDR-L1

<400> SEQUENCE: 28

Arg Ala Ser Gln Ser Ile Ser Ser Trp Leu Ala
1               5                   10

<210> SEQ ID NO 29
<211> LENGTH: 12
<212> TYPE: PRT
<213> ORGANISM: Artificial sequence
<220> FEATURE:
<223> OTHER INFORMATION: OX40(CLC-563, CLC564)  CDR-L1

<400> SEQUENCE: 29

Arg Ala Ser Gln Ser Val Ser Ser Ser Tyr Leu Ala
1               5                   10

<210> SEQ ID NO 30
```

```
<211> LENGTH: 11
<212> TYPE: PRT
<213> ORGANISM: Artificial sequence
<220> FEATURE:
<223> OTHER INFORMATION: OX40(17A9) CDR-L1

<400> SEQUENCE: 30

Gln Gly Asp Ser Leu Arg Ser Tyr Tyr Ala Ser
1               5                   10

<210> SEQ ID NO 31
<211> LENGTH: 7
<212> TYPE: PRT
<213> ORGANISM: Artificial sequence
<220> FEATURE:
<223> OTHER INFORMATION: OX40(8H9,49B4,1G4, 20B7)  CDR-L2

<400> SEQUENCE: 31

Asp Ala Ser Ser Leu Glu Ser
1               5

<210> SEQ ID NO 32
<211> LENGTH: 7
<212> TYPE: PRT
<213> ORGANISM: Artificial sequence
<220> FEATURE:
<223> OTHER INFORMATION: OX40(CLC-563, CLC564)  CDR-L2

<400> SEQUENCE: 32

Gly Ala Ser Ser Arg Ala Thr
1               5

<210> SEQ ID NO 33
<211> LENGTH: 7
<212> TYPE: PRT
<213> ORGANISM: Artificial sequence
<220> FEATURE:
<223> OTHER INFORMATION: OX40(17A9) CDR-L2

<400> SEQUENCE: 33

Gly Lys Asn Asn Arg Pro Ser
1               5

<210> SEQ ID NO 34
<211> LENGTH: 10
<212> TYPE: PRT
<213> ORGANISM: Artificial sequence
<220> FEATURE:
<223> OTHER INFORMATION: OX40(8H9) CDR-L3

<400> SEQUENCE: 34

Gln Gln Tyr Leu Thr Tyr Ser Arg Phe Thr
1               5                   10

<210> SEQ ID NO 35
<211> LENGTH: 9
<212> TYPE: PRT
<213> ORGANISM: Artificial sequence
<220> FEATURE:
<223> OTHER INFORMATION: OX40(49B4) CDR-L3

<400> SEQUENCE: 35

Gln Gln Tyr Ser Ser Gln Pro Tyr Thr
1               5

<210> SEQ ID NO 36
<211> LENGTH: 10
```

```
<212> TYPE: PRT
<213> ORGANISM: Artificial sequence
<220> FEATURE:
<223> OTHER INFORMATION: OX40(1G4) CDR-L3

<400> SEQUENCE: 36

Gln Gln Tyr Ile Ser Tyr Ser Met Leu Thr
1               5                   10

<210> SEQ ID NO 37
<211> LENGTH: 9
<212> TYPE: PRT
<213> ORGANISM: Artificial sequence
<220> FEATURE:
<223> OTHER INFORMATION: OX40(20B7) CDR-L3

<400> SEQUENCE: 37

Gln Gln Tyr Gln Ala Phe Ser Leu Thr
1               5

<210> SEQ ID NO 38
<211> LENGTH: 9
<212> TYPE: PRT
<213> ORGANISM: Artificial sequence
<220> FEATURE:
<223> OTHER INFORMATION: OX40(CLC-563, CLC-164) CDR-L3

<400> SEQUENCE: 38

Gln Gln Tyr Gly Ser Ser Pro Leu Thr
1               5

<210> SEQ ID NO 39
<211> LENGTH: 10
<212> TYPE: PRT
<213> ORGANISM: Artificial sequence
<220> FEATURE:
<223> OTHER INFORMATION: OX40(17A9) CDR-L3

<400> SEQUENCE: 39

Asn Ser Arg Val Met Pro His Asn Arg Val
1               5                   10

<210> SEQ ID NO 40
<211> LENGTH: 116
<212> TYPE: PRT
<213> ORGANISM: Artificial sequence
<220> FEATURE:
<223> OTHER INFORMATION: OX40(8H9) VH

<400> SEQUENCE: 40

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Gly Trp Met Asp Tyr Trp Gly Gln Gly Thr Thr Val
            100                 105                 110
```

Thr Val Ser Ser
         115

<210> SEQ ID NO 41
<211> LENGTH: 108
<212> TYPE: PRT
<213> ORGANISM: Artificial sequence
<220> FEATURE:
<223> OTHER INFORMATION: OX40(8H9) VL

<400> SEQUENCE: 41

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Leu Thr Tyr Ser Arg
                85                  90                  95

Phe Thr Phe Gly Gln Gly Thr Lys Val Glu Ile Lys
            100                 105

<210> SEQ ID NO 42
<211> LENGTH: 118
<212> TYPE: PRT
<213> ORGANISM: Artificial sequence
<220> FEATURE:
<223> OTHER INFORMATION: OX40(49B4) VH

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser
         115

<210> SEQ ID NO 43
<211> LENGTH: 107
<212> TYPE: PRT
<213> ORGANISM: Artificial sequence
<220> FEATURE:
<223> OTHER INFORMATION: OX40(49B4) VL

<400> SEQUENCE: 43

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Gln Pro Tyr
                85                  90                  95

Thr Phe Gly Gln Gly Thr Lys Val Glu Ile Lys
            100                 105

<210> SEQ ID NO 44
<211> LENGTH: 116
<212> TYPE: PRT
<213> ORGANISM: Artificial sequence
<220> FEATURE:
<223> OTHER INFORMATION: OX40(1G4) VH

<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Gly Ser Met Asp Tyr Trp Gly Gln Gly Thr Thr Val
            100                 105                 110

Thr Val Ser Ser
        115

<210> SEQ ID NO 45
<211> LENGTH: 108
<212> TYPE: PRT
<213> ORGANISM: Artificial sequence
<220> FEATURE:
<223> OTHER INFORMATION: OX40(1G4) VL

<400> SEQUENCE: 45

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ile Ser Tyr Ser Met
                85                  90                  95

Leu Thr Phe Gly Gln Gly Thr Lys Val Glu Ile Lys
            100                 105

<210> SEQ ID NO 46
<211> LENGTH: 122
<212> TYPE: PRT
<213> ORGANISM: Artificial sequence
<220> FEATURE:
<223> OTHER INFORMATION: OX40(20B7) VH

<400> SEQUENCE: 46

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Tyr Pro Tyr Ser Tyr Trp Gly Asp Phe Asp Tyr Trp
            100                 105                 110

Gly Gln Gly Thr Thr Val Thr Val Ser Ser
        115                 120

<210> SEQ ID NO 47
<211> LENGTH: 107
<212> TYPE: PRT
<213> ORGANISM: Artificial sequence
<220> FEATURE:
<223> OTHER INFORMATION: OX40(20B7) VL

<400> SEQUENCE: 47

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gln Ala Phe Ser Leu
                85                  90                  95

Thr Phe Gly Gln Gly Thr Lys Val Glu Ile Lys
            100                 105

<210> SEQ ID NO 48
<211> LENGTH: 116
<212> TYPE: PRT

<213> ORGANISM: Artificial sequence
<220> FEATURE:
<223> OTHER INFORMATION: OX40(CLC-563) VH

<400> SEQUENCE: 48

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Asp Val Gly Ala Phe Asp Tyr Trp Gly Gln Gly Ala Leu Val
            100                 105                 110

Thr Val Ser Ser
            115
```

<210> SEQ ID NO 49
<211> LENGTH: 108
<212> TYPE: PRT
<213> ORGANISM: Artificial sequence
<220> FEATURE:
<223> OTHER INFORMATION: OX40(CLC-563) VL

<400> SEQUENCE: 49

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys
            100                 105
```

<210> SEQ ID NO 50
<211> LENGTH: 116
<212> TYPE: PRT
<213> ORGANISM: Artificial sequence
<220> FEATURE:
<223> OTHER INFORMATION: OX40(CLC-564) VH

<400> SEQUENCE: 50

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Phe Asp Val Gly Pro Phe Asp Tyr Trp Gly Gln Gly Thr Leu Val
               100                 105                 110

Thr Val Ser Ser
        115

<210> SEQ ID NO 51
<211> LENGTH: 108
<212> TYPE: PRT
<213> ORGANISM: Artificial sequence
<220> FEATURE:
<223> OTHER INFORMATION: OX40(CLC-564)  VL

<400> SEQUENCE: 51

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys
               100                 105

<210> SEQ ID NO 52
<211> LENGTH: 120
<212> TYPE: PRT
<213> ORGANISM: Artificial sequence
<220> FEATURE:
<223> OTHER INFORMATION: OX40(17A9)  VH

<400> SEQUENCE: 52

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95
```

```
Ala Arg Val Phe Tyr Arg Gly Gly Val Ser Met Asp Tyr Trp Gly Gln
                100                 105                 110

Gly Thr Leu Val Thr Val Ser Ser
        115                 120

<210> SEQ ID NO 53
<211> LENGTH: 106
<212> TYPE: PRT
<213> ORGANISM: Artificial sequence
<220> FEATURE:
<223> OTHER INFORMATION: OX40(17A9)  VL

<400> SEQUENCE: 53

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Val Met Pro His Asn Arg
                85                  90                  95

Val Phe Gly Gly Gly Thr Lys Leu Thr Val
            100                 105

<210> SEQ ID NO 54
<211> LENGTH: 916
<212> TYPE: PRT
<213> ORGANISM: Artificial Sequence
<220> FEATURE:
<223> OTHER INFORMATION: first fusion polypeptide (Fc knob) CD134-0093

<400> SEQUENCE: 54

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
                100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160
```

```
Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Gly Gly Gly
    210                 215                 220

Gly Ser Gly Gly Gly Gly Ser Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Gly Ala Pro Ile Glu Lys Thr Ile Ser Lys Ala Lys Gly
            340                 345                 350

Gln Pro Arg Glu Pro Gln Val Tyr Thr Leu Pro Pro Cys Arg Asp Glu
        355                 360                 365

Leu Thr Lys Asn Gln Val Ser Leu Trp Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys Gly Gly Gly Gly Ser Gly
    450                 455                 460

Gly Gly Gly Ser Asp Ile Gln Met Thr Gln Ser Pro Ser Thr Leu Ser
465                 470                 475                 480

Ala Ser Val Gly Asp Arg Val Thr Ile Thr Cys Arg Ala Ser Gln Ser
                485                 490                 495

Ile Ser Ser Trp Leu Ala Trp Tyr Gln Gln Lys Pro Gly Lys Ala Pro
            500                 505                 510

Lys Leu Leu Ile Tyr Asp Ala Ser Ser Leu Glu Ser Gly Val Pro Ser
        515                 520                 525

Arg Phe Ser Gly Ser Gly Ser Gly Thr Glu Phe Thr Leu Thr Ile Ser
    530                 535                 540

Ser Leu Gln Pro Asp Asp Phe Ala Thr Tyr Tyr Cys Gln Gln Tyr Ser
545                 550                 555                 560

Ser Gln Pro Tyr Thr Phe Gly Gln Gly Thr Lys Val Glu Ile Lys Arg
                565                 570                 575
```

```
Thr Val Ala Ala Pro Ser Val Phe Ile Phe Pro Ser Asp Glu Gln
                580                 585                 590

Leu Lys Ser Gly Thr Ala Ser Val Val Cys Leu Leu Asn Asn Phe Tyr
        595                 600                 605

Pro Arg Glu Ala Lys Val Gln Trp Lys Val Asp Asn Ala Leu Gln Ser
610                 615                 620

Gly Asn Ser Gln Glu Ser Val Thr Glu Gln Asp Ser Lys Asp Ser Thr
625                 630                 635                 640

Tyr Ser Leu Ser Ser Thr Leu Thr Leu Ser Lys Ala Asp Tyr Glu Lys
                645                 650                 655

His Lys Val Tyr Ala Cys Glu Val Thr His Gln Gly Leu Ser Ser Pro
            660                 665                 670

Val Thr Lys Ser Phe Asn Arg Gly Glu Cys Gly Gly Gly Ser Gly
        675                 680                 685

Gly Gly Gly Ser Glu Val Gln Leu Leu Glu Ser Gly Gly Gly Leu Val
        690                 695                 700

Gln Pro Gly Gly Ser Leu Arg Leu Ser Cys Ala Ala Ser Gly Phe Thr
705                 710                 715                 720

Phe Ser Ser Tyr Ala Met Ser Trp Val Arg Gln Ala Pro Gly Lys Gly
                725                 730                 735

Leu Glu Trp Val Ser Ala Ile Ile Gly Ser Gly Ala Ser Thr Tyr Tyr
            740                 745                 750

Ala Asp Ser Val Lys Gly Arg Phe Thr Ile Ser Arg Asp Asn Ser Lys
        755                 760                 765

Asn Thr Leu Tyr Leu Gln Met Asn Ser Leu Arg Ala Glu Asp Thr Ala
770                 775                 780

Val Tyr Tyr Cys Ala Lys Gly Trp Phe Gly Gly Phe Asn Tyr Trp Gly
785                 790                 795                 800

Gln Gly Thr Leu Val Thr Val Ser Ser Ala Ser Val Ala Ala Pro Ser
                805                 810                 815

Val Phe Ile Phe Pro Pro Ser Asp Glu Gln Leu Lys Ser Gly Thr Ala
            820                 825                 830

Ser Val Val Cys Leu Leu Asn Asn Phe Tyr Pro Arg Glu Ala Lys Val
        835                 840                 845

Gln Trp Lys Val Asp Asn Ala Leu Gln Ser Gly Asn Ser Gln Glu Ser
850                 855                 860

Val Thr Glu Gln Asp Ser Lys Asp Ser Thr Tyr Ser Leu Ser Ser Thr
865                 870                 875                 880

Leu Thr Leu Ser Lys Ala Asp Tyr Glu Lys His Lys Val Tyr Ala Cys
                885                 890                 895

Glu Val Thr His Gln Gly Leu Ser Ser Pro Val Thr Lys Ser Phe Asn
            900                 905                 910

Arg Gly Glu Cys
        915

<210> SEQ ID NO 55
<211> LENGTH: 905
<212> TYPE: PRT
<213> ORGANISM: Artificial Sequence
<220> FEATURE:
<223> OTHER INFORMATION: second fusion polypeptide (Fc hole) CD134-0093

<400> SEQUENCE: 55

Gln Val Gln Leu Val Gln Ser Gly Ala Glu Val Lys Lys Pro Gly Ser
1               5                   10                  15
```

```
Ser Val Lys Val Ser Cys Lys Ala Ser Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Gly Gly Gly
    210                 215                 220

Gly Ser Gly Gly Gly Gly Ser Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Gly Ala Pro Ile Glu Lys Thr Ile Ser Lys Ala Lys Gly
            340                 345                 350

Gln Pro Arg Glu Pro Gln Val Cys Thr Leu Pro Pro Ser Arg Asp Glu
        355                 360                 365

Leu Thr Lys Asn Gln Val Ser Leu Ser Cys Ala Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
            420                 425                 430
```

```
Val Phe Ser Cys Ser Val Met His Glu Ala Leu His Asn His Tyr Thr
            435                 440                 445
Gln Lys Ser Leu Ser Leu Ser Pro Gly Lys Gly Gly Gly Gly Ser Gly
        450                 455                 460
Gly Gly Gly Ser Asp Ile Gln Met Thr Gln Ser Pro Ser Thr Leu Ser
465                 470                 475                 480
Ala Ser Val Gly Asp Arg Val Thr Ile Thr Cys Arg Ala Ser Gln Ser
                485                 490                 495
Ile Ser Ser Trp Leu Ala Trp Tyr Gln Gln Lys Pro Gly Lys Ala Pro
            500                 505                 510
Lys Leu Leu Ile Tyr Asp Ala Ser Ser Leu Glu Ser Gly Val Pro Ser
        515                 520                 525
Arg Phe Ser Gly Ser Gly Ser Gly Thr Glu Phe Thr Leu Thr Ile Ser
    530                 535                 540
Ser Leu Gln Pro Asp Asp Phe Ala Thr Tyr Tyr Cys Gln Gln Tyr Ser
545                 550                 555                 560
Ser Gln Pro Tyr Thr Phe Gly Gln Gly Thr Lys Val Glu Ile Lys Arg
                565                 570                 575
Thr Val Ala Ala Pro Ser Val Phe Ile Phe Pro Pro Ser Asp Glu Gln
            580                 585                 590
Leu Lys Ser Gly Thr Ala Ser Val Val Cys Leu Leu Asn Asn Phe Tyr
        595                 600                 605
Pro Arg Glu Ala Lys Val Gln Trp Lys Val Asp Asn Ala Leu Gln Ser
    610                 615                 620
Gly Asn Ser Gln Glu Ser Val Thr Glu Gln Asp Ser Lys Asp Ser Thr
625                 630                 635                 640
Tyr Ser Leu Ser Ser Thr Leu Thr Leu Ser Lys Ala Asp Tyr Glu Lys
                645                 650                 655
His Lys Val Tyr Ala Cys Glu Val Thr His Gln Gly Leu Ser Ser Pro
            660                 665                 670
Val Thr Lys Ser Phe Asn Arg Gly Glu Cys Gly Gly Gly Gly Ser Gly
        675                 680                 685
Gly Gly Gly Ser Glu Ile Val Leu Thr Gln Ser Pro Gly Thr Leu Ser
    690                 695                 700
Leu Ser Pro Gly Glu Arg Ala Thr Leu Ser Cys Arg Ala Ser Gln Ser
705                 710                 715                 720
Val Thr Ser Ser Tyr Leu Ala Trp Tyr Gln Gln Lys Pro Gly Gln Ala
                725                 730                 735
Pro Arg Leu Leu Ile Asn Val Gly Ser Arg Arg Ala Thr Gly Ile Pro
            740                 745                 750
Asp Arg Phe Ser Gly Ser Gly Ser Gly Thr Asp Phe Thr Leu Thr Ile
        755                 760                 765
Ser Arg Leu Glu Pro Glu Asp Phe Ala Val Tyr Tyr Cys Gln Gln Gly
    770                 775                 780
Ile Met Leu Pro Pro Thr Phe Gly Gln Gly Thr Lys Val Glu Ile Lys
785                 790                 795                 800
Ser Ser Ala Ser Thr Lys Gly Pro Ser Val Phe Pro Leu Ala Pro Ser
                805                 810                 815
Ser Lys Ser Thr Ser Gly Gly Thr Ala Ala Leu Gly Cys Leu Val Lys
            820                 825                 830
Asp Tyr Phe Pro Glu Pro Val Thr Val Ser Trp Asn Ser Gly Ala Leu
        835                 840                 845
```

```
Thr Ser Gly Val His Thr Phe Pro Ala Val Leu Gln Ser Ser Gly Leu
    850                 855                 860

Tyr Ser Leu Ser Ser Val Val Thr Val Pro Ser Ser Ser Leu Gly Thr
865                 870                 875                 880

Gln Thr Tyr Ile Cys Asn Val Asn His Lys Pro Ser Asn Thr Lys Val
                885                 890                 895

Asp Lys Lys Val Glu Pro Lys Ser Cys
            900                 905

<210> SEQ ID NO 56
<211> LENGTH: 910
<212> TYPE: PRT
<213> ORGANISM: Artificial Sequence
<220> FEATURE:
<223> OTHER INFORMATION: first fusion polypeptide (Fc knob) CD134-0094

<400> SEQUENCE: 56

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Val Ala Ala Pro Ser Val Phe Ile
        115                 120                 125

Phe Pro Pro Ser Asp Glu Gln Leu Lys Ser Gly Thr Ala Ser Val Val
    130                 135                 140

Cys Leu Leu Asn Asn Phe Tyr Pro Arg Glu Ala Lys Val Gln Trp Lys
145                 150                 155                 160

Val Asp Asn Ala Leu Gln Ser Gly Asn Ser Gln Glu Ser Val Thr Glu
                165                 170                 175

Gln Asp Ser Lys Asp Ser Thr Tyr Ser Leu Ser Ser Thr Leu Thr Leu
            180                 185                 190

Ser Lys Ala Asp Tyr Glu Lys His Lys Val Tyr Ala Cys Glu Val Thr
        195                 200                 205

His Gln Gly Leu Ser Ser Pro Val Thr Lys Ser Phe Asn Arg Gly Glu
    210                 215                 220

Cys Asp Gly Gly Gly Gly Ser Gly Gly Gly Gly Ser Asp Lys Thr His
225                 230                 235                 240

Thr Cys Pro Pro Cys Pro Ala Pro Glu Ala Ala Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300
```

```
Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
            325                 330                 335

Cys Lys Val Ser Asn Lys Ala Leu Gly Ala Pro Ile Glu Lys Thr Ile
                340                 345                 350

Ser Lys Ala Lys Gly Gln Pro Arg Glu Pro Gln Val Tyr Thr Leu Pro
            355                 360                 365

Pro Cys Arg Asp Glu Leu Thr Lys Asn Gln Val Ser Leu Trp Cys Leu
        370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
                420                 425                 430

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro Gly Lys Gly
        450                 455                 460

Gly Gly Gly Ser Gly Gly Gly Ser Asp Ile Gln Met Thr Gln Ser
465                 470                 475                 480

Pro Ser Thr Leu Ser Ala Ser Val Gly Asp Arg Val Thr Ile Thr Cys
                485                 490                 495

Arg Ala Ser Gln Ser Ile Ser Ser Trp Leu Ala Trp Tyr Gln Gln Lys
            500                 505                 510

Pro Gly Lys Ala Pro Lys Leu Leu Ile Tyr Asp Ala Ser Ser Leu Glu
        515                 520                 525

Ser Gly Val Pro Ser Arg Phe Ser Gly Ser Gly Ser Gly Thr Glu Phe
        530                 535                 540

Thr Leu Thr Ile Ser Ser Leu Gln Pro Asp Asp Phe Ala Thr Tyr Tyr
545                 550                 555                 560

Cys Gln Gln Tyr Ser Ser Gln Pro Tyr Thr Phe Gly Gln Gly Thr Lys
                565                 570                 575

Val Glu Ile Lys Ser Ser Ala Ser Thr Lys Gly Pro Ser Val Phe Pro
            580                 585                 590

Leu Ala Pro Ser Ser Lys Ser Thr Ser Gly Gly Thr Ala Ala Leu Gly
        595                 600                 605

Cys Leu Val Lys Asp Tyr Phe Pro Glu Pro Val Thr Val Ser Trp Asn
610                 615                 620

Ser Gly Ala Leu Thr Ser Gly Val His Thr Phe Pro Ala Val Leu Gln
625                 630                 635                 640

Ser Ser Gly Leu Tyr Ser Leu Ser Ser Val Val Thr Val Pro Ser Ser
                645                 650                 655

Ser Leu Gly Thr Gln Thr Tyr Ile Cys Asn Val Asn His Lys Pro Ser
            660                 665                 670

Asn Thr Lys Val Asp Lys Lys Val Glu Pro Lys Ser Cys Gly Gly Gly
        675                 680                 685

Gly Ser Gly Gly Gly Gly Ser Glu Ile Val Leu Thr Gln Ser Pro Gly
        690                 695                 700

Thr Leu Ser Leu Ser Pro Gly Glu Arg Ala Thr Leu Ser Cys Arg Ala
705                 710                 715                 720
```

Ser Gln Ser Val Thr Ser Ser Tyr Leu Ala Trp Tyr Gln Gln Lys Pro
            725                 730                 735

Gly Gln Ala Pro Arg Leu Leu Ile Asn Val Gly Ser Arg Arg Ala Thr
            740                 745                 750

Gly Ile Pro Asp Arg Phe Ser Gly Ser Gly Ser Gly Thr Asp Phe Thr
            755                 760                 765

Leu Thr Ile Ser Arg Leu Glu Pro Glu Asp Phe Ala Val Tyr Tyr Cys
            770                 775                 780

Gln Gln Gly Ile Met Leu Pro Pro Thr Phe Gly Gln Gly Thr Lys Val
785                 790                 795                 800

Glu Ile Lys Arg Thr Val Ala Ala Pro Ser Val Phe Ile Phe Pro Pro
            805                 810                 815

Ser Asp Glu Gln Leu Lys Ser Gly Thr Ala Ser Val Val Cys Leu Leu
            820                 825                 830

Asn Asn Phe Tyr Pro Arg Glu Ala Lys Val Gln Trp Lys Val Asp Asn
            835                 840                 845

Ala Leu Gln Ser Gly Asn Ser Gln Glu Ser Val Thr Glu Gln Asp Ser
            850                 855                 860

Lys Asp Ser Thr Tyr Ser Leu Ser Ser Thr Leu Thr Leu Ser Lys Ala
865                 870                 875                 880

Asp Tyr Glu Lys His Lys Val Tyr Ala Cys Glu Val Thr His Gln Gly
            885                 890                 895

Leu Ser Ser Pro Val Thr Lys Ser Phe Asn Arg Gly Glu Cys
            900                 905                 910

<210> SEQ ID NO 57
<211> LENGTH: 915
<212> TYPE: PRT
<213> ORGANISM: Artificial Sequence
<220> FEATURE:
<223> OTHER INFORMATION: second fusion polypeptide (Fc hole) CD134-0094

<400> SEQUENCE: 57

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Val Ala Ala Pro Ser Val Phe Ile
            115                 120                 125

Phe Pro Pro Ser Asp Glu Gln Leu Lys Ser Gly Thr Ala Ser Val Val
            130                 135                 140

Cys Leu Leu Asn Asn Phe Tyr Pro Arg Glu Ala Lys Val Gln Trp Lys
145                 150                 155                 160

Val Asp Asn Ala Leu Gln Ser Gly Asn Ser Gln Glu Ser Val Thr Glu
            165                 170                 175

-continued

```
Gln Asp Ser Lys Asp Ser Thr Tyr Ser Leu Ser Ser Thr Leu Thr Leu
            180                 185                 190

Ser Lys Ala Asp Tyr Glu Lys His Lys Val Tyr Ala Cys Glu Val Thr
        195                 200                 205

His Gln Gly Leu Ser Ser Pro Val Thr Lys Ser Phe Asn Arg Gly Glu
210                 215                 220

Cys Asp Gly Gly Gly Gly Ser Gly Gly Gly Ser Asp Lys Thr His
225                 230                 235                 240

Thr Cys Pro Pro Cys Pro Ala Pro Glu Ala Ala Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Gly Ala Pro Ile Glu Lys Thr Ile
            340                 345                 350

Ser Lys Ala Lys Gly Gln Pro Arg Glu Pro Gln Val Cys Thr Leu Pro
        355                 360                 365

Pro Ser Arg Asp Glu Leu Thr Lys Asn Gln Val Ser Leu Ser Cys Ala
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys Gly
    450                 455                 460

Gly Gly Gly Ser Gly Gly Gly Gly Ser Asp Ile Gln Met Thr Gln Ser
465                 470                 475                 480

Pro Ser Thr Leu Ser Ala Ser Val Gly Asp Arg Val Thr Ile Thr Cys
                485                 490                 495

Arg Ala Ser Gln Ser Ile Ser Ser Trp Leu Ala Trp Tyr Gln Gln Lys
            500                 505                 510

Pro Gly Lys Ala Pro Lys Leu Leu Ile Tyr Asp Ala Ser Ser Leu Glu
        515                 520                 525

Ser Gly Val Pro Ser Arg Phe Ser Gly Ser Gly Ser Gly Thr Glu Phe
    530                 535                 540

Thr Leu Thr Ile Ser Ser Leu Gln Pro Asp Asp Phe Ala Thr Tyr Tyr
545                 550                 555                 560

Cys Gln Gln Tyr Ser Ser Gln Pro Tyr Thr Phe Gly Gln Gly Thr Lys
                565                 570                 575

Val Glu Ile Lys Ser Ser Ala Ser Thr Lys Gly Pro Ser Val Phe Pro
            580                 585                 590
```

```
Leu Ala Pro Ser Ser Lys Ser Thr Ser Gly Gly Thr Ala Ala Leu Gly
            595                 600                 605

Cys Leu Val Lys Asp Tyr Phe Pro Glu Pro Val Thr Val Ser Trp Asn
610                 615                 620

Ser Gly Ala Leu Thr Ser Gly Val His Thr Phe Pro Ala Val Leu Gln
625                 630                 635                 640

Ser Ser Gly Leu Tyr Ser Leu Ser Ser Val Val Thr Val Pro Ser Ser
            645                 650                 655

Ser Leu Gly Thr Gln Thr Tyr Ile Cys Asn Val Asn His Lys Pro Ser
            660                 665                 670

Asn Thr Lys Val Asp Lys Lys Val Glu Pro Lys Ser Cys Gly Gly Gly
            675                 680                 685

Gly Ser Gly Gly Gly Gly Ser Glu Val Gln Leu Leu Glu Ser Gly Gly
690                 695                 700

Gly Leu Val Gln Pro Gly Gly Ser Leu Arg Leu Ser Cys Ala Ala Ser
705                 710                 715                 720

Gly Phe Thr Phe Ser Ser Tyr Ala Met Ser Trp Val Arg Gln Ala Pro
            725                 730                 735

Gly Lys Gly Leu Glu Trp Val Ser Ala Ile Ile Gly Ser Gly Ala Ser
            740                 745                 750

Thr Tyr Tyr Ala Asp Ser Val Lys Gly Arg Phe Thr Ile Ser Arg Asp
            755                 760                 765

Asn Ser Lys Asn Thr Leu Tyr Leu Gln Met Asn Ser Leu Arg Ala Glu
            770                 775                 780

Asp Thr Ala Val Tyr Tyr Cys Ala Lys Gly Trp Phe Gly Gly Phe Asn
785                 790                 795                 800

Tyr Trp Gly Gln Gly Thr Leu Val Thr Val Ser Ser Ala Ser Thr Lys
            805                 810                 815

Gly Pro Ser Val Phe Pro Leu Ala Pro Ser Ser Lys Ser Thr Ser Gly
            820                 825                 830

Gly Thr Ala Ala Leu Gly Cys Leu Val Lys Asp Tyr Phe Pro Glu Pro
            835                 840                 845

Val Thr Val Ser Trp Asn Ser Gly Ala Leu Thr Ser Gly Val His Thr
850                 855                 860

Phe Pro Ala Val Leu Gln Ser Ser Gly Leu Tyr Ser Leu Ser Ser Val
865                 870                 875                 880

Val Thr Val Pro Ser Ser Ser Leu Gly Thr Gln Thr Tyr Ile Cys Asn
            885                 890                 895

Val Asn His Lys Pro Ser Asn Thr Lys Val Asp Lys Lys Val Glu Pro
            900                 905                 910

Lys Ser Cys
        915

<210> SEQ ID NO 58
<211> LENGTH: 924
<212> TYPE: PRT
<213> ORGANISM: Artificial Sequence
<220> FEATURE:
<223> OTHER INFORMATION: first fusion polypeptide (Fc knob) P1AE0085

<400> SEQUENCE: 58

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30
```

```
Ala Ile Ser Trp Val Arg Gln Ala Pro Gly Gln Gly Leu Glu Trp Met
         35                  40                  45
Gly Gly Ile Ile Pro Ile Phe Gly Thr Ala Asn Tyr Ala Gln Lys Phe
 50                  55                  60
Gln Gly Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Glu Tyr Tyr Arg Gly Pro Tyr Asp Tyr Trp Gly Gln Gly Thr
                100                 105                 110
Thr Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Gly Gly Gly
    210                 215                 220
Gly Ser Gly Gly Gly Gly Ser Asp Lys Thr His Thr Cys Pro Pro Cys
225                 230                 235                 240
Pro Ala Pro Glu Ala Ala Gly Gly Pro Ser Val Phe Leu Phe Pro Pro
                245                 250                 255
Lys Pro Lys Asp Thr Leu Met Ile Ser Arg Thr Pro Glu Val Thr Cys
            260                 265                 270
Val Val Val Asp Val Ser His Glu Asp Pro Glu Val Lys Phe Asn Trp
        275                 280                 285
Tyr Val Asp Gly Val Glu Val His Asn Ala Lys Thr Lys Pro Arg Glu
    290                 295                 300
Glu Gln Tyr Asn Ser Thr Tyr Arg Val Val Ser Val Leu Thr Val Leu
305                 310                 315                 320
His Gln Asp Trp Leu Asn Gly Lys Glu Tyr Lys Cys Lys Val Ser Asn
                325                 330                 335
Lys Ala Leu Gly Ala Pro Ile Glu Lys Thr Ile Ser Lys Ala Lys Gly
            340                 345                 350
Gln Pro Arg Glu Pro Gln Val Tyr Thr Leu Pro Pro Cys Arg Asp Glu
        355                 360                 365
Leu Thr Lys Asn Gln Val Ser Leu Trp Cys Leu Val Lys Gly Phe Tyr
    370                 375                 380
Pro Ser Asp Ile Ala Val Glu Trp Glu Ser Asn Gly Gln Pro Glu Asn
385                 390                 395                 400
Asn Tyr Lys Thr Thr Pro Pro Val Leu Asp Ser Asp Gly Ser Phe Phe
                405                 410                 415
Leu Tyr Ser Lys Leu Thr Val Asp Lys Ser Arg Trp Gln Gln Gly Asn
            420                 425                 430
Val Phe Ser Cys Ser Val Met His Glu Ala Leu His Asn His Tyr Thr
        435                 440                 445
```

-continued

```
Gln Lys Ser Leu Ser Leu Ser Pro Gly Lys Gly Gly Gly Ser Gly
    450                 455                 460
Gly Gly Gly Ser Asp Ile Gln Met Thr Gln Ser Pro Ser Thr Leu Ser
465                 470                 475                 480
Ala Ser Val Gly Asp Arg Val Thr Ile Thr Cys Arg Ala Ser Gln Ser
                485                 490                 495
Ile Ser Ser Trp Leu Ala Trp Tyr Gln Gln Lys Pro Gly Lys Ala Pro
            500                 505                 510
Lys Leu Leu Ile Tyr Asp Ala Ser Ser Leu Glu Ser Gly Val Pro Ser
        515                 520                 525
Arg Phe Ser Gly Ser Gly Ser Gly Thr Glu Phe Thr Leu Thr Ile Ser
    530                 535                 540
Ser Leu Gln Pro Asp Asp Phe Ala Thr Tyr Tyr Cys Gln Gln Tyr Ser
545                 550                 555                 560
Ser Gln Pro Tyr Thr Phe Gly Gln Gly Thr Lys Val Glu Ile Lys Arg
                565                 570                 575
Thr Val Ala Ala Pro Ser Val Phe Ile Phe Pro Pro Ser Asp Glu Gln
            580                 585                 590
Leu Lys Ser Gly Thr Ala Ser Val Val Cys Leu Leu Asn Asn Phe Tyr
        595                 600                 605
Pro Arg Glu Ala Lys Val Gln Trp Lys Val Asp Asn Ala Leu Gln Ser
    610                 615                 620
Gly Asn Ser Gln Glu Ser Val Thr Glu Gln Asp Ser Lys Asp Ser Thr
625                 630                 635                 640
Tyr Ser Leu Ser Ser Thr Leu Thr Leu Ser Lys Ala Asp Tyr Glu Lys
                645                 650                 655
His Lys Val Tyr Ala Cys Glu Val Thr His Gln Gly Leu Ser Ser Pro
            660                 665                 670
Val Thr Lys Ser Phe Asn Arg Gly Glu Cys Gly Gly Gly Gly Ser Gly
        675                 680                 685
Gly Gly Gly Ser Gly Gly Ser Gly Gly Gly Gly Ser Glu Val Gln
    690                 695                 700
Leu Leu Glu Ser Gly Gly Gly Leu Val Gln Pro Gly Gly Ser Leu Arg
705                 710                 715                 720
Leu Ser Cys Ala Ala Ser Gly Phe Thr Phe Ser Ser His Ala Met Ser
                725                 730                 735
Trp Val Arg Gln Ala Pro Gly Lys Gly Leu Glu Trp Val Ser Ala Ile
            740                 745                 750
Trp Ala Ser Gly Glu Gln Tyr Tyr Ala Asp Ser Val Lys Gly Arg Phe
        755                 760                 765
Thr Ile Ser Arg Asp Asn Ser Lys Asn Thr Leu Tyr Leu Gln Met Asn
    770                 775                 780
Ser Leu Arg Ala Glu Asp Thr Ala Val Tyr Tyr Cys Ala Lys Gly Trp
785                 790                 795                 800
Leu Gly Asn Phe Asp Tyr Trp Gly Gln Gly Thr Leu Val Thr Val Ser
                805                 810                 815
Ser Ala Ser Val Ala Ala Pro Ser Val Phe Ile Phe Pro Pro Ser Asp
            820                 825                 830
Glu Gln Leu Lys Ser Gly Thr Ala Ser Val Val Cys Leu Leu Asn Asn
        835                 840                 845
Phe Tyr Pro Arg Glu Ala Lys Val Gln Trp Lys Val Asp Asn Ala Leu
    850                 855                 860
```

Gln Ser Gly Asn Ser Gln Glu Ser Val Thr Glu Gln Asp Ser Lys Asp
865                 870                 875                 880

Ser Thr Tyr Ser Leu Ser Ser Thr Leu Thr Leu Ser Lys Ala Asp Tyr
            885                 890                 895

Glu Lys His Lys Val Tyr Ala Cys Glu Val Thr His Gln Gly Leu Ser
        900                 905                 910

Ser Pro Val Thr Lys Ser Phe Asn Arg Gly Glu Cys
        915                 920

<210> SEQ ID NO 59
<211> LENGTH: 914
<212> TYPE: PRT
<213> ORGANISM: Artificial Sequence
<220> FEATURE:
<223> OTHER INFORMATION: second fusion polypeptide (Fc hole) P1AE0085

<400> SEQUENCE: 59

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Gly Gly Gly
    210                 215                 220

Gly Ser Gly Gly Gly Gly Ser Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

-continued

```
Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
            325                 330                 335

Lys Ala Leu Gly Ala Pro Ile Glu Lys Thr Ile Ser Lys Ala Lys Gly
        340                 345                 350

Gln Pro Arg Glu Pro Gln Val Cys Thr Leu Pro Pro Ser Arg Asp Glu
    355                 360                 365

Leu Thr Lys Asn Gln Val Ser Leu Ser Cys Ala Val Lys Gly Phe Tyr
370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415

Leu Val Ser Lys Leu Thr Val Asp Lys Ser Arg Trp Gln Gln Gly Asn
        420                 425                 430

Val Phe Ser Cys Ser Val Met His Glu Ala Leu His Asn His Tyr Thr
    435                 440                 445

Gln Lys Ser Leu Ser Leu Ser Pro Gly Lys Gly Gly Gly Ser Gly
450                 455                 460

Gly Gly Gly Ser Asp Ile Gln Met Thr Gln Ser Pro Ser Thr Leu Ser
465                 470                 475                 480

Ala Ser Val Gly Asp Arg Val Thr Ile Thr Cys Arg Ala Ser Gln Ser
            485                 490                 495

Ile Ser Ser Trp Leu Ala Trp Tyr Gln Gln Lys Pro Gly Lys Ala Pro
        500                 505                 510

Lys Leu Leu Ile Tyr Asp Ala Ser Ser Leu Glu Ser Gly Val Pro Ser
    515                 520                 525

Arg Phe Ser Gly Ser Gly Ser Gly Thr Glu Phe Thr Leu Thr Ile Ser
530                 535                 540

Ser Leu Gln Pro Asp Asp Phe Ala Thr Tyr Tyr Cys Gln Gln Tyr Ser
545                 550                 555                 560

Ser Gln Pro Tyr Thr Phe Gly Gln Gly Thr Lys Val Glu Ile Lys Arg
            565                 570                 575

Thr Val Ala Ala Pro Ser Val Phe Ile Phe Pro Pro Ser Asp Glu Gln
        580                 585                 590

Leu Lys Ser Gly Thr Ala Ser Val Val Cys Leu Leu Asn Asn Phe Tyr
    595                 600                 605

Pro Arg Glu Ala Lys Val Gln Trp Lys Val Asp Asn Ala Leu Gln Ser
610                 615                 620

Gly Asn Ser Gln Glu Ser Val Thr Glu Gln Asp Ser Lys Asp Ser Thr
625                 630                 635                 640

Tyr Ser Leu Ser Ser Thr Leu Thr Leu Ser Lys Ala Asp Tyr Glu Lys
            645                 650                 655

His Lys Val Tyr Ala Cys Glu Val Thr His Gln Gly Leu Ser Ser Pro
        660                 665                 670

Val Thr Lys Ser Phe Asn Arg Gly Glu Cys Gly Gly Gly Gly Ser Gly
    675                 680                 685

Gly Gly Ser Gly Gly Gly Ser Gly Gly Gly Ser Glu Ile Val
690                 695                 700

Leu Thr Gln Ser Pro Gly Thr Leu Ser Leu Ser Pro Gly Glu Arg Ala
705                 710                 715                 720
```

-continued

```
Thr Leu Ser Cys Arg Ala Ser Gln Ser Val Ser Arg Ser Tyr Leu Ala
            725                 730                 735

Trp Tyr Gln Gln Lys Pro Gly Gln Ala Pro Arg Leu Leu Ile Ile Gly
        740                 745                 750

Ala Ser Thr Arg Ala Thr Gly Ile Pro Asp Arg Phe Ser Gly Ser Gly
        755                 760                 765

Ser Gly Thr Asp Phe Thr Leu Thr Ile Ser Arg Leu Glu Pro Glu Asp
        770                 775                 780

Phe Ala Val Tyr Tyr Cys Gln Gln Gly Gln Val Ile Pro Pro Thr Phe
785                 790                 795                 800

Gly Gln Gly Thr Lys Val Glu Ile Lys Ser Ser Ala Ser Thr Lys Gly
            805                 810                 815

Pro Ser Val Phe Pro Leu Ala Pro Ser Ser Lys Ser Thr Ser Gly Gly
            820                 825                 830

Thr Ala Ala Leu Gly Cys Leu Val Lys Asp Tyr Phe Pro Glu Pro Val
            835                 840                 845

Thr Val Ser Trp Asn Ser Gly Ala Leu Thr Ser Gly Val His Thr Phe
            850                 855                 860

Pro Ala Val Leu Gln Ser Ser Gly Leu Tyr Ser Leu Ser Ser Val Val
865                 870                 875                 880

Thr Val Pro Ser Ser Leu Gly Thr Gln Thr Tyr Ile Cys Asn Val
            885                 890                 895

Asn His Lys Pro Ser Asn Thr Lys Val Asp Lys Lys Val Glu Pro Lys
            900                 905                 910

Ser Cys

<210> SEQ ID NO 60
<211> LENGTH: 925
<212> TYPE: PRT
<213> ORGANISM: Artificial Sequence
<220> FEATURE:
<223> OTHER INFORMATION: first fusion polypeptide (Fc knob) P1AE0086

<400> SEQUENCE: 60

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160
```

```
Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Gly Gly Gly
            210                 215                 220

Gly Ser Gly Gly Gly Ser Asp Lys Thr His Thr Cys Pro Pro Cys
225                 230                 235                 240

Pro Ala Pro Glu Ala Ala Gly Gly Pro Ser Val Phe Leu Phe Pro Pro
            245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
            275                 280                 285

Tyr Val Asp Gly Val Glu Val His Asn Ala Lys Thr Lys Pro Arg Glu
            290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
            325                 330                 335

Lys Ala Leu Gly Ala Pro Ile Glu Lys Thr Ile Ser Lys Ala Lys Gly
            340                 345                 350

Gln Pro Arg Glu Pro Gln Val Tyr Thr Leu Pro Pro Cys Arg Asp Glu
            355                 360                 365

Leu Thr Lys Asn Gln Val Ser Leu Trp Cys Leu Val Lys Gly Phe Tyr
            370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
            435                 440                 445

Gln Lys Ser Leu Ser Leu Ser Pro Gly Lys Gly Gly Gly Gly Ser Gly
            450                 455                 460

Gly Gly Gly Ser Asp Ile Gln Met Thr Gln Ser Pro Ser Thr Leu Ser
465                 470                 475                 480

Ala Ser Val Gly Asp Arg Val Thr Ile Thr Cys Arg Ala Ser Gln Ser
            485                 490                 495

Ile Ser Ser Trp Leu Ala Trp Tyr Gln Gln Lys Pro Gly Lys Ala Pro
            500                 505                 510

Lys Leu Leu Ile Tyr Asp Ala Ser Ser Leu Glu Ser Gly Val Pro Ser
            515                 520                 525

Arg Phe Ser Gly Ser Gly Ser Gly Thr Glu Phe Thr Leu Thr Ile Ser
            530                 535                 540

Ser Leu Gln Pro Asp Asp Phe Ala Thr Tyr Tyr Cys Gln Gln Tyr Ser
545                 550                 555                 560

Ser Gln Pro Tyr Thr Phe Gly Gln Gly Thr Lys Val Glu Ile Lys Arg
            565                 570                 575
```

Thr Val Ala Ala Pro Ser Val Phe Ile Phe Pro Ser Asp Glu Gln
            580                 585                 590

Leu Lys Ser Gly Thr Ala Ser Val Val Cys Leu Leu Asn Asn Phe Tyr
        595                 600                 605

Pro Arg Glu Ala Lys Val Gln Trp Lys Val Asp Asn Ala Leu Gln Ser
    610                 615                 620

Gly Asn Ser Gln Glu Ser Val Thr Glu Gln Asp Ser Lys Asp Ser Thr
625                 630                 635                 640

Tyr Ser Leu Ser Ser Thr Leu Thr Leu Ser Lys Ala Asp Tyr Glu Lys
                645                 650                 655

His Lys Val Tyr Ala Cys Glu Val Thr His Gln Gly Leu Ser Ser Pro
            660                 665                 670

Val Thr Lys Ser Phe Asn Arg Gly Glu Cys Gly Gly Gly Gly Ser Gly
        675                 680                 685

Gly Gly Ser Gly Gly Gly Ser Gly Gly Gly Ser Glu Val Gln
    690                 695                 700

Leu Leu Glu Ser Gly Gly Gly Leu Val Gln Pro Gly Gly Ser Leu Arg
705                 710                 715                 720

Leu Ser Cys Ala Ala Ser Gly Phe Thr Phe Ser Ser Tyr Ala Met Ser
                725                 730                 735

Trp Val Arg Gln Ala Pro Gly Lys Gly Leu Glu Trp Val Ser Ala Ile
            740                 745                 750

Ile Gly Ser Gly Ala Ser Thr Tyr Tyr Ala Asp Ser Val Lys Gly Arg
        755                 760                 765

Phe Thr Ile Ser Arg Asp Asn Ser Lys Asn Thr Leu Tyr Leu Gln Met
    770                 775                 780

Asn Ser Leu Arg Ala Glu Asp Thr Ala Val Tyr Tyr Cys Ala Lys Gly
785                 790                 795                 800

Trp Phe Gly Gly Phe Asn Tyr Trp Gly Gln Gly Thr Leu Val Thr Val
                805                 810                 815

Ser Ser Ala Ser Val Ala Ala Pro Ser Val Phe Ile Phe Pro Pro Ser
            820                 825                 830

Asp Glu Gln Leu Lys Ser Gly Thr Ala Ser Val Val Cys Leu Leu Asn
        835                 840                 845

Asn Phe Tyr Pro Arg Glu Ala Lys Val Gln Trp Lys Val Asp Asn Ala
    850                 855                 860

Leu Gln Ser Gly Asn Ser Gln Glu Ser Val Thr Glu Gln Asp Ser Lys
865                 870                 875                 880

Asp Ser Thr Tyr Ser Leu Ser Ser Thr Leu Thr Leu Ser Lys Ala Asp
                885                 890                 895

Tyr Glu Lys His Lys Val Tyr Ala Cys Glu Val Thr His Gln Gly Leu
            900                 905                 910

Ser Ser Pro Val Thr Lys Ser Phe Asn Arg Gly Glu Cys
        915                 920                 925

<210> SEQ ID NO 61
<211> LENGTH: 914
<212> TYPE: PRT
<213> ORGANISM: Artificial Sequence
<220> FEATURE:
<223> OTHER INFORMATION: second fusion polypeptide (Fc hole) P1AE0086

<400> SEQUENCE: 61

Gln Val Gln Leu Val Gln Ser Gly Ala Glu Val Lys Lys Pro Gly Ser
1               5                   10                  15

```
Ser Val Lys Val Ser Cys Lys Ala Ser Gly Gly Thr Phe Ser Ser Tyr
         20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Gly Gly Gly
    210                 215                 220

Gly Ser Gly Gly Gly Gly Ser Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Gly Ala Pro Ile Glu Lys Thr Ile Ser Lys Ala Lys Gly
            340                 345                 350

Gln Pro Arg Glu Pro Gln Val Cys Thr Leu Pro Pro Ser Arg Asp Glu
        355                 360                 365

Leu Thr Lys Asn Gln Val Ser Leu Ser Cys Ala Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
            420                 425                 430
```

```
Val Phe Ser Cys Ser Val Met His Glu Ala Leu His Asn His Tyr Thr
        435                 440                 445

Gln Lys Ser Leu Ser Leu Ser Pro Gly Lys Gly Gly Gly Ser Gly
    450                 455                 460

Gly Gly Gly Ser Asp Ile Gln Met Thr Gln Ser Pro Ser Thr Leu Ser
465                 470                 475                 480

Ala Ser Val Gly Asp Arg Val Thr Ile Thr Cys Arg Ala Ser Gln Ser
                485                 490                 495

Ile Ser Ser Trp Leu Ala Trp Tyr Gln Gln Lys Pro Gly Lys Ala Pro
                500                 505                 510

Lys Leu Leu Ile Tyr Asp Ala Ser Ser Leu Glu Ser Gly Val Pro Ser
        515                 520                 525

Arg Phe Ser Gly Ser Gly Ser Gly Thr Glu Phe Thr Leu Thr Ile Ser
    530                 535                 540

Ser Leu Gln Pro Asp Asp Phe Ala Thr Tyr Tyr Cys Gln Gln Tyr Ser
545                 550                 555                 560

Ser Gln Pro Tyr Thr Phe Gly Gln Gly Thr Lys Val Glu Ile Lys Arg
                565                 570                 575

Thr Val Ala Ala Pro Ser Val Phe Ile Phe Pro Pro Ser Asp Glu Gln
                580                 585                 590

Leu Lys Ser Gly Thr Ala Ser Val Val Cys Leu Leu Asn Asn Phe Tyr
        595                 600                 605

Pro Arg Glu Ala Lys Val Gln Trp Lys Val Asp Asn Ala Leu Gln Ser
    610                 615                 620

Gly Asn Ser Gln Glu Ser Val Thr Glu Gln Asp Ser Lys Asp Ser Thr
625                 630                 635                 640

Tyr Ser Leu Ser Ser Thr Leu Thr Leu Ser Lys Ala Asp Tyr Glu Lys
                645                 650                 655

His Lys Val Tyr Ala Cys Glu Val Thr His Gln Gly Leu Ser Ser Pro
                660                 665                 670

Val Thr Lys Ser Phe Asn Arg Gly Glu Cys Gly Gly Gly Gly Ser Gly
        675                 680                 685

Gly Gly Gly Ser Gly Gly Ser Gly Gly Gly Ser Glu Ile Val
    690                 695                 700

Leu Thr Gln Ser Pro Gly Thr Leu Ser Leu Ser Pro Gly Glu Arg Ala
705                 710                 715                 720

Thr Leu Ser Cys Arg Ala Ser Gln Ser Val Thr Ser Ser Tyr Leu Ala
                725                 730                 735

Trp Tyr Gln Gln Lys Pro Gly Gln Ala Pro Arg Leu Leu Ile Asn Val
                740                 745                 750

Gly Ser Arg Arg Ala Thr Gly Ile Pro Asp Arg Phe Ser Gly Ser Gly
        755                 760                 765

Ser Gly Thr Asp Phe Thr Leu Thr Ile Ser Arg Leu Glu Pro Glu Asp
    770                 775                 780

Phe Ala Val Tyr Tyr Cys Gln Gln Gly Ile Met Leu Pro Pro Thr Phe
785                 790                 795                 800

Gly Gln Gly Thr Lys Val Glu Ile Lys Ser Ser Ala Ser Thr Lys Gly
                805                 810                 815

Pro Ser Val Phe Pro Leu Ala Pro Ser Ser Lys Ser Thr Ser Gly Gly
                820                 825                 830

Thr Ala Ala Leu Gly Cys Leu Val Lys Asp Tyr Phe Pro Glu Pro Val
        835                 840                 845
```

```
Thr Val Ser Trp Asn Ser Gly Ala Leu Thr Ser Gly Val His Thr Phe
    850                 855                 860

Pro Ala Val Leu Gln Ser Ser Gly Leu Tyr Ser Leu Ser Ser Val Val
865                 870                 875                 880

Thr Val Pro Ser Ser Ser Leu Gly Thr Gln Thr Tyr Ile Cys Asn Val
                885                 890                 895

Asn His Lys Pro Ser Asn Thr Lys Val Asp Lys Lys Val Glu Pro Lys
                900                 905                 910

Ser Cys

<210> SEQ ID NO 62
<211> LENGTH: 919
<212> TYPE: PRT
<213> ORGANISM: Artificial Sequence
<220> FEATURE:
<223> OTHER INFORMATION: first fusion polypeptide (Fc knob) P1AE0087

<400> SEQUENCE: 62

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Val Ala Ala Pro Ser Val Phe Ile
        115                 120                 125

Phe Pro Pro Ser Asp Glu Gln Leu Lys Ser Gly Thr Ala Ser Val Val
    130                 135                 140

Cys Leu Leu Asn Asn Phe Tyr Pro Arg Glu Ala Lys Val Gln Trp Lys
145                 150                 155                 160

Val Asp Asn Ala Leu Gln Ser Gly Asn Ser Gln Glu Ser Val Thr Glu
                165                 170                 175

Gln Asp Ser Lys Asp Ser Thr Tyr Ser Leu Ser Ser Thr Leu Thr Leu
            180                 185                 190

Ser Lys Ala Asp Tyr Glu Lys His Lys Val Tyr Ala Cys Glu Val Thr
        195                 200                 205

His Gln Gly Leu Ser Ser Pro Val Thr Lys Ser Phe Asn Arg Gly Glu
    210                 215                 220

Cys Asp Gly Gly Gly Gly Ser Gly Gly Gly Gly Ser Asp Lys Thr His
225                 230                 235                 240

Thr Cys Pro Pro Cys Pro Ala Pro Glu Ala Ala Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285
```

-continued

```
Val Lys Phe Asn Trp Tyr Val Asp Gly Val Glu Val His Asn Ala Lys
    290                 295                 300
Thr Lys Pro Arg Glu Glu Gln Tyr Asn Ser Thr Tyr Arg Val Val Ser
305                 310                 315                 320
Val Leu Thr Val Leu His Gln Asp Trp Leu Asn Gly Lys Glu Tyr Lys
                325                 330                 335
Cys Lys Val Ser Asn Lys Ala Leu Gly Ala Pro Ile Glu Lys Thr Ile
            340                 345                 350
Ser Lys Ala Lys Gly Gln Pro Arg Glu Pro Gln Val Tyr Thr Leu Pro
        355                 360                 365
Pro Cys Arg Asp Glu Leu Thr Lys Asn Gln Val Ser Leu Trp Cys Leu
370                 375                 380
Val Lys Gly Phe Tyr Pro Ser Asp Ile Ala Val Glu Trp Glu Ser Asn
385                 390                 395                 400
Gly Gln Pro Glu Asn Asn Tyr Lys Thr Thr Pro Pro Val Leu Asp Ser
                405                 410                 415
Asp Gly Ser Phe Phe Leu Tyr Ser Lys Leu Thr Val Asp Lys Ser Arg
            420                 425                 430
Trp Gln Gln Gly Asn Val Phe Ser Cys Ser Val Met His Glu Ala Leu
        435                 440                 445
His Asn His Tyr Thr Gln Lys Ser Leu Ser Leu Ser Pro Gly Lys Gly
    450                 455                 460
Gly Gly Gly Ser Gly Gly Gly Gly Ser Asp Ile Gln Met Thr Gln Ser
465                 470                 475                 480
Pro Ser Thr Leu Ser Ala Ser Val Gly Asp Arg Val Thr Ile Thr Cys
                485                 490                 495
Arg Ala Ser Gln Ser Ile Ser Ser Trp Leu Ala Trp Tyr Gln Gln Lys
            500                 505                 510
Pro Gly Lys Ala Pro Lys Leu Leu Ile Tyr Asp Ala Ser Ser Leu Glu
        515                 520                 525
Ser Gly Val Pro Ser Arg Phe Ser Gly Ser Gly Ser Gly Thr Glu Phe
530                 535                 540
Thr Leu Thr Ile Ser Ser Leu Gln Pro Asp Asp Phe Ala Thr Tyr Tyr
545                 550                 555                 560
Cys Gln Gln Tyr Ser Ser Gln Pro Tyr Thr Phe Gly Gln Gly Thr Lys
                565                 570                 575
Val Glu Ile Lys Ser Ser Ala Ser Thr Lys Gly Pro Ser Val Phe Pro
            580                 585                 590
Leu Ala Pro Ser Ser Lys Ser Thr Ser Gly Gly Thr Ala Ala Leu Gly
        595                 600                 605
Cys Leu Val Lys Asp Tyr Phe Pro Glu Pro Val Thr Val Ser Trp Asn
610                 615                 620
Ser Gly Ala Leu Thr Ser Gly Val His Thr Phe Pro Ala Val Leu Gln
625                 630                 635                 640
Ser Ser Gly Leu Tyr Ser Leu Ser Ser Val Val Thr Val Pro Ser Ser
                645                 650                 655
Ser Leu Gly Thr Gln Thr Tyr Ile Cys Asn Val Asn His Lys Pro Ser
            660                 665                 670
Asn Thr Lys Val Asp Lys Lys Val Glu Pro Lys Ser Cys Gly Gly Gly
        675                 680                 685
Gly Ser Gly Gly Gly Gly Ser Gly Gly Gly Ser Gly Gly Gly Gly Ser
690                 695                 700
```

-continued

```
Glu Ile Val Leu Thr Gln Ser Pro Gly Thr Leu Ser Leu Ser Pro Gly
705                 710                 715                 720

Glu Arg Ala Thr Leu Ser Cys Arg Ala Ser Gln Ser Val Ser Arg Ser
                725                 730                 735

Tyr Leu Ala Trp Tyr Gln Gln Lys Pro Gly Gln Ala Pro Arg Leu Leu
            740                 745                 750

Ile Ile Gly Ala Ser Thr Arg Ala Thr Gly Ile Pro Asp Arg Phe Ser
        755                 760                 765

Gly Ser Gly Ser Gly Thr Asp Phe Thr Leu Thr Ile Ser Arg Leu Glu
    770                 775                 780

Pro Glu Asp Phe Ala Val Tyr Tyr Cys Gln Gln Gly Gln Val Ile Pro
785                 790                 795                 800

Pro Thr Phe Gly Gln Gly Thr Lys Val Glu Ile Lys Arg Thr Val Ala
                805                 810                 815

Ala Pro Ser Val Phe Ile Phe Pro Pro Ser Asp Glu Gln Leu Lys Ser
            820                 825                 830

Gly Thr Ala Ser Val Val Cys Leu Leu Asn Asn Phe Tyr Pro Arg Glu
        835                 840                 845

Ala Lys Val Gln Trp Lys Val Asp Asn Ala Leu Gln Ser Gly Asn Ser
    850                 855                 860

Gln Glu Ser Val Thr Glu Gln Asp Ser Lys Asp Ser Thr Tyr Ser Leu
865                 870                 875                 880

Ser Ser Thr Leu Thr Leu Ser Lys Ala Asp Tyr Glu Lys His Lys Val
                885                 890                 895

Tyr Ala Cys Glu Val Thr His Gln Gly Leu Ser Ser Pro Val Thr Lys
            900                 905                 910

Ser Phe Asn Arg Gly Glu Cys
        915

<210> SEQ ID NO 63
<211> LENGTH: 923
<212> TYPE: PRT
<213> ORGANISM: Artificial Sequence
<220> FEATURE:
<223> OTHER INFORMATION: second fusion polypeptide (Fc hole) P1AE0087

<400> SEQUENCE: 63

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Val Ala Ala Pro Ser Val Phe Ile
        115                 120                 125

Phe Pro Pro Ser Asp Glu Gln Leu Lys Ser Gly Thr Ala Ser Val Val
    130                 135                 140
```

-continued

```
Cys Leu Leu Asn Asn Phe Tyr Pro Arg Glu Ala Lys Val Gln Trp Lys
145                 150                 155                 160

Val Asp Asn Ala Leu Gln Ser Gly Asn Ser Gln Glu Ser Val Thr Glu
            165                 170                 175

Gln Asp Ser Lys Asp Ser Thr Tyr Ser Leu Ser Ser Thr Leu Thr Leu
            180                 185                 190

Ser Lys Ala Asp Tyr Glu Lys His Lys Val Tyr Ala Cys Glu Val Thr
            195                 200                 205

His Gln Gly Leu Ser Ser Pro Val Thr Lys Ser Phe Asn Arg Gly Glu
            210                 215                 220

Cys Asp Gly Gly Gly Ser Gly Gly Gly Ser Asp Lys Thr His
225                 230                 235                 240

Thr Cys Pro Pro Cys Pro Ala Pro Glu Ala Ala Gly Gly Pro Ser Val
                245                 250                 255

Phe Leu Phe Pro Pro Lys Pro Lys Asp Thr Leu Met Ile Ser Arg Thr
                260                 265                 270

Pro Glu Val Thr Cys Val Val Val Asp Val Ser His Glu Asp Pro Glu
            275                 280                 285

Val Lys Phe Asn Trp Tyr Val Asp Gly Val Glu Val His Asn Ala Lys
290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Gly Ala Pro Ile Glu Lys Thr Ile
                340                 345                 350

Ser Lys Ala Lys Gly Gln Pro Arg Glu Pro Gln Val Cys Thr Leu Pro
            355                 360                 365

Pro Ser Arg Asp Glu Leu Thr Lys Asn Gln Val Ser Leu Ser Cys Ala
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
                420                 425                 430

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro Gly Lys Gly
    450                 455                 460

Gly Gly Gly Ser Gly Gly Gly Ser Asp Ile Gln Met Thr Gln Ser
465                 470                 475                 480

Pro Ser Thr Leu Ser Ala Ser Val Gly Asp Arg Val Thr Ile Thr Cys
                485                 490                 495

Arg Ala Ser Gln Ser Ile Ser Ser Trp Leu Ala Trp Tyr Gln Gln Lys
            500                 505                 510

Pro Gly Lys Ala Pro Lys Leu Leu Ile Tyr Asp Ala Ser Ser Leu Glu
    515                 520                 525

Ser Gly Val Pro Ser Arg Phe Ser Gly Ser Gly Ser Gly Thr Glu Phe
    530                 535                 540

Thr Leu Thr Ile Ser Ser Leu Gln Pro Asp Asp Phe Ala Thr Tyr Tyr
545                 550                 555                 560
```

```
Cys Gln Gln Tyr Ser Ser Gln Pro Tyr Thr Phe Gly Gln Gly Thr Lys
                565                 570                 575

Val Glu Ile Lys Ser Ser Ala Ser Thr Lys Gly Pro Ser Val Phe Pro
            580                 585                 590

Leu Ala Pro Ser Ser Lys Ser Thr Ser Gly Gly Thr Ala Ala Leu Gly
            595                 600                 605

Cys Leu Val Lys Asp Tyr Phe Pro Glu Pro Val Thr Val Ser Trp Asn
        610                 615                 620

Ser Gly Ala Leu Thr Ser Gly Val His Thr Phe Pro Ala Val Leu Gln
625                 630                 635                 640

Ser Ser Gly Leu Tyr Ser Leu Ser Ser Val Val Thr Val Pro Ser Ser
                645                 650                 655

Ser Leu Gly Thr Gln Thr Tyr Ile Cys Asn Val Asn His Lys Pro Ser
                660                 665                 670

Asn Thr Lys Val Asp Lys Lys Val Glu Pro Lys Ser Cys Gly Gly Gly
            675                 680                 685

Gly Ser Gly Gly Gly Gly Ser Gly Gly Ser Gly Gly Gly Gly Ser
690                 695                 700

Glu Val Gln Leu Leu Glu Ser Gly Gly Gly Leu Val Gln Pro Gly Gly
705                 710                 715                 720

Ser Leu Arg Leu Ser Cys Ala Ala Ser Gly Phe Thr Phe Ser Ser His
                725                 730                 735

Ala Met Ser Trp Val Arg Gln Ala Pro Gly Lys Gly Leu Glu Trp Val
            740                 745                 750

Ser Ala Ile Trp Ala Ser Gly Glu Gln Tyr Tyr Ala Asp Ser Val Lys
            755                 760                 765

Gly Arg Phe Thr Ile Ser Arg Asp Asn Ser Lys Asn Thr Leu Tyr Leu
        770                 775                 780

Gln Met Asn Ser Leu Arg Ala Glu Asp Thr Ala Val Tyr Tyr Cys Ala
785                 790                 795                 800

Lys Gly Trp Leu Gly Asn Phe Asp Tyr Trp Gly Gln Gly Thr Leu Val
                805                 810                 815

Thr Val Ser Ser Ala Ser Thr Lys Gly Pro Ser Val Phe Pro Leu Ala
                820                 825                 830

Pro Ser Ser Lys Ser Thr Ser Gly Gly Thr Ala Ala Leu Gly Cys Leu
            835                 840                 845

Val Lys Asp Tyr Phe Pro Glu Pro Val Thr Val Ser Trp Asn Ser Gly
        850                 855                 860

Ala Leu Thr Ser Gly Val His Thr Phe Pro Ala Val Leu Gln Ser Ser
865                 870                 875                 880

Gly Leu Tyr Ser Leu Ser Ser Val Val Thr Val Pro Ser Ser Ser Leu
                885                 890                 895

Gly Thr Gln Thr Tyr Ile Cys Asn Val Asn His Lys Pro Ser Asn Thr
            900                 905                 910

Lys Val Asp Lys Lys Val Glu Pro Lys Ser Cys
        915                 920

<210> SEQ ID NO 64
<211> LENGTH: 919
<212> TYPE: PRT
<213> ORGANISM: Artificial Sequence
<220> FEATURE:
<223> OTHER INFORMATION: first fusion polypeptide (Fc knob) P1AE0839
```

<400> SEQUENCE: 64

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
                20                  25                  30
Ala Ile Ser Trp Val Arg Gln Ala Pro Gly Gln Gly Leu Glu Trp Met
            35                  40                  45
Gly Gly Ile Ile Pro Ile Phe Gly Thr Ala Asn Tyr Ala Gln Lys Phe
        50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Tyr Tyr Arg Gly Pro Tyr Asp Tyr Trp Gly Gln Gly Thr
            100                 105                 110
Thr Val Thr Val Ser Ser Ala Ser Val Ala Ala Pro Ser Val Phe Ile
        115                 120                 125
Phe Pro Pro Ser Asp Glu Gln Leu Lys Ser Gly Thr Ala Ser Val Val
130                 135                 140
Cys Leu Leu Asn Asn Phe Tyr Pro Arg Glu Ala Lys Val Gln Trp Lys
145                 150                 155                 160
Val Asp Asn Ala Leu Gln Ser Gly Asn Ser Gln Glu Ser Val Thr Glu
                165                 170                 175
Gln Asp Ser Lys Asp Ser Thr Tyr Ser Leu Ser Ser Thr Leu Thr Leu
            180                 185                 190
Ser Lys Ala Asp Tyr Glu Lys His Lys Val Tyr Ala Cys Glu Val Thr
        195                 200                 205
His Gln Gly Leu Ser Ser Pro Val Thr Lys Ser Phe Asn Arg Gly Glu
    210                 215                 220
Cys Asp Gly Gly Gly Gly Ser Gly Gly Gly Gly Ser Asp Lys Thr His
225                 230                 235                 240
Thr Cys Pro Pro Cys Pro Ala Pro Glu Ala Ala Gly Gly Pro Ser Val
                245                 250                 255
Phe Leu Phe Pro Pro Lys Pro Lys Asp Thr Leu Met Ile Ser Arg Thr
            260                 265                 270
Pro Glu Val Thr Cys Val Val Val Asp Val Ser His Glu Asp Pro Glu
        275                 280                 285
Val Lys Phe Asn Trp Tyr Val Asp Gly Val Glu Val His Asn Ala Lys
290                 295                 300
Thr Lys Pro Arg Glu Glu Gln Tyr Asn Ser Thr Tyr Arg Val Val Ser
305                 310                 315                 320
Val Leu Thr Val Leu His Gln Asp Trp Leu Asn Gly Lys Glu Tyr Lys
                325                 330                 335
Cys Lys Val Ser Asn Lys Ala Leu Gly Ala Pro Ile Glu Lys Thr Ile
            340                 345                 350
Ser Lys Ala Lys Gly Gln Pro Arg Glu Pro Gln Val Tyr Thr Leu Pro
        355                 360                 365
Pro Cys Arg Asp Glu Leu Thr Lys Asn Gln Val Ser Leu Trp Cys Leu
370                 375                 380
Val Lys Gly Phe Tyr Pro Ser Asp Ile Ala Val Glu Trp Glu Ser Asn
385                 390                 395                 400
```

-continued

```
Gly Gln Pro Glu Asn Asn Tyr Lys Thr Thr Pro Val Leu Asp Ser
            405                 410                 415

Asp Gly Ser Phe Phe Leu Tyr Ser Lys Leu Thr Val Asp Lys Ser Arg
        420                 425                 430

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro Gly Lys Gly
450                 455                 460

Gly Gly Gly Ser Gly Gly Gly Ser Asp Ile Gln Met Thr Gln Ser
465                 470                 475                 480

Pro Ser Thr Leu Ser Ala Ser Val Gly Asp Arg Val Thr Ile Thr Cys
            485                 490                 495

Arg Ala Ser Gln Ser Ile Ser Ser Trp Leu Ala Trp Tyr Gln Gln Lys
            500                 505                 510

Pro Gly Lys Ala Pro Lys Leu Leu Ile Tyr Asp Ala Ser Ser Leu Glu
        515                 520                 525

Ser Gly Val Pro Ser Arg Phe Ser Gly Ser Gly Ser Gly Thr Glu Phe
        530                 535                 540

Thr Leu Thr Ile Ser Ser Leu Gln Pro Asp Asp Phe Ala Thr Tyr Tyr
545                 550                 555                 560

Cys Gln Gln Tyr Ser Ser Gln Pro Tyr Thr Phe Gly Gln Gly Thr Lys
                565                 570                 575

Val Glu Ile Lys Ser Ser Ala Ser Thr Lys Gly Pro Ser Val Phe Pro
            580                 585                 590

Leu Ala Pro Ser Ser Lys Ser Thr Ser Gly Gly Thr Ala Ala Leu Gly
            595                 600                 605

Cys Leu Val Lys Asp Tyr Phe Pro Glu Pro Val Thr Val Ser Trp Asn
    610                 615                 620

Ser Gly Ala Leu Thr Ser Gly Val His Thr Phe Pro Ala Val Leu Gln
625                 630                 635                 640

Ser Ser Gly Leu Tyr Ser Leu Ser Ser Val Val Thr Val Pro Ser Ser
            645                 650                 655

Ser Leu Gly Thr Gln Thr Tyr Ile Cys Asn Val Asn His Lys Pro Ser
            660                 665                 670

Asn Thr Lys Val Asp Lys Lys Val Glu Pro Lys Ser Cys Gly Gly Gly
            675                 680                 685

Gly Ser Gly Gly Gly Gly Ser Gly Gly Gly Ser Gly Gly Gly Gly Ser
        690                 695                 700

Glu Ile Val Leu Thr Gln Ser Pro Gly Thr Leu Ser Leu Ser Pro Gly
705                 710                 715                 720

Glu Arg Ala Thr Leu Ser Cys Arg Ala Ser Gln Ser Val Thr Ser Ser
                725                 730                 735

Tyr Leu Ala Trp Tyr Gln Gln Lys Pro Gly Gln Ala Pro Arg Leu Leu
            740                 745                 750

Ile Asn Val Gly Ser Arg Arg Ala Thr Gly Ile Pro Asp Arg Phe Ser
            755                 760                 765

Gly Ser Gly Ser Gly Thr Asp Phe Thr Leu Thr Ile Ser Arg Leu Glu
    770                 775                 780

Pro Glu Asp Phe Ala Val Tyr Tyr Cys Gln Gln Gly Ile Met Leu Pro
785                 790                 795                 800

Pro Thr Phe Gly Gln Gly Thr Lys Val Glu Ile Lys Arg Thr Val Ala
            805                 810                 815
```

```
Ala Pro Ser Val Phe Ile Phe Pro Pro Ser Asp Glu Gln Leu Lys Ser
                820                 825                 830

Gly Thr Ala Ser Val Val Cys Leu Leu Asn Asn Phe Tyr Pro Arg Glu
            835                 840                 845

Ala Lys Val Gln Trp Lys Val Asp Asn Ala Leu Gln Ser Gly Asn Ser
        850                 855                 860

Gln Glu Ser Val Thr Glu Gln Asp Ser Lys Asp Ser Thr Tyr Ser Leu
865                 870                 875                 880

Ser Ser Thr Leu Thr Leu Ser Lys Ala Asp Tyr Glu Lys His Lys Val
                885                 890                 895

Tyr Ala Cys Glu Val Thr His Gln Gly Leu Ser Ser Pro Val Thr Lys
            900                 905                 910

Ser Phe Asn Arg Gly Glu Cys
        915

<210> SEQ ID NO 65
<211> LENGTH: 924
<212> TYPE: PRT
<213> ORGANISM: Artificial Sequence
<220> FEATURE:
<223> OTHER INFORMATION: second fusion polypeptide (Fc hole) P1AE0839

<400> SEQUENCE: 65

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Val Ala Ala Pro Ser Val Phe Ile
        115                 120                 125

Phe Pro Pro Ser Asp Glu Gln Leu Lys Ser Gly Thr Ala Ser Val Val
130                 135                 140

Cys Leu Leu Asn Asn Phe Tyr Pro Arg Glu Ala Lys Val Gln Trp Lys
145                 150                 155                 160

Val Asp Asn Ala Leu Gln Ser Gly Asn Ser Gln Glu Ser Val Thr Glu
                165                 170                 175

Gln Asp Ser Lys Asp Ser Thr Tyr Ser Leu Ser Ser Thr Leu Thr Leu
            180                 185                 190

Ser Lys Ala Asp Tyr Glu Lys His Lys Val Tyr Ala Cys Glu Val Thr
        195                 200                 205

His Gln Gly Leu Ser Ser Pro Val Thr Lys Ser Phe Asn Arg Gly Glu
    210                 215                 220

Cys Asp Gly Gly Gly Ser Gly Gly Gly Ser Asp Lys Thr His
225                 230                 235                 240

Thr Cys Pro Pro Cys Pro Ala Pro Glu Ala Ala Gly Gly Pro Ser Val
                245                 250                 255
```

-continued

```
Phe Leu Phe Pro Pro Lys Pro Lys Asp Thr Leu Met Ile Ser Arg Thr
            260                 265                 270

Pro Glu Val Thr Cys Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Gly Ala Pro Ile Glu Lys Thr Ile
            340                 345                 350

Ser Lys Ala Lys Gly Gln Pro Arg Glu Pro Gln Val Cys Thr Leu Pro
        355                 360                 365

Pro Ser Arg Asp Glu Leu Thr Lys Asn Gln Val Ser Leu Ser Cys Ala
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Val Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys Gly
    450                 455                 460

Gly Gly Gly Ser Gly Gly Gly Gly Ser Asp Ile Gln Met Thr Gln Ser
465                 470                 475                 480

Pro Ser Thr Leu Ser Ala Ser Val Gly Asp Arg Val Thr Ile Thr Cys
                485                 490                 495

Arg Ala Ser Gln Ser Ile Ser Ser Trp Leu Ala Trp Tyr Gln Gln Lys
            500                 505                 510

Pro Gly Lys Ala Pro Lys Leu Leu Ile Tyr Asp Ala Ser Ser Leu Glu
        515                 520                 525

Ser Gly Val Pro Ser Arg Phe Ser Gly Ser Gly Ser Gly Thr Glu Phe
    530                 535                 540

Thr Leu Thr Ile Ser Ser Leu Gln Pro Asp Asp Phe Ala Thr Tyr Tyr
545                 550                 555                 560

Cys Gln Gln Tyr Ser Ser Gln Pro Tyr Thr Phe Gly Gln Gly Thr Lys
                565                 570                 575

Val Glu Ile Lys Ser Ser Ala Ser Thr Lys Gly Pro Ser Val Phe Pro
            580                 585                 590

Leu Ala Pro Ser Ser Lys Ser Thr Ser Gly Gly Thr Ala Ala Leu Gly
        595                 600                 605

Cys Leu Val Lys Asp Tyr Phe Pro Glu Pro Val Thr Val Ser Trp Asn
    610                 615                 620

Ser Gly Ala Leu Thr Ser Gly Val His Thr Phe Pro Ala Val Leu Gln
625                 630                 635                 640

Ser Ser Gly Leu Tyr Ser Leu Ser Ser Val Val Thr Val Pro Ser Ser
                645                 650                 655

Ser Leu Gly Thr Gln Thr Tyr Ile Cys Asn Val Asn His Lys Pro Ser
            660                 665                 670
```

-continued

```
Asn Thr Lys Val Asp Lys Lys Val Glu Pro Lys Ser Cys Gly Gly
            675                 680                 685
Gly Ser Gly Gly Gly Ser Gly Gly Gly Ser Gly Gly Gly Ser
    690                 695                 700
Glu Val Gln Leu Leu Glu Ser Gly Gly Gly Leu Val Gln Pro Gly Gly
705                 710                 715                 720
Ser Leu Arg Leu Ser Cys Ala Ala Ser Gly Phe Thr Phe Ser Ser Tyr
                725                 730                 735
Ala Met Ser Trp Val Arg Gln Ala Pro Gly Lys Gly Leu Glu Trp Val
            740                 745                 750
Ser Ala Ile Ile Gly Ser Gly Ala Ser Thr Tyr Tyr Ala Asp Ser Val
            755                 760                 765
Lys Gly Arg Phe Thr Ile Ser Arg Asp Asn Ser Lys Asn Thr Leu Tyr
        770                 775                 780
Leu Gln Met Asn Ser Leu Arg Ala Glu Asp Thr Ala Val Tyr Tyr Cys
785                 790                 795                 800
Ala Lys Gly Trp Phe Gly Phe Asn Tyr Trp Gly Gln Gly Thr Leu
                805                 810                 815
Val Thr Val Ser Ser Ala Ser Thr Lys Gly Pro Ser Val Phe Pro Leu
            820                 825                 830
Ala Pro Ser Ser Lys Ser Thr Ser Gly Gly Thr Ala Ala Leu Gly Cys
            835                 840                 845
Leu Val Lys Asp Tyr Phe Pro Glu Pro Val Thr Val Ser Trp Asn Ser
        850                 855                 860
Gly Ala Leu Thr Ser Gly Val His Thr Phe Pro Ala Val Leu Gln Ser
865                 870                 875                 880
Ser Gly Leu Tyr Ser Leu Ser Val Val Thr Val Pro Ser Ser Ser
                885                 890                 895
Leu Gly Thr Gln Thr Tyr Ile Cys Asn Val Asn His Lys Pro Ser Asn
            900                 905                 910
Thr Lys Val Asp Lys Lys Val Glu Pro Lys Ser Cys
        915                 920
```

<210> SEQ ID NO 66
<211> LENGTH: 925
<212> TYPE: PRT
<213> ORGANISM: Artificial Sequence
<220> FEATURE:
<223> OTHER INFORMATION: first fusion polypeptide (Fc knob) P1AE0821

<400> SEQUENCE: 66

```
Asp Ile Gln Met Thr Gln Ser Pro Ser Thr Leu Ser Ala Ser Val Gly
1               5                   10                  15
Asp Arg Val Thr Ile Thr Cys Arg Ala Ser Gln Ser Ile Ser Ser Trp
            20                  25                  30
Leu Ala Trp Tyr Gln Gln Lys Pro Gly Lys Ala Pro Lys Leu Leu Ile
        35                  40                  45
Tyr Asp Ala Ser Ser Leu Glu Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Asp Asp Phe Ala Thr Tyr Tyr Cys Gln Gln Tyr Ser Ser Gln Pro Tyr
                85                  90                  95
Thr Phe Gly Gln Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Gly Gly Gly Ser Gly Gly Gly Gly Ser
210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Asp Glu Leu Thr Lys Asn Gln Val Ser
            355                 360                 365

Leu Trp Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys Gly Gly Gly Gly Ser Gly Gly Gly Gly Ser Gln Val Gln
            450                 455                 460

Leu Val Gln Ser Gly Ala Glu Val Lys Lys Pro Gly Ser Ser Val Lys
465                 470                 475                 480

Val Ser Cys Lys Ala Ser Gly Gly Thr Phe Ser Ser Tyr Ala Ile Ser
                485                 490                 495

Trp Val Arg Gln Ala Pro Gly Gln Gly Leu Glu Trp Met Gly Gly Ile
            500                 505                 510

Ile Pro Ile Phe Gly Thr Ala Asn Tyr Ala Gln Lys Phe Gln Gly Arg
            515                 520                 525
```

Val Thr Ile Thr Ala Asp Lys Ser Thr Ser Thr Ala Tyr Met Glu Leu
            530                 535                 540

Ser Ser Leu Arg Ser Glu Asp Thr Ala Val Tyr Tyr Cys Ala Arg Glu
545                 550                 555                 560

Tyr Tyr Arg Gly Pro Tyr Asp Tyr Trp Gly Gln Gly Thr Thr Val Thr
                565                 570                 575

Val Ser Ser Ala Ser Thr Lys Gly Pro Ser Val Phe Pro Leu Ala Pro
            580                 585                 590

Ser Ser Lys Ser Thr Ser Gly Gly Thr Ala Ala Leu Gly Cys Leu Val
        595                 600                 605

Lys Asp Tyr Phe Pro Glu Pro Val Thr Val Ser Trp Asn Ser Gly Ala
    610                 615                 620

Leu Thr Ser Gly Val His Thr Phe Pro Ala Val Leu Gln Ser Ser Gly
625                 630                 635                 640

Leu Tyr Ser Leu Ser Ser Val Val Thr Val Pro Ser Ser Ser Leu Gly
                645                 650                 655

Thr Gln Thr Tyr Ile Cys Asn Val Asn His Lys Pro Ser Asn Thr Lys
            660                 665                 670

Val Asp Lys Lys Val Glu Pro Lys Ser Cys Gly Gly Gly Gly Ser Gly
        675                 680                 685

Gly Gly Gly Ser Gly Gly Gly Ser Gly Gly Gly Gly Ser Glu Val Gln
    690                 695                 700

Leu Leu Glu Ser Gly Gly Gly Leu Val Gln Pro Gly Gly Ser Leu Arg
705                 710                 715                 720

Leu Ser Cys Ala Ala Ser Gly Phe Thr Phe Ser Ser Tyr Ala Met Ser
                725                 730                 735

Trp Val Arg Gln Ala Pro Gly Lys Gly Leu Glu Trp Val Ser Ala Ile
            740                 745                 750

Ile Gly Ser Gly Ala Ser Thr Tyr Tyr Ala Asp Ser Val Lys Gly Arg
        755                 760                 765

Phe Thr Ile Ser Arg Asp Asn Ser Lys Asn Thr Leu Tyr Leu Gln Met
    770                 775                 780

Asn Ser Leu Arg Ala Glu Asp Thr Ala Val Tyr Tyr Cys Ala Lys Gly
785                 790                 795                 800

Trp Phe Gly Gly Phe Asn Tyr Trp Gly Gln Gly Thr Leu Val Thr Val
                805                 810                 815

Ser Ser Ala Ser Val Ala Ala Pro Ser Val Phe Ile Phe Pro Pro Ser
            820                 825                 830

Asp Glu Gln Leu Lys Ser Gly Thr Ala Ser Val Val Cys Leu Leu Asn
        835                 840                 845

Asn Phe Tyr Pro Arg Glu Ala Lys Val Gln Trp Lys Val Asp Asn Ala
    850                 855                 860

Leu Gln Ser Gly Asn Ser Gln Glu Ser Val Thr Glu Gln Asp Ser Lys
865                 870                 875                 880

Asp Ser Thr Tyr Ser Leu Ser Ser Thr Leu Thr Leu Ser Lys Ala Asp
                885                 890                 895

Tyr Glu Lys His Lys Val Tyr Ala Cys Glu Val Thr His Gln Gly Leu
            900                 905                 910

Ser Ser Pro Val Thr Lys Ser Phe Asn Arg Gly Glu Cys
        915                 920                 925

<210> SEQ ID NO 67
<211> LENGTH: 914
<212> TYPE: PRT

<213> ORGANISM: Artificial Sequence
<220> FEATURE:
<223> OTHER INFORMATION: second fusion polypeptide (Fc hole) P1AE0821

<400> SEQUENCE: 67

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Gln Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
370                 375                 380
```

```
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys Gly Gly Gly Ser Gly Gly Gly Ser Gln Val Gln
450                 455                 460

Leu Val Gln Ser Gly Ala Glu Val Lys Lys Pro Gly Ser Ser Val Lys
465                 470                 475                 480

Val Ser Cys Lys Ala Ser Gly Gly Thr Phe Ser Ser Tyr Ala Ile Ser
            485                 490                 495

Trp Val Arg Gln Ala Pro Gly Gln Gly Leu Glu Trp Met Gly Gly Ile
            500                 505                 510

Ile Pro Ile Phe Gly Thr Ala Asn Tyr Ala Gln Lys Phe Gln Gly Arg
            515                 520                 525

Val Thr Ile Thr Ala Asp Lys Ser Thr Ser Thr Ala Tyr Met Glu Leu
            530                 535                 540

Ser Ser Leu Arg Ser Glu Asp Thr Ala Val Tyr Tyr Cys Ala Arg Glu
545                 550                 555                 560

Tyr Tyr Arg Gly Pro Tyr Asp Tyr Trp Gly Gln Gly Thr Thr Val Thr
            565                 570                 575

Val Ser Ser Ala Ser Thr Lys Gly Pro Ser Val Phe Pro Leu Ala Pro
            580                 585                 590

Ser Ser Lys Ser Thr Ser Gly Gly Thr Ala Ala Leu Gly Cys Leu Val
            595                 600                 605

Lys Asp Tyr Phe Pro Glu Pro Val Thr Val Ser Trp Asn Ser Gly Ala
            610                 615                 620

Leu Thr Ser Gly Val His Thr Phe Pro Ala Val Leu Gln Ser Ser Gly
625                 630                 635                 640

Leu Tyr Ser Leu Ser Ser Val Val Thr Val Pro Ser Ser Ser Leu Gly
            645                 650                 655

Thr Gln Thr Tyr Ile Cys Asn Val Asn His Lys Pro Ser Asn Thr Lys
            660                 665                 670

Val Asp Lys Lys Val Glu Pro Lys Ser Cys Gly Gly Gly Gly Ser Gly
            675                 680                 685

Gly Gly Gly Ser Gly Gly Gly Gly Ser Gly Gly Gly Gly Ser Glu Ile Val
            690                 695                 700

Leu Thr Gln Ser Pro Gly Thr Leu Ser Leu Ser Pro Gly Glu Arg Ala
705                 710                 715                 720

Thr Leu Ser Cys Arg Ala Ser Gln Ser Val Thr Ser Ser Tyr Leu Ala
            725                 730                 735

Trp Tyr Gln Gln Lys Pro Gly Gln Ala Pro Arg Leu Leu Ile Asn Val
            740                 745                 750

Gly Ser Arg Arg Ala Thr Gly Ile Pro Asp Arg Phe Ser Gly Ser Gly
            755                 760                 765

Ser Gly Thr Asp Phe Thr Leu Thr Ile Ser Arg Leu Glu Pro Glu Asp
            770                 775                 780

Phe Ala Val Tyr Tyr Cys Gln Gln Gly Ile Met Leu Pro Pro Thr Phe
785                 790                 795                 800
```

Gly Gln Gly Thr Lys Val Glu Ile Lys Ser Ala Ser Thr Lys Gly
                    805                 810                 815

Pro Ser Val Phe Pro Leu Ala Pro Ser Ser Lys Ser Thr Ser Gly Gly
            820                 825                 830

Thr Ala Ala Leu Gly Cys Leu Val Lys Asp Tyr Phe Pro Glu Pro Val
        835                 840                 845

Thr Val Ser Trp Asn Ser Gly Ala Leu Thr Ser Gly Val His Thr Phe
    850                 855                 860

Pro Ala Val Leu Gln Ser Ser Gly Leu Tyr Ser Leu Ser Ser Val Val
865                 870                 875                 880

Thr Val Pro Ser Ser Leu Gly Thr Gln Thr Tyr Ile Cys Asn Val
            885                 890                 895

Asn His Lys Pro Ser Asn Thr Lys Val Asp Lys Val Glu Pro Lys
        900                 905                 910

Ser Cys

<210> SEQ ID NO 68
<211> LENGTH: 583
<212> TYPE: PRT
<213> ORGANISM: Artificial Sequence
<220> FEATURE:
<223> OTHER INFORMATION: (49B4) VHCH1 Fc knob VH (28H1) (heavy chain 1)

<400> SEQUENCE: 68

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

```
Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Asp Glu Leu Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Gly
        435                 440                 445

Gly Gly Gly Ser Gly Gly Gly Gly Ser Gly Gly Gly Gly Ser Gly Gly
    450                 455                 460

Gly Gly Ser Glu Val Gln Leu Leu Glu Ser Gly Gly Gly Leu Val Gln
465                 470                 475                 480

Pro Gly Gly Ser Leu Arg Leu Ser Cys Ala Ala Ser Gly Phe Thr Phe
                485                 490                 495

Ser Ser His Ala Met Ser Trp Val Arg Gln Ala Pro Gly Lys Gly Leu
            500                 505                 510

Glu Trp Val Ser Ala Ile Trp Ala Ser Gly Glu Gln Tyr Tyr Ala Asp
        515                 520                 525

Ser Val Lys Gly Arg Phe Thr Ile Ser Arg Asp Asn Ser Lys Asn Thr
    530                 535                 540

Leu Tyr Leu Gln Met Asn Ser Leu Arg Ala Glu Asp Thr Ala Val Tyr
545                 550                 555                 560

Tyr Cys Ala Lys Gly Trp Leu Gly Asn Phe Asp Tyr Trp Gly Gln Gly
                565                 570                 575

Thr Leu Val Thr Val Ser Ser
            580

<210> SEQ ID NO 69
<211> LENGTH: 575
<212> TYPE: PRT
<213> ORGANISM: Artificial Sequence
<220> FEATURE:
<223> OTHER INFORMATION: (49B4) VHCH1 Fc hole VL (28H1) (heavy chain 2)

<400> SEQUENCE: 69

Gln Val Gln Leu Val Gln Ser Gly Ala Glu Val Lys Lys Pro Gly Ser
1               5                   10                  15
```

```
Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Lys Ser Thr Ser Thr Ala Tyr
65                   70                  75                  80

Met Glu Leu Ser Ser Leu Arg Ser Glu Asp Thr Ala Val Tyr Tyr Cys
             85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
            355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430
```

```
Leu His Asn His Tyr Thr Gln Lys Ser Leu Ser Leu Ser Pro Gly Gly
            435                 440                 445

Gly Gly Gly Ser Gly Gly Gly Ser Gly Gly Gly Ser Gly Gly
450                 455                 460

Gly Gly Ser Glu Ile Val Leu Thr Gln Ser Pro Gly Thr Leu Ser Leu
465                 470                 475                 480

Ser Pro Gly Glu Arg Ala Thr Leu Ser Cys Arg Ala Ser Gln Ser Val
                485                 490                 495

Ser Arg Ser Tyr Leu Ala Trp Tyr Gln Gln Lys Pro Gly Gln Ala Pro
                500                 505                 510

Arg Leu Leu Ile Ile Gly Ala Ser Thr Arg Ala Thr Gly Ile Pro Asp
            515                 520                 525

Arg Phe Ser Gly Ser Gly Ser Gly Thr Asp Phe Thr Leu Thr Ile Ser
            530                 535                 540

Arg Leu Glu Pro Glu Asp Phe Ala Val Tyr Tyr Cys Gln Gln Gly Gln
545                 550                 555                 560

Val Ile Pro Pro Thr Phe Gly Gln Gly Thr Lys Val Glu Ile Lys
                565                 570                 575

<210> SEQ ID NO 70
<211> LENGTH: 214
<212> TYPE: PRT
<213> ORGANISM: Artificial Sequence
<220> FEATURE:
<223> OTHER INFORMATION: (49B4) VLCL-light chain

<400> SEQUENCE: 70

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Gln Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 71
<211> LENGTH: 584
<212> TYPE: PRT
<213> ORGANISM: Artificial Sequence
<220> FEATURE:
<223> OTHER INFORMATION: (49B4) VHCH1 Fc knob VH (4B9) (heavy chain 1)

<400> SEQUENCE: 71

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Asp Glu Leu Thr Lys Asn Gln Val Ser Leu Trp Cys
        355                 360                 365
```

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Gly
    435                 440                 445

Gly Gly Gly Ser Gly Gly Gly Ser Gly Gly Gly Ser Gly Gly
450                 455                 460

Gly Gly Ser Glu Val Gln Leu Leu Glu Ser Gly Gly Gly Leu Val Gln
465                 470                 475                 480

Pro Gly Gly Ser Leu Arg Leu Ser Cys Ala Ala Ser Gly Phe Thr Phe
            485                 490                 495

Ser Ser Tyr Ala Met Ser Trp Val Arg Gln Ala Pro Gly Lys Gly Leu
        500                 505                 510

Glu Trp Val Ser Ala Ile Ile Gly Ser Gly Ala Ser Thr Tyr Tyr Ala
    515                 520                 525

Asp Ser Val Lys Gly Arg Phe Thr Ile Ser Arg Asp Asn Ser Lys Asn
530                 535                 540

Thr Leu Tyr Leu Gln Met Asn Ser Leu Arg Ala Glu Asp Thr Ala Val
545                 550                 555                 560

Tyr Tyr Cys Ala Lys Gly Trp Phe Gly Gly Phe Asn Tyr Trp Gly Gln
            565                 570                 575

Gly Thr Leu Val Thr Val Ser Ser
            580

<210> SEQ ID NO 72
<211> LENGTH: 575
<212> TYPE: PRT
<213> ORGANISM: Artificial Sequence
<220> FEATURE:
<223> OTHER INFORMATION: (49B4) VHCH1 Fc hole VL (4B9) (heavy chain 2)

<400> SEQUENCE: 72

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
            325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
            355                 360                 365

Ala Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Gly
            435                 440                 445

Gly Gly Gly Ser Gly Gly Gly Ser Gly Gly Gly Gly Ser Gly Gly
450                 455                 460

Gly Gly Ser Glu Ile Val Leu Thr Gln Ser Pro Gly Thr Leu Ser Leu
465                 470                 475                 480

Ser Pro Gly Glu Arg Ala Thr Leu Ser Cys Arg Ala Ser Gln Ser Val
            485                 490                 495

Thr Ser Ser Tyr Leu Ala Trp Tyr Gln Gln Lys Pro Gly Gln Ala Pro
            500                 505                 510

Arg Leu Leu Ile Asn Val Gly Ser Arg Arg Ala Thr Gly Ile Pro Asp
            515                 520                 525

Arg Phe Ser Gly Ser Gly Ser Gly Thr Asp Phe Thr Leu Thr Ile Ser
            530                 535                 540

Arg Leu Glu Pro Glu Asp Phe Ala Val Tyr Tyr Cys Gln Gln Gly Ile
545                 550                 555                 560
```

```
                                    -continued

Met Leu Pro Pro Thr Phe Gly Gln Gly Thr Lys Val Glu Ile Lys
                565                 570                 575

<210> SEQ ID NO 73
<211> LENGTH: 582
<212> TYPE: PRT
<213> ORGANISM: Artificial Sequence
<220> FEATURE:
<223> OTHER INFORMATION: (49B4) VHCH1 Fc knob VH (DP47) (heavy chain 1)

<400> SEQUENCE: 73

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Tyr Thr Leu
            340                 345                 350
```

-continued

```
Pro Pro Cys Arg Asp Glu Leu Thr Lys Asn Gln Val Ser Leu Trp Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Gly
        435                 440                 445

Gly Gly Gly Ser Gly Gly Gly Ser Gly Gly Gly Ser Gly Gly
        450                 455                 460

Gly Gly Ser Glu Val Gln Leu Leu Glu Ser Gly Gly Leu Val Gln
465                 470                 475                 480

Pro Gly Gly Ser Leu Arg Leu Ser Cys Ala Ala Ser Gly Phe Thr Phe
                485                 490                 495

Ser Ser Tyr Ala Met Ser Trp Val Arg Gln Ala Pro Lys Gly Leu
        500                 505                 510

Glu Trp Val Ser Ala Ile Ser Gly Ser Gly Gly Ser Thr Tyr Tyr Ala
            515                 520                 525

Asp Ser Val Lys Gly Arg Phe Thr Ile Ser Arg Asp Asn Ser Lys Asn
530                 535                 540

Thr Leu Tyr Leu Gln Met Asn Ser Leu Arg Ala Glu Asp Thr Ala Val
545                 550                 555                 560

Tyr Tyr Cys Ala Lys Gly Ser Gly Phe Asp Tyr Trp Gly Gln Gly Thr
                565                 570                 575

Leu Val Thr Val Ser Ser
            580

<210> SEQ ID NO 74
<211> LENGTH: 575
<212> TYPE: PRT
<213> ORGANISM: Artificial Sequence
<220> FEATURE:
<223> OTHER INFORMATION: (49B4) VHCH1 Fc hole VL (DP47) (heavy chain 2)

<400> SEQUENCE: 74

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125
```

```
Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Gly
        435                 440                 445

Gly Gly Gly Ser Gly Gly Gly Ser Gly Gly Gly Gly Ser Gly Gly Gly
    450                 455                 460

Gly Gly Ser Glu Ile Val Leu Thr Gln Ser Pro Gly Thr Leu Ser Leu
465                 470                 475                 480

Ser Pro Gly Glu Arg Ala Thr Leu Ser Cys Arg Ala Ser Gln Ser Val
                485                 490                 495

Ser Ser Ser Tyr Leu Ala Trp Tyr Gln Gln Lys Pro Gly Gln Ala Pro
            500                 505                 510

Arg Leu Leu Ile Tyr Gly Ala Ser Ser Arg Ala Thr Gly Ile Pro Asp
        515                 520                 525

Arg Phe Ser Gly Ser Gly Ser Gly Thr Asp Phe Thr Leu Thr Ile Ser
    530                 535                 540
```

-continued

Arg Leu Glu Pro Glu Asp Phe Ala Val Tyr Tyr Cys Gln Gln Tyr Gly
545                 550                 555                 560

Ser Ser Pro Leu Thr Phe Gly Gln Gly Thr Lys Val Glu Ile Lys
            565                 570                 575

<210> SEQ ID NO 75
<211> LENGTH: 816
<212> TYPE: PRT
<213> ORGANISM: Artificial Sequence
<220> FEATURE:
<223> OTHER INFORMATION: HC 1(49B4) VHCH1_VHCH1 Fc knob VH (4B9)

<400> SEQUENCE: 75

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Gly Gly
    210                 215                 220

Gly Gly Ser Gly Gly Gly Gly Ser Gln Val Gln Leu Val Gln Ser Gly
225                 230                 235                 240

Ala Glu Val Lys Lys Pro Gly Ser Ser Val Lys Val Ser Cys Lys Ala
                245                 250                 255

Ser Gly Gly Thr Phe Ser Ser Tyr Ala Ile Ser Trp Val Arg Gln Ala
            260                 265                 270

Pro Gly Gln Gly Leu Glu Trp Met Gly Gly Ile Ile Pro Ile Phe Gly
        275                 280                 285

Thr Ala Asn Tyr Ala Gln Lys Phe Gln Gly Arg Val Thr Ile Thr Ala
    290                 295                 300

Asp Lys Ser Thr Ser Thr Ala Tyr Met Glu Leu Ser Ser Leu Arg Ser
305                 310                 315                 320

Glu Asp Thr Ala Val Tyr Tyr Cys Ala Arg Glu Tyr Tyr Arg Gly Pro
                325                 330                 335

-continued

```
Tyr Asp Tyr Trp Gly Gln Gly Thr Thr Val Thr Val Ser Ser Ala Ser
            340                 345                 350

Thr Lys Gly Pro Ser Val Phe Pro Leu Ala Pro Ser Ser Lys Ser Thr
        355                 360                 365

Ser Gly Gly Thr Ala Ala Leu Gly Cys Leu Val Lys Asp Tyr Phe Pro
370                 375                 380

Glu Pro Val Thr Val Ser Trp Asn Ser Gly Ala Leu Thr Ser Gly Val
385                 390                 395                 400

His Thr Phe Pro Ala Val Leu Gln Ser Ser Gly Leu Tyr Ser Leu Ser
                405                 410                 415

Ser Val Val Thr Val Pro Ser Ser Ser Leu Gly Thr Gln Thr Tyr Ile
            420                 425                 430

Cys Asn Val Asn His Lys Pro Ser Asn Thr Lys Val Asp Lys Lys Val
        435                 440                 445

Glu Pro Lys Ser Cys Asp Lys Thr His Thr Cys Pro Pro Cys Pro Ala
450                 455                 460

Pro Glu Ala Ala Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
                485                 490                 495

Val Asp Val Ser His Glu Asp Pro Glu Val Lys Phe Asn Trp Tyr Val
            500                 505                 510

Asp Gly Val Glu Val His Asn Ala Lys Thr Lys Pro Arg Glu Glu Gln
        515                 520                 525

Tyr Asn Ser Thr Tyr Arg Val Val Ser Val Leu Thr Val Leu His Gln
530                 535                 540

Asp Trp Leu Asn Gly Lys Glu Tyr Lys Cys Lys Val Ser Asn Lys Ala
545                 550                 555                 560

Leu Gly Ala Pro Ile Glu Lys Thr Ile Ser Lys Ala Lys Gly Gln Pro
                565                 570                 575

Arg Glu Pro Gln Val Tyr Thr Leu Pro Pro Cys Arg Asp Glu Leu Thr
            580                 585                 590

Lys Asn Gln Val Ser Leu Trp Cys Leu Val Lys Gly Phe Tyr Pro Ser
        595                 600                 605

Asp Ile Ala Val Glu Trp Glu Ser Asn Gly Gln Pro Glu Asn Asn Tyr
610                 615                 620

Lys Thr Thr Pro Pro Val Leu Asp Ser Asp Gly Ser Phe Phe Leu Tyr
625                 630                 635                 640

Ser Lys Leu Thr Val Asp Lys Ser Arg Trp Gln Gln Gly Asn Val Phe
                645                 650                 655

Ser Cys Ser Val Met His Glu Ala Leu His Asn His Tyr Thr Gln Lys
            660                 665                 670

Ser Leu Ser Leu Ser Pro Gly Gly Gly Gly Ser Gly Gly Gly Gly
        675                 680                 685

Ser Gly Gly Gly Gly Ser Gly Gly Gly Gly Ser Glu Val Gln Leu Leu
690                 695                 700

Glu Ser Gly Gly Gly Leu Val Gln Pro Gly Gly Ser Leu Arg Leu Ser
705                 710                 715                 720

Cys Ala Ala Ser Gly Phe Thr Phe Ser Ser Tyr Ala Met Ser Trp Val
                725                 730                 735

Arg Gln Ala Pro Gly Lys Gly Leu Glu Trp Val Ser Ala Ile Ile Gly
            740                 745                 750
```

-continued

Ser Gly Ala Ser Thr Tyr Tyr Ala Asp Ser Val Lys Gly Arg Phe Thr
        755                 760                 765

Ile Ser Arg Asp Asn Ser Lys Asn Thr Leu Tyr Leu Gln Met Asn Ser
    770                 775                 780

Leu Arg Ala Glu Asp Thr Ala Val Tyr Tyr Cys Ala Lys Gly Trp Phe
785                 790                 795                 800

Gly Gly Phe Asn Tyr Trp Gly Gln Gly Thr Leu Val Thr Val Ser Ser
                805                 810                 815

<210> SEQ ID NO 76
<211> LENGTH: 807
<212> TYPE: PRT
<213> ORGANISM: Artificial Sequence
<220> FEATURE:
<223> OTHER INFORMATION: HC 2 (49B4) VHCH1_VHCH1 Fc hole VL (4B9)

<400> SEQUENCE: 76

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Gly Gly
    210                 215                 220

Gly Gly Ser Gly Gly Gly Ser Gln Val Gln Leu Val Gln Ser Gly
225                 230                 235                 240

Ala Glu Val Lys Lys Pro Gly Ser Ser Val Lys Val Ser Cys Lys Ala
                245                 250                 255

Ser Gly Gly Thr Phe Ser Ser Tyr Ala Ile Ser Trp Val Arg Gln Ala
            260                 265                 270

Pro Gly Gln Gly Leu Glu Trp Met Gly Gly Ile Ile Pro Ile Phe Gly
        275                 280                 285

Thr Ala Asn Tyr Ala Gln Lys Phe Gln Gly Arg Val Thr Ile Thr Ala
    290                 295                 300

```
Asp Lys Ser Thr Ser Thr Ala Tyr Met Glu Leu Ser Ser Leu Arg Ser
305                 310                 315                 320

Glu Asp Thr Ala Val Tyr Tyr Cys Ala Arg Glu Tyr Tyr Arg Gly Pro
            325                 330                 335

Tyr Asp Tyr Trp Gly Gln Gly Thr Thr Val Thr Val Ser Ser Ala Ser
        340                 345                 350

Thr Lys Gly Pro Ser Val Phe Pro Leu Ala Pro Ser Ser Lys Ser Thr
    355                 360                 365

Ser Gly Gly Thr Ala Ala Leu Gly Cys Leu Val Lys Asp Tyr Phe Pro
370                 375                 380

Glu Pro Val Thr Val Ser Trp Asn Ser Gly Ala Leu Thr Ser Gly Val
385                 390                 395                 400

His Thr Phe Pro Ala Val Leu Gln Ser Ser Gly Leu Tyr Ser Leu Ser
            405                 410                 415

Ser Val Val Thr Val Pro Ser Ser Leu Gly Thr Gln Thr Tyr Ile
        420                 425                 430

Cys Asn Val Asn His Lys Pro Ser Asn Thr Lys Val Asp Lys Lys Val
    435                 440                 445

Glu Pro Lys Ser Cys Asp Lys Thr His Thr Cys Pro Pro Cys Pro Ala
450                 455                 460

Pro Glu Ala Ala Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
            485                 490                 495

Val Asp Val Ser His Glu Asp Pro Glu Val Lys Phe Asn Trp Tyr Val
        500                 505                 510

Asp Gly Val Glu Val His Asn Ala Lys Thr Lys Pro Arg Glu Glu Gln
    515                 520                 525

Tyr Asn Ser Thr Tyr Arg Val Val Ser Val Leu Thr Val Leu His Gln
530                 535                 540

Asp Trp Leu Asn Gly Lys Glu Tyr Lys Cys Lys Val Ser Asn Lys Ala
545                 550                 555                 560

Leu Gly Ala Pro Ile Glu Lys Thr Ile Ser Lys Ala Lys Gly Gln Pro
            565                 570                 575

Arg Glu Pro Gln Val Cys Thr Leu Pro Pro Ser Arg Asp Glu Leu Thr
        580                 585                 590

Lys Asn Gln Val Ser Leu Ser Cys Ala Val Lys Gly Phe Tyr Pro Ser
    595                 600                 605

Asp Ile Ala Val Glu Trp Glu Ser Asn Gly Gln Pro Glu Asn Asn Tyr
610                 615                 620

Lys Thr Thr Pro Pro Val Leu Asp Ser Asp Gly Ser Phe Phe Leu Val
625                 630                 635                 640

Ser Lys Leu Thr Val Asp Lys Ser Arg Trp Gln Gln Gly Asn Val Phe
            645                 650                 655

Ser Cys Ser Val Met His Glu Ala Leu His Asn His Tyr Thr Gln Lys
        660                 665                 670

Ser Leu Ser Leu Ser Pro Gly Gly Gly Gly Ser Gly Gly Gly Gly
    675                 680                 685

Ser Gly Gly Gly Gly Ser Gly Gly Gly Gly Ser Glu Ile Val Leu Thr
690                 695                 700

Gln Ser Pro Gly Thr Leu Ser Leu Ser Pro Gly Glu Arg Ala Thr Leu
705                 710                 715                 720
```

-continued

```
Ser Cys Arg Ala Ser Gln Ser Val Thr Ser Ser Tyr Leu Ala Trp Tyr
            725                 730                 735

Gln Gln Lys Pro Gly Gln Ala Pro Arg Leu Leu Ile Asn Val Gly Ser
            740                 745                 750

Arg Arg Ala Thr Gly Ile Pro Asp Arg Phe Ser Gly Ser Gly Ser Gly
            755                 760                 765

Thr Asp Phe Thr Leu Thr Ile Ser Arg Leu Glu Pro Glu Asp Phe Ala
            770                 775                 780

Val Tyr Tyr Cys Gln Gln Gly Ile Met Leu Pro Pro Thr Phe Gly Gln
785                 790                 795                 800

Gly Thr Lys Val Glu Ile Lys
                805
```

<210> SEQ ID NO 77
<211> LENGTH: 5
<212> TYPE: PRT
<213> ORGANISM: Artificial Sequence
<220> FEATURE:
<223> OTHER INFORMATION: Peptide linker G4S

<400> SEQUENCE: 77

```
Gly Gly Gly Gly Ser
1               5
```

<210> SEQ ID NO 78
<211> LENGTH: 10
<212> TYPE: PRT
<213> ORGANISM: Artificial Sequence
<220> FEATURE:
<223> OTHER INFORMATION: Peptide linker (G4S)2

<400> SEQUENCE: 78

```
Gly Gly Gly Gly Ser Gly Gly Gly Gly Ser
1               5                   10
```

<210> SEQ ID NO 79
<211> LENGTH: 10
<212> TYPE: PRT
<213> ORGANISM: Artificial Sequence
<220> FEATURE:
<223> OTHER INFORMATION: Peptide linker (SG4)2

<400> SEQUENCE: 79

```
Ser Gly Gly Gly Gly Ser Gly Gly Gly Gly
1               5                   10
```

<210> SEQ ID NO 80
<211> LENGTH: 17
<212> TYPE: PRT
<213> ORGANISM: Artificial Sequence
<220> FEATURE:
<223> OTHER INFORMATION: Peptide linker particular

<400> SEQUENCE: 80

```
Gly Gly Gly Gly Gly Ser Gly Gly Gly Gly Ser Ser Gly Gly Gly Gly
1               5                   10                  15

Ser
```

<210> SEQ ID NO 81
<211> LENGTH: 15
<212> TYPE: PRT
<213> ORGANISM: Artificial Sequence
<220> FEATURE:
<223> OTHER INFORMATION: Peptide linker (G4S)3

```
<400> SEQUENCE: 81

Gly Gly Gly Gly Ser Gly Gly Gly Gly Ser Gly Gly Gly Gly Ser
1               5                   10                  15

<210> SEQ ID NO 82
<211> LENGTH: 14
<212> TYPE: PRT
<213> ORGANISM: Artificial Sequence
<220> FEATURE:
<223> OTHER INFORMATION: Peptide linker G4(SG4)2

<400> SEQUENCE: 82

Gly Gly Gly Gly Ser Gly Gly Gly Gly Ser Gly Gly Gly Gly
1               5                   10

<210> SEQ ID NO 83
<211> LENGTH: 20
<212> TYPE: PRT
<213> ORGANISM: Artificial Sequence
<220> FEATURE:
<223> OTHER INFORMATION: Peptide linker (G4S)4

<400> SEQUENCE: 83

Gly Gly Gly Gly Ser Gly Gly Gly Gly Ser Gly Gly Gly Gly Ser Gly
1               5                   10                  15

Gly Gly Gly Ser
            20

<210> SEQ ID NO 84
<211> LENGTH: 19
<212> TYPE: PRT
<213> ORGANISM: Artificial Sequence
<220> FEATURE:
<223> OTHER INFORMATION: Peptide linker GGGGSGGGGSGGGSGGGGS

<400> SEQUENCE: 84

Gly Gly Gly Gly Ser Gly Gly Gly Gly Ser Gly Gly Gly Ser Gly Gly
1               5                   10                  15

Gly Gly Ser

<210> SEQ ID NO 85
<211> LENGTH: 10
<212> TYPE: PRT
<213> ORGANISM: Artificial Sequence
<220> FEATURE:
<223> OTHER INFORMATION: Peptide linker GSPGSSSSGS

<400> SEQUENCE: 85

Gly Ser Pro Gly Ser Ser Ser Ser Gly Ser
1               5                   10

<210> SEQ ID NO 86
<211> LENGTH: 8
<212> TYPE: PRT
<213> ORGANISM: Artificial Sequence
<220> FEATURE:
<223> OTHER INFORMATION: Peptide linker GSGSGSGS

<400> SEQUENCE: 86

Gly Ser Gly Ser Gly Ser Gly Ser
1               5

<210> SEQ ID NO 87
<211> LENGTH: 8
```

```
<212> TYPE: PRT
<213> ORGANISM: Artificial Sequence
<220> FEATURE:
<223> OTHER INFORMATION: Peptide linker GSGSGNGS

<400> SEQUENCE: 87

Gly Ser Gly Ser Gly Asn Gly Ser
1               5

<210> SEQ ID NO 88
<211> LENGTH: 8
<212> TYPE: PRT
<213> ORGANISM: Artificial Sequence
<220> FEATURE:
<223> OTHER INFORMATION: Peptide linker GGSGSGSG

<400> SEQUENCE: 88

Gly Gly Ser Gly Ser Gly Ser Gly
1               5

<210> SEQ ID NO 89
<211> LENGTH: 6
<212> TYPE: PRT
<213> ORGANISM: Artificial Sequence
<220> FEATURE:
<223> OTHER INFORMATION: Peptide linker GGSGSG

<400> SEQUENCE: 89

Gly Gly Ser Gly Ser Gly
1               5

<210> SEQ ID NO 90
<211> LENGTH: 4
<212> TYPE: PRT
<213> ORGANISM: Artificial Sequence
<220> FEATURE:
<223> OTHER INFORMATION: Peptide linker GGSG

<400> SEQUENCE: 90

Gly Gly Ser Gly
1

<210> SEQ ID NO 91
<211> LENGTH: 8
<212> TYPE: PRT
<213> ORGANISM: Artificial Sequence
<220> FEATURE:
<223> OTHER INFORMATION: GGSGNGSG

<400> SEQUENCE: 91

Gly Gly Ser Gly Asn Gly Ser Gly
1               5

<210> SEQ ID NO 92
<211> LENGTH: 8
<212> TYPE: PRT
<213> ORGANISM: Artificial Sequence
<220> FEATURE:
<223> OTHER INFORMATION: Peptide inker GGNGSGSG

<400> SEQUENCE: 92

Gly Gly Asn Gly Ser Gly Ser Gly
1               5

<210> SEQ ID NO 93
<211> LENGTH: 6
<212> TYPE: PRT
```

<213> ORGANISM: Artificial Sequence
<220> FEATURE:
<223> OTHER INFORMATION: Peptide linker GGNGSG

<400> SEQUENCE: 93

Gly Gly Asn Gly Ser Gly
1               5

<210> SEQ ID NO 94
<211> LENGTH: 98
<212> TYPE: PRT
<213> ORGANISM: Homo sapiens

<400> SEQUENCE: 94

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 95
<211> LENGTH: 107
<212> TYPE: PRT
<213> ORGANISM: Homo sapiens

<400> SEQUENCE: 95

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Trp Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Glu Ser Thr Tyr Arg Trp Ser Val Leu Thr Val Leu His Gln Asp Trp
65                  70                  75                  80

Leu Asn Gly Lys Glu Tyr Lys Cys Lys Val Ser Asn Lys Ala Leu Pro
                85                  90                  95

Ala Pro Ile Glu Lys Thr Ile Ser Lys Ala Lys
            100                 105

<210> SEQ ID NO 96
<211> LENGTH: 106
<212> TYPE: PRT
<213> ORGANISM: Homo sapiens

<400> SEQUENCE: 96

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

```
Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 97
<211> LENGTH: 760
<212> TYPE: PRT
<213> ORGANISM: Homo sapiens

<400> SEQUENCE: 97

Met Lys Thr Trp Val Lys Ile Val Phe Gly Val Ala Thr Ser Ala Val
 1               5                  10                  15

Leu Ala Leu Leu Val Met Cys Ile Val Leu Arg Pro Ser Arg Val His
            20                  25                  30

Asn Ser Glu Glu Asn Thr Met Arg Ala Leu Thr Leu Lys Asp Ile Leu
            35                  40                  45

Asn Gly Thr Phe Ser Tyr Lys Thr Phe Phe Pro Asn Trp Ile Ser Gly
 50                  55                  60

Gln Glu Tyr Leu His Gln Ser Ala Asp Asn Asn Ile Val Leu Tyr Asn
 65                  70                  75                  80

Ile Glu Thr Gly Gln Ser Tyr Thr Ile Leu Ser Asn Arg Thr Met Lys
                85                  90                  95

Ser Val Asn Ala Ser Asn Tyr Gly Leu Ser Pro Asp Arg Gln Phe Val
            100                 105                 110

Tyr Leu Glu Ser Asp Tyr Ser Lys Leu Trp Arg Tyr Ser Tyr Thr Ala
            115                 120                 125

Thr Tyr Tyr Ile Tyr Asp Leu Ser Asn Gly Glu Phe Val Arg Gly Asn
            130                 135                 140

Glu Leu Pro Arg Pro Ile Gln Tyr Leu Cys Trp Ser Pro Val Gly Ser
145                 150                 155                 160

Lys Leu Ala Tyr Val Tyr Gln Asn Asn Ile Tyr Leu Lys Gln Arg Pro
                165                 170                 175

Gly Asp Pro Pro Phe Gln Ile Thr Phe Asn Gly Arg Glu Asn Lys Ile
            180                 185                 190

Phe Asn Gly Ile Pro Asp Trp Val Tyr Glu Glu Met Leu Ala Thr
            195                 200                 205

Lys Tyr Ala Leu Trp Trp Ser Pro Asn Gly Lys Phe Leu Ala Tyr Ala
            210                 215                 220

Glu Phe Asn Asp Thr Asp Ile Pro Val Ile Ala Tyr Ser Tyr Tyr Gly
225                 230                 235                 240

Asp Glu Gln Tyr Pro Arg Thr Ile Asn Ile Pro Tyr Pro Lys Ala Gly
                245                 250                 255

Ala Lys Asn Pro Val Val Arg Ile Phe Ile Ile Asp Thr Thr Tyr Pro
            260                 265                 270

Ala Tyr Val Gly Pro Gln Glu Val Pro Val Pro Ala Met Ile Ala Ser
            275                 280                 285
```

```
Ser Asp Tyr Tyr Phe Ser Trp Leu Thr Trp Val Thr Asp Glu Arg Val
    290                 295                 300
Cys Leu Gln Trp Leu Lys Arg Val Gln Asn Val Ser Val Leu Ser Ile
305                 310                 315                 320
Cys Asp Phe Arg Glu Asp Trp Gln Thr Trp Asp Cys Pro Lys Thr Gln
            325                 330                 335
Glu His Ile Glu Glu Ser Arg Thr Gly Trp Ala Gly Gly Phe Phe Val
            340                 345                 350
Ser Thr Pro Val Phe Ser Tyr Asp Ala Ile Ser Tyr Lys Ile Phe
            355                 360                 365
Ser Asp Lys Asp Gly Tyr Lys His Ile His Tyr Ile Lys Asp Thr Val
370                 375                 380
Glu Asn Ala Ile Gln Ile Thr Ser Gly Lys Trp Glu Ala Ile Asn Ile
385                 390                 395                 400
Phe Arg Val Thr Gln Asp Ser Leu Phe Tyr Ser Ser Asn Glu Phe Glu
            405                 410                 415
Glu Tyr Pro Gly Arg Arg Asn Ile Tyr Arg Ile Ser Ile Gly Ser Tyr
            420                 425                 430
Pro Pro Ser Lys Lys Cys Val Thr Cys His Leu Arg Lys Glu Arg Cys
            435                 440                 445
Gln Tyr Tyr Thr Ala Ser Phe Ser Asp Tyr Ala Lys Tyr Tyr Ala Leu
    450                 455                 460
Val Cys Tyr Gly Pro Gly Ile Pro Ile Ser Thr Leu His Asp Gly Arg
465                 470                 475                 480
Thr Asp Gln Glu Ile Lys Ile Leu Glu Glu Asn Lys Glu Leu Glu Asn
            485                 490                 495
Ala Leu Lys Asn Ile Gln Leu Pro Lys Glu Ile Lys Lys Leu Glu
            500                 505                 510
Val Asp Glu Ile Thr Leu Trp Tyr Lys Met Ile Leu Pro Pro Gln Phe
            515                 520                 525
Asp Arg Ser Lys Lys Tyr Pro Leu Leu Ile Gln Val Tyr Gly Gly Pro
                    535                 540
Cys Ser Gln Ser Val Arg Ser Val Phe Ala Val Asn Trp Ile Ser Tyr
545                 550                 555                 560
Leu Ala Ser Lys Glu Gly Met Val Ile Ala Leu Val Asp Gly Arg Gly
                565                 570                 575
Thr Ala Phe Gln Gly Asp Lys Leu Leu Tyr Ala Val Tyr Arg Lys Leu
            580                 585                 590
Gly Val Tyr Glu Val Glu Asp Gln Ile Thr Ala Val Arg Lys Phe Ile
            595                 600                 605
Glu Met Gly Phe Ile Asp Glu Lys Arg Ile Ala Ile Trp Gly Trp Ser
    610                 615                 620
Tyr Gly Gly Tyr Val Ser Ser Leu Ala Leu Ala Ser Gly Thr Gly Leu
625                 630                 635                 640
Phe Lys Cys Gly Ile Ala Val Ala Pro Val Ser Ser Trp Glu Tyr Tyr
            645                 650                 655
Ala Ser Val Tyr Thr Glu Arg Phe Met Gly Leu Pro Thr Lys Asp Asp
            660                 665                 670
Asn Leu Glu His Tyr Lys Asn Ser Thr Val Met Ala Arg Ala Glu Tyr
            675                 680                 685
Phe Arg Asn Val Asp Tyr Leu Leu Ile His Gly Thr Ala Asp Asp Asn
    690                 695                 700
```

-continued

Val His Phe Gln Asn Ser Ala Gln Ile Ala Lys Ala Leu Val Asn Ala
705                 710                 715                 720

Gln Val Asp Phe Gln Ala Met Trp Tyr Ser Asp Gln Asn His Gly Leu
            725                 730                 735

Ser Gly Leu Ser Thr Asn His Leu Tyr Thr His Met Thr His Phe Leu
            740                 745                 750

Lys Gln Cys Phe Ser Leu Ser Asp
            755                 760

<210> SEQ ID NO 98
<211> LENGTH: 761
<212> TYPE: PRT
<213> ORGANISM: Mus musculus

<400> SEQUENCE: 98

Met Lys Thr Trp Leu Lys Thr Val Phe Gly Val Thr Thr Leu Ala Ala
1               5                   10                  15

Leu Ala Leu Val Val Ile Cys Ile Val Leu Arg Pro Ser Arg Val Tyr
            20                  25                  30

Lys Pro Glu Gly Asn Thr Lys Arg Ala Leu Thr Leu Lys Asp Ile Leu
            35                  40                  45

Asn Gly Thr Phe Ser Tyr Lys Thr Tyr Phe Pro Asn Trp Ile Ser Glu
50                  55                  60

Gln Glu Tyr Leu His Gln Ser Glu Asp Asn Ile Val Phe Tyr Asn
65                  70                  75                  80

Ile Glu Thr Arg Glu Ser Tyr Ile Ile Leu Ser Asn Ser Thr Met Lys
            85                  90                  95

Ser Val Asn Ala Thr Asp Tyr Gly Leu Ser Pro Asp Arg Gln Phe Val
            100                 105                 110

Tyr Leu Glu Ser Asp Tyr Ser Lys Leu Trp Arg Tyr Ser Tyr Thr Ala
            115                 120                 125

Thr Tyr Tyr Ile Tyr Asp Leu Gln Asn Gly Glu Phe Val Arg Gly Tyr
            130                 135                 140

Glu Leu Pro Arg Pro Ile Gln Tyr Leu Cys Trp Ser Pro Val Gly Ser
145                 150                 155                 160

Lys Leu Ala Tyr Val Tyr Gln Asn Asn Ile Tyr Leu Lys Gln Arg Pro
            165                 170                 175

Gly Asp Pro Pro Phe Gln Ile Thr Tyr Thr Gly Arg Glu Asn Arg Ile
            180                 185                 190

Phe Asn Gly Ile Pro Asp Trp Val Tyr Glu Glu Glu Met Leu Ala Thr
            195                 200                 205

Lys Tyr Ala Leu Trp Trp Ser Pro Asp Gly Lys Phe Leu Ala Tyr Val
210                 215                 220

Glu Phe Asn Asp Ser Asp Ile Pro Ile Ile Ala Tyr Ser Tyr Tyr Gly
225                 230                 235                 240

Asp Gly Gln Tyr Pro Arg Thr Ile Asn Ile Pro Tyr Pro Lys Ala Gly
            245                 250                 255

Ala Lys Asn Pro Val Val Arg Val Phe Ile Val Asp Thr Thr Tyr Pro
            260                 265                 270

His His Val Gly Pro Met Glu Val Pro Val Pro Glu Met Ile Ala Ser
            275                 280                 285

Ser Asp Tyr Tyr Phe Ser Trp Leu Thr Trp Val Ser Ser Glu Arg Val
            290                 295                 300

Cys Leu Gln Trp Leu Lys Arg Val Gln Asn Val Ser Val Leu Ser Ile
305                 310                 315                 320

-continued

Cys Asp Phe Arg Glu Asp Trp His Ala Trp Glu Cys Pro Lys Asn Gln
                325                 330                 335

Glu His Val Glu Glu Ser Arg Thr Gly Trp Ala Gly Gly Phe Phe Val
                340                 345                 350

Ser Thr Pro Ala Phe Ser Gln Asp Ala Thr Ser Tyr Tyr Lys Ile Phe
                355                 360                 365

Ser Asp Lys Asp Gly Tyr Lys His Ile His Tyr Ile Lys Asp Thr Val
            370                 375                 380

Glu Asn Ala Ile Gln Ile Thr Ser Gly Lys Trp Glu Ala Ile Tyr Ile
385                 390                 395                 400

Phe Arg Val Thr Gln Asp Ser Leu Phe Tyr Ser Asn Glu Phe Glu
                405                 410                 415

Gly Tyr Pro Gly Arg Arg Asn Ile Tyr Arg Ile Ser Ile Gly Asn Ser
                420                 425                 430

Pro Pro Ser Lys Lys Cys Val Thr Cys His Leu Arg Lys Glu Arg Cys
                435                 440                 445

Gln Tyr Tyr Thr Ala Ser Phe Ser Tyr Lys Ala Lys Tyr Tyr Ala Leu
            450                 455                 460

Val Cys Tyr Gly Pro Gly Leu Pro Ile Ser Thr Leu His Asp Gly Arg
465                 470                 475                 480

Thr Asp Gln Glu Ile Gln Val Leu Glu Glu Asn Lys Glu Leu Glu Asn
                485                 490                 495

Ser Leu Arg Asn Ile Gln Leu Pro Lys Val Glu Ile Lys Lys Leu Lys
                500                 505                 510

Asp Gly Gly Leu Thr Phe Trp Tyr Lys Met Ile Leu Pro Pro Gln Phe
            515                 520                 525

Asp Arg Ser Lys Lys Tyr Pro Leu Leu Ile Gln Val Tyr Gly Gly Pro
            530                 535                 540

Cys Ser Gln Ser Val Lys Ser Val Phe Ala Val Asn Trp Ile Thr Tyr
545                 550                 555                 560

Leu Ala Ser Lys Glu Gly Ile Val Ile Ala Leu Val Asp Gly Arg Gly
                565                 570                 575

Thr Ala Phe Gln Gly Asp Lys Phe Leu His Ala Val Tyr Arg Lys Leu
                580                 585                 590

Gly Val Tyr Glu Val Glu Asp Gln Leu Thr Ala Val Arg Lys Phe Ile
            595                 600                 605

Glu Met Gly Phe Ile Asp Glu Arg Ile Ala Ile Trp Gly Trp Ser
610                 615                 620

Tyr Gly Gly Tyr Val Ser Ser Leu Ala Leu Ala Ser Gly Thr Gly Leu
625                 630                 635                 640

Phe Lys Cys Gly Ile Ala Val Ala Pro Val Ser Ser Trp Glu Tyr Tyr
                645                 650                 655

Ala Ser Ile Tyr Ser Glu Arg Phe Met Gly Leu Pro Thr Lys Asp Asp
            660                 665                 670

Asn Leu Glu His Tyr Lys Asn Ser Thr Val Met Ala Arg Ala Glu Tyr
                675                 680                 685

Phe Arg Asn Val Asp Tyr Leu Leu Ile His Gly Thr Ala Asp Asp Asn
            690                 695                 700

Val His Phe Gln Asn Ser Ala Gln Ile Ala Lys Ala Leu Val Asn Ala
705                 710                 715                 720

Gln Val Asp Phe Gln Ala Met Trp Tyr Ser Asp Gln Asn His Gly Ile
                725                 730                 735

```
Ser Ser Gly Arg Ser Gln Asn His Leu Tyr Thr His Met Thr His Phe
        740                 745                 750

Leu Lys Gln Cys Phe Ser Leu Ser Asp
        755                 760

<210> SEQ ID NO 99
<211> LENGTH: 5
<212> TYPE: PRT
<213> ORGANISM: Artificial Sequence
<220> FEATURE:
<223> OTHER INFORMATION: CH1 connector

<400> SEQUENCE: 99

Glu Pro Lys Ser Cys
1               5

<210> SEQ ID NO 100
<211> LENGTH: 10
<212> TYPE: PRT
<213> ORGANISM: Artificial Sequence
<220> FEATURE:
<223> OTHER INFORMATION: hinge with X being S or P
<220> FEATURE:
<221> NAME/KEY: X
<222> LOCATION: (8)..(8)
<223> OTHER INFORMATION: X is S or P

<400> SEQUENCE: 100

Asp Lys Thr His Thr Cys Pro Xaa Cys Pro
1               5                   10

<210> SEQ ID NO 101
<211> LENGTH: 7
<212> TYPE: PRT
<213> ORGANISM: Artificial Sequence
<220> FEATURE:
<223> OTHER INFORMATION: hinge with X being S or P
<220> FEATURE:
<221> NAME/KEY: X
<222> LOCATION: (5)..(5)
<223> OTHER INFORMATION: X is S or P

<400> SEQUENCE: 101

His Thr Cys Pro Xaa Cys Pro
1               5

<210> SEQ ID NO 102
<211> LENGTH: 5
<212> TYPE: PRT
<213> ORGANISM: Artificial Sequence
<220> FEATURE:
<223> OTHER INFORMATION: hinge with X being S or P
<220> FEATURE:
<221> NAME/KEY: X
<222> LOCATION: (3)..(3)
<223> OTHER INFORMATION: X is S or P

<400> SEQUENCE: 102

Cys Pro Xaa Cys Pro
1               5

<210> SEQ ID NO 103
<211> LENGTH: 330
<212> TYPE: PRT
<213> ORGANISM: Homo sapiens
```

<400> SEQUENCE: 103

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 104
<211> LENGTH: 330
<212> TYPE: PRT
<213> ORGANISM: Homo sapiens

<400> SEQUENCE: 104

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 105
<211> LENGTH: 326
<212> TYPE: PRT
<213> ORGANISM: Homo sapiens

<400> SEQUENCE: 105

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

```
Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 106
<211> LENGTH: 377
<212> TYPE: PRT
<213> ORGANISM: Homo sapiens

<400> SEQUENCE: 106

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
 65                 70                  75                  80

Tyr Thr Cys Asn Val Asn His Lys Pro Ser Asn Thr Lys Val Asp Lys
                85                  90                  95
```

```
Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
        130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 107
<211> LENGTH: 327
<212> TYPE: PRT
<213> ORGANISM: Homo sapiens

<400> SEQUENCE: 107

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80
```

```
Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 108
<211> LENGTH: 277
<212> TYPE: PRT
<213> ORGANISM: Homo sapiens

<400> SEQUENCE: 108

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110
```

```
Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
        130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
        210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 109
<211> LENGTH: 255
<212> TYPE: PRT
<213> ORGANISM: Homo sapiens

<400> SEQUENCE: 109

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190
```

```
Ala Leu Thr Ser Thr Ala Leu Leu Phe Leu Leu Phe Leu Thr Leu
            195                 200                 205

Arg Phe Ser Val Val Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 110
<211> LENGTH: 260
<212> TYPE: PRT
<213> ORGANISM: Homo sapiens

<400> SEQUENCE: 110

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu His Gln Arg Arg Lys Tyr Arg Ser Asn Lys Gly Glu Ser
    210                 215                 220

Pro Val Glu Pro Ala Glu Pro Cys His Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255

Ala Cys Ser Pro
            260

<210> SEQ ID NO 111
<211> LENGTH: 283
<212> TYPE: PRT
<213> ORGANISM: Homo sapiens
```

-continued

```
<400> SEQUENCE: 111

Met Glu Pro Pro Gly Asp Trp Gly Pro Pro Trp Arg Ser Thr Pro
1               5                   10                  15

Lys Thr Asp Val Leu Arg Leu Val Leu Tyr Leu Thr Phe Leu Gly Ala
                20                  25                  30

Pro Cys Tyr Ala Pro Ala Leu Pro Ser Cys Lys Glu Asp Glu Tyr Pro
                35                  40                  45

Val Gly Ser Glu Cys Cys Pro Lys Cys Ser Pro Gly Tyr Arg Val Lys
    50                  55                  60

Glu Ala Cys Gly Glu Leu Thr Gly Thr Val Cys Glu Pro Cys Pro Pro
65              70                  75                  80

Gly Thr Tyr Ile Ala His Leu Asn Gly Leu Ser Lys Cys Leu Gln Cys
                    85                  90                  95

Gln Met Cys Asp Pro Ala Met Gly Leu Arg Ala Ser Arg Asn Cys Ser
                100                 105                 110

Arg Thr Glu Asn Ala Val Cys Gly Cys Ser Pro Gly His Phe Cys Ile
                115                 120                 125

Val Gln Asp Gly Asp His Cys Ala Ala Cys Arg Ala Tyr Ala Thr Ser
130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
                180                 185                 190

Gly Ala Gly Thr Ser Ser Ser His Trp Val Trp Trp Phe Leu Ser Gly
                195                 200                 205

Ser Leu Val Ile Val Ile Val Cys Ser Thr Val Gly Leu Ile Ile Cys
210                 215                 220

Val Lys Arg Arg Lys Pro Arg Gly Asp Val Val Lys Val Ile Val Ser
225                 230                 235                 240

Val Gln Arg Lys Arg Gln Glu Ala Glu Gly Glu Ala Thr Val Ile Glu
                245                 250                 255

Ala Leu Gln Ala Pro Pro Asp Val Thr Thr Val Ala Val Glu Glu Thr
                260                 265                 270

Ile Pro Ser Phe Thr Gly Arg Ser Pro Asn His
                275                 280

<210> SEQ ID NO 112
<211> LENGTH: 595
<212> TYPE: PRT
<213> ORGANISM: Homo sapiens

<400> SEQUENCE: 112

Met Arg Val Leu Leu Ala Ala Leu Gly Leu Leu Phe Leu Gly Ala Leu
1               5                   10                  15

Arg Ala Phe Pro Gln Asp Arg Pro Phe Glu Asp Thr Cys His Gly Asn
                20                  25                  30

Pro Ser His Tyr Tyr Asp Lys Ala Val Arg Arg Cys Cys Tyr Arg Cys
                35                  40                  45

Pro Met Gly Leu Phe Pro Thr Gln Gln Cys Pro Gln Arg Pro Thr Asp
            50                  55                  60

Cys Arg Lys Gln Cys Glu Pro Asp Tyr Tyr Leu Asp Glu Ala Asp Arg
65                  70                  75                  80
```

```
Cys Thr Ala Cys Val Thr Cys Ser Arg Asp Asp Leu Val Glu Lys Thr
                85                  90                  95

Pro Cys Ala Trp Asn Ser Ser Arg Val Cys Glu Cys Arg Pro Gly Met
            100                 105                 110

Phe Cys Ser Thr Ser Ala Val Asn Ser Cys Ala Arg Cys Phe Phe His
        115                 120                 125

Ser Val Cys Pro Ala Gly Met Ile Val Lys Phe Pro Gly Thr Ala Gln
    130                 135                 140

Lys Asn Thr Val Cys Glu Pro Ala Ser Pro Gly Val Ser Pro Ala Cys
145                 150                 155                 160

Ala Ser Pro Glu Asn Cys Lys Glu Pro Ser Ser Gly Thr Ile Pro Gln
                165                 170                 175

Ala Lys Pro Thr Pro Val Ser Pro Ala Thr Ser Ser Ala Ser Thr Met
            180                 185                 190

Pro Val Arg Gly Gly Thr Arg Leu Ala Gln Glu Ala Ala Ser Lys Leu
        195                 200                 205

Thr Arg Ala Pro Asp Ser Pro Ser Ser Val Gly Arg Pro Ser Ser Asp
    210                 215                 220

Pro Gly Leu Ser Pro Thr Gln Pro Cys Pro Glu Gly Ser Gly Asp Cys
225                 230                 235                 240

Arg Lys Gln Cys Glu Pro Asp Tyr Tyr Leu Asp Glu Ala Gly Arg Cys
                245                 250                 255

Thr Ala Cys Val Ser Cys Ser Arg Asp Asp Leu Val Glu Lys Thr Pro
            260                 265                 270

Cys Ala Trp Asn Ser Ser Arg Thr Cys Glu Cys Arg Pro Gly Met Ile
        275                 280                 285

Cys Ala Thr Ser Ala Thr Asn Ser Cys Ala Arg Cys Val Pro Tyr Pro
    290                 295                 300

Ile Cys Ala Ala Glu Thr Val Thr Lys Pro Gln Asp Met Ala Glu Lys
305                 310                 315                 320

Asp Thr Thr Phe Glu Ala Pro Pro Leu Gly Thr Gln Pro Asp Cys Asn
                325                 330                 335

Pro Thr Pro Glu Asn Gly Glu Ala Pro Ala Ser Thr Ser Pro Thr Gln
            340                 345                 350

Ser Leu Leu Val Asp Ser Gln Ala Ser Lys Thr Leu Pro Ile Pro Thr
        355                 360                 365

Ser Ala Pro Val Ala Leu Ser Ser Thr Gly Lys Pro Val Leu Asp Ala
    370                 375                 380

Gly Pro Val Leu Phe Trp Val Ile Leu Val Leu Val Val Val Val Gly
385                 390                 395                 400

Ser Ser Ala Phe Leu Leu Cys His Arg Arg Ala Cys Arg Lys Arg Ile
                405                 410                 415

Arg Gln Lys Leu His Leu Cys Tyr Pro Val Gln Thr Ser Gln Pro Lys
            420                 425                 430

Leu Glu Leu Val Asp Ser Arg Pro Arg Arg Ser Ser Thr Gln Leu Arg
        435                 440                 445

Ser Gly Ala Ser Val Thr Glu Pro Val Ala Glu Glu Arg Gly Leu Met
    450                 455                 460

Ser Gln Pro Leu Met Glu Thr Cys His Ser Val Gly Ala Ala Tyr Leu
465                 470                 475                 480

Glu Ser Leu Pro Leu Gln Asp Ala Ser Pro Ala Gly Gly Pro Ser Ser
                485                 490                 495
```

```
Pro Arg Asp Leu Pro Glu Pro Arg Val Ser Thr Glu His Thr Asn Asn
            500                 505                 510

Lys Ile Glu Lys Ile Tyr Ile Met Lys Ala Asp Thr Val Ile Val Gly
        515                 520                 525

Thr Val Lys Ala Glu Leu Pro Glu Gly Arg Gly Leu Ala Gly Pro Ala
    530                 535                 540

Glu Pro Glu Leu Glu Glu Leu Glu Ala Asp His Thr Pro His Tyr
545                 550                 555                 560

Pro Glu Gln Glu Thr Glu Pro Pro Leu Gly Ser Cys Ser Asp Val Met
                565                 570                 575

Leu Ser Val Glu Glu Gly Lys Glu Asp Pro Leu Pro Thr Ala Ala
            580                 585                 590

Ser Gly Lys
        595

<210> SEQ ID NO 113
<211> LENGTH: 241
<212> TYPE: PRT
<213> ORGANISM: Homo sapiens

<400> SEQUENCE: 113

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Leu Gly Thr Gly Thr Asp Ala Arg
        35                  40                  45

Cys Cys Arg Val His Thr Thr Arg Cys Cys Arg Asp Tyr Pro Gly Glu
    50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Ser Gln Cys Met Trp Pro Arg Glu Thr Gln Leu Leu Leu Glu Val
        195                 200                 205

Pro Pro Ser Thr Glu Asp Ala Arg Ser Cys Gln Phe Pro Glu Glu Glu
    210                 215                 220

Arg Gly Glu Arg Ser Ala Glu Glu Lys Gly Arg Leu Gly Asp Leu Trp
225                 230                 235                 240

Val

<210> SEQ ID NO 114
<211> LENGTH: 272
```

```
<212> TYPE: PRT
<213> ORGANISM: Mus musculus

<400> SEQUENCE: 114

Met Tyr Val Trp Val Gln Gln Pro Thr Ala Leu Leu Leu Ala Leu
1               5                   10                  15

Thr Leu Gly Val Thr Ala Arg Arg Leu Asn Cys Val Lys His Thr Tyr
            20                  25                  30

Pro Ser Gly His Lys Cys Cys Arg Glu Cys Gln Pro Gly His Gly Met
            35                  40                  45

Val Ser Arg Cys Asp His Thr Arg Asp Thr Leu Cys His Pro Cys Glu
        50                  55                  60

Thr Gly Phe Tyr Asn Glu Ala Val Asn Tyr Asp Thr Cys Lys Gln Cys
65              70                  75                  80

Thr Gln Cys Asn His Arg Ser Gly Ser Glu Leu Lys Gln Asn Cys Thr
                85                  90                  95

Pro Thr Gln Asp Thr Val Cys Arg Cys Arg Pro Gly Thr Gln Pro Arg
            100                 105                 110

Gln Asp Ser Gly Tyr Lys Leu Gly Val Asp Cys Val Pro Cys Pro Pro
        115                 120                 125

Gly His Phe Ser Pro Gly Asn Asn Gln Ala Cys Lys Pro Trp Thr Asn
    130                 135                 140

Cys Thr Leu Ser Gly Lys Gln Thr Arg His Pro Ala Ser Asp Ser Leu
145             150                 155                 160

Asp Ala Val Cys Glu Asp Arg Ser Leu Leu Ala Thr Leu Leu Trp Glu
                165                 170                 175

Thr Gln Arg Pro Thr Phe Arg Pro Thr Thr Val Gln Ser Thr Thr Val
            180                 185                 190

Trp Pro Arg Thr Ser Glu Leu Pro Ser Pro Pro Thr Leu Val Thr Pro
        195                 200                 205

Glu Gly Pro Ala Phe Ala Val Leu Leu Gly Leu Gly Leu Gly Leu Leu
    210                 215                 220

Ala Pro Leu Thr Val Leu Leu Ala Leu Tyr Leu Leu Arg Lys Ala Trp
225             230                 235                 240

Arg Leu Pro Asn Thr Pro Lys Pro Cys Trp Gly Asn Ser Phe Arg Thr
                245                 250                 255

Pro Ile Gln Glu Glu His Thr Asp Ala His Phe Thr Leu Ala Lys Ile
            260                 265                 270

<210> SEQ ID NO 115
<211> LENGTH: 277
<212> TYPE: PRT
<213> ORGANISM: Homo sapiens

<400> SEQUENCE: 115

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
        50                  55                  60

Ser Glu Phe Leu Asp Thr Trp Asn Arg Glu Thr His Cys His Gln His
65              70                  75                  80
```

```
Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
            115                 120                 125

Phe Gly Val Lys Gln Ile Ala Thr Gly Val Ser Asp Thr Ile Cys Glu
            130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
            195                 200                 205

Leu Leu Val Leu Val Phe Ile Lys Lys Val Ala Lys Lys Pro Thr Asn
            210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
            275

<210> SEQ ID NO 116
<211> LENGTH: 914
<212> TYPE: PRT
<213> ORGANISM: Artificial Sequence
<220> FEATURE:
<223> OTHER INFORMATION: first fusion polypeptide (Fc knob) P1AE1122

<400> SEQUENCE: 116

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160
```

```
Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Gly Gly Gly
                210                 215                 220

Gly Ser Gly Gly Gly Gly Ser Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
                260                 265                 270

Val Val Val Asp Val Ser His Glu Asp Pro Glu Val Lys Phe Asn Trp
                275                 280                 285

Tyr Val Asp Gly Val Glu Val His Asn Ala Lys Thr Lys Pro Arg Glu
                290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Gly Ala Pro Ile Glu Lys Thr Ile Ser Lys Ala Lys Gly
                340                 345                 350

Gln Pro Arg Glu Pro Gln Val Tyr Thr Leu Pro Pro Cys Arg Asp Glu
                355                 360                 365

Leu Thr Lys Asn Gln Val Ser Leu Trp Cys Leu Val Lys Gly Phe Tyr
                370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
                420                 425                 430

Val Phe Ser Cys Ser Val Met His Glu Ala Leu His Asn His Tyr Thr
                435                 440                 445

Gln Lys Ser Leu Ser Leu Ser Pro Gly Lys Gly Gly Gly Gly Ser Gly
                450                 455                 460

Gly Gly Gly Ser Asp Ile Gln Met Thr Gln Ser Pro Ser Thr Leu Ser
465                 470                 475                 480

Ala Ser Val Gly Asp Arg Val Thr Ile Thr Cys Arg Ala Ser Gln Ser
                485                 490                 495

Ile Ser Ser Trp Leu Ala Trp Tyr Gln Gln Lys Pro Gly Lys Ala Pro
                500                 505                 510

Lys Leu Leu Ile Tyr Asp Ala Ser Ser Leu Glu Ser Gly Val Pro Ser
                515                 520                 525

Arg Phe Ser Gly Ser Gly Ser Gly Thr Glu Phe Thr Leu Thr Ile Ser
                530                 535                 540

Ser Leu Gln Pro Asp Asp Phe Ala Thr Tyr Tyr Cys Gln Gln Tyr Ser
545                 550                 555                 560

Ser Gln Pro Tyr Thr Phe Gly Gln Gly Thr Lys Val Glu Ile Lys Arg
                565                 570                 575
```

```
Thr Val Ala Ala Pro Ser Val Phe Ile Phe Pro Ser Asp Glu Gln
            580                 585                 590

Leu Lys Ser Gly Thr Ala Ser Val Val Cys Leu Leu Asn Asn Phe Tyr
        595                 600                 605

Pro Arg Glu Ala Lys Val Gln Trp Lys Val Asp Asn Ala Leu Gln Ser
    610                 615                 620

Gly Asn Ser Gln Glu Ser Val Thr Glu Gln Asp Ser Lys Asp Ser Thr
625                 630                 635                 640

Tyr Ser Leu Ser Ser Thr Leu Thr Leu Ser Lys Ala Asp Tyr Glu Lys
            645                 650                 655

His Lys Val Tyr Ala Cys Glu Val Thr His Gln Gly Leu Ser Ser Pro
        660                 665                 670

Val Thr Lys Ser Phe Asn Arg Gly Glu Cys Gly Gly Gly Gly Ser Gly
    675                 680                 685

Gly Gly Gly Ser Gly Gly Gly Ser Gly Gly Gly Ser Glu Ile Val
690                 695                 700

Leu Thr Gln Ser Pro Gly Thr Leu Ser Leu Ser Pro Gly Glu Arg Ala
705                 710                 715                 720

Thr Leu Ser Cys Arg Ala Ser Gln Ser Val Thr Ser Ser Tyr Leu Ala
            725                 730                 735

Trp Tyr Gln Gln Lys Pro Gly Gln Ala Pro Arg Leu Leu Ile Asn Val
        740                 745                 750

Gly Ser Arg Arg Ala Thr Gly Ile Pro Asp Arg Phe Ser Gly Ser Gly
    755                 760                 765

Ser Gly Thr Asp Phe Thr Leu Thr Ile Ser Arg Leu Glu Pro Glu Asp
770                 775                 780

Phe Ala Val Tyr Tyr Cys Gln Gln Gly Ile Met Leu Pro Pro Thr Phe
785                 790                 795                 800

Gly Gln Gly Thr Lys Val Glu Ile Lys Ser Ser Ala Ser Thr Lys Gly
            805                 810                 815

Pro Ser Val Phe Pro Leu Ala Pro Ser Ser Lys Ser Thr Ser Gly Gly
        820                 825                 830

Thr Ala Ala Leu Gly Cys Leu Val Lys Asp Tyr Phe Pro Glu Pro Val
    835                 840                 845

Thr Val Ser Trp Asn Ser Gly Ala Leu Thr Ser Gly Val His Thr Phe
850                 855                 860

Pro Ala Val Leu Gln Ser Ser Gly Leu Tyr Ser Leu Ser Ser Val Val
865                 870                 875                 880

Thr Val Pro Ser Ser Ser Leu Gly Thr Gln Thr Tyr Ile Cys Asn Val
            885                 890                 895

Asn His Lys Pro Ser Asn Thr Lys Val Asp Lys Lys Val Glu Pro Lys
        900                 905                 910

Ser Cys

<210> SEQ ID NO 117
<211> LENGTH: 925
<212> TYPE: PRT
<213> ORGANISM: Artificial Sequence
<220> FEATURE:
<223> OTHER INFORMATION: second fusion polypeptide (Fc hole) P1AE1122

<400> SEQUENCE: 117

Gln Val Gln Leu Val Gln Ser Gly Ala Glu Val Lys Lys Pro Gly Ser
1               5                   10                  15
```

```
Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
                100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Gly Gly Gly
        210                 215                 220

Gly Ser Gly Gly Gly Gly Ser Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
                260                 265                 270

Val Val Val Asp Val Ser His Glu Asp Pro Glu Val Lys Phe Asn Trp
            275                 280                 285

Tyr Val Asp Gly Val Glu Val His Asn Ala Lys Thr Lys Pro Arg Glu
        290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Gly Ala Pro Ile Glu Lys Thr Ile Ser Lys Ala Lys Gly
                340                 345                 350

Gln Pro Arg Glu Pro Gln Val Cys Thr Leu Pro Pro Ser Arg Asp Glu
            355                 360                 365

Leu Thr Lys Asn Gln Val Ser Leu Ser Cys Ala Val Lys Gly Phe Tyr
        370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
                420                 425                 430
```

```
Val Phe Ser Cys Ser Val Met His Glu Ala Leu His Asn His Tyr Thr
            435                 440                 445

Gln Lys Ser Leu Ser Leu Ser Pro Gly Lys Gly Gly Gly Gly Ser Gly
        450                 455                 460

Gly Gly Gly Ser Asp Ile Gln Met Thr Gln Ser Pro Ser Thr Leu Ser
465                 470                 475                 480

Ala Ser Val Gly Asp Arg Val Thr Ile Thr Cys Arg Ala Ser Gln Ser
                485                 490                 495

Ile Ser Ser Trp Leu Ala Trp Tyr Gln Gln Lys Pro Gly Lys Ala Pro
                500                 505                 510

Lys Leu Leu Ile Tyr Asp Ala Ser Ser Leu Glu Ser Gly Val Pro Ser
        515                 520                 525

Arg Phe Ser Gly Ser Gly Ser Gly Thr Glu Phe Thr Leu Thr Ile Ser
    530                 535                 540

Ser Leu Gln Pro Asp Asp Phe Ala Thr Tyr Tyr Cys Gln Gln Tyr Ser
545                 550                 555                 560

Ser Gln Pro Tyr Thr Phe Gly Gln Gly Thr Lys Val Glu Ile Lys Arg
                565                 570                 575

Thr Val Ala Ala Pro Ser Val Phe Ile Phe Pro Pro Ser Asp Glu Gln
            580                 585                 590

Leu Lys Ser Gly Thr Ala Ser Val Val Cys Leu Leu Asn Asn Phe Tyr
        595                 600                 605

Pro Arg Glu Ala Lys Val Gln Trp Lys Val Asp Asn Ala Leu Gln Ser
    610                 615                 620

Gly Asn Ser Gln Glu Ser Val Thr Glu Gln Asp Ser Lys Asp Ser Thr
625                 630                 635                 640

Tyr Ser Leu Ser Ser Thr Leu Thr Leu Ser Lys Ala Asp Tyr Glu Lys
                645                 650                 655

His Lys Val Tyr Ala Cys Glu Val Thr His Gln Gly Leu Ser Ser Pro
            660                 665                 670

Val Thr Lys Ser Phe Asn Arg Gly Glu Cys Gly Gly Gly Gly Ser Gly
        675                 680                 685

Gly Gly Gly Ser Gly Gly Ser Gly Gly Gly Ser Glu Val Gln
        690                 695                 700

Leu Leu Glu Ser Gly Gly Gly Leu Val Gln Pro Gly Gly Ser Leu Arg
705                 710                 715                 720

Leu Ser Cys Ala Ala Ser Gly Phe Thr Phe Ser Ser Tyr Ala Met Ser
                725                 730                 735

Trp Val Arg Gln Ala Pro Gly Lys Gly Leu Glu Trp Val Ser Ala Ile
            740                 745                 750

Ile Gly Ser Gly Ala Ser Thr Tyr Tyr Ala Asp Ser Val Lys Gly Arg
        755                 760                 765

Phe Thr Ile Ser Arg Asp Asn Ser Lys Asn Thr Leu Tyr Leu Gln Met
    770                 775                 780

Asn Ser Leu Arg Ala Glu Asp Thr Ala Val Tyr Tyr Cys Ala Lys Gly
785                 790                 795                 800

Trp Phe Gly Gly Phe Asn Tyr Trp Gly Gln Gly Thr Leu Val Thr Val
                805                 810                 815

Ser Ser Ala Ser Val Ala Ala Pro Ser Val Phe Ile Phe Pro Pro Ser
            820                 825                 830

Asp Glu Gln Leu Lys Ser Gly Thr Ala Ser Val Val Cys Leu Leu Asn
        835                 840                 845
```

Asn Phe Tyr Pro Arg Glu Ala Lys Val Gln Trp Lys Val Asp Asn Ala
850                 855                 860

Leu Gln Ser Gly Asn Ser Gln Glu Ser Val Thr Glu Gln Asp Ser Lys
865                 870                 875                 880

Asp Ser Thr Tyr Ser Leu Ser Ser Thr Leu Thr Leu Ser Lys Ala Asp
                885                 890                 895

Tyr Glu Lys His Lys Val Tyr Ala Cys Glu Val Thr His Gln Gly Leu
            900                 905                 910

Ser Ser Pro Val Thr Lys Ser Phe Asn Arg Gly Glu Cys
            915                 920                 925

<210> SEQ ID NO 118
<211> LENGTH: 914
<212> TYPE: PRT
<213> ORGANISM: Artificial Sequence
<220> FEATURE:
<223> OTHER INFORMATION: first fusion polypeptide (Fc knob) P1AE1942

<400> SEQUENCE: 118

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Gln Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

```
His Asn Ala Lys Thr Lys Pro Arg Glu Glu Gln Tyr Asn Ser Thr Tyr
290                 295                 300

Arg Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Asp Glu Leu Thr Lys Asn Gln Val Ser
                355                 360                 365

Leu Trp Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys Gly Gly Gly Gly Ser Gly Gly Gly Ser Gln Val Gln
450                 455                 460

Leu Val Gln Ser Gly Ala Glu Val Lys Lys Pro Gly Ser Ser Val Lys
465                 470                 475                 480

Val Ser Cys Lys Ala Ser Gly Gly Thr Phe Ser Ser Tyr Ala Ile Ser
                485                 490                 495

Trp Val Arg Gln Ala Pro Gly Gln Gly Leu Glu Trp Met Gly Gly Ile
                500                 505                 510

Ile Pro Ile Phe Gly Thr Ala Asn Tyr Ala Gln Lys Phe Gln Gly Arg
                515                 520                 525

Val Thr Ile Thr Ala Asp Lys Ser Thr Ser Thr Ala Tyr Met Glu Leu
                530                 535                 540

Ser Ser Leu Arg Ser Glu Asp Thr Ala Val Tyr Tyr Cys Ala Arg Glu
545                 550                 555                 560

Tyr Tyr Arg Gly Pro Tyr Asp Tyr Trp Gly Gln Gly Thr Thr Val Thr
                565                 570                 575

Val Ser Ser Ala Ser Thr Lys Gly Pro Ser Val Phe Pro Leu Ala Pro
                580                 585                 590

Ser Ser Lys Ser Thr Ser Gly Gly Thr Ala Ala Leu Gly Cys Leu Val
                595                 600                 605

Lys Asp Tyr Phe Pro Glu Pro Val Thr Val Ser Trp Asn Ser Gly Ala
                610                 615                 620

Leu Thr Ser Gly Val His Thr Phe Pro Ala Val Leu Gln Ser Ser Gly
625                 630                 635                 640

Leu Tyr Ser Leu Ser Ser Val Val Thr Val Pro Ser Ser Ser Leu Gly
                645                 650                 655

Thr Gln Thr Tyr Ile Cys Asn Val Asn His Lys Pro Ser Asn Thr Lys
                660                 665                 670

Val Asp Lys Lys Val Glu Pro Lys Ser Cys Gly Gly Gly Gly Ser Gly
                675                 680                 685

Gly Gly Gly Ser Gly Gly Gly Ser Gly Gly Gly Gly Ser Glu Ile Val
690                 695                 700
```

```
Leu Thr Gln Ser Pro Gly Thr Leu Ser Leu Ser Pro Gly Glu Arg Ala
705                 710                 715                 720

Thr Leu Ser Cys Arg Ala Ser Gln Ser Val Thr Ser Ser Tyr Leu Ala
            725                 730                 735

Trp Tyr Gln Gln Lys Pro Gly Gln Ala Pro Arg Leu Leu Ile Asn Val
        740                 745                 750

Gly Ser Arg Arg Ala Thr Gly Ile Pro Asp Arg Phe Ser Gly Ser Gly
    755                 760                 765

Ser Gly Thr Asp Phe Thr Leu Thr Ile Ser Arg Leu Glu Pro Glu Asp
770                 775                 780

Phe Ala Val Tyr Tyr Cys Gln Gln Gly Ile Met Leu Pro Pro Thr Phe
785                 790                 795                 800

Gly Gln Gly Thr Lys Val Glu Ile Lys Ser Ser Ala Ser Thr Lys Gly
            805                 810                 815

Pro Ser Val Phe Pro Leu Ala Pro Ser Ser Lys Ser Thr Ser Gly Gly
        820                 825                 830

Thr Ala Ala Leu Gly Cys Leu Val Lys Asp Tyr Phe Pro Glu Pro Val
    835                 840                 845

Thr Val Ser Trp Asn Ser Gly Ala Leu Thr Ser Gly Val His Thr Phe
850                 855                 860

Pro Ala Val Leu Gln Ser Ser Gly Leu Tyr Ser Leu Ser Ser Val Val
865                 870                 875                 880

Thr Val Pro Ser Ser Ser Leu Gly Thr Gln Thr Tyr Ile Cys Asn Val
            885                 890                 895

Asn His Lys Pro Ser Asn Thr Lys Val Asp Lys Lys Val Glu Pro Lys
        900                 905                 910

Ser Cys

<210> SEQ ID NO 119
<211> LENGTH: 925
<212> TYPE: PRT
<213> ORGANISM: Artificial Sequence
<220> FEATURE:
<223> OTHER INFORMATION: second fusion polypeptide (Fc hole) P1AE1942

<400> SEQUENCE: 119

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Gln Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Gly Ser Gln Val Gln
    450                 455                 460

Leu Val Gln Ser Gly Ala Glu Val Lys Lys Pro Gly Ser Ser Val Lys
465                 470                 475                 480

Val Ser Cys Lys Ala Ser Gly Gly Thr Phe Ser Ser Tyr Ala Ile Ser
                485                 490                 495

Trp Val Arg Gln Ala Pro Gly Gln Gly Leu Glu Trp Met Gly Gly Ile
            500                 505                 510

Ile Pro Ile Phe Gly Thr Ala Asn Tyr Ala Gln Lys Phe Gln Gly Arg
        515                 520                 525

Val Thr Ile Thr Ala Asp Lys Ser Thr Ser Thr Ala Tyr Met Glu Leu
    530                 535                 540

Ser Ser Leu Arg Ser Glu Asp Thr Ala Val Tyr Tyr Cys Ala Arg Glu
545                 550                 555                 560
```

-continued

```
Tyr Tyr Arg Gly Pro Tyr Asp Tyr Trp Gly Gln Gly Thr Thr Val Thr
            565                 570                 575

Val Ser Ser Ala Ser Thr Lys Gly Pro Ser Val Phe Pro Leu Ala Pro
        580                 585                 590

Ser Ser Lys Ser Thr Ser Gly Gly Thr Ala Ala Leu Gly Cys Leu Val
            595                 600                 605

Lys Asp Tyr Phe Pro Glu Pro Val Thr Val Ser Trp Asn Ser Gly Ala
610                 615                 620

Leu Thr Ser Gly Val His Thr Phe Pro Ala Val Leu Gln Ser Ser Gly
625                 630                 635                 640

Leu Tyr Ser Leu Ser Ser Val Val Thr Val Pro Ser Ser Ser Leu Gly
            645                 650                 655

Thr Gln Thr Tyr Ile Cys Asn Val Asn His Lys Pro Ser Asn Thr Lys
            660                 665                 670

Val Asp Lys Lys Val Glu Pro Lys Ser Cys Gly Gly Gly Ser Gly
            675                 680                 685

Gly Gly Gly Ser Gly Gly Ser Gly Gly Gly Ser Glu Val Gln
    690                 695                 700

Leu Leu Glu Ser Gly Gly Gly Leu Val Gln Pro Gly Gly Ser Leu Arg
705                 710                 715                 720

Leu Ser Cys Ala Ala Ser Gly Phe Thr Phe Ser Ser Tyr Ala Met Ser
                725                 730                 735

Trp Val Arg Gln Ala Pro Gly Lys Gly Leu Glu Trp Val Ser Ala Ile
                740                 745                 750

Ile Gly Ser Gly Ala Ser Thr Tyr Tyr Ala Asp Ser Val Lys Gly Arg
            755                 760                 765

Phe Thr Ile Ser Arg Asp Asn Ser Lys Asn Thr Leu Tyr Leu Gln Met
770                 775                 780

Asn Ser Leu Arg Ala Glu Asp Thr Ala Val Tyr Tyr Cys Ala Lys Gly
785                 790                 795                 800

Trp Phe Gly Gly Phe Asn Tyr Trp Gly Gln Gly Thr Leu Val Thr Val
                805                 810                 815

Ser Ser Ala Ser Val Ala Ala Pro Ser Val Phe Ile Phe Pro Pro Ser
            820                 825                 830

Asp Glu Gln Leu Lys Ser Gly Thr Ala Ser Val Val Cys Leu Leu Asn
            835                 840                 845

Asn Phe Tyr Pro Arg Glu Ala Lys Val Gln Trp Lys Val Asp Asn Ala
850                 855                 860

Leu Gln Ser Gly Asn Ser Gln Glu Ser Val Thr Glu Gln Asp Ser Lys
865                 870                 875                 880

Asp Ser Thr Tyr Ser Leu Ser Ser Thr Leu Thr Leu Ser Lys Ala Asp
                885                 890                 895

Tyr Glu Lys His Lys Val Tyr Ala Cys Glu Val Thr His Gln Gly Leu
                900                 905                 910

Ser Ser Pro Val Thr Lys Ser Phe Asn Arg Gly Glu Cys
            915                 920                 925

<210> SEQ ID NO 120
<211> LENGTH: 925
<212> TYPE: PRT
<213> ORGANISM: Artificial Sequence
<220> FEATURE:
<223> OTHER INFORMATION: first fusion polypeptide (Fc knob) P1AE1887
```

<400> SEQUENCE: 120

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Gln Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Ser
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Asp Glu Leu Thr Lys Asn Gln Val Ser
        355                 360                 365

Leu Trp Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

```
Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys Gly Gly Gly Gly Ser Gly Gly Gly Gly Ser Gln Val Gln
    450                 455                 460

Leu Val Gln Ser Gly Ala Glu Val Lys Lys Pro Gly Ser Ser Val Lys
465                 470                 475                 480

Val Ser Cys Lys Ala Ser Gly Gly Thr Phe Ser Ser Tyr Ala Ile Ser
                485                 490                 495

Trp Val Arg Gln Ala Pro Gly Gln Gly Leu Glu Trp Met Gly Gly Ile
            500                 505                 510

Ile Pro Ile Phe Gly Thr Ala Asn Tyr Ala Gln Lys Phe Gln Gly Arg
            515                 520                 525

Val Thr Ile Thr Ala Asp Lys Ser Thr Ser Thr Ala Tyr Met Glu Leu
            530                 535                 540

Ser Ser Leu Arg Ser Glu Asp Thr Ala Val Tyr Tyr Cys Ala Arg Glu
545                 550                 555                 560

Tyr Tyr Arg Gly Pro Tyr Asp Tyr Trp Gly Gln Gly Thr Thr Val Thr
                565                 570                 575

Val Ser Ser Ala Ser Thr Lys Gly Pro Ser Val Phe Pro Leu Ala Pro
            580                 585                 590

Ser Ser Lys Ser Thr Ser Gly Gly Thr Ala Ala Leu Gly Cys Leu Val
            595                 600                 605

Lys Asp Tyr Phe Pro Glu Pro Val Thr Val Ser Trp Asn Ser Gly Ala
            610                 615                 620

Leu Thr Ser Gly Val His Thr Phe Pro Ala Val Leu Gln Ser Ser Gly
625                 630                 635                 640

Leu Tyr Ser Leu Ser Ser Val Val Thr Val Pro Ser Ser Ser Leu Gly
                645                 650                 655

Thr Gln Thr Tyr Ile Cys Asn Val Asn His Lys Pro Ser Asn Thr Lys
            660                 665                 670

Val Asp Lys Lys Val Glu Pro Lys Ser Cys Gly Gly Gly Gly Ser Gly
            675                 680                 685

Gly Gly Gly Ser Gly Gly Gly Gly Ser Gly Gly Gly Gly Ser Glu Val Gln
    690                 695                 700

Leu Leu Glu Ser Gly Gly Gly Leu Val Gln Pro Gly Gly Ser Leu Arg
705                 710                 715                 720

Leu Ser Cys Ala Ala Ser Gly Phe Thr Phe Ser Ser Tyr Ala Met Ser
                725                 730                 735

Trp Val Arg Gln Ala Pro Gly Lys Gly Leu Glu Trp Val Ser Ala Ile
            740                 745                 750

Ile Gly Ser Gly Ala Ser Thr Tyr Tyr Ala Asp Ser Val Lys Gly Arg
            755                 760                 765

Phe Thr Ile Ser Arg Asp Asn Ser Lys Asn Thr Leu Tyr Leu Gln Met
            770                 775                 780

Asn Ser Leu Arg Ala Glu Asp Thr Ala Val Tyr Tyr Cys Ala Lys Gly
785                 790                 795                 800

Trp Phe Gly Gly Phe Asn Tyr Trp Gly Gln Gly Thr Leu Val Thr Val
                805                 810                 815
```

```
Ser Ser Ala Ser Val Ala Ala Pro Ser Val Phe Ile Phe Pro Pro Ser
                820                 825                 830

Asp Glu Gln Leu Lys Ser Gly Thr Ala Ser Val Val Cys Leu Leu Asn
            835                 840                 845

Asn Phe Tyr Pro Arg Glu Ala Lys Val Gln Trp Lys Val Asp Asn Ala
        850                 855                 860

Leu Gln Ser Gly Asn Ser Gln Glu Ser Val Thr Glu Gln Asp Ser Lys
865                 870                 875                 880

Asp Ser Thr Tyr Ser Leu Ser Ser Thr Leu Thr Leu Ser Lys Ala Asp
                885                 890                 895

Tyr Glu Lys His Lys Val Tyr Ala Cys Glu Val Thr His Gln Gly Leu
            900                 905                 910

Ser Ser Pro Val Thr Lys Ser Phe Asn Arg Gly Glu Cys
        915                 920                 925

<210> SEQ ID NO 121
<211> LENGTH: 914
<212> TYPE: PRT
<213> ORGANISM: Artificial Sequence
<220> FEATURE:
<223> OTHER INFORMATION: second fusion polypeptide (Fc hole) P1AE1887

<400> SEQUENCE: 121

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Gly Gly Gly
    210                 215                 220

Gly Ser Gly Gly Gly Gly Ser Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255
```

-continued

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Gly Ala Pro Ile Glu Lys Thr Ile Ser Lys Ala Lys Gly
            340                 345                 350

Gln Pro Arg Glu Pro Gln Val Cys Thr Leu Pro Pro Ser Arg Asp Glu
        355                 360                 365

Leu Thr Lys Asn Gln Val Ser Leu Ser Cys Ala Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys Gly Gly Gly Gly Ser Gly
    450                 455                 460

Gly Gly Gly Ser Asp Ile Gln Met Thr Gln Ser Pro Ser Thr Leu Ser
465                 470                 475                 480

Ala Ser Val Gly Asp Arg Val Thr Ile Thr Cys Arg Ala Ser Gln Ser
                485                 490                 495

Ile Ser Ser Trp Leu Ala Trp Tyr Gln Gln Lys Pro Gly Lys Ala Pro
            500                 505                 510

Lys Leu Leu Ile Tyr Asp Ala Ser Ser Leu Glu Ser Gly Val Pro Ser
        515                 520                 525

Arg Phe Ser Gly Ser Gly Ser Gly Thr Glu Phe Thr Leu Thr Ile Ser
    530                 535                 540

Ser Leu Gln Pro Asp Asp Phe Ala Thr Tyr Tyr Cys Gln Gln Tyr Ser
545                 550                 555                 560

Ser Gln Pro Tyr Thr Phe Gly Gln Gly Thr Lys Val Glu Ile Lys Arg
                565                 570                 575

Thr Val Ala Ala Pro Ser Val Phe Ile Phe Pro Pro Ser Asp Glu Gln
            580                 585                 590

Leu Lys Ser Gly Thr Ala Ser Val Val Cys Leu Leu Asn Asn Phe Tyr
        595                 600                 605

Pro Arg Glu Ala Lys Val Gln Trp Lys Val Asp Asn Ala Leu Gln Ser
    610                 615                 620

Gly Asn Ser Gln Glu Ser Val Thr Glu Gln Asp Ser Lys Asp Ser Thr
625                 630                 635                 640

Tyr Ser Leu Ser Ser Thr Leu Thr Leu Ser Lys Ala Asp Tyr Glu Lys
                645                 650                 655

His Lys Val Tyr Ala Cys Glu Val Thr His Gln Gly Leu Ser Ser Pro
            660                 665                 670

Val Thr Lys Ser Phe Asn Arg Gly Glu Cys Gly Gly Gly Ser Gly
            675                 680                 685

Gly Gly Gly Ser Gly Gly Ser Gly Gly Gly Ser Glu Ile Val
    690                 695                 700

Leu Thr Gln Ser Pro Gly Thr Leu Ser Leu Ser Pro Gly Glu Arg Ala
705                 710                 715                 720

Thr Leu Ser Cys Arg Ala Ser Gln Ser Val Thr Ser Ser Tyr Leu Ala
                725                 730                 735

Trp Tyr Gln Gln Lys Pro Gly Gln Ala Pro Arg Leu Leu Ile Asn Val
            740                 745                 750

Gly Ser Arg Arg Ala Thr Gly Ile Pro Asp Arg Phe Ser Gly Ser Gly
            755                 760                 765

Ser Gly Thr Asp Phe Thr Leu Thr Ile Ser Arg Leu Glu Pro Glu Asp
            770                 775                 780

Phe Ala Val Tyr Tyr Cys Gln Gln Gly Ile Met Leu Pro Pro Thr Phe
785                 790                 795                 800

Gly Gln Gly Thr Lys Val Glu Ile Lys Ser Ser Ala Ser Thr Lys Gly
                805                 810                 815

Pro Ser Val Phe Pro Leu Ala Pro Ser Ser Lys Ser Thr Ser Gly Gly
            820                 825                 830

Thr Ala Ala Leu Gly Cys Leu Val Lys Asp Tyr Phe Pro Glu Pro Val
            835                 840                 845

Thr Val Ser Trp Asn Ser Gly Ala Leu Thr Ser Gly Val His Thr Phe
            850                 855                 860

Pro Ala Val Leu Gln Ser Ser Gly Leu Tyr Ser Leu Ser Ser Val Val
865                 870                 875                 880

Thr Val Pro Ser Ser Ser Leu Gly Thr Gln Thr Tyr Ile Cys Asn Val
                885                 890                 895

Asn His Lys Pro Ser Asn Thr Lys Val Asp Lys Lys Val Glu Pro Lys
            900                 905                 910

Ser Cys

<210> SEQ ID NO 122
<211> LENGTH: 925
<212> TYPE: PRT
<213> ORGANISM: Artificial Sequence
<220> FEATURE:
<223> OTHER INFORMATION: first fusion polypeptide (Fc knob) P1AE1888

<400> SEQUENCE: 122

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

```
Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
    195                 200                 205

Asn Thr Lys Val Asp Lys Lys Val Glu Pro Lys Ser Cys Gly Gly Gly
210                 215                 220

Gly Ser Gly Gly Gly Gly Ser Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
    275                 280                 285

Tyr Val Asp Gly Val Glu Val His Asn Ala Lys Thr Lys Pro Arg Glu
            290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Gly Ala Pro Ile Glu Lys Thr Ile Ser Lys Ala Lys Gly
            340                 345                 350

Gln Pro Arg Glu Pro Gln Val Tyr Thr Leu Pro Pro Cys Arg Asp Glu
    355                 360                 365

Leu Thr Lys Asn Gln Val Ser Leu Trp Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
    435                 440                 445

Gln Lys Ser Leu Ser Leu Ser Pro Gly Lys Gly Gly Gly Gly Ser Gly
    450                 455                 460

Gly Gly Gly Ser Asp Ile Gln Met Thr Gln Ser Pro Ser Thr Leu Ser
465                 470                 475                 480

Ala Ser Val Gly Asp Arg Val Thr Ile Thr Cys Arg Ala Ser Gln Ser
                485                 490                 495

Ile Ser Ser Trp Leu Ala Trp Tyr Gln Gln Lys Pro Gly Lys Ala Pro
            500                 505                 510

Lys Leu Leu Ile Tyr Asp Ala Ser Ser Leu Glu Ser Gly Val Pro Ser
    515                 520                 525
```

```
Arg Phe Ser Gly Ser Gly Ser Gly Thr Glu Phe Thr Leu Thr Ile Ser
            530                 535                 540

Ser Leu Gln Pro Asp Asp Phe Ala Thr Tyr Tyr Cys Gln Gln Tyr Ser
545                 550                 555                 560

Ser Gln Pro Tyr Thr Phe Gly Gln Gly Thr Lys Val Glu Ile Lys Arg
                565                 570                 575

Thr Val Ala Ala Pro Ser Val Phe Ile Phe Pro Pro Ser Asp Glu Gln
            580                 585                 590

Leu Lys Ser Gly Thr Ala Ser Val Val Cys Leu Leu Asn Asn Phe Tyr
        595                 600                 605

Pro Arg Glu Ala Lys Val Gln Trp Lys Val Asp Asn Ala Leu Gln Ser
    610                 615                 620

Gly Asn Ser Gln Glu Ser Val Thr Glu Gln Asp Ser Lys Asp Ser Thr
625                 630                 635                 640

Tyr Ser Leu Ser Ser Thr Leu Thr Leu Ser Lys Ala Asp Tyr Glu Lys
                645                 650                 655

His Lys Val Tyr Ala Cys Glu Val Thr His Gln Gly Leu Ser Ser Pro
            660                 665                 670

Val Thr Lys Ser Phe Asn Arg Gly Glu Cys Gly Gly Gly Gly Ser Gly
        675                 680                 685

Gly Gly Gly Ser Gly Gly Ser Gly Gly Gly Ser Glu Val Gln
690                 695                 700

Leu Leu Glu Ser Gly Gly Gly Leu Val Gln Pro Gly Gly Ser Leu Arg
705                 710                 715                 720

Leu Ser Cys Ala Ala Ser Gly Phe Thr Phe Ser Ser Tyr Ala Met Ser
                725                 730                 735

Trp Val Arg Gln Ala Pro Gly Lys Gly Leu Glu Trp Val Ser Ala Ile
            740                 745                 750

Ile Gly Ser Gly Ala Ser Thr Tyr Tyr Ala Asp Ser Val Lys Gly Arg
        755                 760                 765

Phe Thr Ile Ser Arg Asp Asn Ser Lys Asn Thr Leu Tyr Leu Gln Met
    770                 775                 780

Asn Ser Leu Arg Ala Glu Asp Thr Ala Val Tyr Tyr Cys Ala Lys Gly
785                 790                 795                 800

Trp Phe Gly Gly Phe Asn Tyr Trp Gly Gln Gly Thr Leu Val Thr Val
                805                 810                 815

Ser Ser Ala Ser Val Ala Ala Pro Ser Val Phe Ile Phe Pro Pro Ser
            820                 825                 830

Asp Glu Gln Leu Lys Ser Gly Thr Ala Ser Val Val Cys Leu Leu Asn
        835                 840                 845

Asn Phe Tyr Pro Arg Glu Ala Lys Val Gln Trp Lys Val Asp Asn Ala
    850                 855                 860

Leu Gln Ser Gly Asn Ser Gln Glu Ser Val Thr Glu Gln Asp Ser Lys
865                 870                 875                 880

Asp Ser Thr Tyr Ser Leu Ser Ser Thr Leu Thr Leu Ser Lys Ala Asp
                885                 890                 895

Tyr Glu Lys His Lys Val Tyr Ala Cys Glu Val Thr His Gln Gly Leu
            900                 905                 910

Ser Ser Pro Val Thr Lys Ser Phe Asn Arg Gly Glu Cys
        915                 920                 925

<210> SEQ ID NO 123
<211> LENGTH: 914
```

```
<212> TYPE: PRT
<213> ORGANISM: Artificial Sequence
<220> FEATURE:
<223> OTHER INFORMATION: second fusion polypeptide (Fc hole) P1AE1888

<400> SEQUENCE: 123

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Gln Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
370                 375                 380
```

```
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys Gly Gly Gly Ser Gly Gly Gly Ser Gln Val Gln
            450                 455                 460

Leu Val Gln Ser Gly Ala Glu Val Lys Lys Pro Gly Ser Ser Val Lys
465                 470                 475                 480

Val Ser Cys Lys Ala Ser Gly Gly Thr Phe Ser Ser Tyr Ala Ile Ser
            485                 490                 495

Trp Val Arg Gln Ala Pro Gly Gln Gly Leu Glu Trp Met Gly Gly Ile
            500                 505                 510

Ile Pro Ile Phe Gly Thr Ala Asn Tyr Ala Gln Lys Phe Gln Gly Arg
            515                 520                 525

Val Thr Ile Thr Ala Asp Lys Ser Thr Ser Thr Ala Tyr Met Glu Leu
            530                 535                 540

Ser Ser Leu Arg Ser Glu Asp Thr Ala Val Tyr Tyr Cys Ala Arg Glu
545                 550                 555                 560

Tyr Tyr Arg Gly Pro Tyr Asp Tyr Trp Gly Gln Gly Thr Thr Val Thr
            565                 570                 575

Val Ser Ser Ala Ser Thr Lys Gly Pro Ser Val Phe Pro Leu Ala Pro
            580                 585                 590

Ser Ser Lys Ser Thr Ser Gly Gly Thr Ala Ala Leu Gly Cys Leu Val
            595                 600                 605

Lys Asp Tyr Phe Pro Glu Pro Val Thr Val Ser Trp Asn Ser Gly Ala
            610                 615                 620

Leu Thr Ser Gly Val His Thr Phe Pro Ala Val Leu Gln Ser Ser Gly
625                 630                 635                 640

Leu Tyr Ser Leu Ser Ser Val Val Thr Val Pro Ser Ser Ser Leu Gly
            645                 650                 655

Thr Gln Thr Tyr Ile Cys Asn Val Asn His Lys Pro Ser Asn Thr Lys
            660                 665                 670

Val Asp Lys Lys Val Glu Pro Lys Ser Cys Gly Gly Gly Gly Ser Gly
            675                 680                 685

Gly Gly Gly Ser Gly Gly Gly Ser Gly Gly Gly Gly Ser Glu Ile Val
            690                 695                 700

Leu Thr Gln Ser Pro Gly Thr Leu Ser Leu Ser Pro Gly Glu Arg Ala
705                 710                 715                 720

Thr Leu Ser Cys Arg Ala Ser Gln Ser Val Thr Ser Ser Tyr Leu Ala
            725                 730                 735

Trp Tyr Gln Gln Lys Pro Gly Gln Ala Pro Arg Leu Leu Ile Asn Val
            740                 745                 750

Gly Ser Arg Arg Ala Thr Gly Ile Pro Asp Arg Phe Ser Gly Ser Gly
            755                 760                 765

Ser Gly Thr Asp Phe Thr Leu Thr Ile Ser Arg Leu Glu Pro Glu Asp
            770                 775                 780

Phe Ala Val Tyr Tyr Cys Gln Gln Gly Ile Met Leu Pro Pro Thr Phe
785                 790                 795                 800
```

```
Gly Gln Gly Thr Lys Val Glu Ile Lys Ser Ser Ala Ser Thr Lys Gly
                805                 810                 815

Pro Ser Val Phe Pro Leu Ala Pro Ser Ser Lys Ser Thr Ser Gly Gly
            820                 825                 830

Thr Ala Ala Leu Gly Cys Leu Val Lys Asp Tyr Phe Pro Glu Pro Val
            835                 840                 845

Thr Val Ser Trp Asn Ser Gly Ala Leu Thr Ser Gly Val His Thr Phe
        850                 855                 860

Pro Ala Val Leu Gln Ser Ser Gly Leu Tyr Ser Leu Ser Ser Val Val
865                 870                 875                 880

Thr Val Pro Ser Ser Ser Leu Gly Thr Gln Thr Tyr Ile Cys Asn Val
                885                 890                 895

Asn His Lys Pro Ser Asn Thr Lys Val Asp Lys Lys Val Glu Pro Lys
                900                 905                 910

Ser Cys

<210> SEQ ID NO 124
<211> LENGTH: 925
<212> TYPE: PRT
<213> ORGANISM: Artificial Sequence
<220> FEATURE:
<223> OTHER INFORMATION: first fusion polypeptide (Fc knob) P1AE2254

<400> SEQUENCE: 124

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Glu Lys Val Glu Pro Lys Ser Cys Gly Gly Gly
    210                 215                 220

Gly Ser Gly Gly Gly Gly Ser Asp Lys Thr His Thr Cys Pro Pro Cys
225                 230                 235                 240
```

-continued

```
Pro Ala Pro Glu Ala Gly Gly Pro Ser Val Phe Leu Phe Pro Pro
            245                 250                 255

Lys Pro Lys Asp Thr Leu Met Ile Ser Arg Thr Pro Glu Val Thr Cys
        260                 265                 270

Val Val Val Asp Val Ser His Glu Asp Pro Glu Val Lys Phe Asn Trp
    275                 280                 285

Tyr Val Asp Gly Val Glu Val His Asn Ala Lys Thr Lys Pro Arg Glu
290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Gly Ala Pro Ile Glu Lys Thr Ile Ser Lys Ala Lys Gly
            340                 345                 350

Gln Pro Arg Glu Pro Gln Val Tyr Thr Leu Pro Pro Cys Arg Asp Glu
        355                 360                 365

Leu Thr Lys Asn Gln Val Ser Leu Trp Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys Gly Gly Gly Gly Ser Gly
    450                 455                 460

Gly Gly Gly Ser Asp Ile Gln Met Thr Gln Ser Pro Ser Thr Leu Ser
465                 470                 475                 480

Ala Ser Val Gly Asp Arg Val Thr Ile Thr Cys Arg Ala Ser Gln Ser
                485                 490                 495

Ile Ser Ser Trp Leu Ala Trp Tyr Gln Gln Lys Pro Gly Lys Ala Pro
            500                 505                 510

Lys Leu Leu Ile Tyr Asp Ala Ser Ser Leu Glu Ser Gly Val Pro Ser
        515                 520                 525

Arg Phe Ser Gly Ser Gly Ser Gly Thr Glu Phe Thr Leu Thr Ile Ser
    530                 535                 540

Ser Leu Gln Pro Asp Asp Phe Ala Thr Tyr Tyr Cys Gln Gln Tyr Ser
545                 550                 555                 560

Ser Gln Pro Tyr Thr Phe Gly Gln Gly Thr Lys Val Glu Ile Lys Arg
                565                 570                 575

Thr Val Ala Ala Pro Ser Val Phe Ile Phe Pro Pro Ser Asp Arg Lys
            580                 585                 590

Leu Lys Ser Gly Thr Ala Ser Val Val Cys Leu Leu Asn Asn Phe Tyr
        595                 600                 605

Pro Arg Glu Ala Lys Val Gln Trp Lys Val Asp Asn Ala Leu Gln Ser
    610                 615                 620

Gly Asn Ser Gln Glu Ser Val Thr Glu Gln Asp Ser Lys Asp Ser Thr
625                 630                 635                 640

Tyr Ser Leu Ser Ser Thr Leu Thr Leu Ser Lys Ala Asp Tyr Glu Lys
                645                 650                 655
```

His Lys Val Tyr Ala Cys Glu Val Thr His Gln Gly Leu Ser Ser Pro
                660                 665                 670

Val Thr Lys Ser Phe Asn Arg Gly Glu Cys Gly Gly Gly Ser Gly
        675                 680                 685

Gly Gly Gly Ser Gly Gly Ser Gly Gly Gly Ser Glu Val Gln
690                 695                 700

Leu Leu Glu Ser Gly Gly Gly Leu Val Gln Pro Gly Gly Ser Leu Arg
705                 710                 715                 720

Leu Ser Cys Ala Ala Ser Gly Phe Thr Phe Ser Ser Tyr Ala Met Ser
                725                 730                 735

Trp Val Arg Gln Ala Pro Gly Lys Gly Leu Glu Trp Val Ser Ala Ile
                740                 745                 750

Ile Gly Ser Gly Ala Ser Thr Tyr Tyr Ala Asp Ser Val Lys Gly Arg
                755                 760                 765

Phe Thr Ile Ser Arg Asp Asn Ser Lys Asn Thr Leu Tyr Leu Gln Met
                770                 775                 780

Asn Ser Leu Arg Ala Glu Asp Thr Ala Val Tyr Tyr Cys Ala Lys Gly
785                 790                 795                 800

Trp Phe Gly Gly Phe Asn Tyr Trp Gly Gln Gly Thr Leu Val Thr Val
                805                 810                 815

Ser Ser Ala Ser Val Ala Ala Pro Ser Val Phe Ile Phe Pro Pro Ser
                820                 825                 830

Asp Glu Gln Leu Lys Ser Gly Thr Ala Ser Val Val Cys Leu Leu Asn
                835                 840                 845

Asn Phe Tyr Pro Arg Glu Ala Lys Val Gln Trp Lys Val Asp Asn Ala
                850                 855                 860

Leu Gln Ser Gly Asn Ser Gln Glu Ser Val Thr Glu Gln Asp Ser Lys
865                 870                 875                 880

Asp Ser Thr Tyr Ser Leu Ser Ser Thr Leu Thr Leu Ser Lys Ala Asp
                885                 890                 895

Tyr Glu Lys His Lys Val Tyr Ala Cys Glu Val Thr His Gln Gly Leu
                900                 905                 910

Ser Ser Pro Val Thr Lys Ser Phe Asn Arg Gly Glu Cys
                915                 920                 925

<210> SEQ ID NO 125
<211> LENGTH: 914
<212> TYPE: PRT
<213> ORGANISM: Artificial Sequence
<220> FEATURE:
<223> OTHER INFORMATION: second fusion polypeptide (Fc hole) P1AE2254

<400> SEQUENCE: 125

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

-continued

```
Ala Arg Glu Tyr Tyr Arg Gly Pro Tyr Asp Tyr Trp Gly Gln Gly Thr
            100                 105                 110
Thr Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
130                 135                 140
Cys Leu Val Glu Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Glu Lys Val Glu Pro Lys Ser Cys Gly Gly Gly
    210                 215                 220
Gly Ser Gly Gly Gly Gly Ser Asp Lys Thr His Thr Cys Pro Pro Cys
225                 230                 235                 240
Pro Ala Pro Glu Ala Ala Gly Gly Pro Ser Val Phe Leu Phe Pro Pro
                245                 250                 255
Lys Pro Lys Asp Thr Leu Met Ile Ser Arg Thr Pro Glu Val Thr Cys
            260                 265                 270
Val Val Val Asp Val Ser His Glu Asp Pro Glu Val Lys Phe Asn Trp
        275                 280                 285
Tyr Val Asp Gly Val Glu Val His Asn Ala Lys Thr Lys Pro Arg Glu
    290                 295                 300
Glu Gln Tyr Asn Ser Thr Tyr Arg Val Val Ser Val Leu Thr Val Leu
305                 310                 315                 320
His Gln Asp Trp Leu Asn Gly Lys Glu Tyr Lys Cys Lys Val Ser Asn
                325                 330                 335
Lys Ala Leu Gly Ala Pro Ile Glu Lys Thr Ile Ser Lys Ala Lys Gly
            340                 345                 350
Gln Pro Arg Glu Pro Gln Val Cys Thr Leu Pro Pro Ser Arg Asp Glu
        355                 360                 365
Leu Thr Lys Asn Gln Val Ser Leu Ser Cys Ala Val Lys Gly Phe Tyr
    370                 375                 380
Pro Ser Asp Ile Ala Val Glu Trp Glu Ser Asn Gly Gln Pro Glu Asn
385                 390                 395                 400
Asn Tyr Lys Thr Thr Pro Pro Val Leu Asp Ser Asp Gly Ser Phe Phe
                405                 410                 415
Leu Val Ser Lys Leu Thr Val Asp Lys Ser Arg Trp Gln Gln Gly Asn
            420                 425                 430
Val Phe Ser Cys Ser Val Met His Glu Ala Leu His Asn His Tyr Thr
        435                 440                 445
Gln Lys Ser Leu Ser Leu Ser Pro Gly Lys Gly Gly Gly Gly Ser Gly
    450                 455                 460
Gly Gly Gly Ser Asp Ile Gln Met Thr Gln Ser Pro Ser Thr Leu Ser
465                 470                 475                 480
Ala Ser Val Gly Asp Arg Val Thr Ile Thr Cys Arg Ala Ser Gln Ser
                485                 490                 495
Ile Ser Ser Trp Leu Ala Trp Tyr Gln Gln Lys Pro Gly Lys Ala Pro
            500                 505                 510
```

```
Lys Leu Leu Ile Tyr Asp Ala Ser Ser Leu Glu Ser Gly Val Pro Ser
            515                 520                 525

Arg Phe Ser Gly Ser Gly Ser Gly Thr Glu Phe Thr Leu Thr Ile Ser
530                 535                 540

Ser Leu Gln Pro Asp Asp Phe Ala Thr Tyr Tyr Cys Gln Gln Tyr Ser
545                 550                 555                 560

Ser Gln Pro Tyr Thr Phe Gly Gln Gly Thr Lys Val Glu Ile Lys Arg
                565                 570                 575

Thr Val Ala Ala Pro Ser Val Phe Ile Phe Pro Pro Ser Asp Arg Lys
            580                 585                 590

Leu Lys Ser Gly Thr Ala Ser Val Val Cys Leu Leu Asn Asn Phe Tyr
595                 600                 605

Pro Arg Glu Ala Lys Val Gln Trp Lys Val Asp Asn Ala Leu Gln Ser
610                 615                 620

Gly Asn Ser Gln Glu Ser Val Thr Glu Gln Asp Ser Lys Asp Ser Thr
625                 630                 635                 640

Tyr Ser Leu Ser Ser Thr Leu Thr Leu Ser Lys Ala Asp Tyr Glu Lys
                645                 650                 655

His Lys Val Tyr Ala Cys Glu Val Thr His Gln Gly Leu Ser Ser Pro
            660                 665                 670

Val Thr Lys Ser Phe Asn Arg Gly Glu Cys Gly Gly Gly Ser Gly
            675                 680                 685

Gly Gly Gly Ser Gly Gly Ser Gly Gly Gly Ser Glu Ile Val
            690                 695                 700

Leu Thr Gln Ser Pro Gly Thr Leu Ser Leu Ser Pro Gly Glu Arg Ala
705                 710                 715                 720

Thr Leu Ser Cys Arg Ala Ser Gln Ser Val Thr Ser Ser Tyr Leu Ala
                725                 730                 735

Trp Tyr Gln Gln Lys Pro Gly Gln Ala Pro Arg Leu Leu Ile Asn Val
            740                 745                 750

Gly Ser Arg Arg Ala Thr Gly Ile Pro Asp Arg Phe Ser Gly Ser Gly
            755                 760                 765

Ser Gly Thr Asp Phe Thr Leu Thr Ile Ser Arg Leu Glu Pro Glu Asp
770                 775                 780

Phe Ala Val Tyr Tyr Cys Gln Gln Gly Ile Met Leu Pro Pro Thr Phe
785                 790                 795                 800

Gly Gln Gly Thr Lys Val Glu Ile Lys Ser Ala Ser Thr Lys Gly
                805                 810                 815

Pro Ser Val Phe Pro Leu Ala Pro Ser Ser Lys Ser Thr Ser Gly Gly
            820                 825                 830

Thr Ala Ala Leu Gly Cys Leu Val Lys Asp Tyr Phe Pro Glu Pro Val
            835                 840                 845

Thr Val Ser Trp Asn Ser Gly Ala Leu Thr Ser Gly Val His Thr Phe
850                 855                 860

Pro Ala Val Leu Gln Ser Ser Gly Leu Tyr Ser Leu Ser Ser Val Val
865                 870                 875                 880

Thr Val Pro Ser Ser Ser Leu Gly Thr Gln Thr Tyr Ile Cys Asn Val
                885                 890                 895

Asn His Lys Pro Ser Asn Thr Lys Val Asp Lys Lys Val Glu Pro Lys
            900                 905                 910

Ser Cys

<210> SEQ ID NO 126
```

<211> LENGTH: 925
<212> TYPE: PRT
<213> ORGANISM: Artificial Sequence
<220> FEATURE:
<223> OTHER INFORMATION: first fusion polypeptide (Fc knob) P1AE2340

<400> SEQUENCE: 126

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Glu Lys Val Glu Pro Lys Ser Cys Gly Gly Gly
    210                 215                 220

Gly Ser Gly Gly Gly Gly Ser Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Gly Ala Pro Ile Glu Lys Thr Ile Ser Lys Ala Lys Gly
            340                 345                 350

Gln Pro Arg Glu Pro Gln Val Tyr Thr Leu Pro Pro Cys Arg Asp Glu
        355                 360                 365

Leu Thr Lys Asn Gln Val Ser Leu Trp Cys Leu Val Lys Gly Phe Tyr
    370                 375                 380
```

-continued

```
Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys Gly Gly Gly Ser Gly
    450                 455                 460

Gly Gly Gly Ser Asp Ile Gln Met Thr Gln Ser Pro Ser Thr Leu Ser
465                 470                 475                 480

Ala Ser Val Gly Asp Arg Val Thr Ile Thr Cys Arg Ala Ser Gln Ser
                485                 490                 495

Ile Ser Ser Trp Leu Ala Trp Tyr Gln Gln Lys Pro Gly Lys Ala Pro
            500                 505                 510

Lys Leu Leu Ile Tyr Asp Ala Ser Ser Leu Glu Ser Gly Val Pro Ser
        515                 520                 525

Arg Phe Ser Gly Ser Gly Ser Gly Thr Glu Phe Thr Leu Thr Ile Ser
    530                 535                 540

Ser Leu Gln Pro Asp Asp Phe Ala Thr Tyr Tyr Cys Gln Gln Tyr Ser
545                 550                 555                 560

Ser Gln Pro Tyr Thr Phe Gly Gln Gly Thr Lys Val Glu Ile Lys Arg
                565                 570                 575

Thr Val Ala Ala Pro Ser Val Phe Ile Phe Pro Pro Ser Asp Arg Lys
            580                 585                 590

Leu Lys Ser Gly Thr Ala Ser Val Val Cys Leu Leu Asn Asn Phe Tyr
        595                 600                 605

Pro Arg Glu Ala Lys Val Gln Trp Lys Val Asp Asn Ala Leu Gln Ser
    610                 615                 620

Gly Asn Ser Gln Glu Ser Val Thr Glu Gln Asp Ser Lys Asp Ser Thr
625                 630                 635                 640

Tyr Ser Leu Ser Ser Thr Leu Thr Leu Ser Lys Ala Asp Tyr Glu Lys
                645                 650                 655

His Lys Val Tyr Ala Cys Glu Val Thr His Gln Gly Leu Ser Ser Pro
            660                 665                 670

Val Thr Lys Ser Phe Asn Arg Gly Glu Cys Gly Gly Gly Gly Ser Gly
        675                 680                 685

Gly Gly Gly Ser Gly Gly Ser Gly Gly Gly Ser Glu Val Gln
    690                 695                 700

Leu Leu Glu Ser Gly Gly Gly Leu Val Gln Pro Gly Gly Ser Leu Arg
705                 710                 715                 720

Leu Ser Cys Ala Ala Ser Gly Phe Thr Phe Ser Ser Tyr Ala Met Ser
                725                 730                 735

Trp Val Arg Gln Ala Pro Gly Lys Gly Leu Glu Trp Val Ser Ala Ile
            740                 745                 750

Ile Gly Ser Gly Ala Ser Thr Tyr Tyr Ala Asp Ser Val Lys Gly Arg
        755                 760                 765

Phe Thr Ile Ser Arg Asp Asn Ser Lys Asn Thr Leu Tyr Leu Gln Met
    770                 775                 780

Asn Ser Leu Arg Ala Glu Asp Thr Ala Val Tyr Tyr Cys Ala Lys Gly
785                 790                 795                 800
```

Trp Phe Gly Gly Phe Asn Tyr Trp Gly Gln Gly Thr Leu Val Thr Val
                805                 810                 815

Ser Ser Ala Ser Val Ala Ala Pro Ser Val Phe Ile Phe Pro Pro Ser
            820                 825                 830

Asp Glu Gln Leu Lys Ser Gly Thr Ala Ser Val Val Cys Leu Leu Asn
            835                 840                 845

Asn Phe Tyr Pro Arg Glu Ala Lys Val Gln Trp Lys Val Asp Asn Ala
850                 855                 860

Leu Gln Ser Gly Asn Ser Gln Glu Ser Val Thr Glu Gln Asp Ser Lys
865                 870                 875                 880

Asp Ser Thr Tyr Ser Leu Ser Ser Thr Leu Thr Leu Ser Lys Ala Asp
                885                 890                 895

Tyr Glu Lys His Lys Val Tyr Ala Cys Glu Val Thr His Gln Gly Leu
                900                 905                 910

Ser Ser Pro Val Thr Lys Ser Phe Asn Arg Gly Glu Cys
                915                 920                 925

<210> SEQ ID NO 127
<211> LENGTH: 688
<212> TYPE: PRT
<213> ORGANISM: Artificial Sequence
<220> FEATURE:
<223> OTHER INFORMATION: second fusion polypeptide (Fc hole) P1AE2340

<400> SEQUENCE: 127

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Glu Lys Val Glu Pro Lys Ser Cys Gly Gly Gly
    210                 215                 220

Gly Ser Gly Gly Gly Gly Ser Asp Lys Thr His Thr Cys Pro Pro Cys
225                 230                 235                 240

-continued

```
Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Gly Ala Pro Ile Glu Lys Thr Ile Ser Lys Ala Lys Gly
            340                 345                 350

Gln Pro Arg Glu Pro Gln Val Cys Thr Leu Pro Pro Ser Arg Asp Glu
        355                 360                 365

Leu Thr Lys Asn Gln Val Ser Leu Ser Cys Ala Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys Gly Gly Gly Gly Ser Gly
    450                 455                 460

Gly Gly Gly Ser Asp Ile Gln Met Thr Gln Ser Pro Ser Thr Leu Ser
465                 470                 475                 480

Ala Ser Val Gly Asp Arg Val Thr Ile Thr Cys Arg Ala Ser Gln Ser
                485                 490                 495

Ile Ser Ser Trp Leu Ala Trp Tyr Gln Gln Lys Pro Gly Lys Ala Pro
            500                 505                 510

Lys Leu Leu Ile Tyr Asp Ala Ser Ser Leu Glu Ser Gly Val Pro Ser
        515                 520                 525

Arg Phe Ser Gly Ser Gly Ser Gly Thr Glu Phe Thr Leu Thr Ile Ser
    530                 535                 540

Ser Leu Gln Pro Asp Asp Phe Ala Thr Tyr Tyr Cys Gln Gln Tyr Ser
545                 550                 555                 560

Ser Gln Pro Tyr Thr Phe Gly Gln Gly Thr Lys Val Glu Ile Lys Arg
                565                 570                 575

Thr Val Ala Ala Pro Ser Val Phe Ile Phe Pro Pro Ser Asp Arg Lys
            580                 585                 590

Leu Lys Ser Gly Thr Ala Ser Val Val Cys Leu Leu Asn Asn Phe Tyr
        595                 600                 605

Pro Arg Glu Ala Lys Val Gln Trp Lys Val Asp Asn Ala Leu Gln Ser
    610                 615                 620

Gly Asn Ser Gln Glu Ser Val Thr Glu Gln Asp Ser Val Thr Glu Gln
625                 630                 635                 640

Asp Ser Lys Asp Ser Thr Tyr Ser Leu Ser Ser Thr Leu Thr Leu Ser
                645                 650                 655
```

```
Lys Ala Asp Tyr Glu Lys His Lys Val Tyr Ala Cys Glu Val Thr His
            660                 665                 670

Gln Gly Leu Ser Ser Pro Val Thr Lys Ser Phe Asn Arg Gly Glu Cys
        675                 680                 685
```

<210> SEQ ID NO 128
<211> LENGTH: 213
<212> TYPE: PRT
<213> ORGANISM: Artificial Sequence
<220> FEATURE:
<223> OTHER INFORMATION: Light Chain P1AE2340

<400> SEQUENCE: 128

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys
    210
```

<210> SEQ ID NO 129
<211> LENGTH: 925
<212> TYPE: PRT
<213> ORGANISM: Artificial Sequence
<220> FEATURE:
<223> OTHER INFORMATION: first fusion polypeptide (Fc knob) P1AE2735

<400> SEQUENCE: 129

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

-continued

```
Ser Ala Ile Ile Gly Ser Gly Ala Ser Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Gly Trp Phe Gly Gly Phe Asn Tyr Trp Gly Gln Gly Thr Leu
                100                 105                 110
Val Thr Val Ser Ser Ala Ser Val Ala Ala Pro Ser Val Phe Ile Phe
                115                 120                 125
Pro Pro Ser Asp Glu Gln Leu Lys Ser Gly Thr Ala Ser Val Val Cys
130                 135                 140
Leu Leu Asn Asn Phe Tyr Pro Arg Glu Ala Lys Val Gln Trp Lys Val
145                 150                 155                 160
Asp Asn Ala Leu Gln Ser Gly Asn Ser Gln Glu Ser Val Thr Glu Gln
                165                 170                 175
Asp Ser Lys Asp Ser Thr Tyr Ser Leu Ser Ser Thr Leu Thr Leu Ser
                180                 185                 190
Lys Ala Asp Tyr Glu Lys His Lys Val Tyr Ala Cys Glu Val Thr His
                195                 200                 205
Gln Gly Leu Ser Ser Pro Val Thr Lys Ser Phe Asn Arg Gly Glu Cys
210                 215                 220
Gly Gly Gly Gly Ser Gly Gly Gly Gly Ser Gly Gly Gly Ser Gly Gly
225                 230                 235                 240
Gly Gly Ser Gln Val Gln Leu Val Gln Ser Gly Ala Glu Val Lys Lys
                245                 250                 255
Pro Gly Ser Ser Val Lys Val Ser Cys Lys Ala Ser Gly Gly Thr Phe
                260                 265                 270
Ser Ser Tyr Ala Ile Ser Trp Val Arg Gln Ala Pro Gly Gln Gly Leu
                275                 280                 285
Glu Trp Met Gly Gly Ile Ile Pro Ile Phe Gly Thr Ala Asn Tyr Ala
                290                 295                 300
Gln Lys Phe Gln Gly Arg Val Thr Ile Thr Ala Asp Lys Ser Thr Ser
305                 310                 315                 320
Thr Ala Tyr Met Glu Leu Ser Ser Leu Arg Ser Glu Asp Thr Ala Val
                325                 330                 335
Tyr Tyr Cys Ala Arg Glu Tyr Tyr Arg Gly Pro Tyr Asp Tyr Trp Gly
                340                 345                 350
Gln Gly Thr Thr Val Thr Val Ser Ala Ser Thr Lys Gly Pro Ser
                355                 360                 365
Val Phe Pro Leu Ala Pro Ser Ser Lys Ser Thr Ser Gly Gly Thr Ala
370                 375                 380
Ala Leu Gly Cys Leu Val Lys Asp Tyr Phe Pro Glu Pro Val Thr Val
385                 390                 395                 400
Ser Trp Asn Ser Gly Ala Leu Thr Ser Gly Val His Thr Phe Pro Ala
                405                 410                 415
Val Leu Gln Ser Ser Gly Leu Tyr Ser Leu Ser Ser Val Val Thr Val
                420                 425                 430
Pro Ser Ser Ser Leu Gly Thr Gln Thr Tyr Ile Cys Asn Val Asn His
                435                 440                 445
Lys Pro Ser Asn Thr Lys Val Asp Lys Lys Val Glu Pro Lys Ser Cys
450                 455                 460
```

```
Gly Gly Gly Gly Ser Gly Gly Gly Ser Asp Lys Thr His Thr Cys
465                 470                 475                 480

Pro Pro Cys Pro Ala Pro Glu Ala Ala Gly Gly Pro Ser Val Phe Leu
            485                 490                 495

Phe Pro Pro Lys Pro Lys Asp Thr Leu Met Ile Ser Arg Thr Pro Glu
        500                 505                 510

Val Thr Cys Val Val Val Asp Val Ser His Glu Asp Pro Glu Val Lys
        515                 520                 525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Lys
            565                 570                 575

Val Ser Asn Lys Ala Leu Gly Ala Pro Ile Glu Lys Thr Ile Ser Lys
        580                 585                 590

Ala Lys Gly Gln Pro Arg Glu Pro Gln Val Tyr Thr Leu Pro Pro Cys
    595                 600                 605

Arg Asp Glu Leu Thr Lys Asn Gln Val Ser Leu Trp Cys Leu Val Lys
    610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
            645                 650                 655

Ser Phe Phe Leu Tyr Ser Lys Leu Thr Val Asp Lys Ser Arg Trp Gln
        660                 665                 670

Gln Gly Asn Val Phe Ser Cys Ser Val Met His Glu Ala Leu His Asn
    675                 680                 685

His Tyr Thr Gln Lys Ser Leu Ser Leu Ser Pro Gly Lys Gly Gly Gly
            690                 695                 700

Gly Ser Gly Gly Gly Gly Ser Asp Ile Gln Met Thr Gln Ser Pro Ser
705                 710                 715                 720

Thr Leu Ser Ala Ser Val Gly Asp Arg Val Thr Ile Thr Cys Arg Ala
            725                 730                 735

Ser Gln Ser Ile Ser Ser Trp Leu Ala Trp Tyr Gln Gln Lys Pro Gly
        740                 745                 750

Lys Ala Pro Lys Leu Leu Ile Tyr Asp Ala Ser Ser Leu Glu Ser Gly
    755                 760                 765

Val Pro Ser Arg Phe Ser Gly Ser Gly Ser Gly Thr Glu Phe Thr Leu
770                 775                 780

Thr Ile Ser Ser Leu Gln Pro Asp Asp Phe Ala Thr Tyr Tyr Cys Gln
785                 790                 795                 800

Gln Tyr Ser Ser Gln Pro Tyr Thr Phe Gly Gln Gly Thr Lys Val Glu
            805                 810                 815

Ile Lys Arg Thr Val Ala Ala Pro Ser Val Phe Ile Phe Pro Pro Ser
        820                 825                 830

Asp Glu Gln Leu Lys Ser Gly Thr Ala Ser Val Val Cys Leu Leu Asn
    835                 840                 845

Asn Phe Tyr Pro Arg Glu Ala Lys Val Gln Trp Lys Val Asp Asn Ala
    850                 855                 860

Leu Gln Ser Gly Asn Ser Gln Glu Ser Val Thr Glu Gln Asp Ser Lys
865                 870                 875                 880
```

-continued

Asp Ser Thr Tyr Ser Leu Ser Ser Thr Leu Thr Leu Ser Lys Ala Asp
                885                 890                 895

Tyr Glu Lys His Lys Val Tyr Ala Cys Glu Val Thr His Gln Gly Leu
            900                 905                 910

Ser Ser Pro Val Thr Lys Ser Phe Asn Arg Gly Glu Cys
        915                 920                 925

<210> SEQ ID NO 130
<211> LENGTH: 914
<212> TYPE: PRT
<213> ORGANISM: Artificial Sequence
<220> FEATURE:
<223> OTHER INFORMATION: second fusion polypeptide (Fc hole) P1AE2735

<400> SEQUENCE: 130

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys Gly Gly Gly Ser Gly Gly Gly Gly Ser Gly
    210                 215                 220

Gly Gly Ser Gly Gly Gly Ser Gln Val Gln Leu Val Gln Ser Gly
225                 230                 235                 240

Ala Glu Val Lys Lys Pro Gly Ser Ser Val Lys Val Ser Cys Lys Ala
                245                 250                 255

Ser Gly Gly Thr Phe Ser Ser Tyr Ala Ile Ser Trp Val Arg Gln Ala
            260                 265                 270

Pro Gly Gln Gly Leu Glu Trp Met Gly Gly Ile Ile Pro Ile Phe Gly
        275                 280                 285

Thr Ala Asn Tyr Ala Gln Lys Phe Gln Gly Arg Val Thr Ile Thr Ala
    290                 295                 300

Asp Lys Ser Thr Ser Thr Ala Tyr Met Glu Leu Ser Ser Leu Arg Ser
305                 310                 315                 320

```
Glu Asp Thr Ala Val Tyr Tyr Cys Ala Arg Glu Tyr Arg Gly Pro
                325                 330             335

Tyr Asp Tyr Trp Gly Gln Gly Thr Thr Val Thr Val Ser Ser Ala Ser
            340             345             350

Thr Lys Gly Pro Ser Val Phe Pro Leu Ala Pro Ser Ser Lys Ser Thr
        355             360             365

Ser Gly Gly Thr Ala Ala Leu Gly Cys Leu Val Lys Asp Tyr Phe Pro
    370             375             380

Glu Pro Val Thr Val Ser Trp Asn Ser Gly Ala Leu Thr Ser Gly Val
385             390             395             400

His Thr Phe Pro Ala Val Leu Gln Ser Ser Gly Leu Tyr Ser Leu Ser
            405             410             415

Ser Val Val Thr Val Pro Ser Ser Ser Leu Gly Thr Gln Thr Tyr Ile
            420             425             430

Cys Asn Val Asn His Lys Pro Ser Asn Thr Lys Val Asp Lys Lys Val
            435             440             445

Glu Pro Lys Ser Cys Gly Gly Gly Ser Gly Gly Gly Ser Asp
    450             455             460

Lys Thr His Thr Cys Pro Pro Cys Pro Ala Pro Glu Ala Ala Gly Gly
465             470             475             480

Pro Ser Val Phe Leu Phe Pro Pro Lys Pro Lys Asp Thr Leu Met Ile
            485             490             495

Ser Arg Thr Pro Glu Val Thr Cys Val Val Val Asp Val Ser His Glu
            500             505             510

Asp Pro Glu Val Lys Phe Asn Trp Tyr Val Asp Gly Val Glu Val His
            515             520             525

Asn Ala Lys Thr Lys Pro Arg Glu Glu Gln Tyr Asn Ser Thr Tyr Arg
            530             535             540

Val Val Ser Val Leu Thr Val Leu His Gln Asp Trp Leu Asn Gly Lys
545             550             555             560

Glu Tyr Lys Cys Lys Val Ser Asn Lys Ala Leu Gly Ala Pro Ile Glu
            565             570             575

Lys Thr Ile Ser Lys Ala Lys Gly Gln Pro Arg Glu Pro Gln Val Cys
            580             585             590

Thr Leu Pro Pro Ser Arg Asp Glu Leu Thr Lys Asn Gln Val Ser Leu
            595             600             605

Ser Cys Ala Val Lys Gly Phe Tyr Pro Ser Asp Ile Ala Val Glu Trp
    610             615             620

Glu Ser Asn Gly Gln Pro Glu Asn Asn Tyr Lys Thr Thr Pro Pro Val
625             630             635             640

Leu Asp Ser Asp Gly Ser Phe Phe Leu Val Ser Lys Leu Thr Val Asp
            645             650             655

Lys Ser Arg Trp Gln Gln Gly Asn Val Phe Ser Cys Ser Val Met His
            660             665             670

Glu Ala Leu His Asn His Tyr Thr Gln Lys Ser Leu Ser Leu Ser Pro
            675             680             685

Gly Lys Gly Gly Gly Gly Ser Gly Gly Gly Ser Asp Ile Gln Met
    690             695             700

Thr Gln Ser Pro Ser Thr Leu Ser Ala Ser Val Gly Asp Arg Val Thr
705             710             715             720

Ile Thr Cys Arg Ala Ser Gln Ser Ile Ser Ser Trp Leu Ala Trp Tyr
            725             730             735
```

```
Gln Gln Lys Pro Gly Lys Ala Pro Lys Leu Leu Ile Tyr Asp Ala Ser
            740                 745                 750

Ser Leu Glu Ser Gly Val Pro Ser Arg Phe Ser Gly Ser Gly Ser Gly
        755                 760                 765

Thr Glu Phe Thr Leu Thr Ile Ser Ser Leu Gln Pro Asp Asp Phe Ala
    770                 775                 780

Thr Tyr Tyr Cys Gln Gln Tyr Ser Ser Gln Pro Tyr Thr Phe Gly Gln
785                 790                 795                 800

Gly Thr Lys Val Glu Ile Lys Arg Thr Val Ala Ala Pro Ser Val Phe
                805                 810                 815

Ile Phe Pro Pro Ser Asp Glu Gln Leu Lys Ser Gly Thr Ala Ser Val
            820                 825                 830

Val Cys Leu Leu Asn Asn Phe Tyr Pro Arg Glu Ala Lys Val Gln Trp
        835                 840                 845

Lys Val Asp Asn Ala Leu Gln Ser Gly Asn Ser Gln Glu Ser Val Thr
    850                 855                 860

Glu Gln Asp Ser Lys Asp Ser Thr Tyr Ser Leu Ser Ser Thr Leu Thr
865                 870                 875                 880

Leu Ser Lys Ala Asp Tyr Glu Lys His Lys Val Tyr Ala Cys Glu Val
                885                 890                 895

Thr His Gln Gly Leu Ser Ser Pro Val Thr Lys Ser Phe Asn Arg Gly
            900                 905                 910

Glu Cys

<210> SEQ ID NO 131
<211> LENGTH: 925
<212> TYPE: PRT
<213> ORGANISM: Artificial Sequence
<220> FEATURE:
<223> OTHER INFORMATION: first fusion polypeptide (Fc knob) P1AE2743

<400> SEQUENCE: 131

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Val Ala Ala Pro Ser Val Phe Ile Phe
        115                 120                 125

Pro Pro Ser Asp Glu Gln Leu Lys Ser Gly Thr Ala Ser Val Val Cys
    130                 135                 140

Leu Leu Asn Asn Phe Tyr Pro Arg Glu Ala Lys Val Gln Trp Lys Val
145                 150                 155                 160

Asp Asn Ala Leu Gln Ser Gly Asn Ser Gln Glu Ser Val Thr Glu Gln
                165                 170                 175
```

```
Asp Ser Lys Asp Ser Thr Tyr Ser Leu Ser Ser Thr Leu Thr Leu Ser
            180                 185                 190

Lys Ala Asp Tyr Glu Lys His Lys Val Tyr Ala Cys Glu Val Thr His
        195                 200                 205

Gln Gly Leu Ser Ser Pro Val Thr Lys Ser Phe Asn Arg Gly Glu Cys
    210                 215                 220

Gly Gly Gly Gly Ser Gly Gly Gly Ser Gly Gly Gly Ser Gly Gly
225                 230                 235                 240

Gly Gly Ser Asp Ile Gln Met Thr Gln Ser Pro Ser Thr Leu Ser Ala
            245                 250                 255

Ser Val Gly Asp Arg Val Thr Ile Thr Cys Arg Ala Ser Gln Ser Ile
            260                 265                 270

Ser Ser Trp Leu Ala Trp Tyr Gln Gln Lys Pro Gly Lys Ala Pro Lys
        275                 280                 285

Leu Leu Ile Tyr Asp Ala Ser Ser Leu Glu Ser Gly Val Pro Ser Arg
    290                 295                 300

Phe Ser Gly Ser Gly Ser Gly Thr Glu Phe Thr Leu Thr Ile Ser Ser
305                 310                 315                 320

Leu Gln Pro Asp Asp Phe Ala Thr Tyr Tyr Cys Gln Gln Tyr Ser Ser
            325                 330                 335

Gln Pro Tyr Thr Phe Gly Gln Gly Thr Lys Val Glu Ile Lys Arg Thr
        340                 345                 350

Val Ala Ala Pro Ser Val Phe Ile Phe Pro Pro Ser Asp Glu Gln Leu
    355                 360                 365

Lys Ser Gly Thr Ala Ser Val Val Cys Leu Leu Asn Asn Phe Tyr Pro
        370                 375                 380

Arg Glu Ala Lys Val Gln Trp Lys Val Asp Asn Ala Leu Gln Ser Gly
385                 390                 395                 400

Asn Ser Gln Glu Ser Val Thr Glu Gln Asp Ser Lys Asp Ser Thr Tyr
            405                 410                 415

Ser Leu Ser Ser Thr Leu Thr Leu Ser Lys Ala Asp Tyr Glu Lys His
        420                 425                 430

Lys Val Tyr Ala Cys Glu Val Thr His Gln Gly Leu Ser Ser Pro Val
    435                 440                 445

Thr Lys Ser Phe Asn Arg Gly Glu Cys Gly Gly Gly Gly Ser Gly Gly
        450                 455                 460

Gly Gly Ser Asp Lys Thr His Thr Cys Pro Pro Cys Pro Ala Pro Glu
465                 470                 475                 480

Ala Ala Gly Gly Pro Ser Val Phe Leu Phe Pro Pro Lys Pro Lys Asp
            485                 490                 495

Thr Leu Met Ile Ser Arg Thr Pro Glu Val Thr Cys Val Val Val Asp
        500                 505                 510

Val Ser His Glu Asp Pro Glu Val Lys Phe Asn Trp Tyr Val Asp Gly
    515                 520                 525

Val Glu Val His Asn Ala Lys Thr Lys Pro Arg Glu Glu Gln Tyr Asn
        530                 535                 540

Ser Thr Tyr Arg Val Val Ser Val Leu Thr Val Leu His Gln Asp Trp
545                 550                 555                 560

Leu Asn Gly Lys Glu Tyr Lys Cys Lys Val Ser Asn Lys Ala Leu Gly
            565                 570                 575

Ala Pro Ile Glu Lys Thr Ile Ser Lys Ala Lys Gly Gln Pro Arg Glu
            580                 585                 590
```

```
Pro Gln Val Tyr Thr Leu Pro Pro Cys Arg Asp Glu Leu Thr Lys Asn
            595                 600                 605

Gln Val Ser Leu Trp Cys Leu Val Lys Gly Phe Tyr Pro Ser Asp Ile
    610                 615                 620

Ala Val Glu Trp Glu Ser Asn Gly Gln Pro Glu Asn Asn Tyr Lys Thr
625                 630                 635                 640

Thr Pro Pro Val Leu Asp Ser Asp Gly Ser Phe Phe Leu Tyr Ser Lys
                645                 650                 655

Leu Thr Val Asp Lys Ser Arg Trp Gln Gln Gly Asn Val Phe Ser Cys
            660                 665                 670

Ser Val Met His Glu Ala Leu His Asn His Tyr Thr Gln Lys Ser Leu
    675                 680                 685

Ser Leu Ser Pro Gly Lys Gly Gly Gly Ser Gly Gly Gly Gly Ser
690                 695                 700

Gln Val Gln Leu Val Gln Ser Gly Ala Glu Val Lys Lys Pro Gly Ser
705                 710                 715                 720

Ser Val Lys Val Ser Cys Lys Ala Ser Gly Gly Thr Phe Ser Ser Tyr
                725                 730                 735

Ala Ile Ser Trp Val Arg Gln Ala Pro Gly Gln Gly Leu Glu Trp Met
            740                 745                 750

Gly Gly Ile Ile Pro Ile Phe Gly Thr Ala Asn Tyr Ala Gln Lys Phe
    755                 760                 765

Gln Gly Arg Val Thr Ile Thr Ala Asp Lys Ser Thr Ser Thr Ala Tyr
770                 775                 780

Met Glu Leu Ser Ser Leu Arg Ser Glu Asp Thr Ala Val Tyr Tyr Cys
785                 790                 795                 800

Ala Arg Glu Tyr Tyr Arg Gly Pro Tyr Asp Tyr Trp Gly Gln Gly Thr
                805                 810                 815

Thr Val Thr Val Ser Ser Ala Ser Thr Lys Gly Pro Ser Val Phe Pro
            820                 825                 830

Leu Ala Pro Ser Ser Lys Ser Thr Ser Gly Gly Thr Ala Ala Leu Gly
    835                 840                 845

Cys Leu Val Lys Asp Tyr Phe Pro Glu Pro Val Thr Val Ser Trp Asn
850                 855                 860

Ser Gly Ala Leu Thr Ser Gly Val His Thr Phe Pro Ala Val Leu Gln
865                 870                 875                 880

Ser Ser Gly Leu Tyr Ser Leu Ser Ser Val Val Thr Val Pro Ser Ser
                885                 890                 895

Ser Leu Gly Thr Gln Thr Tyr Ile Cys Asn Val Asn His Lys Pro Ser
            900                 905                 910

Asn Thr Lys Val Asp Lys Lys Val Glu Pro Lys Ser Cys
    915                 920                 925

<210> SEQ ID NO 132
<211> LENGTH: 914
<212> TYPE: PRT
<213> ORGANISM: Artificial Sequence
<220> FEATURE:
<223> OTHER INFORMATION: second fusion polypeptide (Fc hole) P1AE2743

<400> SEQUENCE: 132

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30
```

```
Tyr Leu Ala Trp Tyr Gln Gln Lys Pro Gly Gln Ala Pro Arg Leu Leu
         35                  40                  45

Ile Asn Val Gly Ser Arg Arg Ala Thr Gly Ile Pro Asp Arg Phe Ser
 50                      55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Ile Met Leu Pro
                 85                  90                  95

Pro Thr Phe Gly Gln Gly Thr Lys Val Glu Ile Lys Ser Ser Ala Ser
             100                 105                 110

Thr Lys Gly Pro Ser Val Phe Pro Leu Ala Pro Ser Ser Lys Ser Thr
         115                 120                 125

Ser Gly Gly Thr Ala Ala Leu Gly Cys Leu Val Lys Asp Tyr Phe Pro
     130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                 165                 170                 175

Ser Val Val Thr Val Pro Ser Ser Ser Leu Gly Thr Gln Thr Tyr Ile
                 180                 185                 190

Cys Asn Val Asn His Lys Pro Ser Asn Thr Lys Val Asp Lys Lys Val
             195                 200                 205

Glu Pro Lys Ser Cys Gly Gly Gly Ser Gly Gly Gly Ser Gly
         210                 215                 220

Gly Gly Ser Gly Gly Gly Ser Asp Ile Gln Met Thr Gln Ser Pro
225                 230                 235                 240

Ser Thr Leu Ser Ala Ser Val Gly Asp Arg Val Thr Ile Thr Cys Arg
                 245                 250                 255

Ala Ser Gln Ser Ile Ser Ser Trp Leu Ala Trp Tyr Gln Gln Lys Pro
             260                 265                 270

Gly Lys Ala Pro Lys Leu Leu Ile Tyr Asp Ala Ser Ser Leu Glu Ser
         275                 280                 285

Gly Val Pro Ser Arg Phe Ser Gly Ser Gly Ser Gly Thr Glu Phe Thr
     290                 295                 300

Leu Thr Ile Ser Ser Leu Gln Pro Asp Asp Phe Ala Thr Tyr Tyr Cys
305                 310                 315                 320

Gln Gln Tyr Ser Ser Gln Pro Tyr Thr Phe Gly Gln Gly Thr Lys Val
                 325                 330                 335

Glu Ile Lys Arg Thr Val Ala Ala Pro Ser Val Phe Ile Phe Pro Pro
             340                 345                 350

Ser Asp Glu Gln Leu Lys Ser Gly Thr Ala Ser Val Val Cys Leu Leu
         355                 360                 365

Asn Asn Phe Tyr Pro Arg Glu Ala Lys Val Gln Trp Lys Val Asp Asn
     370                 375                 380

Ala Leu Gln Ser Gly Asn Ser Gln Glu Ser Val Thr Glu Gln Asp Ser
385                 390                 395                 400

Lys Asp Ser Thr Tyr Ser Leu Ser Ser Thr Leu Thr Leu Ser Lys Ala
                 405                 410                 415

Asp Tyr Glu Lys His Lys Val Tyr Ala Cys Glu Val Thr His Gln Gly
             420                 425                 430

Leu Ser Ser Pro Val Thr Lys Ser Phe Asn Arg Gly Glu Cys Gly Gly
         435                 440                 445
```

```
Gly Gly Ser Gly Gly Gly Ser Asp Lys Thr His Thr Cys Pro Pro
    450             455             460
Cys Pro Ala Pro Glu Ala Ala Gly Gly Pro Ser Val Phe Leu Phe Pro
465             470             475             480
Pro Lys Pro Lys Asp Thr Leu Met Ile Ser Arg Thr Pro Glu Val Thr
                485             490             495
Cys Val Val Val Asp Val Ser His Glu Asp Pro Glu Val Lys Phe Asn
                500             505             510
Trp Tyr Val Asp Gly Val Glu Val His Asn Ala Lys Thr Lys Pro Arg
            515             520             525
Glu Glu Gln Tyr Asn Ser Thr Tyr Arg Val Val Ser Val Leu Thr Val
            530             535             540
Leu His Gln Asp Trp Leu Asn Gly Lys Glu Tyr Lys Cys Lys Val Ser
545             550             555             560
Asn Lys Ala Leu Gly Ala Pro Ile Glu Lys Thr Ile Ser Lys Ala Lys
                565             570             575
Gly Gln Pro Arg Glu Pro Gln Val Cys Thr Leu Pro Pro Ser Arg Asp
            580             585             590
Glu Leu Thr Lys Asn Gln Val Ser Leu Ser Cys Ala Val Lys Gly Phe
            595             600             605
Tyr Pro Ser Asp Ile Ala Val Glu Trp Glu Ser Asn Gly Gln Pro Glu
            610             615             620
Asn Asn Tyr Lys Thr Thr Pro Pro Val Leu Asp Ser Asp Gly Ser Phe
625             630             635             640
Phe Leu Val Ser Lys Leu Thr Val Asp Lys Ser Arg Trp Gln Gln Gly
                645             650             655
Asn Val Phe Ser Cys Ser Val Met His Glu Ala Leu His Asn His Tyr
            660             665             670
Thr Gln Lys Ser Leu Ser Leu Ser Pro Gly Lys Gly Gly Gly Gly Ser
            675             680             685
Gly Gly Gly Gly Ser Gln Val Gln Leu Val Gln Ser Gly Ala Glu Val
690             695             700
Lys Lys Pro Gly Ser Ser Val Lys Val Ser Cys Lys Ala Ser Gly Gly
705             710             715             720
Thr Phe Ser Ser Tyr Ala Ile Ser Trp Val Arg Gln Ala Pro Gly Gln
            725             730             735
Gly Leu Glu Trp Met Gly Gly Ile Ile Pro Ile Phe Gly Thr Ala Asn
            740             745             750
Tyr Ala Gln Lys Phe Gln Gly Arg Val Thr Ile Thr Ala Asp Lys Ser
            755             760             765
Thr Ser Thr Ala Tyr Met Glu Leu Ser Ser Leu Arg Ser Glu Asp Thr
770             775             780
Ala Val Tyr Tyr Cys Ala Arg Glu Tyr Arg Gly Pro Tyr Asp Tyr
785             790             795             800
Trp Gly Gln Gly Thr Thr Val Thr Val Ser Ser Ala Ser Thr Lys Gly
            805             810             815
Pro Ser Val Phe Pro Leu Ala Pro Ser Ser Lys Ser Thr Ser Gly Gly
            820             825             830
Thr Ala Ala Leu Gly Cys Leu Val Lys Asp Tyr Phe Pro Glu Pro Val
            835             840             845
Thr Val Ser Trp Asn Ser Gly Ala Leu Thr Ser Gly Val His Thr Phe
            850             855             860
```

```
Pro Ala Val Leu Gln Ser Ser Gly Leu Tyr Ser Leu Ser Val Val
865                 870                 875                 880

Thr Val Pro Ser Ser Leu Gly Thr Gln Thr Tyr Ile Cys Asn Val
                885                 890                 895

Asn His Lys Pro Ser Asn Thr Lys Val Asp Lys Lys Val Glu Pro Lys
            900                 905                 910

Ser Cys

<210> SEQ ID NO 133
<211> LENGTH: 919
<212> TYPE: PRT
<213> ORGANISM: Artificial Sequence
<220> FEATURE:
<223> OTHER INFORMATION: first fusion polypeptide (Fc knob) P1AE2762

<400> SEQUENCE: 133

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
                20                  25                  30

Tyr Leu Ala Trp Tyr Gln Gln Lys Pro Gly Gln Ala Pro Arg Leu Leu
            35                  40                  45

Ile Asn Val Gly Ser Arg Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Gly Ser Gly Gly Gly Gly
210                 215                 220

Ser Gly Gly Gly Ser Gly Gly Gly Ser Gln Val Gln Leu Val Gln
225                 230                 235                 240

Ser Gly Ala Glu Val Lys Lys Pro Gly Ser Ser Val Lys Val Ser Cys
                245                 250                 255

Lys Ala Ser Gly Gly Thr Phe Ser Ser Tyr Ala Ile Ser Trp Val Arg
            260                 265                 270

Gln Ala Pro Gly Gln Gly Leu Glu Trp Met Gly Gly Ile Ile Pro Ile
        275                 280                 285

Phe Gly Thr Ala Asn Tyr Ala Gln Lys Phe Gln Gly Arg Val Thr Ile
290                 295                 300
```

```
Thr Ala Asp Lys Ser Thr Ser Thr Ala Tyr Met Glu Leu Ser Ser Leu
305                 310                 315                 320

Arg Ser Glu Asp Thr Ala Val Tyr Tyr Cys Ala Arg Glu Tyr Tyr Arg
            325                 330                 335

Gly Pro Tyr Asp Tyr Trp Gly Gln Gly Thr Thr Val Thr Val Ser Ser
            340                 345                 350

Ala Ser Val Ala Ala Pro Ser Val Phe Ile Phe Pro Ser Asp Glu
            355                 360                 365

Gln Leu Lys Ser Gly Thr Ala Ser Val Val Cys Leu Leu Asn Asn Phe
370                 375                 380

Tyr Pro Arg Glu Ala Lys Val Gln Trp Lys Val Asp Asn Ala Leu Gln
385                 390                 395                 400

Ser Gly Asn Ser Gln Glu Ser Val Thr Glu Gln Asp Ser Lys Asp Ser
            405                 410                 415

Thr Tyr Ser Leu Ser Ser Thr Leu Thr Leu Ser Lys Ala Asp Tyr Glu
            420                 425                 430

Lys His Lys Val Tyr Ala Cys Glu Val Thr His Gln Gly Leu Ser Ser
            435                 440                 445

Pro Val Thr Lys Ser Phe Asn Arg Gly Glu Cys Asp Gly Gly Gly Gly
450                 455                 460

Ser Gly Gly Gly Gly Ser Asp Lys Thr His Thr Cys Pro Pro Cys Pro
465                 470                 475                 480

Ala Pro Glu Ala Ala Gly Gly Pro Ser Val Phe Leu Phe Pro Pro Lys
            485                 490                 495

Pro Lys Asp Thr Leu Met Ile Ser Arg Thr Pro Glu Val Thr Cys Val
            500                 505                 510

Val Val Asp Val Ser His Glu Asp Pro Glu Val Lys Phe Asn Trp Tyr
            515                 520                 525

Val Asp Gly Val Glu Val His Asn Ala Lys Thr Lys Pro Arg Glu Glu
            530                 535                 540

Gln Tyr Asn Ser Thr Tyr Arg Val Val Ser Val Leu Thr Val Leu His
545                 550                 555                 560

Gln Asp Trp Leu Asn Gly Lys Glu Tyr Lys Cys Lys Val Ser Asn Lys
            565                 570                 575

Ala Leu Gly Ala Pro Ile Glu Lys Thr Ile Ser Lys Ala Lys Gly Gln
            580                 585                 590

Pro Arg Glu Pro Gln Val Tyr Thr Leu Pro Pro Cys Arg Asp Glu Leu
            595                 600                 605

Thr Lys Asn Gln Val Ser Leu Trp Cys Leu Val Lys Gly Phe Tyr Pro
            610                 615                 620

Ser Asp Ile Ala Val Glu Trp Glu Ser Asn Gly Gln Pro Glu Asn Asn
625                 630                 635                 640

Tyr Lys Thr Thr Pro Pro Val Leu Asp Ser Asp Gly Ser Phe Phe Leu
            645                 650                 655

Tyr Ser Lys Leu Thr Val Asp Lys Ser Arg Trp Gln Gln Gly Asn Val
            660                 665                 670

Phe Ser Cys Ser Val Met His Glu Ala Leu His Asn His Tyr Thr Gln
            675                 680                 685

Lys Ser Leu Ser Leu Ser Pro Gly Lys Gly Gly Gly Ser Gly Gly
            690                 695                 700

Gly Gly Ser Asp Ile Gln Met Thr Gln Ser Pro Ser Thr Leu Ser Ala
705                 710                 715                 720
```

```
Ser Val Gly Asp Arg Val Thr Ile Thr Cys Arg Ala Ser Gln Ser Ile
            725                 730                 735

Ser Ser Trp Leu Ala Trp Tyr Gln Gln Lys Pro Gly Lys Ala Pro Lys
        740                 745                 750

Leu Leu Ile Tyr Asp Ala Ser Ser Leu Glu Ser Gly Val Pro Ser Arg
            755                 760                 765

Phe Ser Gly Ser Gly Ser Gly Thr Glu Phe Thr Leu Thr Ile Ser Ser
    770                 775                 780

Leu Gln Pro Asp Asp Phe Ala Thr Tyr Tyr Cys Gln Gln Tyr Ser Ser
785                 790                 795                 800

Gln Pro Tyr Thr Phe Gly Gln Gly Thr Lys Val Glu Ile Lys Ser Ser
                805                 810                 815

Ala Ser Thr Lys Gly Pro Ser Val Phe Pro Leu Ala Pro Ser Ser Lys
            820                 825                 830

Ser Thr Ser Gly Gly Thr Ala Ala Leu Gly Cys Leu Val Lys Asp Tyr
        835                 840                 845

Phe Pro Glu Pro Val Thr Val Ser Trp Asn Ser Gly Ala Leu Thr Ser
    850                 855                 860

Gly Val His Thr Phe Pro Ala Val Leu Gln Ser Ser Gly Leu Tyr Ser
865                 870                 875                 880

Leu Ser Ser Val Val Thr Val Pro Ser Ser Ser Leu Gly Thr Gln Thr
                885                 890                 895

Tyr Ile Cys Asn Val Asn His Lys Pro Ser Asn Thr Lys Val Asp Lys
            900                 905                 910

Lys Val Glu Pro Lys Ser Cys
        915
```

<210> SEQ ID NO 134
<211> LENGTH: 924
<212> TYPE: PRT
<213> ORGANISM: Artificial Sequence
<220> FEATURE:
<223> OTHER INFORMATION: second fusion polypeptide (Fc hole) P1AE2762

<400> SEQUENCE: 134

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Gly Trp Phe Gly Gly Phe Asn Tyr Trp Gly Gln Gly Thr Leu
        100                 105                 110

Val Thr Val Ser Ser Ala Ser Thr Lys Gly Pro Ser Val Phe Pro Leu
    115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160
```

-continued

```
Gly Ala Leu Thr Ser Gly Val His Thr Phe Pro Ala Val Leu Gln Ser
            165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
            195                 200                 205
Thr Lys Val Asp Lys Lys Val Glu Pro Lys Ser Cys Gly Gly Gly Gly
210                 215                 220
Ser Gly Gly Gly Gly Ser Gly Gly Ser Gly Gly Gly Ser Gln
225                 230                 235                 240
Val Gln Leu Val Gln Ser Gly Ala Glu Val Lys Lys Pro Gly Ser Ser
            245                 250                 255
Val Lys Val Ser Cys Lys Ala Ser Gly Gly Thr Phe Ser Ser Tyr Ala
            260                 265                 270
Ile Ser Trp Val Arg Gln Ala Pro Gly Gln Gly Leu Glu Trp Met Gly
            275                 280                 285
Gly Ile Ile Pro Ile Phe Gly Thr Ala Asn Tyr Ala Gln Lys Phe Gln
            290                 295                 300
Gly Arg Val Thr Ile Thr Ala Asp Lys Ser Thr Ser Thr Ala Tyr Met
305                 310                 315                 320
Glu Leu Ser Ser Leu Arg Ser Glu Asp Thr Ala Val Tyr Tyr Cys Ala
            325                 330                 335
Arg Glu Tyr Tyr Arg Gly Pro Tyr Asp Tyr Trp Gly Gln Gly Thr Thr
            340                 345                 350
Val Thr Val Ser Ser Ala Ser Val Ala Ala Pro Ser Val Phe Ile Phe
            355                 360                 365
Pro Pro Ser Asp Glu Gln Leu Lys Ser Gly Thr Ala Ser Val Val Cys
            370                 375                 380
Leu Leu Asn Asn Phe Tyr Pro Arg Glu Ala Lys Val Gln Trp Lys Val
385                 390                 395                 400
Asp Asn Ala Leu Gln Ser Gly Asn Ser Gln Glu Ser Val Thr Glu Gln
            405                 410                 415
Asp Ser Lys Asp Ser Thr Tyr Ser Leu Ser Ser Thr Leu Thr Leu Ser
            420                 425                 430
Lys Ala Asp Tyr Glu Lys His Lys Val Tyr Ala Cys Glu Val Thr His
            435                 440                 445
Gln Gly Leu Ser Ser Pro Val Thr Lys Ser Phe Asn Arg Gly Glu Cys
            450                 455                 460
Asp Gly Gly Gly Gly Ser Gly Gly Gly Gly Ser Asp Lys Thr His Thr
465                 470                 475                 480
Cys Pro Pro Cys Pro Ala Pro Glu Ala Ala Gly Gly Pro Ser Val Phe
            485                 490                 495
Leu Phe Pro Pro Lys Pro Lys Asp Thr Leu Met Ile Ser Arg Thr Pro
            500                 505                 510
Glu Val Thr Cys Val Val Val Asp Val Ser His Glu Asp Pro Glu Val
            515                 520                 525
Lys Phe Asn Trp Tyr Val Asp Gly Val Glu Val His Asn Ala Lys Thr
            530                 535                 540
Lys Pro Arg Glu Glu Gln Tyr Asn Ser Thr Tyr Arg Val Val Ser Val
545                 550                 555                 560
Leu Thr Val Leu His Gln Asp Trp Leu Asn Gly Lys Glu Tyr Lys Cys
            565                 570                 575
```

```
Lys Val Ser Asn Lys Ala Leu Gly Ala Pro Ile Glu Lys Thr Ile Ser
            580                 585                 590

Lys Ala Lys Gly Gln Pro Arg Glu Pro Gln Val Cys Thr Leu Pro Pro
        595                 600                 605

Ser Arg Asp Glu Leu Thr Lys Asn Gln Val Ser Leu Ser Cys Ala Val
    610                 615                 620

Lys Gly Phe Tyr Pro Ser Asp Ile Ala Val Glu Trp Glu Ser Asn Gly
625                 630                 635                 640

Gln Pro Glu Asn Asn Tyr Lys Thr Thr Pro Pro Val Leu Asp Ser Asp
                645                 650                 655

Gly Ser Phe Phe Leu Val Ser Lys Leu Thr Val Asp Lys Ser Arg Trp
            660                 665                 670

Gln Gln Gly Asn Val Phe Ser Cys Ser Val Met His Glu Ala Leu His
        675                 680                 685

Asn His Tyr Thr Gln Lys Ser Leu Ser Leu Ser Pro Gly Lys Gly Gly
    690                 695                 700

Gly Gly Ser Gly Gly Gly Gly Ser Asp Ile Gln Met Thr Gln Ser Pro
705                 710                 715                 720

Ser Thr Leu Ser Ala Ser Val Gly Asp Arg Val Thr Ile Thr Cys Arg
                725                 730                 735

Ala Ser Gln Ser Ile Ser Ser Trp Leu Ala Trp Tyr Gln Gln Lys Pro
            740                 745                 750

Gly Lys Ala Pro Lys Leu Leu Ile Tyr Asp Ala Ser Ser Leu Glu Ser
        755                 760                 765

Gly Val Pro Ser Arg Phe Ser Gly Ser Gly Ser Gly Thr Glu Phe Thr
    770                 775                 780

Leu Thr Ile Ser Ser Leu Gln Pro Asp Asp Phe Ala Thr Tyr Tyr Cys
785                 790                 795                 800

Gln Gln Tyr Ser Ser Gln Pro Tyr Thr Phe Gly Gln Gly Thr Lys Val
                805                 810                 815

Glu Ile Lys Ser Ser Ala Ser Thr Lys Gly Pro Ser Val Phe Pro Leu
            820                 825                 830

Ala Pro Ser Ser Lys Ser Thr Ser Gly Gly Thr Ala Ala Leu Gly Cys
        835                 840                 845

Leu Val Lys Asp Tyr Phe Pro Glu Pro Val Thr Val Ser Trp Asn Ser
    850                 855                 860

Gly Ala Leu Thr Ser Gly Val His Thr Phe Pro Ala Val Leu Gln Ser
865                 870                 875                 880

Ser Gly Leu Tyr Ser Leu Ser Ser Val Val Thr Val Pro Ser Ser Ser
                885                 890                 895

Leu Gly Thr Gln Thr Tyr Ile Cys Asn Val Asn His Lys Pro Ser Asn
            900                 905                 910

Thr Lys Val Asp Lys Lys Val Glu Pro Lys Ser Cys
        915                 920
```

<210> SEQ ID NO 135
<211> LENGTH: 5
<212> TYPE: PRT
<213> ORGANISM: Artificial Sequence
<220> FEATURE:
<223> OTHER INFORMATION: 4-1BB (20H4.9) CDR-H1

<400> SEQUENCE: 135

```
Gly Tyr Tyr Trp Ser
1               5
```

<210> SEQ ID NO 136
<211> LENGTH: 16
<212> TYPE: PRT
<213> ORGANISM: Artificial Sequence
<220> FEATURE:
<223> OTHER INFORMATION: 4-1BB (20H4.9) CDR-H2

<400> SEQUENCE: 136

Glu Ile Asn His Gly Gly Tyr Val Thr Tyr Asn Pro Ser Leu Glu Ser
1               5                   10                  15

<210> SEQ ID NO 137
<211> LENGTH: 13
<212> TYPE: PRT
<213> ORGANISM: Artificial Sequence
<220> FEATURE:
<223> OTHER INFORMATION: 4-1BB (20H4.9) CDR-H3

<400> SEQUENCE: 137

Asp Tyr Gly Pro Gly Asn Tyr Asp Trp Tyr Phe Asp Leu
1               5                   10

<210> SEQ ID NO 138
<211> LENGTH: 11
<212> TYPE: PRT
<213> ORGANISM: Artificial Sequence
<220> FEATURE:
<223> OTHER INFORMATION: 4-1BB (20H4.9) CDR-L1

<400> SEQUENCE: 138

Arg Ala Ser Gln Ser Val Ser Ser Tyr Leu Ala
1               5                   10

<210> SEQ ID NO 139
<211> LENGTH: 7
<212> TYPE: PRT
<213> ORGANISM: Artificial Sequence
<220> FEATURE:
<223> OTHER INFORMATION: 4-1BB (20H4.9) CDR-L2

<400> SEQUENCE: 139

Asp Ala Ser Asn Arg Ala Thr
1               5

<210> SEQ ID NO 140
<211> LENGTH: 11
<212> TYPE: PRT
<213> ORGANISM: Artificial Sequence
<220> FEATURE:
<223> OTHER INFORMATION: 4-1BB (20H4.9) CDR-L3

<400> SEQUENCE: 140

Gln Gln Arg Ser Asn Trp Pro Pro Ala Leu Thr
1               5                   10

<210> SEQ ID NO 141
<211> LENGTH: 121
<212> TYPE: PRT
<213> ORGANISM: Artificial Sequence
<220> FEATURE:
<223> OTHER INFORMATION: 4-1BB (20H4.9) VH

<400> SEQUENCE: 141

Gln Val Gln Leu Gln Gln Trp Gly Ala Gly Leu Leu Lys Pro Ser Glu
1               5                   10                  15

```
Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser
            115                 120

<210> SEQ ID NO 142
<211> LENGTH: 109
<212> TYPE: PRT
<213> ORGANISM: Artificial Sequence
<220> FEATURE:
<223> OTHER INFORMATION: 4-1BB (20H4.9) VL

<400> SEQUENCE: 142

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys
            100                 105

<210> SEQ ID NO 143
<211> LENGTH: 930
<212> TYPE: PRT
<213> ORGANISM: Artificial Sequence
<220> FEATURE:
<223> OTHER INFORMATION: first fusion polypeptide (Fc knob) P1AE1899

<400> SEQUENCE: 143

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

-continued

Arg Asp Tyr Gly Pro Gly Asn Tyr Asp Trp Tyr Phe Asp Leu Trp Gly
                100                 105                 110

Arg Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
        210                 215                 220

Gly Gly Gly Gly Ser Gly Gly Gly Gly Ser Asp Lys Thr His Thr Cys
225                 230                 235                 240

Pro Pro Cys Pro Ala Pro Glu Ala Ala Gly Gly Pro Ser Val Phe Leu
                245                 250                 255

Phe Pro Pro Lys Pro Lys Asp Thr Leu Met Ile Ser Arg Thr Pro Glu
                260                 265                 270

Val Thr Cys Val Val Val Asp Val Ser His Glu Asp Pro Glu Val Lys
            275                 280                 285

Phe Asn Trp Tyr Val Asp Gly Val Glu Val His Asn Ala Lys Thr Lys
        290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Gly Ala Pro Ile Glu Lys Thr Ile Ser Lys
                340                 345                 350

Ala Lys Gly Gln Pro Arg Glu Pro Gln Val Tyr Thr Leu Pro Pro Cys
            355                 360                 365

Arg Asp Glu Leu Thr Lys Asn Gln Val Ser Leu Trp Cys Leu Val Lys
        370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
                420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Gly Lys Gly Gly Gly
        450                 455                 460

Gly Ser Gly Gly Gly Gly Ser Glu Ile Val Leu Thr Gln Ser Pro Ala
465                 470                 475                 480

Thr Leu Ser Leu Ser Pro Gly Glu Arg Ala Thr Leu Ser Cys Arg Ala
                485                 490                 495

Ser Gln Ser Val Ser Ser Tyr Leu Ala Trp Tyr Gln Gln Lys Pro Gly
                500                 505                 510

-continued

```
Gln Ala Pro Arg Leu Leu Ile Tyr Asp Ala Ser Asn Arg Ala Thr Gly
            515                 520                 525
Ile Pro Ala Arg Phe Ser Gly Ser Gly Ser Gly Thr Asp Phe Thr Leu
        530                 535                 540
Thr Ile Ser Ser Leu Glu Pro Glu Asp Phe Ala Val Tyr Tyr Cys Gln
545                 550                 555                 560
Gln Arg Ser Asn Trp Pro Pro Ala Leu Thr Phe Gly Gly Gly Thr Lys
                565                 570                 575
Val Glu Ile Lys Arg Thr Val Ala Ala Pro Ser Val Phe Ile Phe Pro
            580                 585                 590
Pro Ser Asp Glu Gln Leu Lys Ser Gly Thr Ala Ser Val Val Cys Leu
            595                 600                 605
Leu Asn Asn Phe Tyr Pro Arg Glu Ala Lys Val Gln Trp Lys Val Asp
        610                 615                 620
Asn Ala Leu Gln Ser Gly Asn Ser Gln Glu Ser Val Thr Glu Gln Asp
625                 630                 635                 640
Ser Lys Asp Ser Thr Tyr Ser Leu Ser Ser Thr Leu Thr Leu Ser Lys
                645                 650                 655
Ala Asp Tyr Glu Lys His Lys Val Tyr Ala Cys Glu Val Thr His Gln
            660                 665                 670
Gly Leu Ser Ser Pro Val Thr Lys Ser Phe Asn Arg Gly Glu Cys Gly
            675                 680                 685
Gly Gly Gly Ser Gly Gly Gly Gly Ser Gly Gly Gly Ser Gly Gly Gly
        690                 695                 700
Gly Ser Glu Val Gln Leu Leu Glu Ser Gly Gly Gly Leu Val Gln Pro
705                 710                 715                 720
Gly Gly Ser Leu Arg Leu Ser Cys Ala Ala Ser Gly Phe Thr Phe Ser
                725                 730                 735
Ser Tyr Ala Met Ser Trp Val Arg Gln Ala Pro Gly Lys Gly Leu Glu
            740                 745                 750
Trp Val Ser Ala Ile Ile Gly Ser Gly Ala Ser Thr Tyr Tyr Ala Asp
            755                 760                 765
Ser Val Lys Gly Arg Phe Thr Ile Ser Arg Asp Asn Ser Lys Asn Thr
        770                 775                 780
Leu Tyr Leu Gln Met Asn Ser Leu Arg Ala Glu Asp Thr Ala Val Tyr
785                 790                 795                 800
Tyr Cys Ala Lys Gly Trp Phe Gly Gly Phe Asn Tyr Trp Gln Gly Gly
                805                 810                 815
Thr Leu Val Thr Val Ser Ser Ala Ser Val Ala Ala Pro Ser Val Phe
            820                 825                 830
Ile Phe Pro Pro Ser Asp Glu Gln Leu Lys Ser Gly Thr Ala Ser Val
            835                 840                 845
Val Cys Leu Leu Asn Asn Phe Tyr Pro Arg Glu Ala Lys Val Gln Trp
        850                 855                 860
Lys Val Asp Asn Ala Leu Gln Ser Gly Asn Ser Gln Glu Ser Val Thr
865                 870                 875                 880
Glu Gln Asp Ser Lys Asp Ser Thr Tyr Ser Leu Ser Ser Thr Leu Thr
                885                 890                 895
Leu Ser Lys Ala Asp Tyr Glu Lys His Lys Val Tyr Ala Cys Glu Val
            900                 905                 910
```

-continued

Thr His Gln Gly Leu Ser Ser Pro Val Thr Lys Ser Phe Asn Arg Gly
        915                 920                 925

Glu Cys
    930

<210> SEQ ID NO 144
<211> LENGTH: 919
<212> TYPE: PRT
<213> ORGANISM: Artificial Sequence
<220> FEATURE:
<223> OTHER INFORMATION: second fusion polypeptide (Fc hole) P1AE1899

<400> SEQUENCE: 144

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Gly Gly Gly Gly Ser Gly Gly Gly Ser Asp Lys Thr His Thr Cys
225                 230                 235                 240

Pro Pro Cys Pro Ala Pro Glu Ala Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

```
Val Ser Asn Lys Ala Leu Gly Ala Pro Ile Glu Lys Thr Ile Ser Lys
                340                 345                 350

Ala Lys Gly Gln Pro Arg Glu Pro Gln Val Cys Thr Leu Pro Pro Ser
            355                 360                 365

Arg Asp Glu Leu Thr Lys Asn Gln Val Ser Leu Ser Cys Ala Val Lys
        370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Val Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys Gly Gly Gly
    450                 455                 460

Gly Ser Gly Gly Gly Gly Ser Glu Ile Val Leu Thr Gln Ser Pro Ala
465                 470                 475                 480

Thr Leu Ser Leu Ser Pro Gly Glu Arg Ala Thr Leu Ser Cys Arg Ala
                485                 490                 495

Ser Gln Ser Val Ser Ser Tyr Leu Ala Trp Tyr Gln Gln Lys Pro Gly
            500                 505                 510

Gln Ala Pro Arg Leu Leu Ile Tyr Asp Ala Ser Asn Arg Ala Thr Gly
        515                 520                 525

Ile Pro Ala Arg Phe Ser Gly Ser Gly Ser Gly Thr Asp Phe Thr Leu
    530                 535                 540

Thr Ile Ser Ser Leu Glu Pro Glu Asp Phe Ala Val Tyr Tyr Cys Gln
545                 550                 555                 560

Gln Arg Ser Asn Trp Pro Pro Ala Leu Thr Phe Gly Gly Gly Thr Lys
                565                 570                 575

Val Glu Ile Lys Arg Thr Val Ala Ala Pro Ser Val Phe Ile Phe Pro
            580                 585                 590

Pro Ser Asp Glu Gln Leu Lys Ser Gly Thr Ala Ser Val Val Cys Leu
        595                 600                 605

Leu Asn Asn Phe Tyr Pro Arg Glu Ala Lys Val Gln Trp Lys Val Asp
    610                 615                 620

Asn Ala Leu Gln Ser Gly Asn Ser Gln Glu Ser Val Thr Glu Gln Asp
625                 630                 635                 640

Ser Lys Asp Ser Thr Tyr Ser Leu Ser Ser Thr Leu Thr Leu Ser Lys
                645                 650                 655

Ala Asp Tyr Glu Lys His Lys Val Tyr Ala Cys Glu Val Thr His Gln
            660                 665                 670

Gly Leu Ser Ser Pro Val Thr Lys Ser Phe Asn Arg Gly Glu Cys Gly
        675                 680                 685

Gly Gly Gly Ser Gly Gly Gly Gly Ser Gly Gly Gly Ser Gly Gly Gly
    690                 695                 700

Gly Ser Glu Ile Val Leu Thr Gln Ser Pro Gly Thr Leu Ser Leu Ser
705                 710                 715                 720

Pro Gly Glu Arg Ala Thr Leu Ser Cys Arg Ala Ser Gln Ser Val Thr
                725                 730                 735

Ser Ser Tyr Leu Ala Trp Tyr Gln Gln Lys Pro Gly Gln Ala Pro Arg
            740                 745                 750
```

```
Leu Leu Ile Asn Val Gly Ser Arg Arg Ala Thr Gly Ile Pro Asp Arg
            755                 760                 765

Phe Ser Gly Ser Gly Ser Gly Thr Asp Phe Thr Leu Thr Ile Ser Arg
    770                 775                 780

Leu Glu Pro Glu Asp Phe Ala Val Tyr Tyr Cys Gln Gln Gly Ile Met
785                 790                 795                 800

Leu Pro Pro Thr Phe Gly Gln Gly Thr Lys Val Glu Ile Lys Ser Ser
                805                 810                 815

Ala Ser Thr Lys Gly Pro Ser Val Phe Pro Leu Ala Pro Ser Ser Lys
            820                 825                 830

Ser Thr Ser Gly Gly Thr Ala Ala Leu Gly Cys Leu Val Lys Asp Tyr
            835                 840                 845

Phe Pro Glu Pro Val Thr Val Ser Trp Asn Ser Gly Ala Leu Thr Ser
    850                 855                 860

Gly Val His Thr Phe Pro Ala Val Leu Gln Ser Ser Gly Leu Tyr Ser
865                 870                 875                 880

Leu Ser Ser Val Val Thr Val Pro Ser Ser Leu Gly Thr Gln Thr
                885                 890                 895

Tyr Ile Cys Asn Val Asn His Lys Pro Ser Asn Thr Lys Val Asp Lys
                900                 905                 910

Lys Val Glu Pro Lys Ser Cys
        915

<210> SEQ ID NO 145
<211> LENGTH: 930
<212> TYPE: PRT
<213> ORGANISM: Artificial Sequence
<220> FEATURE:
<223> OTHER INFORMATION: first fusion polypeptide (Fc knob) P1AE2051

<400> SEQUENCE: 145

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
        195                 200                 205

Lys Pro Ser Asn Thr Lys Val Asp Glu Lys Val Glu Pro Lys Ser Cys
210                 215                 220

Gly Gly Gly Gly Ser Gly Gly Gly Ser Asp Lys Thr His Thr Cys
225                 230                 235                 240

Pro Pro Cys Pro Ala Pro Glu Ala Ala Gly Gly Pro Ser Val Phe Leu
            245                 250                 255

Phe Pro Pro Lys Pro Lys Asp Thr Leu Met Ile Ser Arg Thr Pro Glu
        260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
        290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Gly Ala Pro Ile Glu Lys Thr Ile Ser Lys
                340                 345                 350

Ala Lys Gly Gln Pro Arg Glu Pro Gln Val Tyr Thr Leu Pro Pro Cys
            355                 360                 365

Arg Asp Glu Leu Thr Lys Asn Gln Val Ser Leu Trp Cys Leu Val Lys
        370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
                420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Gly Lys Gly Gly Gly
        450                 455                 460

Gly Ser Gly Gly Gly Gly Ser Glu Ile Val Leu Thr Gln Ser Pro Ala
465                 470                 475                 480

Thr Leu Ser Leu Ser Pro Gly Glu Arg Ala Thr Leu Ser Cys Arg Ala
                485                 490                 495

Ser Gln Ser Val Ser Ser Tyr Leu Ala Trp Tyr Gln Gln Lys Pro Gly
            500                 505                 510

Gln Ala Pro Arg Leu Leu Ile Tyr Asp Ala Ser Asn Arg Ala Thr Gly
        515                 520                 525

Ile Pro Ala Arg Phe Ser Gly Ser Gly Ser Gly Thr Asp Phe Thr Leu
        530                 535                 540

Thr Ile Ser Ser Leu Glu Pro Glu Asp Phe Ala Val Tyr Tyr Cys Gln
545                 550                 555                 560

Gln Arg Ser Asn Trp Pro Pro Ala Leu Thr Phe Gly Gly Gly Thr Lys
                565                 570                 575

Val Glu Ile Lys Arg Thr Val Ala Ala Pro Ser Val Phe Ile Phe Pro
                580                 585                 590

Pro Ser Asp Arg Lys Leu Lys Ser Gly Thr Ala Ser Val Val Cys Leu
            595                 600                 605
```

```
Leu Asn Asn Phe Tyr Pro Arg Glu Ala Lys Val Gln Trp Lys Val Asp
610                 615                 620

Asn Ala Leu Gln Ser Gly Asn Ser Gln Glu Ser Val Thr Glu Gln Asp
625                 630                 635                 640

Ser Lys Asp Ser Thr Tyr Ser Leu Ser Ser Thr Leu Thr Leu Ser Lys
                645                 650                 655

Ala Asp Tyr Glu Lys His Lys Val Tyr Ala Cys Glu Val Thr His Gln
                660                 665                 670

Gly Leu Ser Ser Pro Val Thr Lys Ser Phe Asn Arg Gly Glu Cys Gly
                675                 680                 685

Gly Gly Gly Ser Gly Gly Gly Ser Gly Gly Gly Ser Gly Gly Gly
            690                 695                 700

Gly Ser Glu Val Gln Leu Leu Glu Ser Gly Gly Gly Leu Val Gln Pro
705                 710                 715                 720

Gly Gly Ser Leu Arg Leu Ser Cys Ala Ala Ser Gly Phe Thr Phe Ser
                725                 730                 735

Ser Tyr Ala Met Ser Trp Val Arg Gln Ala Pro Gly Lys Gly Leu Glu
                740                 745                 750

Trp Val Ser Ala Ile Ile Gly Ser Gly Ala Ser Thr Tyr Tyr Ala Asp
                755                 760                 765

Ser Val Lys Gly Arg Phe Thr Ile Ser Arg Asp Asn Ser Lys Asn Thr
770                 775                 780

Leu Tyr Leu Gln Met Asn Ser Leu Arg Ala Glu Asp Thr Ala Val Tyr
785                 790                 795                 800

Tyr Cys Ala Lys Gly Trp Phe Gly Gly Phe Asn Tyr Trp Gly Gln Gly
                805                 810                 815

Thr Leu Val Thr Val Ser Ser Ala Ser Val Ala Ala Pro Ser Val Phe
                820                 825                 830

Ile Phe Pro Pro Ser Asp Glu Gln Leu Lys Ser Gly Thr Ala Ser Val
                835                 840                 845

Val Cys Leu Leu Asn Asn Phe Tyr Pro Arg Glu Ala Lys Val Gln Trp
                850                 855                 860

Lys Val Asp Asn Ala Leu Gln Ser Gly Asn Ser Gln Glu Ser Val Thr
865                 870                 875                 880

Glu Gln Asp Ser Lys Asp Ser Thr Tyr Ser Leu Ser Ser Thr Leu Thr
                885                 890                 895

Leu Ser Lys Ala Asp Tyr Glu Lys His Lys Val Tyr Ala Cys Glu Val
                900                 905                 910

Thr His Gln Gly Leu Ser Ser Pro Val Thr Lys Ser Phe Asn Arg Gly
                915                 920                 925

Glu Cys
   930

<210> SEQ ID NO 146
<211> LENGTH: 919
<212> TYPE: PRT
<213> ORGANISM: Artificial Sequence
<220> FEATURE:
<223> OTHER INFORMATION: second fusion polypeptide (Fc hole) P1AE2051

<400> SEQUENCE: 146

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30
```

```
Tyr Trp Ser Trp Ile Arg Gln Ser Pro Glu Lys Gly Leu Glu Trp Ile
         35                  40                  45

Gly Glu Ile Asn His Gly Gly Tyr Val Thr Tyr Asn Pro Ser Leu Glu
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Tyr Gly Pro Gly Asn Tyr Asp Trp Tyr Phe Asp Leu Trp Gly
                100                 105                 110

Arg Gly Thr Leu Val Thr Val Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Glu Lys Val Glu Pro Lys Ser Cys
    210                 215                 220

Gly Gly Gly Gly Ser Gly Gly Gly Ser Asp Lys Thr His Thr Cys
225                 230                 235                 240

Pro Pro Cys Pro Ala Pro Glu Ala Ala Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Gly Ala Pro Ile Glu Lys Thr Ile Ser Lys
            340                 345                 350

Ala Lys Gly Gln Pro Arg Glu Pro Gln Val Cys Thr Leu Pro Pro Ser
        355                 360                 365

Arg Asp Glu Leu Thr Lys Asn Gln Val Ser Leu Ser Cys Ala Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Val Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445
```

-continued

```
His Tyr Thr Gln Lys Ser Leu Ser Leu Ser Pro Gly Lys Gly Gly
    450                 455                 460
Gly Ser Gly Gly Gly Ser Glu Ile Val Leu Thr Gln Ser Pro Ala
465                 470                 475                 480
Thr Leu Ser Leu Ser Pro Gly Glu Arg Ala Thr Leu Ser Cys Arg Ala
                    485                 490                 495
Ser Gln Ser Val Ser Ser Tyr Leu Ala Trp Tyr Gln Gln Lys Pro Gly
                500                 505                 510
Gln Ala Pro Arg Leu Leu Ile Tyr Asp Ala Ser Asn Arg Ala Thr Gly
            515                 520                 525
Ile Pro Ala Arg Phe Ser Gly Ser Gly Ser Gly Thr Asp Phe Thr Leu
530                 535                 540
Thr Ile Ser Ser Leu Glu Pro Glu Asp Phe Ala Val Tyr Tyr Cys Gln
545                 550                 555                 560
Gln Arg Ser Asn Trp Pro Pro Ala Leu Thr Phe Gly Gly Gly Thr Lys
                565                 570                 575
Val Glu Ile Lys Arg Thr Val Ala Ala Pro Ser Val Phe Ile Phe Pro
            580                 585                 590
Pro Ser Asp Arg Lys Leu Lys Ser Gly Thr Ala Ser Val Val Cys Leu
            595                 600                 605
Leu Asn Asn Phe Tyr Pro Arg Glu Ala Lys Val Gln Trp Lys Val Asp
610                 615                 620
Asn Ala Leu Gln Ser Gly Asn Ser Gln Glu Ser Val Thr Glu Gln Asp
625                 630                 635                 640
Ser Lys Asp Ser Thr Tyr Ser Leu Ser Ser Thr Leu Thr Leu Ser Lys
                645                 650                 655
Ala Asp Tyr Glu Lys His Lys Val Tyr Ala Cys Glu Val Thr His Gln
            660                 665                 670
Gly Leu Ser Ser Pro Val Thr Lys Ser Phe Asn Arg Gly Glu Cys Gly
            675                 680                 685
Gly Gly Gly Ser Gly Gly Gly Gly Ser Gly Gly Gly Ser Gly Gly Gly
            690                 695                 700
Gly Ser Glu Ile Val Leu Thr Gln Ser Pro Gly Thr Leu Ser Leu Ser
705                 710                 715                 720
Pro Gly Glu Arg Ala Thr Leu Ser Cys Arg Ala Ser Gln Ser Val Thr
                725                 730                 735
Ser Ser Tyr Leu Ala Trp Tyr Gln Gln Lys Pro Gly Gln Ala Pro Arg
                740                 745                 750
Leu Leu Ile Asn Val Gly Ser Arg Arg Ala Thr Gly Ile Pro Asp Arg
            755                 760                 765
Phe Ser Gly Ser Gly Ser Gly Thr Asp Phe Thr Leu Thr Ile Ser Arg
770                 775                 780
Leu Glu Pro Glu Asp Phe Ala Val Tyr Tyr Cys Gln Gln Gly Ile Met
785                 790                 795                 800
Leu Pro Pro Thr Phe Gly Gln Gly Thr Lys Val Glu Ile Lys Ser Ser
                805                 810                 815
Ala Ser Thr Lys Gly Pro Ser Val Phe Pro Leu Ala Pro Ser Ser Lys
            820                 825                 830
Ser Thr Ser Gly Gly Thr Ala Ala Leu Gly Cys Leu Val Lys Asp Tyr
            835                 840                 845
Phe Pro Glu Pro Val Thr Val Ser Trp Asn Ser Gly Ala Leu Thr Ser
850                 855                 860
```

```
Gly Val His Thr Phe Pro Ala Val Leu Gln Ser Ser Gly Leu Tyr Ser
865                 870                 875                 880

Leu Ser Ser Val Val Thr Val Pro Ser Ser Ser Leu Gly Thr Gln Thr
                885                 890                 895

Tyr Ile Cys Asn Val Asn His Lys Pro Ser Asn Thr Lys Val Asp Lys
            900                 905                 910

Lys Val Glu Pro Lys Ser Cys
        915
```

```
<210> SEQ ID NO 147
<211> LENGTH: 5
<212> TYPE: PRT
<213> ORGANISM: Artificial Sequence
<220> FEATURE:
<223> OTHER INFORMATION: hu CD40  CDR-H1

<400> SEQUENCE: 147

Gly Tyr Tyr Ile His
1               5

<210> SEQ ID NO 148
<211> LENGTH: 17
<212> TYPE: PRT
<213> ORGANISM: Artificial Sequence
<220> FEATURE:
<223> OTHER INFORMATION: hu CD40  CDR-H2

<400> SEQUENCE: 148

Arg Val Ile Pro Asn Ala Gly Gly Thr Ser Tyr Asn Gln Lys Phe Lys
1               5                   10                  15

Gly

<210> SEQ ID NO 149
<211> LENGTH: 5
<212> TYPE: PRT
<213> ORGANISM: Artificial Sequence
<220> FEATURE:
<223> OTHER INFORMATION: hu CD40  CDR-H3

<400> SEQUENCE: 149

Glu Gly Ile Tyr Trp
1               5

<210> SEQ ID NO 150
<211> LENGTH: 16
<212> TYPE: PRT
<213> ORGANISM: Artificial Sequence
<220> FEATURE:
<223> OTHER INFORMATION: hu CD40  CDR-L1

<400> SEQUENCE: 150

Arg Ser Ser Gln Ser Leu Val His Ser Asn Gly Asn Thr Phe Leu His
1               5                   10                  15

<210> SEQ ID NO 151
<211> LENGTH: 7
<212> TYPE: PRT
<213> ORGANISM: Artificial Sequence
<220> FEATURE:
<223> OTHER INFORMATION: hu CD40  CDR-L2

<400> SEQUENCE: 151

Thr Val Ser Asn Arg Phe Ser
1               5
```

<210> SEQ ID NO 152
<211> LENGTH: 9
<212> TYPE: PRT
<213> ORGANISM: Artificial Sequence
<220> FEATURE:
<223> OTHER INFORMATION: hu CD40 CDR-L3

<400> SEQUENCE: 152

Ser Gln Thr Thr His Val Pro Trp Thr
1               5

<210> SEQ ID NO 153
<211> LENGTH: 114
<212> TYPE: PRT
<213> ORGANISM: Artificial Sequence
<220> FEATURE:
<223> OTHER INFORMATION: hu CD40 VH

<400> SEQUENCE: 153

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45

Ala Arg Val Ile Pro Asn Ala Gly Gly Thr Ser Tyr Asn Gln Lys Phe
    50                  55                  60

Lys Gly Arg Phe Thr Leu Ser Val Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Tyr Trp Trp Gly Gln Gly Thr Leu Val Thr Val
            100                 105                 110

Ser Ser

<210> SEQ ID NO 154
<211> LENGTH: 112
<212> TYPE: PRT
<213> ORGANISM: Artificial Sequence
<220> FEATURE:
<223> OTHER INFORMATION: hu CD40 VL

<400> SEQUENCE: 154

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Phe Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Phe Cys Ser Gln Thr
                85                  90                  95

Thr His Val Pro Trp Thr Phe Gly Gln Gly Thr Lys Val Glu Ile Lys
            100                 105                 110

```
<210> SEQ ID NO 155
<211> LENGTH: 926
<212> TYPE: PRT
<213> ORGANISM: Artificial Sequence
<220> FEATURE:
<223> OTHER INFORMATION: first fusion polypeptide (Fc knob) P1AE1799

<400> SEQUENCE: 155
```

| | | | | | | | | | | | | | | | |
|---|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Tyr | Ser | Phe | Thr | Gly | Tyr |
| | | | 20 | | | | | 25 | | | | | 30 | | |
| Tyr | Ile | His | Trp | Val | Arg | Gln | Ala | Pro | Gly | Lys | Gly | Leu | Glu | Trp | Val |
| | | | 35 | | | | | 40 | | | | | 45 | | |
| Gly | Arg | Val | Ile | Pro | Asn | Ala | Gly | Gly | Thr | Ser | Tyr | Asn | Gln | Lys | Phe |
| | 50 | | | | | 55 | | | | | 60 | | | | |
| Lys | Gly | Arg | Phe | Thr | Ile | Ser | Val | Asp | Asn | Ser | Lys | Asn | Thr | Ala | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Glu | Gly | Ile | Tyr | Trp | Trp | Gly | Gln | Gly | Thr | Thr | Val | Thr | Val |
| | | | 100 | | | | | 105 | | | | | 110 | | |
| Ser | Ser | Ala | Ser | Thr | Lys | Gly | Pro | Ser | Val | Phe | Pro | Leu | Ala | Pro | Ser |
| | | | 115 | | | | | 120 | | | | | 125 | | |
| Ser | Lys | Ser | Thr | Ser | Gly | Gly | Thr | Ala | Ala | Leu | Gly | Cys | Leu | Val | Lys |
| | | 130 | | | | | 135 | | | | | 140 | | | |
| Asp | Tyr | Phe | Pro | Glu | Pro | Val | Thr | Val | Ser | Trp | Asn | Ser | Gly | Ala | Leu |
| 145 | | | | | 150 | | | | | 155 | | | | | 160 |
| Thr | Ser | Gly | Val | His | Thr | Phe | Pro | Ala | Val | Leu | Gln | Ser | Ser | Gly | Leu |
| | | | | 165 | | | | | 170 | | | | | 175 | |
| Tyr | Ser | Leu | Ser | Ser | Val | Val | Thr | Val | Pro | Ser | Ser | Ser | Leu | Gly | Thr |
| | | | 180 | | | | | 185 | | | | | 190 | | |
| Gln | Thr | Tyr | Ile | Cys | Asn | Val | Asn | His | Lys | Pro | Ser | Asn | Thr | Lys | Val |
| | | | 195 | | | | | 200 | | | | | 205 | | |
| Asp | Lys | Lys | Val | Glu | Pro | Lys | Ser | Cys | Gly | Gly | Gly | Ser | Gly | Gly | |
| | | 210 | | | | | 215 | | | | | 220 | | | |
| Gly | Gly | Ser | Asp | Lys | Thr | His | Thr | Cys | Pro | Pro | Cys | Pro | Ala | Pro | Glu |
| 225 | | | | | 230 | | | | | 235 | | | | | 240 |
| Ala | Ala | Gly | Gly | Pro | Ser | Val | Phe | Leu | Phe | Pro | Pro | Lys | Pro | Lys | Asp |
| | | | | 245 | | | | | 250 | | | | | 255 | |
| Thr | Leu | Met | Ile | Ser | Arg | Thr | Pro | Glu | Val | Thr | Cys | Val | Val | Val | Asp |
| | | | 260 | | | | | 265 | | | | | 270 | | |
| Val | Ser | His | Glu | Asp | Pro | Glu | Val | Lys | Phe | Asn | Trp | Tyr | Val | Asp | Gly |
| | | 275 | | | | | 280 | | | | | 285 | | | |
| Val | Glu | Val | His | Asn | Ala | Lys | Thr | Lys | Pro | Arg | Glu | Glu | Gln | Tyr | Asn |
| | 290 | | | | | 295 | | | | | 300 | | | | |
| Ser | Thr | Tyr | Arg | Val | Val | Ser | Val | Leu | Thr | Val | Leu | His | Gln | Asp | Trp |
| 305 | | | | | 310 | | | | | 315 | | | | | 320 |
| Leu | Asn | Gly | Lys | Glu | Tyr | Lys | Cys | Lys | Val | Ser | Asn | Lys | Ala | Leu | Gly |
| | | | | 325 | | | | | 330 | | | | | 335 | |
| Ala | Pro | Ile | Glu | Lys | Thr | Ile | Ser | Lys | Ala | Lys | Gly | Gln | Pro | Arg | Glu |
| | | | 340 | | | | | 345 | | | | | 350 | | |
| Pro | Gln | Val | Tyr | Thr | Leu | Pro | Pro | Cys | Arg | Asp | Glu | Leu | Thr | Lys | Asn |
| | | | 355 | | | | | 360 | | | | | 365 | | |

-continued

```
Gln Val Ser Leu Trp Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro Gly Lys Gly Gly Gly Ser Gly Gly Gly Gly Ser
    450                 455                 460
Asp Ile Gln Met Thr Gln Ser Pro Ser Ser Leu Ser Ala Ser Val Gly
465                 470                 475                 480
Asp Arg Val Thr Ile Thr Cys Arg Ser Ser Gln Ser Leu Val His Ser
                485                 490                 495
Asn Gly Asn Thr Phe Leu His Trp Tyr Gln Gln Lys Pro Gly Lys Ala
            500                 505                 510
Pro Lys Leu Leu Ile Tyr Thr Val Ser Asn Arg Phe Ser Gly Val Pro
        515                 520                 525
Ser Arg Phe Ser Gly Ser Gly Ser Gly Thr Asp Phe Thr Leu Thr Ile
    530                 535                 540
Ser Ser Leu Gln Pro Glu Asp Phe Ala Thr Tyr Phe Cys Ser Gln Thr
545                 550                 555                 560
Thr His Val Pro Trp Thr Phe Gly Gly Gly Thr Lys Val Glu Ile Lys
                565                 570                 575
Arg Thr Val Ala Ala Pro Ser Val Phe Ile Phe Pro Pro Ser Asp Glu
            580                 585                 590
Gln Leu Lys Ser Gly Thr Ala Ser Val Val Cys Leu Leu Asn Asn Phe
        595                 600                 605
Tyr Pro Arg Glu Ala Lys Val Gln Trp Lys Val Asp Asn Ala Leu Gln
    610                 615                 620
Ser Gly Asn Ser Gln Glu Ser Val Thr Glu Gln Asp Ser Lys Asp Ser
625                 630                 635                 640
Thr Tyr Ser Leu Ser Ser Thr Leu Thr Leu Ser Lys Ala Asp Tyr Glu
                645                 650                 655
Lys His Lys Val Tyr Ala Cys Glu Val Thr His Gln Gly Leu Ser Ser
            660                 665                 670
Pro Val Thr Lys Ser Phe Asn Arg Gly Glu Cys Gly Gly Gly Gly Ser
        675                 680                 685
Gly Gly Gly Gly Ser Gly Gly Gly Ser Gly Gly Gly Gly Ser Glu Val
    690                 695                 700
Gln Leu Leu Glu Ser Gly Gly Gly Leu Val Gln Pro Gly Gly Ser Leu
705                 710                 715                 720
Arg Leu Ser Cys Ala Ala Ser Gly Phe Thr Phe Ser Ser Tyr Ala Met
                725                 730                 735
Ser Trp Val Arg Gln Ala Pro Gly Lys Gly Leu Glu Trp Val Ser Ala
            740                 745                 750
Ile Ile Gly Ser Gly Ala Ser Thr Tyr Tyr Ala Asp Ser Val Lys Gly
        755                 760                 765
Arg Phe Thr Ile Ser Arg Asp Asn Ser Lys Asn Thr Leu Tyr Leu Gln
    770                 775                 780
```

```
Met Asn Ser Leu Arg Ala Glu Asp Thr Ala Val Tyr Tyr Cys Ala Lys
785                 790                 795                 800

Gly Trp Phe Gly Gly Phe Asn Tyr Trp Gly Gln Gly Thr Leu Val Thr
            805                 810                 815

Val Ser Ser Ala Ser Val Ala Ala Pro Ser Val Phe Ile Phe Pro Pro
        820                 825                 830

Ser Asp Glu Gln Leu Lys Ser Gly Thr Ala Ser Val Val Cys Leu Leu
    835                 840                 845

Asn Asn Phe Tyr Pro Arg Glu Ala Lys Val Gln Trp Lys Val Asp Asn
850                 855                 860

Ala Leu Gln Ser Gly Asn Ser Gln Glu Ser Val Thr Glu Gln Asp Ser
865                 870                 875                 880

Lys Asp Ser Thr Tyr Ser Leu Ser Ser Thr Leu Thr Leu Ser Lys Ala
                885                 890                 895

Asp Tyr Glu Lys His Lys Val Tyr Ala Cys Glu Val Thr His Gln Gly
                900                 905                 910

Leu Ser Ser Pro Val Thr Lys Ser Phe Asn Arg Gly Glu Cys
                915                 920                 925

<210> SEQ ID NO 156
<211> LENGTH: 915
<212> TYPE: PRT
<213> ORGANISM: Artificial Sequence
<220> FEATURE:
<223> OTHER INFORMATION: second fusion polypeptide (Fc hole) P1AE1799

<400> SEQUENCE: 156

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45

Gly Arg Val Ile Pro Asn Ala Gly Gly Thr Ser Tyr Asn Gln Lys Phe
    50                  55                  60

Lys Gly Arg Phe Thr Ile Ser Val Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Tyr Trp Trp Gly Gln Gly Thr Thr Val Thr Val
                100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Gln Thr Tyr Ile Cys Asn Val Asn His Lys Pro Ser Asn Thr Lys Val
            195                 200                 205

Asp Lys Lys Val Glu Pro Lys Ser Cys Gly Gly Gly Gly Ser Gly Gly
    210                 215                 220
```

```
Gly Gly Ser Asp Lys Thr His Thr Cys Pro Pro Cys Pro Ala Pro Glu
225                 230                 235                 240

Ala Ala Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
        260                 265                 270

Val Ser His Glu Asp Pro Glu Val Lys Phe Asn Trp Tyr Val Asp Gly
    275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Gly
            325                 330                 335

Ala Pro Ile Glu Lys Thr Ile Ser Lys Ala Lys Gly Gln Pro Arg Glu
        340                 345                 350

Pro Gln Val Cys Thr Leu Pro Pro Ser Arg Asp Glu Leu Thr Lys Asn
    355                 360                 365

Gln Val Ser Leu Ser Cys Ala Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Val Ser Lys
            405                 410                 415

Leu Thr Val Asp Lys Ser Arg Trp Gln Gln Gly Asn Val Phe Ser Cys
        420                 425                 430

Ser Val Met His Glu Ala Leu His Asn His Tyr Thr Gln Lys Ser Leu
    435                 440                 445

Ser Leu Ser Pro Gly Lys Gly Gly Gly Ser Gly Gly Gly Gly Ser
450                 455                 460

Asp Ile Gln Met Thr Gln Ser Pro Ser Ser Leu Ser Ala Ser Val Gly
465                 470                 475                 480

Asp Arg Val Thr Ile Thr Cys Arg Ser Ser Gln Ser Leu Val His Ser
            485                 490                 495

Asn Gly Asn Thr Phe Leu His Trp Tyr Gln Gln Lys Pro Gly Lys Ala
        500                 505                 510

Pro Lys Leu Leu Ile Tyr Thr Val Ser Asn Arg Phe Ser Gly Val Pro
    515                 520                 525

Ser Arg Phe Ser Gly Ser Gly Ser Gly Thr Asp Phe Thr Leu Thr Ile
530                 535                 540

Ser Ser Leu Gln Pro Glu Asp Phe Ala Thr Tyr Phe Cys Ser Gln Thr
545                 550                 555                 560

Thr His Val Pro Trp Thr Phe Gly Gly Gly Thr Lys Val Glu Ile Lys
            565                 570                 575

Arg Thr Val Ala Ala Pro Ser Val Phe Ile Phe Pro Pro Ser Asp Glu
        580                 585                 590

Gln Leu Lys Ser Gly Thr Ala Ser Val Val Cys Leu Leu Asn Asn Phe
    595                 600                 605

Tyr Pro Arg Glu Ala Lys Val Gln Trp Lys Val Asp Asn Ala Leu Gln
    610                 615                 620

Ser Gly Asn Ser Gln Glu Ser Val Thr Glu Gln Asp Ser Lys Asp Ser
625                 630                 635                 640
```

Thr Tyr Ser Leu Ser Ser Thr Leu Thr Leu Ser Lys Ala Asp Tyr Glu
            645                 650                 655

Lys His Lys Val Tyr Ala Cys Glu Val Thr His Gln Gly Leu Ser Ser
        660                 665                 670

Pro Val Thr Lys Ser Phe Asn Arg Gly Glu Cys Gly Gly Gly Gly Ser
            675                 680                 685

Gly Gly Gly Gly Ser Gly Gly Gly Ser Gly Gly Gly Gly Ser Glu Ile
        690                 695                 700

Val Leu Thr Gln Ser Pro Gly Thr Leu Ser Leu Ser Pro Gly Glu Arg
705                 710                 715                 720

Ala Thr Leu Ser Cys Arg Ala Ser Gln Ser Val Thr Ser Ser Tyr Leu
            725                 730                 735

Ala Trp Tyr Gln Gln Lys Pro Gly Gln Ala Pro Arg Leu Leu Ile Asn
        740                 745                 750

Val Gly Ser Arg Arg Ala Thr Gly Ile Pro Asp Arg Phe Ser Gly Ser
            755                 760                 765

Gly Ser Gly Thr Asp Phe Thr Leu Thr Ile Ser Arg Leu Glu Pro Glu
        770                 775                 780

Asp Phe Ala Val Tyr Tyr Cys Gln Gln Gly Ile Met Leu Pro Pro Thr
785                 790                 795                 800

Phe Gly Gln Gly Thr Lys Val Glu Ile Lys Ser Ser Ala Ser Thr Lys
            805                 810                 815

Gly Pro Ser Val Phe Pro Leu Ala Pro Ser Ser Lys Ser Thr Ser Gly
        820                 825                 830

Gly Thr Ala Ala Leu Gly Cys Leu Val Lys Asp Tyr Phe Pro Glu Pro
            835                 840                 845

Val Thr Val Ser Trp Asn Ser Gly Ala Leu Thr Ser Gly Val His Thr
        850                 855                 860

Phe Pro Ala Val Leu Gln Ser Ser Gly Leu Tyr Ser Leu Ser Ser Val
865                 870                 875                 880

Val Thr Val Pro Ser Ser Ser Leu Gly Thr Gln Thr Tyr Ile Cys Asn
            885                 890                 895

Val Asn His Lys Pro Ser Asn Thr Lys Val Asp Lys Lys Val Glu Pro
        900                 905                 910

Lys Ser Cys
        915

<210> SEQ ID NO 157
<211> LENGTH: 915
<212> TYPE: PRT
<213> ORGANISM: Artificial Sequence
<220> FEATURE:
<223> OTHER INFORMATION: first fusion polypeptide (Fc knob) P1AE1902

<400> SEQUENCE: 157

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45

Gly Arg Val Ile Pro Asn Ala Gly Gly Thr Ser Tyr Asn Gln Lys Phe
    50                  55                  60

Lys Gly Arg Phe Thr Ile Ser Val Asp Asn Ser Lys Asn Thr Ala Tyr
65                  70                  75                  80

-continued

```
Leu Gln Met Asn Ser Leu Arg Ala Glu Asp Thr Ala Val Tyr Tyr Cys
                85                  90                  95
Ala Arg Glu Gly Ile Tyr Trp Trp Gly Gln Gly Thr Thr Val Thr Val
            100                 105                 110
Ser Ser Ala Ser Thr Lys Gly Pro Ser Val Phe Pro Leu Ala Pro Ser
            115                 120                 125
Ser Lys Ser Thr Ser Gly Gly Thr Ala Ala Leu Gly Cys Leu Val Lys
130                 135                 140
Asp Tyr Phe Pro Glu Pro Val Thr Val Ser Trp Asn Ser Gly Ala Leu
145                 150                 155                 160
Thr Ser Gly Val His Thr Phe Pro Ala Val Leu Gln Ser Ser Gly Leu
                165                 170                 175
Tyr Ser Leu Ser Ser Val Val Thr Val Pro Ser Ser Ser Leu Gly Thr
            180                 185                 190
Gln Thr Tyr Ile Cys Asn Val Asn His Lys Pro Ser Asn Thr Lys Val
            195                 200                 205
Asp Lys Lys Val Glu Pro Lys Ser Cys Gly Gly Gly Ser Gly Gly
210                 215                 220
Gly Gly Ser Asp Lys Thr His Thr Cys Pro Pro Cys Pro Ala Pro Glu
225                 230                 235                 240
Ala Ala Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
            275                 280                 285
Val Glu Val His Asn Ala Lys Thr Lys Pro Arg Glu Glu Gln Tyr Asn
290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Gly
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Cys Arg Asp Glu Leu Thr Lys Asn
            355                 360                 365
Gln Val Ser Leu Trp Cys Leu Val Lys Gly Phe Tyr Pro Ser Asp Ile
370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
            435                 440                 445
Ser Leu Ser Pro Gly Lys Gly Gly Gly Ser Gly Gly Gly Gly Ser
450                 455                 460
Asp Ile Gln Met Thr Gln Ser Pro Ser Ser Leu Ser Ala Ser Val Gly
465                 470                 475                 480
Asp Arg Val Thr Ile Thr Cys Arg Ser Ser Gln Ser Leu Val His Ser
                485                 490                 495
```

```
Asn Gly Asn Thr Phe Leu His Trp Tyr Gln Gln Lys Pro Gly Lys Ala
            500                 505                 510

Pro Lys Leu Leu Ile Tyr Thr Val Ser Asn Arg Phe Ser Gly Val Pro
        515                 520                 525

Ser Arg Phe Ser Gly Ser Gly Ser Gly Thr Asp Phe Thr Leu Thr Ile
    530                 535                 540

Ser Ser Leu Gln Pro Glu Asp Phe Ala Thr Tyr Phe Cys Ser Gln Thr
545                 550                 555                 560

Thr His Val Pro Trp Thr Phe Gly Gly Gly Thr Lys Val Glu Ile Lys
                565                 570                 575

Arg Thr Val Ala Ala Pro Ser Val Phe Ile Phe Pro Pro Ser Asp Glu
            580                 585                 590

Gln Leu Lys Ser Gly Thr Ala Ser Val Val Cys Leu Leu Asn Asn Phe
        595                 600                 605

Tyr Pro Arg Glu Ala Lys Val Gln Trp Lys Val Asp Asn Ala Leu Gln
    610                 615                 620

Ser Gly Asn Ser Gln Glu Ser Val Thr Glu Gln Asp Ser Lys Asp Ser
625                 630                 635                 640

Thr Tyr Ser Leu Ser Ser Thr Leu Thr Leu Ser Lys Ala Asp Tyr Glu
                645                 650                 655

Lys His Lys Val Tyr Ala Cys Glu Val Thr His Gln Gly Leu Ser Ser
            660                 665                 670

Pro Val Thr Lys Ser Phe Asn Arg Gly Glu Cys Gly Gly Gly Gly Ser
        675                 680                 685

Gly Gly Gly Gly Ser Gly Gly Ser Gly Gly Gly Ser Glu Ile
690                 695                 700

Val Leu Thr Gln Ser Pro Gly Thr Leu Ser Leu Ser Pro Gly Glu Arg
705                 710                 715                 720

Ala Thr Leu Ser Cys Arg Ala Ser Gln Ser Val Thr Ser Ser Tyr Leu
                725                 730                 735

Ala Trp Tyr Gln Gln Lys Pro Gly Gln Ala Pro Arg Leu Leu Ile Asn
            740                 745                 750

Val Gly Ser Arg Arg Ala Thr Gly Ile Pro Asp Arg Phe Ser Gly Ser
        755                 760                 765

Gly Ser Gly Thr Asp Phe Thr Leu Thr Ile Ser Arg Leu Glu Pro Glu
    770                 775                 780

Asp Phe Ala Val Tyr Tyr Cys Gln Gln Gly Ile Met Leu Pro Pro Thr
785                 790                 795                 800

Phe Gly Gln Gly Thr Lys Val Glu Ile Lys Ser Ser Ala Ser Thr Lys
                805                 810                 815

Gly Pro Ser Val Phe Pro Leu Ala Pro Ser Ser Lys Ser Thr Ser Gly
            820                 825                 830

Gly Thr Ala Ala Leu Gly Cys Leu Val Lys Asp Tyr Phe Pro Glu Pro
        835                 840                 845

Val Thr Val Ser Trp Asn Ser Gly Ala Leu Thr Ser Gly Val His Thr
    850                 855                 860

Phe Pro Ala Val Leu Gln Ser Ser Gly Leu Tyr Ser Leu Ser Ser Val
865                 870                 875                 880

Val Thr Val Pro Ser Ser Ser Leu Gly Thr Gln Thr Tyr Ile Cys Asn
                885                 890                 895
```

```
Val Asn His Lys Pro Ser Asn Thr Lys Val Asp Lys Lys Val Glu Pro
            900                 905                 910
Lys Ser Cys
        915

<210> SEQ ID NO 158
<211> LENGTH: 926
<212> TYPE: PRT
<213> ORGANISM: Artificial Sequence
<220> FEATURE:
<223> OTHER INFORMATION: second fusion polypeptide (Fc hole) P1AE1902

<400> SEQUENCE: 158

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45

Gly Arg Val Ile Pro Asn Ala Gly Gly Thr Ser Tyr Asn Gln Lys Phe
    50                  55                  60

Lys Gly Arg Phe Thr Ile Ser Val Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Tyr Trp Trp Gly Gln Gly Thr Thr Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Gly Gly Gly Gly Ser Gly Gly
    210                 215                 220

Gly Gly Ser Asp Lys Thr His Thr Cys Pro Pro Cys Pro Ala Pro Glu
225                 230                 235                 240

Ala Ala Gly Gly Pro Ser Val Phe Leu Phe Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Gly
                325                 330                 335
```

```
Ala Pro Ile Glu Lys Thr Ile Ser Lys Ala Lys Gly Gln Pro Arg Glu
            340                 345                 350

Pro Gln Val Cys Thr Leu Pro Pro Ser Arg Asp Glu Leu Thr Lys Asn
            355                 360                 365

Gln Val Ser Leu Ser Cys Ala Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Val Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys Gly Gly Gly Gly Ser Gly Gly Gly Gly Ser
            450                 455                 460

Asp Ile Gln Met Thr Gln Ser Pro Ser Ser Leu Ser Ala Ser Val Gly
465                 470                 475                 480

Asp Arg Val Thr Ile Thr Cys Arg Ser Ser Gln Ser Leu Val His Ser
                485                 490                 495

Asn Gly Asn Thr Phe Leu His Trp Tyr Gln Gln Lys Pro Gly Lys Ala
            500                 505                 510

Pro Lys Leu Leu Ile Tyr Thr Val Ser Asn Arg Phe Ser Gly Val Pro
            515                 520                 525

Ser Arg Phe Ser Gly Ser Gly Ser Gly Thr Asp Phe Thr Leu Thr Ile
545                 550                 555                 560

Ser Ser Leu Gln Pro Glu Asp Phe Ala Thr Tyr Phe Cys Ser Gln Thr
545                 550                 555                 560

Thr His Val Pro Trp Thr Phe Gly Gly Gly Thr Lys Val Glu Ile Lys
            565                 570                 575

Arg Thr Val Ala Ala Pro Ser Val Phe Ile Phe Pro Pro Ser Asp Glu
            580                 585                 590

Gln Leu Lys Ser Gly Thr Ala Ser Val Val Cys Leu Leu Asn Asn Phe
            595                 600                 605

Tyr Pro Arg Glu Ala Lys Val Gln Trp Lys Val Asp Asn Ala Leu Gln
            610                 615                 620

Ser Gly Asn Ser Gln Glu Ser Val Thr Glu Gln Asp Ser Lys Asp Ser
625                 630                 635                 640

Thr Tyr Ser Leu Ser Ser Thr Leu Thr Leu Ser Lys Ala Asp Tyr Glu
                645                 650                 655

Lys His Lys Val Tyr Ala Cys Glu Val Thr His Gln Gly Leu Ser Ser
            660                 665                 670

Pro Val Thr Lys Ser Phe Asn Arg Gly Glu Cys Gly Gly Gly Gly Ser
            675                 680                 685

Gly Gly Gly Gly Ser Gly Gly Gly Gly Gly Ser Glu Val
            690                 695                 700

Gln Leu Leu Glu Ser Gly Gly Gly Leu Val Gln Pro Gly Gly Ser Leu
705                 710                 715                 720

Arg Leu Ser Cys Ala Ala Ser Gly Phe Thr Phe Ser Ser Tyr Ala Met
                725                 730                 735

Ser Trp Val Arg Gln Ala Pro Gly Lys Gly Leu Glu Trp Val Ser Ala
            740                 745                 750
```

```
Ile Ile Gly Ser Gly Ala Ser Thr Tyr Tyr Ala Asp Ser Val Lys Gly
            755                 760                 765

Arg Phe Thr Ile Ser Arg Asp Asn Ser Lys Asn Thr Leu Tyr Leu Gln
770                 775                 780

Met Asn Ser Leu Arg Ala Glu Asp Thr Ala Val Tyr Tyr Cys Ala Lys
785                 790                 795                 800

Gly Trp Phe Gly Gly Phe Asn Tyr Trp Gly Gln Gly Thr Leu Val Thr
                805                 810                 815

Val Ser Ser Ala Ser Val Ala Ala Pro Ser Val Phe Ile Phe Pro Pro
            820                 825                 830

Ser Asp Glu Gln Leu Lys Ser Gly Thr Ala Ser Val Val Cys Leu Leu
        835                 840                 845

Asn Asn Phe Tyr Pro Arg Glu Ala Lys Val Gln Trp Lys Val Asp Asn
850                 855                 860

Ala Leu Gln Ser Gly Asn Ser Gln Glu Ser Val Thr Glu Gln Asp Ser
865                 870                 875                 880

Lys Asp Ser Thr Tyr Ser Leu Ser Ser Thr Leu Thr Leu Ser Lys Ala
                885                 890                 895

Asp Tyr Glu Lys His Lys Val Tyr Ala Cys Glu Val Thr His Gln Gly
                900                 905                 910

Leu Ser Ser Pro Val Thr Lys Ser Phe Asn Arg Gly Glu Cys
            915                 920                 925

<210> SEQ ID NO 159
<211> LENGTH: 926
<212> TYPE: PRT
<213> ORGANISM: Artificial Sequence
<220> FEATURE:
<223> OTHER INFORMATION: first fusion polypeptide (Fc knob) P1AE1800

<400> SEQUENCE: 159

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45

Gly Arg Val Ile Pro Asn Ala Gly Gly Thr Ser Tyr Asn Gln Lys Phe
    50                  55                  60

Lys Gly Arg Phe Thr Ile Ser Val Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Tyr Trp Trp Gly Gln Gly Thr Thr Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190
```

-continued

```
Gln Thr Tyr Ile Cys Asn Val Asn His Lys Pro Ser Asn Thr Lys Val
            195                 200                 205

Asp Lys Lys Val Glu Pro Lys Ser Cys Gly Gly Gly Ser Gly Gly
210                 215                 220

Gly Gly Ser Asp Lys Thr His Thr Cys Pro Pro Cys Pro Ala Pro Glu
225                 230                 235                 240

Ala Ala Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Gly
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Cys Arg Asp Glu Leu Thr Lys Asn
        355                 360                 365

Gln Val Ser Leu Trp Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys Gly Gly Gly Ser Gly Gly Gly Gly Ser
    450                 455                 460

Asp Ile Gln Met Thr Gln Ser Pro Ser Ser Leu Ser Ala Ser Val Gly
465                 470                 475                 480

Asp Arg Val Thr Ile Thr Cys Arg Ser Ser Gln Ser Leu Val His Ser
                485                 490                 495

Asn Gly Asn Thr Phe Leu His Trp Tyr Gln Gln Lys Pro Gly Lys Ala
            500                 505                 510

Pro Lys Leu Leu Ile Tyr Thr Val Ser Asn Arg Phe Ser Gly Val Pro
        515                 520                 525

Ser Arg Phe Ser Gly Ser Gly Ser Gly Thr Asp Phe Thr Leu Thr Ile
    530                 535                 540

Ser Ser Leu Gln Pro Glu Asp Phe Ala Thr Tyr Phe Cys Ser Gln Thr
545                 550                 555                 560

Thr His Val Pro Trp Thr Phe Gly Gly Gly Thr Lys Val Glu Ile Lys
                565                 570                 575

Arg Thr Val Ala Ala Pro Ser Val Phe Ile Phe Pro Pro Ser Asp Glu
            580                 585                 590

Gln Leu Lys Ser Gly Thr Ala Ser Val Val Cys Leu Leu Asn Asn Phe
        595                 600                 605
```

Tyr Pro Arg Glu Ala Lys Val Gln Trp Lys Val Asp Asn Ala Leu Gln
610 615 620

Ser Gly Asn Ser Gln Glu Ser Val Thr Glu Gln Asp Ser Lys Asp Ser
625 630 635 640

Thr Tyr Ser Leu Ser Ser Thr Leu Thr Leu Ser Lys Ala Asp Tyr Glu
645 650 655

Lys His Lys Val Tyr Ala Cys Glu Val Thr His Gln Gly Leu Ser Ser
660 665 670

Pro Val Thr Lys Ser Phe Asn Arg Gly Glu Cys Gly Gly Gly Gly Ser
675 680 685

Gly Gly Gly Gly Ser Gly Gly Ser Gly Gly Gly Gly Ser Glu Val
690 695 700

Gln Leu Leu Glu Ser Gly Gly Gly Leu Val Gln Pro Gly Gly Ser Leu
705 710 715 720

Arg Leu Ser Cys Ala Ala Ser Gly Phe Thr Phe Ser Ser Tyr Ala Met
725 730 735

Ser Trp Val Arg Gln Ala Pro Gly Lys Gly Leu Glu Trp Val Ser Ala
740 745 750

Ile Ile Gly Ser Gly Ala Ser Thr Tyr Tyr Ala Asp Ser Val Lys Gly
755 760 765

Arg Phe Thr Ile Ser Arg Asp Asn Ser Lys Asn Thr Leu Tyr Leu Gln
770 775 780

Met Asn Ser Leu Arg Ala Glu Asp Thr Ala Val Tyr Tyr Cys Ala Lys
785 790 795 800

Gly Trp Phe Gly Gly Phe Asn Tyr Trp Gly Gln Gly Thr Leu Val Thr
805 810 815

Val Ser Ser Ala Ser Val Ala Ala Pro Ser Val Phe Ile Phe Pro Pro
820 825 830

Ser Asp Glu Gln Leu Lys Ser Gly Thr Ala Ser Val Val Cys Leu Leu
835 840 845

Asn Asn Phe Tyr Pro Arg Glu Ala Lys Val Gln Trp Lys Val Asp Asn
850 855 860

Ala Leu Gln Ser Gly Asn Ser Gln Glu Ser Val Thr Glu Gln Asp Ser
865 870 875 880

Lys Asp Ser Thr Tyr Ser Leu Ser Ser Thr Leu Thr Leu Ser Lys Ala
885 890 895

Asp Tyr Glu Lys His Lys Val Tyr Ala Cys Glu Val Thr His Gln Gly
900 905 910

Leu Ser Ser Pro Val Thr Lys Ser Phe Asn Arg Gly Glu Cys
915 920 925

<210> SEQ ID NO 160
<211> LENGTH: 915
<212> TYPE: PRT
<213> ORGANISM: Artificial Sequence
<220> FEATURE:
<223> OTHER INFORMATION: second fusion polypeptide (Fc hole) P1AE1800

<400> SEQUENCE: 160

Asp Ile Gln Met Thr Gln Ser Pro Ser Ser Leu Ser Ala Ser Val Gly
1 5 10 15

Asp Arg Val Thr Ile Thr Cys Arg Ser Ser Gln Ser Leu Val His Ser
20 25 30

Asn Gly Asn Thr Phe Leu His Trp Tyr Gln Gln Lys Pro Gly Lys Ala
35 40 45

-continued

```
Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Phe Cys Ser Gln Thr
                85                  90                  95

Thr His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Gly Ala Pro Ile Glu Lys Thr Ile Ser Lys Ala Lys Gly Gln Pro
            340                 345                 350

Arg Glu Pro Gln Val Cys Thr Leu Pro Pro Ser Arg Asp Glu Leu Thr
        355                 360                 365

Lys Asn Gln Val Ser Leu Ser Cys Ala Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys Gly Gly Gly Ser Gly Gly Gly Gly
    450                 455                 460
```

-continued

Gly Ser Glu Val Gln Leu Leu Glu Ser Gly Gly Leu Val Gln Pro
465                 470                 475                 480

Gly Gly Ser Leu Arg Leu Ser Cys Ala Ala Ser Gly Tyr Ser Phe Thr
            485                 490                 495

Gly Tyr Tyr Ile His Trp Val Arg Gln Ala Pro Gly Lys Gly Leu Glu
                500                 505                 510

Trp Val Gly Arg Val Ile Pro Asn Ala Gly Gly Thr Ser Tyr Asn Gln
            515                 520                 525

Lys Phe Lys Gly Arg Phe Thr Ile Ser Val Asp Asn Ser Lys Asn Thr
    530                 535                 540

Ala Tyr Leu Gln Met Asn Ser Leu Arg Ala Glu Asp Thr Ala Val Tyr
545                 550                 555                 560

Tyr Cys Ala Arg Glu Gly Ile Tyr Trp Trp Gly Gln Gly Thr Thr Val
            565                 570                 575

Thr Val Ser Ser Ala Ser Thr Lys Gly Pro Ser Val Phe Pro Leu Ala
            580                 585                 590

Pro Ser Ser Lys Ser Thr Ser Gly Gly Thr Ala Ala Leu Gly Cys Leu
    595                 600                 605

Val Lys Asp Tyr Phe Pro Glu Pro Val Thr Val Ser Trp Asn Ser Gly
    610                 615                 620

Ala Leu Thr Ser Gly Val His Thr Phe Pro Ala Val Leu Gln Ser Ser
625                 630                 635                 640

Gly Leu Tyr Ser Leu Ser Ser Val Val Thr Val Pro Ser Ser Ser Leu
            645                 650                 655

Gly Thr Gln Thr Tyr Ile Cys Asn Val Asn His Lys Pro Ser Asn Thr
            660                 665                 670

Lys Val Asp Lys Lys Val Glu Pro Lys Ser Cys Gly Gly Gly Gly Ser
    675                 680                 685

Gly Gly Gly Gly Ser Gly Gly Gly Ser Gly Gly Gly Gly Ser Glu Ile
            690                 695                 700

Val Leu Thr Gln Ser Pro Gly Thr Leu Ser Leu Ser Pro Gly Glu Arg
705                 710                 715                 720

Ala Thr Leu Ser Cys Arg Ala Ser Gln Ser Val Thr Ser Ser Tyr Leu
            725                 730                 735

Ala Trp Tyr Gln Gln Lys Pro Gly Gln Ala Pro Arg Leu Leu Ile Asn
            740                 745                 750

Val Gly Ser Arg Arg Ala Thr Gly Ile Pro Asp Arg Phe Ser Gly Ser
            755                 760                 765

Gly Ser Gly Thr Asp Phe Thr Leu Thr Ile Ser Arg Leu Glu Pro Glu
    770                 775                 780

Asp Phe Ala Val Tyr Tyr Cys Gln Gln Gly Ile Met Leu Pro Pro Thr
785                 790                 795                 800

Phe Gly Gln Gly Thr Lys Val Glu Ile Lys Ser Ser Ala Ser Thr Lys
            805                 810                 815

Gly Pro Ser Val Phe Pro Leu Ala Pro Ser Ser Lys Ser Thr Ser Gly
            820                 825                 830

Gly Thr Ala Ala Leu Gly Cys Leu Val Lys Asp Tyr Phe Pro Glu Pro
    835                 840                 845

Val Thr Val Ser Trp Asn Ser Gly Ala Leu Thr Ser Gly Val His Thr
    850                 855                 860

Phe Pro Ala Val Leu Gln Ser Ser Gly Leu Tyr Ser Leu Ser Ser Val
865                 870                 875                 880

```
Val Thr Val Pro Ser Ser Leu Gly Thr Gln Thr Tyr Ile Cys Asn
                885                 890                 895

Val Asn His Lys Pro Ser Asn Thr Lys Val Asp Lys Lys Val Glu Pro
            900                 905                 910

Lys Ser Cys
        915

<210> SEQ ID NO 161
<211> LENGTH: 926
<212> TYPE: PRT
<213> ORGANISM: Artificial Sequence
<220> FEATURE:
<223> OTHER INFORMATION: first fusion polypeptide (Fc knob) P1AE2052

<400> SEQUENCE: 161

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Phe Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Phe Cys Ser Gln Thr
                85                  90                  95

Thr His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320
```

Asp Trp Leu Asn Gly Lys Glu Tyr Lys Cys Lys Val Ser Asn Lys Ala
            325                 330                 335

Leu Gly Ala Pro Ile Glu Lys Thr Ile Ser Lys Ala Lys Gly Gln Pro
            340                 345                 350

Arg Glu Pro Gln Val Tyr Thr Leu Pro Pro Cys Arg Asp Glu Leu Thr
            355                 360                 365

Lys Asn Gln Val Ser Leu Trp Cys Leu Val Lys Gly Phe Tyr Pro Ser
            370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly Lys Gly Gly Gly Ser Gly Gly Gly
            450                 455                 460

Gly Ser Glu Val Gln Leu Leu Glu Ser Gly Gly Gly Leu Val Gln Pro
465                 470                 475                 480

Gly Gly Ser Leu Arg Leu Ser Cys Ala Ala Ser Gly Tyr Ser Phe Thr
            485                 490                 495

Gly Tyr Tyr Ile His Trp Val Arg Gln Ala Pro Gly Lys Gly Leu Glu
            500                 505                 510

Trp Val Gly Arg Val Ile Pro Asn Ala Gly Gly Thr Ser Tyr Asn Gln
            515                 520                 525

Lys Phe Lys Gly Arg Phe Thr Ile Ser Val Asp Asn Ser Lys Asn Thr
            530                 535                 540

Ala Tyr Leu Gln Met Asn Ser Leu Arg Ala Glu Asp Thr Ala Val Tyr
545                 550                 555                 560

Tyr Cys Ala Arg Glu Gly Ile Tyr Trp Trp Gly Gln Gly Thr Thr Val
            565                 570                 575

Thr Val Ser Ser Ala Ser Thr Lys Gly Pro Ser Val Phe Pro Leu Ala
            580                 585                 590

Pro Ser Ser Lys Ser Thr Ser Gly Gly Thr Ala Ala Leu Gly Cys Leu
            595                 600                 605

Val Lys Asp Tyr Phe Pro Glu Pro Val Thr Val Ser Trp Asn Ser Gly
            610                 615                 620

Ala Leu Thr Ser Gly Val His Thr Phe Pro Ala Val Leu Gln Ser Ser
625                 630                 635                 640

Gly Leu Tyr Ser Leu Ser Ser Val Val Thr Val Pro Ser Ser Ser Leu
            645                 650                 655

Gly Thr Gln Thr Tyr Ile Cys Asn Val Asn His Lys Pro Ser Asn Thr
            660                 665                 670

Lys Val Asp Lys Lys Val Glu Pro Lys Ser Cys Gly Gly Gly Gly Ser
            675                 680                 685

Gly Gly Gly Gly Ser Gly Gly Ser Gly Gly Gly Ser Glu Val
            690                 695                 700

Gln Leu Leu Glu Ser Gly Gly Leu Val Gln Pro Gly Gly Ser Leu
705                 710                 715                 720

Arg Leu Ser Cys Ala Ala Ser Gly Phe Thr Phe Ser Ser Tyr Ala Met
            725                 730                 735

```
Ser Trp Val Arg Gln Ala Pro Gly Lys Gly Leu Glu Trp Val Ser Ala
            740                 745                 750

Ile Ile Gly Ser Gly Ala Ser Thr Tyr Tyr Ala Asp Ser Val Lys Gly
        755                 760                 765

Arg Phe Thr Ile Ser Arg Asp Asn Ser Lys Asn Thr Leu Tyr Leu Gln
    770                 775                 780

Met Asn Ser Leu Arg Ala Glu Asp Thr Ala Val Tyr Tyr Cys Ala Lys
785                 790                 795                 800

Gly Trp Phe Gly Gly Phe Asn Tyr Trp Gly Gln Gly Thr Leu Val Thr
                805                 810                 815

Val Ser Ser Ala Ser Val Ala Ala Pro Ser Val Phe Ile Phe Pro Pro
            820                 825                 830

Ser Asp Glu Gln Leu Lys Ser Gly Thr Ala Ser Val Val Cys Leu Leu
        835                 840                 845

Asn Asn Phe Tyr Pro Arg Glu Ala Lys Val Gln Trp Lys Val Asp Asn
    850                 855                 860

Ala Leu Gln Ser Gly Asn Ser Gln Glu Ser Val Thr Glu Gln Asp Ser
865                 870                 875                 880

Lys Asp Ser Thr Tyr Ser Leu Ser Ser Thr Leu Thr Leu Ser Lys Ala
                885                 890                 895

Asp Tyr Glu Lys His Lys Val Tyr Ala Cys Glu Val Thr His Gln Gly
            900                 905                 910

Leu Ser Ser Pro Val Thr Lys Ser Phe Asn Arg Gly Glu Cys
        915                 920                 925

<210> SEQ ID NO 162
<211> LENGTH: 915
<212> TYPE: PRT
<213> ORGANISM: Artificial Sequence
<220> FEATURE:
<223> OTHER INFORMATION: second fusion polypeptide (Fc hole) P1AE2052

<400> SEQUENCE: 162

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Phe Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Phe Cys Ser Gln Thr
                85                  90                  95

Thr His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

-continued

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200             205

Pro Val Thr Lys Ser Phe Asn Arg Gly Glu Cys Gly Gly Gly Gly Ser
            210                 215             220

Gly Gly Gly Gly Ser Asp Lys Thr His Thr Cys Pro Pro Cys Pro Ala
225                     230             235                 240

Pro Glu Ala Ala Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265             270

Val Asp Val Ser His Glu Asp Pro Glu Val Lys Phe Asn Trp Tyr Val
            275                 280             285

Asp Gly Val Glu Val His Asn Ala Lys Thr Lys Pro Arg Glu Glu Gln
            290                 295             300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Gly Ala Pro Ile Glu Lys Thr Ile Ser Lys Ala Lys Gly Gln Pro
            340                 345             350

Arg Glu Pro Gln Val Cys Thr Leu Pro Pro Ser Arg Asp Glu Leu Thr
            355                 360             365

Lys Asn Gln Val Ser Leu Ser Cys Ala Val Lys Gly Phe Tyr Pro Ser
            370                 375             380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
            420                 425             430

Ser Cys Ser Val Met His Glu Ala Leu His Asn His Tyr Thr Gln Lys
            435                 440             445

Ser Leu Ser Leu Ser Pro Gly Lys Gly Gly Gly Ser Gly Gly Gly
            450                 455             460

Gly Ser Glu Val Gln Leu Leu Glu Ser Gly Gly Gly Leu Val Gln Pro
465                 470                 475                 480

Gly Gly Ser Leu Arg Leu Ser Cys Ala Ala Ser Gly Tyr Ser Phe Thr
                485                 490                 495

Gly Tyr Tyr Ile His Trp Val Arg Gln Ala Pro Gly Lys Gly Leu Glu
            500                 505             510

Trp Val Gly Arg Val Ile Pro Asn Ala Gly Gly Thr Ser Tyr Asn Gln
            515                 520             525

Lys Phe Lys Gly Arg Phe Thr Ile Ser Val Asp Asn Ser Lys Asn Thr
            530                 535             540

Ala Tyr Leu Gln Met Asn Ser Leu Arg Ala Glu Asp Thr Ala Val Tyr
545                 550                 555                 560

Tyr Cys Ala Arg Glu Gly Ile Tyr Trp Trp Gly Gln Gly Thr Thr Val
                565                 570                 575

Thr Val Ser Ser Ala Ser Thr Lys Gly Pro Ser Val Phe Pro Leu Ala
            580                 585             590
```

```
Pro Ser Ser Lys Ser Thr Ser Gly Gly Thr Ala Ala Leu Gly Cys Leu
        595                 600                 605

Val Lys Asp Tyr Phe Pro Glu Pro Val Thr Val Ser Trp Asn Ser Gly
610                 615                 620

Ala Leu Thr Ser Gly Val His Thr Phe Pro Ala Val Leu Gln Ser Ser
625                 630                 635                 640

Gly Leu Tyr Ser Leu Ser Ser Val Val Thr Val Pro Ser Ser Ser Leu
                645                 650                 655

Gly Thr Gln Thr Tyr Ile Cys Asn Val Asn His Lys Pro Ser Asn Thr
            660                 665                 670

Lys Val Asp Lys Lys Val Glu Pro Lys Ser Cys Gly Gly Gly Gly Ser
        675                 680                 685

Gly Gly Gly Gly Ser Gly Gly Gly Ser Gly Gly Gly Gly Ser Glu Ile
    690                 695                 700

Val Leu Thr Gln Ser Pro Gly Thr Leu Ser Leu Ser Pro Gly Glu Arg
705                 710                 715                 720

Ala Thr Leu Ser Cys Arg Ala Ser Gln Ser Val Thr Ser Ser Tyr Leu
                725                 730                 735

Ala Trp Tyr Gln Gln Lys Pro Gly Gln Ala Pro Arg Leu Leu Ile Asn
            740                 745                 750

Val Gly Ser Arg Arg Ala Thr Gly Ile Pro Asp Arg Phe Ser Gly Ser
        755                 760                 765

Gly Ser Gly Thr Asp Phe Thr Leu Thr Ile Ser Arg Leu Glu Pro Glu
    770                 775                 780

Asp Phe Ala Val Tyr Tyr Cys Gln Gln Gly Ile Met Leu Pro Pro Thr
785                 790                 795                 800

Phe Gly Gln Gly Thr Lys Val Glu Ile Lys Ser Ser Ala Ser Thr Lys
                805                 810                 815

Gly Pro Ser Val Phe Pro Leu Ala Pro Ser Ser Lys Ser Thr Ser Gly
            820                 825                 830

Gly Thr Ala Ala Leu Gly Cys Leu Val Lys Asp Tyr Phe Pro Glu Pro
        835                 840                 845

Val Thr Val Ser Trp Asn Ser Gly Ala Leu Thr Ser Gly Val His Thr
    850                 855                 860

Phe Pro Ala Val Leu Gln Ser Ser Gly Leu Tyr Ser Leu Ser Ser Val
865                 870                 875                 880

Val Thr Val Pro Ser Ser Ser Leu Gly Thr Gln Thr Tyr Ile Cys Asn
                885                 890                 895

Val Asn His Lys Pro Ser Asn Thr Lys Val Asp Lys Lys Val Glu Pro
            900                 905                 910

Lys Ser Cys
        915

<210> SEQ ID NO 163
<211> LENGTH: 915
<212> TYPE: PRT
<213> ORGANISM: Artificial Sequence
<220> FEATURE:
<223> OTHER INFORMATION: first fusion polypeptide (Fc knob) P1AE1901

<400> SEQUENCE: 163

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30
```

```
Asn Gly Asn Thr Phe Leu His Trp Tyr Gln Gln Lys Pro Gly Lys Ala
             35                  40                  45

Pro Lys Leu Leu Ile Tyr Thr Val Ser Asn Arg Phe Ser Gly Val Pro
 50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Phe Cys Ser Gln Thr
                 85                  90                  95

Thr His Val Pro Trp Thr Phe Gly Gly Gly Thr Lys Val Glu Ile Lys
                100                 105                 110

Arg Thr Val Ala Ala Pro Ser Val Phe Ile Phe Pro Pro Ser Asp Glu
             115                 120                 125

Gln Leu Lys Ser Gly Thr Ala Ser Val Val Cys Leu Leu Asn Asn Phe
             130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
             180                 185                 190

Lys His Lys Val Tyr Ala Cys Glu Val Thr His Gln Gly Leu Ser Ser
             195                 200                 205

Pro Val Thr Lys Ser Phe Asn Arg Gly Glu Cys Gly Gly Gly Gly Ser
             210                 215                 220

Gly Gly Gly Gly Ser Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
             260                 265                 270

Val Asp Val Ser His Glu Asp Pro Glu Val Lys Phe Asn Trp Tyr Val
             275                 280                 285

Asp Gly Val Glu Val His Asn Ala Lys Thr Lys Pro Arg Glu Glu Gln
             290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Gly Ala Pro Ile Glu Lys Thr Ile Ser Lys Ala Lys Gly Gln Pro
             340                 345                 350

Arg Glu Pro Gln Val Tyr Thr Leu Pro Pro Cys Arg Asp Glu Leu Thr
             355                 360                 365

Lys Asn Gln Val Ser Leu Trp Cys Leu Val Lys Gly Phe Tyr Pro Ser
 370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
             420                 425                 430

Ser Cys Ser Val Met His Glu Ala Leu His Asn His Tyr Thr Gln Lys
             435                 440                 445
```

```
Ser Leu Ser Leu Ser Pro Gly Lys Gly Gly Gly Ser Gly Gly Gly
450                 455                 460

Gly Ser Glu Val Gln Leu Leu Glu Ser Gly Gly Gly Leu Val Gln Pro
465                 470                 475                 480

Gly Gly Ser Leu Arg Leu Ser Cys Ala Ala Ser Gly Tyr Ser Phe Thr
                485                 490                 495

Gly Tyr Tyr Ile His Trp Val Arg Gln Ala Pro Gly Lys Gly Leu Glu
                500                 505                 510

Trp Val Gly Arg Val Ile Pro Asn Ala Gly Gly Thr Ser Tyr Asn Gln
                515                 520                 525

Lys Phe Lys Gly Arg Phe Thr Ile Ser Val Asp Asn Ser Lys Asn Thr
530                 535                 540

Ala Tyr Leu Gln Met Asn Ser Leu Arg Ala Glu Asp Thr Ala Val Tyr
545                 550                 555                 560

Tyr Cys Ala Arg Glu Gly Ile Tyr Trp Trp Gly Gln Gly Thr Thr Val
                565                 570                 575

Thr Val Ser Ser Ala Ser Thr Lys Gly Pro Ser Val Phe Pro Leu Ala
                580                 585                 590

Pro Ser Ser Lys Ser Thr Ser Gly Gly Thr Ala Ala Leu Gly Cys Leu
                595                 600                 605

Val Lys Asp Tyr Phe Pro Glu Pro Val Thr Val Ser Trp Asn Ser Gly
610                 615                 620

Ala Leu Thr Ser Gly Val His Thr Phe Pro Ala Val Leu Gln Ser Ser
625                 630                 635                 640

Gly Leu Tyr Ser Leu Ser Ser Val Val Thr Val Pro Ser Ser Ser Leu
                645                 650                 655

Gly Thr Gln Thr Tyr Ile Cys Asn Val Asn His Lys Pro Ser Asn Thr
                660                 665                 670

Lys Val Asp Lys Lys Val Glu Pro Lys Ser Cys Gly Gly Gly Gly Ser
                675                 680                 685

Gly Gly Gly Gly Ser Gly Gly Ser Gly Gly Gly Gly Ser Glu Ile
                690                 695                 700

Val Leu Thr Gln Ser Pro Gly Thr Leu Ser Leu Ser Pro Gly Glu Arg
705                 710                 715                 720

Ala Thr Leu Ser Cys Arg Ala Ser Gln Ser Val Thr Ser Ser Tyr Leu
                725                 730                 735

Ala Trp Tyr Gln Gln Lys Pro Gly Gln Ala Pro Arg Leu Leu Ile Asn
                740                 745                 750

Val Gly Ser Arg Arg Ala Thr Gly Ile Pro Asp Arg Phe Ser Gly Ser
                755                 760                 765

Gly Ser Gly Thr Asp Phe Thr Leu Thr Ile Ser Arg Leu Glu Pro Glu
                770                 775                 780

Asp Phe Ala Val Tyr Tyr Cys Gln Gln Gly Ile Met Leu Pro Pro Thr
785                 790                 795                 800

Phe Gly Gln Gly Thr Lys Val Glu Ile Lys Ser Ser Ala Ser Thr Lys
                805                 810                 815

Gly Pro Ser Val Phe Pro Leu Ala Pro Ser Ser Lys Ser Thr Ser Gly
                820                 825                 830

Gly Thr Ala Ala Leu Gly Cys Leu Val Lys Asp Tyr Phe Pro Glu Pro
                835                 840                 845

Val Thr Val Ser Trp Asn Ser Gly Ala Leu Thr Ser Gly Val His Thr
850                 855                 860
```

```
Phe Pro Ala Val Leu Gln Ser Ser Gly Leu Tyr Ser Leu Ser Ser Val
865                 870                 875                 880

Val Thr Val Pro Ser Ser Ser Leu Gly Thr Gln Thr Tyr Ile Cys Asn
            885                 890                 895

Val Asn His Lys Pro Ser Asn Thr Lys Val Asp Lys Lys Val Glu Pro
        900                 905                 910

Lys Ser Cys
        915

<210> SEQ ID NO 164
<211> LENGTH: 926
<212> TYPE: PRT
<213> ORGANISM: Artificial Sequence
<220> FEATURE:
<223> OTHER INFORMATION: second fusion polypeptide (Fc hole) P1AE1901

<400> SEQUENCE: 164

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Phe Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Phe Cys Ser Gln Thr
                85                  90                  95

Thr His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300
```

```
Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
            325                 330                 335

Leu Gly Ala Pro Ile Glu Lys Thr Ile Ser Lys Ala Lys Gly Gln Pro
                340                 345                 350

Arg Glu Pro Gln Val Cys Thr Leu Pro Pro Ser Arg Asp Glu Leu Thr
            355                 360                 365

Lys Asn Gln Val Ser Leu Ser Cys Ala Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly Lys Gly Gly Gly Ser Gly Gly Gly
450                 455                 460

Gly Ser Glu Val Gln Leu Leu Glu Ser Gly Gly Gly Leu Val Gln Pro
465                 470                 475                 480

Gly Gly Ser Leu Arg Leu Ser Cys Ala Ala Ser Gly Tyr Ser Phe Thr
            485                 490                 495

Gly Tyr Tyr Ile His Trp Val Arg Gln Ala Pro Gly Lys Gly Leu Glu
                500                 505                 510

Trp Val Gly Arg Val Ile Pro Asn Ala Gly Gly Thr Ser Tyr Asn Gln
            515                 520                 525

Lys Phe Lys Gly Arg Phe Thr Ile Ser Val Asp Asn Ser Lys Asn Thr
530                 535                 540

Ala Tyr Leu Gln Met Asn Ser Leu Arg Ala Glu Asp Thr Ala Val Tyr
545                 550                 555                 560

Tyr Cys Ala Arg Glu Gly Ile Tyr Trp Trp Gly Gln Gly Thr Thr Val
            565                 570                 575

Thr Val Ser Ser Ala Ser Thr Lys Gly Pro Ser Val Phe Pro Leu Ala
            580                 585                 590

Pro Ser Ser Lys Ser Thr Ser Gly Gly Thr Ala Ala Leu Gly Cys Leu
            595                 600                 605

Val Lys Asp Tyr Phe Pro Glu Pro Val Thr Val Ser Trp Asn Ser Gly
            610                 615                 620

Ala Leu Thr Ser Gly Val His Thr Phe Pro Ala Val Leu Gln Ser Ser
625                 630                 635                 640

Gly Leu Tyr Ser Leu Ser Ser Val Val Thr Val Pro Ser Ser Ser Leu
                645                 650                 655

Gly Thr Gln Thr Tyr Ile Cys Asn Val Asn His Lys Pro Ser Asn Thr
                660                 665                 670

Lys Val Asp Lys Lys Val Glu Pro Lys Ser Cys Gly Gly Gly Gly Ser
            675                 680                 685

Gly Gly Gly Gly Ser Gly Gly Gly Ser Gly Gly Gly Gly Ser Glu Val
            690                 695                 700

Gln Leu Leu Glu Ser Gly Gly Gly Leu Val Gln Pro Gly Gly Ser Leu
705                 710                 715                 720
```

-continued

```
Arg Leu Ser Cys Ala Ala Ser Gly Phe Thr Phe Ser Ser Tyr Ala Met
                725                 730                 735

Ser Trp Val Arg Gln Ala Pro Gly Lys Gly Leu Glu Trp Val Ser Ala
            740                 745                 750

Ile Ile Gly Ser Gly Ala Ser Thr Tyr Tyr Ala Asp Ser Val Lys Gly
            755                 760                 765

Arg Phe Thr Ile Ser Arg Asp Asn Ser Lys Asn Thr Leu Tyr Leu Gln
        770                 775                 780

Met Asn Ser Leu Arg Ala Glu Asp Thr Ala Val Tyr Tyr Cys Ala Lys
785                 790                 795                 800

Gly Trp Phe Gly Gly Phe Asn Tyr Trp Gly Gln Gly Thr Leu Val Thr
                805                 810                 815

Val Ser Ser Ala Ser Val Ala Ala Pro Ser Val Phe Ile Phe Pro Pro
            820                 825                 830

Ser Asp Glu Gln Leu Lys Ser Gly Thr Ala Ser Val Val Cys Leu Leu
        835                 840                 845

Asn Asn Phe Tyr Pro Arg Glu Ala Lys Val Gln Trp Lys Val Asp Asn
    850                 855                 860

Ala Leu Gln Ser Gly Asn Ser Gln Glu Ser Val Thr Glu Gln Asp Ser
865                 870                 875                 880

Lys Asp Ser Thr Tyr Ser Leu Ser Ser Thr Leu Thr Leu Ser Lys Ala
                885                 890                 895

Asp Tyr Glu Lys His Lys Val Tyr Ala Cys Glu Val Thr His Gln Gly
            900                 905                 910

Leu Ser Ser Pro Val Thr Lys Ser Phe Asn Arg Gly Glu Cys
        915                 920                 925

<210> SEQ ID NO 165
<211> LENGTH: 926
<212> TYPE: PRT
<213> ORGANISM: Artificial Sequence
<220> FEATURE:
<223> OTHER INFORMATION: first fusion polypeptide (Fc knob) P1AE2255

<400> SEQUENCE: 165

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45

Gly Arg Val Ile Pro Asn Ala Gly Gly Thr Ser Tyr Asn Gln Lys Phe
    50                  55                  60

Lys Gly Arg Phe Thr Ile Ser Val Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Tyr Trp Trp Gly Gln Gly Thr Thr Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Glu
    130                 135                 140

Asp Tyr Phe Pro Glu Pro Val Thr Val Ser Trp Asn Ser Gly Ala Leu
145                 150                 155                 160
```

```
Thr Ser Gly Val His Thr Phe Pro Ala Val Leu Gln Ser Ser Gly Leu
                165                 170                 175
Tyr Ser Leu Ser Ser Val Val Thr Val Pro Ser Ser Ser Leu Gly Thr
            180                 185                 190
Gln Thr Tyr Ile Cys Asn Val Asn His Lys Pro Ser Asn Thr Lys Val
        195                 200                 205
Asp Glu Lys Val Glu Pro Lys Ser Cys Gly Gly Gly Ser Gly Gly
    210                 215                 220
Gly Gly Ser Asp Lys Thr His Thr Cys Pro Pro Cys Pro Ala Pro Glu
225                 230                 235                 240
Ala Ala Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
        275                 280                 285
Val Glu Val His Asn Ala Lys Thr Lys Pro Arg Glu Glu Gln Tyr Asn
    290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Gly
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Cys Arg Asp Glu Leu Thr Lys Asn
        355                 360                 365
Gln Val Ser Leu Trp Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro Gly Lys Gly Gly Gly Ser Gly Gly Gly Gly Ser
    450                 455                 460
Asp Ile Gln Met Thr Gln Ser Pro Ser Ser Leu Ser Ala Ser Val Gly
465                 470                 475                 480
Asp Arg Val Thr Ile Thr Cys Arg Ser Ser Gln Ser Leu Val His Ser
                485                 490                 495
Asn Gly Asn Thr Phe Leu His Trp Tyr Gln Gln Lys Pro Gly Lys Ala
            500                 505                 510
Pro Lys Leu Leu Ile Tyr Thr Val Ser Asn Arg Phe Ser Gly Val Pro
        515                 520                 525
Ser Arg Phe Ser Gly Ser Gly Ser Gly Thr Asp Phe Thr Leu Thr Ile
    530                 535                 540
Ser Ser Leu Gln Pro Glu Asp Phe Ala Thr Tyr Phe Cys Ser Gln Thr
545                 550                 555                 560
Thr His Val Pro Trp Thr Phe Gly Gly Gly Thr Lys Val Glu Ile Lys
                565                 570                 575
```

```
Arg Thr Val Ala Ala Pro Ser Val Phe Ile Phe Pro Ser Asp Arg
            580                 585                 590
Lys Leu Lys Ser Gly Thr Ala Ser Val Val Cys Leu Leu Asn Asn Phe
        595                 600                 605
Tyr Pro Arg Glu Ala Lys Val Gln Trp Lys Val Asp Asn Ala Leu Gln
    610                 615                 620
Ser Gly Asn Ser Gln Glu Ser Val Thr Glu Gln Asp Ser Lys Asp Ser
625                 630                 635                 640
Thr Tyr Ser Leu Ser Ser Thr Leu Thr Leu Ser Lys Ala Asp Tyr Glu
                645                 650                 655
Lys His Lys Val Tyr Ala Cys Glu Val Thr His Gln Gly Leu Ser Ser
            660                 665                 670
Pro Val Thr Lys Ser Phe Asn Arg Gly Glu Cys Gly Gly Gly Gly Ser
        675                 680                 685
Gly Gly Gly Gly Ser Gly Gly Ser Gly Gly Gly Gly Ser Glu Val
    690                 695                 700
Gln Leu Leu Glu Ser Gly Gly Gly Leu Val Gln Pro Gly Gly Ser Leu
705                 710                 715                 720
Arg Leu Ser Cys Ala Ala Ser Gly Phe Thr Phe Ser Ser Tyr Ala Met
                725                 730                 735
Ser Trp Val Arg Gln Ala Pro Gly Lys Gly Leu Glu Trp Val Ser Ala
            740                 745                 750
Ile Ile Gly Ser Gly Ala Ser Thr Tyr Tyr Ala Asp Ser Val Lys Gly
        755                 760                 765
Arg Phe Thr Ile Ser Arg Asp Asn Ser Lys Asn Thr Leu Tyr Leu Gln
    770                 775                 780
Met Asn Ser Leu Arg Ala Glu Asp Thr Ala Val Tyr Tyr Cys Ala Lys
785                 790                 795                 800
Gly Trp Phe Gly Gly Phe Asn Tyr Trp Gly Gln Gly Thr Leu Val Thr
                805                 810                 815
Val Ser Ser Ala Ser Val Ala Ala Pro Ser Val Phe Ile Phe Pro Pro
            820                 825                 830
Ser Asp Glu Gln Leu Lys Ser Gly Thr Ala Ser Val Val Cys Leu Leu
        835                 840                 845
Asn Asn Phe Tyr Pro Arg Glu Ala Lys Val Gln Trp Lys Val Asp Asn
    850                 855                 860
Ala Leu Gln Ser Gly Asn Ser Gln Glu Ser Val Thr Glu Gln Asp Ser
865                 870                 875                 880
Lys Asp Ser Thr Tyr Ser Leu Ser Ser Thr Leu Thr Leu Ser Lys Ala
                885                 890                 895
Asp Tyr Glu Lys His Lys Val Tyr Ala Cys Glu Val Thr His Gln Gly
            900                 905                 910
Leu Ser Ser Pro Val Thr Lys Ser Phe Asn Arg Gly Glu Cys
        915                 920                 925

<210> SEQ ID NO 166
<211> LENGTH: 915
<212> TYPE: PRT
<213> ORGANISM: Artificial Sequence
<220> FEATURE:
<223> OTHER INFORMATION: second fusion polypeptide (Fc hole) P1AE2255

<400> SEQUENCE: 166

Glu Val Gln Leu Leu Glu Ser Gly Gly Gly Leu Val Gln Pro Gly Gly
1               5                   10                  15
```

-continued

```
Ser Leu Arg Leu Ser Cys Ala Ala Ser Gly Tyr Ser Phe Thr Gly Tyr
         20                  25                  30

Tyr Ile His Trp Val Arg Gln Ala Pro Gly Lys Gly Leu Glu Trp Val
         35                  40                  45

Gly Arg Val Ile Pro Asn Ala Gly Gly Thr Ser Tyr Asn Gln Lys Phe
 50                  55                  60

Lys Gly Arg Phe Thr Ile Ser Val Asp Asn Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ile Tyr Trp Trp Gly Gln Gly Thr Thr Val Thr Val
                100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Glu
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Val Glu Pro Lys Ser Cys Gly Gly Gly Ser Gly Gly
210                 215                 220

Gly Gly Ser Asp Lys Thr His Thr Cys Pro Pro Cys Pro Ala Pro Glu
225                 230                 235                 240

Ala Ala Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Gly
                325                 330                 335

Ala Pro Ile Glu Lys Thr Ile Ser Lys Ala Lys Gly Gln Pro Arg Glu
            340                 345                 350

Pro Gln Val Cys Thr Leu Pro Pro Ser Arg Asp Glu Leu Thr Lys Asn
        355                 360                 365

Gln Val Ser Leu Ser Cys Ala Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Val Ser Lys
                405                 410                 415

Leu Thr Val Asp Lys Ser Arg Trp Gln Gln Gly Asn Val Phe Ser Cys
            420                 425                 430
```

```
Ser Val Met His Glu Ala Leu His Asn His Tyr Thr Gln Lys Ser Leu
        435                 440                 445

Ser Leu Ser Pro Gly Lys Gly Gly Gly Ser Gly Gly Gly Gly Ser
    450                 455                 460

Asp Ile Gln Met Thr Gln Ser Pro Ser Ser Leu Ser Ala Ser Val Gly
465                 470                 475                 480

Asp Arg Val Thr Ile Thr Cys Arg Ser Ser Gln Ser Leu Val His Ser
                485                 490                 495

Asn Gly Asn Thr Phe Leu His Trp Tyr Gln Gln Lys Pro Gly Lys Ala
            500                 505                 510

Pro Lys Leu Leu Ile Tyr Thr Val Ser Asn Arg Phe Ser Gly Val Pro
        515                 520                 525

Ser Arg Phe Ser Gly Ser Gly Ser Gly Thr Asp Phe Thr Leu Thr Ile
    530                 535                 540

Ser Ser Leu Gln Pro Glu Asp Phe Ala Thr Tyr Phe Cys Ser Gln Thr
545                 550                 555                 560

Thr His Val Pro Trp Thr Phe Gly Gly Gly Thr Lys Val Glu Ile Lys
                565                 570                 575

Arg Thr Val Ala Ala Pro Ser Val Phe Ile Phe Pro Pro Ser Asp Arg
            580                 585                 590

Lys Leu Lys Ser Gly Thr Ala Ser Val Val Cys Leu Leu Asn Asn Phe
        595                 600                 605

Tyr Pro Arg Glu Ala Lys Val Gln Trp Lys Val Asp Asn Ala Leu Gln
    610                 615                 620

Ser Gly Asn Ser Gln Glu Ser Val Thr Glu Gln Asp Ser Lys Asp Ser
625                 630                 635                 640

Thr Tyr Ser Leu Ser Ser Thr Leu Thr Leu Ser Lys Ala Asp Tyr Glu
                645                 650                 655

Lys His Lys Val Tyr Ala Cys Glu Val Thr His Gln Gly Leu Ser Ser
            660                 665                 670

Pro Val Thr Lys Ser Phe Asn Arg Gly Glu Cys Gly Gly Gly Gly Ser
        675                 680                 685

Gly Gly Gly Gly Ser Gly Gly Gly Ser Gly Gly Gly Gly Ser Glu Ile
    690                 695                 700

Val Leu Thr Gln Ser Pro Gly Thr Leu Ser Leu Ser Pro Gly Glu Arg
705                 710                 715                 720

Ala Thr Leu Ser Cys Arg Ala Ser Gln Ser Val Thr Ser Ser Tyr Leu
                725                 730                 735

Ala Trp Tyr Gln Gln Lys Pro Gly Gln Ala Pro Arg Leu Leu Ile Asn
            740                 745                 750

Val Gly Ser Arg Arg Ala Thr Gly Ile Pro Asp Arg Phe Ser Gly Ser
        755                 760                 765

Gly Ser Gly Thr Asp Phe Thr Leu Thr Ile Ser Arg Leu Glu Pro Glu
    770                 775                 780

Asp Phe Ala Val Tyr Tyr Cys Gln Gln Gly Ile Met Leu Pro Pro Thr
785                 790                 795                 800

Phe Gly Gln Gly Thr Lys Val Glu Ile Lys Ser Ser Ala Ser Thr Lys
                805                 810                 815

Gly Pro Ser Val Phe Pro Leu Ala Pro Ser Ser Lys Ser Thr Ser Gly
            820                 825                 830

Gly Thr Ala Ala Leu Gly Cys Leu Val Lys Asp Tyr Phe Pro Glu Pro
        835                 840                 845
```

Val Thr Val Ser Trp Asn Ser Gly Ala Leu Thr Ser Gly Val His Thr
            850                 855                 860

Phe Pro Ala Val Leu Gln Ser Ser Gly Leu Tyr Ser Leu Ser Ser Val
865                 870                 875                 880

Val Thr Val Pro Ser Ser Leu Gly Thr Gln Thr Tyr Ile Cys Asn
            885                 890                 895

Val Asn His Lys Pro Ser Asn Thr Lys Val Asp Lys Lys Val Glu Pro
            900                 905                 910

Lys Ser Cys
        915

<210> SEQ ID NO 167
<211> LENGTH: 114
<212> TYPE: PRT
<213> ORGANISM: Artificial Sequence
<220> FEATURE:
<223> OTHER INFORMATION: VH1a (CD40)

<400> SEQUENCE: 167

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Gln Ser Leu Glu Trp Met
        35                  40                  45

Gly Arg Val Ile Pro Asn Ala Gly Gly Thr Ser Tyr Asn Gln Lys Phe
    50                  55                  60

Lys Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Ile Tyr Trp Trp Gly Gln Gly Thr Thr Val Thr Val
            100                 105                 110

Ser Ser

<210> SEQ ID NO 168
<211> LENGTH: 114
<212> TYPE: PRT
<213> ORGANISM: Artificial Sequence
<220> FEATURE:
<223> OTHER INFORMATION: VH1b (CD40)

<400> SEQUENCE: 168

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Lys Ser Leu Glu Trp Met
        35                  40                  45

Gly Arg Val Ile Pro Asn Ala Gly Gly Thr Ser Tyr Asn Gln Lys Phe
    50                  55                  60

Lys Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

```
Ala Arg Glu Gly Ile Tyr Trp Trp Gly Gln Gly Thr Thr Val Thr Val
            100                 105                 110
Ser Ser

<210> SEQ ID NO 169
<211> LENGTH: 114
<212> TYPE: PRT
<213> ORGANISM: Artificial Sequence
<220> FEATURE:
<223> OTHER INFORMATION: VH1c (CD40)

<400> SEQUENCE: 169

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Gln Ser Leu Glu Trp Met
        35                  40                  45

Gly Arg Val Ile Pro Asn Ala Gly Gly Thr Ser Tyr Asn Gln Lys Phe
    50                  55                  60

Lys Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Ile Tyr Trp Trp Gly His Gly Thr Thr Val Thr Val
            100                 105                 110
Ser Ser

<210> SEQ ID NO 170
<211> LENGTH: 114
<212> TYPE: PRT
<213> ORGANISM: Artificial Sequence
<220> FEATURE:
<223> OTHER INFORMATION: VH1d (CD40)

<400> SEQUENCE: 170

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Gln Ser Leu Glu Trp Met
        35                  40                  45

Gly Arg Val Ile Pro Asn Ala Gly Gly Thr Ser Tyr Asn Gln Lys Phe
    50                  55                  60

Lys Gly Arg Val Thr Leu Ser Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Ile Tyr Trp Trp Gly Gln Gly Thr Thr Val Thr Val
            100                 105                 110
Ser Ser

<210> SEQ ID NO 171
<211> LENGTH: 112
<212> TYPE: PRT
<213> ORGANISM: Artificial Sequence
<220> FEATURE:
<223> OTHER INFORMATION: VL1a (CD40)
```

<400> SEQUENCE: 171

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Phe Leu His Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Thr His Val Pro Trp Thr Phe Gly Gly Gly Thr Lys Val Glu Ile Lys
            100                 105                 110

<210> SEQ ID NO 172
<211> LENGTH: 112
<212> TYPE: PRT
<213> ORGANISM: Artificial Sequence
<220> FEATURE:
<223> OTHER INFORMATION: VL1b (CD40)

<400> SEQUENCE: 172

Asp Ile Val Val Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Phe Leu His Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Thr His Val Pro Trp Thr Phe Gly Gly Gly Thr Lys Val Glu Ile Lys
            100                 105                 110

<210> SEQ ID NO 173
<211> LENGTH: 112
<212> TYPE: PRT
<213> ORGANISM: Artificial Sequence
<220> FEATURE:
<223> OTHER INFORMATION: VL1c (CD40)

<400> SEQUENCE: 173

Asp Val Val Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Phe Leu His Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Val Gly Val Tyr Phe Cys Ser Gln Thr
            85                  90                  95

Thr His Val Pro Trp Thr Phe Gly Gly Gly Thr Lys Val Glu Ile Lys
            100                 105                 110

<210> SEQ ID NO 174
<211> LENGTH: 112
<212> TYPE: PRT
<213> ORGANISM: Artificial Sequence
<220> FEATURE:
<223> OTHER INFORMATION: VL1d (CD40)

<400> SEQUENCE: 174

Asp Val Val Val Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Phe Leu His Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
            85                  90                  95

Thr His Val Pro Trp Thr Phe Gly Gly Gly Thr Lys Leu Glu Ile Lys
            100                 105                 110

<210> SEQ ID NO 175
<211> LENGTH: 114
<212> TYPE: PRT
<213> ORGANISM: Artificial Sequence
<220> FEATURE:
<223> OTHER INFORMATION: VH2a (CD40)

<400> SEQUENCE: 175

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45

Gly Arg Val Ile Pro Asn Ala Gly Gly Thr Ser Tyr Asn Gln Lys Phe
    50                  55                  60

Lys Gly Arg Phe Thr Ile Ser Val Asp Asn Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Glu Gly Ile Tyr Trp Trp Gly Gln Gly Thr Thr Val Thr Val
            100                 105                 110

Ser Ser

<210> SEQ ID NO 176
<211> LENGTH: 114
<212> TYPE: PRT
<213> ORGANISM: Artificial Sequence
<220> FEATURE:
<223> OTHER INFORMATION: VH2b (CD40)
```

-continued

```
<400> SEQUENCE: 176

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Ser Leu Glu Trp Val
        35                  40                  45

Gly Arg Val Ile Pro Asn Ala Gly Gly Thr Ser Tyr Asn Gln Lys Phe
    50                  55                  60

Lys Gly Arg Phe Thr Ile Ser Val Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Tyr Trp Trp Gly Gln Gly Thr Thr Val Thr Val
            100                 105                 110

Ser Ser

<210> SEQ ID NO 177
<211> LENGTH: 114
<212> TYPE: PRT
<213> ORGANISM: Artificial Sequence
<220> FEATURE:
<223> OTHER INFORMATION: VH2c (CD40)

<400> SEQUENCE: 177

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45

Gly Arg Val Ile Pro Asn Ala Gly Gly Thr Ser Tyr Asn Gln Lys Phe
    50                  55                  60

Lys Gly Arg Phe Thr Ile Ser Val Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Tyr Trp Trp Gly His Gly Thr Thr Val Thr Val
            100                 105                 110

Ser Ser

<210> SEQ ID NO 178
<211> LENGTH: 114
<212> TYPE: PRT
<213> ORGANISM: Artificial Sequence
<220> FEATURE:
<223> OTHER INFORMATION: VH2d (CD40)

<400> SEQUENCE: 178

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Tyr Ile His Trp Val Arg Gln Ala Pro Gly Lys Gly Leu Glu Trp Val
        35                  40                  45

Gly Arg Val Ile Pro Asn Ala Gly Gly Thr Ser Tyr Gly Asp Ser Val
    50                  55                  60
```

```
Lys Gly Arg Phe Thr Ile Ser Val Asp Asn Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ile Tyr Trp Trp Gly Gln Gly Thr Thr Val Thr Val
            100                 105                 110

Ser Ser

<210> SEQ ID NO 179
<211> LENGTH: 114
<212> TYPE: PRT
<213> ORGANISM: Artificial Sequence
<220> FEATURE:
<223> OTHER INFORMATION: VH2ab (CD40)

<400> SEQUENCE: 179

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
                20                  25                  30

Tyr Met His Trp Val Arg Gln Ala Pro Gly Lys Gly Leu Glu Trp Val
             35                  40                  45

Gly Arg Val Ile Pro Asn Ala Gly Gly Thr Ser Tyr Asn Gln Lys Phe
 50                  55                  60

Lys Gly Arg Phe Thr Ile Ser Val Asp Asn Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ile Tyr Trp Trp Gly Gln Gly Thr Thr Val Thr Val
            100                 105                 110

Ser Ser

<210> SEQ ID NO 180
<211> LENGTH: 114
<212> TYPE: PRT
<213> ORGANISM: Artificial Sequence
<220> FEATURE:
<223> OTHER INFORMATION: VH2ac (CD40)

<400> SEQUENCE: 180

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
                20                  25                  30

Tyr Ile His Trp Val Arg Gln Ala Pro Gly Lys Gly Leu Glu Trp Val
             35                  40                  45

Gly Arg Val Ile Pro Asn Ala Gly Gly Thr Ser Tyr Asn Gln Lys Val
 50                  55                  60

Lys Gly Arg Phe Thr Ile Ser Val Asp Asn Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ile Tyr Trp Trp Gly Gln Gly Thr Thr Val Thr Val
            100                 105                 110

Ser Ser
```

```
<210> SEQ ID NO 181
<211> LENGTH: 112
<212> TYPE: PRT
<213> ORGANISM: Artificial Sequence
<220> FEATURE:
<223> OTHER INFORMATION: VL2a (CD40)

<400> SEQUENCE: 181

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Phe Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Phe Cys Ser Gln Thr
                85                  90                  95

Thr His Val Pro Trp Thr Phe Gly Gly Gly Thr Lys Val Glu Ile Lys
            100                 105                 110

<210> SEQ ID NO 182
<211> LENGTH: 112
<212> TYPE: PRT
<213> ORGANISM: Artificial Sequence
<220> FEATURE:
<223> OTHER INFORMATION: VL2b (CD40)

<400> SEQUENCE: 182

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Phe Leu His Trp Tyr Gln Gln Lys Pro Gly Gln Ser
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Phe Cys Ser Gln Thr
                85                  90                  95

Thr His Val Pro Trp Thr Phe Gly Gly Gly Thr Lys Val Glu Ile Lys
            100                 105                 110

<210> SEQ ID NO 183
<211> LENGTH: 112
<212> TYPE: PRT
<213> ORGANISM: Artificial Sequence
<220> FEATURE:
<223> OTHER INFORMATION: VL2ab (CD40)

<400> SEQUENCE: 183

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Leu Val His Ser
            20                  25                  30
```

```
Asn Gly Asn Thr Phe Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                      70                  75                  80

Ser Ser Leu Gln Pro Glu Asp Phe Ala Thr Tyr Phe Cys Ser Gln Thr
                85                  90                  95

Thr His Val Pro Trp Thr Phe Gly Gly Gly Thr Lys Val Glu Ile Lys
                100                 105                 110

<210> SEQ ID NO 184
<211> LENGTH: 112
<212> TYPE: PRT
<213> ORGANISM: Artificial Sequence
<220> FEATURE:
<223> OTHER INFORMATION: VL2ac (CD40)

<400> SEQUENCE: 184

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
                20                  25                  30

Asn Gly Asn Thr Phe Leu His Trp Tyr Gln Gln Lys Pro Gly Lys Ala
        35                  40                  45

Pro Lys Leu Leu Ile Tyr Thr Val Ser Asn Arg Phe Ser Gly Val Pro
    50                  55                  60

Ser Arg Phe Ser Gly Ser Gly Ser Gly Thr Asp Phe Thr Leu Thr Ile
65                      70                  75                  80

Ser Ser Leu Gln Pro Glu Asp Phe Ala Thr Tyr Phe Cys Ser Gln Thr
                85                  90                  95

Thr His Val Pro Trp Thr Phe Gly Gly Gly Thr Lys Val Glu Ile Lys
                100                 105                 110
```